(12) United States Patent
Gossett et al.

(10) Patent No.: US 7,282,501 B2
(45) Date of Patent: *Oct. 16, 2007

(54) MODULATORS OF PEROXISOME PROLIFERATOR ACTIVATED RECEPTORS (PPAR)

(75) Inventors: Lynn Stacy Gossett, Indianapolis, IN (US); Jonathan Edward Green, Greencastle, IN (US); James Robert Henry, Indianapolis, IN (US); Winton Dennis Jones, Carmel, IN (US); Donald Paul Matthews, Indianapolis, IN (US); Quanrong Shen, Fishers, IN (US); Daryl Lynn Smith, Fishers, IN (US); Jennifer Ann Vance, San Jose, CA (US); Alan M. Warshawsky, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 407 days.

This patent is subject to a terminal disclaimer.

(21) Appl. No.: 10/477,405

(22) PCT Filed: May 24, 2002

(86) PCT No.: PCT/US02/15143

§ 371 (c)(1),
(2), (4) Date: Nov. 12, 2003

(87) PCT Pub. No.: WO02/100403

PCT Pub. Date: Dec. 19, 2002

(65) Prior Publication Data

US 2005/0075378 A1  Apr. 7, 2005

Related U.S. Application Data

(60) Provisional application No. 60/296,701, filed on Jun. 7, 2001.

(51) Int. Cl.
| | |
|---|---|
| *A61K 31/535* | (2006.01) |
| *A61K 31/42* | (2006.01) |
| *A61K 31/445* | (2006.01) |
| *A61K 31/4965* | (2006.01) |
| *C07D 263/34* | (2006.01) |
| *C07D 275/04* | (2006.01) |
| *C07D 413/10* | (2006.01) |

(52) U.S. Cl. .................. 514/236.8; 514/374; 514/326; 514/256; 514/255.05; 514/340; 548/236; 548/209; 544/137; 544/333; 544/405; 546/271.4

(58) Field of Classification Search ................ 548/236, 548/209; 514/374, 236.8, 326, 256, 255.05, 514/340; 544/137, 333, 405; 546/209, 271.4
See application file for complete search history.

(56) References Cited

U.S. PATENT DOCUMENTS

| | | |
|---|---|---|
| 5,089,514 A | 2/1992 | Hulin |
| 5,232,945 A | 8/1993 | Hulin |
| 5,306,726 A | 4/1994 | Hulin |
| 5,902,726 A | 5/1999 | Kliewer et al. |
| 5,994,554 A | 11/1999 | Kliewer et al. |
| 6,982,278 B2 * | 1/2006 | Brooks et al. ............... 514/374 |

FOREIGN PATENT DOCUMENTS

| | | |
|---|---|---|
| EP | 0 930 229 A | 7/1999 |
| EP | 1 216 980 A | 6/2002 |
| GB | 2 359 082 A | 8/2001 |
| WO | WO97 28115 | 8/1997 |
| WO | WO97 31907 A | 9/1997 |
| WO | WO99 46232 A | 9/1999 |
| WO | WO 01 00566 A | 1/2001 |
| WO | WO 01 16120 A | 3/2001 |
| WO | WO 02 16332 A | 2/2002 |
| WO | WO 02 18355 A | 3/2002 |
| WO | WO 02 100813 | 12/2002 |

OTHER PUBLICATIONS

Obach R. S., Drug-drug interactions: An important negative attribute in drugs, Drugs of Today, 39(5), 301-38, (2003).*
Sarges, R., et al.: "Glucose Transport-Enhancing and Hypoglycemic Activity of 2-Methyl-2-Phenoxy-3-Phenylpropanoic Acids"; Journal of Medicinal Chemistry, vol. 39, No. 24, Nov. 22, 1996, pp. 4783-4803.
Cobb, J. E., et al.: "N-(2-Benzoylphenyl)-L-Tyrosine PPARGamma Agonists. 3. Structure-Activity Relationship and Optimization of the N-Aryl Substituent"; Journal of Medicinal Chemistry, vol. 41, No. 25, Dec. 3, 1998, pp. 5055-5069.
Bright, S.W., et. al.: "Competitive Particle Concentration Fluorescence Immunoassays for Measuring Anti-Diabetic Drug Levels in Mouse Plasma"; Journal of Immunological Methods, vol. 207, No. 1, Aug. 22, 1997, pp. 23-31.
Brooks, D., et al.: "Design and Synthesis of 2-methyl-2-{4-'2-'5-methyl-2-aryloxazol-4-yl)ethoxylphenoxy}propionic acids: A New Class of Dual PPARAlpha/Gamma Agonists"; Journal of Medicinal Chemistry, vol. 44, No. 13, Jun. 21, 2001, pp. 2061-2064.
Shinkai, H. et al.: "Isoxazolidine-3,5-dione and Noncyclic 1,3-dicarbonyl Compounds as Hypoglycemic Agents"; Journal of Medicinal Chemistry, vol. 41, No. 11, May 21, 1998, pp. 1927-1933.
Murugesan, N., et al.: "Biphenylsulfonamide Endothelin Receptor Antogonists 2. Discovery of 4'-oxazoly-lbiphenylsulfonamides as a New Class of Poent, Highly Selective ET(A) Antagonists"; Journal of Medicinal Chemistry, vol. 43, No. 16, Aug. 10, 2000, pp. 3111-3117.
Malamas, M.S., et al.: "Azole Phenoxy Hydroxyureas as Selective and Orally Active Inhibitors fo 5-Lipoxygenase"; Journal of Medicinal Chemistry, vol. 39, No. 1, Jan. 5, 1996, pp. 237-245.
Merguro, K., et al.: "Studies on Antidiabetic Agents. VII. Synthesis and Hypoglycemic Activity fo 4-Oxazoleacetic Acid Derivatives"; Chemical & Pharmaceutical Bulletin, vol. 34, No. 7, 1986, pp. 2840-2851.

* cited by examiner

*Primary Examiner*—Rebecca Anderson
(74) *Attorney, Agent, or Firm*—MaCharri Vorndran-Jones; Soonhee Jang

(57) ABSTRACT

The present invention is directed to a compound of formula I, and pharmaceutically acceptable salts, solvates, hydrates or stereoisomer thereof, which are useful in treating Syndrome X, Type II diabetes, hyperglycemia, hyperlipidemia, obesity, coagaulopathy, hypertension, arteriosclerosis, and other disorders related to Syndrome X as well as cardiovascular diseases.

18 Claims, No Drawings

MODULATORS OF PEROXISOME PROLIFERATOR ACTIVATED RECEPTORS (PPAR)

This is the national stage application under 35 USC 371 for PCT/US02/15143, filed May 24, 2002, which claims the benefit of U.S. Provisional Application Ser. No. 60/296,701, filed Jun. 7, 2001.

FIELD OF THE INVENTION

The present invention relates to a compound of peroxisome proliferator activated receptor (PPAR) agonists, which are useful for the treatment and/or prevention of disorders modulated by a PPAR.

BACKGROUND OF THE INVENTION

The peroxisome proliferator activated receptors (PPARs) are members of the nuclear receptor gene family that are activated by fatty acids and fatty acid metabolites. The PPARs belong to the subset of nuclear receptors that function as heterodimers with the 9-cis retinoic acid receptor (RXR). Three subtypes, designated PPARα, PPARγ and PPARδ, are found in species ranging from *Xenopus* to humans.

PPARα is the main subtype in the liver and has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also involved with the activity of fibrates and fatty acids in rodents and humans. Fibric acid derivatives such as clofibrate, fenofibrate, bezafibrate, ciprofibrate, beclofibrate and etofibrate, as well as gemfibrozil, produce a substantial reduction in plasma triglycerides along with moderate reduction in low-density lipoprotein (LDL) cholesterol, and they are used particularly for the treatment of hypertriglyceridemia.

PPARγ is the main subtype in adipose tissue and involved in activating the program of adipocyte differentiation. PPARγ is not involved in stimulating peroxisome proliferation in the liver. There are two isomers of PPARγ: PPARγ1 and PPARγ2, which differ only in that PPARγ2 contains an additional 28 amino acids present at the amino terminus. The DNA sequences for the PPARγ receptors are described in Elbrecht, et al., BBRC 224;431-437 (1996). Although peroxisome proliferators, including the fibrates and fatty acids, activate the transcriptional activity of PPAR's, only prostaglandin $J_2$ derivatives have been identified as natural ligands for PPARγ, which also binds the anti-diabetic agents thiazolidinediones with high affinity. The physiological functions of PPARα and PPARγ in lipid and carbohydrate metabolism were uncovered once it was recognized that they were the receptors for the fibrate and glitazone drugs, repectively.

PPARα and PPARγ receptors have been implicated in diabetes mellitus, cardiovascular disease, obesity, and gastrointestinal disease, such as inflammatory bowel disease and other inflammation related illnesses. Such inflammation related illnesses include, but are not limited to Alzheimer's disease, Crohn's disease, rheumatoid arthritis, psoriasis, and ischemia reprofusion injury.

By contrast, PPARδ (also referred to as PPARβ and NUC1) is not reported to be receptor for any known class of drug molecules, and its role in mammalian physiology has remained undefined. The human nuclear receptor gene PPARδ (hPPARδ) has been cloned from a human osteosarcoma cell cDNA library and is fully described in A. Schmidt et al., *Molecular Endocrinology*, 6:1634-1641 (1992).

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes, which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL (known as the "bad" cholesterol) which are risk factors in cardiovascular diseases. The constellation of symptoms which includes hyperinsulemia combined with hypertension, elevated body weight, elevated triglycerides and elevated LDL is known as Syndrome X.

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. One form of hyperlipidemia is hypercholesterolemia, characterized by the existence of elevated LDL cholesterol levels. The initial treatment for hypercholesterolemia is often a diet low in fat and cholesterol coupled with appropriate physical exercise. Drug intervention is initiated if LDL-lowering goals are not met by diet and exercise alone. It is desirable to lower elevated levels of LDL cholesterol and increase levels of HDL cholesterol. Generally, it has been found that increased levels of HDL are associated with lower risk for coronary heart disease (CHD). See Gordon, et al., *Am. J. Med.*, 62, 707-714 (1977); Stampfer, et al., *N. England J. Med.*, 325, 373-381 (1991); and Kannel, et al., *Ann. Internal Med.*, 90, 85-91 (1979). An example of an HDL raising agent is nicotinic acid, but the quantities needed to achieve HDL elevation are associated with undesirable effects, such as flushing.

There are several treatments currently available for treating diabetes mellitus but these treatments still remain unsatisfactory and have limitations. While physical exercise and reduction in dietary intake of calories will improve the diabetic condition, compliance with this approach can be poor because of sedentary lifestyles and excess food consumption, in particular high fat-containing food. Therefore, treatment with hypoglycemics, such as sulfonylureas (e.g., chlorpropamide, tolbutamide, tolazamide and acetohexamide) and biguanides (e.g. phenformin and metformin) are often necessary as the disease progresses. Sulfonylureas stimulate the β cells of the pancreas to secrete more insulin as the disease progresses. However, the response of the β cells eventually fails and treatment with insulin injections is necessary. In addition, both sulfonylurea treatment and insulin injection have the life threatening side effect of hypoglycemic coma, and thus patients using these treatments must carefully control dosage.

It has been well established that improved glycemic control in patients with diabetes (Type I and Type II) is accompanied by decreased microvasclular complications (DCCT and UKPDS). Due to difficulty in maintaining adequate glycemic control over time in patients with Type II diabetes, the use of insulin sensitizers in the therapy of Type II diabetes is growing. There is also a growing body of evidence that PPARγ agonist, insulin sensitizer, may have benefits in the treatment of Type II diabetes beyond their effects in improving glycemic control.

In the last decade a class of compounds known as thiazolidinediones (e.g. U.S. Pat. Nos. 5,089,514; 4,342,771; 4,367,234; 4,340,605; and 5,306,726) have emerged as effective anidiabetic agents that have been shown to increase the sensitivity of insulin sensitive tissues, such as skeletal muscle, liver and adipose, to insulin. Increasing insulin sensitivity rather than the amount of insulin in the blood reduces the likelihood of hypoglycemic coma. Although thiazolidinediones have been shown to increase insulin sensitivity by binding to PPARγ receptors, this treatment also produces unwanted side effects such as weight gain and, for troglitazone, liver toxicity.

In view of the above, there exists a need for new pharmaceutical agents which modulate these receptors to prevent, treat and/or alleviate these diseases or conditions while ameliorating side effects of current treatments.

SUMMARY OF THE INVENTION

The present invention relates to compound of novel peroxisome proliferator activated receptor agonists having a structural formula I,

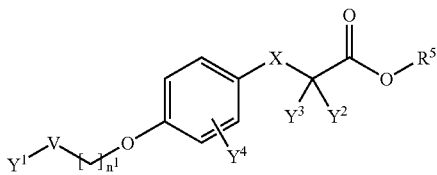

and pharmaceutically acceptable salts, solvates, hydrates or stereoisomers thereof, wherein:
$n^1$ is 2, 3, 4 or 5;
V is a bond or O;
X is $CH_2$ or O;
p is 0 or 1;
m is 1-4;
$Y^1$ is:

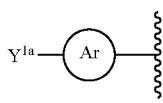

wherein,

is: aryl or heteroaryl,
  wherein aryl and heteroaryl are optionally substituted with one or more groups independently selected from the group consisting of:
  hydrogen, $C_1$-$C_6$ alkyl, $C_1$-$C_6$ alkoxy, halo, haloalkyl and haloalkyloxy;

$Y^{1a}$ is: hydrogen,
  ($C_0$-$C_3$)alkyl-aryl,
  C(O)-aryl,
  heteroaryl,
  cycloalkyl,
  heterocycloalkyl,
  aryloxy,
  $NR^5(CH_2)_mOR^5$,
  aryl-Z-aryl,
  aryl-Z-heteroaryl,
  aryl-Z-cycloalkyl,
  aryl-Z-heterocycloalkyl,
  heteroaryl-Z-aryl,
  heteroaryl-Z-heterocycloalkyl or
  heterocycloalkyl-Z-aryl,
  wherein aryl, cycloalkyl, aryloxy, heteroaryl, and heterocycloalkyl are optionally substituted with one or more substituents independently selected from the group consisting of:
    halo,
    hydroxyl,
    nitro,
    cyano,
    $C_1$-$C_6$ alkyl,
    $C_1$-$C_6$ alkoxy optionally substituted with $N(R^5)_2$,
    haloalkyl,
    $N(R^5)_2$,
    $N[C(O)R^5]_2$,
    $N[S(O)_2R^5]_2$,
    $NR^5S(O)_2R^5$,
    $NR^5C(O)R^5$,
    $NR^5C(O)OR^5$,
    $C(O)N(R^5)_2$,
    $C(O)OR^5$ and
    $C(O)R^5$;
Z is: a bond,
  -oxygen-
  —$C(O)NR^5$—
  —$NR^5C(O)$—,
  —$NR^5C(O)O$—,
  —$C(O)$—,
  —$NR^5$—,
  —$[O]_p(CH_2)_m$—,
  —$(CH_2)_m[O]_p$—,
  —$NR^5(CH_2)_m$— or
  —$(CH_2)_mNR^5$—;
$Y^2$ and $Y^3$ are each independently:
  hydrogen,
  $C_1$-$C_6$ alkyl or
  $C_1$-$C_6$ alkoxy;
$Y^4$ is: ($C_1$-$C_3$)alkyl-$NR^5C(O)$—($C_0$-$C_5$)alkyl-$Y^7$,
  ($C_1$-$C_3$)alkyl-$NR^5C(O)$—($C_2$-$C_5$)alkenyl-$Y^7$,
  ($C_1$-$C_3$)alkyl-$NR^5C(O)$—($C_2$-$C_5$)alkynyl-$Y^7$;
  ($C_1$-$C_3$)alkyl-$NR^5C(O)O$—($C_0$-$C_5$)alkyl-$Y^7$,
  ($C_1$-$C_3$)alkyl-$NR^5C(O)NR^5$—($C_0$-$C_5$)alkyl-$Y^7$,
  ($C_1$-$C_3$)alkyl-$NR^5C(S)NR^5$—($C_0$-$C_5$)alkyl-$Y^7$,
  ($C_0$-$C_3$)alkyl-$C(O)NR^5$—($C_0$-$C_5$)alkyl-$Y^7$,
  ($C_{1-3}$)alkyl-$OC(O)NY^{10}Y^{11}$,
  ($C_1$-$C_3$)alkyl-$NY^{10}Y^{11}$,
  ($C_1$-$C_3$)alkyl-O—($C_0$-$C_5$)alkyl-$Y^7$,
  ($C_1$-$C_3$)alkyl-S—($C_0$-$C_5$)alkyl-$Y^7$ or
  CN;
$Y^7$ is: hydrogen,
  aryl,
  heteroaryl,
  $C_1$-$C_{12}$ alkyl,
  $C_1$-$C_6$ alkoxy, cycloalkyl,
heterocycloalkyl,
aryloxy,
C(O)-heteroaryl or
SR⁶,
wherein alkyl, aryl, aryloxy, alkoxy, heteroaryl, cycloalkyl, and heterocycloalkyl are optionally substituted with one or more groups independently selected from $R^7$:
$Y^{10}$ and $Y^{11}$ are each independently:
hydrogen,
aryl,
heteroaryl,
$C_1$-$C_{10}$alkyl,
cycloalkyl,
$SO_2(R^6)$; or
$Y^{10}$ and $Y^{11}$ together are a 5- to 10-membered heterocycloalkyl ring or heterocycloalkyl ring fused with aryl, and the heterocycloalkyl ring optionally containing one or more heteroatoms selected from N, O or S; and wherein, aryl, heteroaryl, heterocycloalkyl and alkyl are optionally substituted with one or more substituents independently selected from $R^7$;
$R^5$ is: hydrogen or $C_1$-$C_6$ alkyl;
$R^6$ is: hydrogen,
$C_1$-$C_{10}$ alkyl,
cycloalkyl,
aryl, or
heteroaryl,
wherein alkyl, cycloalkyl, aryl and heteroaryl are optionally substituted with one or more substituents independently selected from $R^7$;
$R^7$ is: halo,
nitro,
oxo,
cyano,
hydroxyl,
benzyl,
phenyl,
phenoxy,
heteroaryl,
$C(O)R^6$,
$C_1$-$C_{10}$ alkyl,
$C_1$-$C_6$ alkoxy,
$C_1$-$C_6$ haloalkyl,
$C_1$-$C_6$ haloalkyloxy,
$O(CH_2)_m$-phenyl,
$(CH_2)_mOC(O)$-aryl,
$C(O)OR^5$,
$S(O)_2R^5$,
$S(O)_2N(R^5)_2$,
$SR^5$ or
$N(R^5)_2$,
wherein phenyl and phenoxy are optionally substituted with one or more groups independently selected from halo or trifluoromethyl.

The compounds of the present invention are useful in the treatment or prevention of diseases or condition relates to hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component.

In one embodiment, the present invention also relates to pharmaceutical compositions which comprising at least one compound of the present invention, or a pharmaceutically acceptable salt, solvate, hydrate thereof and a pharmaceutically acceptable carrier. Within the scope of this invention also include a pharmaceutical composition containing additional therapeutic agent as well as at least one compound of the present invention, or a pharmaceutically acceptable salt, solvate, hydrate thereof and a pharmaceutically acceptable carrier.

In another embodiment, the present invention relates to a method of modulating a peroxisome proliferator activated receptor by contacting the receptor with at least one compound of Formula I, and pharmaceutically acceptable salts, solvates and hydrates thereof.

DETAILED DESCRIPTION OF THE INVENTION

The compounds of the present invention are directed to peroxisome proliferator activated receptor (PPAR) agonists, which are useful for the treatment and/or prevention of disorders modulated by a PPAR.

An embodiment of the present invention is a compound of structural formula I:

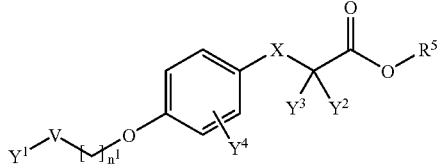

I and pharmaceutically acceptable salts, solvates, hydrates or stereoisomers thereof, wherein:
$n^1$ is 2, 3, 4 or 5;
V is a bond or O;
X is $CH_2$ or O;
p is 0 or 1;
m is 1-4;
$Y^1$ is:

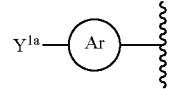

wherein,

is: aryl or heteroaryl,
wherein aryl and heteroaryl are optionally substituted with one or more groups independently selected from the group consisting of:
hydrogen, $C_1$-$C_6$ alkyl, $C_1$-$C_6$ alkoxy, halo, haloalkyl and haloalkyloxy;
$Y^{1a}$ is: hydrogen,
$(C_0$-$C_3)$alkyl-aryl,
C(O)-aryl,
heteroaryl,
cycloalkyl,
heterocycloalkyl,
aryloxy, $NR^5(CH_2)_mOR^5$,
aryl-Z-aryl,
aryl-Z-heteroaryl,
aryl-Z-cycloalkyl,
aryl-Z-heterocycloalkyl,
heteroaryl-Z-aryl,
heteroaryl-Z-heterocycloalkyl or
heterocycloalkyl-Z-aryl,
wherein aryl, cycloalkyl, aryloxy, heteroaryl, and heterocycloalkyl are optionally substituted with one or more substituents independently selected from the group consisting of:
halo,
hydroxyl,
nitro,
cyano,
$C_1$-$C_6$ alkyl,
$C_1$-$C_6$ alkoxy optionally substituted with $N(R^5)_2$,
haloalkyl,
$N(R^5)_2$,
$N[C(O)R^5]_2$,
$N[S(O)_2R^5]_2$,
$NR^5S(O)_2R^5$,
$NR^5C(O)R^5$,
$NR^5C(O)OR^5$,
$C(O)N(R^5)_2$,
$C(O)OR^5$ and
$C(O)R^5$;
Z is: a bond,
—oxygen—
—$C(O)NR^5$—
—$NR^5C(O)$—,
—$NR^5C(O)O$—,
—$C(O)$—,
—$NR^5$—,
—$[O]_p(CH_2)_m$—,
—$(CH_2)_m[O]_p$—,
—$NR^5(CH_2)_m$— or
—$(CH_2)_mNR^5$—;
$Y^2$ and $Y^3$ are each independently:
hydrogen,
$C_1$-$C_6$ alkyl or
$C_1$-$C_6$ alkoxy;
$Y^4$ is: $(C_1$-$C_3)$alkyl-$NR^5C(O)$—$(C_0$-$C_5)$alkyl-$Y^7$,
$(C_1$-$C_3)$alkyl-$NR^5C(O)$—$(C_2$-$C_5)$alkenyl-$Y^7$,
$(C_1$-$C_3)$alkyl-$NR^5C(O)$—$(C_2$-$C_5)$alkynyl-$Y^7$;
$(C_1$-$C_3)$alkyl-$NR^5C(O)O$—$(C_0$-$C_5)$alkyl-$Y^7$,
$(C_1$-$C_3)$alkyl-$NR^5C(O)NR^5$—$(C_0$-$C_5)$alkyl-$Y^7$,
$(C_1$-$C_3)$alkyl-$NR^5C(S)NR^5$—$(C_0$-$C_5)$alkyl-$Y^7$,
$(C_0$-$C_3)$alkyl-$C(O)NR^5$—$(C_0$-$C_5)$alkyl-$Y^7$,
$(C_1$-$C_3)$alkyl-$OC(O)NY^{10}Y^{11}$,
$(C_1$-$C_3)$alkyl-$NY^{10}Y^{11}$,
$(C_1$-$C_3)$alkyl-$O$—$(C_0$-$C_5)$alkyl-$Y^7$,
$(C_1$-$C_3)$alkyl-$S$—$(C_0$-$C_5)$alkyl-$Y^7$ or
CN;
$Y^7$ is: hydrogen,
aryl,
heteroaryl,
$C_1$-$C_{12}$ alkyl,
$C_1$-$C_6$ alkoxy,
cycloalkyl,
heterocycloalkyl,
aryloxy,
C(O)-heteroaryl or
$SR^6$, wherein alkyl, aryl, aryloxy, alkoxy, heteroaryl, cycloalkyl, and heterocycloalkyl are optionally substituted with one or more groups independently selected from $R^7$;
$Y^{10}$ and $Y^{11}$ are each independently:
hydrogen,
aryl,
heteroaryl,
$C_1$-$C_{10}$ alkyl,
cycloalkyl,
$SO_2(R^6)$; or
$Y^{10}$ and $Y^{11}$ together are a 5- to 10-membered heterocycloalkyl ring or heterocycloalkyl ring fused with aryl, and the heterocycloalkyl ring optionally containing one or more heteroatoms selected from N, O or S; and wherein, aryl, heteroaryl, heterocycloalkyl and alkyl are optionally substituted with one or more substituents independently selected from $R^7$;
$R^5$ is: hydrogen or $C_1$-$C_6$ alkyl;
$R^6$ is: hydrogen,
$C_1$-$C_{10}$ alkyl,
cycloalkyl,
aryl, or
heteroaryl,
wherein alkyl, cycloalkyl, aryl and heteroaryl are optionally substituted with one or more substituents independently selected from $R^7$;
$R^7$ is: halo,
nitro,
oxo,
cyano,
hydroxyl,
benzyl,
phenyl,
phenoxy,
heteroaryl,
$C(O)R^6$,
$C_1$-$C_{10}$ alkyl,
$C_1$-$C_6$ alkoxy,
$C_1$-$C_6$ haloalkyl,
$C_1$-$C_6$ haloalkyloxy,
$O(CH_2)_m$-phenyl,
$(CH_2)_mOC(O)$-aryl,
$C(O)OR^5$,
$S(O)_2R^5$,
$S(O)_2N(R^5)_2$,
$SR^5$ or
$N(R^5)_2$,
wherein phenyl and phenoxy are optionally substituted with one or more groups independently selected from halo or trifluoromethyl.

An embodiment of the present invention also include a compound represented by the structural Formula Ia:

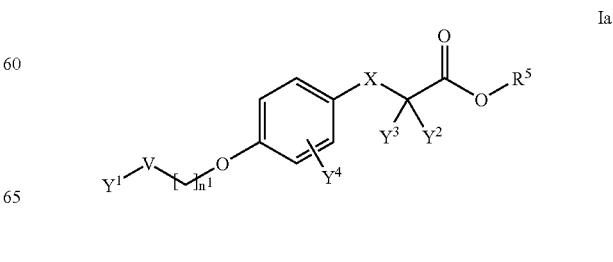

Ia or a pharmaceutically acceptable salt, hydrate or solvate thereof, wherein:

$Y^1$ is an unsubstituted or substituted group selected from the group consisting of:

aryl, heteroaryl, cycloalkyl, heterocycloalkyl, aryl-$C_1$-$C_4$ alkyl, heteroaryl-$C_1$-$C_4$ alkyl, cycloalkyl-$C_1$-$C_4$ alkyl, and t-butyl;

$Y^2$ is selected from the group consisting of:

H, $C_1$-$C_{10}$ alkyl, cycloalkyl, ($C_1$-$C_{10}$ alkyl)-$Y^5$, O—$Y^6$;

$Y^5$ is selected from the group consisting of:

an aryl, substituted aryl group, —COR$^4$, —COOR$^4$, —CONR$^6$R$^7$, —CSR$^4$, and —C(S)NR$^6$R$^7$;

$Y^6$ is selected from the group consisting of:

an aliphatic group, a substituted aliphatic group, an aryl, substituted aryl group, —COR$^4$, —COOR$^4$, —CONR$^6$R$^7$, —CSR$^4$, and —C(S)NR$^6$R$^7$;

$R^4$, $R^6$ and $R^7$ are each independently selected from the group consisting of:

H, an aliphatic group, a substituted aliphatic group, an aryl group and a substituted aryl group;

$Y^3$ is selected from the group consisting of:

H, aliphatic, substituted aliphatic, aryl, substituted aryl, heteroaryl, substituted heteroaryl, and ($C_1$-$C_{10}$ alkyl)-R$^8$; $R^8$ is selected from the group consisting of aryl, substituted aryl, heteroaryl, and substituted heteroaryl; and $R^5$ is selected from the group consisting of:

H, aliphatic group, a substituted aliphatic group, heteroaryl, substituted heteroaryl, an aryl, a substituted aryl, and ($C_1$-$C_{10}$ alkyl)-R$^9$;

$R^9$ is selected from the group consisting of:

aryl, substituted aryl, heteroaryl, and substituted heteroaryl, aminoalkyl, and cycloalkyl;

V is a bond or O;

X is $CH_2$ or O;

$Y^4$ is selected from the group consisting of:

—($C_1$-$C_3$)alkyl-O—W—$Y^7$, —C(O)NY$^8$Y$^9$, —($C_1$-$C_3$) alkyl-NY$^{10}$Y$^{11}$, and —($C_1$-$C_3$)alkylN(Y$^{13}$)W—($C_0$-$C_5$) alkyl-Y$^{14}$;

W is selected from the group consisting of:

a bond, —CONY$^{12}$, —C(O)—, —OCH$_2$—, $C_1$-$C_6$ alkyl, —CO$_2$—, —CHOY$^{15}$—, —CSNY$^{16}$ and —SO$_2$—;

$Y^7$ is selected from the group consisting of:

aryl, substituted aryl, heteroaryl, substituted heteroaryl, aliphatic, branched aliphatic and substituted ($C_1$-$C_{10}$)alkyl;

$Y^8$, $Y^9$, $Y^{10}$, $Y^{11}$, $Y^{12}$, $Y^{13}$, $Y^{14}$, $Y^{15}$, and $Y^{16}$ are each independently selected from the group consisting of:

aryl, substituted aryl, heteroaryl, substituted heteroaryl, aliphatic, branched aliphatic and substituted ($C_1$-$C_{10}$)alkyl; and $n^1$ are 2, 3, 4 or 5.

The substituent $Y^1$ of the compound represented by a formula Ia includes

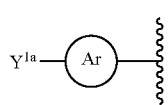

where $Y^{1a}$ and

are defined above in formula I, and substituted group includes the substituents recited above and as defined in the embodiment.

The compound of present invention as recited above, wherein $Y^{1a}$ is selected from the group consisting of: aryl, heteroaryl, cycloalkyl, heterocycloalkyl, aryloxy,

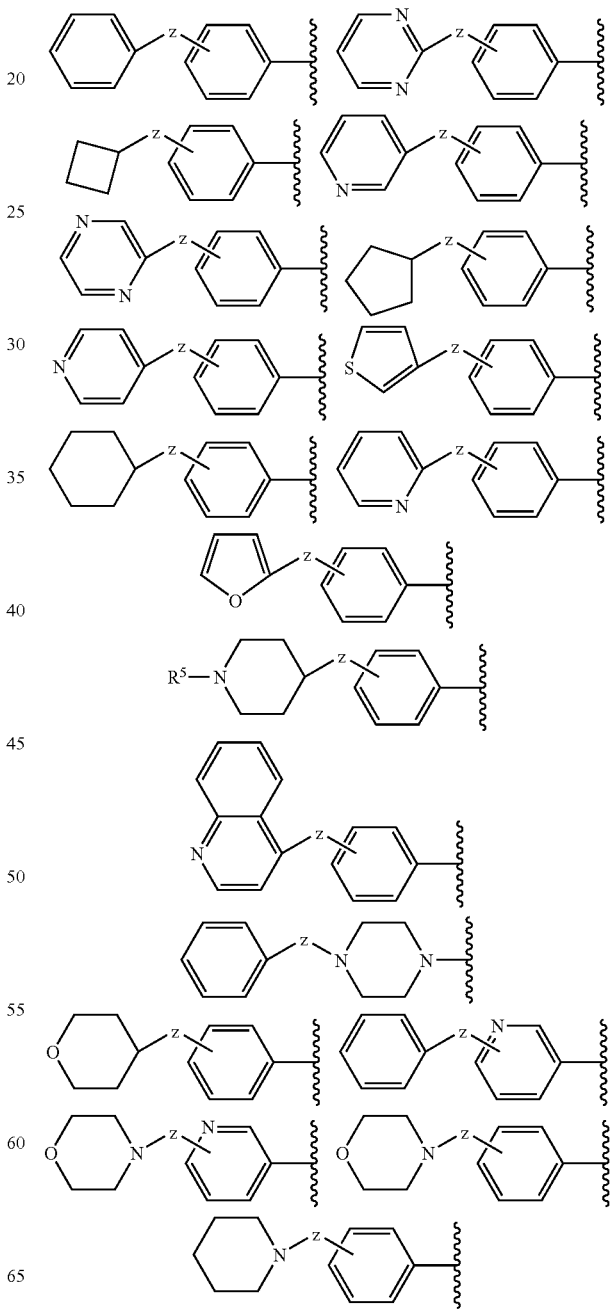

-continued

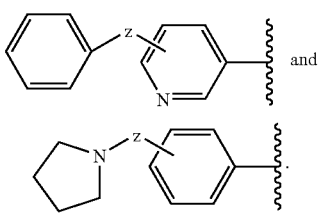
and

A preferred embodiment of the present invention is a compound represented by the following structural formula,

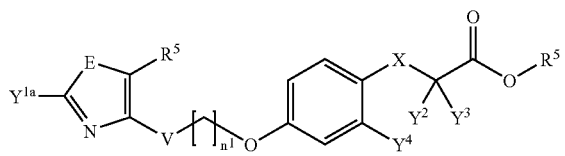

wherein E is O or S.

Another preferred embodiment of the present invention is a compound represented by the following structural formula,

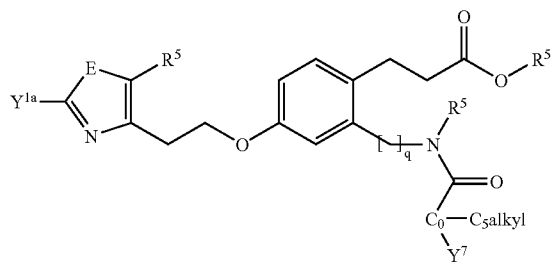

wherein q is 1 or 2; and each $R^5$ is independently hydrogen or methyl.

Another preferred embodiment of the present invention is a compound represented by the following structural formula,

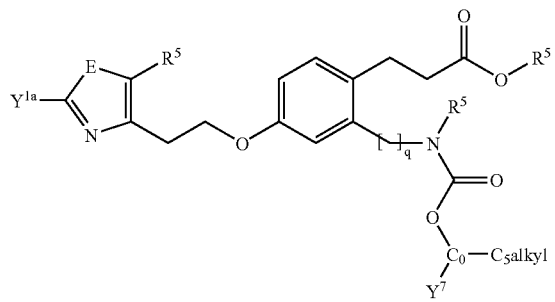

wherein q is 1 or 2; and each $R^5$ is independently hydrogen or methyl.

Another preferred embodiment of the present invention is a compound represented by the following structural formula,

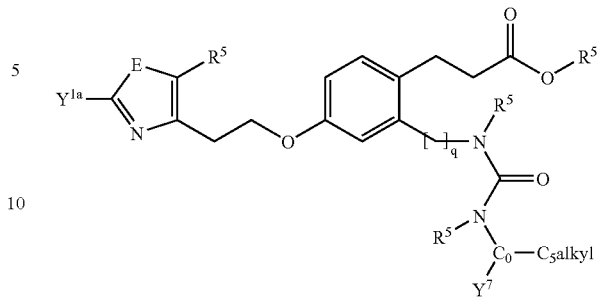

wherein q is 1 or 2; and each $R^5$ is independently hydrogen or methyl.

Another preferred embodiment of the present invention is a compound represented by the following structural formula,

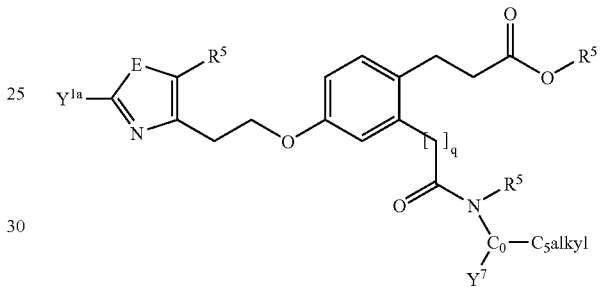

wherein q is 0 or 1; and each $R^5$ is independently hydrogen or methyl.

Another preferred embodiment of the present invention is a compound represented by the following structural formula,

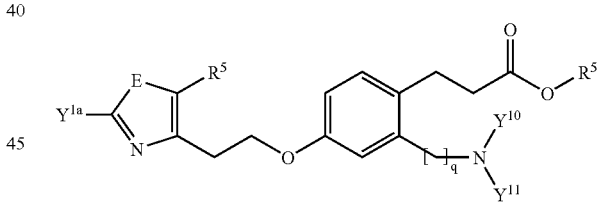

wherein q is 1 or 2; and each $R^5$ is independently hydrogen or methyl.

Another preferred embodiment of the present invention is a compound represented by the following structural formula,

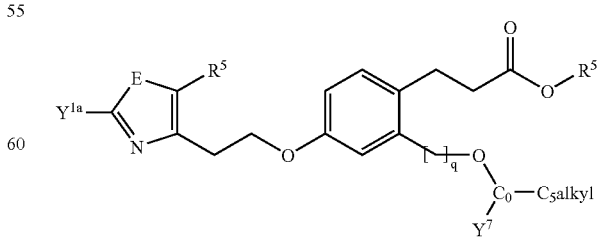

wherein q is 1 or 2; and each $R^5$ is independently hydrogen or methyl.

Another preferred embodiment of the present invention is a compound represented by the following structural formula,

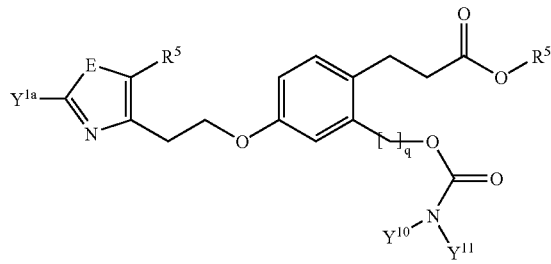

wherein q is 1 or 2; and each R⁵ is independently hydrogen or methyl.

Another preferred embodiment of the present invention is a compound represented by the following structural formula,

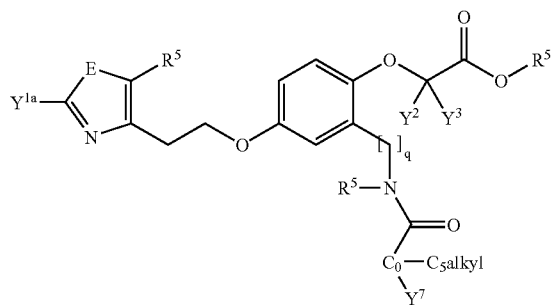

wherein q is 1 or 2; and each $R^5$, $Y^2$ and $Y^3$ are independently hydrogen or methyl.

Another preferred embodiment of the present invention is a compound represented by the following structural formula,

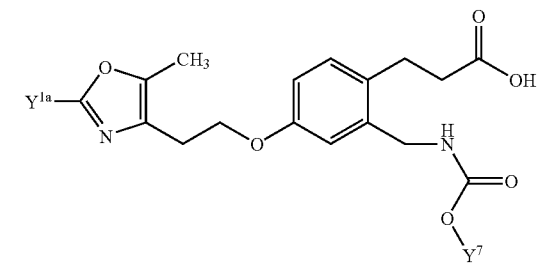

wherein $Y^{1a}$ is optionally substituted phenyl, naphthyl,

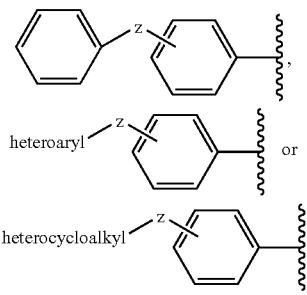

and Z is a bond, oxygen, —NH—, —N(CH₃)—, —NHC(O)— or —C(O)NH—.

Another preferred embodiment of the present invention is a compound represented by the following structural formula,

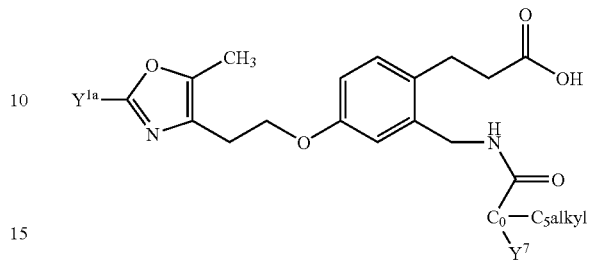

wherein $Y^{1a}$ is optionally substituted phenyl, naphthyl or

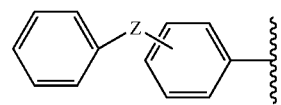

and Z is a bond, oxygen, —NH—, —N(CH₃)—, —NHC(O)— or —C(O)NH—.

Another preferred embodiment of the present invention is a compound represented by the following structural formula,

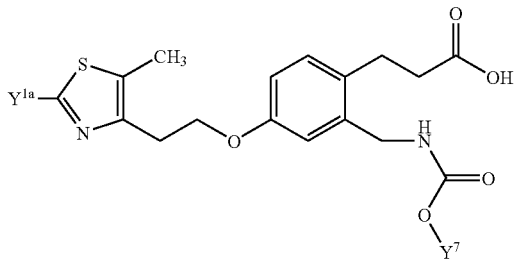

wherein $Y^{1a}$ is optionally substituted aryl, heteroaryl, heterocycloalkyl, heteroaryl-Z-heterocycloalkyl or heteroaryl-Z-aryl.

Another preferred embodiment of the present invention is a compound represented by the following structural formula,

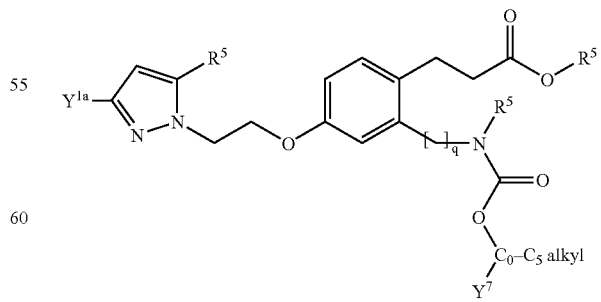

wherein q is 1 or 2; and each R⁵ is independently hydrogen or methyl.

Another preferred embodiment of the present invention is a compound represented by the following structural formula,

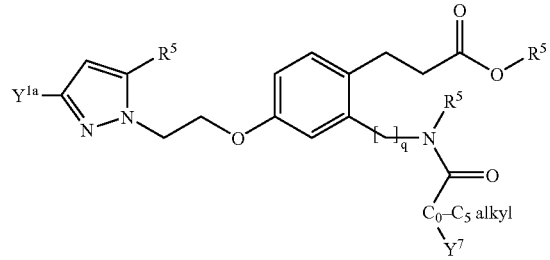

wherein q is 1 or 2; and each $R^5$ is independently hydrogen or methyl.

Another preferred embodiment of the present invention is a compound represented by the following structural formula,

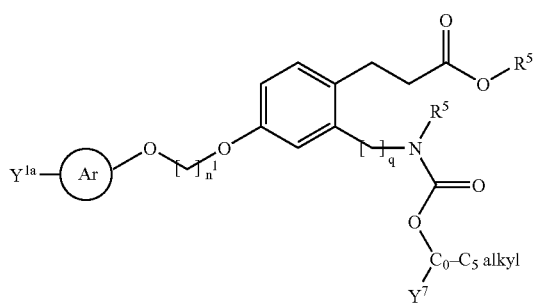

wherein, $Y^{1a}$ is hydrogen, aryl, heteroaryl, or aryloxy; q is 1 or 2; and $n^1$ is 2, 3, or 4.

Another preferred embodiment of the present invention is a compound represented by the following structural formula,

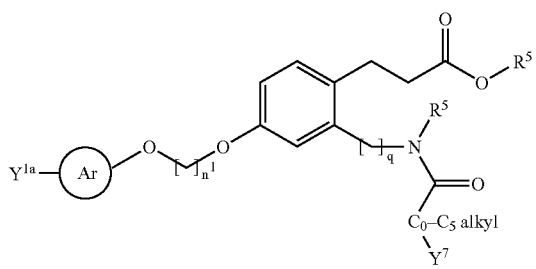

wherein, $Y^{1a}$ is hydrogen, aryl, heteroaryl or aryloxy; q is 1 or 2; and $n^1$ is 2, 3, or 4.

A preferred compound is a compound represented by the following structural formula,

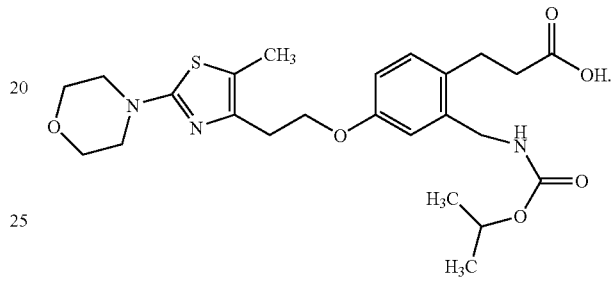

A preferred compound is a compound represented by the following structural formula,

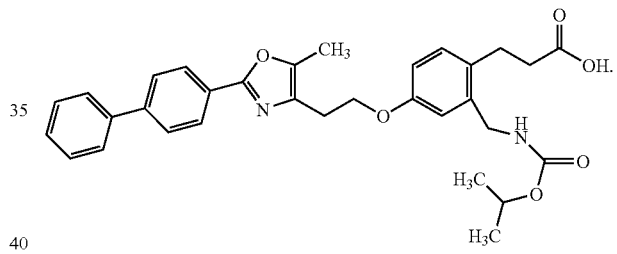

More preferred compounds of the present invention are listed below:

| No. | Compound | name |
|---|---|---|
| 1 | 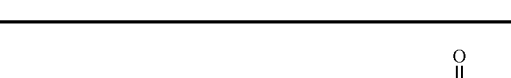 | 3-{2-(Diphenylacetyl-aminomethyl)-4-[2-(5-methyl-2-phenyloxazol-4-yl)ethoxy]phenyl} propionic acid |

-continued

| No. | Compound | name |
|---|---|---|
| 2 | | 3-{2-[(2-Cyclopropylacetylamino)methyl]-4-[2-(5-methyl-2-phenyloxazol-4-yl)ethoxy]phenyl} propionic acid |
| 3 | | 3-{2-[(3-Methoxybenzoylamino)methyl]-4-[2-(5-methyl-2-phenyloxazol-04-yl)ethoxy] phenyl} propionic acid |
| 4 | | 3-{2-{[(Biphenyl-2-carbonyl)amino]methyl}-4-[2-(5-methyl-2-phenyloxazol-4-yl)ethoxy]phenyl} propionic acid |
| 5 | | 3-(4-[2-(2-Biphenyl-4-yl-5-methyloxazol-4-yl)ethoxy]-2-{[(2,5-dichlorothiophene-3-carbonyl)amino]methyl}phenyl) propionic acid |
| 6 | | 3-{2-(Isopropoxycarbonyl-aminomethyl)-4-[2-(5-methyl-2-phenyloxazol-4-yl)ethoxy] phenyl} propionic acid |

| No. | Compound | name |
|---|---|---|
| 7 | | 3-{2-(1,3-Dioxo-1,3-dihydroisoindol-2-ylmethyl)-4-[2-(5-methyl-2-phenyloxazol-4-yl)ethoxy]phenyl} propionic acid |
| 8 | | 3-{4-0[2-(5-Methyl-2-phenyloxazol-4-yl)ethoxy]-2-[(3-phenylureido)methyl] phenyl} propionic acid |
| 9 | | 3-[4-[2-(2-Biphenyl-4-yl-5-methyloxazol-4-yl)ethoxy]-2-(isopropoxycarbonylaminomethyl)phenyl] propionic acid |
| 10 | | 3-{2-(Isopropoxycarbonyl-aminomethyl)-4-[2-(5-methyl-2-morpholin-4-ylthiazol-4-yl)ethoxy]phenyl} propionic acid |

| No. | Compound | name |
| --- | --- | --- |
| 11 | | 3-{2-(Benzoylaminomethyl)-4-[3-(biphenyl-4-yloxy)propoxy]phenyl} propionic acid |
| 12 | | 3-(4-[3-(Biphenyl-4-yloxy)propoxy]-2-{[(pyridine-2-carbonyl)amino]methyl}phenyl) propionic acid |
| 13 | | 3-{2-Benzylcarbamoyl-4-[2-(5-methyl-2-phenyloxazol-4-yl)ethoxy]phenyl} propionic acid |
| 14 | | 3-{2-Benzoylcarbamoyl-4-[2-(2-biphenyl-4-yl-5-methyloxazol-4-yl)ethoxy]phenyl} propionic acid |
| 15 | | 3-{4-[2-(2-Biphenyl-4-yl-5-methyloxazol-4-yl)ethoxy]-2-cyanophenyl} propionic acid |

-continued

| No. | Compound | name |
|---|---|---|
| 16 | 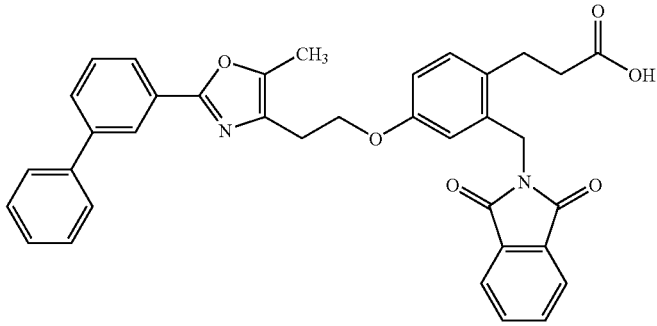 | 3-[4-[2-(2-Biphenyl-3-yl-5-methyloxazol-4-yl)ethoxy]-2-(1,3-dioxo-1,3-dihydroisoindol-2-ylmethyl)phenyl] propionic acid |
| 17 | 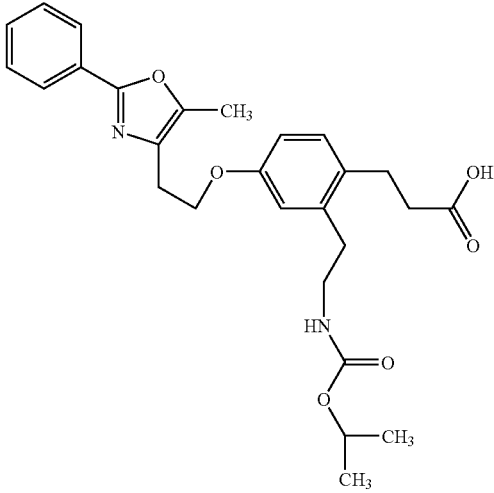 | 3-{2-(2-Isopropoxycarbonyyl-aminoethyl)-4-[2-(5-methyl-2-phenyloxazol-4-yl)ethoxy]phenyl} propionic acid |
| 18 | 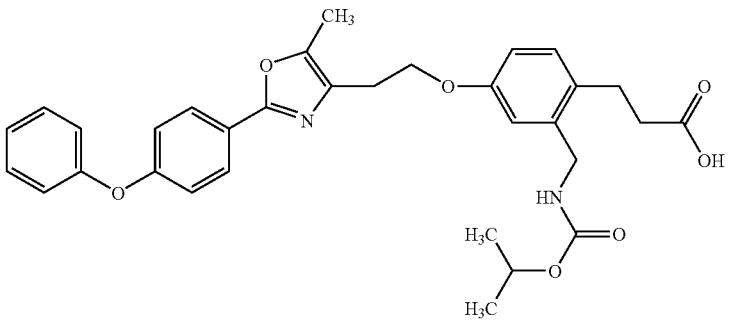 | 3-(2-(Isopropoxycarbonyl-aminomethyl)-4-{2-[5-methyl-2-(4-phenoxyphenyl)oxazol-4-yl]ethoxy}phenyl) propionic acid |
| 19 | 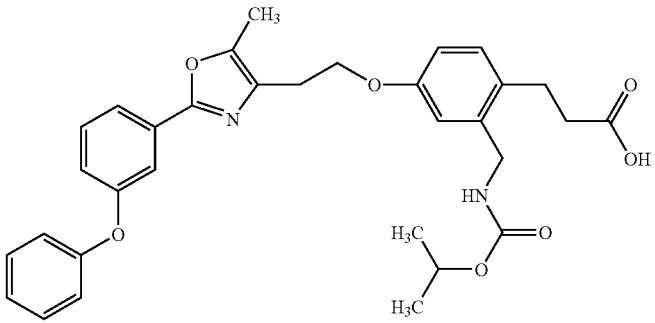 | 3-(2-(Isopropoxycarbonyl-aminomethyl)-4-p{2-[5-methyl-2-(3-phenoxyphenyl)oxazol-4-yl]ethoxy}phenyl) propionic acid |

| No. | Compound | name |
|---|---|---|
| 20 | 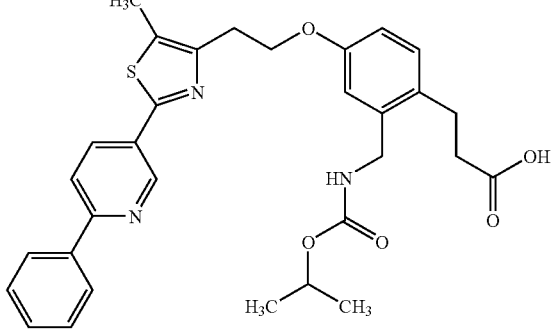 | 3-(2-(Isopropoxycarbonyl-aminomethyl)-4-{2-[5-methyl-2-(6-phenylpyridin-3-yl)thiazol-4-yl]ethoxy}phenyl) propionic acid |
| 21 | 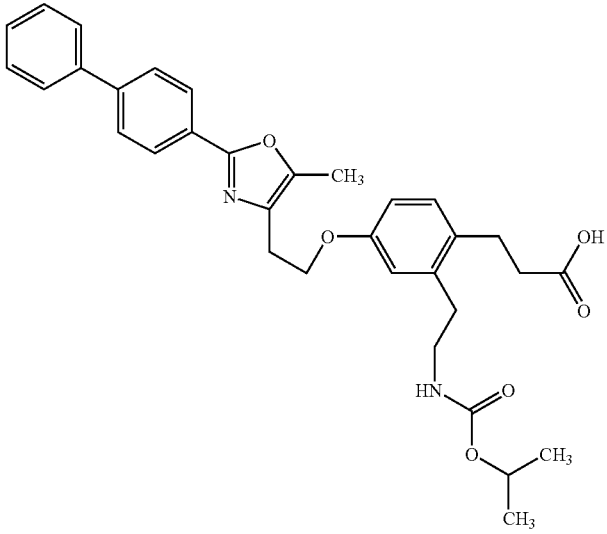 | 3-[4-[2-(2-Biphenyl-4-yl-5-methylisoxazol-4-yl)ethoxy]-2-(2-isopropoxycarbonylaminoethyl)phenyl] propionic acid |
| 22 | 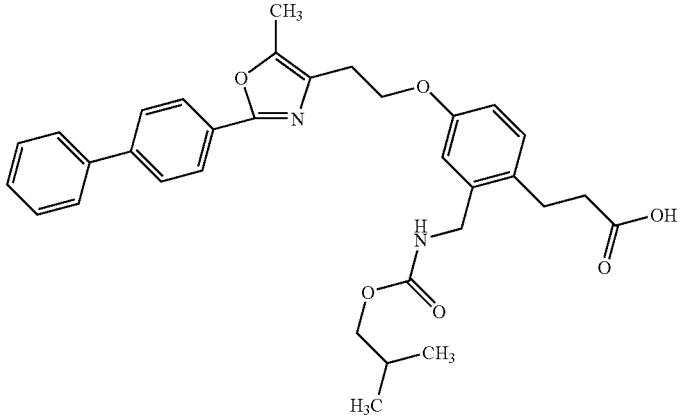 | 3-[4-[2-(2-Biphenyl-4-yl-5-methyloxazol-4-yl)ethoxy]-2-(isobutoxycarbonylaminomethyl)phenyl] propionic acid |

-continued

| No. | Compound | name |
|---|---|---|
| 23 | | 3-[4-[2-(2-Biphenyl-4-yl-5-methyloxazol-4-yl)ethoxy]-2-(cyclopentyloxycarbonyl-aminomethyl)phenyl] propionic acid |
| 24 | | 3-(2-Isopropoxycarbonyl-aminomethyl)-4-{2-[2-(4-isopropoxyphenyl)-5-methyloxazol-4-yl]ethoxy} phenyl) propionic acid |
| 25 | | 3-(2-Benzylcarbamoyl-4-{2-[5-meethyl-2-(4-phenoxyphenyl)oxazol-4-yl]ethoxy}phenyl) propionic acid |
| 26 | | 3-(2-(Isopropoxycarbonyl-aminomethyl)-4-{2-[5-methyl-2-(4-morpholin-4-ylphenyl)oxazol-4-yl]ethoxy}phenyl) propionic acid |

-continued

| No. | Compound | name |
|---|---|---|
| 27 | | 3-(2-(Isopropoxycarbonyl-aminomethyl)-4-{2-[5-methyl-2-(4-piperidin-1-ylphenyl)oxazol-4-yl]ethoxy}phenyl) propionic acid |
| 28 | | 3-(2-(Isopropoxycarbonyl-aminomethyl)-4-{2-[5-methyl-2-(4-pyrimidin-2-ylphenyl)oxazol-4-yl]ethoxy}phenyl) propionic acid |
| 29 | | 3-(2-(Isopropoxycarbonyl-aminomethyl)-4-{2-[5-methyl-2-(4-pyrazin-2-ylphenyl)oxazol-4-yl]ethoxy}phenyl) propionic acid |
| 30 | | 3-(2-(Isopropoxycarbonyl-aminomethyl)-4-{2-[5-methyl-2-(6-phenoxypyridin-3-yl)thiazol-4-yl]ethoxy}phenyl) propionic acid |

-continued

| No. | Compound | name |
|---|---|---|
| 31 | | 3-{2-Cyclohexylcarbamoyl-oxymethyl-4-[2-(5-methyl-2-phenyloxazol-4-yl)ethoxy]phenyl} propionic acid |
| 32 | | 3-(2-Isopropoxycarbonyl-aminomethyl)-4-{2-[5-methyl-2-(4-phenylaminophenyl)oxazol-4-yl]ethoxy}phenyl) propionic acid |
| 33 | | 3-(4-{2-[5-Methyl-2-(6-phenylpyridin-3-yl)thiazol-4-yl]ethoxy}-2-{[(pyridin-2-carbonyl)amino]meethyl}phenyl) propionic acid HCl salt |
| 34 | | 3-{4-[2-(2-Biphenyl-4-yl-5-methyloxazol-4-yl)ethoxy]-2-[(3-methylbutyrylamino)methyl]phenyl} propionic acid |

-continued

| No. | Compound | name |
|---|---|---|
| 35 | | 3-{2-(Isopropoxycarbonyl-aminomethyl)-4-[2-(5-methoxy-2-phenyloxazol-4-yl)ethoxy]phenyl} propionic acid |
| 36 | | 3-(2-Isopropoxycarbonyl-aminomethyl)-4-{2-[5-methyl-2-(6-phenoxypyridin-3-yl)oxazol-4-yl]ethoxy}phenyl) propionic acid |
| 37 | | 3-{4-[2-(2-Biphenyl-4-yl-5-methyloxazol-4-yl)ethoxy]-2-cyclohexylcarbamoyloxy-methylphenyl} propionic acid |
| 38 | | 3-{2-Cyclohexylcarbamoyl-oxymethyl-4-[2-(5-methyl-2-morpholin-4-ylthiazol-4-yl)ethoxy]phenyl} propionic acid |

-continued

| No. | Compound | name |
|---|---|---|
| 39 | | 3-(2-Cyclohexylcarbamoyl-oxymethyl-4-{2-[5-methyl-2-(4-phenoxxyphenyl)oxazol-4-yl]ethoxy}phenyl) propionic acid |
| 40 | | 3-(2-Cyclohexylcarbamoyl-oxymethyl-4-{2-[5-meethyl-2-(4-morpholin-4-ylphenyl)oxazol-4-yl]ethoxy}phenyl) propionic acid |
| 41 | | 3-[2-(Isopropoxycarbonyl-aminomethyl)-4-(2-{5-methyl-2-[3-(tetrahydropyran-4-yloxy)phenyl]oxazol-4-yl}ethoxy)phenyl] propionic acid |
| 42 | | 3-[4-[2-(3-Biphenyl-4-yl-5-methyloxazol-4-yl)ethoxy]-2-(cyclopropylmethoxycarbonyl-aminomethyl)phenyl] propionic acid |

-continued

| No. | Compound | name |
|---|---|---|
| 43 | 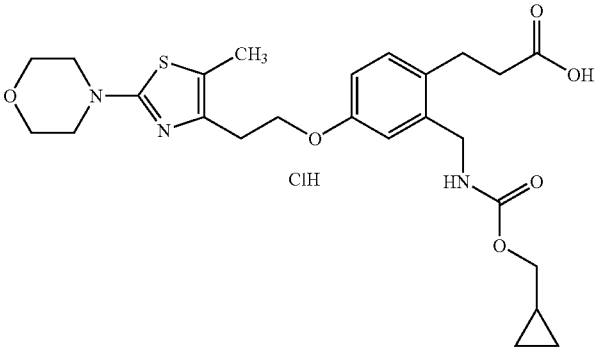 | 3-{2-(Cyclopropylmethoxy-carbonylaminomethyl)-4-[2-(5-methyl-2-morpholin-4-ylthiazol-4-yl)ethoxy]phenyl} propionic acid HCl salt |
| 44 | 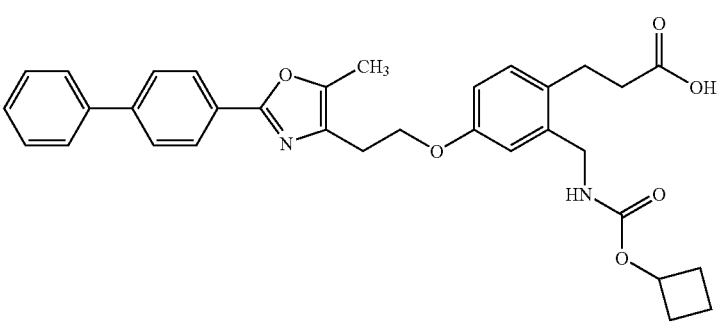 | 3-[4-[2-(2-Biphenyl-4-yl-5-methyloxazol-4-yl)ethoxy]-2-(cyclobutylcarbonyl-aminomethyl)phenyl]propionic acid HCl salt |
| 45 | 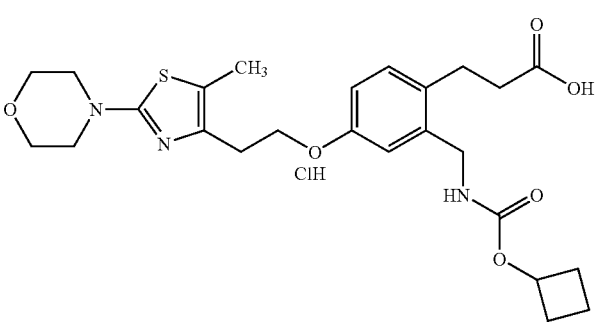 | 3-{2-(Cyclobutoxycarbonyl-aminomethyl)-4-[2-(5-methyl-2-morpholin-4-ylthiazol-4-yl)ethoxy]phenyl} propionic acid HCl salt |
| 46 | 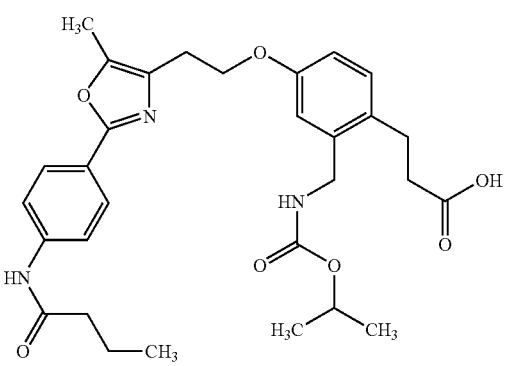 | 3-[4-{2-[2-(4-Butyrylaminophenyl)-5-methyloxazol-4-yl]ethoxy}-2-(isopropoxycarbonylaminomethyl)phenyl] propionic acid |

-continued

| No. | Compound | name |
|---|---|---|
| 47 | | 3-{2-(Isopropoxycarbonyl- amino-methyl)-4-[2-(5-methyl-2-{4-[(pyridine-2-carbonyl)-amino]-phenyl}-oxazol-4-yl)-ethoxy]-phenyl}-propionic acid |
| 48 | | 3-(4-[2-(2-Biphenyl-4-yl-5-methyloxazol-4-yl)ethoxy]-2-{[(pyrazine-2-carbonyl) amino]meethyl}phenyl) propionic acid |
| 49 | | 3-[4-{2-[2-(3-Cyclohexylcarbamoylphenyl)-5-methyloxazol-4-yl]ethoxy}-2-(isopropoxycarbonylaminomethyl) phenyl] propionic acid |
| 50 | | 3-(2-Isopropoxycarbonyl-aminomethyl)-4-{2-[5-methyl-2-(2-phenoxyphenyl)oxazol-4-yl]ethoxy}phenyl) propionic acid |

-continued

| No. | Compound | name |
|---|---|---|
| 51 | | 3-(2-Cyano-4-{2-[5-methyl-2-(4-phenoxy-phenyl)-oxazol-4-yl]-ethoxy}-phenyl) propionic acid |
| 52 | | 3-[2-(Isopropoxycarbonyl-aminomethyl)-4-(2-{5-methyl-2-[4-(pyridin-2-yloxy)phenyl]oxazol-4-yl}ethoxy)phenyl] propionic acid |
| 53 | | 3-[4-[2-(2-Biphenyl-4-yl-5-methyloxazol-4-yl)ethoxy]-2-(4-trifluoromethylphenoxymethyl)phenyl] propionic acid |
| 54 | | 3-{2-(Isobutoxycarbonyl-aminomethyl)-4-[2-(5-methyl-2-morpholin-4-ylthiazol-4-yl)ethoxy]phenyl} propionic acid |

-continued

| No. | Compound | name |
|---|---|---|
| 55 | | 3-[2-(Isopropoxycarbonyl-aminomethyl)-4-(2-{5-methyl-2-[4-(pyrimidin-3-yloxy)phenyl]oxazol-4-yl}ethoxy)phenyl] propionic acid |
| 56 | | 3-[4-[2-(2-Biphenyl-4-yl-5-methoxyoxazol-4-yl)ethoxy]-2-(isopropoxycarbonylaminomethyl)phenyl] propionic acid |
| 57 | | 3-(4-[2-(5-Methyl-2-phenyl-oxazol-4-yl)-ethoxy]-2-{[(pyridine-2-carbonyl)-amino]-methyl}-phenyl)-propionic acid |
| 58 | | 3-{4-[2-(5-Methyl-2-phenyl-oxazol-4-yl)-ethoxy]-2-[(2,4,5-trifluoro-benzoylamino)-methyl]-phenyl}-propionic acid |
| 59 | | 3-{2-[(2,4-Difluoro-benzoylamino)-methyl]-04-[2-(5-methyl-2-phenyl-oxazol-4-yl)-ethoxy]-phenyl}-propionic acid |

| No. | Compound | name |
|---|---|---|
| 60 | | 3-(4-[2-(5-Methyl-2-phenyl-oxazol-4-yl)-ethoxy]-2-{[(thiophene-2-carbonyl)-amino]-methyl}-phenyl)-propionic acid |
| 61 | | 3-(4-[2-(5-Methyl-2-phenyl-oxazol-4-yl)-ethoxy]-2-{[(thiophene-2-carbonyl)-amino]-methyl}-phenyl)-propionic acid |
| 62 | | 3-{2-(Butyrylamino-methyl)-4-[2-(5-methyl-2-phenyl-oxazol-4-yl)-ethoxy]-phenyl}-propionic acid |
| 63 | | 3-{2-[(Cyclobutanecarbonyl-amino)-methyl]-4-[2-(5-methyl-2-phenyl-oxazol-4-yl)-ethoxy]-phenyl}-propionic acid |
| 64 | | 3-{21-(Benzyloxycarbonylamino-meethyl)-4-[2-(5-methyl-2-phenyl-oxazol-4-yl)-ethoxy]-phenyl}-propionic acid |

| No. | Compound | name |
|---|---|---|
| 65 | | 3-{2-(tert-Butoxycarbonylamino-methyl)-4-[2-(5-methyl-2-phenyl-oxazol-4-yl)-ethoxy]-phenyl}-propionic acid |
| 66 | | 3-{4-[2-(5-Methyl-2-phenyl-oxazol-4-yl)-ethoxy]-2-[(2-phenoxy-acetylamino)-methyl]-phenyl}-propionic acid |
| 67 | | 3-{2-[(Cyclopentanecarbonyl-amino)-methyl]-4-[2-(5-methyl-2-phenyl-oxazol-4-yl)-ethoxy]-phenyl}-propionic acid |

Also encompassed by the present invention is a pharmaceutical composition, comprising a pharmaceutically acceptable carrier and at least one compound of the present invention or a pharmaceutically acceptable salt, solvate or hydrate thereof.

Also encompassed by the present invention is a pharmaceutical composition comprising: (1) a compound of formula I according to Claim 1 or a pharmaceutically acceptable salt, solvate, hydrate or stereoisomer thereof; (2) a second therapeutic agent selected from the group consisting of insulin sensitizers, sulfonylureas, biguanides, thiazolidinediones, α-glucosidase inhibitors, insulin secretogogues, insulin, antihyperlipidemic agents, plasma HDL-raising agents, HMG-CoA reductase inhibitors, statins, acryl CoA:cholestrol acyltransferase inhibitors, antiobesity compounds, antihypercholesterolemic agents, fibrates, vitamins and aspirin; and (3) a pharmaceutically acceptable carrier.

Also encompassed by the present invention is a method of modulating a peroxisome proliferator activated receptor (PPAR), comprising the step of contacting the receptor with at least one compound of the present invention or a pharmaceutically acceptable salt, solvate or hydrate thereof. The peroxisome proliferator activated receptor is an alpha-receptor or a gamma-receptor.

Also encompassed by the present invention is a method for treating or preventing a peroxisome proliferator activated receptor-gamma mediated disease or condition comprising the step of administering a compound of Formula I or Formula Ia.

Also encompassed by the present invention is a method for lowering blood-glucose comprising the step of administering an effective amount of a compound of formula I or formula Ia.

Also encompassed by the present invention is a method of treating or preventing disease or condition selected from the group consisting of hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component, comprising the step of administering an effective amount of a compound of formula I or formula Ia.

Also encompassed by the present invention is a method of treating or preventing diabetes mellitus in a mammal comprising the step of administering to a mammal a therapeutically effective amount of at least one compound of formula I or formula Ia.

Also encompassed by the present invention is a method of treating or preventing cardiovascular disease in a mammal comprising the step of administering to a mammal a therapeutically effective amount of at least one compound of formula I or formula Ia, or a pharmaceutically acceptable salt, solvate, hydrate or stereoisomer thereof.

Also encompassed by the present invention is a method of treating or preventing syndrome X in a mammal, comprising the step of administering to the mammal a therapeutically effective amount of at least one compound of formula I or formula Ia, or a pharmaceutically acceptable salt, solvate, hydrate or stereoisomer thereof.

Also encompassed by the present invention is a method of treating or preventing disease or condition selected from the group consisting of hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component, comprising the step of administering an effective amount of a compound of formula I or Ia, and an effective amount of second therapeutic agent selected from the group consisting of insulin sensitizers, sulfonylureas, biguanides, thiazolidinediones, α-glucosidase inhibitors, insulin secretogogues, insulin, antihyperlipidemic agents, plasma HDL-raising agents, HMG-CoA reductase inhibitors, statins, acryl CoA:cholestrol acyltransferase inhibitors, antiobesity compounds, antihypercholesterolemic agents, fibrates, vitamins and aspirin.

Also encompassed by the present invention is use of a compound of formula I or formula Ia and pharmaceutically acceptable salt, solvate, hydrate or stereoisomer thereof, for the manufacture of a medicament for the treatment of a condition modulated by a PPAR.

An embodiment of the present invention also includes the compounds having a structural formula II to IX as shown below. These compounds are within the scope of the compound represented by a structural Formula Ia. The substituent $Y^1$ of these compound includes

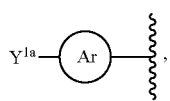

where $Y^{1a}$ and

are defined above in formula I, and substituted groups includes substituents recited above and as defined in the embodiment herein.

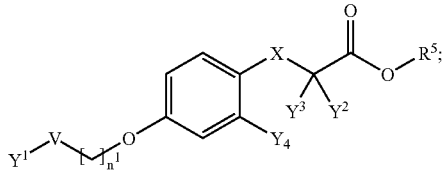

II

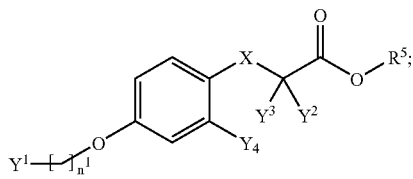

III

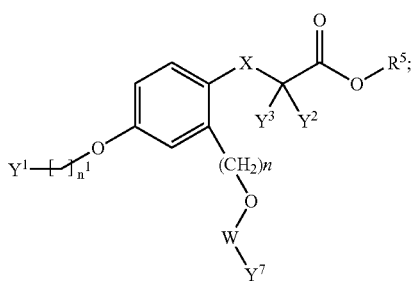

IV

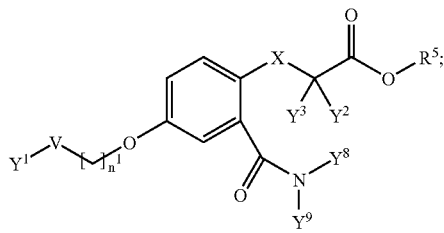

V

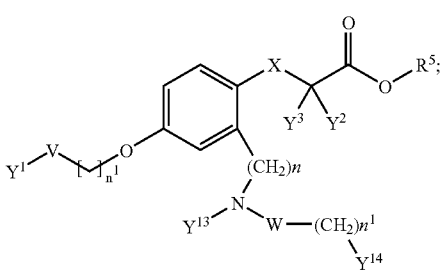

VI

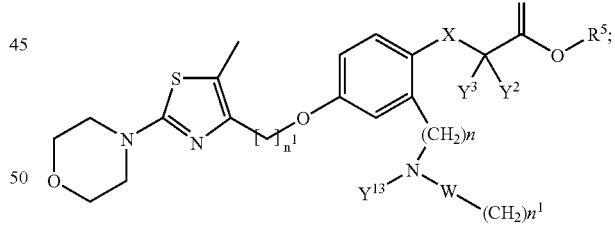

VII

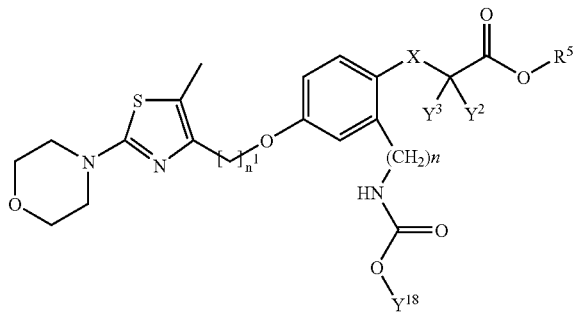

VIII wherein $Y^{18}$ is ($C_1$-$C_6$) straight or branched alkyl; and

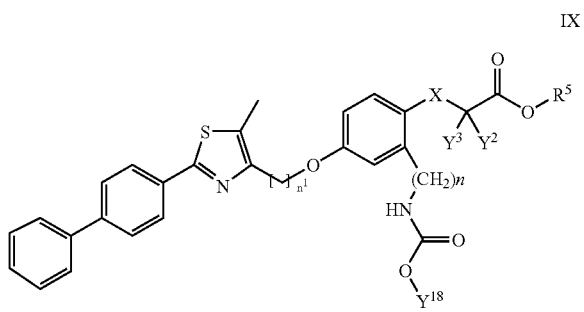

IX wherein $Y^{18}$ is ($C_1$-$C_6$) straight or branched alkyl.

The terms used to describe the instant invention have the following meanings.

As used herein, the term "aliphatic" or "aliphatic group" is a non-aromatic, consisting solely of carbon and hydrogen and may optionally contain one or more units of saturation, e.g., double and/or triple bonds (also refer herein as "alkenyl" and "alkynyl"). An aliphatic or aliphatic group may be straight chained, branched (also refer herein as "alkyl") or cyclic (also refer herein as "cycloalkyl"). When straight chained or branched, an aliphatic group typically contains between about 1 and about 10 carbon atoms, more typically between about 1 and about 6 carbon atoms. When cyclic, an aliphatic typically contains between about 3 and about 10 carbon atoms, more typically between about 3 and about 7 carbon atoms. Aliphatics are preferably $C_1$-$C_{10}$ straight chained or branched alkyl groups (i.e. completely saturated aliphatic groups), more preferably $C_1$-$C_6$ straight chained or branched alkyl groups. Examples include, but are not limited to methyl, ethyl, propyl, n-propyl, iso-propyl, n-butyl, sec-butyl, and tert-butyl. Additional examples include, but are not limited to, cyclopropyl, cyclopentyl, cyclohexyl, cyclopentyl, cyclohexylyl and the like.

The term "alkyl," unless otherwise indicated, refers to those alkyl groups of a designated number of carbon atoms of either a straight or branched saturated configuration. Examples of "alkyl" include, but are not limited to, methyl, ethyl, n-propyl, isopropyl, n-butyl, isobutyl, sec-butyl and tert-butyl, pentyl, hexyl, isopentyl and the like. Alkyl as defined above may be optionally substituted with a designated number of substituents as set forth in the embodiment recited above.

The term "alkenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with designated number of substituents as set forth in the embodiment recited above.

The term "alkynyl" means hydrocarbon chain of a specified number of carbon atoms of either a straight or branched configuration and having at least one carbon-carbon triple bond, which may occur at any point along the chain. Example of alkynyl is acetylene. Alkynyl as defined above may be optionally substituted with designated number of substituents as set forth in the embodiment recited above.

The term "cycloalkyl" refers to a saturated or partially saturated carbocycle containing one or more rings of from 3 to 12 carbon atoms. Examples of cycloalkyl includes, but are not limited to cyclopropyl, cyclobutyl, cyclopentyl, cyclohexyl and cycloheptyl, and the like. Cycloalkyl as defined above also includes a tricycle, such as adamantyl. Cycloalkyl as defined above may be optionally substituted with a designated number of substituents as set forth in the embodiment recited above.

The term "halo" refers to fluoro, chloro, bromo and iodo.

The term "haloalkyl" is a $C_1$-$C_6$ alkyl group, which is substituted with one or more halo atoms selected from F, Br, Cl and I. An example of a haloalkyl group is trifluoromethyl.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "haloalkyloxy" represents a $C_1$-$C_6$ haloalkyl group attached through an oxygen bridge, such as $OCF_3$. The "haloalkyloxy" as defined above may be optionally substituted with a designated number of substituents as set forth in the embodiment recited above.

The term "aryl" includes carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3, 4-tetrahydronaphthyl). "Aryl" as defined above may be optionally substituted with a designated number of substituents as set forth in the embodiment recited above.

The term "heteroaryl" group, as used herein, is an aromatic ring system having at least one heteroatom such as nitrogen, sulfur or oxygen and includes monocyclic, bicyclic or tricyclic aromatic ring of 5- to 14-carbon atoms containing one or more heteroatoms selected from O, N, or S. The "heteroaryl" as defined above may be optionally substituted with a designated number of substituents as set forth in the embodiment recited above. Examples of heteroaryl are, but are not limited to, furanyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline and the like.

The term "heterocycloalkyl" refers to a non-aromatic ring which contains one or more oxygen, nitrogen or sulfur and includes a monocyclic, bicyclic or tricyclic non-aromatic ring of 5 to 14 carbon atoms containing one or more heteroatoms selected from O, N or S. The "heterocycloalkyl" as defined above may be optionally substituted with a designated number of substituents as set forth in the embodiment recited above. Examples of heterocycloalkyl include, but are not limited to, morpholine, piperidine, piperazine, pyrrolidine, and thiomorpholine. The preferred heterocycloalkyl group is morpholine.

An aryl-$C_1$-$C_4$-alkyl group, as used herein, is an aryl substituent that is linked to a compound by an alkyl group having from one to four carbon atoms.

A heteroaryl-$C_1$-$C_4$-alkyl group, as used herein, is a heteroaryl substituent that is linked to a compound by an alkyl group having from one to four carbon atoms.

A cycloalkyl-$C_1$-$C_4$-alkyl group, as used herein, is a cycloalkyl substituent that is linked to a compound by an alkyl group having from one to four carbon atoms.

An aminoalkyl group is an alkyl group having from one to six carbon atoms, which is substituted with at least one amine represented by $NR^{12}R^{12}$ where each $R^{12}$ is independently a $C_1$-$C_6$ alkyl or both $R^{12}$ taken together with the nitrogen to which they are attached form a five or six membered heterocycloalkyl.

Unless otherwise indicated, substituents for alkyl, alkenyl, cycloalkyl, aryl, heteroaryl and heterocycloalkyl also include halo, carboxyl, $C_1$-$C_6$ alkyl, $C_1$-$C_6$ alkoxy, $C_1$-$C_6$ haloalkyl, $C_1$-$C_6$ haloalkoxy, nitro, cyano, CHO, hydroxyl, $C_1$-$C_6$ alkanoic acid and —C(O)NR$^{13}$R$^{13}$ where each R$^{13}$ is independently hydrogen or a $C_1$-$C_6$ alkyl.

Substituents for thiophen-2,5-diyl and phenylene include H, $C_1$-$C_4$ alkyl, $C_1$-$C_4$ alkoxy, $C_1$-$C_4$ haloalkyl and $C_1$-$C_4$ haloalkoxy.

The term "active ingredient" means the compounds generically described by formula I as well as the salts, solvates and prodrugs of such compounds.

The term "pharmaceutically acceptable" means that the carrier, diluents, excipients and salt must be compatible with the other ingredients of the composition, and not deleterious to the recipient thereof. Pharmaceutical compositions of the present invention are prepared by procedures known in the art using well-known and readily available ingredients.

"Preventing" refers to reducing the likelihood that the recipient will incur or develop any of the pathological conditions described herein.

"Treating" refers to mediating a disease or condition, and preventing or mitigating its further progression or ameliorate the symptoms associated with the disease or condition.

"Pharmaceutically-effective amount" means that amount of a compound of the present invention, or of its salt, solvate, hydrate or prodrug thereof that will elicit the biological or medical response of a tissue, system or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount, which is sufficient to modulate a PPAR receptor such as a PPARα or PPARγ receptor to mediate a disease or condition. Conditions mediated by PPARα or PPARγ receptors include, for example, diabetes mellitus, cardiovascular disease, Syndrome X, obesity and gastrointestinal disease. Additional conditions associated with the modulation of a PPAR receptor include inflammation related conditions which include, for example, IBD (inflammatory bowel disease), rheumatoid arthritis, psoriasis, Alzheimer's disease, Chrohn's disease and ischemia reprofusion injury (stroke and miocardial infarction).

A "mammal" is an individual animal that is a member of the taxonomic class Mammalia. The class Mammalia includes humans, monkeys, chimpanzees, gorillas, cattle, swine, horses, sheep, dogs, cats, mice, rats and the like.

Administration to a human is most preferred. A human to whom the compounds and compositions of the present invention are administered has a disease or condition in which control blood glucose levels are not adequately controlled without medical intervention, but wherein there is endogenous insulin present in the human's blood. Non-insulin dependent diabetes mellitus (NIDDM) is a chronic disease or condition characterized by the presence of insulin in the blood, even at levels above normal, but resistance or lack of sensitivity to insulin action at the tissues.

Those skilled in the art will recognize that sterocenters exist in compound of Formula I and Formula Ia. Accordingly, the present invention includes all possible stereoisomers and geometric isomers of formula I including racemic compounds and the optically active isomers.

The compounds of Formula I and Formula Ia contain one or more chiral centers and exist in different optically active forms. When compounds of formula I contain one chiral center, the compounds exist in two enantiomeric forms and the present invention includes both enantiomers and mixtures of enantiomers, such as racemic mixtures. Resolution of the final product, an intermediate or a starting material may be effected by any suitable method known in the art, for example by formation of diastereoisomeric salts which may be separated by crystallization; formation of diastereoisomeric derivatives or complexes which may be separated by crystallization and gas-liquid or liquid chromatography; selective reaction of one enantiomer with an enantiomer-specific reagent such as enzymatic esterification; and gas-liquid or liquid chromatography in a chiral environment such as on a chiral support, for example silica with a bound chiral ligand or in the presence of a chiral solvent. See also *Sterochemistry of Carbon Compounds* by E. L. Eliel (Mcgraw Hill, 1962) and *Tables of Resolving Agents* by S. H. Wilen. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation. In a more preferred embodiment, the compounds of the present invention are S-enantiomers.

When a compound of Formula I or Formula Ia has more than one chiral substituents, it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of formula I or Ia may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and Ia and mixtures thereof.

Certain compound of formula I or Ia may exist in zwitterionic form, and the present invention includes each zwitterionic form of compounds of formula I or Ia and mixtures thereof.

Certain compounds of formula I or Ia and their salts may exist in more than one crystal form. Polymorphs of compounds of formula I form part of the present invention and may be prepared by crystallization of a compound of formula I or Ia under different conditions, such as using different solvents or different solvent mixtures for recrystallization; crystallization at different temperatures; and various modes of cooling ranging from very fast to very slow cooling during crystallization. Polymorphs may also be obtained by heating or melting a compound of Formula I or Formula Ia followed by gradual or fast cooling. The presence of polymorphs may be determined by solid probe NMR spectroscopy, IR spectroscopy, differential scanning calorimetry, powder X-ray diffraction or other available techniques.

Certain compounds of formula I or Ia and their salts may exist in more than one crystal form, and the present invention includes each crystal form and mixtures thereof.

Certain compounds of formula I or Ia and their salts may also exist in the form of solvates, for example hydrates, and the present invention includes each solvate and mixtures thereof.

"Pharmaceutically-acceptable salt" refers to salts of the compounds of formula I or Ia which are substantially non-toxic to mammals. Typical pharmaceutically acceptable salts include those salts prepared by reaction of the compounds of the present invention with a mineral, organic acid: an organic base or inorganic base. Such salts are known as base addition salts, respectively. It should be recognized that the particular counterion forming a part of any salt of the present invention is not of a critical nature so long as the salt as a whole is pharmaceutically acceptable and the counterion does not contribute undesired qualities to the salt as a whole.

By virtue of its acidic moiety, a compound of formula I or Ia forms salts with pharmaceutically acceptable bases. Some examples of base addition salts include metal salts such as aluminum; alkali metal salts such as lithium, sodium or potassium; and alkaline earth metal salts such as calcium, magnesium, ammonium, or substituted ammonium salts. Examples of substituted ammonium salts include, for instance, those with lower alkylamines such as trimethylamine and triethylamine; hydroxyalkylamines such as 2-hydroxyethylamine, bis-(2-hydroxyethyl)-amine or tri-(2-hydroxyethyl)-amine; cycloalkylamines such as bicyclohexylamine or dibenzylpiperidine, N-benzyl-β-phenethylamine, dehydroabietylamine, N,N'-bisdehydro-abietylamine, glucamine, N-piperazine methylglucamine; bases of the pyridine type such as pyridine, collidine, quinine or quinoline; and salts of basic amino acids such as lysine and arginine.

Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Compounds of formula I or Ia, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid. These salts may be prepared by methods known to those skilled in the art.

Certain compounds of formula I or Ia and their salts may also exist in the form of solvates, for example hydrates, and the present invention includes each solvate and mixtures thereof.

The compounds of present invention, which bind to and activate the PPARs, lower one or more of glucose, insulin, triglycerides, fatty acids and/or cholesterol, and are therefore useful for the treatment and/or prevention of hyperglycemia, dyslipidemia and in particular Type II diabetes as well as other diseases including syndrome X, Type I diabetes, hypertriglyceridemia, insulin resistance, diabetic dyslipidemia, hyperlipidemia, hypercholesteremia, heart failure, coagaulopathy, hypertension, and cardiovascular diseases, especially arteriosclerosis. In addition, these compounds are indicated to be useful for the regulation of appetite and food intake in subjects suffering from disorders such as obesity, anorexia bulimia and anorexia nervosa.

The compounds and compositions of the present invention are also useful to treat acute or transient disorders in insulin sensitivity, which sometimes occurs following a surgery, trauma, myocardial infarction and the like. The compounds and compositions of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who can benefit from administration of the compounds and compositions of the present invention.

The present invention further provides a method for the treatment and/or prophylaxis of hyperglycemia in a human or non-human mammal which comprises administering an effective, non-toxic amount of a compound of formula I, or a tautomeric form thereof and/or a pharmaceutically acceptable salt thereof and/or a pharmaceutically acceptable solvate thereof to a hyperglycemic human or non-human mammal in need thereof.

The compounds of the present invention are useful as therapeutic substances in preventing or treating Syndrome X, diabetes mellitus and related endocrine and cardiovascular disorders and diseases in human or non-human animals.

The present invention also relates to the use of a compound of formula I as described above for the manufacture of a medicament for treating a PPARα or PPARγ mediated condition, separately or in combination.

A therapeutically effective amount of a compound of formula I can be used for the preparation of a medicament useful for treating Syndrome X, diabetes, treating obesity, lowering tryglyceride levels, raising the plasma level of high density lipoprotein, and for treating, preventing or reducing the risk of developing arteriosclerosis, and for preventing or reducing the risk of having a first or subsequent atherosclerotic disease event in mammals, particularly in humans. In general, a therapeutically effective amount of a compound of formula I of the present invention typically reduces serum glucose levels, more specifically HbA1c, of a patient by about 0.7% or more; typically reduces serum triglyceride levels of a patient by about 20% or more; and increases serum HDL levels in a patient. Preferably, HDL levels can be increased by about 30% or more.

Additionally, an effective amount of a compound of formula I and a therapeutically effective amount of one or more active agents selected from antihyperlipidemic agent, plasma HDL-raising agents, antihypercholesterolemic agents, fibrates, vitamins, aspirin, insulin secretogogues, insulin and the like can be used together for the preparation of a medicament useful for the above described treatments.

Advantageously, compositions containing the compound of formula I or the salts thereof may be provided in dosage unit form, preferably each dosage unit containing from about 1 to about 500 mg. It is understood that the amount of the compounds or compounds of formula I that will be administered is determined by a physician considering of all the relevant circumstances.

Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially arteriosclerosis.

The compositions are formulated and administered in the same general manner as detailed herein. The compounds of the present invention may be used effectively alone or in combination with one or more additional active agents depending on the desired target therapy. Combination therapy includes administration of a single pharmaceutical dosage composition, which contains a compound of formula I and one or more additional active agents, as well as administration of a compound of formula I and each active agent in its own separate pharmaceutical dosage formulation. For example, a compound of formula I or thereof and an insulin secretogogue such as biguanides, thiazolidinediones, sulfonylureas, insulin or α-glucosidose inhibitors can be administered to the patient together in a single oral dosage composition such as a tablet or capsule, or each agent administered in separate oral dosage formulations. Where separate dosage formulations are used, a compound of formula I and one or more additional active agents can be administered at essentially the same time, i.e., concurrently or at separately staggered times, i.e., sequentially; combination therapy is understood to include all these regimens.

An example of combination treatment or prevention of arteriosclerosis may involve administration of a compound of formula I or salts thereof in combination with one or more of second active therapeutic agents: antihyperlipidemic agents; plasma HDL-raising agents; antihypercholesterolemic agents, fibrates, vitamins, aspirin and the like. As noted above, the compounds of formula I can be administered in combination with more than one additional active agent.

Another example of combination therapy can be seen in treating diabetes and related disorders wherein the compounds of formula I or salts thereof can be effectively used in combination with second active therapeutic, such as sulfonylureas, biguanides, thiazolidinediones, α-glucosidase inhibitors, other insulin secretogogues, insulin as well as the active agents discussed above for treating arteriosclerosis.

The examples of second therapeutic agents are insulin sensitizers, PPARγ agonists, glitazones, troglitazone, pioglitazone, englitazone, MCC-555, BRL 49653, biguanides, metformin, phenformin, insulin, insulin minetics, sufonylureas, tolbutamide, glipizide, alpha-glucosidase inhibitors, acarbose, cholesterol lowering agent, HMG-CoA reductase inhibitors, lovastatin, simvastatin, pravastatin, fluvastatin, atrovastatin, rivastatin, other statins, sequestrates, cholestyramine, colestipol, dialkylaminoalkyl derivatives of a cross-linked dextran, nicotinyl alcohol, nicotinic acid: a nicotinic acid salt, PPARα agonists, fenofibric acid derivatives, gemfibrozil, clofibrate, fenofibrate, benzafibrate, inhibitors of cholesterol absorption, beta-sitosterol, acryl CoA:cholesterol acyltransferase inhibitors, melinamide, probucol, PPARδ agonists, antiobesity compounds, fenfluramine, dexfenfluramine, phentiramine, sulbitramine, orlistat, neuropeptide Y5 inhibitors, $\beta_3$ adrenergic receptor agonists, and ileal bile acid transporter inhibitors.

The compounds of the present invention and the pharmaceutically acceptable salts, solvates and hydrates thereof have valuable pharmacological properties and can be used in pharmaceutical compositions containing a therapeutically effective amount of a compound of the present invention, or pharmaceutically acceptable salts, esters or prodrugs thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient, which is a compound of the present invention.

Preferably, the pharmaceutical formulation is in unit dosage form. A "unit dosage form" is a physically discrete unit containing a unit dose suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts considering various factors, such as without limitation, the species, age, weight, sex, medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses of two, three or more times per day. Where delivery is via transdermal forms, administration is continuous.

Suitable routes of administration of pharmaceutical compositions of the present invention include, for example, oral, eye drop, rectal, transmucosal, topical or intestinal administration; parenteral delivery (bolus or infusion), including intramuscular, subcutaneous, intramedullary injections, as well as intrathecal, direct intraven-tricular, intravenous, intraperitoneal, intranasal, or intraocular injections. The compounds of the present invention can also be administered in a targeted drug delivery system, such as in a liposome coated with endothelial cell-specific antibody.

For oral administration, the compounds of the present invention can be formulated readily by combining the active compounds with pharmaceutically acceptable carriers well known in the art. Such carriers enable the compounds of the present invention to be formulated as tablets, pills, powders, sachets, granules, dragees, capsules, liquids, elixirs, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid: or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid: sodium oleate, sodium benzoate, sodium acetate, sodium chloride, talc, and the like. When a dosage unit form is a capsule, it may contain, in addition to materials of the above type, a liquid carrier such as a fatty oil.

Solid form formulations include powders, tablets and capsules. A solid carrier can be one or more substances, which may also act as flavoring agents, lubricants, solubilisers, suspending agents, binders, tablet disintegrating agents and encapsulating material.

In powders, the carrier is a finely divided solid which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration the compounds of the present invention or salts thereof can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks' solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the art. The active compounds can also be administered intranasally as, for example, liquid drops or spray.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing for example up to 10% by weight of the active compound. The compounds of the present invention are preferably formulated prior to administration.

The following pharmaceutical formulations 1 through 8 are illustrative only and are not intended to limit the scope of the invention in any way. "Active Ingredient" refers to a compound of the present invention according to formula I and/or Ia or salts thereof.

Formulation 1

Hard gelatin capsules are prepared using the following ingredients:

|  | Quantity (mg/capsule) |
| --- | --- |
| Active Ingredient | 250 |
| Starch, dried | 200 |

-continued

| | Quantity (mg/capsule) |
|---|---|
| Magnesium stearate | 10 |
| Total | 460 mg |

Formulation 2

A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

| | Weight |
|---|---|
| Active Ingredient | 0.25 |
| Ethanol | 25.75 |
| Propellant 22 (chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| | |
|---|---|
| Active Ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

| | |
|---|---|
| Active Ingredient | 225 mg |
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacities and allowed to cool.

Formulation 7

Suspensions each containing 50 mg of Active Ingredient per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active Ingredient | 100 mg |
| Isotonic saline | 1,000 ml |

The solution of the above materials generally is administered intravenously to a subject at a rate of 1 ml per minute.

In yet another embodiment of the present invention, the compound is radiolabelled, such as with carbon-14 or tritiated. Said radiolabelled or tritiated compounds are useful as reference standards for in vitro assays to identify new PPARα and PPARγ agonists.

Binding and Cotransfection Studies

The in vitro potency of compounds in modulating PPARγ, PPARα and PPARδ receptors are determined by the procedures detailed below. DNA-dependent binding (ABCD binding) is carried out using Scintillation Proximity Assay (SPA) technology with PPAR receptors. Tritium-labeled PPARα and PPARγ agonists are used as radioligands for generating displacement curves and $IC_{50}$ values with compounds of the present invention. Cotransfection assays are carried out in CV-1 cells. The reporter plasmid contains an acylCoA oxidase (AOX) PPRE and TK promoter upstream of the luciferase reporter cDNA. Appropriate PPARs and RXRα are constitutively expressed using plasmids containing the CMV promoter. Since for PPARα and PPARβ, interference by endogenous PPARγ in CV-1 cells is an issue, in order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist and PPARγ agonist reference molecules. Efficacies are determined by computer fit to a concentration-response curve, or in some cases at a single high concentration of agonist (10 µM). A typical range for concentration determination ($IC_{50}$) is from 1 nM to 10 µM. For binding or cotransfection studies with receptors other than PPARs, similar assays are carried out using appropriate ligands, receptors, reporter constructs and etc. for that particular receptor.

These studies are carried out to evaluate the ability of compounds of the present invention to bind to and/or activate various nuclear transcription factors, particularly huPPARα ("hu" indicates "human"), huPPARγ and huPPARδ. These studies provide in-vitro data concerning efficacy and selectivity of compounds of the present invention. Furthermore, binding and cotransfection data for compounds of the present invention are compared with corresponding data for reference compounds that act on either huPPARα or huPPARγ. The typical range of concentration for binding is from 1 nM to 10 µM. The concentration of test compound required to effect 50% maximal activation of PPARα ($IC_{50}α$) and PPARγ ($IC_{50}γ$) is determined.

Evaluation of Triglyceride and Cholesterol Level in HuapoAI Transgenic Mice

Five to six week old male mice, transgenic for human apoAI [C57Bl/6-tgn(apoa1)1rub, Jackson Laboratory, Bar Harbor, Me.] are housed five per cage (10"×20"×8" with aspen chip bedding) with food (Purina 5001) and water available at all times. After an acclimation period of 2 weeks, animals are individually identified by ear notches, weighed and assigned to groups based on body weight. Beginning the following morning, mice are dosed daily by oral gavage for 7 days using a 20 gauge, 1½" curved disposable feeding needle. Treatments are test compounds (30 mg/kg), a positive control (fenofibrate, 100 mg/kg) or vehicle [1% carboxymethylcellulose (w/v)/0.25% Tween80 (w/v); 0.2 ml/mouse]. Prior to termination on day 7, mice are weighed and dosed. Three hours after dosing, animals are anesthetized by inhalation of isoflurane (2-4%) and blood obtained via cardiac puncture (0.7-1.0 ml). Whole blood is transferred to serum separator tubes (Vacutainer SST), chilled on ice and permitted to clot. Serum is obtained after centrifugation at 4° C. and frozen until analysis for triglycerides, total cholesterol, compound levels and serum lipoprotein profile by fast protein liquid chromatography (FPLC) coupled to an inline detection system. After sacrifice by cervical dislocation, the liver, heart and epididymal fat pads are excised and weighed.

The animals dosed with vehicle have average triglycerides values of about 60 to 80 mg/dl, which are reduced by the positive control fenofibrate (33-58 mg/dl with a mean reduction of 37%). The animals dosed with vehicle have average total serum cholesterol values of about 140 to 180 mg/dl, which are increased by fenofibrate (about 190 to 280 mg/dl with a mean elevation of 41%). When subject to FPLC analysis, pooled sera from vehicle-treated hu apoAI transgenic mice have a high-density lipoprotein cholesterol (HDLc) peak area which ranges from 47 v-sec to 62 v-sec. Fenofibrate increases the amount of HDLc (68-96 v-sec with a mean percent increase of 48%). Test compounds evaluated in terms of percent increase in the area under the curve. Representative compounds of the present invention are tested using the above methods or substantially similar methods.

Evaluation of Glucose Levels in db/db Mice

Five week old male diabetic (db/db) mice [C57BlKs/j-m +/+ Lepr(db), Jackson Laboratory, Bar Harbor, Me.] or lean littermates (db+) are housed 6 per cage (10"×20"×8" with aspen chip bedding) with food (Purina 5015) and water available at all times. After an acclimation period of 2 weeks, animals are individually identified by ear notches, weighed and bled via the tail vein for determination of initial glucose levels. Blood is collected (100 µl) from unfasted animals by wrapping each mouse in a towel, cutting the tip of the tail with a scalpel, and milking blood from the tail into a heparinized capillary tube balanced on the edge of the bench. Sample is discharged into a heparinized microtainer with gel separator (VWR) and retained on ice. Plasma is obtained after centrifugation at 4° C. and glucose is measured immediately. Remaining plasma is frozen until the completion of the experiment, and glucose and triglycerides are assayed in all samples. Animals are grouped based on initial glucose levels and body weights. Beginning the following morning, mice are dosed daily by oral gavage for 7 days using a 20 gauge, 1½" curved disposable feeding needle. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) for about 3 hours after dosing. Twenty-four hours after the $7^{th}$ dose (i.e., day 8), animals are bled again (tail vein). Samples obtained from conscious animals on days 0, 7 and 8 are assayed for glucose. After 24 hour bleed, animals are weighed and dosed for the final time. Three hours after dosing on day 8, animals are anesthetized by inhalation of isoflurane, and blood obtained is via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

The animals dosed with vehicle have average triglycerides values of about 170 to 230 mg/dl, which are reduced by the positive PPARγ control (about 70 to 120 mg/dl with a mean reduction of 50%). Male db/db mice are hyperglycemic (average glucose of about 680 to 730 mg/dl on the $7^{th}$ day of treatment), while lean animals have average glucose levels between about 190 and 230 mg/dl. Treatment with the positive control agent reduces glucose significantly (about 350 to 550 mg/dl with a mean decrease towards normalization of 56%).

Glucose is measured calorimetrically by using commercially purchased reagents (Sigma #315-500). According to the manufacturers, the procedures are modified from published work (McGowan et al. *Clin Chem*, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte coupled with a color reaction first described by Trinder (Trinder, P. *Ann Clin*

Biochem, 6:24 (1969)). The absorbance of the dye produced is linearly related to the analyte in the sample. The assays are further modified for use in a 96 well format. Standards (Sigma #339-11, Sigma #16-11, and Sigma #CC0534 for glucose, triglycerides and total cholesterol, respectively), quality control plasma (Sigma # A2034), and samples (2 or 5 µl/well) are measured in duplicate using 200 µl of reagent. An additional aliquot of sample, pipetted to a third well and diluted in 200 µl water, provided a blank for each specimen. Plates are incubated at room temperature (18, 15, and 10 minutes for glucose, triglycerides and total cholesterol, respectively) on a plate shaker and absorbance read at 500 nm (glucose and total cholesterol) or 540 nm (triglycerides) on a plate reader. Sample absorbance is compared to a standard curve (100-800, 10-500, and 100-400 mg/dl for glucose, triglycerides and total cholesterol, respectively). Values for the quality control sample are consistently within the expected range and the coefficient of variation for samples is below 10%. All samples from an experiment are assayed at the same time to minimize inter-assay variability.

Serum lipoproteins are separated and cholesterol is quantitated with an in-line detection system. Sample is applied to a Superose® 6 HR 10/30-size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min is mixed with the column effluent through a T-connection, and the mixture is passed through a 15 m×0.5 mm id knitted tubing reactor immersed in a 37° C. water bath. The colored product produced in the presence of cholesterol is monitored in the flow stream at 505 nm, and the analog voltage from the monitor is converted to a digital signal for collection and analysis. The change in voltage corresponding to change in cholesterol concentration is plotted against time, and the area under the curve corresponding to the elution of VLDL, LDL and HDL is calculated (Perkin Elmer Turbochrome software).

The compounds of the present invention can be prepared according to the procedures of the following schemes and examples, which may further illustrate details for the preparation of the compounds of the present invention. The compounds illustrated in the schemes and examples are, however, not to be construed as forming the only genus that is considered as the present invention.

General Reaction Scheme:

The compounds of the present invention, in general, may be prepared according to the Reaction Schemes described below. When describing various aspects of the present compounds, the terms "Tail" and "Head" are used as their concept is illustrated below.

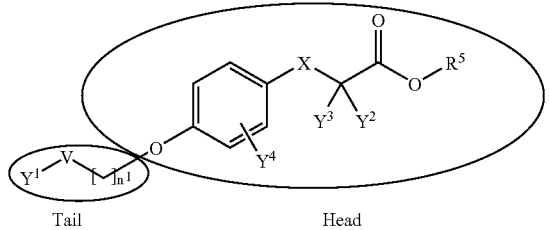

Tail                    Head

Reaction Scheme 1:

Tail-$Z_1$+HO-Head'→Tail-Head $Z_1$=leaving group
Head'=modified headpiece to show OH substitution As shown in Reaction Scheme I, the compounds of the present invention, in general, can be divided into Tail and Head regions where a nucleophilic headpiece is coupled with an electrophilic tailpiece. These regions can be further modified as shown in the following reaction schemes.

Reaction Scheme 2:
Oxazole tailpiece

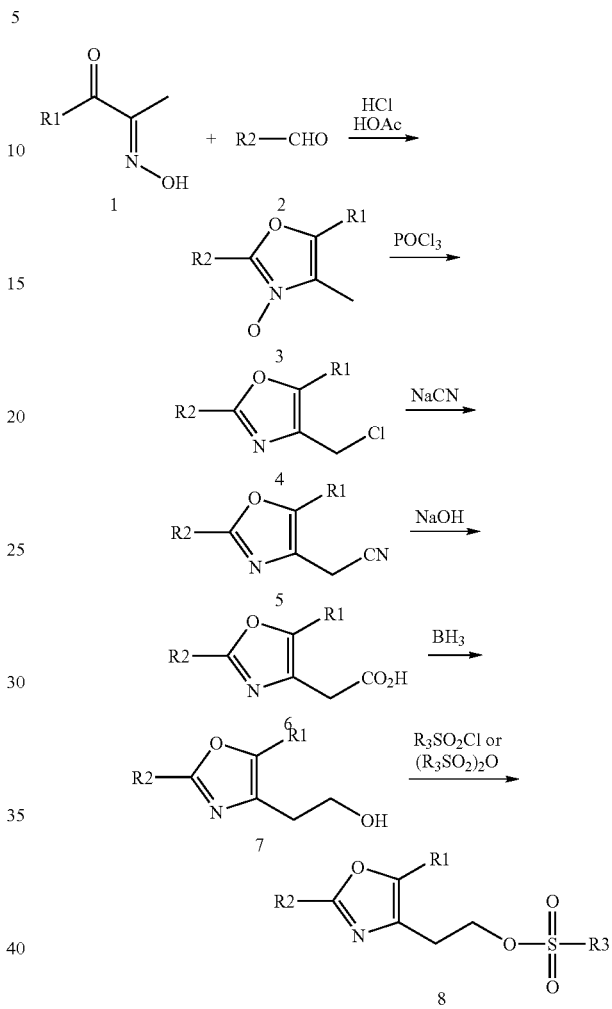

R1 is H, $C_1$-$C_6$ alkyl, $C_1$-$C_6$ alkoxy, halo, haloalkyl or haloalkoxy;

R2 is $Y^{1a}$;

R3 is alkyl (methyl) or tolyl.

As shown in Reaction Scheme 2, an intermediate oxazole tailpiece can be prepared by a condensation of dionemonoxime (1) with aldehyde (2) such as bromobenzaldehyde in the presence of acid such as hydrochloric acid or acetic acid to give an oxazole n-oxide compound (3). The oxazole n-oxide is then treated with phosphorous oxychloride in an organic solvent to form chloromethyl substituted-oxazole (4). Compound (4) is further treated with a cyanide to form cyanomethyl oxazole compound (5). The cyano group of compound (5) is converted to a carboxylic acid group by treatment with an alkali metal hydroxide such as NaOH to form carboxymethyl substituted oxazole (6), which is further treated with a carboxylic acid reducing agent, such as borane or lithium aluminum hydride (LAH) to form compound (7). Compound (7) can be converted to oxazolyl sulfonyl ester (8) in the presence of a base by treatment with a sulfonyl halide or sulfonyl anhydride ($R_3SO_2Cl$ or ($R_3SO_2)_2O$), such as tosyl anhydride, mesyl anhydride, tosyl chloride or mesyl chloride.

Reaction Scheme 3:
Oxazole tailpiece

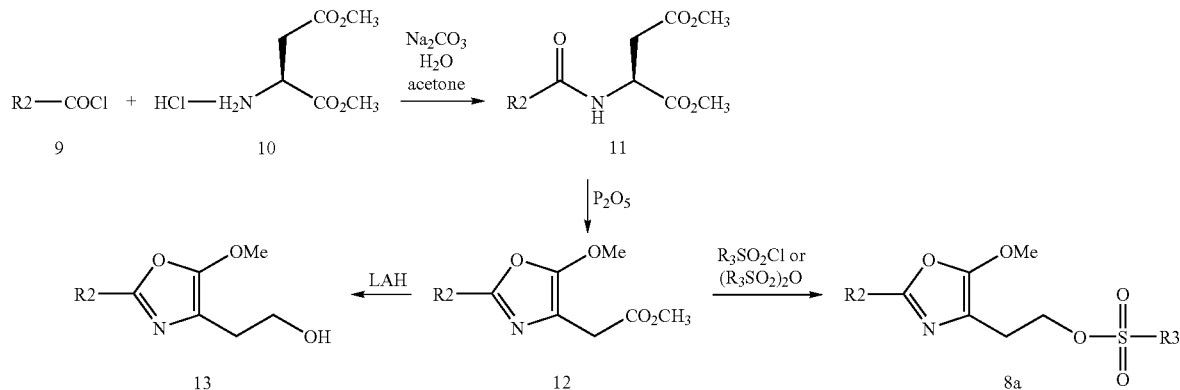

Alternatively, an intermediate of oxazole tailpiece can be prepared as shown in Reaction Scheme 3. Acid chloride (9) is reacted with L-aspartic acid dimethyl ester (10) to give amide compound (11), which undergoes cyclization to form an oxazole ring (12) by treatment with a dehydrating agent such as $P_2O_5$. The ester compound (12) is reduced by treating with LAH to give alcohol (13), which is then converted to oxazolyl sulfonyl ester (8a) as described above in Reaction Scheme 2.

Another route to an intermediate of oxazole tailpiece is shown in Reaction Scheme 4. Acid chloride (9) and L-aspartic acid monomethyl ester (10) are reacted to give amide compound (11), which is further reacted to give ketone (14). The ketone compound undergoes a cyclization in the presence of dehydrating agent such as $POCl_3$ or $H_2SO_4$/acetic anhydride to form oxazole ring (15). Compound (15) under- Reaction Scheme 4:
Oxazole tailpiece

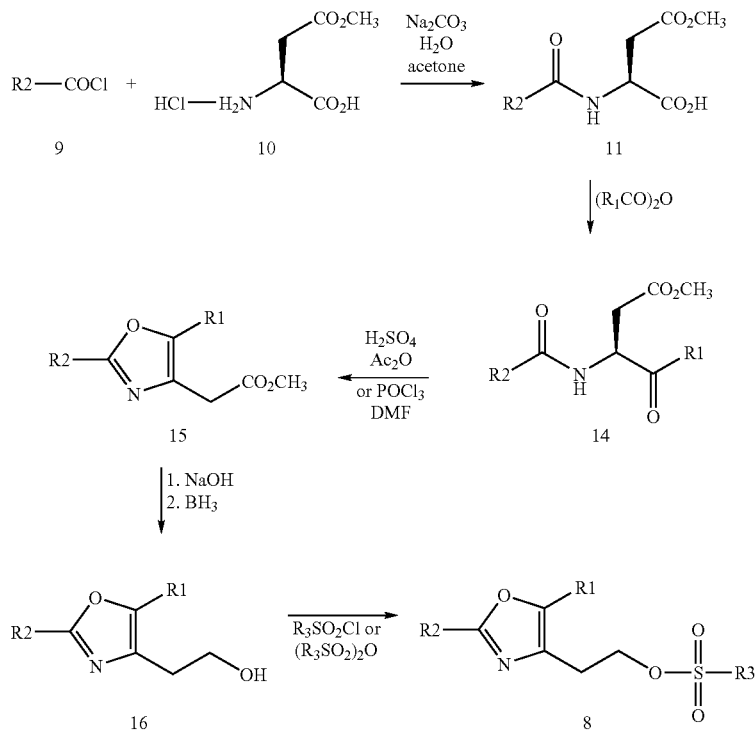

goes reduction to give alcohol (16), which is then converted to oxazolyl sulfonyl ester (8) as described above in Reaction Scheme 2.

Reaction Scheme 5:
Oxazole tailpiece

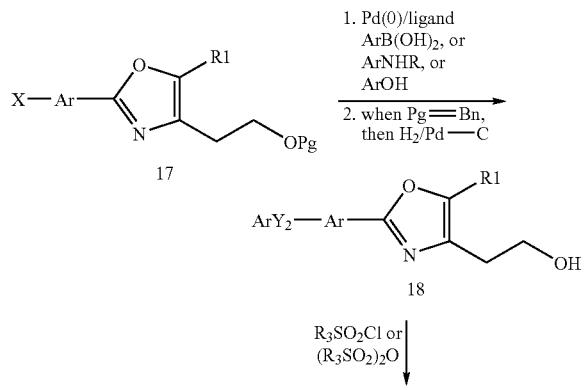

X = OTf, I, Br, Cl
R = H, or alkyl
Pg = protecting group, e.g. benzyl
$Y_2$ = bond, N, or O
$ArY_2—Ar = Y^{1a}$ Another route to an intermediate of the oxazole tailpiece is shown in Reaction Scheme 5. The oxazole compound (17) can undergo a coupling reaction in the presence of palladium catalyst with an aryl boronic acid, aryl alcohol or aryl amine followed by deprotection to yield the corresponding compound (18). Compound (18) is then converted to oxazolyl sulfonyl ester (19) as described above in Reaction Scheme 2.

Reaction Scheme 6:
Thiazole tailpiece

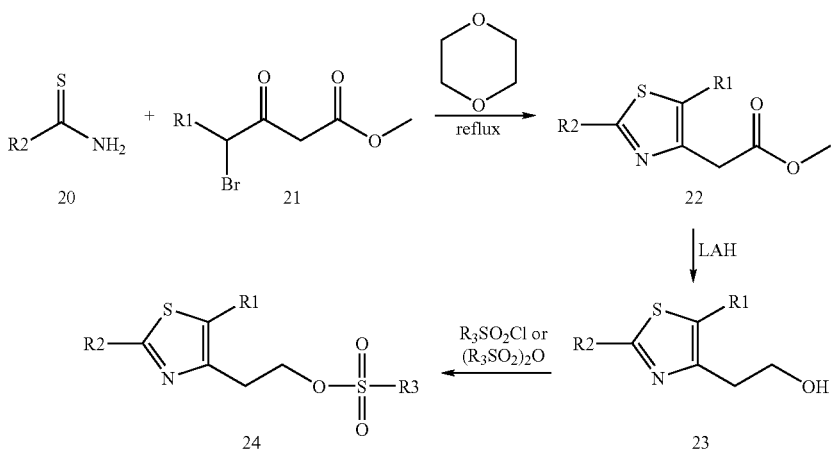

As shown in Reaction Scheme 6, an intermediate thiazole tailpiece can be prepared by the condensation of compound (20) with bromo alkyl ester (21) in the presence of 1,4-dioxane followed by cyclization to give thiazole compound (22). The thiazole (22) then undergoes an ester reduction to give alcohol (13), which is further converted to thiazole sulfonyl ester (8) as described above in Reaction Scheme 2.

Reaction Scheme 7:
Pyrazole tailpiece

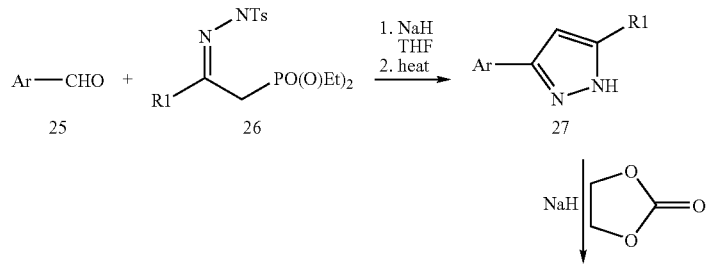

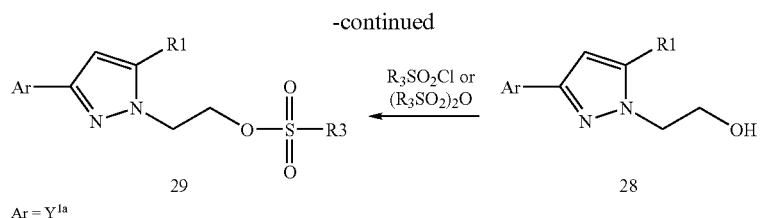

Ar = Y$^{1a}$

As shown in Reaction Scheme 7, an intermediate pyrazole tailpiece can be prepared by the condensation of arylaldehyde (25) with compound (26) in the presence of base followed by cyclization to give pyrazole compound (27). Compound (27) is treated with ethylene carbonate in the presence of base such as NaH to give alkylated compound (28), which is then converted to pyrazole sulfonyl ester (29) as described above in Reaction Scheme 2.

Reaction Scheme 8:
Preparation of arylether bromide

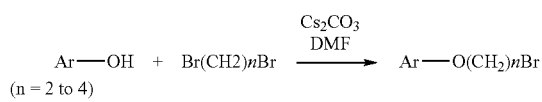

(n = 2 to 4)

Reaction Scheme 8 shows the preparation of arylether bromide by a nucleophilic substitution reaction of an aryl alcohol with a dibromide in the presence of a base.

Reaction Scheme 9:
Preparation of Aminomethyldihydrocinnamate

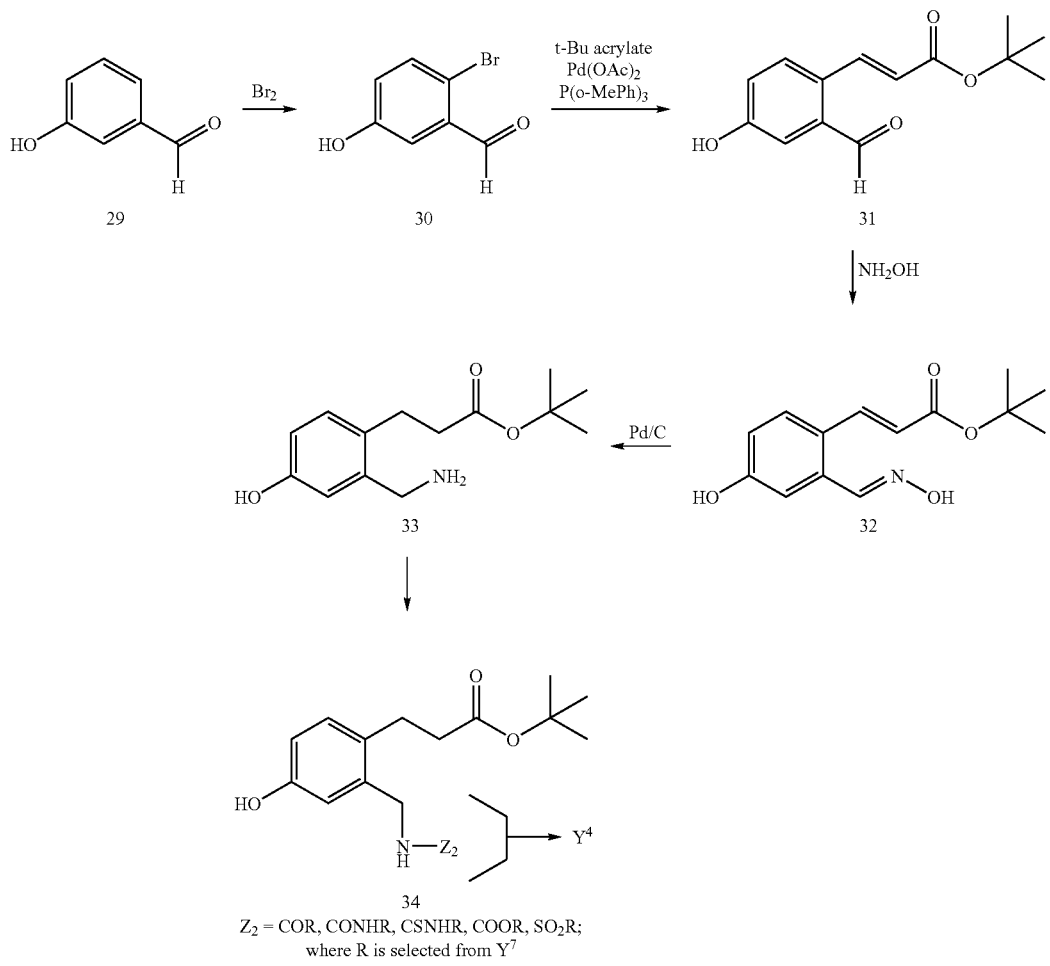

$Z_2$ = COR, CONHR, CSNHR, COOR, SO$_2$R;
where R is selected from Y$^7$

Reaction Scheme 9 shows the synthetic route to prepare aminomethyldihydrocinnamate headpiece. 3-Hydroxybenzaldehyde (29) is reacted with bromine to give 2-bromo-5-hydroxybenzaldehyde (30), which is then coupled to t-butylacrylate to give the compound (31). Compound (31) is treated with NH$_2$OH to give oxime (32), which undergoes hydrogenation to give aminomethyldihydrocinnamate (33). Various functional groups (Z$_2$) can be introduced at the aminomethyl portion of compound (33) to afford compound (34).

Reaction Scheme 10:
N-alkyl headpiece

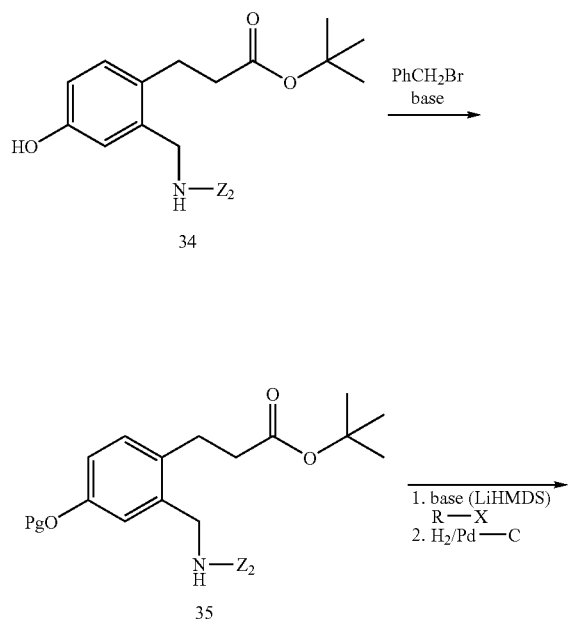

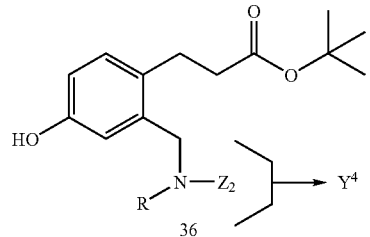

As shown in Reaction Scheme 10, aminomethyl portion of the headpiece compound (34) can be further modified. Phenol (34) is protected with a protecting group such as a benzyl group to give compound (35). Compound (35) undergoes a nucleophilic substitution reaction with an alkyl halide (RX) under basic conditions followed by a deprotection to give phenol compound (36).

Reaction Scheme 11:
Tranesterification

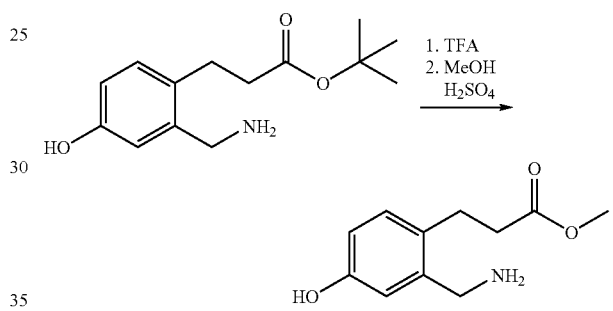

Reaction Scheme 11 illustrates a transesterification reaction of the compound as shown above. The tert-butyl ester can be cleaved under acidic conditions such as TFA. The corresponding carboxylic acid group can be re-esterified with an appropriate alcohol, such as methanol in the presence of an acid such as H$_2$SO$_4$.

Reaction Scheme 12:
Tail-Head coupling with aminomethyldihydrocinnamates
Path A

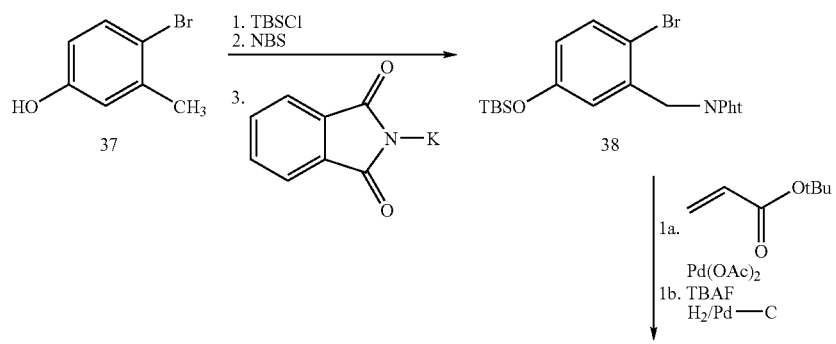

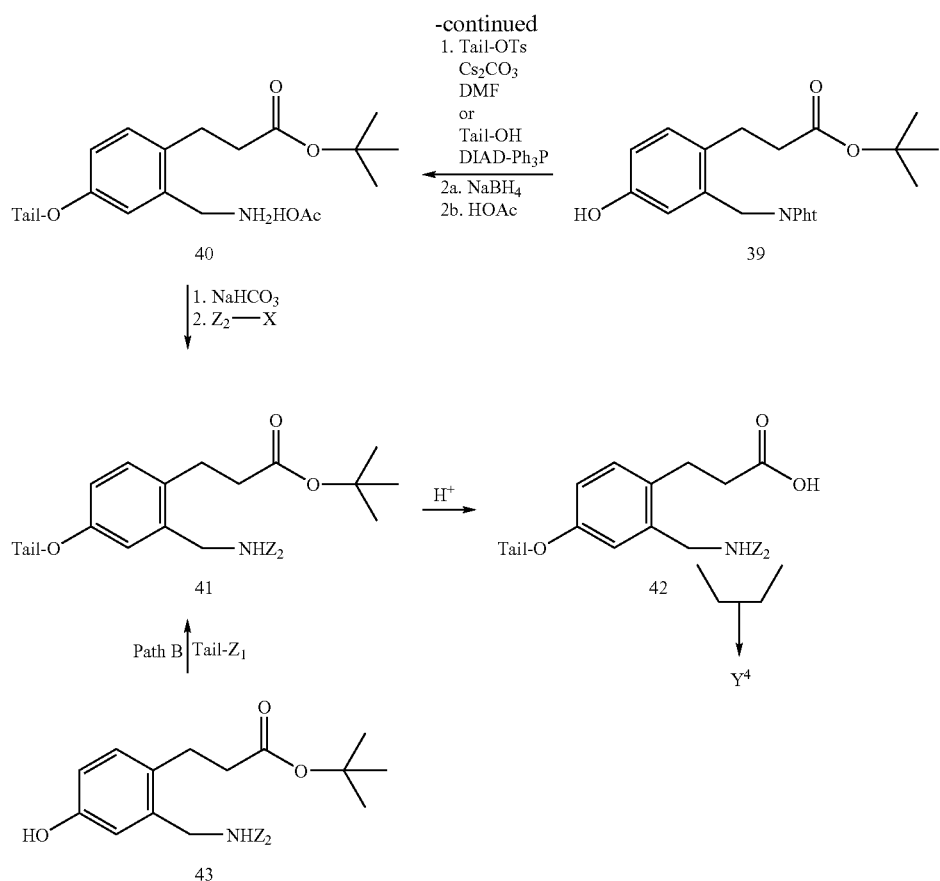

As shown in Reaction Scheme 12, headpiece and tailpiece can be modified to introduce various functional groups. In Path A, the protecting group (TBS) is first attached to the phenol of compound (37) and then radical bromination followed by alkylation with potassium phthalimide yields compound (38). Compound (38) undergoes a Heck coupling reaction with tert-butyl acrylate in the presence of palladium catalyst and then deprotection of silyl group followed by hydrogenation to give compound (39). Compound (39) is coupled with a tailpiece and removal of phthaloyl group yields compound (40). After neutralization, the amino function of (40) can be modified to give (41). Eaester hydrolysis under acidic conditions gives (42). Alternatively, as shown in Path B, compound (42) can be obtained by coupling headpiece (43) with a tailpiece to give compound (41) followed by ester hydrolysis.

Reaction Scheme 13:
Synthesis of meta-aminomethyldihydrocinnamates

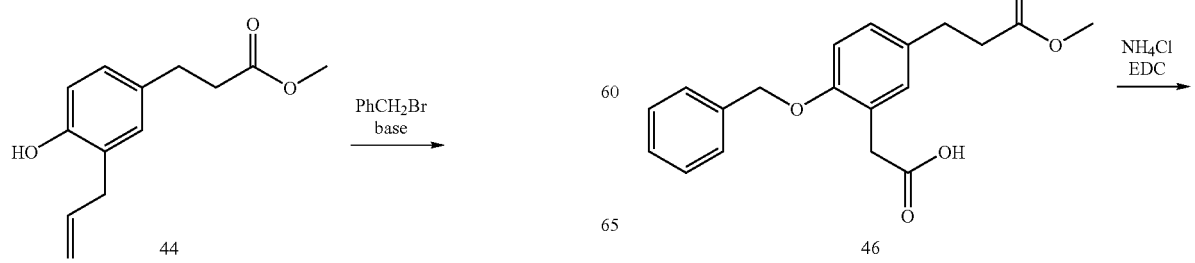

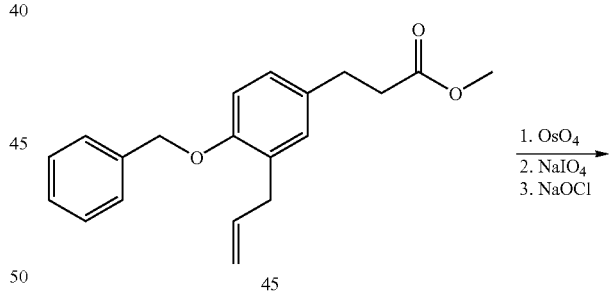

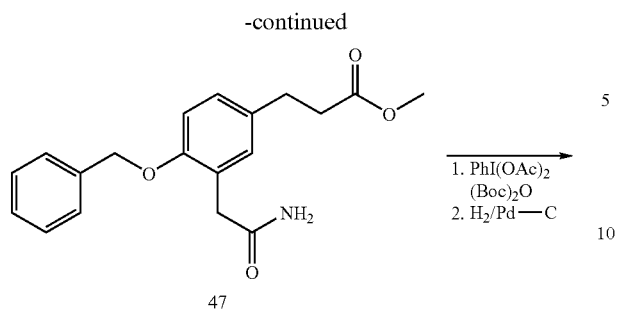

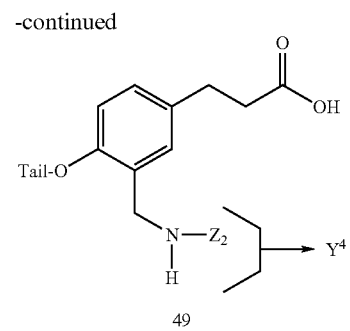

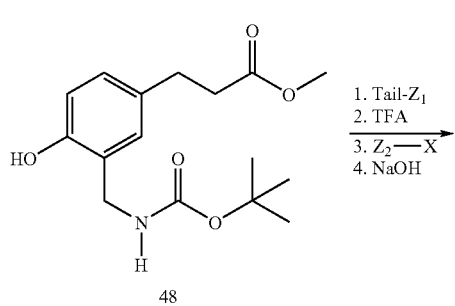

Reaction Scheme 13 shows a synthesis for meta-substituted aminomethyldihydrocinnamates. A protecting group such as benzyl is attached to the phenol of compound (44) to give protected compound (45). Compound (45) undergoes glycol formation followed by cleavage and oxidation reactions to give carboxylic acid compound (46), which is then converted to amide compound (47). Compound (47) undergoes a rearrangement and subsequent amine protection with Boc anhydride followed by deprotection of benzyl ether to afford phenol (48). Compound (48) is coupled with a tail-piece followed by deprotection to give the intermediate, which then undergoes further modification at the aminomethyl portion of the compound followed by hydrolysis to give compound (49).

Reaction Scheme 14:
Synthesis of Aminoethyldihydrocinnamates

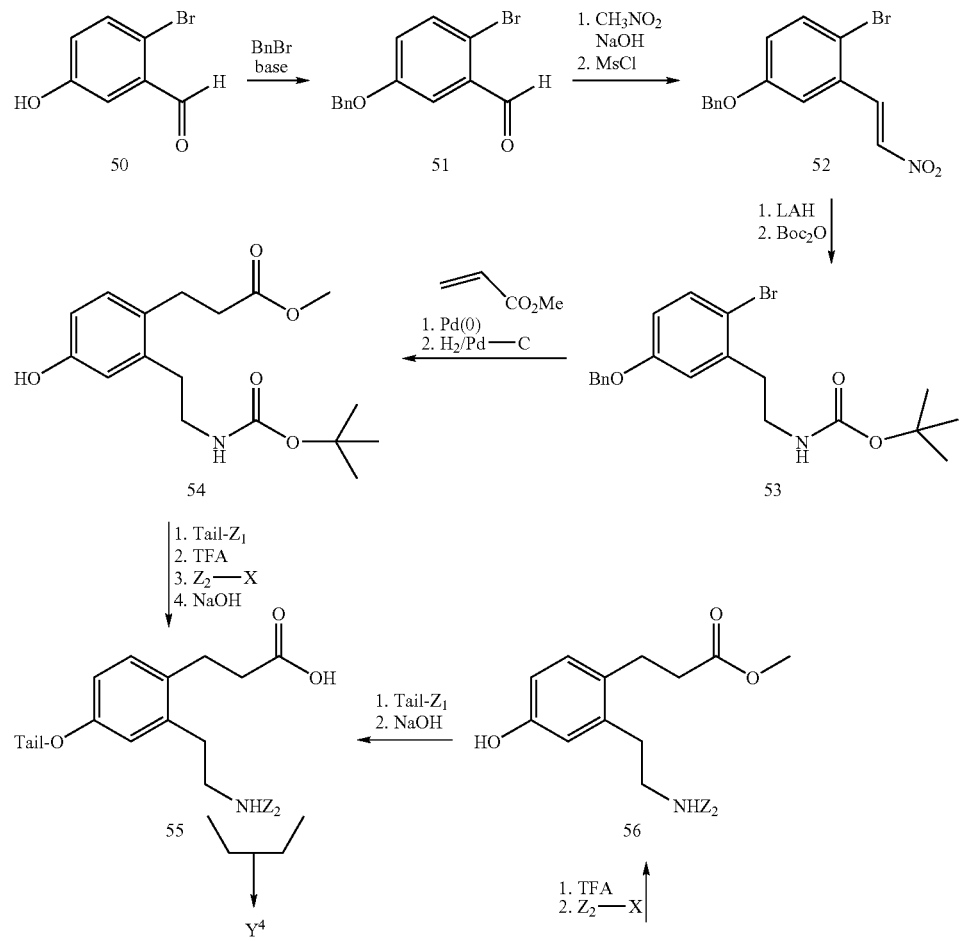

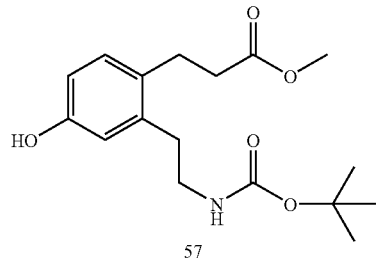

Reaction Scheme 14 shows the synthetic route to prepare aminoethyldihydrocinnamate headpiece. A protecting group such as benzyl is attached to aryl alcohol of compound (50) to give protected compound (51), which is then converted to nitro-olefin compound (52). Compound (52) undergoes reduction of the nitro-olefin by treatment with LAH followed by introduction of an amine protecting group such as Boc to give compound (53). Compound (53) undergoes a coupling reaction with methyl acrylate in the presence of a palladium catalyst followed by deprotection of phenol group to give the phenol compound (54). Compound (54) is then coupled with a tailpiece followed by deprotection of Boc group to give the intermediate compound, which then can undergo further modification at the aminoethyl portion of the compound followed by hydrolysis to give compound (55). Alternatively, compound (57) is deprotected followed by modification at the aminoethyl portion of the compound to give compound (56). Compound (56) can be coupled with a tailpiece followed by ester hydrolysis to afford compound (55).

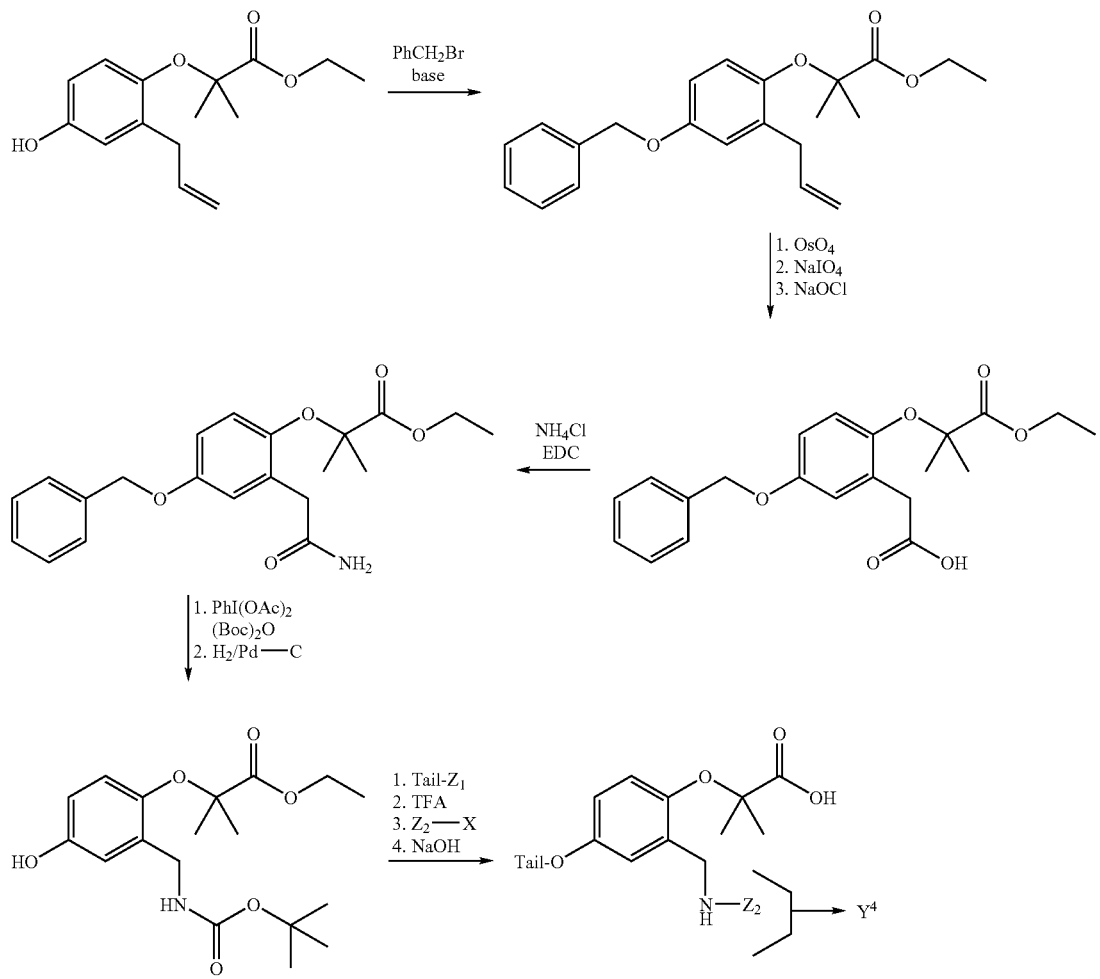

Reaction Scheme 15 shows a synthetic route to prepare aminomethylfibrate compounds. The reaction is carried out by following a substantially similar synthetic route as described in Reaction Scheme 13.

compound (59). Compound (59) is oxidized to give carboxylic acid compound (60), which then undergoes esterification followed by deprotection of the phenol to give compound (61). Compound (61) is coupled with a tailpiece Reaction Scheme 16:
Synthesis of Carboxamidodihydrocinnamates

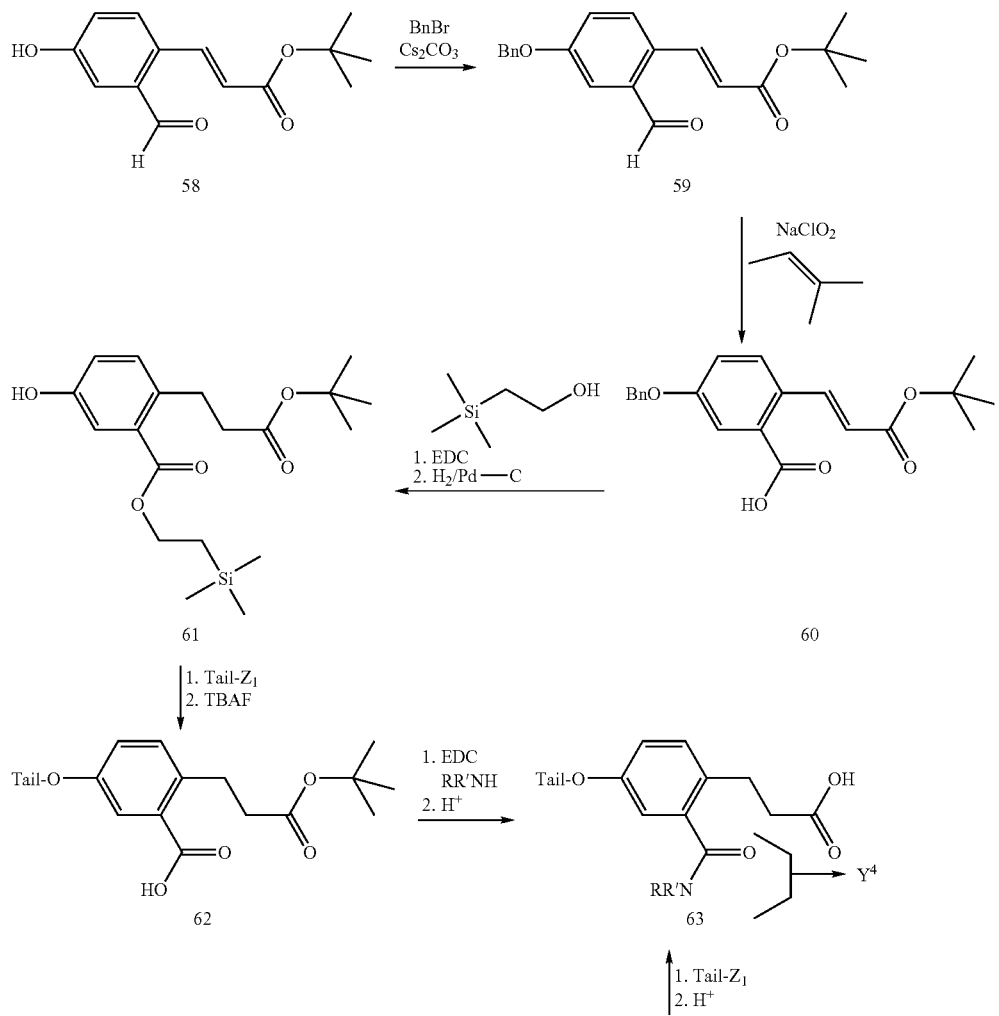

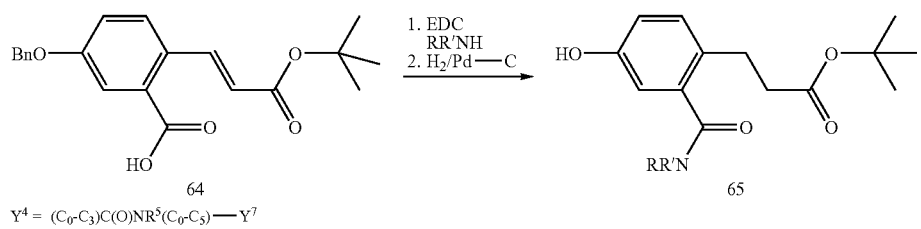

Reaction Scheme 16 shows the synthetic routes to carboxamidodihydrocinnamates by Path A or Path B. Path A allows for rapic amide variation and Path B for tailpiece variation. In path A, the protecting group such as benzyl is attached to the phenol of compound (58) to give protected followed by deprotection of carboxylic acid group to give compound (62), which then undergoes amide formation followed by ester hydrolysis to afford compound (63). Alternatively as shown in path B, compound (64) can undergo an amide formation followed by reduction and deprotection of phenol group to give compound (65). Compound (65) then can be coupled with a tailpiece followed by ester hydrolysis to yield compound (63).

Reaction Scheme 17:
Synthesis of Cyanodihydrocinnamates

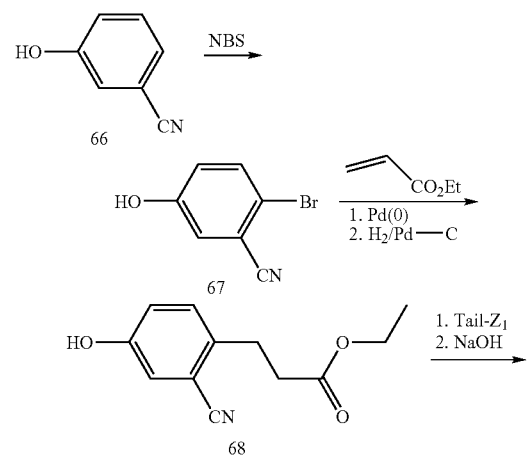

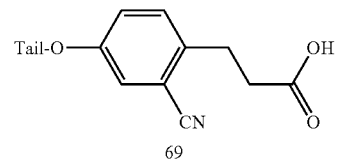

Cyanodihydrocinnamates can be prepared as shown in Reaction Scheme 17. Compound (66) is brominated with a brominating agent such as NBS to give compound (67), which is then undergoes a Heck coupling reaction with ethyl acrylate in the presence of palladium catalyst followed by hydrogenation to give compound (68). Compound (68) is coupled with a tailpiece followed by ester hydrolysis to yield carboxylic acid compound (69).

Reaction Scheme 18:
Synthesis of alkoxydihydrocinnamates

Route (a)

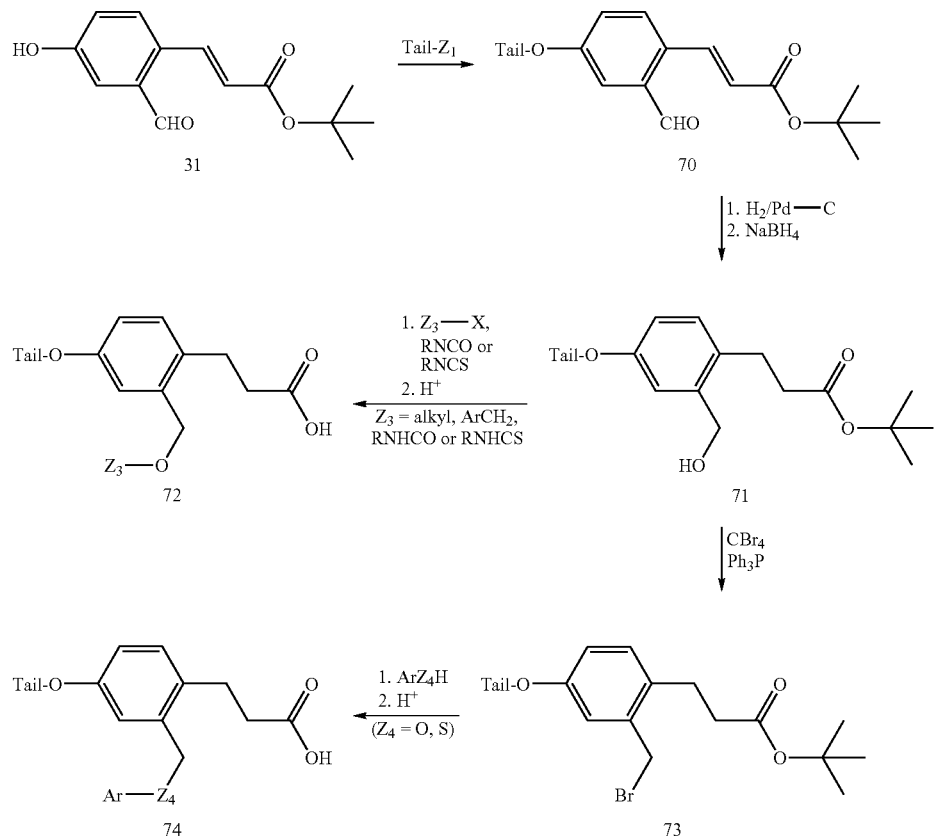

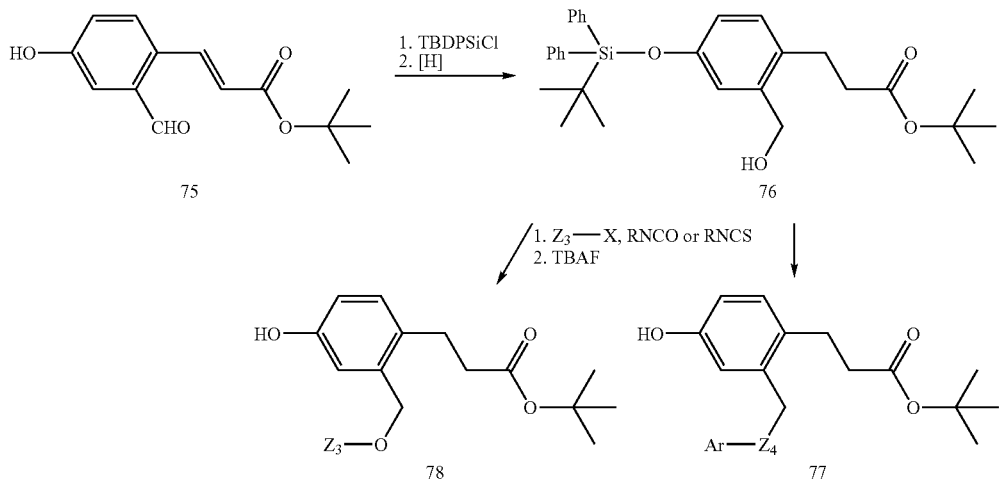

Alkoxydihydrocinnamates can be prepared as shown in Reaction Scheme 18. In route (a), compound (31) is coupled with a tailpiece to give compound (70), which then undergoes sequential reduction of double bond and aldehyde to give alcohol compound (71). Compound (71) undergoes the condensation reaction with an isocyanate or thioisocyanate, alkyl halide or arylic halide followed by ester hydrolysis to give compound (72). Alternatively, compound (71) can be converted to the corresponding halide (73) using a carbon tetrahalide and triphenylphosphine. A nucleophilic substitution reaction followed by ester hydrolysis affords compound (74).

In route (b), the protecting group such as TBDPSi is attached to the aryl alcohol of compound (75) to give compound (76), which then undergoes a similar reaction sequence as described in route (a) to give phenol (77). Alternatively, compound (76) can undergo the condensation reaction with $Z_3$-X followed by deprotection to afford phenol (78). Phenol compounds (77) and (78) can be taken separately to final compounds by reaction with a tailpiece followed by acid hydrolysis.

Reaction Scheme 19:
Synthesis of Alkoxyalkylfibrates

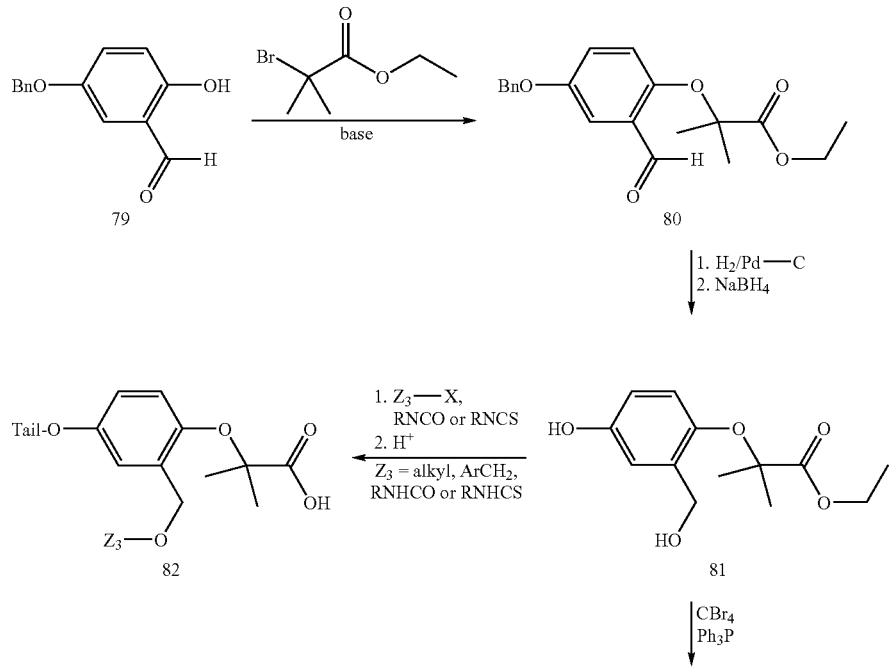

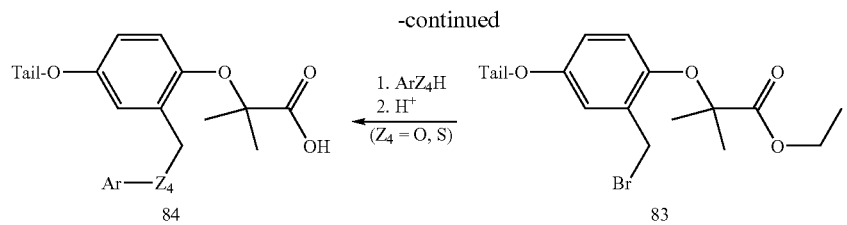

Reaction Scheme 19 illustrates a synthetic route to prepare alkoxyalkylfibrate compounds. Compound (79) is reacted with ethyl 2-bromoisobutyrate in the presence of base to give compound (80). The phenol of compound (80) is deprotected followed by aldehyde reduction in the presence of a reducing agent such as $NaBH_4$ to give compound (81). Phenol (81) then can undergo reaction with $Z_3$-X followed by hydrolysis to give alkoxyalkylfibrate compound (82). Alternatively, phenol compound (81) can be converted to the corresponding halide (83) using a carbon tetrahalide and triphenylphosphine. Treatment of compound (83) with $ArZ_4H$ followed by ester hydrolysis affords compound (84).

Reaction Scheme 20 illustrates the synthetic routes to compounds with modified tailpieces. Oxazole compound (85) can undergo a coupling reaction with an arylboronic, aryl alcohol, aryl amine or secondary amine in the presence of palladium catalyst to give modified tailpiece compound (86). Alternatively, compound (85) undergoes a coupling reaction with pinacol diborane in the presence of palladium catalyst to give compound (87), which then is further coupled with arylhalide to give biaryl compound (88). Alternatively, the compound (87) can be oxidized to give phenol (89), which is then coupled with arylhalide in the Reaction Scheme 20:
Modification to the tailpiece

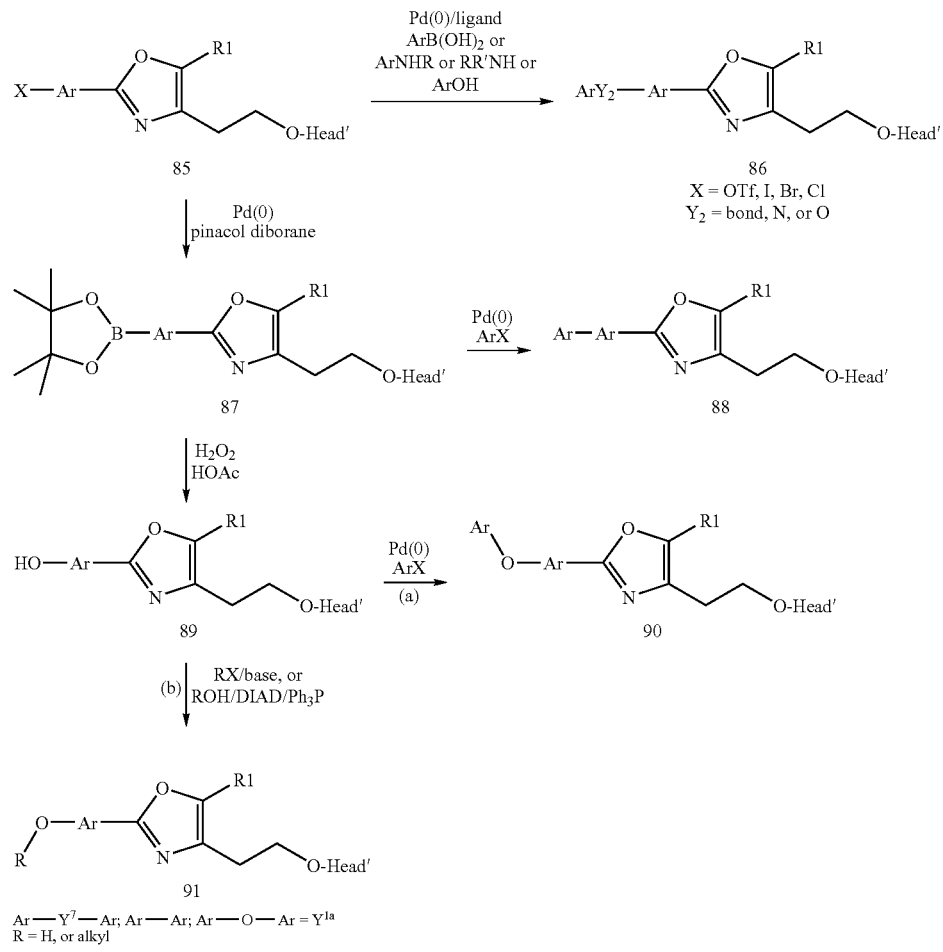

presence of palladium catalyst to give aryl-aryloxy compound (90) as shown in route (a). Alternatively, compound (89) can undergo a nucleophilic reaction with an alkyl halide or alcohol as shown in route (b) to form ether compound (91).

give carboxylic acid compound (93), which is converted to the acid chloride followed by reaction with an amine to form amide compound (94). Similarly in route (b), modified compound (94) is achieved by palladium catalyzed carbo- Reaction Scheme 21:
Modification to the tailpiece

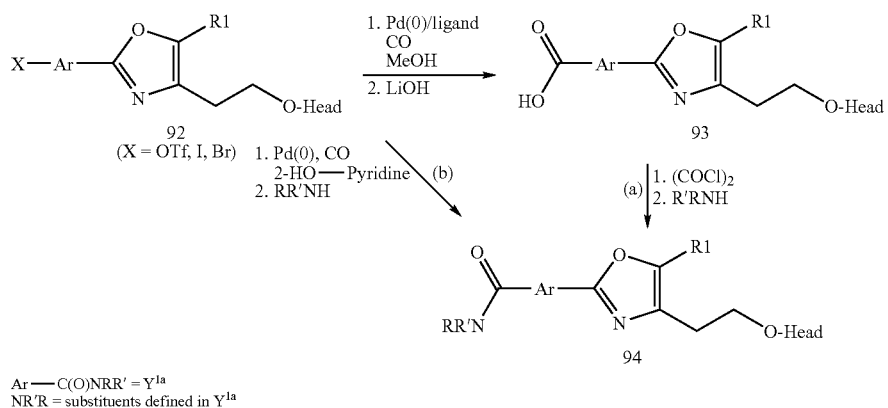

Reaction Scheme 21 shows a synthetic route to modify the tailpiece of the present compounds. In route (a), the oxazole tailpiece compound (92) undergoes carbonylation to give carboxylic acid compound (93), which is converted to the acid chloride followed by reaction with an amine to form amide compound (94). Similarly in route (b), modified compound (94) is achieved by palladium catalyzed carbonylation to form an intermediate hydroxypyridine ester followed by a reaction with amine to form amide compound.

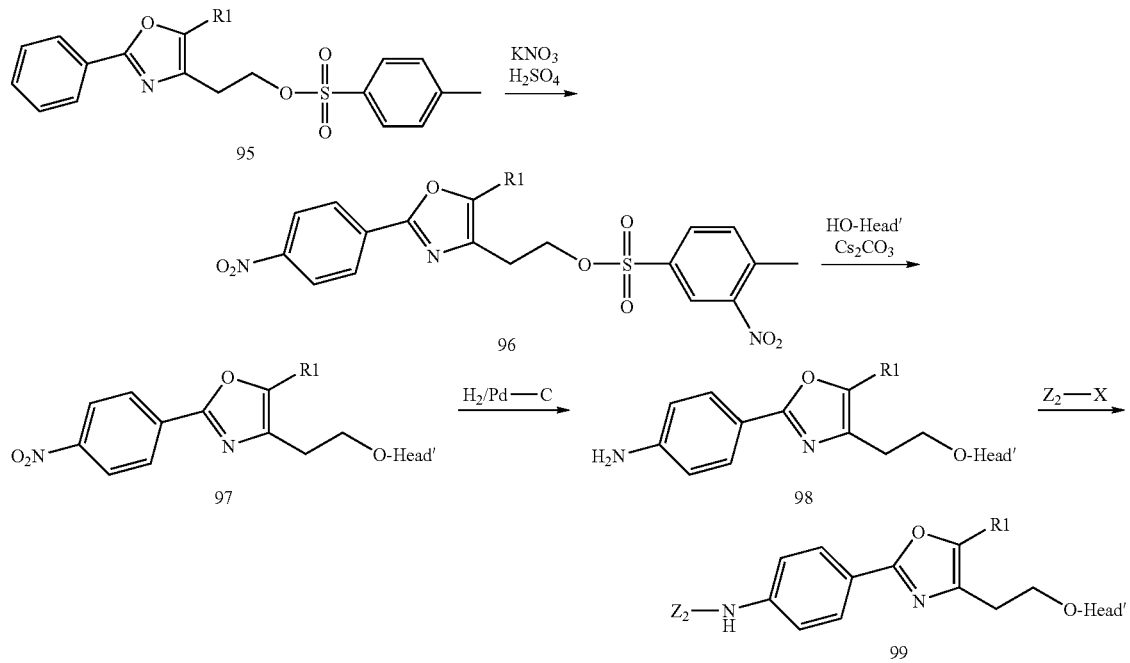

Reaction Scheme 22 shows a synthetic route to modify the tailpiece of the present compounds. Compound oxazolyl sulfonyl ester (95) is nitrated to give compound (96), which then undergoes a coupling reaction with a headpiece to give compound (97). The nitro group of the phenyl ring is reduced to give aniline compound, which is modified to give compound (99).

route (b) with $Z_2$ as a trifluoro acetyl group, alkylation under basic conditions followed by aqueous base hydrolysis gives secondary amine compound (104). Subsequent functionalization of the amine with $Z_2$-X followed by acid hydrolysis affords compound (105).

Reaction Scheme 23:
Modification to the headpiece N

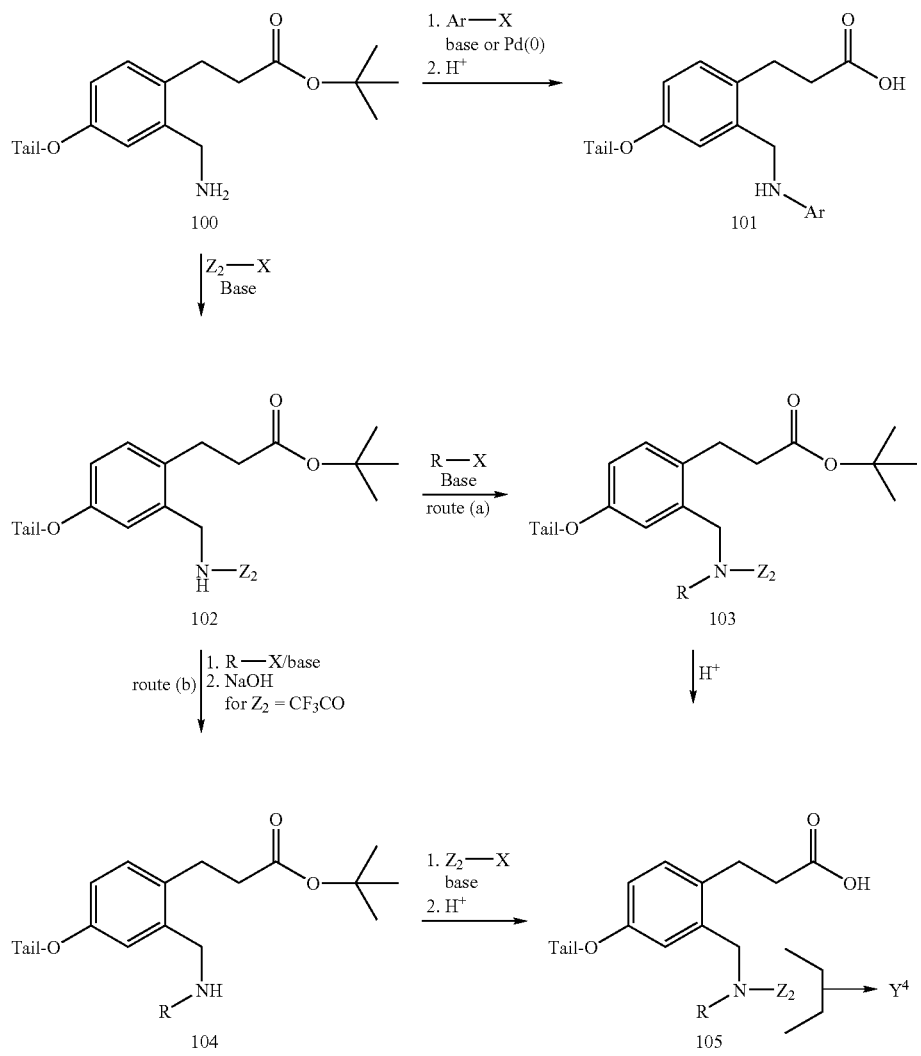

Reaction Scheme 23 shows a synthetic route to modify the headpiece of the present compounds. The headpiece compound (100) can be modified by coupling with arylhalide (Ar—X) in the presence of palladium catalyst followed by ester hydrolysis to give the compound (101). Alternatively, compound (100) can be reacted with $Z_2$-X in the presence of base to give the modified aminomethyl compound (102). In route (a), compound (102) can undergo nucleophilic substitution at the amine followed by ester hydrolysis to give acid compound (105). Alternatively, by Reaction Scheme 24:
Oxazole tailpiece

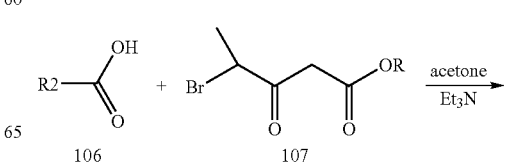

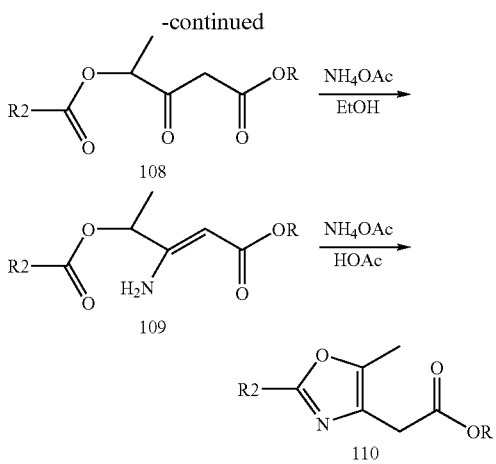

R2 = Y$^{1a}$ such as aryl, aryl—Z—aryl or heteroaryl—Z—aryl, or alkyl
R = alkyl An alternative synthetic route to oxazole tailpiece is shown in Reaction Scheme 24. Carboxylic acid (106) is condensed with 2-bromo-3-oxopentanoate (preferably methyl ester) (107) to give ketoester (108). The latter is converted to an intermediate enamine (109) by treatment with anhydrous ammonium acetate. Subsequent cyclization of compound (109) in acetic acid in the presence of anhydrous ammonium acetate gives compound (110). The use of anhydrous ammonium acetate obtained by azeotropic evaporation with ethanol eliminates water in the reaction, which causes decarboxylation of compound (110). Additionally, some of the water liberated in the reaction is removed at the enamine stage. These modifications along with a simplified isolation procedure lead to higher yields of oxazole (110).

In the Schemes, Preparations and Examples below, various reagent symbols and abbreviations have the following meanings:

| | |
|---|---|
| BINAP | 2,2'-Bis(diphenylphosphino)-1,1'-binaphthyl |
| Boc | t-butoxycarbonyl |
| CBZ | benzyloxycarbonyl |
| DCM | dichloromethane |
| DEAD | diethyl azodicarboxylate |
| DI | deionized |
| DIAD | diisopropyl azodicarboxylate |
| DIPEA | diisopropylethylamine |
| DMAP | 4-dimethylamino pyridine |
| DMF | N,N-dimethylformamide |
| DMSO | dimethylsulfoxide |
| eq. (equiv) | equivalent(s) |
| EDC | 1-(3-dimethylaminopropyl)-3-ethylcarbodiimide HCl |
| ESI-MS | electron spray ion-mass spectroscopy |
| Et | ethyl |
| EtOAc | ethyl acetate |
| FMOC | 9-Flurorenylmethyl carbamate |
| HATU | O-(7-azabenzotriazol-1-yl)-N,N,N',N'-tetramethyluronium hexafluorophosphate |
| HOAc | acetic acid |
| HOAT: | 1-hydroxy-7-azabenzotriazole |
| HOBT | 1-hydroxybenzotriazole hydrate |
| HPLC | high performance liquid chromatography |
| HRMS | high resolution mass |
| h | hour(s) |
| LRMS | low resolution mass |
| LAH | lithium aluminum hydride |
| Me | methyl |
| Ms | methanesulfonyl |
| NBS | N-bromosuccinimide |
| Pd$_2$(dba)$_3$ | tris(dibenzylideneacetone) dipalladium(0) |
| Ph | phenyl |
| Phe | phenylalanine |
| Pr | propyl |
| r.t. | room temperature |
| TBAF | tetrabutylammonium fluoride |
| TBS | tertbutyldimethylsilyl |
| TFA | trifluoroacetic acid |
| TEA | triethylamine |
| THF | tetrahydrofuran |
| TLC | thin-layer chromatography |

Standard Procedure

The following standard procedures (A) to (E) are used for preparing the compounds of the present invention as illustrated in Examples below.

Standard Procedure (A): Coupling Aryl Alcohol Headpieces with Bromide or Tosylate Tailpieces 3-[2-(1,3-dioxo-1,3-dihydro-isoindol-2-ylmethyl)-4-hydroxy-phenyl]-propionic acid tert-butyl ester (67.9 g, 0.178 mol), toluene-4-sulfonic acid 2-(5-methyl-2-phenyl-oxazol-4-yl)-ethyl ester (76.6 g, 0.214 mol) and DMF (680 mL). Cesium carbonate (75.4 g, 0.231 mol) was added, and the reaction mixture was heated at 55° C. for 18 h. After cooling, ethyl acetate (890 mL) and DI water (1200 mL) were added, the mixture was agitated, and the layers were seperated. The aqueous layer was back-extracted with ethyl acetate (740 mL). The organic layers were combined and washed with 1N NaOH (375 mL) then saturated NaCl solution (2×375 mL). The organic solution was dried (Na$_2$SO$_4$), filtered, and concentrated to an oil (107 g).

Standard Procedure (B): Mitsunobu Coupling of Aryl Alcohol Headpieces with Alcohol Tailpieces A mixture of 2-(5-methyl-2-naphthalen-2-yl-oxazol-4-yl)-ethanol (12 mg, 0.442 mmol, 1 equiv), 3-[4-hydroxy-2-(isopropoxycarbonylamino-methyl)-phenyl]-propionic acid tert-butyl ester (150 mg, 0.445 mmol, 1.00 equiv), and triphenylphosphine (116 mg, 0.442 mmol, 1.00 equiv) in toluene (10 mL) at room temperature was treated with diisopropyl azodicarboxylate (90 μL, 92 mg, 0.46 mmol, 1.0 equiv) over a period of about 3 minutes. The mixture was stirred for about 23 hours and concentrated. The crude material was purified by silica gel chromatography.

Standard Procedure (C): Ester Hydrolysis Under Acidic Conditions

A solution of tert-butyl ester-containing compound (0.5 mmol) in CH$_2$Cl$_2$ (6 mL) was treated with 90% trifluoroacetic acid/water (3 mL) and stirred at ambient temperature for about 3 hours and then concentrated to give the corresponding carboxylic acid compound. The crude material was purified by silica gel chromatography if necessary.

Standard Procedure (D): Ester Hydrolysis Under Acidic Conditions

A mixture of tert-butyl ester-containing compound (0.2 mmol) in 4 M HCl in 1,4-dioxane (5 mL) was stirred at ambient temperature for about 16 hours and concentrated to give the corresponding carboxylic acid compound. The crude material was purified by silica gel chromatography if necessary.

Standard Procedure (E): Ester Hydrolysis Under Basic Conditions

A solution of ester (0.25 mmol) in MeOH (3 mL) and THF (1.5 mL) was treated with 2N NaOH (1 mL) and heated at 55° C. for about 2 hours. The mixture was cooled and concentrated. The residue was partitioned between $CH_2Cl_2$ (10 mL), brine (5 mL) and 5N HCl (1 mL). The organic layer was dried ($Na_2SO_4$) and concentrated. The crude material was purified by silica gel chromatography if necessary.

PREPARATION OF INTERMEDIATES

Tailpiece Preparation—Oxazoles

Preparation 1

Toluene-4-sulfonic acid 2-(2-biphenyl-4-yl-5-methyl-oxazol-4-yl)ethyl ester

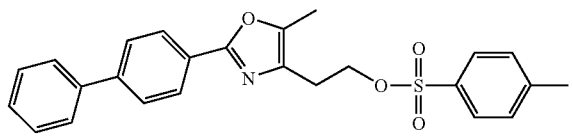

Step A: 4,5-Dimethyl-2-(4-bromophenyl)-oxazole oxide

A solution of 2,3-butanedione monooxime (50 g, 0.49 mol) and 4-bromo-benzaldehyde (101 g, 0.54 mol) in acetic acid (500 mL) was cooled to 0° C. and then gaseous HCl was bubbled through the solution for 35 min while the reaction was stirred in an ice bath. Diethyl ether (500 mL) was added to the reaction to precipitate the product, and the resultant slurry was stirred 45 min at 0° C. before being filtered. The solids were rinsed with $Et_2O$ (50 mL), taken up in water (1 L), and conc. $NH_4OH$ (60 mL) was added to the slurry. This mixture was extracted with $CHCl_3$. The organic layer was dried ($MgSO_4$) and concentrated to give 97.4 g (74%) of 4,5-dimethyl-2-(4-bromophenyl)-oxazole oxide as a white solid. This compound should be used directly within 24-48 h. $^1$H NMR (500 MHz, $CDCl_3$) 8.34 (d, J=9.0 Hz, 2H), 7.61 (d, J=9.0 Hz, 2H), 2.35 (s, 3H), 2.20 (s, 3H); $^{13}$C (125 MHz, $CDCl_3$) 142.1, 131.9, 129.5, 126.3, 124.1, 122.2, 11.1, 6.2; IR (KBr) 1685, 1529, 1418, 1377, 1233, 1165 $cm^{-1}$; UV (EtOH)$_{max}$ 307 nm (24371); HRMS (TOF) m/z calculated for $C_{11}H_{11}^{79}BrNO_2$: 267.997, found 267.9951.

Step B: 2-(4-Bromophenyl-4-(chloromethyl)-5-methyloxazole

A solution of 4,5-dimethyl-2-(4-bromophenyl)-oxazole oxide (96.6 g, 0.36 mol) in $CHCl_3$ (0.90 L) was treated dropwise with phosphorous oxychloride (61.1 g, 0.40 mol) allowing the reaction to exotherm and then was stirred at reflux for 30 min. The reaction was cooled to room temperature and washed with water (2×1 L). The combined aqueous washes were back extracted with $CH_2Cl_2$ (2×400 mL). The organic layers were dried ($MgSO_4$) and concentrated to give crude product that was recrystallized from hot hexanes (300 mL), decanting the hot supernatant away from a dark oily material. The remaining dark oil was agitated in additional hot hexanes (200 mL), and the combined supernatants were cooled to 0° C. The product was isolated by filtration as a lime-green powder (74.2 g, 72%): Rf=0.39 in 20% ethyl acetate/hexanes. $^1$H NMR (500 MHz, $CDCl_3$) 7.88-7.86 (m, 2H), 7.59-7.56 (m, 2H), 4.54 (s, 2H), 2.42 (s, 3H); $^{13}$C (125 MHz, $CDCl_3$) 159.2, 146.9, 133.2, 132.0, 127.6, 126.1, 124.7, 37.1, 11.5; IR (KBr) 2970, 1633, 1599, 1481, 1401, 1258, 1117, 1008 $cm^{-1}$; UV (EtOH)$_{max}$ 281 nm (21349); HRMS (FAB) m/z calculated for $C_{11}H_{10}^{79}BrClNO$: 285.9634, found 285.9641; Anal. Calculated for $C_{11}H_9ClBrNO$: C, 46.11; H, 3.17; N, 4.89; Cl, 12.37; Br, 27.88. Found C, 46.28; H, 3.07; N, 4.81; Cl, 12.36; Br, 27.88.

Step C: 2-(4-Bromophenyl)-5-methyl-4-oxazoleacetic acid

To a solution of 2-(4-bromophenyl-4-(chloromethyl)-5-methyloxazole (64.8 g, 0.23 mol) in DMF (400 mL) was added powdered potassium cyanide (22.1 g, 0.34 mol) and potassium iodide (28.6 g, 0.17 mol), and the resultant mixture was heated to 85° C. for 3.5 h. The reaction mixture was cooled to room temperature. Potassium carbonate (5 g) was dissolved in water (800 mL) and added dropwise to the reaction to precipitate 2-(4-bromophenyl)-4-(cyanomethyl)-5-methyloxazole (stir vigorously 15 min following addition) which was isolated by filtration and washed with water (2×400 mL). The crude 2-(4-bromophenyl-4-(cyanomethyl)-5-methyloxazole was used in the next step without purification. $^1$H NMR (300 MHz, $CDCl_3$) 7.85 (m, 2H), 7.58 (m, 2H), 3.64 (s, 3H), 2.43 (s, 3H).

The crude 2-(4-bromophenyl)-4-(cyanomethyl)-5-methyloxazole (assume 0.22 mol) was combined with 2-methoxyethanol (630 mL) and 85% solid KOH (74.6 g, 1.33 mol) in water (360 mL) was added to the reaction. The mixture was heated to reflux for 3 h, cooled, quenched with 2 M HCl (500 mL), and extracted with $CH_2Cl_2$. The organic layer was dried ($MgSO_4$) and concentrated, using toluene to remove residual 2-methoxyethanol azeotropically. The crude product (57.3 g) was recrystallized from toluene (450 mL) to give 39.8 g (60%) of 2-(4-bromophenyl)-5-methyl-4-oxazoleacetic acid as an off-white powder. Rf=0.23 in 10% MeOH/$CH_2Cl_2$; $^1$H NMR (500 MHz, $CDCl_3$) 9.00 (br s, 1H), 7.85-7.83 (m, 2H), 7.58-7.56 (m, 2H), 3.62 (s, 3H), 2.36 (s, 3H); $^{13}$C (125 MHz, $CDCl_3$) 173.8, 159.0, 146.2, 132.0, 129.1, 127.6, 125.9, 124.7, 31.5, 10.2; IR ($CHCl_3$) 2923, 1699, 1641, 1481, 1428, 1306, 1234, 1010, 829, 727 $cm^{-1}$; UV (EtOH)$_{max}$ 288 nm (19626).

Step D: 2-(4-Bromophenyl)-5-methyl-4-oxazoleethanol

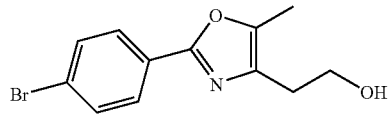

A solution of 2-(4-bromophenyl)-5-methyl-4-oxazoleacetic acid (39.1 g, 0.13 mol) in dry THF (175 mL) was treated dropwise with borane/THF complex (227 mL of a 1.0 M solution in THF, 1.3 mol) over 2 h at about 35° C. After stirring 2 h at room temperature under $N_2$, the reaction was quenched with slow addition of methanol (60 mL) and stirred overnight at room temperature. The reaction was diluted with 1 N NaOH (50 mL) and extracted with $CH_2Cl_2$ (2×200 mL). The organic layer was washed with $H_2O$ (3×100 mL), dried ($MgSO_4$), and concentrated. The crude product (38.7 g) was recrystallized from toluene (200 mL, wash solid with cold hexanes) to give 26.9 g (72%) of 2-(4-bromophenyl)-5-methyl-4-oxazoleethanol as a white powder. Rf=0.37 in 10% MeOH/$CH_2Cl_2$. $^1$H NMR (500 MHz, $CDCl_3$) 7.84-7.82 (m, 2H), 7.57-7.55 (m, 2H), 3.91 (q, J=5.5 Hz, 2H), 3.14 (t, J=6 Hz, OH), 2.72 (t, J=5.5 Hz, 2H), 2.33 (s, 3H); $^{13}$C (125 MHz, $CDCl_3$) 158.7, 144.5, 134.2, 131.9, 127.4, 126.4, 124.3, 61.8, 28.1, 10.1; IR (KBr) 3293, 2948, 1642, 15985, 1480, 1472, 1401, 1053, 1003, 836, 734 $cm^{-1}$; UV (EtOH) max 290 nm (20860); Anal. Calculated for $C_{12}H_{12}BrNO_2$: C, 51.09; H, 4.29; N, 4.96; Br, 28.32. Found C, 51.31; H, 4.06; N, 4.90; Br, 28.19.

Step E: 2-(Biphenyl-4-yl-5-methyl-oxazol-4-yl)ethanol

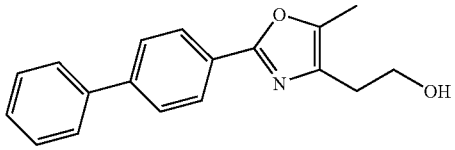

2-(4-Bromophenyl)-5-methyl-4-oxazoleethanol (10.0 g, 35.0 mmol) and phenylboronic acid (4.5 g, 38.0 mmol) were dissolved in n-propanol (120 mL) before adding triphenylphosphine (165.2 mg, 0.63 mmol), palladium acetate (46 mg, 2.1 mmol), and $Na_2CO_3$ (4.5 g, 42 mmol dissolved in 30 mL distilled $H_2O$). The solution was heated at reflux and stirred for 1.5 h. After cooling to ambient temperature, the mixture was concentrated and then partitioned between $CH_2Cl_2$ (100 mL) and 1N NaOH (100 mL). The aqueous phase was extracted with $CH_2Cl_2$ (2×50 mL). The combined organic phases were dried ($MgSO_4$) and concentrated under reduced pressure to provide 2-(4-biphenyl)-5-methyl-4-oxazoleethanol (9.5 g, 97% yield) as a white solid which was used directly without further purification. $^1$H NMR (500 MHz, $CDCl_3$) 8.01 (d, 2H), 7.77-7.50 (m, 4H), 7.46 (m, 2H), 7.38 (m, 1H), 3.91 (q, J=5.5 Hz, 2H), 3.18 (t, J=6 Hz, OH), 2.72 (t, J=5.5 Hz, 2H), 2.33 (s, 3H).

Step F: Toluene-4-sulfonic acid 2-(2-biphenyl-4-yl-5-methyl-oxazol-4-yl)ethyl ester To a solution of 2-(biphenyl-4-yl-5-methyl-oxazol-4-yl)ethanol (15.8 g, 56.6 mmol) in $CH_2Cl_2$ (250 mL) at room temperature under $N_2$ was added pyridine (14.7 g, 185 mmol, 15.0 mL), DMAP (2.03 g, 16.6 mmol), and then tosyl anhydride (24.57 g, 75.2 mmol) portion wise. The reaction exothermed to 32° C. and was stirred 30 min before additional tosyl anhydride (2.3 g) was added. The mixture was diluted with $CH_2Cl_2$ (100 mL) and stirred vigorously with 1N HCl (150 mL) for 15 min. The organic phase was dried ($MgSO_4$) and filtered through a pad of silica gel (100 mL, packed with $CH_2Cl_2$). The silica gel was eluted with ethyl acetate (100 mL), and the solution was concentrated to give toluene-4-sulfonic acid 2-(2-biphenyl-4-yl-5-methyl-oxazol-4-yl)ethyl ester as a white solid (23.3 g, 95%). Rf=0.51 in 60% ethyl acetate/hexanes. $^1$H NMR (400 MHz, $CDCl_3$) 7.97 (d, 2H), 7.70 (d, 2H), 7.66 (t, 2H), 7.65 (d, 2H), 7.51 (t, 1H), 7.42 (d, 2H), 7.24 (d, 2H), 4.37 (t, 2H), 2.88 (t, 2H), 2.37 (s, 3H), 2.26 (s, 3H).

Preparation 2

Toluene-4-sulfonic acid 2-(4-Bromophenyl-5-methyl-oxazol-4-yl)ethyl ester

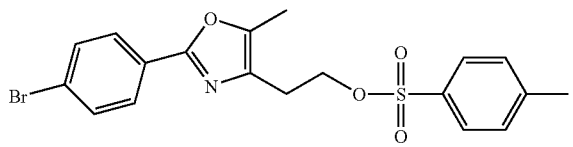

The title compound was prepared from 2-(4-bromophenyl)-5-methyl-4-oxazoleethanol according to Procedure 1, Step F: MS (ESI) m/z 436.0 $(M+H)^+$.

The following intermediate compounds are prepared by a substantially similar manner as described in Preparations 1 and 2.

2-(3-Bromophenyl)-5-methyl-4-oxazoleethanol

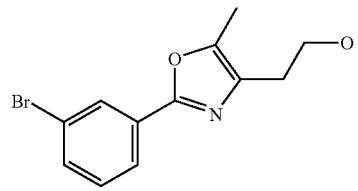

$^1$H NMR (300 MHz, $d_6$-DMSO) δ 7.99 (s, 1H), 7.88 (d, J=7.7 Hz, 1H), 7.64 (d, J=7.7 Hz, 1H), 7.44 (t, J=7.7 Hz, 1H), 4.61 (t, J=5.5 Hz, OH), 3.63 (q, J=5.5 Hz, 2H), 2.60 (t, J=6.6 Hz, 2H), 2.32 (s, 3H);

Toluene-4-sulfonic acid 2-(3-bromophenyl-5-methyl-oxazol-4-yl)ethyl ester

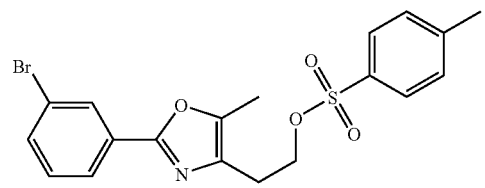

$^1$H NMR (400 MHz, $CDCl_3$) δ 8.01 (t, J=1.6 Hz, 1H) 7.80 (dt, J=7.6 Hz, J=1.6 Hz, 1H), 7.66 (d, J=8.4 Hz, 2H), 7.53 (dt, J=7.6 Hz, J=1.6 Hz, 1H), 7.30 (t, J=7.6 Hz, 1H), 7.19 (d, J=8.4 Hz, 2H), 4.30 (t, J=6.4 Hz, 2H), 2.82 (t, J=6.4 Hz, 2H), 2.31 (s, 3H), 2.24 (s, 3H); MS (ESI) m/z 436.0 $(M+H)^+$.

Toluene-4-sulfonic acid 2-(2-biphenyl-3-yl-5-methyl-oxazol-4-yl)ethyl ester

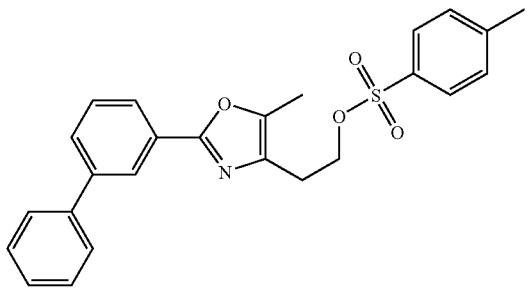

$^1$H NMR (300 MHz, $CDCl_3$) δ 7.99 (s, 1H), 7.80 (d, J=8.0 Hz, 1H), 7.64 (d, 8.0 Hz, 1H), 7.51 (d, J=9.0 Hz, 1H), 7.30 (t, J=8.0 Hz, 1H), 7.20 (d, J=9.0 Hz, 1H), 4.30 (t, J=7.0 Hz, 2H), 2.80 (t, J=7.0 Hz, 2H), 2.30 (s, 3H), 2.23 (s, 3H).

2-(5-Methyl-2-thiophen-2-yl-4-oxazoleethanol

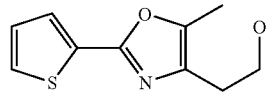

$^1$H NMR (500 MHz, $CDCl_3$): δ 7.54 (m, 1H), 7.33 (m, 1H), 7.03 (m, 1H), 3.87 (t, J=5.8 Hz, 2H), 3.5 (s, 1H), 2.67 (t, J=5.8 Hz, 2H), 2.25 (s, 3H)

Toluene-4-sulfonic acid 2-(5-methyl-2-thiophen-2-yloxazol-4-yl)ethyl ester

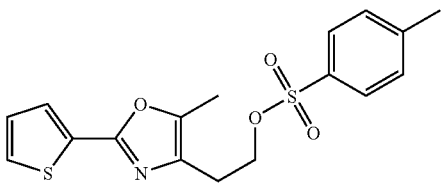

¹H NMR (400 MHz, CDCl₃): δ 7.67 (d, J=8.3 Hz, 2H), 7.51 (dd, J=3.8, 1.4 Hz, 1H), 7.37 (dd, J=4.9, 1.2 Hz, 1H), 7.21 (d, J=7.9 Hz, 2H), 7.08 (dd, J=4.8, 3.5 Hz, 1H), 4.28 (t, J=6.3 Hz, 2H), 2.80 (t, J=6.3 Hz, 2H), 2.28 (s, 3H), 2.26 (s, 3H); mp 107-109° C.

2-[2-(4-Benzyloxy-phenyl)-5-methyl-oxazol-4-yl]-ethanol

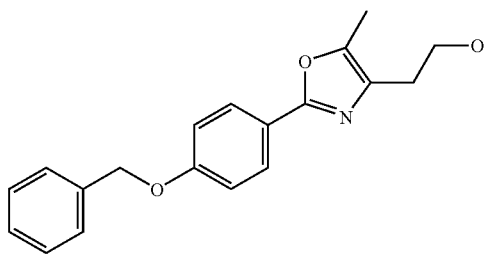

¹H NMR (500 MHz, CDCl₃) δ 7.91 (d, 2H, J=8.60 Hz), 7.45-34 (m, 5H), 7.02 (d, 2H, J=8.60 Hz), 5.11 (s, 2H), 3.91 (t, 2H, J=5.7 Hz), 2.71 (t, 2H, J=5.7 Hz), 2.31 (s, 3H); MS (ES⁺) Calculated for C₁₉H₂₀NO₃: Found m/e 310 (M+1, 100%).

Toluene-4-sulfonic acid 2-[2-(4-benzyloxy-phenyl)-5-methyl-oxazol-4-yl]-ethyl ester

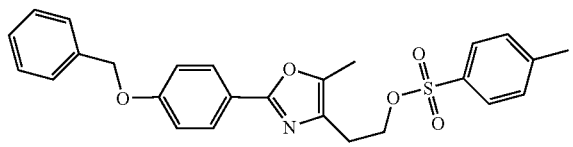

¹H NMR (500 MHz, CDCl₃) δ 7.80-7.78 (m, 2H), 7.67-7.65 (m, 2H), 7.45-7.34 (m, 5H), 7.25-7.17 (m, 2H), 7.02-6.99 (m, 2H), 5.12 (s, 2H), 4.29 (t, 2H, J=6.45 Hz), 2.80 (t, 2H, J=6.45 Hz), 2.27 (s, 3H), 2.22 (s, 3H); HRMS (ES⁺) m/z exact mass calculated for C₂₆H₂₆NO₅S 464.1532, found 464.1531; Anal. Calculated for C₂₆H₂₁NO₅S: C, 67.37; H, 5.44; N, 3.02. Found C, 66.59; H, 5.33; N, 3.06.

Preparation 3

Toluene-4-sulfonic acid 2-(5-methyl-2-phenethyl-oxazol-4-yl)-ethyl ester

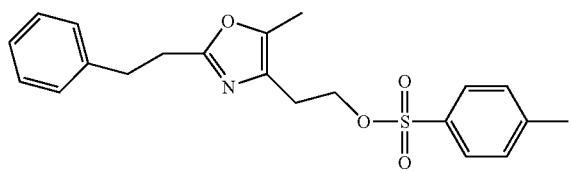

Step A: 2-(3-Phenyl-propionylamino)-succinic acid 4-methyl ester

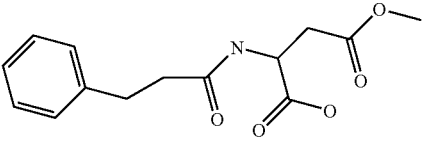

Methyl L-aspartate (15.0 g, 0.082 mol), DI water (245 mL), acetone (20 mL), and Na₂CO₃ (30.8 g, 0.286 mol) were combined and cooled the solution to 5° C. The compound 3-phenyl-propionyl chloride (13.3 mL, 0.089 mol) was added dropwise via addition funnel over 10 min. The reaction was allowed to warm to ambient temperature and stir for 2 h. Conc. HCl (50 mL) was added to the thick slurry until the pH was ≦4.0. The reaction mixture was extracted with CH₂Cl₂ (3×100 mL). The combined organic layers were washed with water, dried (MgSO₄), filtered, and concentrated. The clear, colorless oil was used without further purification. ¹H NMR (400 MHz, CDCl₃) δ 7.92 (br s, 1H), 7.28-7.17 (m, 5H), 6.57 (d, J=7.6 Hz, 1H), 4.87 (m, 1H), 3.67 (s, 3H), 2.96 (t, J=7.6 Hz, 2H), 2.89 (A of ABX, $J_{AB}$=17.6 Hz, $J_{AX}$=4.8 Hz, 1H), 2.88 (B of ABX, $J_{BA}$=17.6 Hz, $J_{BX}$=4.0 Hz, 1H), 2.69 (t, J=7.6 Hz, 2H); MS (EI+) 280 (M+H), 302 (M+H+Na).

Step B: 4-Oxo-3-(3-phenyl-propionylamino)-pentanoic acid methyl ester

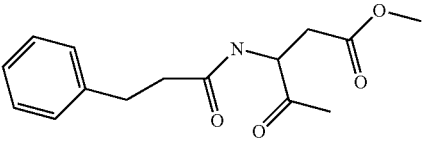

2-(3-Phenyl-propionylamino)-succinic acid 4-methyl ester (10 g, 36 mmol), pyridine (50 mL) and acetic anhydride (45 mL) were combined in a 500 mL flask. The reaction mixture was heated at 90° C. for 2 h and then cooled to ambient temperature. After concentrating the reaction mixture under reduced pressure, DI water was added (100 mL). The reaction mixture was partitioned between water and CH₂Cl₂ (200 mL). The organic phase was washed with 1N HCl (50 mL), dried (MgSO₄), filtered, and concentrated. The material was used without further purification. ¹H NMR (400 MHz, CDCl₃) δ 7.31-7.20 (m, 5H), 6.79 (br d, J=7.6 Hz, 1H), 4.72 (X of ABX, 1H), 3.65 (s, 3H), 3.01-2.93 (m, 3H), 2.71-2.62 (m, 3H), 2.11 (s, 3H); MS (EI) 278.1 (M+H).

Step C: (5-Methyl-2-phenethyl-oxazol-4-yl)-acetic acid methyl ester

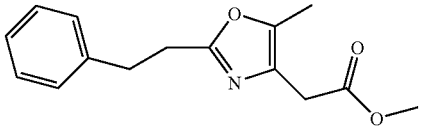

In a 100 mL flask, 4-oxo-3-(3-phenyl-propionylamino)-pentanoic acid methyl ester (10 g, 36 mmol) and acetic anhydride (28 mL) were combined. Following addition of concentrated H₂SO₄ (1 mL), the solution was heated to 90° C. for 30 min and cooled to ambient temperature. The reaction was slowly diluted with DI water (30 mL, potential exotherm). The reaction mixture was partitioned between CH₂Cl₂ (150 mL) and water (150 mL). The organic phase was washed with DI water, 10% NaHCO₃ (aq), brine (150 mL), and then was dried (MgSO₄) and concentrated to a brown oil. The residue was purified by column chromatography (600 mL SiO₂, 35% EtOAc/hexanes) to provide the desired product (3.25 g) as a pale yellow oil. ¹H NMR (400

MHz, CDCl$_3$) δ 7.33-7.20 (m, 5H), 3.72 (s, 3H), 3.47 (s, 2H), 3.08-2.96 (m, 4H), 2.24 (s, 3H); MS (EI+) 260 (M+H).

Step D: (5-Methyl-2-phenethyl-oxazol-4-yl)-acetic acid

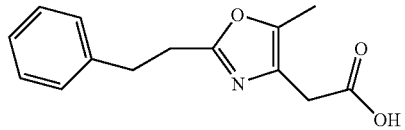

(5-Methyl-2-phenethyl-oxazol-4-yl)-acetic acid methyl ester (8.75 g, 33.8 mmol), in MeOH (120 mL) was treated with 5N NaOH (40 mL), and then the solution was warmed to 40° C. After 40 min, the reaction mixture was concentrated. The residue was suspended in water (75 ml) and acidified to pH=1 with 5N HCl. The mixture was extracted with EtOAc (2×), dried (MgSO$_4$), and concentrated to provide 5.25 g (63%) of the product as an off-white solid. $^1$H NMR (400 MHz, CDCl$_3$) δ$^1$H NMR (400 MHz, CDCl$_3$) δ 7.33-7.20 (m, 5H), 3.52 (s, 2H), 3.06-3.03 (m, 4H), 2.24 (s, 3H).

Step E: 2-(5-Methyl-2-phenethyl-oxazol-4-yl)-ethanol

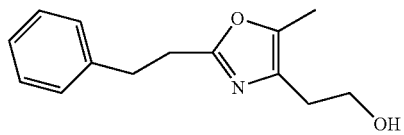

BH$_3$-THF complex (49 mL of a 1.0 M solution in THF) was added dropwise via addition funnel over 50 min to a solution of (5-methyl-2-phenethyl-oxazol-4-yl)-acetic acid (5.05 g, 20.6 mmol) in THF (35 mL). The reaction mixture was stirred at ambient temperature for 3 h, and then quenched with MeOH (12 mL). After heating at 50° C. for 2 h, the reaction mixture was cooled to ambient temperature, and then partitioned between CH$_2$Cl$_2$ and 1N NaOH. The organic phase was washed with brine (1×50 mL), dried over MgSO$_4$ and concentrated to obtain a residue, which was purified by column chromatography (500 mL SiO$_2$, 35% EtOAc/hexanes) to provide 3.99 g (84%) of the desired product as a clear, colorless oil. $^1$H NMR (400 MHz, CDCl$_3$) δ 7.33-7.20 (m, 5H), 3.84 (q, J=5.6 Hz, 2H), 3.06-2.67 (m, 4H), 2.62 (t, J=5.6 Hz, 2H), 2.22 (s, 3H); MS (EI+) 232.19 (M+H); 254.15 (M+H+Na).

Step F: Toluene-4-sulfonic acid 2-(5-methyl-2-phenethyl-oxazol-4-yl)-ethyl ester A solution of 2-(5-methyl-2-phenethyl-oxazol-4-yl)-ethanol (1.2 g, 5.19 mmol) in CH$_2$Cl$_2$ at 0° C. was treated with pyridine (1.64 g, 20.7 mmol, 1.68 mL), DMAP (190 mg, 1.56 mmol), and tosyl anhydride (2.2 g, 6.75 mmol). The reaction was warmed to ambient temperature and, after 90 min, the solution was filtered through a pad of silica gel (rinsed with CH$_2$Cl$_2$). The product was used without further purification. $^1$H NMR (400 MHz, CDCl$_3$) δ 7.73 (d, J=8.4 Hz, 2H), 7.31-7.17 (m, 7H), 4.21 (t, J=6.8 Hz, 2H), 3.01-2.88 (m, 4H), 2.75 (t, J=6.8 Hz, 2H), 2.43 (s, 3H), 2.19 (s, 3H).

The following intermediate compounds are prepared by a substantially similar manner as described in Preparations 3.

2-(2-Cyclohexyl-5-methyl-oxazol-4-yl)-ethanol

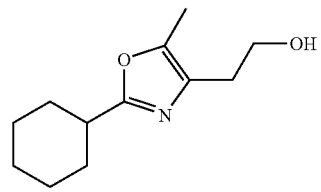

$^1$H NMR (400 MHz, CDCl$_3$) δ3.73 (t, J=6.8 Hz, 2H), 2.58 (tt, J=11.6, 3.6 Hz, 1H), 2.54 (t, J=6.8 Hz, 2H), 2.13 (s, 3H), 1.93-1.89 (m, 2H), 1.74 (dt, J=12.8, 3.6 Hz, 2H), 1.67-1.62 (m, 1H), 1.41 (qd, J=12.0, 3.2 Hz, 1H), 1.33-1.17 (m, 4H); MS (EI+) 210.1 (M+H).

Toluene-4-sulfonic acid 2-(2-cyclohexyl-5-methyl-oxazol-4-yl)-ethyl ester

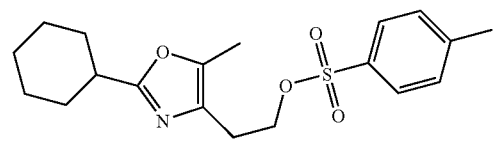

$^1$H NMR (400 MHz, CDCl$_3$) δ7.67 (d, J=8.4 Hz, 2H), 7.27 (d, J=8.4 Hz, 2H), 4.16 (t, J=6.8 Hz, 2H), 2.70 (t, J=6.8 Hz, 2H), 2.56 (tt, J=11.6, 3.6 Hz, 1H), 2.39 (s, 3H), 2.13 (s, 3H), 1.93-1.89 (m, 2H), 1.74 (dt, J=12.8, 3.6 Hz, 2H), 1.67-1.62 (m, 1H), 1.41 (qd, J=12.0, 3.2 Hz, 1H), 1.33-1.17 (m, 4H); MS (EI+) 364.1 (M+H)$^+$.

2-[5-Methyl-2-(1-methylcyclohexyl)oxazol-4-yl] ethanol

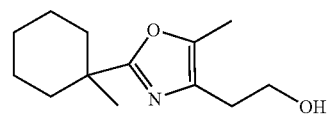

MS (EI+) 224.1 (M+H)$^+$.

Toluene-4-sulfonic acid 2-[5-methyl-2-(1-methylcyclohexyl)oxazol-4-yl]ethyl ester

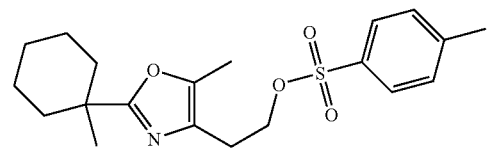

$^1$H NMR (400 MHz, CDCl$_3$) δ 7.73 (d, J=8.4 Hz, 2H), 7.30 (t, J=8.4 Hz, 2H), 4.12 (t, J=6.6 Hz, 2H), 2.76 (t, J=6.6 Hz, 2H), 2.42 (s, 3H), 2.17 (s, 3H), 2.61-2.02 (m, 2H), 1.56-1.30 (m, 8H), 1.19 (s, 3H); MS (EI) 378.2 (M+H)$^+$.

2-[5-Methyl-2-(tetrahydro-pyran-4-yl)-oxazol-4-yl]-ethanol

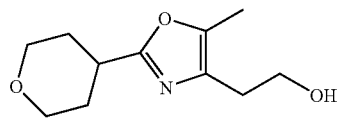

MS (EI) 212.2 (M+H)+.

Toluene-4-sulfonic acid 2-[5-methyl-2-(tetrahydro-pyran-4-yl)-oxazol-4-yl]-ethyl ester

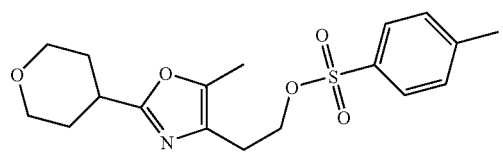

MS (EI) 366.2 (M+H)+.

2-(2-Benzyl-5-methyl-oxazol-4-yl)-ethanol

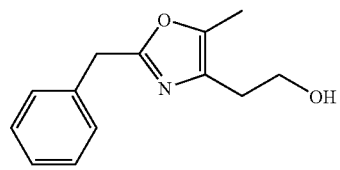

MS (EI) 218.0 (M+H)+.

Toluene-4-sulfonic acid 2-(2-benzyl-5-methyl-oxazol-4-yl)-ethyl ester

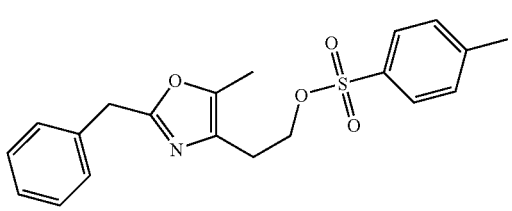

MS (EI) 372.1 (M+H)+.

2-(2-Benzo[b]thiophen-2-yl-5-methyl-oxazol-4-yl)-ethanol

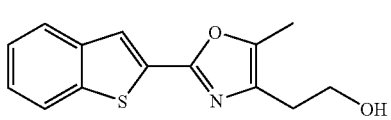

$^1$H NMR (CDCl$_3$) δ 7.81 (m, 3H), 7.38 (m, 2H), 3.94 (m, 2H), 3.07 (br s, 1H), 2.73 (t, 2H, J=6 Hz), 2.34 (s, 3H); $^{13}$C NMR (CDCl$_3$) δ 155.9, 145.0, 140.5, 139.8, 134.5, 129.9, 125.9, 125.1, 124.7, 123.7, 122.7, 61.9, 28.5, 10.4; MS (EI) 260.1 (M+H)+.

Toluene-4-sulfonic acid 2-(2-benzo[b]thiophen-2-yl-5-methyl-oxazol-4-yl)-ethyl ester

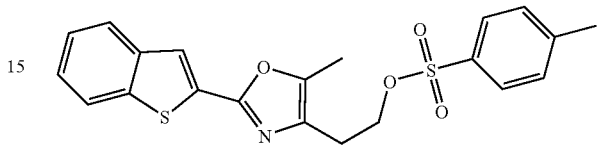

$^1$H NMR (CDCl$_3$) δ 7.85 (m, 1H), 7.84 (m, 1H), 7.75 (s, 1H), 7.67 (d, 2H, J=8 Hz), 7.39 (m, 2H), 7.21 (m, 2H), 4.31 (t, 2H, J=2 Hz), 2.83 (t, 2H, J=6 Hz), 2.32 (s, 3H), 2.19 (s, 3H).

2-(5-Methyl-2-naphthalen-2-yl-oxazol-4-yl)-ethanol

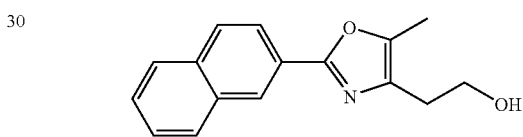

HRMS Calcd for C$_{16}$H$_{16}$NO$_2$: m/z 254.1181. Found: 254.1167.

2-[5-Methyl-2-(4-trifluoromethyl-phenyl)-oxazol-4-yl]-ethanol

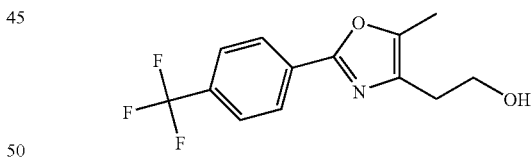

MS (EI) 272 (M+H)+.

Toluene-4-sulfonic acid 2-[5-methyl-2-(4-trifluoromethyl-phenyl)-oxazol-4-yl]-ethyl ester

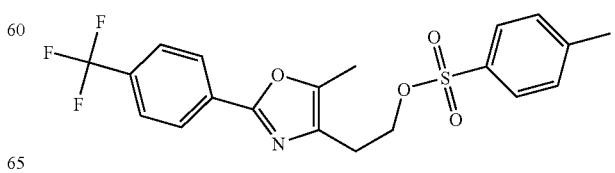

MS (EI) 426 (M+H)+; mp 110.2° C.

2-[2-(4-Butoxy-phenyl)-5-methyl-oxazol-4-yl]-ethanol

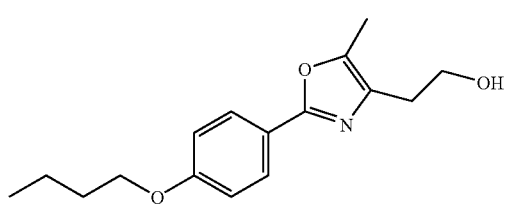

MS (EI) 276 (M+H)$^+$.

Toluene-4-sulfonic acid 2-[2-(4-butoxy-phenyl)-5-methyl-oxazol-4-yl]-ethyl ester

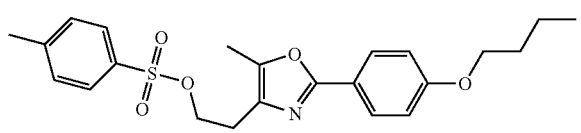

MS (EI) 430 (M+H)$^+$; mp 84.9° C.

2-(2-Bromophenyl-5-methyl-oxazol-4-yl)-ethanol

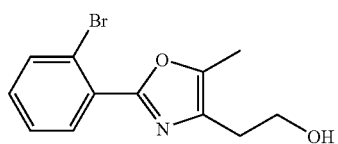

MS (EI) 282.1 (M+H)$^+$.

Toluene-4-sulfonic acid 2-(2-bromophenyl-5-methyl-oxazol-4-yl)ethyl ester

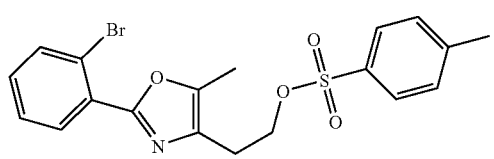

MS (EI) 438.1 (M+H)$^+$.

Preparation 4

Toluene-4-sulfonic acid 2-[2-(6-chloro-pyridn-3-yl)-5-methyl-oxaxol-4-yl]-ethyl ester

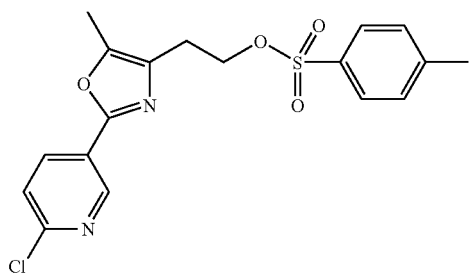

Step A: 3-[2-(6-Chloro-pyridin-3-yl)-5-methyl-oxazole-4-yl]-acetic acid methyl ester

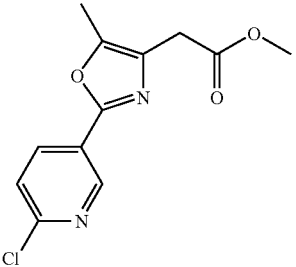

According to Preparation 3, Steps A to C, 6-chloronicotinic acid was converted into the title compound. MS (ESI) m/z 267 (M+H)$^+$.

Step B: 3-[2-(6-Chloro-pyridin-3-yl)-5-methyl-oxazole-4-yl]-ethanol

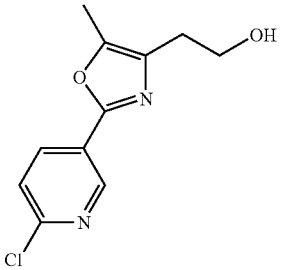

A solution of 3-[2-(6-chloro-pyridin-3-yl)-5-methyl-oxazole-4-yl]-acetic acid methyl ester (500 mg, 1.88 mmol) in THF (20 mL) at 0° C. was treated LAH (90 mg, 2.3 mmol). The reaction mixture was stirred for 1 h and was quenched with water (0.1 mL), 15% NaOH (0.1 mL), and water (0.3 mL). The mixture was filtered through Celite and concentrated to give the title alcohol which as used in the next step without further purification. MS (ESI) m/z 239 (M+H)$^+$.

Step C: Toluene-4-sulfonic acid 2-[2-(6-chloro-pyridn-3-yl)-5-methyl-oxaxol-4-yl]-ethyl ester A solution of crude 3-[2-(6-chloro-pyridin-3-yl)-5-methyl-oxazole-4-yl]-ethanol (1.88 mmol max) in CH$_2$Cl$_2$ (10 mL) was treated with para-toluenesulfonyl chloride (0.4 g, 2.3 mmol), DMAP (40 mg), and triethylamine (0.4 mL, 2.82 mmol). The reaction mixture was stirred at ambient temperature overnight and was diluted with CH$_2$Cl$_2$ (20 mL). The mixture was washed with water, and the organic layer was dried (MgSO$_4$), filtered, and concentrated. The crude product was purified by silica gel chromatography (hexanes/EtOAc 10/1 to 2/1) to afford the title compound (295 mg, 40% over two steps). MS (ESI) m/z 393 (M+H)$^+$.

Preparation 5

Toluene-4-sulfonic acid 2-{5-methyl-2-[4-(methyl-phenyl-amino)-phenyl]-oxazol-4-yl}-ethyl ester

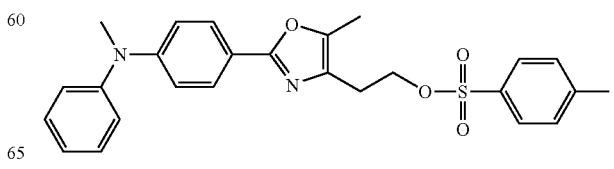

Step A: 4-(2-Benzyloxy-ethyl)-2-(4-bromo-phenyl)-5-methyl-oxazole

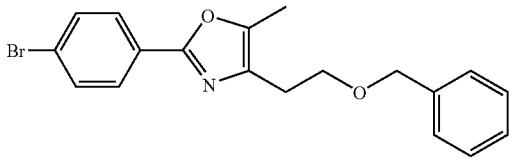

A solution of 2-[2-(4-bromo-phenyl)-5-methyl-oxazol-4-yl]-ethanol (3.17 g, 11.2 mmol) in DMF (25 mL) was treated with NaH (0.67 g, 60% oil dispersion) at 0° C. and stirred for 5 min. Benzyl bromide (2.90 g, 16.9 mmol) was added, and the resulting mixture was stirred at room temperature for 3 h. The reaction was quenched with water, and the mixture was extracted with EtOAc (2×150 mL). The combined organics were dried ($Na_2SO_4$), concentrated, and purified by silica gel chromatography column (10% EtOAc/hexanes) to yield the title compound as an oil (2.50 g, 60%).

Step B: {4-[4-(2-Benzyloxy-ethyl)-5-methyl-oxazol-2-yl]-phenyl}-methyl-phenyl-amine

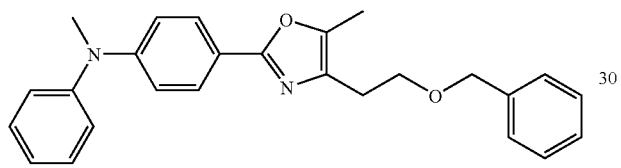

A solution of 4-(2-benzyloxy-ethyl)-2-(4-bromo-phenyl)-5-methyl-oxazole (200 mg, 0.538 mmol) in toluene (5.0 mL) in a seal tube under nitrogen gas flow was treated with Pd(OAc)$_2$ (50 mg), 2-(di-t-butylphosphino)biphenyl (20 mg), N-methyl aniline (115 mg, 1.08 mmol), and sodium t-butoxide (104 mg, 1.08 mmol). The tube was sealed and heated at 105° C. for 14 h. The mixture was cooled and purified directly by silica gel column chromatography (30-50% EtOAc/hexanes) to yield the title compound (195 mg, 91%). MS (ESI) m/z 399.3 (M+H)$^+$.

Step C: 2-{5-Methyl-2-[4-(methyl-phenyl-amino)-phenyl]-oxazol-4-yl}-ethanol

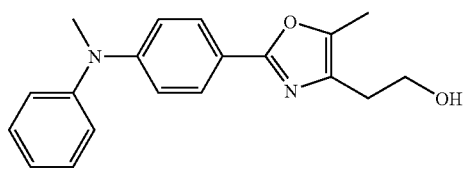

A solution of {4-[4-(2-benzyloxy-ethyl)-5-methyl-oxazol-2-yl]-phenyl}-methyl-phenyl-amine (195 mg, 0.490 mmol) in THF (2 mL) and EtOH (10 mL) was treated a slurry of Pd/C (200 mg) in EtOH (2 mL). The resulting mixture was treated with hydrogen under balloon pressure for 14 h and filtered through a pad of Celite. The filtrate was concentrated, and crude product was purified by silica gel chromatography column (50% EtOAc/hexanes) to yield the title compound (91 mg, 60%).

Step D: Toluene-4-sulfonic acid 2-{5-methyl-2-[4-(methyl-phenyl-amino)-phenyl]-oxazol-4-yl}-ethyl ester A solution of 2-{5-methyl-2-[4-(methyl-phenyl-amino)-phenyl]-oxazol-4-yl}-ethanol (91 mg, 0.30 mmol) in $CH_2Cl_2$ (4.0 mL) was treated with para-toluenesulfonyl chloride (68 mg, 0.36 mmol), triethyl amine (0.20 mL) and a few crystals of DMAP. The resulting mixture was stirred at room temperature for 14 h and was quenched with water (0.2 mL). The mixture was purified directly by silica gel column chromatography (40% EtOAc/hexanes) to yield the title compound (120 mg, 83%). MS (ESI) m/z 463.1 (M+H)$^+$.

The following intermediate compounds are prepared by a substantially similar manner as described in Preparation 5.

Toluene-4-sulfonic acid 2-[5-methyl-2-(4-phenylamino-phenyl)-oxazol-4-yl]-ethyl ester

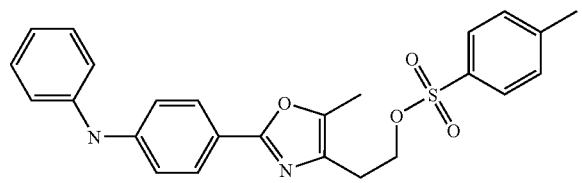

MS (ESI) m/z 449.1 (M+H)$^+$.

Toluene-4-sulfonic acid 2-[5-methyl-2-(4-morpholin-4-yl-phenyl)-oxazol-4-yl]-ethyl ester

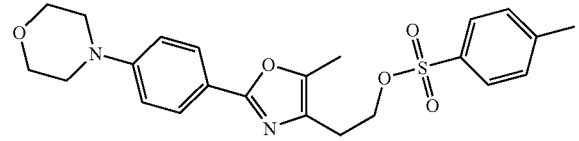

MS (ESI) m/z 443.1 (M+H)$^+$.

Preparation 6

Toluene-4-sulfonic acid 2-[5-methyl-2-(4-phenoxy-phenyl)-oxazol-4-yl]-ethyl ester

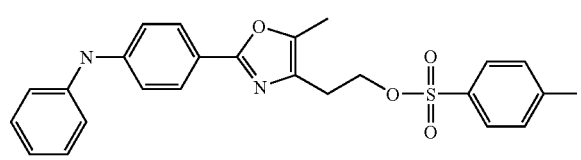

Step A: 4-(2-Benzyloxy-ethyl)-5-methyl-2-(4-phenoxy-phenyl)-oxazole

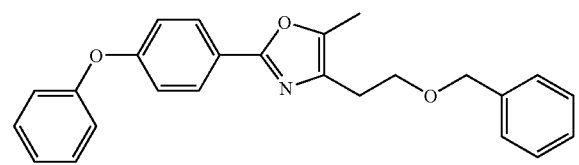

A mixture of 4-(2-benzyloxy-ethyl)-2-(4-bromo-phenyl)-5-methyl-oxazole (0.025 mol, 9.2 g), phenol (0.03 mol, 2.8 g), K$_3$PO$_4$ (0.05 mol, 10.6 g), 2-(di-tert-butylphosphino)biphenyl (1.8 mmol, 0.54 g) and Pd(OAc)$_2$ (1.2 mmol, 0.28 g) in toluene (350 mL) was degassed with nitrogen and heated at 100° C. for 18 h. Additional Pd(OAc)$_2$ (0.5 g) and phosphine ligand (1.0 g) were added, and the mixture was heated 5 h at 100° C. The reaction was concentrated and purified directly by silica gel chromatography (4/1 hexanes/ethyl acetate) to give the title compound (7.6 g).

Step B: Toluene-4-sulfonic acid 2-[5-methyl-2-(4-phenoxy-phenyl)-oxazol-4-yl]-ethyl ester According to Preparation 5, Steps C to D, 4-(2-benzyloxy-ethyl)-5-methyl-2-(4-phenoxy-phenyl)-oxazole was converted into the title compound. $^1$HNMR (400 MHz, CDCl$_3$) δ 7.81 (d, 2H, J=9.1 Hz), 7.67 (d, 21, J=8.2 Hz), 7.37 (t, 2H, J=8.2 Hz), 7.15 (m, 3H), 7.12 (m, 4H), 4.39 (t, 2H, J=6.4 Hz), 2.81 (t, 2H, 6.4 Hz), 2.30 (s, 3H), 2.25 (s, 3H).

Preparation 7

4-Methyl-3-nitro-benzenesulfonic acid 2-[5-methyl-2-(4-nitro-phenyl)-oxazol-4-yl]-ethyl ester

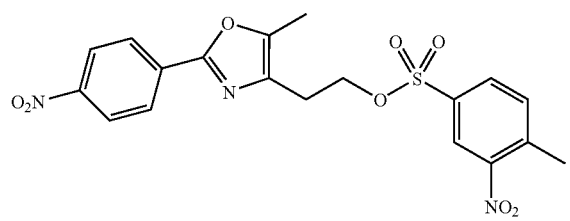

A mixture of potassium nitrate (3.0 g, 30 mmol, 2.7 equiv) and sulfuric acid (10 mL, 18 g, 94 mmol, 17 equiv) was cooled to 0° C. Toluene-4-sulfonic acid 2-(5-methyl-2-phenyl-oxazol-4-yl)-ethyl ester (4.00 g, 11.2 mmol, 1 equiv) was added and the ice bath was removed. The reaction mixture was heated with a heat gun until the tosylate dissolved. After 30 min, the solution was poured into H$_2$O (100 mL) and extracted with EtOAc (100 mL). The organic layer was dried (Na$_2$SO$_4$) and concentrated (75° C.) to an orange oil (4.41 g). The crude product was purified by silica gel flash chromatography (30-50% EtOAc/hexanes) to give the title compound as a yellow solid (3.64 g, 73%). MS (ESI) m/z 447 (M+H)$^+$.

Preparation 8

Toluene-4-sulfonic acid 2-(5-methoxy-2-phenyl-oxazol-4-yl)-ethyl ester

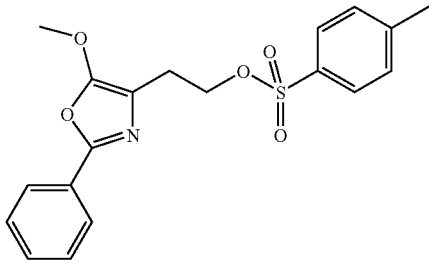

Step A: 2-Benzoylamino-succinic acid dimethyl ester

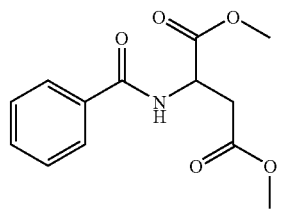

A mixture of benzoyl chloride (3.20 mL, 27.7 mmol), L-aspartic acid dimethyl ester (5.0 g, 25.2 mmol) and triethyl amine (5.3 mL, 38 mmol) in CH$_2$Cl$_2$ (50 mL) was stirred at ambient temperature for 2 h and diluted with water. The organic layer was dried (MgSO$_4$), filtered, and concentrated. The residue was purified by silica gel chromatography (hexanes/EtOAc 1/1) to afford a white solid (5.3 g, 79%). MS (ESI) m/z 266 (M+H)$^+$.

Step B: 3-(5-Methoxy-2-phenyl-oxazol-4-yl)-acetic acid methyl ester

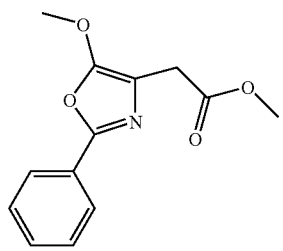

A mixture of 2-benzoylamino-succinic acid dimethyl ester (5.3 g, 20 mmol) in 1,2-dichloroethane (15 mL) was treated with P$_2$O$_5$ (5.3 g, 30 mmol) and Celite (3.2 g) and was heated at 85° C. for 2 h. The solvent was decanted and concentrated. The residue was dissolved in CH$_2$Cl$_2$ and washed with saturated aqueous NaHCO$_3$. The organic layer was dried (MgSO$_4$), filtered, and concentrated. The residue was purified by silica gel chromatography (hexanes/EtOAc 10/1 to 3/1) to afford the title compound (2.9 g, 59%). MS (ESI) m/z 247 (M+H)$^+$.

Step C: 3-(5-Methoxy-2-phenyl-oxazol-4-yl)-ethanol

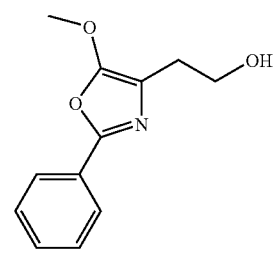

A suspension of LAH (0.56 g, 14.1 mmol) in THF (100 mL) at −78° C. was treated dropwise with a solution of 3-(5-methoxy-2-phenyl-oxazol-4-yl)-acetic acid methyl ester (2.9 g, 11.7 mmol) in THF (100 mL). After the addition was completed, the reaction mixture was warmed up to ambient temperature, cooled to −20° C., and quenched with H$_2$O (0.8 mL), 15% NaOH (0.8 mL), and H$_2$O (2.4 mL). The mixture was filtered through Celite and concentrated to the title compound as an oil. MS (ESI) m/z 220.3 (M+H)$^+$.

Step D: Toluene-4-sulfonic acid 2-(5-methoxy-2-phenyl-oxazol-4-yl)-ethyl ester

A solution of crude 3-(5-methoxy-2-phenyl-oxazol-4-yl)-ethanol (11.7 mmol max) in CH$_2$Cl$_2$ (100 mL) was treated with para-toluenesulfonyl chloride (2.7 g, 14.0 mmol), DMAP (100 mg), and triethylamine (2.5 mL, 17.6 mmol). The reaction mixture was stirred at ambient temperature for 16 h and was washed with water. The organic layer was dried (MgSO$_4$), filtered, and concentrated. The residue was purified by silica gel chromatography (hexanes/EtOAc, 10/1 to 1/1) to afford the title compound (2.0 g, 46% over two steps). MS (ESI) m/z 374 (M+H)$^+$.

The following intermediate compounds are prepared by a substantially similar manner as described in Preparation 8.

2-(2-Biphenyl-4-yl-5-methoxy-oxazol-4-yl)-ethanol

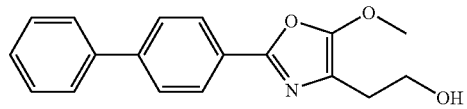

MS (ESI) m/z 296.0 (M+H)$^+$.

Toluene-4-sulfonic acid 2-(2-biphenyl-4-yl-5-methoxy-oxazol-4-yl)-ethyl ester

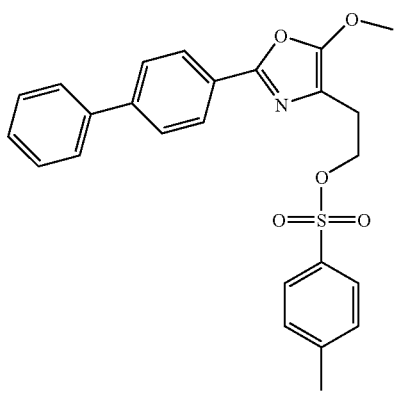

MS (ESI) m/z 450.1 (M+H)$^+$.

Preparation 9

Toluene-4-sulponic acid 2-[5-methyl-2-(6-phenyl-pyridin-3-yl)thiazol-4-yl]ethyl ester

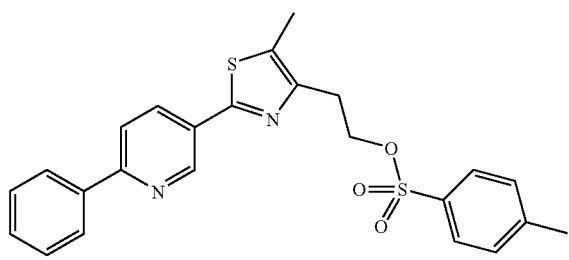

Step A: 2-Phenyl-5-cyanopyridine

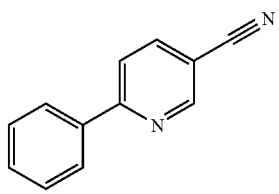

5-Cyano-2-chloropyridine (5.0 g, 36.1 mmol), phenylboronic acid (6.6 g, 54 mmol), tetrakis(triphenylphosphine) palladium (0) (0.5 g), and aqueous Na$_2$CO$_3$ (7.6 g), in toluene (100 mL) were heated at 90° C. for 16 h. The mixture was diluted with EtOAc and washed with H$_2$O. The organic layer was dried (MgSO$_4$), filtered, and concentrated. The residue was purified by silica gel chromatography (hexanes/EtOAc 2/1) to afford the title compound (6.1 g, 94%). MS (ESI) m/z 181 (M+H)$^+$.

Step B

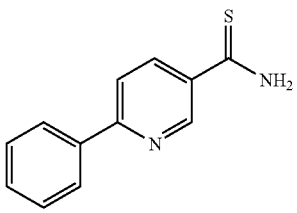

A mixture of 2-phenyl-5-cyanopyridine (6.0 g, 33 mmol) and thioacetamide (4.0 g, 53 mmol) in 4N HCl in 1,4-dioxane (50 mL) was heated at 98° C. for 20 h. The reaction mixture was cooled and poured into aqueous saturated NaHCO$_3$. The precipitate was collected, washed with water, and dried under vacuum (60° C.) to afford the title compound as a yellow solid (7.0 g, 99%).

Step C: [5-Methyl-2-(6-phenyl-pyridin-3-yl)-thiazol-4-yl]-acetic acid methyl ester

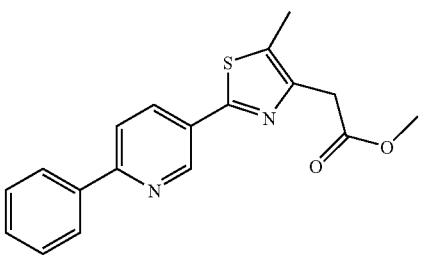

A mixture of 6-phenyl-thionicotinamide (7.0 g) and 4-bromo-3-oxo-pentanoic acid methyl ester (9.15 g, 35 mmol) in 1,4-dioxane (30 mL) was heated at reflux for 4 h. The reaction mixture was cooled, poured into aqueous saturated NaHCO$_3$, and extracted with CH$_2$Cl$_2$. The organic layer was dried (MgSO$_4$), filtered, and concentrated. The residue was purified by silica gel chromatography (hexanes/EtOAc, 2/1) to afford the title compound (6.0 g, 56%). MS (ESI) m/z 325 (M+H)$^+$.

Step D: [5-Methyl-2-(6-phenyl-pyridin-3-yl)-thiazol-4-yl]-ethanol

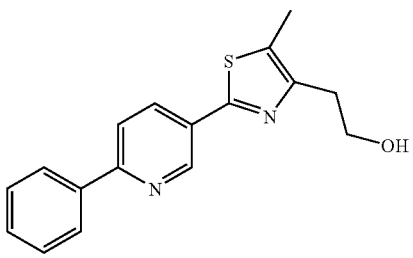

A solution of [5-methyl-2-(6-phenyl-pyridin-3-yl)-thiazol-4-yl]-acetic acid methyl ester (6.0 g, 18.5 mmol) in THF (500 mL) was added dropwise to a suspension of LAH (0.90 g, 22.2 mmol) in THF (300 mL) at −78° C. After the addition was completed, the reaction mixture was allowed to warm to ambient temperature, cooled to −20° C., and quenched sequentially with $H_2O$ (1.1 mL), 15% NaOH (1.1 mL), and $H_2O$ (3.3 mL). The mixture was filtered through Celite, and the filtrated was concentrated to give the title compound as an oil that was used directly in the next step.

Step E: Toluene-4-sulponic acid 2-[5-methyl-2-(6-phenyl-pyridin-3-yl)thiazol-4-yl]ethyl ester A mixture of [5-methyl-2-(6-phenyl-pyridin-3-yl)-thiazol-4-yl]-ethanol (18.5 mmol max), para-toluenesulfonyl chloride (3.89 g, 20.5 mmol), DMAP (500 mg), and triethylamine (4.0 mL, 28.0 mmol) in $CH_2Cl_2$ (300 mL) was stirred at ambient temperature for 2.5 h. The reaction mixture was diluted with water, and the organic layer was separated, dried ($MgSO_4$), filtered, and concentrated. The residue was purified by silica gel chromatography (hexanes/EtOAc, 10/1 to 1/1) to afford the title compound as a solid (2.0 g, 46% over two steps). MS (ESI) m/z 451 (M+H)$^+$.

The following intermediate compounds are prepared by a substantially similar manner as described in Preparation 9.

2-[5-Methyl-2-(5-phenyl-pyridin-3-yl)-thiazol-4-yl]-ethanol

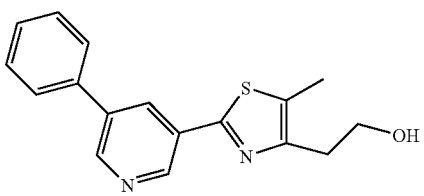

MS (ESI) m/z 297 (M+H)$^+$.

Toluene-4-sulfonic acid 2-[5-methyl-2-(5-phenyl-pyridin-3-yl)thiazol-4-yl]ethyl ester

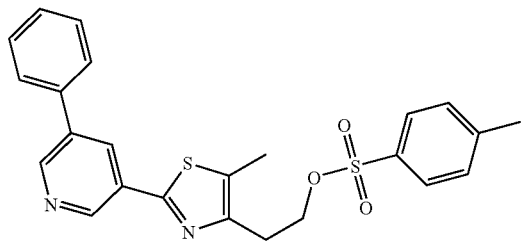

MS (ESI) m/z 451 (M+H)$^+$.

Toluene-4-sulfonic acid 2-[5-methyl-2-(6-phenoxy-pyridin-3-yl)-thiazol-4-yl]-ethyl ester

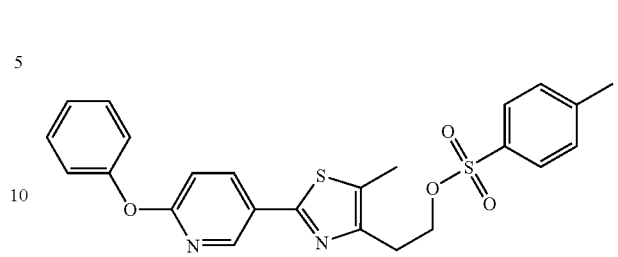

$^1$HNMR 400 MHz (CDCl$_3$) δ8.52 (2, 1H), 8.03 (d, 1H, J=6.9 Hz), 7.63 (d, 2H, J=8.6 Hz), 7.42 (t, 2H, J=7.7 Hz), 7.2 (m, 5H), 6.91 (1H, d, J=7.7 Hz), 4.37 (t, 2H, J=6.3 Hz), 3.02 (t, 2H, J=6.3 Hz), 2.39 (s, 3H), 2.28 (s, 3H).

Toluene-4-sulfonic acid 2-[5-methyl-2-(6-morpholin-4-yl-pyridin-3-yl)-thiazol-4-yl]-ethyl ester

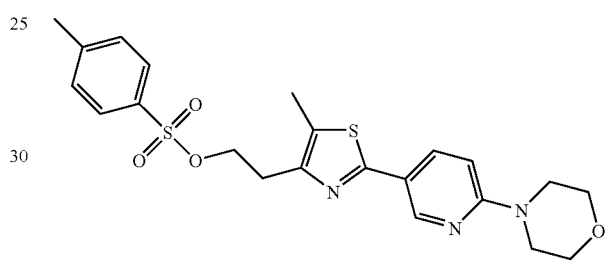

$^1$HNMR 400 MHz (CDCl$_3$) δ8.51 (s, 1H), 7.82 (d, 1H, J=8.5 Hz), 7.63 (d, 2H, J=7.8 Hz), 7.19 (d, 2 h, J=7.8 Hz), 6.61 (d, 1H, J=8.5 Hz), 4.37 (t, 2H, J=6.5 Hz), 3.82 (t, 2H, J=5.2 Hz), 3.58 (t, 2H, J=5.2 Hz), 2.99 (t, 2H, J=6.5 Hz), 2.35 (s, 3H), 2.27 (s, 3H).

4-{5-Methyl-4-[2-(toluene-4-sulfonyloxy)-ethyl]-thiazol-2-yl}-piperazine-1-carboxylic acid tert-butyl ester

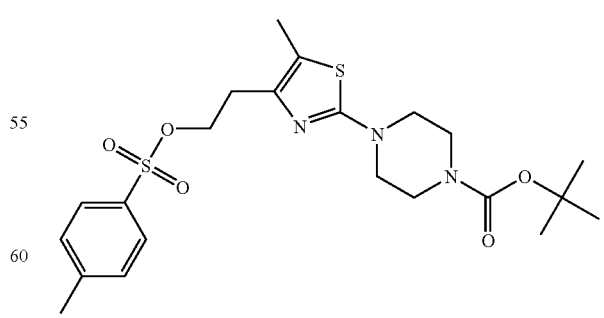

MS (ESI) m/z 482 (M+H)$^+$.

115

Toluene-4-sulfonic acid 2-[5-methyl-2-(4-methyl-piperazin-1-yl)-thiazol-4-yl]-ethyl ester

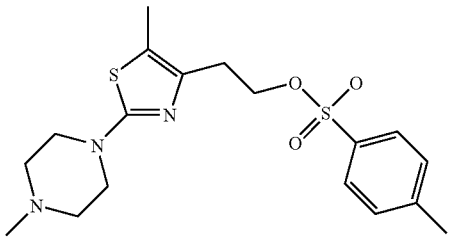

MS (ESI) m/z 396.1 (M+H)$^+$.

Toluene-4-sulfonic acid 2-[5-methyl-2-(4-phenyl-piperazin-1-yl)-thiazol-4-yl]-ethyl ester

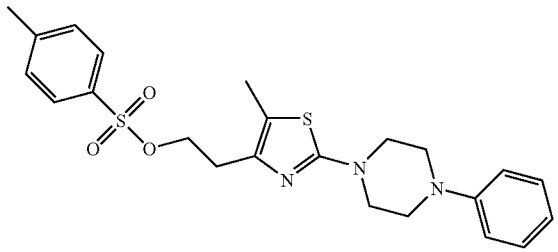

MS (ESI) m/z 458.1 (M+H)$^+$.

2-(5-Methyl-2-phenyl-thiazol-4-yl)-ethanol

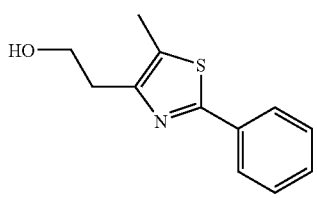

MS (ESI) m/z 220 (M+H)$^+$.

Toluene-4-sulfonic acid 2-(5-methyl-2-phenyl-thiazol-4-yl)-ethyl ester

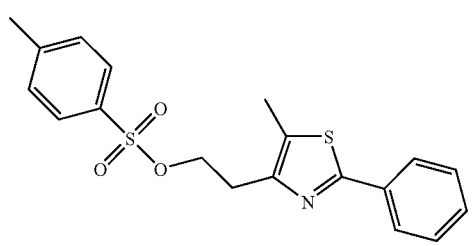

MS (ESI) m/z 374 (M+H)$^+$.

116

2-(2-Biphenyl-4-yl-5-methyl-thiazol-4-yl)-ethanol

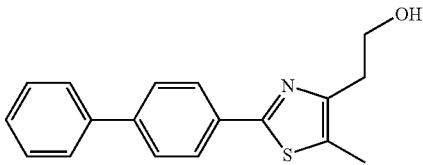

MS (ESI) m/z 296 (M+H)$^+$.

Toluene-4-sulfonic acid 2-(2-biphenyl-4-yl-5-methyl-thiazol-4-yl)-ethyl ester

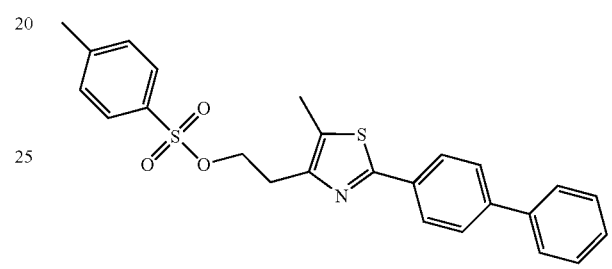

MS (ESI) m/z 450 (M+H)$^+$.

Toluene-4-sulfonic acid 2-(5-methyl-2-pyridin-2-ylthiazol-4-yl)ethyl ester

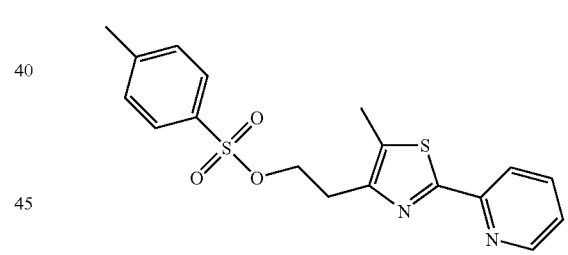

MS (ESI) m/z 375.1 (M+H)$^+$.

Toluene-4-sulfonic acid 2-(5-methyl-2-pyridin-3-ylthiazol-4-yl)ethyl ester

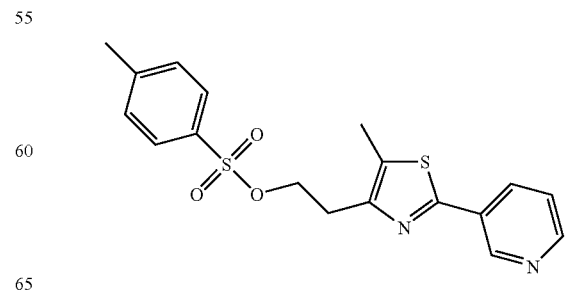

MS (ESI) m/z 375.1 (M+H)$^+$.

Toluene-4-sulfonic acid 2-(5-methyl-2-pyridin-4-ylthiazol-4-yl)ethyl ester

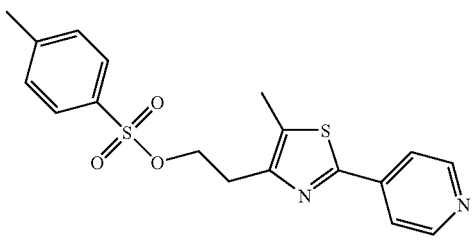

MS (ESI) m/z 375 (M+H)⁺, MS (ESI) m/z 383.1 (M+H)⁺.

Toluene-4-sulfonic acid 2-[2-(2-methoxyethylamino)-5-methylthiazol-4-yl]ethyl ester

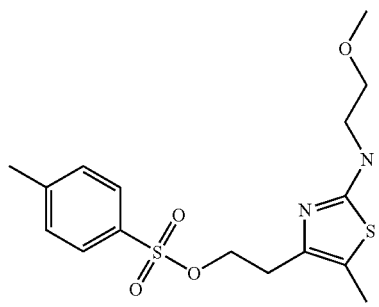

MS (ESI) m/z 371 (M+H)⁺.

Pyrazoles

Preparation 10

Toluene-4-sulfonic acid 2-(5-methyl-3-phenyl-pyrazol-1-yl)-ethyl ester

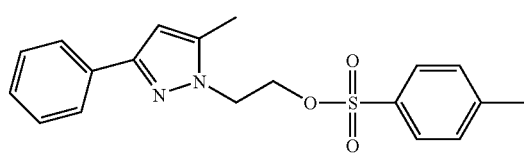

Step A: 5-Methyl-3-phenyl-1H-pyrazole

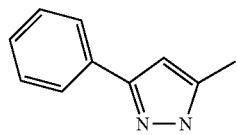

Hydrazine hydrate (9.0 mL, 99 mmol, 35 wt. % in H₂O; 0.64 equiv) was added to a solution of benzoylacetone (25.00 g, 154.1 mmol, 1 equiv) in ethanol (250 mL). After stirring 14 h, more hydrazine hydrate (8.0 mL, 88 mmol, 0.57 equiv) was added. After 2 h, the reaction solution was concentrated (95° C.) to give the title compound as a white solid (24.31 g, 99.7%). HRMS Calculated for $C_{10}H_{11}N_2$: m/z 159.0922. Found: 159.0917.

Step B: 2-(5-Methyl-3-phenyl-pyrazol-1-yl)-ethanol

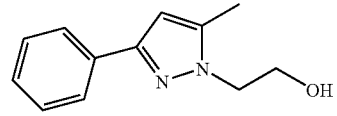

Sodium hydride (2.5 g, 1.5 g NaH, 62 mmol, 1.1 equiv) was added over a period of 3 min to a solution of 5-methyl-3-phenyl-1H-pyrazole (9.00 g, 56.9 mmol, 1 equiv) in DMF (90 mL) cooled to 0° C. in an ice bath. After stirring 15 min, ethylene carbonate (7.6 mL, 10 g, 110 mmol, 2.0 equiv) was added. The bath was removed, and the reaction mixture was stirred for 15 h. The mixture was treated with 4 M aq $K_2CO_3$ (90 mL), heated at reflux for 5 h, and diluted with $H_2O$ (200 mL). After allowing the hot mixture to cool for 15 min, more $H_2O$ (100 mL) and then hexanes (100 mL) were added. The mixture was shaken vigorously and then allowed to separate. Crystals formed and stayed with the top organic layer. The aqueous layer was separated, and the crystals were collected by vacuum filtration and washed with hexanes (2×50 mL). The crystals were dissolved in Et₂O/EtOAc (1:1; 200 mL), and the solution was dried (Na₂SO₄), filtered, and concentrated (75° C.) to give the title compound as an off-white crystalline solid (6.86 g, 59.6%). HRMS Calculated for $C_{12}H_{15}N_2O$: m/z 203.1184. Found: 203.1168.

Step C: Toluene-4-sulfonic acid 2-(5-methyl-3-phenyl-pyrazol-1-yl)-ethyl ester

According to Preparation 9, Step E, 2-(5-methyl-3-phenyl-pyrazol-1-yl)-ethanol was converted into the title compound. MS (ESI) m/z 357 (M+H)⁺.

Preparation 11

2-(3-Biphenyl-4-yl-5-methyl-pyrazol-1-yl)-ethanol

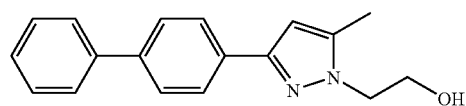

Step A: 5-Biphenyl-4-yl-3-methyl-1H-pyrazole

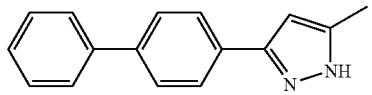

To a stirred mixture of NaH (1.98 g, 0.049 mol, 60% oil dispersion) in dry THF (30 mL) was added a suspension of diethoxyphosphorylacetone tosyl hydrazone (8.97 g, 0.024 mol; N Almirante *Syn. Lett.* 1999, 302.) in a mixture of THF (35 mL) and DMF (5.0 mL) dropwise over 15 min. The yellow suspension was stirred at 0-5° C. for 30 min and was treated with a 4-biphenyl carboxaldehyde (3.10 g, 0.0169 mol) in dry THF (30 mL) at 0-5° C. over 15 min. The orange solution was heated and stirred at reflux for 4 h and stirred at ambient temperature overnight. The mixture was poured into 5% aq. NaH₂PO₄ (350 mL) and extracted with EtOAc (2×200 mL). The organic layers were combined, washed with brine, dried (MgSO₄), filtered, and concentrated to a yellow semi-solid. This material was triturated with hot EtOAc (20 mL) and filtered. The solid was washed with EtOAc (2×10 mL) and dried under high vacuum to give the title compound (2.61 g, 47%): HRMS Calculated for $C_{16}H_{15}N_2$: m/z 235.1235. Found: 235.1230.

Step B: 2-(3-Biphenyl-4-yl-5-methyl-pyrazol-1-yl)-ethanol

The title compound was prepared from 5-biphenyl-4-yl-3-methyl-1H-pyrazole according to the Preparation 10, Step B. HRMS Calculated for $C_{18}H_{19}N_2O$: m/z 279.1497. Found: 279.1496.

The following intermediate compounds are prepared by a substantially similar manner as described in Preparations 10 and 11.

2-[3-(4-Bromo-phenyl)-5-methyl-pyrazol-1-yl]-ethanol

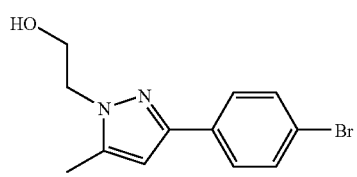

HRMS Calculated for $C_{12}H_{14}BrN_2O$: m/z 281.0289. Found: 281.0288.

3-Methyl-5-naphthalen-2-yl-1H-pyrazole

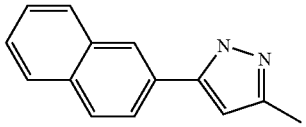

HRMS Calculated for $C_{14}H_{12}N_2$: m/z 208.1001. Found: 208.0981.

2-(5-Methyl-3-naphthalen-2-yl-pyrazol-1-yl)-ethanol

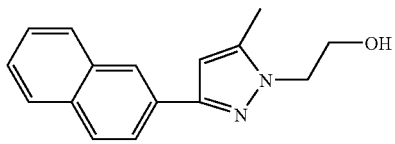

HRMS Calculated for $C_{16}H_{17}N_2O$: m/z 253.1341. Found: 253.1339.

3-Methyl-5-naphthalen-1-yl-1H-pyrazole

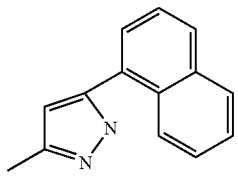

Anal Calculated for $C_{14}H_{12}N_2$: C, 80.74; H, 5.81; N, 13.45. Found: C, 80.93; H, 5.70; N, 13.42. mp 115-117° C.

2-(5-Methyl-3-naphthalen-1-yl-pyrazol-1-yl)-ethanol

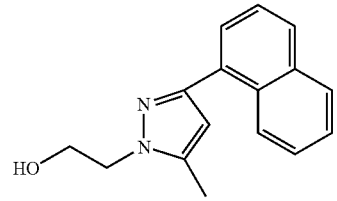

Arylether Bromide Preparations

Preparation 12

2-(2-Bromo-ethoxy)-6-methoxynaphthalene

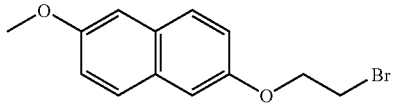

To a solution of 6-methoxynaphthalen-2-ol (1.07 g, 6.14 mmol) in DMF (4 mL) were added cesium carbonate (3.11 g, 9.55 mmol) and dibromoethane (2.5 mL, 29 mmol). The mixture was stirred and heated at 55° C. for 48 h. The reaction mixture was cooled, filtered, diluted with EtOAc, and washed with brine (2×30 mL). The organic layer was dried ($Na_2SO_4$) and concentrated. The crude product was purified using radial chromatography (2:98 to 25:75 EtOAc: Hex) to give the title compound as a white solid (0.52 g, 30%): $^1$H NMR (400 MHz, $CDCl_3$) δ 3.61 (t, J=6.1 Hz, 2H), 3.82 (s, 3H), 4.30 (t, J=6.4 Hz, 2H), 7.01-7.08 (m, 4H), 7.56 (dd, J=12.0, 9.0 Hz, 2H).

The following intermediate compounds are prepared by a substantially similar manner as described in Preparation 12.

6-(2-Bromoethoxy)-3-phenylbenzofuran

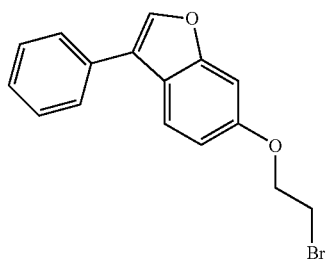

The above compound is prepared from 3-phenylbenzofuran-6-ol (see *Bull. Soc. Chim. Fr.,* 942 (1962)). $^1$H NMR (400 MHz, $CDCl_3$) δ 3.60 (t, J=6.4 Hz, 2H), 4.28 (t, J=6.4 Hz, 2H), 6.88 (dd, J=8.8, 2.4 Hz, 1H), 7.00 (d, J=2.4 Hz, 1H), 7.26-7.30 (m, 1H), 7.36-7.44 (m, 2H), 7.52-7.56 (m, 2H), 7.63 (d, J=9.8 Hz, 2H).

4-(2-Bromoethoxy)-1-phenoxybenzene

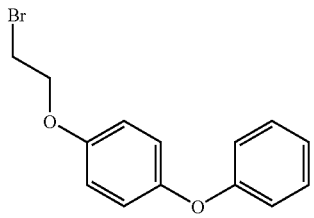

$^1$H NMR (400 MHz, CDCl$_3$) δ 3.55 (t, J=6.4 Hz, 2H), 4.19 (t, J=6.1 Hz, 2H), 6.80-6.90 (m, 6H), 6.96 (t, J=7.3 Hz, 1H), 7.17-7.24 (m, 2H).

4-(3-Bromoethoxy)biphenyl: MS (ESI) m/z 295 (M+NH$_3$)$^+$.

3-(2-Bromoethoxy)biphenyl: $^1$H NMR (400 MHz, CDCl$_3$) δ 3.58 (t, J=6.4 Hz, 2H), 4.27 (t, J=6.4 Hz, 2H), 6.81 (dd, J=8.3, 2.4 Hz, 1H), 6.90 (d, J=8.8 Hz, 1H), 7.13 (dd, J=7.8, 1.0 Hz, 1H), 7.26-7.33 (m, 2H), 7.34-7.37 (m, 2H), 7.43-7.50 (m, 2H).

6-(4-Bromopropoxy)-3-phenylbenzofuran: $^1$H NMR (400 MHz, CDCl$_3$) δ 2.26-2.33 (m, 2H), 3.57 (t, J=6.4 Hz, 2H), 4.11 (t, J=5.9 Hz, 2H), 6.89 (dd, J=8.6, 2.2 Hz, 1H), 7.01 (d, J=2.0 Hz, 1H), 7.29 (t, J=7.6 Hz, 1H), 7.40 (t, J=7.6 Hz, 2H), 7.56 (d, J=6.8 Hz, 2H), 7.57-7.65 (m, 2H).

2-(4-Bromopropoxy)-6-methoxynaphthalene: $^1$H NMR (400 MHz, CDCl$_3$) δ 2.29 (t, J=6.1 Hz, 2H), 3.56 (t, J=6.4 Hz, 2H), 3.81 (4.11 (t, J=5.9 Hz, 2H), 7.01-7.14 (m, 4H), 7.52-7.57 (m, 2H).

3-(4-Bromopropoxy)biphenyl: $^1$H NMR (400 MHz, CDCl$_3$) δ 2.27 (t, J=6.1 Hz, 2H), 3.55 (t, J=6.6 Hz, 2H), 4.09 (t, J=5.9 Hz, 2H), 6.81 (dd, J=2.9, 1.0 Hz, 1H), 7.05 (t, J=2.0 Hz, 1H), 7.07 (t, J=2.0 Hz, 1H), 7.22-7.24 (m, 2H), 7.26-7.37 (m, 2H), 7.43-7.52 (m, 3H).

4-(3-Bromopropoxy)-biphenyl

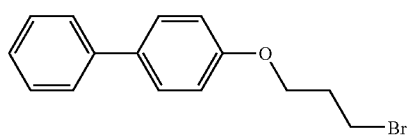

$^1$H-NMR (200.15 MHz, CDCl$_3$): δ7.57-7.29 (m, 7H), 6.98 (dd, 2H, J=6.72, 1.88), 4.15 (t, 2H, J=5.92), 3.62 (t, 2H, J=6.44), 2.34 (qn, 2H, J=5.92).

4-(3-Bromoproxy)-1-phenoxybenzene: $^1$H-NMR (300 MHz, CDCl$_3$): δ 7.3(2H, m), 7.1(2H, m), 7.0(2H, m), 6.9(2H, m), 4.1(2H, m); 3.6(2H, m); 2.3(2H, m).

2-(4-Bromobutoxy)-6-methoxynaphthalene

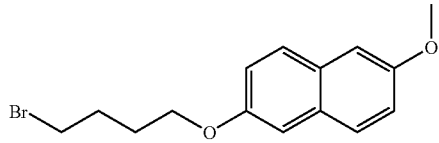

$^1$H NMR (400 MHz, CDCl$_3$) δ1.88-1.97 (m, 2H), 1.99-2.10 (m, 2H), 3.41-3.48 (m, 2H), 3.81 (s, 3H), 4.00 (t, J=5.9 Hz, 2H), 7.00-7.05 (m, 3H), 7.13-7.19 (m, 1H), 7.54 (t, J=8.1 Hz, 2H).

6-(4-Bromobutoxy)-3-phenylbenzofuran

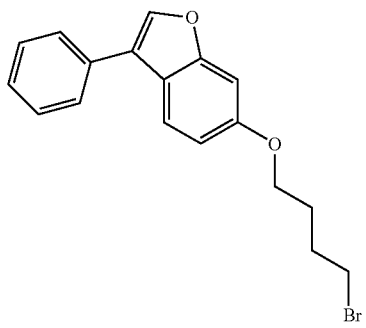

$^1$H NMR (400 MHz, CDCl$_3$) δ 1.90-1.98 (m, 2H), 2.01-2.04 (m, 2H), 3.41-3.44 (m, 2H), 3.94-3.99 (m, 2H), 6.83-6.91 (m, 1H), 6.96-6.97 (m, 1H), 7.27-7.29 (m, 1H), 7.36-7.43 (m, 2H), 7.53-7.62 (m, 4H).

4-(4-Bromobutoxy)biphenyl

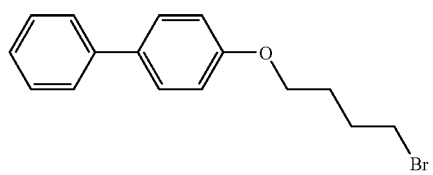

$^1$H NMR (400 MHz, CDCl$_3$) δ 2.03 (t, J=6.8 Hz, 2H), 3.42 (t, J=6.6 Hz, 2H), 3.96 (t, J=6.5 Hz, 2H), 6.87 (d, J=7.8 Hz, 2H), 7.17-7.23 (m, 3H), 7.32 (t, J=7.6 Hz, 1H), 7.42-7.47 (m, 4H).

3-(4-Bromobutoxy)biphenyl

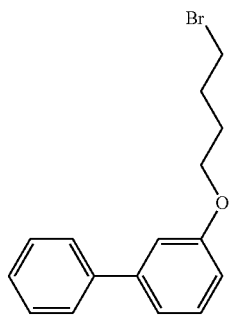

$^1$H NMR (400 MHz, CDCl$_3$) δ 1.86-1.95 (m, 2H), 1.96-2.05 (m, 2H), 2.42 (t, J=6.6 Hz, 2H), 3.98 (t, J=6.1 Hz, 2H), 6.79 (dd, J=7.3, 2.0 Hz, 1H), 7.03-7.11 (m, 1H), 7.26 (t, J=7.8 Hz, 2H), 7.35 (t, J=7.8 Hz, 2H), 7.42-7.51 (m, 2H).

4-(4-Bromobutoxy)-1-phenoxybenzene

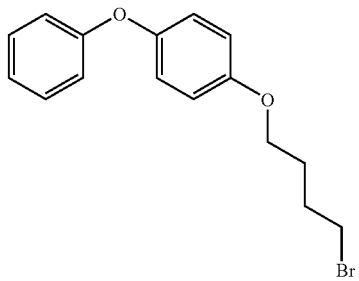

$^1$H NMR (400 MHz, CDCl$_3$) δ 1.83-2.03 (m, 2H), 1.96-2.03 (m, 2H), 3.41 (t, J=6.6 Hz, 2H), 3.90 (t, J=6.5 Hz, 2H), 6.76-6.78 (m, 2H), 6.79-6.90 (m, 4H), 6.94-6.97 (m, 1H), 7.19-7.23 (m, 2H).

Headpiece Preparations

Preparation 13

3-(2-Aminomethyl-4-hydroxy-phenyl)-propionic acid tert-butyl ester

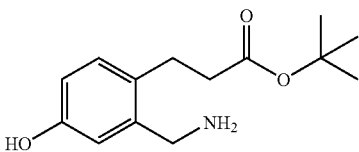

Step A: 2-Bromo-5-hydroxybenzaldehyde

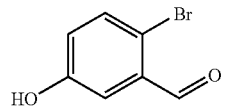

To a suspension of 3-hydroxybenzaldehyde (1 kg, 8.2 mol) in CH$_2$Cl$_2$ (10 L) was added a solution of bromine (1.3 kg, 8.2 mol) in CH$_2$Cl$_2$ (620 mL) over 1 h. After stirring for about 22 h, the solids were isolated by filtration, washed with CH$_2$Cl$_2$ (4 L), and dried under vacuum to afford of 2-bromo-5-hydroxybenzaldehyde as a tan solid (1.05 kg, 63%).

Step B: 3-(2-Formyl-4-hydroxy-phenyl)-acrylic acid tert-butyl ester

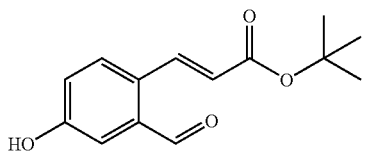

To a solution of 2-bromo-5-hydroxybenzaldehyde (200 g, 1.0 mole) in propionitrile (6 L) under N$_2$ was added tri-o-tolyl phosphine (75.4 g, 0.25 mol) and diisopropylethylamine (350 mL, 260 g, 2.0 mol). The solution was degassed and purged with N$_2$ three times. To this solution was added tert-butylacrylate (440 mL, 385 g, 3.0 mol) and palladium acetate trimer (27.8 g, 0.12 mol). The mixture was degassed three times and heated to 80° C. over 30 min. After 30 min, the reaction was cooled to ambient temperature and filtered. The solids were washed with acetonitrile. The filtrate was transferred to a separatory funnel with acetonitrile (4 L total) and was extracted with hexanes (4×5 L). The propionitrile/acetonitrile layer was concentrated by rotary evaporation. The residue was dissolved in toluene (4 L) and washed successively with 1N HCl (1 L), water (1 L), and brine (1 L). The organic layer was dried (Na$_2$SO$_4$), filtered, and concentrated to afford crude product as a wet brown solid (293 g). The crude product was dissolved in CH$_2$Cl$_2$ (600 mL) with stirring. To this solution was added hexanes (1.8 L) over ~2 h, and the resulting slurry was stirred at ambient temperature for 1 h. The slurry was cooled in an ice water bath and stirred for 1 h. The product was isolated by filtration, washed with hexanes, and dried under vacuum to afford the product as a tan solid (199.5 g, 80.6%).

Step C: 3-[4-Hydroxy-2-(hydroxyimino-methyl)-phenyl]-acrylic acid tert-butyl ester

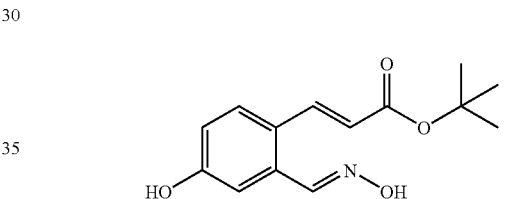

A slurry of hydroxylamine hydrochloride (8.33 g, 0.12 mol), pyridine (9.49 g, 0.12 mol), and ethanol (100 mL) was stirred at ambient temperature for 30 min. 3-(2-Formyl-4-hydroxy-phenyl)-acrylic acid tert-butyl ester (14.90 g, 0.06 mol) was added followed by an ethanol (49 mL) rinse. The resulting brown solution was stirred at ambient temperature for 16 h and concentrated. The residue was suspended in water (150 mL) and extracted with ethyl acetate (3×100 mL). The combined organic layers were washed with saturated NaCl solution (2×100 mL), dried (Na$_2$SO$_4$), and filtered through a plug of silica gel to remove trace polar impurities. The filtrate was concentrated to give crude product (16.04 g). A 13.56 g sample of the crude material was crystallized from heptane (70 mL) and ethyl acetate (80 mL) to the title compound (7.41 g, 55%), mp 146-149° C. $^1$H NMR (CD$_3$OD): δ 1.53 (s, 9H), 4.83 (s, 2H), 6.15-6.23 (d, 1H), 6.82-6.87 (dd, 1H), 7.10-7.12 (d, 1H), 7.52-7.55 (d, 1H), 7.98-8.03 (d, 1H), 8.37 (s, 1H). MS (ES$^+$) m/z 286.1 ([M+Na]$^+$). MS (ES$^-$) m/z 262.2 ([M−H]$^-$). Anal. Calculated for C$_{14}$H$_{17}$NO$_4$: C: 63.8658; H: 6.5081; N: 5.3198. Found: C: 63.71; H: 6.38; N: 5.51.

Step D: 3-(2-Aminomethyl-4-hydroxy-phenyl)-propionic acid tert-butyl ester

A solution of 3-[4-hydroxy-2-(hydroxyimino-methyl)-phenyl]-acrylic acid tert-butyl ester (0.50 g, 1.9 mmol) in ethanol (50 mL) was treated with 10% palladium on carbon (0.25 g). The resulting suspension was treated with hydrogen using a Parr shaker apparatus at ambient temperature and 50 psi for 16 h. The reaction mixture was filtered through Celite, rinsed with ethanol (20 mL), and concentrated. The residue was dissolved in ethyl acetate (50 mL) and washed with 10% $K_2CO_3$ solution (2×25 mL) and 1N NaOH (2×25 mL). The organic layer was dried ($Na_2SO_4$), filtered, and concentrated. The residue was crystallized from isopropyl acetate to give the title compound (0.14 g, 40%), mp 154-157° C. $^1$H NMR ($CD_3OD$): δ 1.37 (s, 9H), 2.44-2.50 (t, 2H), 2.80-2.85 (t, 2H), 3.75 (s, 2H), 4.83 (s, 3H), 6.57-6.63 (dd, 1H), 6.75-6.77 (d, 1H), 6.95-7.00 (d, 1H). MS ($ES^+$) m/z 252.1 ($[M+H]^+$). MS ($ES^-$) m/z 250.2 ($[M-H]^-$). Anal. Calculated for $C_{14}H_{21}NO_3$: C: 66.9069; H: 8.4222; N: 5.5731. Found: C: 66.57; H: 8.29; N: 5.60.

Preparation 14

3-(2-Aminomethyl-4-hydroxy-phenyl)-propionic acid tert-butyl ester Ethandioate (2:1)

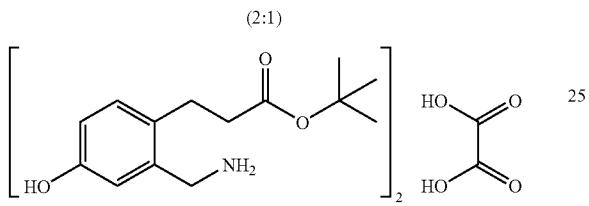

Alternative to the crystallization of 3-(2-Aminomethyl-4-hydroxy-phenyl)-propionic acid tert-butyl ester from isopropyl acetate. The crude tert-butyl-3-[2-(aminomethyl)-4-hydroxyphenyl]propanoate (0.50 g, 0.002 mol) was dissolved in refluxing ethyl acetate (10 mL). A solution of oxalic acid (0.18 g, 0.002 mol) dissolved in ethyl acetate (5 mL) was added and produced a precipitate immediately. The resulting slurry was cooled to 0° C. and filtered. The isolated product was slurred in ethanol (5 mL), cooled to 0° C., and filtered to give 3-(2-aminomethyl-4-hydroxy-phenyl)-propionic acid tert-butyl ester ethandioate (2:1) (0.41 g, 69%). mp 188-190° C. $^1$H NMR (DMSO-$d_6$): δ 1.36 (s, 18H), 2.39-2.45 (t, 4H), 2.47-2.52 (m, 4H), 2.70-2.76 (t, 4H), 3.83 (s, 4H), 6.61-6.65 (dd, 2H), 6.77-6.82 (d, 2H), 6.97-7.01 (d, 2H). MS ($ES^+$) m/z 252.1 ($[M+H]^+$). MS ($ES^-$) m/z 250.2 ($[M-H]^-$). Anal. Calculated for $C_{30}H_{44}N_2O_{10}$: C: 60.80; H: 7.48; N: 4.73. Found: C: 60.79; H: 7.51; N: 4.81.

Preparation 15

3-[2-(tert-Butoxycarbonylamino-methyl)-4-hydroxy-phenyl]-propionic acid methyl ester

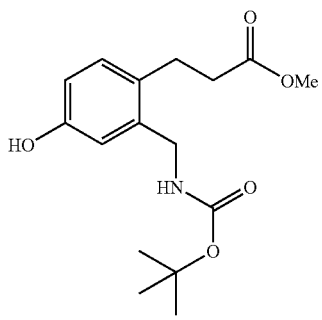

A solution of 3-(2-aminomethyl-4-hydroxy-phenyl)-propionic acid tert-butyl ester (1.00 g, 3.98 mmol) in $CH_2Cl_2$ (10 mL) was treated with water (12 drops) then TFA (10 mL). The solution was stirred at ambient temperature for 6.5 h and concentrated. The residue was diluted with 2,2-dimethoxypropane (40 mL), conc. HCl (4 mL), and then MeOH (10 mL). The solution was stirred for 18 h and concentrated to 3-(2-aminomethyl-4-hydroxy-phenyl)-propionic acid: HCl salt as a tan solid. MS ($ES^-$) m/z 208 [M-1].

The solid was diluted with THF (20 mL) and saturated aq. $NaHCO_3$ solution (12 mL) and was treated with di-tert-butyl dicarbonate (1.09 g, 5.00 mmol). The mixture was stirred for 3 h and concentrated, and the residue was partitioned between EtOAc (75 mL) and 1N HCl (30 ml). The organic layer was dried ($Na_2SO_4$), and concentrated to give the title compound (1.16 g, 94%). MS ($ES^-$) m/z 308 [M-1].

Preparation 16

3-[4-hydroxy-2-(isopropoxycarbonylamino-methyl)-phenyl]-propionic acid tert-butyl ester

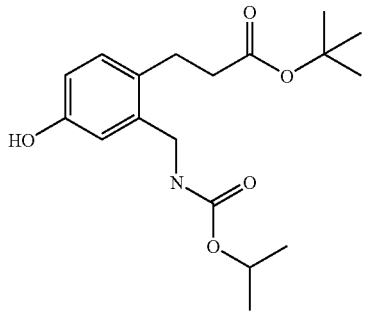

A slurry of 3-(2-aminomethyl-4-hydroxy-phenyl)-propionic acid tert-butyl ester (75.4 g, 0.3 mol) in $CH_2Cl_2$ (900 mL) at 1° C. was treated with triethylamine (60.7 g, 0.6 mol). Isopropyl chloroformate (300 mL, 0.3 mol, 1M in toluene) was added while maintaining the temperature less than 12° C. The resulting solution was stirred 16 h at ambient temperature. After 16 h, additional isopropyl chloroformate (15 mL, 0.015 mol, 1.0M in toluene) was added, and the reaction was stirred for 1 h. The reaction mixture was washed with 1N HCl (2×200 mL) and saturated $NaHCO_3$ solution (2×200 mL). The organic layer was dried ($Na_2SO_4$) and concentrated. The residue was purified by filtration through Merck silica gel 62 (750 grams, $CH_2Cl_2$/MeOH 100/0 to 96/4) to give the title compound (95.48 g, 94.3%). $^1$H NMR (300 MHz, $CDCl_3$): δ 1.20-1.24 (d, 6H), 1.40 (s, 9H), 2.46-2.52 (t, 2H), 2.81-2.86 (t, 2H), 4.29-4.32 (d, 2H), 4.86-4.97 (m, 1H), 5.19-5.28 (m, 1H), 6.67-6.72 (dd, 2H), 6.76 (s, 1H), 6.97-7.00 (d, 1H). MS ($ES^-$) m/z 336.1 $[M-H]^-$.

The following intermediate compounds are prepared by a substantially similar manner as described in Preparation 16.

127

3-[4-Hydroxy-2-(isobutoxycarbonylamino-methyl)-phenyl]-propionic acid tert-butyl ester

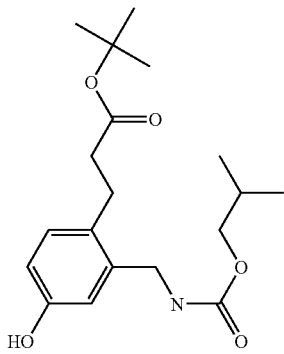

MS (ES⁻) m/z 350 [M–H]⁻.

3-[2-(Cyclopropylmethoxycarbonylamino-methyl)-4-hydroxy-phenyl]-propionic acid tert-butyl ester

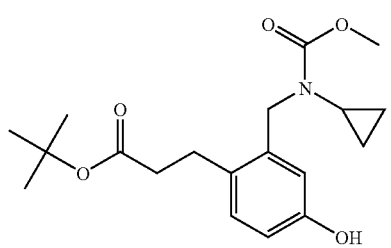

HRMS Calculated for $C_{19}H_{26}NO_5$: m/z 348.1811. Found: 348.1817.

3-[2-(Cyclobutoxycarbonylamino-methyl)-4-hydroxy-phenyl]-propionic acid tert-butyl ester

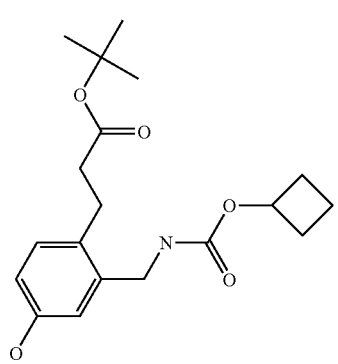

HRMS Calculated for $C_{19}H_{26}NO_5$: m/z 348.1811. Found: 348.1817.

128

3-[2-(Cyclopentyloxycarbonylamino-methyl)-4-hydroxy-phenyl]-propionic acid tert-butyl ester

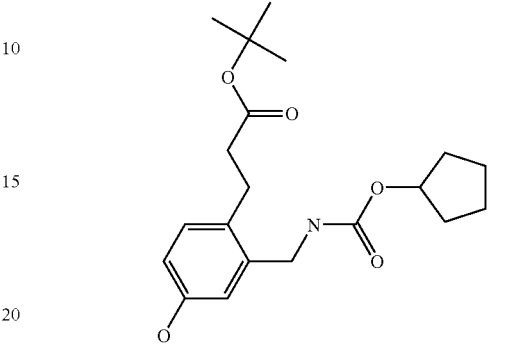

MS (ES⁻) m/z 362 [M–H]⁻.

Preparation 17

3-[4-Hydroxy-2-(isopropoxycarbonylamino-methyl)-phenyl]-propionic acid methyl ester

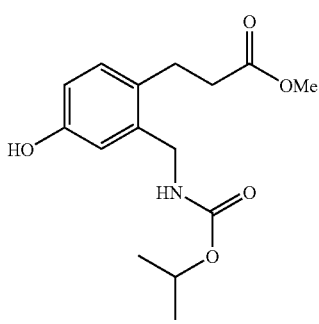

A solution of 3-[4-hydroxy-2-(isopropoxycarbonylamino-methyl)-phenyl]-propionic acid tert-butyl ester (3.0 mmol, 1.0 g) in $CH_2Cl_2$ (10 mL) was treated with 90% $CF_3CO_2H$/$H_2O$ (20 mL) at ambient temperature. The mixture was stirred for 3 h and concentrated. The residue was dissolved in MeOH (20 mL), treated with conc. $H_2SO_4$ (1 mL), and heated at reflux for 14 h. The mixture was cooled and concentrated. The residue was dissolved in water/ethyl acetate and neutralized with $K_2CO_3$. The organic layer was dried ($Na_2SO_4$), and concentrated to give the title compound (0.76 g, 86%). HRMS Calculated for $C_{15}H_{22}NO_5$: m/z 296.1498. Found: 296.1504.

Preparation 18

3-[4-Hydroxy-2-(3-isopropyl-ureidomethyl)-phenyl]-propionic acid tert-butyl ester

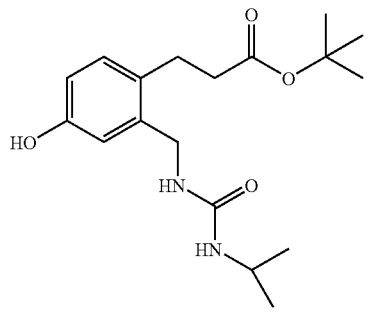

A slurry of 3-(2-aminomethyl-4-hydroxy-phenyl)-propionic acid tert-butyl ester (2.24 g, 8.91 mmol) in $CH_2Cl_2$ (30 mL) was treated with isopropyl isocyanate (1.1 mL, 11 mmol). The reaction mixture was diluted with water, the $CH_2Cl_2$ was removed under reduced pressure, and the aqueous layer was extracted with EtOAc. The organic layer was dried ($MgSO_4$) and concentrated to the title compound as a white solid (2.6 g, 87%). MS ($ES^+$) m/z 337 $[M+H]^+$.

Preparation 19

3-(2-{[(2,5-dichloro-thiophene-3-carbonyl)-amino]-methyl}-4-hydroxy-phenyl)-propionic acid tert-butyl ester

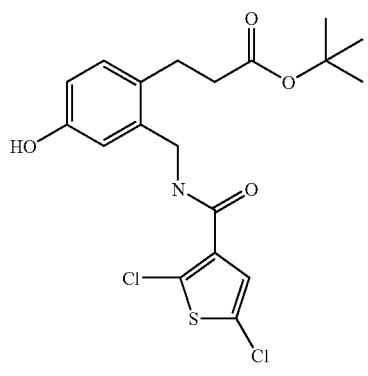

Step A: 2,5-Dichloro-thiophene-3-carboxylic acid

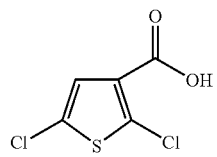

A mixture of the 1-(2,5-dichloro-thiophen-3-yl)-ethanone (10 g, 51.26 mmol) and 9.5% NaOCl (150 mL, 230 mmol, 4.5 eq., commercial bleach) was treated with 5N NaOH (1 mL, 5 mmol, 0.1 eq.). The mixture was stirred vigorously and heated to 55° C. The internal temperature was monitored closely and heat was removed to control the exotherm. After 6 h at 61° C., starting material was completely consumed. The mixture was cooled to 0° C. and carefully quenched with 20% aq. $NaHSO_3$ solution (20 mL). At 0° C., 6M HCl (12 mL) was added to adjust the pH to 1.5. The mixture was extracted with EtOAc (300 mL and 3×50 mL). The combined organic layers were washed with brine (200 mL), dried ($Na_2SO_4$), and concentrated to a white solid (8.8 g).

Step B: 3-(2-{[(2,5-dichloro-thiophene-3-carbonyl)-amino]-methyl}-4-hydroxy-phenyl)-propionic acid tert-butyl ester A solution of the 2,5-dichloro-thiophene-3-carboxylic acid (12.9 g, 65.5 mmol) and 4-methylmorpholine (7.17 mL, 65.2 mmol) in dry THF (400 mL) was cooled to −15° C. Isobutyl chloroformate (8.46 mL, 65.2 mmol) was added. The mixture was stirred 3 min and triethylamine (9.1 mL, 65 mmol) was added. A solution of 3-(2-aminomethyl-4-hydroxy-phenyl)-propionic acid tert-butyl ester (16.4 g, 65.3 mmol) in DMF (130 mL) pre-cooled to −15° C. was added via cannula over 15 min. After stirring 1 h, TLC indicated complete reaction. The reaction mixture was allowed to warm to ambient temperature. Solids were removed by filtration and washed with THF (100 mL). The filtrate was diluted with $Et_2O$ (500 mL) and washed with water (250 mL) then brine (150 mL). The organic layer was dried ($Na_2SO_4$) and concentrated. The crude brown oil was purified by silica gel chromatography (hexanes/EtOAc 2/1) and recrystallization (toluene) to afford the title compound as a white crystalline solid (22.3 g, 79.6%). MS ($ES^+$) m/z 430.1 $[M+H]^+$.

Preparation 20

3-(4-Hydroxy-2-{[(pyrazine-2-carbonyl)-amino]-methyl}-phenyl)-propionic acid tert-butyl ester

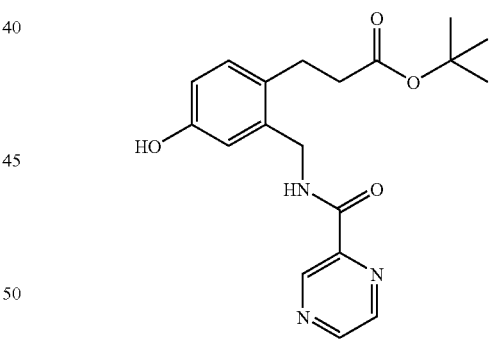

To a solution of pyrazine-2-carboxylic acid (0.570 g, 4.60 mmol) in $CH_2Cl_2$ (50 mL) was added EDC (0.960 g, 5.01 mmol) and HOBt (0.620 g, 4.60 mmol) at room temperature. The mixture was stirred for 10 min, and 3-(2-aminomethyl-4-hydroxy-phenyl)-propionic acid tert-butyl ester (1.05 g, 4.18 mmol) was added. The reaction mixture was stirred for 18 h at room temperature, treated with water (50 mL), and extracted with $CH_2Cl_2$ (2×50 mL). The combined organic layers were dried ($Na_2SO_4$), concentrated, and purified by silica gel chromatography (EtOAc/hexanes, 1:1 to 1:0) to obtain the title compound (1.05 g, 70%). $^1$H NMR (400 MHz, $CDCl_3$): δ 1.40 (s, 9H), 2.52 (t, 2H, J=7.6 Hz), 2.91 (t, 2H, J=7.6 Hz), 4.66 (d, 2H, J=6.4 Hz), 6.73 (dd, 1H, J=2.9, 7.8 Hz), 6.83 (d, 1H, J=2.4 Hz), 7.07 (d, 1H, J=8.3

Hz), 8.17 (br s, 1H), 8.49 (dd, 1H, J=1.5, 2.4 Hz), 8.73 (d, 1H, J=2.4 Hz), 9.41 (d, 1H, J=1.5 Hz). MS (ES) m/z 356.1 ([M−H]⁻).

The following intermediate compounds are prepared by a substantially similar manner as described in Preparation 20.

3-(4-Hydroxy-2-{[(pyridine-2-carbonyl)-amino]-methyl}-phenyl)-propionic acid tert-butyl ester

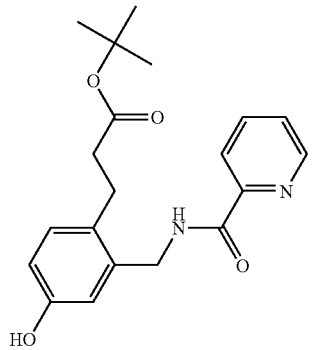

¹H-NMR(CDCl₃): 1.40 (s, 9H), 2.51 (t, J=7.6 Hz, 2H), 2.91 (t, J=7.6 Hz, 2H), 4.64 (d, J=5.9 Hz, 2H), 6.72 (d, J=7.8 Hz, 1H), 6.85 (s, 1H), 7.06 (d, J=8.2 Hz, 1H), 7.41 (t, J=7.6 Hz, 1H), 7.84 (t, J=7.0 Hz, 1H), 8.20 (d, J=7.4 Hz, 1H), 8.38 (br s, 1H), 8.50 (d, J=3.5 Hz, 1H); MS (ES) m/z 348 (M+H).

Preparation 21

3-[2-(benzoylamino-methyl)-4-hydroxy-phenyl]propionic acid tert-butyl ester

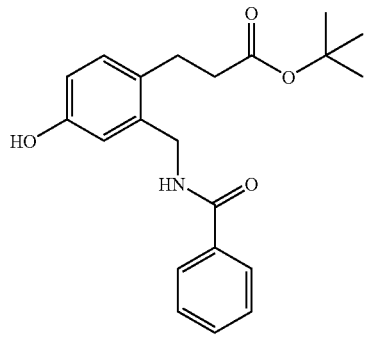

A slurry of 3-(2-aminomethyl-4-hydroxy-phenyl)-propionic acid tert-butyl ester (0.36 g, 1.43 mmol) in CH₂Cl₂ (10 mL) was cooled in an ice-water bath and treated with triethyl amine (0.40 mL, 0.28 mmol) then dropwise with benzoyl chloride (0.18 mL, 1.55 mmol). The resulting solution was stirred 30 min, and the cooling bath was removed. After 30 min, the solution was concentrated, and the residue was partitioned between EtOAc (50 mL) and 1N HCl (10 mL). The organic layer was washed with brine (10 mL), dried (Na₂SO₄), and concentrated to a solid. The crude mixture was purified by radial chromatography (hexanes:EtOAc 3:1 to 2:1) to give the title compound as a white solid (325 mg, 64%): ¹H NMR (400 MHz, CDCl₃) δ1.26 (s, 9H), 2.54 (t, J=7.1 Hz, 2H), 2.81 (t, J=6.8 Hz, 2H), 4.55 (d, J=2H), 6.68 (dd, J=8.3, 2.4 Hz, 1H), 6.86 (d, J=2.9 Hz, 1H), 6.96 (d, J=8.3 Hz, 1H), 7.25-7.29 (m, 2H), 7.34-7.37 (m, 1H), 7.49 (br s, 1H), 7.16-7.79 (m, 2H); MS (ES) m/z 356.2 (M+H).

The following intermediate compound is prepared by a substantially similar manner as described in Preparation 21.

3-{2-[(Cyclobutanecarbonyl-amino)-methyl]-4-hydroxy-phenyl}-propionic acid tert-butyl ester

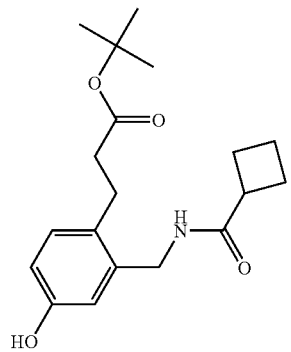

MS (ESI) m/z 334.2 (M+H)⁺.

Preparation 22

3-[2-(1,3-Dioxo-1,3-dihydro-isoindol-2-ylmethyl)-4-hydroxy-phenyl]-propionic acid tert-butyl ester

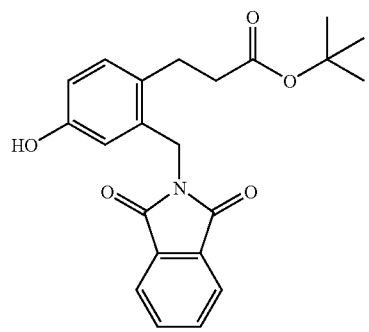

Step A: (4-Bromo-3-methyl-phenoxy)-tert-butyl-dimethyl-silane

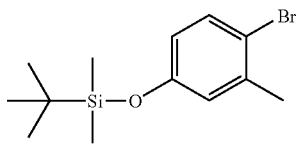

A 12 L flask was charged with 4-bromo-3-methyl phenol (428 g, 2.29 mol), CH₂Cl₂ (7.5 L), triethylamine (480 mL, 3.45 mol), and tert-butyldimethylsilyl chloride (324 g, 2.15 mol). To the solution was added 4-dimethylaminopyridine (15.0 g, 0.123 mol). The reaction mixture was stirred at ambient temperature overnight. The reaction was washed with saturated ammonium chloride (2.2 L) and then DI water (0.9 L). The organic layer was dried (Na₂SO₄), filtered, and concentrated to crude product (699 g). This material was purified by silica gel chromatography (heptane) to give the title compound (637 g, 98.5%).

Step B: (4-Bromo-3-bromomethyl-phenoxy)-tert-butyl-dimethyl-silane

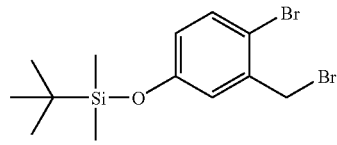

(4-Bromo-3-methyl-phenoxy)-tert-butyl-dimethyl-silane (255 g, 0.846 mol), dichloroethane (2.5 L), N-bromosuccinimide (165 g, 0.927 mol) and 2,2'-azobisisobutyronitrile (19.0 g, 0.116 mol) were combined in a 5 L flask. The mixture was degassed by evacuating and purging with $N_2$ (5×). The reaction mixture was heated to 47° C., and the heat was shut off. An exotherm to 76° C. occurred. GC analysis showed 6.5% unreacted starting material. The heat was applied again, and the reaction was held at reflux (83° C.) for 15 min. After cooling to 8° C., heptane (1.0 L) was added. The resulting slurry was stirred at 4° C. for 30 min and filtered. The filtrate was evaporated to dryness. The residue was treated with heptane (1 L), placed in the freezer overnight, and filtered. The filtrate was concentrated to the title compound (326 g, 101%).

Step C: 2-[2-Bromo-5-(tert-butyl-dimethyl-silanyloxy)-benzyl]-isoindole-1,3-dione

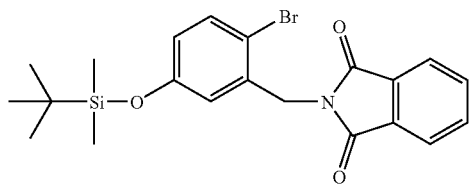

A 12 L flask was charged with (4-bromo-3-bromomethyl-phenoxy)-tert-butyl-dimethyl-silane (568 g 1.49 mol), DMF (3.1 L), and potassium phthalimide (316 g 1.71 mol). An exotherm to 34° C. occurred. After 40 min, the reaction mixture was cooled to 18° C. Ether (6.2 L) and DI water (4.9 L) were added, and the layers were separated. The organic layer was washed with saturated NaCl solution (2 L), dried ($Na_2SO_4$), filtered, and concentrated. The residue was recrystallized from heptane (1.5 L) to give the title compound (454 g, 68%).

Step D: 3-[2-(1,3-Dioxo-1,3-dihydro-isoindol-2-ylmethyl)-4-hydroxy-phenyl]-acrylic acid tert-butyl ester

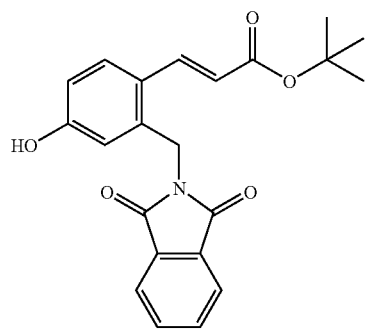

A 12 L flask was charged with 2-[2-bromo-5-(tert-butyl-dimethyl-silanyloxy)-benzyl]-isoindole-1,3-dione (461 g, 1.03 mol), propionitrile (7 L), tri-ortho-tolyl phosphine (76.0 g, 0.250 mol) and diisopropyl ethyl amine (365 mL, 2.10 mol). The reaction mixture was degassed/purged with $N_2$ (3×), and tert-butyl acrylate (465 mL, 3.17 mol) was added. After degassing/purging one time, palladium (II) acetate (28.0 g, 0.125 mol) was added. The stirred mixture was degassed/purged with $N_2$ three times and heated to 95° C. for 20 h. The mixture was filtered through a hyflo cake, washed with acetonitrile, and concentrated to a brown oil (841 g). The residue was dissolved in THF (3.5 L), and tetrabutylammonium fluoride (TBAF, 650 mL, 0.65 mol, 1M in THF) was added. After 1 h, additional TBAF (95 mL) was added. The mixture was rotated on the rotary evaporator for 10 min and was concentrated to crude product (987 g). This material was purified by silica gel chromatography (toluene/ethyl acetate, 100/0 to 75/25) to give the title compound (340 g, 86.8%).

Step E: 3-[2-(1,3-Dioxo-1,3-dihydro-isoindol-2-ylmethyl)-4-hydroxy-phenyl]-propionic acid tert-butyl ester A 1 gallon autoclave was charged with 3-[2-(1,3-dioxo-1,3-dihydro-isoindol-2-ylmethyl)-4-hydroxy-phenyl]-acrylic acid tert-butyl ester (196 g, 0.517 mol), ethyl acetate (2.6 L) and 5% palladium on carbon (75 g). The autoclave was kept at 25° C. under 60 psi of hydrogen for 21 h. The temperature of the reaction was increased to 40° C., and the pressure was increased to 75 psi for 5 h. The mixture was filtered through a pad of hyflo and concentrated to the title compound (186 g, 94.4%): MS (ESI) m/z 380.2 (M−H)⁻.

Preparation 23

3-{4-Hydroxy-2-[(isopropoxycarbonyl-methyl-amino)-methyl]-phenyl}-propionic acid tert-butyl ester

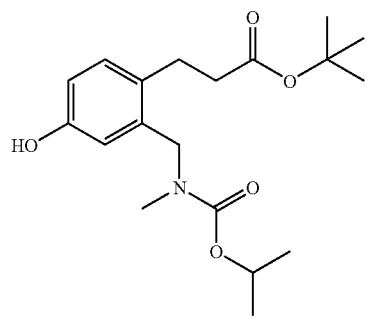

Step A: 3-[5-Benzyloxy-2-(isopropoxycarbonylamino-methyl)-phenyl]-propionic acid tert-butyl ester

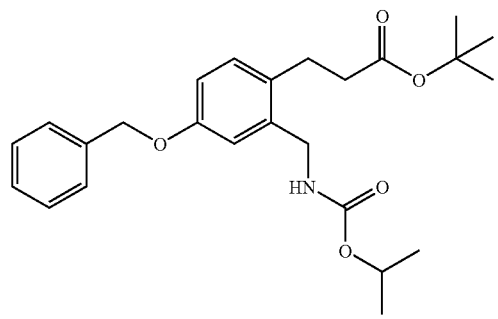

To a solution of 3-[5-hydroxy-2-(isopropoxycarbonylamino-methyl)-phenyl]-propionic acid tert-butyl ester (14.8 mmol) in DMF (100 mL) was added $Cs_2CO_3$ (29.6 mmol) and benzyl bromide (16.3 mmol). The reaction mixture was stirred overnight at ambient temperature and diluted with EtOAc (200 mL). The mixture was washed with brine (100 mL) and water (100 mL). The organic layer was dried ($Na_2SO_4$) and concentrated to a yellow oil (6.8 g). MS [ES] m/z 428 (M+H)⁺.

Step B: 3-{5-Hydroxy-2-[(isopropoxycarbonyl-methyl-amino)-methyl]-phenyl}-propionic acid tert-butyl ester To a solution of 3-[5-benzyloxy-2-(isopropoxycarbonylamino-methyl)-phenyl]-propionic acid tert-butyl ester (6.3 g, 0.015 mol) in DMF (100 mL) was added NaH (29.4 mmol, 60% oil dispersion). The reaction mixture was stirred at 0° C. for 15 min, treated with methyl iodide (4.18 g, 29.4 mmol), and stirred overnight under $N_2$ at ambient temperature. The mixture was concentrated and triturated with hexanes (200 mL). The residue was diluted with EtOAc (200 mL), and the solution was washed with water (200 mL) and brine (200 mL), dried ($Na_2SO_4$), and concentrated to a yellow oil (5.2 g). The material was dissolved in EtOAc (100 mL), and 5% Pd/C (0.725 g) was added. The reaction mixture was shaken under a hydrogen atmosphere in a Parr apparatus at 60 psi overnight at 40° C. The mixture was filtered and concentrated to give the title compound (2.1 g). MS [ES] m/z 352 (M+H)$^+$.

The following intermediate compound is prepared by a substantially similar manner as described in Preparation 23.

3-(5-Hydroxy-2-{[methyl-(pyridine-2-carbonyl)-amino]-methyl}-phenyl)-propionic acid tert-butyl ester

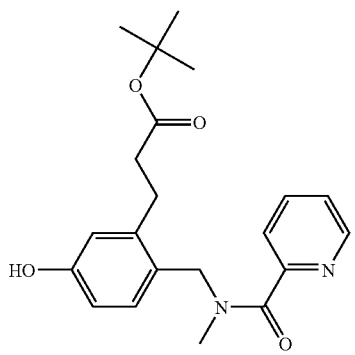

MS [ES] m/z 371 (M+H)$^+$.

The following General Procedures are used to prepare the compounds of present invention as illustrated below.

General Procedures I and II

General Procedure I

General Procedure for the Parallel Synthesis of Carboxamides from Carboxylic Acids

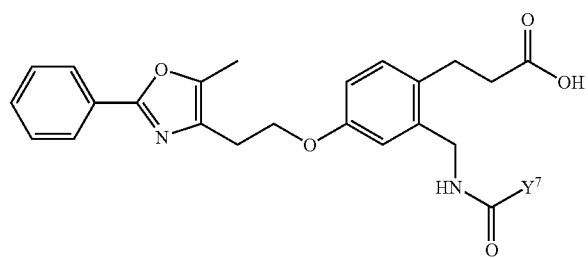

3-{2-Aminomethyl-4-[2-(5-methyl-2-phenyl-oxazol-4-yl)-ethoxy]-phenyl}-propionic acid tert-butyl ester: acetic acid salt (704 mg, 1.4 mmol) was dissolved in $CH_2Cl_2$ (25 mL) and washed with saturated $NaHCO_3$ solution (15 mL). The organic layer was dried ($NaSO_4$), filtered, and concentrated to 3-{2-aminomethyl-4-[2-(5-methyl-2-phenyl-oxazol-4-yl)-ethoxy]-phenyl}-propionic acid tert-butyl ester (636 mg, 1.4 mmol). This amine (0.11 mmol, 0.1 M in $CH_2Cl_2$) was added to a carboxylic acid (1.4 eq) in a 1 dram vial. N-Hydroxybenzotriazole hydrate (1.4 eq, 0.17 M in $CH_2Cl_2$/DMF 10/1; HOBt) and EDC (1.4 eq, 0.18 M $CH_2Cl_2$) were added, and the vials were capped and shaken for 18 h. DMF (0.5 mL) and triethylamine (0.5 mL) were added and the vials were shaken for 72 h. Brine (1 mL) was added, and the mixtures were transferred to a ChemElute cartridge and eluted with $CH_2Cl_2$. The solvent was removed under a stream of $N_2$. The residue was treated with a mixture of $CH_2Cl_2$/TFA/water 60/35/5 (1 mL), agitated briefly, and allowed to stand at ambient temperature for 2 h. The solvent was removed under a stream of $N_2$. The residue was treated with 10% $CCl_4/CH_2Cl_2$ (1 mL) and concentrated under a stream of $N_2$ (2×). The crude products were dried under vacuum and purified by mass-directed HPLC.

General Procedure II

General Procedure for the Parallel Synthesis of Carboxamides, Carbamates, Sulfonamides, Ureas, and Thioureas from Carboxylic Acid Chlorides, Chloroformates, Sulfonyl Chlorides, Isocyanates, and Isothiocyanates

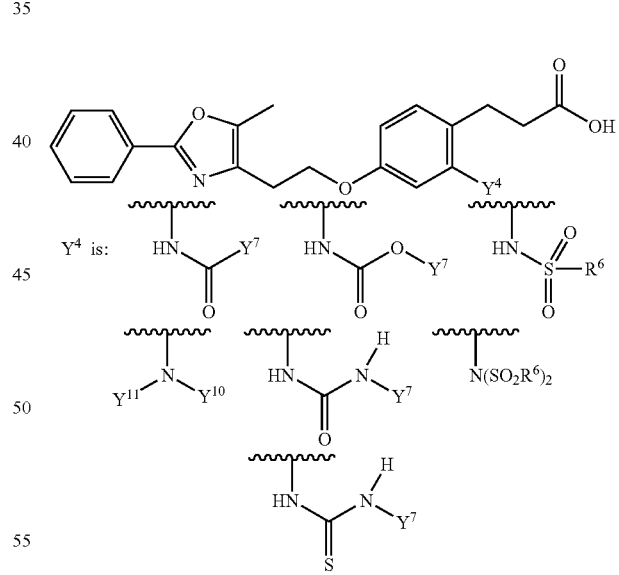

3-{2-Aminomethyl-4-[2-(5-methyl-2-phenyl-oxazol-4-yl)-ethoxy]-phenyl}-propionic acid tert-butyl ester: acetic acid salt (720 mg, 1.4 mmol) was dissolved in $CH_2Cl_2$ (25 mL) and washed with saturated $NaHCO_3$ solution (15 mL). The organic layer was dried ($NaSO_4$), filtered, and concentrated to 3-{2-aminomethyl-4-[2-(5-methyl-2-phenyl-oxazol-4-yl)-ethoxy]-phenyl}-propionic acid tert-butyl ester (586 mg, 92%). This amine (0.1 mmol, 0.1 M in $CH_2Cl_2$) and carboxylic acid chloride, chloroformate, sulfonyl chloride, isocyanate, or thioisocyanate (1 eq), and triethylamine (0.2 mL) were placed in a 1 dram vial. The vials were capped and shaken for 18 h. DMF (0.5 mL) was added to incomplete reaction mixtures, and the vials were shaken for 2 h. Brine (1 mL) was added, and the mixtures were transferred to a ChemElute cartridge and eluted with $CH_2Cl_2$. The solvent was removed under a stream of $N_2$. The residue was treated with a mixture of $CH_2Cl_2$/TFA/water 60/35/5 (1 mL), agitated briefly, and allowed to stand at ambient temperature for 2 h. The solvent was removed under a stream of $N_2$. The residue was treated with 10% $CCl_4/CH_2Cl_2$ (1 mL) and concentrated under a stream of $N_2$ (2×). The crude products were dried under vacuum and purified by mass-directed HPLC.

Example 1

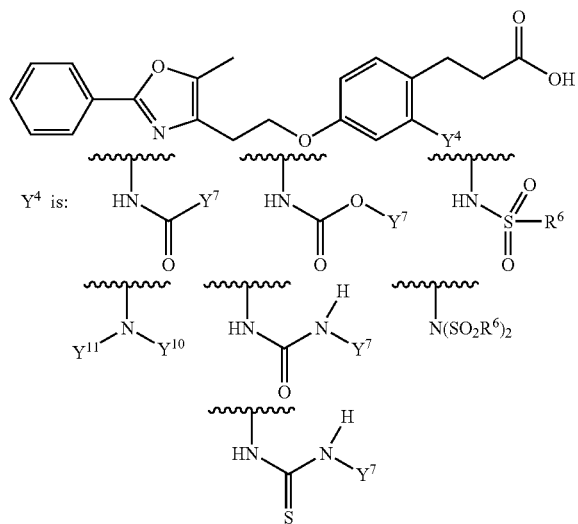

Step A: 3-{2-(1,3-Dioxo-1,3-dihydro-isoindol-2-ylmethyl)-4-[2-(5-methyl-2-phenyl-oxazol-4-yl)-ethoxy]-phenyl}-propionic acid tert-butyl ester

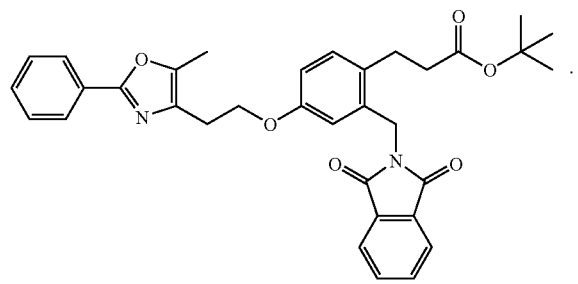

A 2 L 3-neck flask was charged with 3-[2-(1,3-dioxo-1,3-dihydro-isoindol-2-ylmethyl)-4-hydroxy-phenyl]-propionic acid tert-butyl ester (67.9 g, 0.178 mol), toluene-4-sulfonic acid 2-(5-methyl-2-phenyl-oxazol-4-yl)-ethyl ester (76.6 g, 0.214 mol) and DMF (680 mL). Cesium carbonate (75.4 g, 0.231 mol) was added, and the reaction mixture was heated at 55° C. for 18 h. After cooling, ethyl acetate (890 mL) and DI water (1200 mL) were added, the mixture was agitated, and the layers were separated. The aqueous layer was back-extracted with ethyl acetate (740 mL). The organic layers were combined and washed with 1N NaOH (375 mL) then saturated NaCl solution (2×375 mL). The organic solution was dried ($Na_2SO_4$), filtered, and concentrated to an oil (107 g). The crude oil was dissolved in toluene (50 mL), and heptane was added (~100 mL) until cloudiness remained even with agitation. The mixture was warmed to 50° C. on a rotary evaporator to yield a solution. Seed crystals were added, and rotation was continued at ambient temperature overnight. The product slurry was placed in the freezer overnight and filtered. The title compound was dried in a vacuum oven at 35° C. (71.4 g, 70.8%).

Step B: 3-{2-Aminomethyl-4-[2-(5-methyl-2-phenyl-oxazol-4-yl)-ethoxy]-phenyl}-propionic acid tert-butyl ester: acetic acid salt

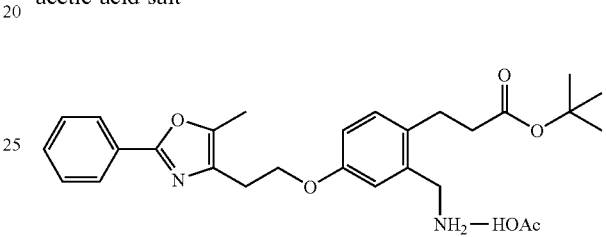

A 3 L 3-neck flask was charged with 3-{2-(1,3-dioxo-1,3-dihydro-isoindol-2-ylmethyl)-4-[2-(5-methyl-2-phenyl-oxazol-4-yl)-ethoxy]-phenyl}-propionic acid tert-butyl ester (71.0 g, 0.125 mol) and isopropanol (IPA, 1.35 L). After warming to 40° C. and adding IPA (250 mL), a solution was still not obtained. After cooling to <30° C., sodium borohydride (25.6 g, 0.677 mol) was added carefully in portions. Tap water was added to the bath, and the reaction was allowed to stir overnight. A spatula was used to break up the solids in the thick slurry, and IPA (200 mL) was added. Glacial acetic acid (130 mL, 2.27 mol) was added dropwise over 2 h. The reaction mixture was heated at reflux for 10 h, allowed to cool over the weekend, and concentrated to crude product (237 g). $CH_2Cl_2$ (100 mL) was added to give a thick gel which was poured onto a column of silica gel 60 equilibrated with $CH_2Cl_2$. Methanol was used to help dissolve the crude material. Eluting with $CH_2Cl_2$/MeOH (1/1) gave the product mixture (182 g). Ethyl acetate (200 mL) was added, and a precipitate formed. The mixture was heated to 40° C., and the solution was cooled to 0° C. The pure product was filtered, washed with heptane/EtOAc (1:1, 2×100 mL), and dried to yield a white fluffy solid (35.4 g, 57%). The filtrate was concentrated (116 g) and purified again by silica gel chromatography ($CH_2Cl_2$/MeOH 100/0 to 80/20) to give additional product as an amber oil (13.9 g, 22%).

EXAMPLES 2-230

Examples 2-230 are prepared by following a substantially similar procedure as described in Example 1 and General Procedures I and II.

| No | Compounds | MS (ES+) | General Procedure |
|---|---|---|---|
| 2 | (structure) | 515.5 FIA | II |
| 3 | (structure) | 513.5 FIA | I |
| 4 | (structure) | 514.4 FIA | II |
| 5 | (structure) | 535.2 FIA | II |
| 6 | (structure) | 501.3 FIA | II |

| No | Compounds | MS (ES+) | General Procedure |
|---|---|---|---|
| 7 | | 557.1 FIA | II |
| 8 | | 505.3 | II |
| 9 | | 491.3 | I |
| 10 | | 493.3 | I |
| 11 | | 451.2 | I |

-continued

| No | Compounds | MS (ES+) | General Procedure |
|---|---|---|---|
| 12 | | 451.2 | II |
| 13 | | 463.3 | II |
| 14 | | 505.3 | II |
| 15 | | 521.6 | II |
| 16 | | 531.6 | II |

-continued

| No | Compounds | MS (ES+) | General Procedure |
|---|---|---|---|
| 17 | | 575.7 | II |
| 18 | | 621.6 | II |
| 19 | | 559.8 | II |
| 20 | | 543.7 | II |

-continued

| No | Compounds | MS (ES+) | General Procedure |
|----|-----------|----------|-------------------|
| 21 | | 555.4 | II |
| 22 | | 525.2 | II |
| 23 | | 529.3 | II |
| 24 | | 515.3 | II |

-continued

| No | Compounds | MS (ES+) | General Procedure |
|---|---|---|---|
| 25 | | 510.6 | II |
| 26 | | 543.7 | II |
| 27 | | 539.3 | II |

| No | Compounds | MS (ES+) | General Procedure |
|---|---|---|---|
| 28 | 5-methyl-2-phenyl-oxazole-CH₂CH₂-O-phenyl(CH₂CH₂COOH)-CH₂-NH-C(O)-phenyl-hexyl | 569.4 | II |
| 29 | 5-methyl-2-phenyl-oxazole-CH₂CH₂-O-phenyl(CH₂CH₂COOH)-CH₂-NH-C(O)-(2-fluoro-4-trifluoromethyl)phenyl | 571.3 | II |
| 30 | 5-methyl-2-phenyl-oxazole-CH₂CH₂-O-phenyl(CH₂CH₂COOH)-CH₂-NH-C(O)-(2,3-dimethyl)phenyl | 513.4 | II |

| No | Compounds | MS (ES+) | General Procedure |
|---|---|---|---|
| 31 | 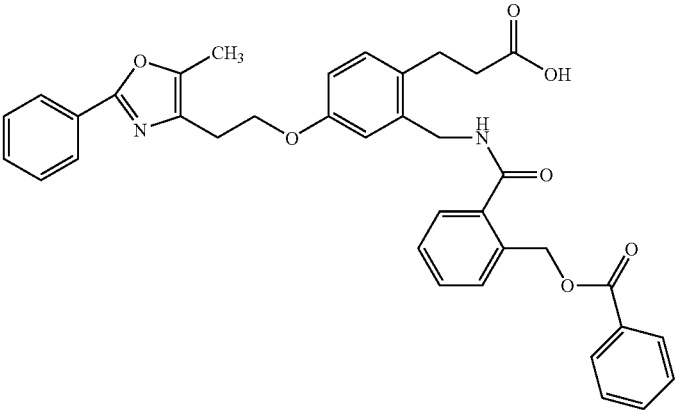 | 619.4 | II |
| 32 | 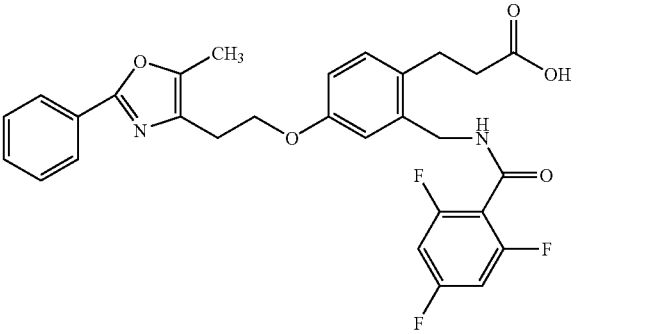 | 539.3 | II |
| 33 | 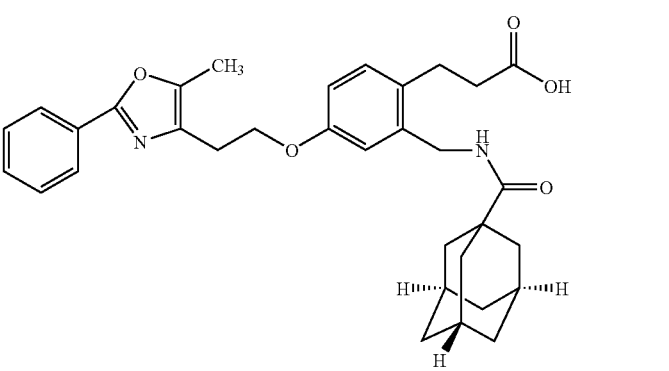 | 543.4 | II |
| 34 | 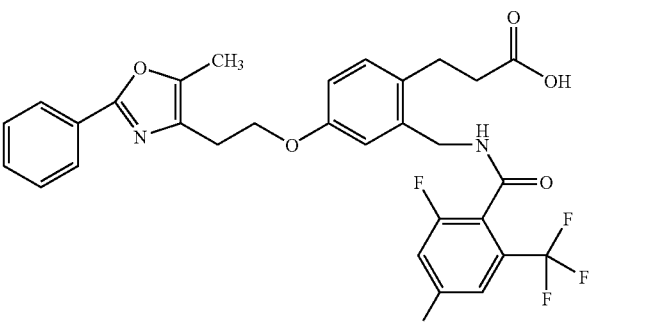 | 571.3 | II |

| No | Compounds | MS (ES+) | General Procedure |
|---|---|---|---|
| 35 | | 589.2 | II |
| 36 | | 577.3 | II |
| 37 | | 529.7 | I |
| 38 | | 505.3 | I |

-continued
| No | Compounds | MS (ES+) | General Procedure |
|---|---|---|---|
| 39 | 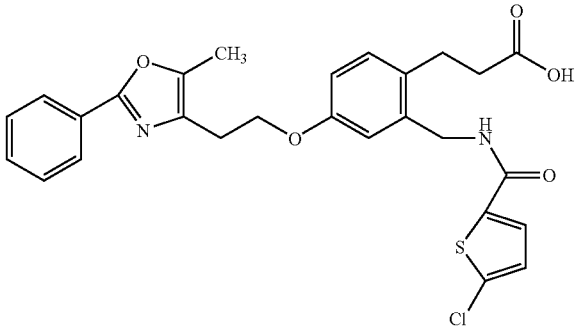 | 525.2 | I |
| 40 | 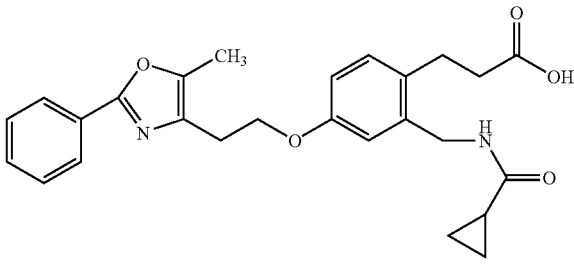 | 549.3 | I |
| 41 | 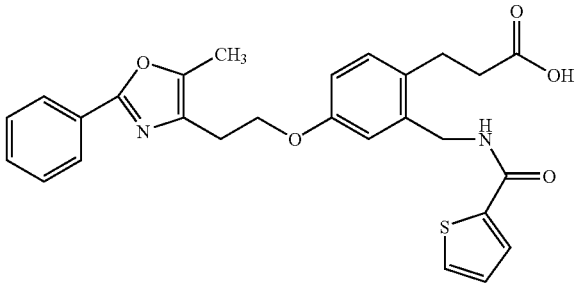 | 491.3 | I |
| 42 | 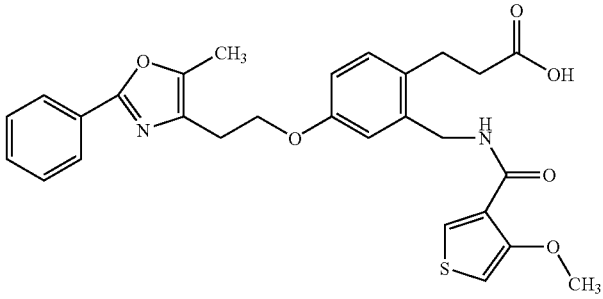 | 521.3 | I |
| 43 | 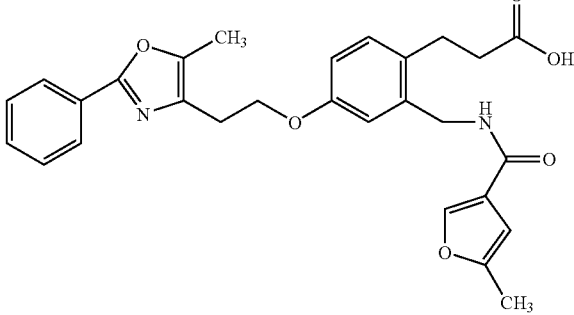 | 489.3 | I |

-continued
| No | Compounds | MS (ES+) | General Procedure |
|---|---|---|---|
| 44 | 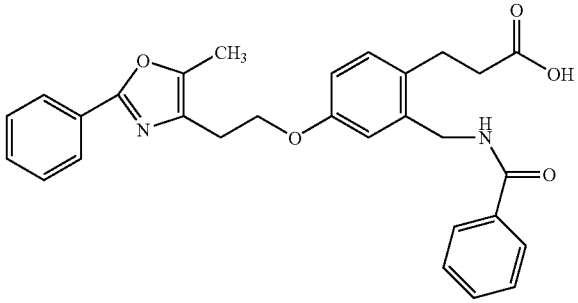 | 485.3 | I |
| 45 | 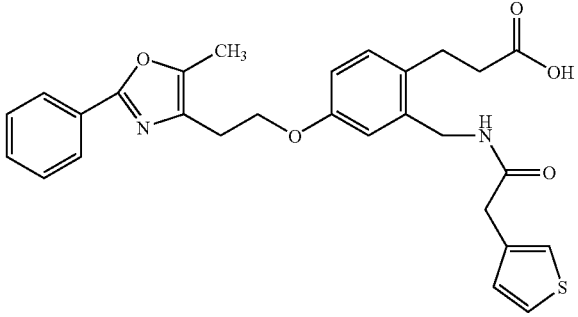 | 505.3 | I |
| 46 | 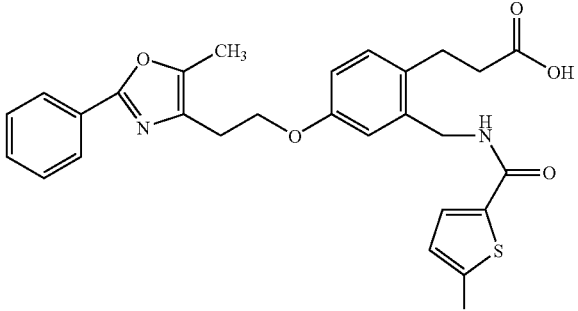 | 505.3 | I |
| 47 | 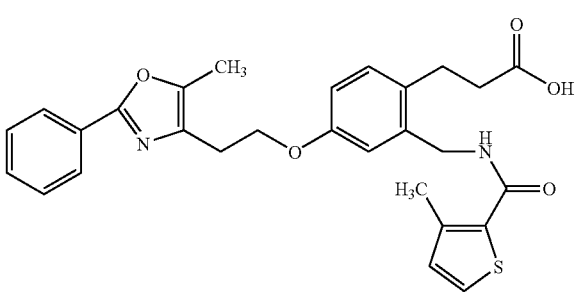 | 505.3 | I |

-continued

| No | Compounds | MS (ES+) | General Procedure |
|----|-----------|----------|-------------------|
| 48 | (5-methyl-2-phenyloxazol-4-yl)ethoxy phenyl propanoic acid with thiophene-3-carboxamide methyl linker | 491.3 | I |
| 49 | (5-methyl-2-phenyloxazol-4-yl)ethoxy phenyl propanoic acid with 3-bromothiophene-2-carboxamide methyl linker | 571.2 | I |
| 50 | (5-methyl-2-phenyloxazol-4-yl)ethoxy phenyl propanoic acid with 3-benzyloxythiophene-2-carboxamide methyl linker | 597.4 | I |
| 51 | (5-methyl-2-phenyloxazol-4-yl)ethoxy phenyl propanoic acid with 4-methylthiophene-2-carboxamide methyl linker | 505.3 | I |
| 52 | (5-methyl-2-phenyloxazol-4-yl)ethoxy phenyl propanoic acid with phenylacetamide methyl linker | 499.3 | I |

-continued
| No | Compounds | MS (ES+) | General Procedure |
|---|---|---|---|
| 53 | 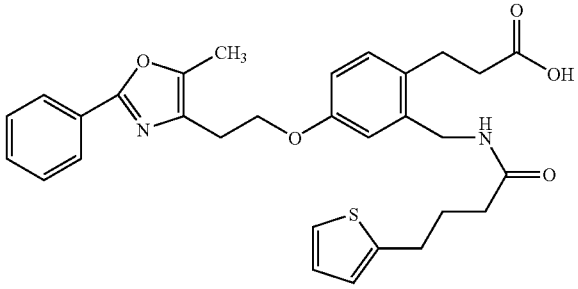 | 533.3 | I |
| 54 | 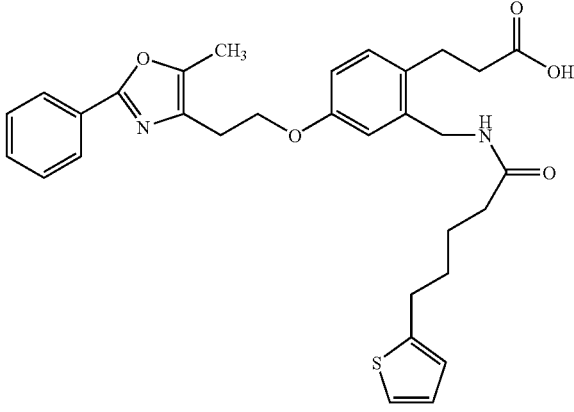 | 547.3 | I |
| 55 | 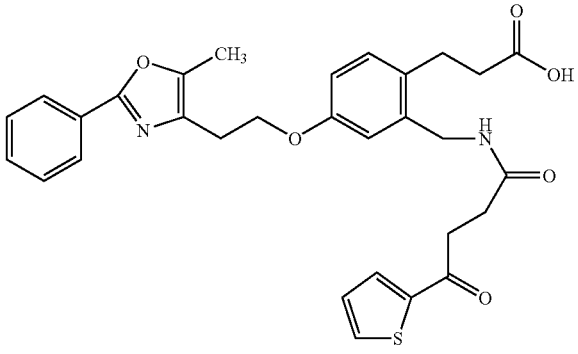 | 547.3 | I |
| 56 | 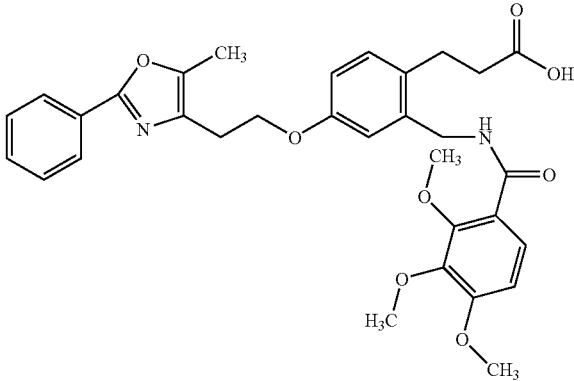 | 575 | I |

| No | Compounds | MS (ES+) | General Procedure |
|---|---|---|---|
| 57 | | 575 | I |
| 58 | | 591 | I |
| 59 | | 521 | I |
| 60 | | 591 | I |

-continued
| No | Compounds | MS (ES+) | General Procedure |
|---|---|---|---|
| 61 | 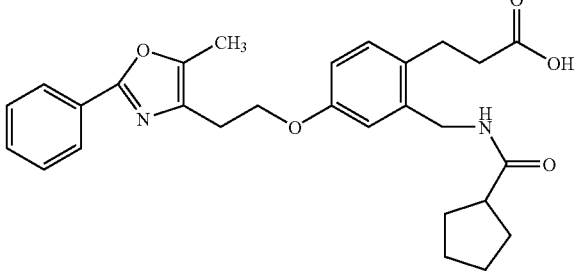 | 477.2 | I |
| 62 | 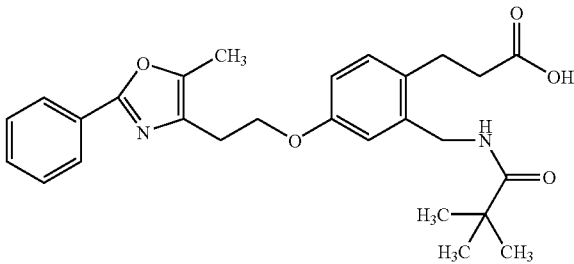 | 465 | I |
| 63 | 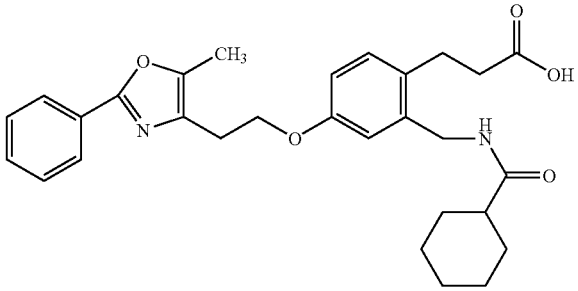 | 491 | I |
| 64 | 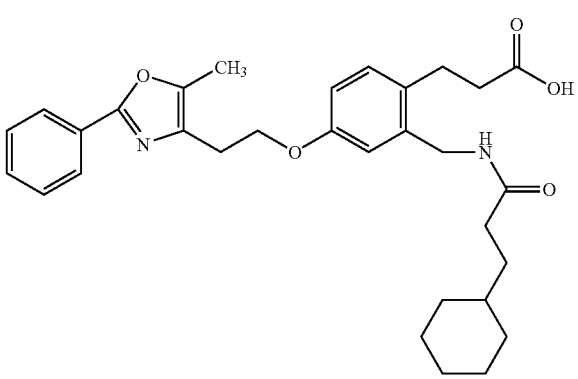 | 519 | I |

|  |  | MS | General |
|---|---|---|---|
| No | Compounds | (ES+) | Procedure |
| 65 | | 541 | I |
| 66 | | 493 | I |
| 67 | | 541 | I |
| 68 | | 554 | I |

-continued

| No | Compounds | MS (ES+) | General Procedure |
|---|---|---|---|
| 69 | | 507 | I |
| 70 | | 527 | I |
| 71 | | 463 | I |
| 72 | | 521 | I |

-continued
| No | Compounds | MS (ES+) | General Procedure |
|---|---|---|---|
| 73 | 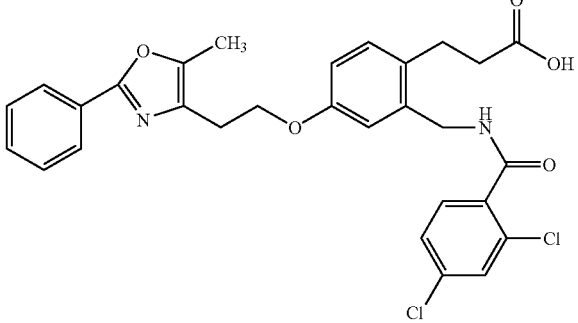 | 554 | I |
| 74 | 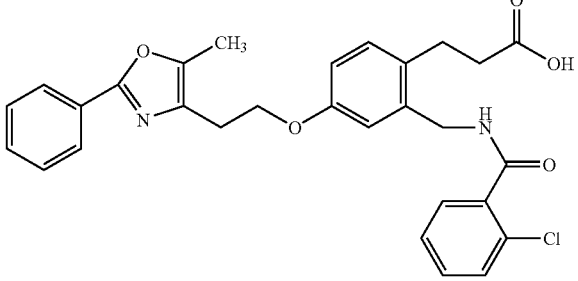 | 520 | I |
| 75 | 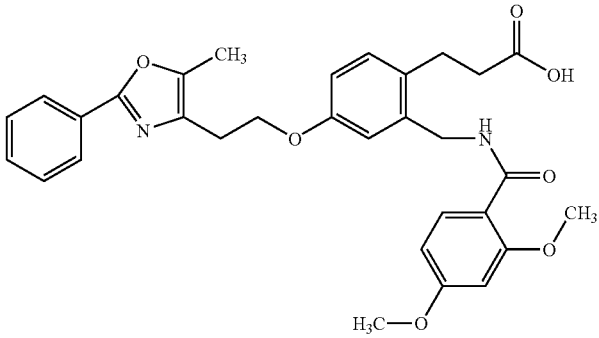 | 545 | I |
| 76 | 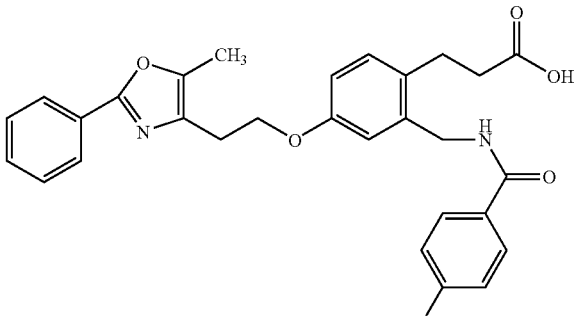 | 503 | I |

-continued
| No | Compounds | MS (ES+) | General Procedure |
|---|---|---|---|
| 77 | 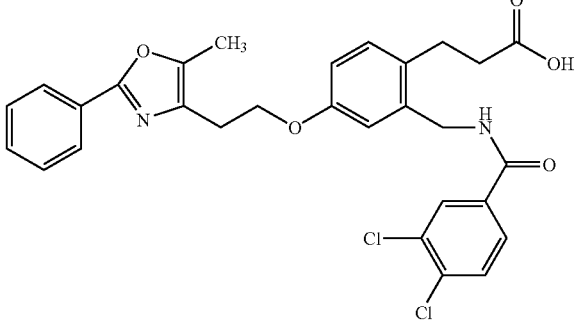 | 554 | I |
| 78 | 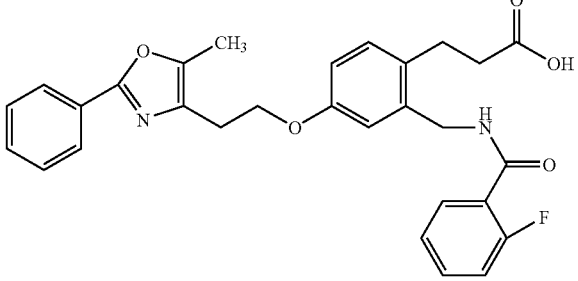 | 503 | I |
| 79 | 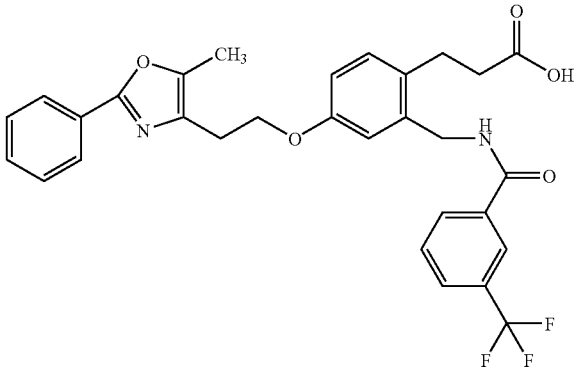 | 553 | I |
| 80 | 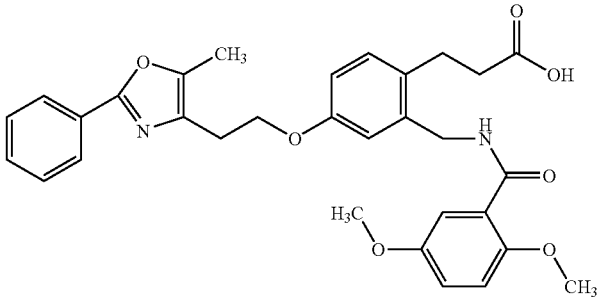 | 545 | I |

-continued
| No | Compounds | MS (ES+) | General Procedure |
|----|-----------|----------|-------------------|
| 81 | 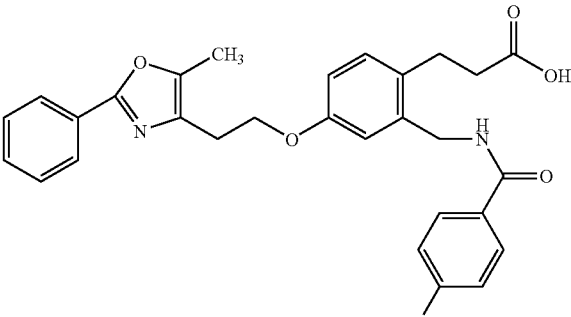 | 499 | I |
| 82 | 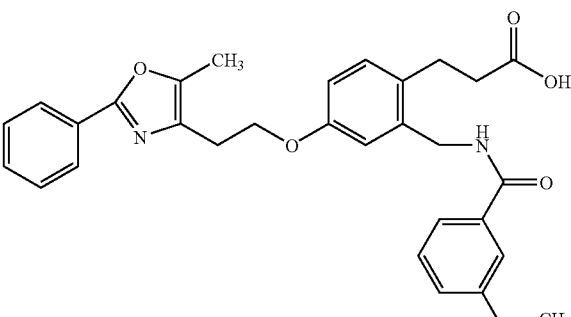 | 515.2 | I |
| 83 | 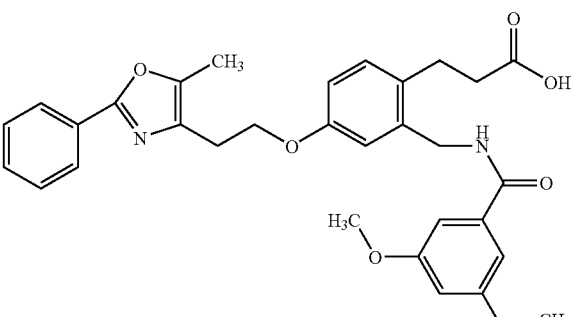 | 545.3 | I |
| 84 | 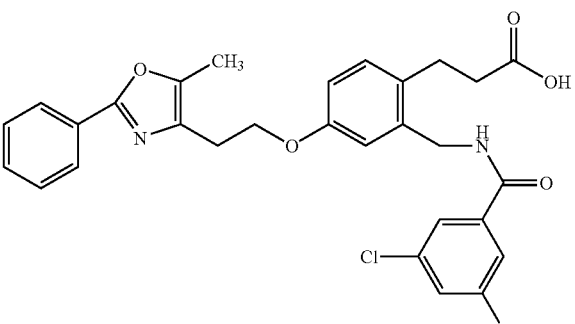 | 554 | I |

-continued

| No | Compounds | MS (ES+) | General Procedure |
|---|---|---|---|
| 85 | | 515 | I |
| 86 | | 554 | I |
| 87 | | 554 | I |
| 88 | | 598 | I |

-continued

| No | Compounds | MS (ES+) | General Procedure |
|---|---|---|---|
| 89 | | 499 | I |
| 90 | | 555 | I |
| 91 | | 529 | I |
| 92 | | 465 | I |

| No | Compounds | MS (ES+) | General Procedure |
|---|---|---|---|
| 93 | | 533 | I |
| 94 | | 465 | I |
| 95 | | 538 | I |
| 96 | | 499 | I |

-continued

| No | Compounds | MS (ES+) | General Procedure |
|---|---|---|---|
| 97 | | 479 | I |
| 98 | | 521 | I |
| 99 | | 538 | I |
| 100 | | 521 | I |

-continued

| No | Compounds | MS (ES+) | General Procedure |
|---|---|---|---|
| 101 | | 553 | I |
| 102 | | 538 | I |
| 103 | | 513 | I |
| 104 | | 513 | I |

| No | Compounds | MS (ES+) | General Procedure |
|---|---|---|---|
| 105 | | 503 | I |
| 106 | | 527 | I |
| 107 | | 513 | I |
| 108 | | 513 | I |

-continued

| No | Compounds | MS (ES+) | General Procedure |
|---|---|---|---|
| 109 | | 513 | I |
| 110 | | 521 | I |
| 111 | | 513 | I |
| 112 | | 535 | I |

-continued

| No | Compounds | MS (ES+) | General Procedure |
|---|---|---|---|
| 113 | | 545 | I |
| 114 | | 545 | I |
| 115 | | 527 | I |
| 116 | | 555 | I |

-continued
| No | Compounds | MS (ES+) | General Procedure |
|----|-----------|----------|-------------------|
| 117 | 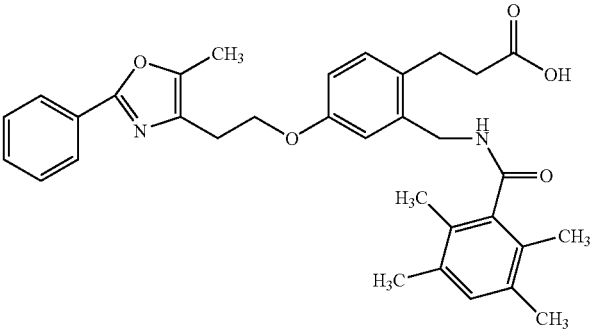 | 541 | I |
| 118 | 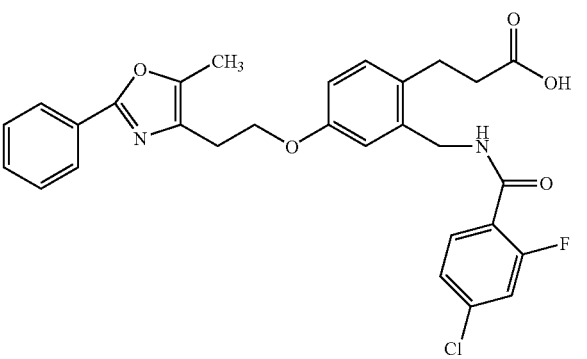 | 538 | I |
| 119 | 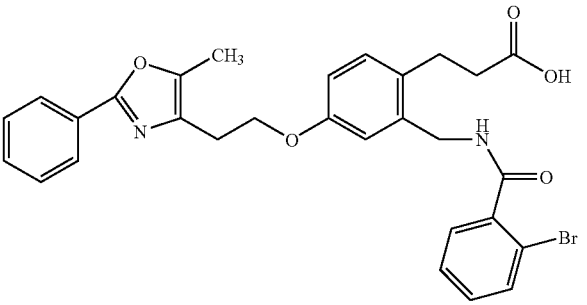 | 564 | I |
| 120 | 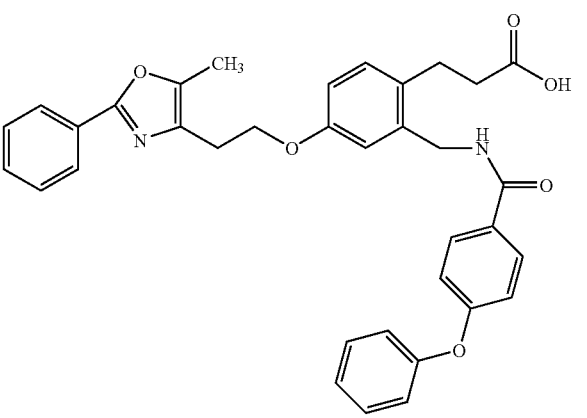 | 577 | I |

-continued

| No | Compounds | MS (ES+) | General Procedure |
|---|---|---|---|
| 121 | | 569 | I |
| 122 | | 564 | I |
| 123 | | 575 | I |
| 124 | | 587 | I |

-continued
| No | Compounds | MS (ES+) | General Procedure |
|---|---|---|---|
| 125 | 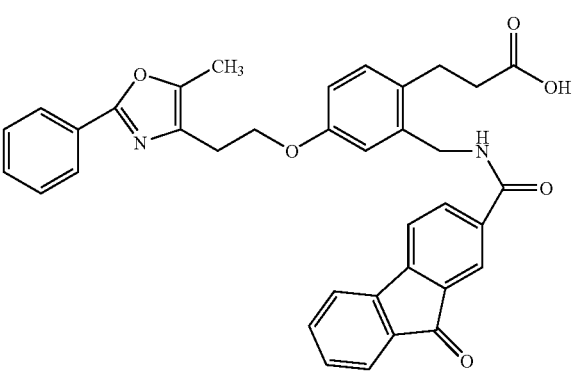 | 587 | I |
| 126 | 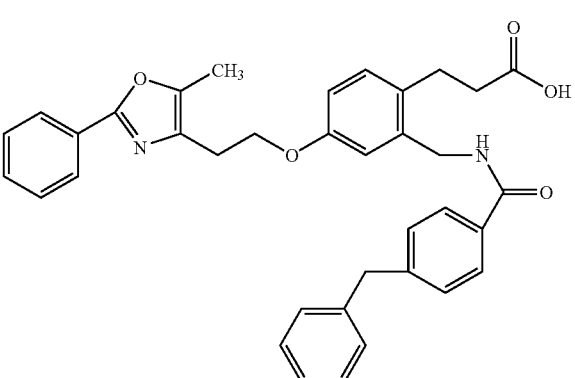 | 575 | I |
| 127 | 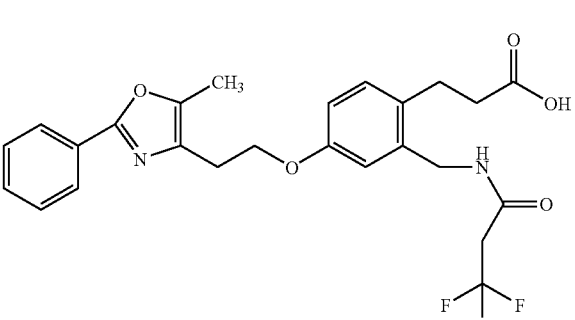 | 491 | I |
| 128 | 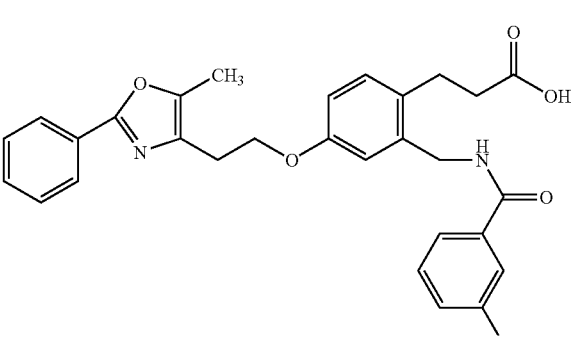 | 564 | I |

-continued
| No | Compounds | MS (ES+) | General Procedure |
|---|---|---|---|
| 129 | 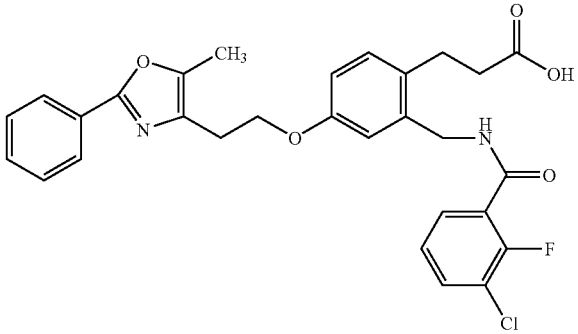 | 538 | I |
| 130 | 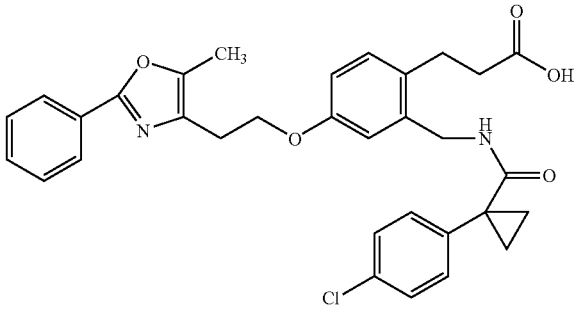 | 560 | I |
| 131 | 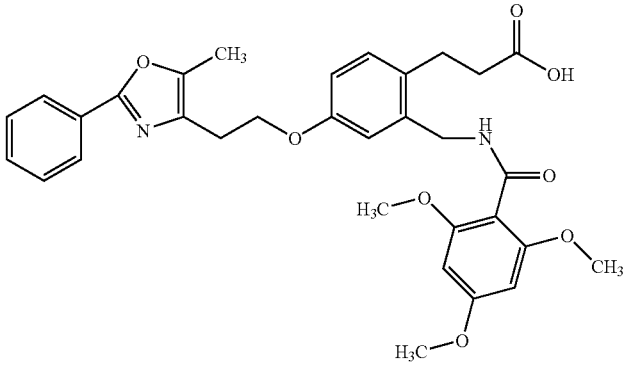 | 575 | I |
| 132 | 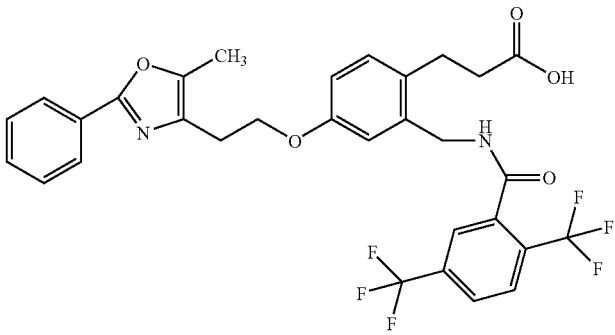 | 621 | I |

-continued

| No | Compounds | MS (ES+) | General Procedure |
|---|---|---|---|
| 133 | | 527 | I |
| 134 | | 569 | I |
| 135 | | 571 | I |
| 136 | | 571 | I |

| No | Compounds | MS (ES+) | General Procedure |
|---|---|---|---|
| 137 | | 597 | I |
| 138 | | 569 | I |
| 139 | | 621 | I |
| 140 | | 571 | I |

-continued
| No | Compounds | MS (ES+) | General Procedure |
|---|---|---|---|
| 141 | 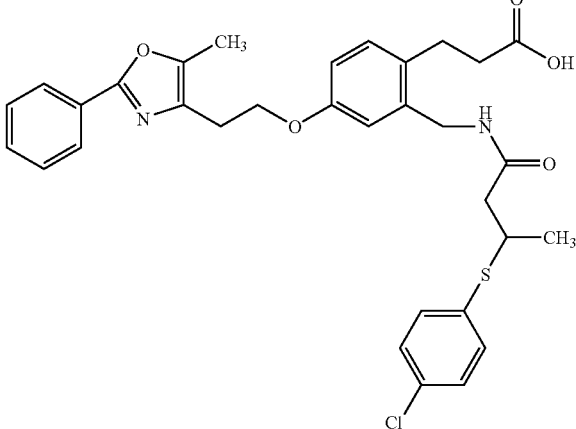 | 594 | I |
| 142 | 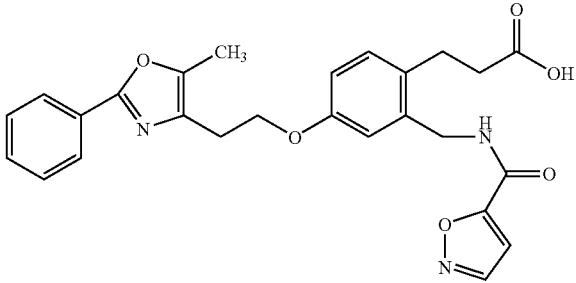 | 476 | I |
| 143 | 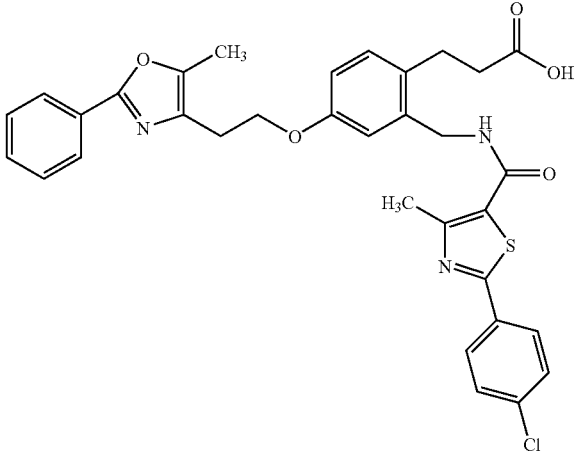 | 617 | I |
| 144 | 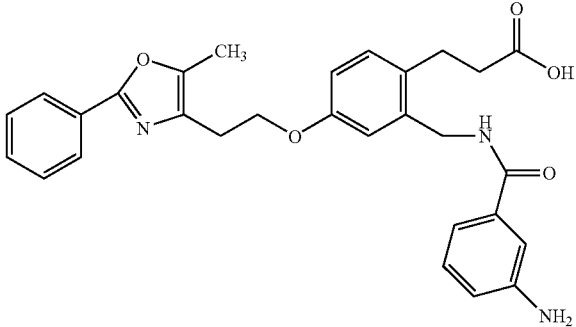 | 500 | I |

-continued
| No | Compounds | MS (ES+) | General Procedure |
|---|---|---|---|
| 145 | 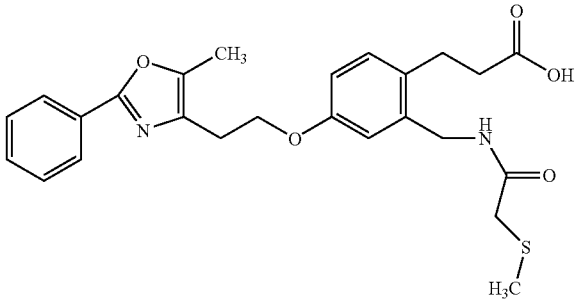 | 469 | I |
| 146 | 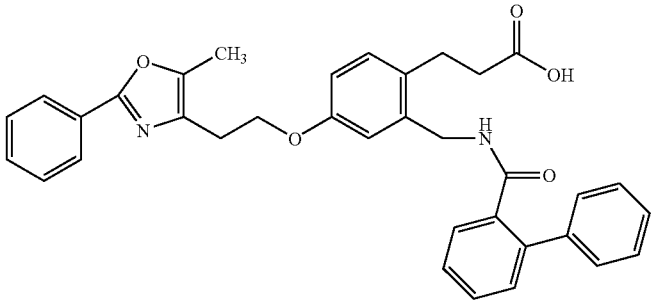 | 561 | I |
| 147 | 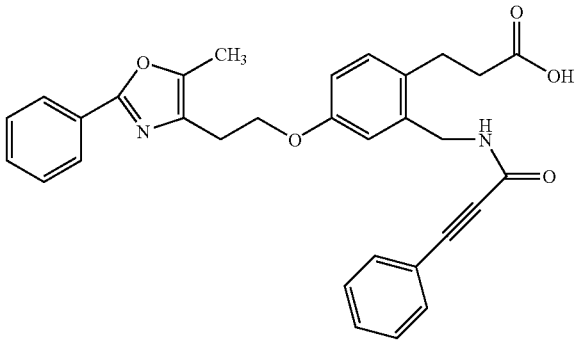 | 509 | I |
| 148 | 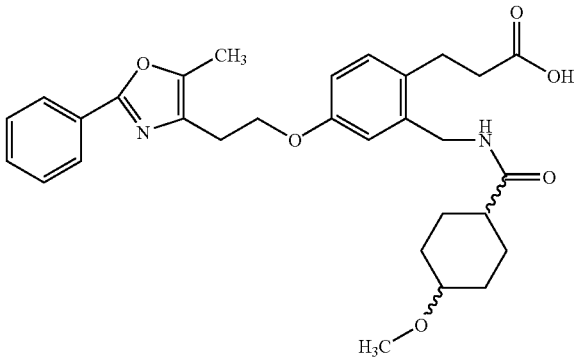 | 521 | I |

-continued

| No | Compounds | MS (ES+) | General Procedure |
|---|---|---|---|
| 149 | | 577 | I |
| 150 | | 589 | I |
| 151 | | 561 | I |
| 152 | | 595 | I |

-continued
| No | Compounds | MS (ES+) | General Procedure |
|---|---|---|---|
| 153 | 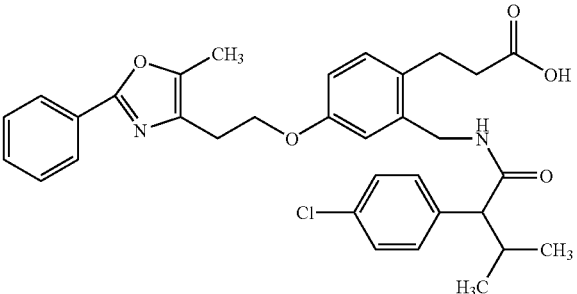 | 575 | I |
| 154 | 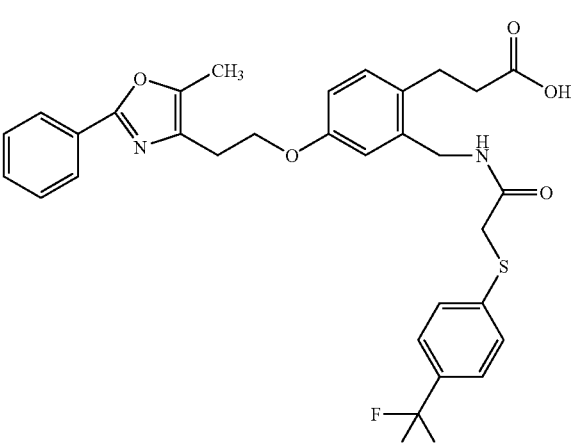 | 599 | I |
| 155 | 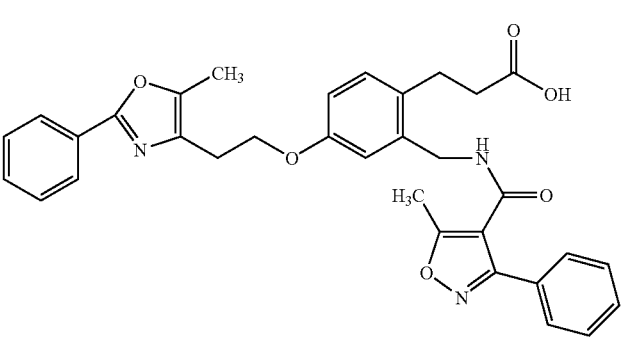 | 566 | I |
| 156 | 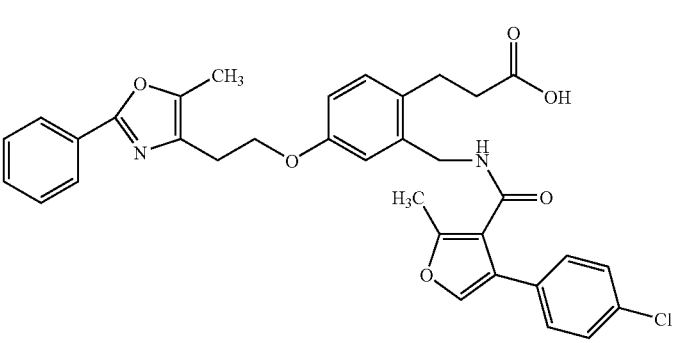 | 599 | I |

| No | Compounds | MS (ES+) | General Procedure |
|---|---|---|---|
| 157 | 5-methyl-2-phenyl-oxazole-CH₂CH₂-O-phenyl(CH₂CH₂COOH)-CH₂-NH-C(O)-furan-CF₃ | 543 | I |
| 158 | 5-methyl-2-phenyl-oxazole-CH₂CH₂-O-phenyl(CH₂CH₂COOH)-CH₂-NH-C(O)-(4-methylthiazole)-phenyl-CF₃ | 650 | I |
| 159 | 5-methyl-2-phenyl-oxazole-CH₂CH₂-O-phenyl(CH₂CH₂COOH)-CH₂-NH-C(O)-furan-phenyl-CF₃ | 619 | I |

-continued

| No | Compounds | MS (ES+) | General Procedure |
|---|---|---|---|
| 160 | | 615 | I |
| 161 | | 437.2 | I |
| 162 | | 571.2 | I |
| 163 | | see text | I |
| 164 | | 493.2 | II |

| No | Compounds | MS (ES+) | General Procedure |
|---|---|---|---|
| 165 | | 483.2 | II |
| 166 | | 551.2 | II |
| 167 | | 467.2 | II |
| 168 | | 481.2 | II |
| 169 | | 501.2 | II |

-continued

| No | Compounds | MS (ES+) | General Procedure |
|---|---|---|---|
| 170 | | 439.2 | II |
| 171 | | 481.3 | II |
| 172 | | 453.2 | II |
| 173 | | 565.4 | II |
| 174 | | 535.2 | II |

-continued

| No | Compounds | MS (ES+) | General Procedure |
|---|---|---|---|
| 175 | (structure: 5-methyl-2-phenyloxazole-ethoxy-phenyl-propanoic acid with furan-2-carboxamide methyl substituent) | 475.2 | I |
| 176 | (structure: 5-methyl-2-phenyloxazole-ethoxy-phenyl-propanoic acid with quinoline-2-carboxamide methyl substituent) | 536.2 | I |
| 177 | (structure: 5-methyl-2-phenyloxazole-ethoxy-phenyl-propanoic acid with 1H-indole-2-carboxamide methyl substituent) | 524.2 | I |
| 178 | (structure: 5-methyl-2-phenyloxazole-ethoxy-phenyl-propanoic acid with pyrazine-2-carboxamide methyl substituent) | 487.2 | I |
| 179 | (structure: 5-methyl-2-phenyloxazole-ethoxy-phenyl-propanoic acid with tetrahydrofuran-2-carboxamide methyl substituent) | 479.2 | I |

-continued

| No | Compounds | MS (ES+) | General Procedure |
|---|---|---|---|
| 180 | | 486.2 | I |
| 181 | | 486.2 | I |
| 182 | | 474.2 | I |
| 183 | | 486.2 | I |
| 184 | | 512 | I |

-continued

| No | Compounds | MS (ES+) | General Procedure |
|----|-----------|----------|-------------------|
| 185 | | 512.2 | I |
| 186 | | 568.1 | I |
| 187 | | 556.1 | I |
| 188 | | 574.1 | I |

| No | Compounds | MS (ES+) | General Procedure |
|----|-----------|----------|-------------------|
| 189 | | 574.1 | I |
| 190 | | 559.1 | I |
| 191 | | 487.3 | II |
| 192 | | 473.0 | II |

| No | Compounds | MS (ES+) | General Procedure |
|---|---|---|---|
| 193 | 5-methyl-2-phenyl-oxazole-CH₂CH₂-O-(phenyl with CH₂CH₂COOH and CH₂-NH-SO₂-CH₂CH₂CH₃) | 487.3 | II |
| 194 | 5-methyl-2-phenyl-oxazole-CH₂CH₂-O-(phenyl with CH₂CH₂COOH and CH₂-NH-SO₂-phenyl) | 521.3 | II |
| 195 | 5-methyl-2-phenyl-oxazole-CH₂CH₂-O-(phenyl with CH₂CH₂COOH and CH₂-NH-SO₂-thiophene) | 527.2 | II |
| 196 | 5-methyl-2-phenyl-oxazole-CH₂CH₂-O-(phenyl with CH₂CH₂COOH and CH₂-NH-C(O)-NH-CH(CH₃)₂) | 466.3 | II |
| 197 | 5-methyl-2-phenyl-oxazole-CH₂CH₂-O-(phenyl with CH₂CH₂COOH and CH₂-NH-C(O)-NH-CH₂CH₂-phenyl) | 528.3 | II |

| No | Compounds | MS (ES+) | General Procedure |
|---|---|---|---|
| 198 | | 534.3 | II |
| 199 | | 480.3 | II |
| 200 | | 535.2 | II |
| 201 | | 611.1 | II |
| 202 | | 539.2 | II |
| 203 | | 539.1 | II |
| 204 | | 557.1 | II |

-continued

| No | Compounds | MS (ES+) | General Procedure |
|---|---|---|---|
| 205 | | 557.1 | II |
| 206 | | 500.2 | II |
| 207 | | 550.2 | II |
| 208 | | 592.2 | II |

-continued
| No | Compounds | MS (ES+) | General Procedure |
|---|---|---|---|
| 209 | 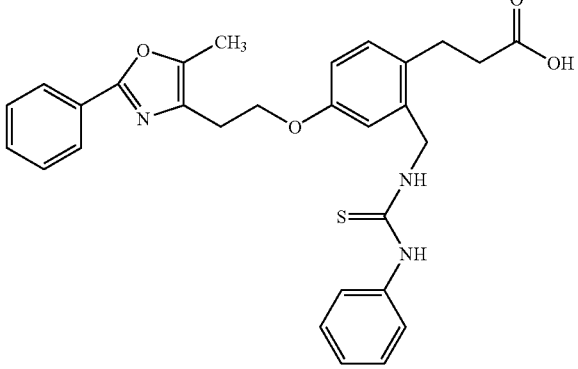 | 516.1 | II |
| 210 | 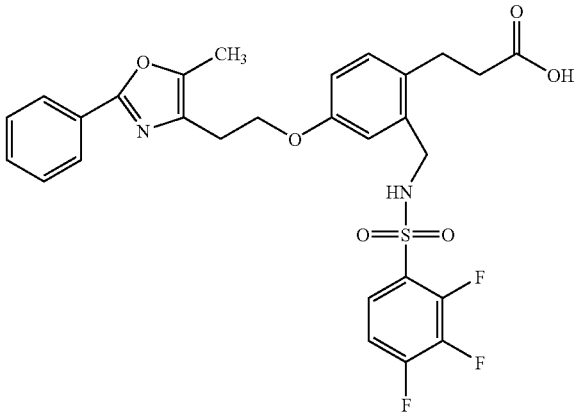 | 575.1 | II |
| 211 | 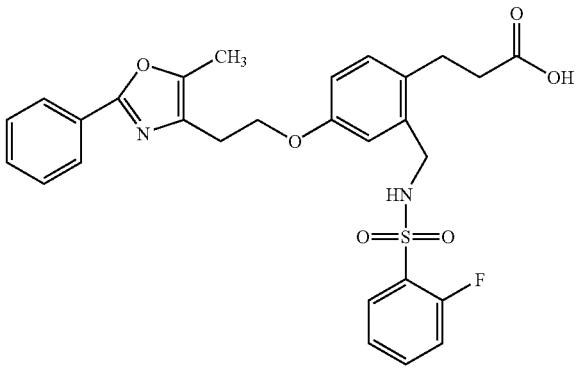 | 539.2 | II |
| 212 | 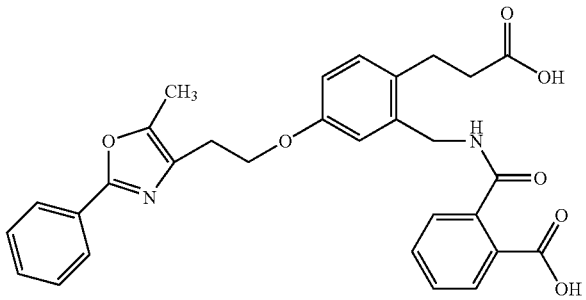 | 529 | II |

-continued
| No | Compounds | MS (ES+) | General Procedure |
|---|---|---|---|
| 213 | 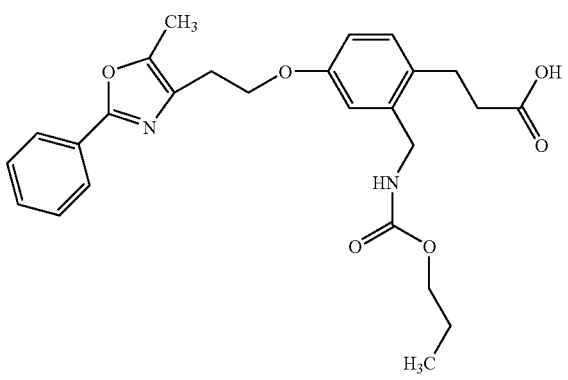 | 467.3 | II |
| 214 | 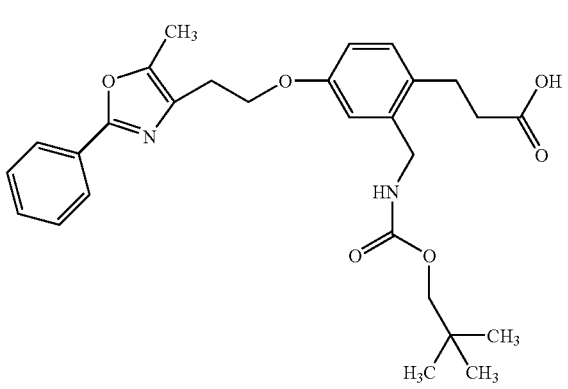 | 495.3 | II |
| 215 | 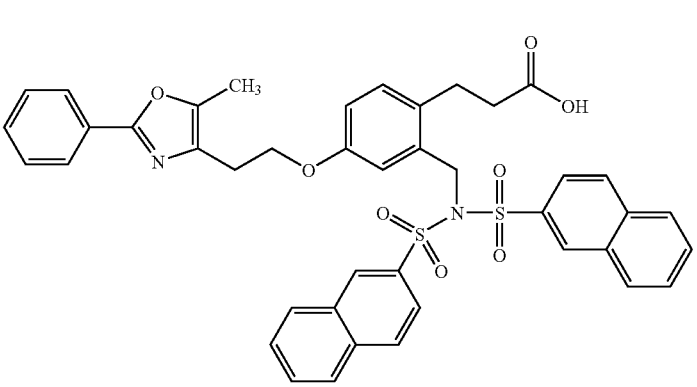 | 761.2 (FIA) | II |
| 216 | 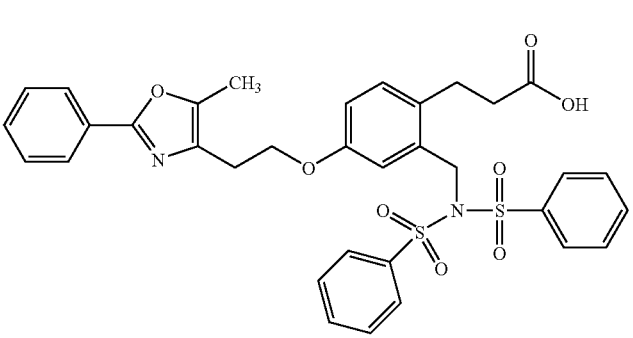 | 661.1 (FIA) | II |

-continued

| No | Compounds | MS (ES+) | General Procedure |
|---|---|---|---|
| 217 | | 459.4 (FIA) | II |
| 218 | | 682 | II |
| 219 | | 423 | I |
| 220 | | 569 | I |
| 221 | | 552 | II |

-continued
| No | Compounds | MS (ES+) | General Procedure |
|---|---|---|---|
| 222 | 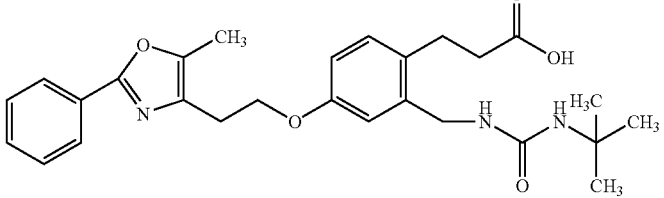 | 480 | II |
| 223 | 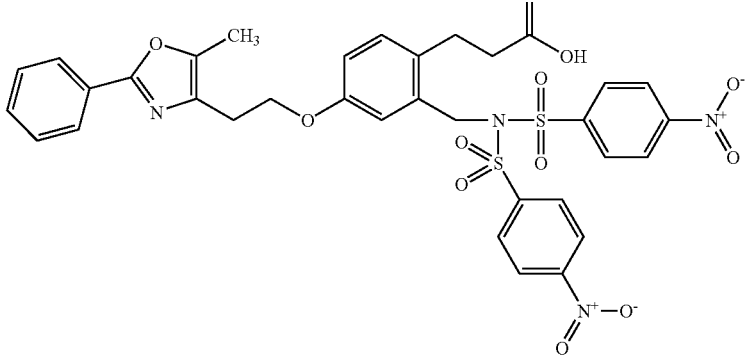 | 751 | II |
| 224 | 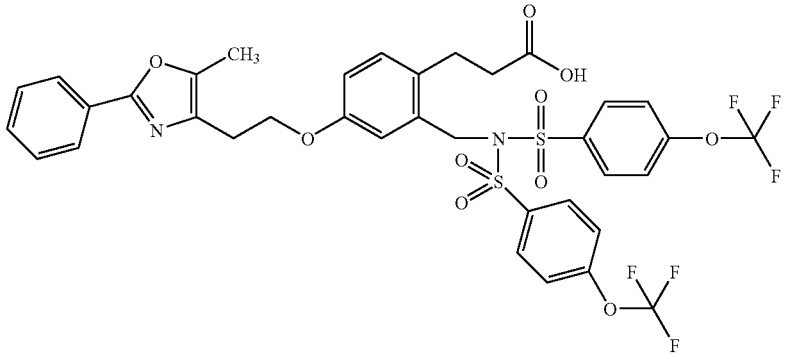 | 829 | II |
| 225 | 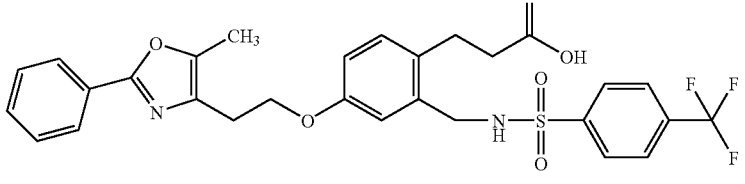 | 589 | II |
| 226 | 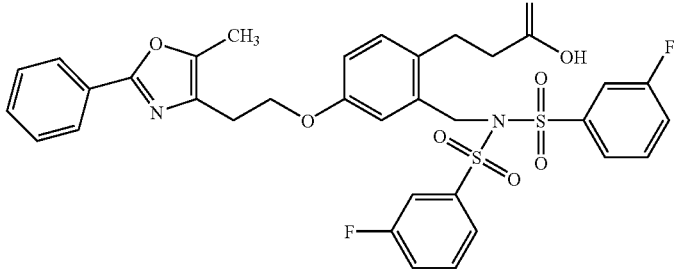 | 697 | II |

-continued

| No | Compounds | MS (ES+) | General Procedure |
|---|---|---|---|
| 227 | | 733 | II |
| 228 | | 733 | II |
| 229 | | 733 | II |
| 230 | | 494.1 | II |

Example 231

3-(4-[2-(2-Biphenyl-4-yl-5-methyl-oxazol-4-yl)-ethoxy]-2-{[(2,5-dichloro-thiophene-3-carbonyl)-amino]-methyl}-phenyl)-propionic acid

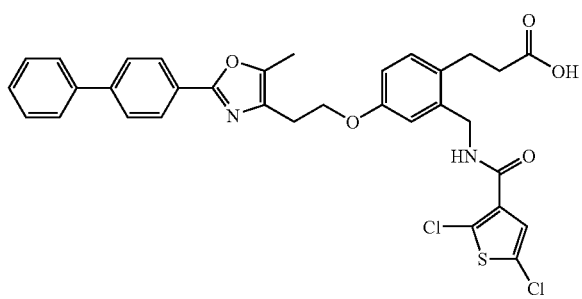

Step A: 3-(4-[2-(2-Biphenyl-4-yl-5-methyl-oxazol-4-yl)-ethoxy]-2-{[(2,5-dichloro-thiophene-3-carbonyl)-amino]-methyl}-phenyl)-propionic acid tert-butyl ester

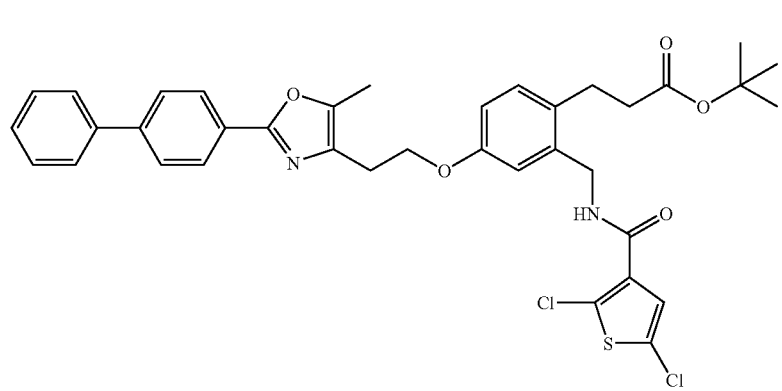

A mixture of 3-(2-{[(2,5-dichloro-thiophene-3-carbonyl)-amino]-methyl}-4-hydroxy-phenyl)-propionic acid tert-butyl ester (280 mg, 0.651 mmol) and toluene-4-sulfonic acid 2-(2-biphenyl-4-yl-5-methyl-oxazol-4-yl)-ethyl ester (498 mg, 1.15 mmol), were reacted according to Standard procedure A to give, after radial chromatography (hexanes/EtOAc 98:2 to 90:10), the title compound as a white solid (367 mg, 82%). $^1$H NMR (400 MHz, CDCl$_3$): δ 1.36 (s, 9H), 2.37 (s, 3H), 2.55 (t, 2H, J=7.3 Hz), 2.87 (t, 2H, J=7.3 Hz), 2.96 (t, 2H, J=6.6 Hz), 4.22 (t, 2H, J=6.8 Hz), 4.58 (d, 2H, J=5.4 Hz), 6.80 (dd, 1H, J=8.3 Hz, J=2.4 Hz), 6.88 (d, 1H, J=2.9 Hz), 6.97 (t, 1H, J=5.9 Hz), 7.10 (d, 1H, J=8.8 Hz), 7.13 (s, 1H), 7.36 (t, 1H, J=7.3 Hz), 7.45 (t, 2H, J=7.8 Hz), 7.63 (d, 2H, J=8.3 Hz), 7.65 (d, 2H, J=6.3 Hz), 8.02 (d, 2H, J=7.8 Hz). MS (ES) m/e 691.2 [M+1].

Step B: 3-(4-[2-(2-Biphenyl-4-yl-5-methyl-oxazol-4-yl)-ethoxy]-2-{[(2,5-dichloro-thiophene-3-carbonyl)-amino]-methyl}-phenyl)-propionic acid A solution of the 3-(4-[2-(2-biphenyl-4-yl-5-methyl-oxazol-4-yl)-ethoxy]-2-{[(2,5-dichloro-thiophene-3-carbonyl)-amino]-methyl}-phenyl)-propionic acid tert-butyl ester (367 mg, 0.531 mmol) in CH$_2$Cl$_2$ (20 mL) was treated with anisole (2.0 mL) then TFA (6.0 mL). The mixture was stirred at room temperature for 2 h and concentrated. The residue was co-evaporated with CCl$_4$ three times, dried under vacuum, triturated with ether, and filtered to obtain the title compound as a white solid (301 mg, 73%). $^1$H NMR (400 MHz, DMSO-d$_6$): δ 2.25 (s, 3H), 2.38 (t, 2H, J=8.3 Hz), 2.71 (t, 2H, J=7.3 Hz), 2.82 (t, 2H, J=6.3 Hz), 4.07 (t, 2H, J=6.6 Hz), 4.28 (d, 2H, J=4.9 Hz), 6.68 (d, 1H, J=9.3 Hz), 6.77 (s, 1H), 7.00 (d, 1H, J=8.3 Hz), 7.24 (s, 1H), 7.29 (t, 1H, J=5.9 Hz), 7.39 (t, 2H, J=7.8 Hz), 7.63 (t, 2H, J=7.8 Hz), 7.71 (d, 2H, J=8.3 Hz), 7.88 (d, 2H, J=8.3 Hz), 8.69 (t, 2H, J=5.9 Hz). MS (ES) m/e 635.1 [M+1].

EXAMPLES 232-318

Examples 232-318 are prepared by following a substantially similar procedure as described in Example 231 and Standard coupling procedure A and Standard hydrolysis procedures C to E.

| No. | Compounds | MS (ES+) |
|---|---|---|
| 232 | 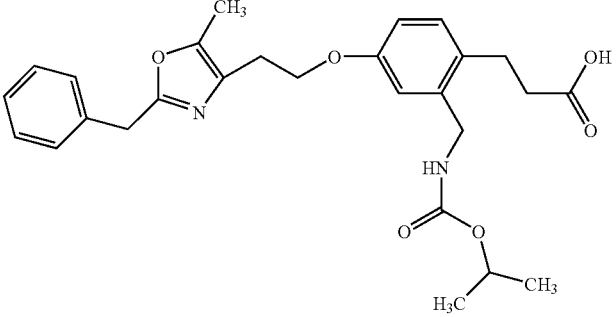 | 481.3 |
| 233 | 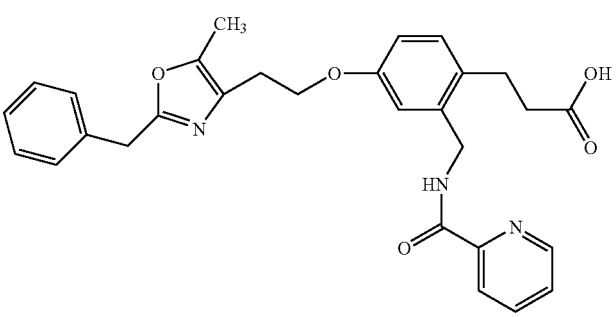 | 500.3 |
| 234 | 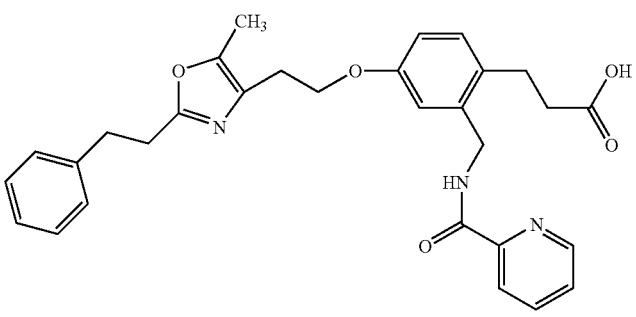 | 514.3 |
| 235 | 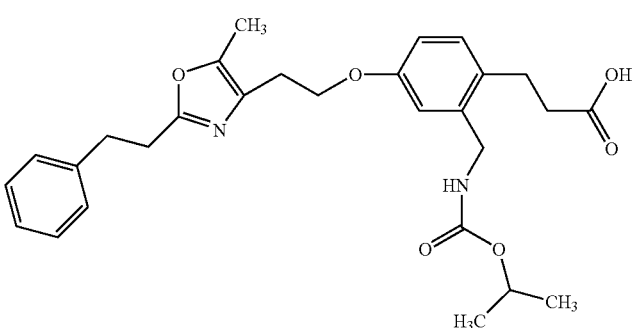 | 495.3 |

-continued

| No. | Compounds | MS (ES+) |
|---|---|---|
| 236 | | 475.1 |
| 237 | | 494.3 |
| 238 | | 542.2 |
| 239 | | 523.3 |

|      | -continued |          |
|------|------------|----------|
| No.  | Compounds  | MS (ES+) |
| 240  |            | 480.3    |
| 241  |            | 499.2    |
| 242  |            | 503      |
| 243  |            | 484      |

-continued

| No. | Compounds | MS (ES+) |
|---|---|---|
| 244 | | 524.4 |
| 245 | | 586.3 |
| 246 | | 567.3 |
| 247 | | 505.3 |

-continued
| No. | Compounds | MS (ES+) |
|---|---|---|
| 248 | 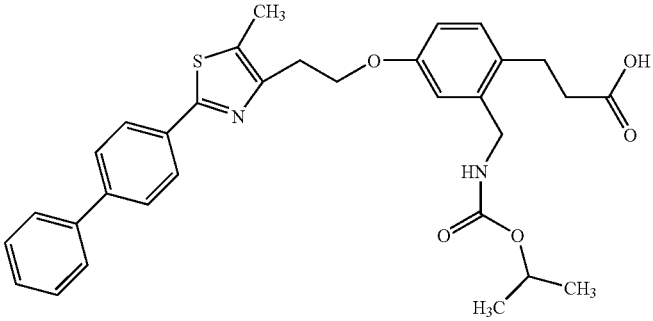 | 559.2 |
| 249 | 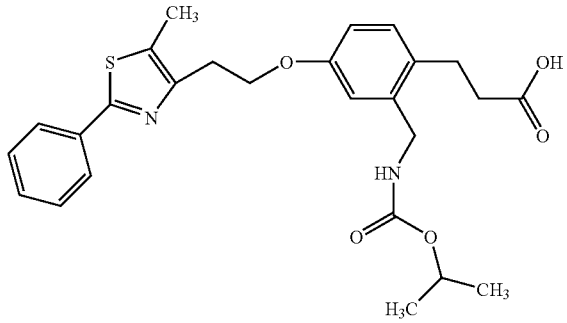 | 483.2 |
| 250 | 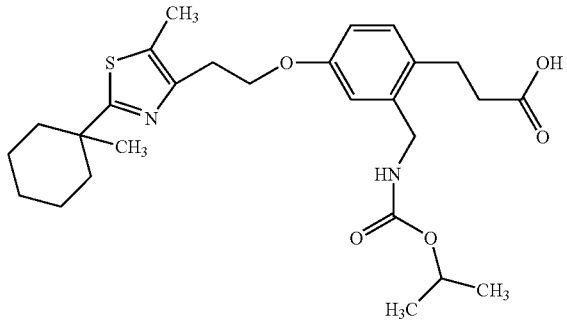 | 487.3 |
| 251 | 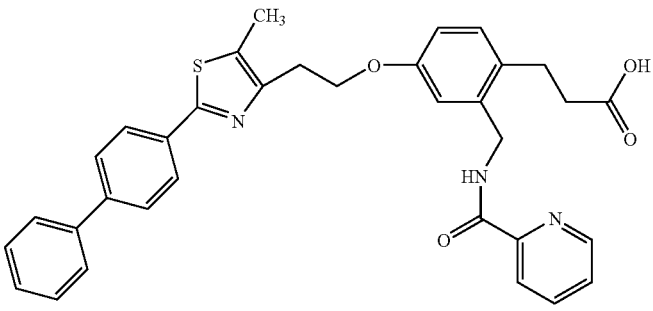 | 578.3 |

-continued
| No. | Compounds | MS (ES+) |
|---|---|---|
| 252 | 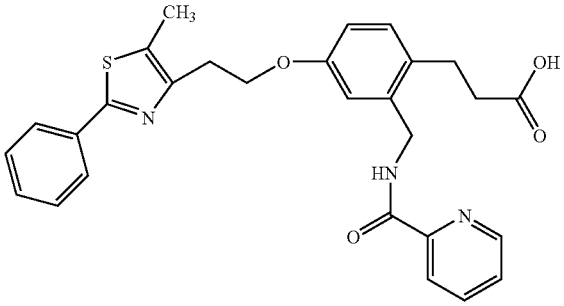 | 502.2 |
| 253 | 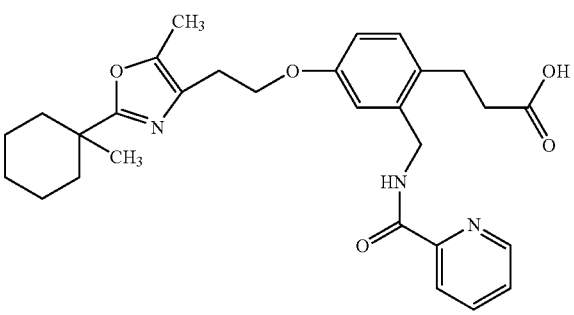 | 503.3 |
| 254 | 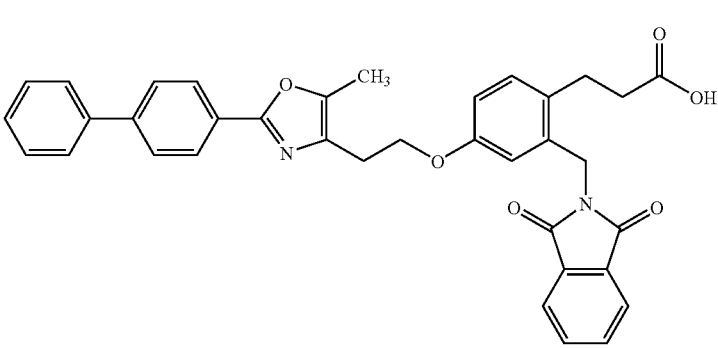 | 587.2 |
| 255 | 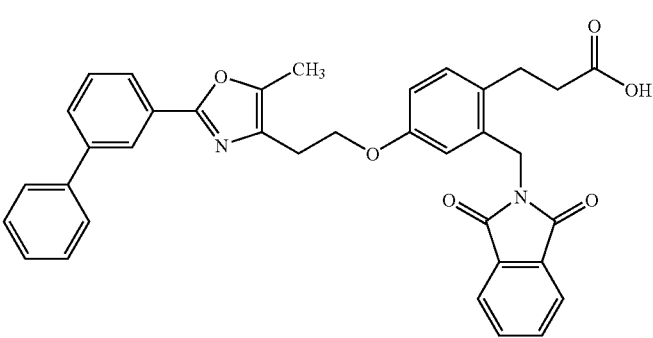 | 587.2 |
| 256 | 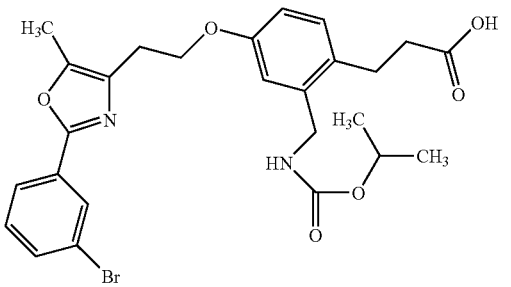 | 545/547 |

-continued

| No. | Compounds | MS (ES+) |
|---|---|---|
| 257 | | 545/547 |
| 258 | | 535 |
| 259 | | 560 |
| 260 | | 579 |

-continued
| No. | Compounds | MS (ES+) |
|---|---|---|
| 261 | 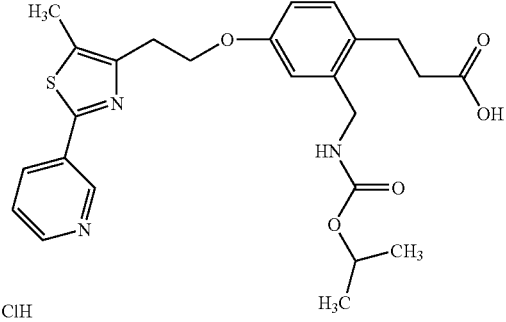 ClH | 484 |
| 262 | 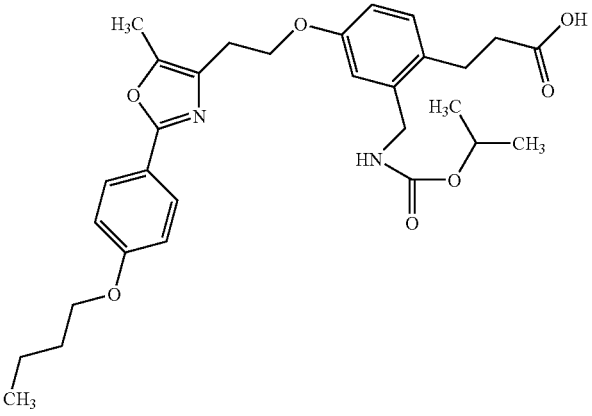 | 539 |
| 263 | 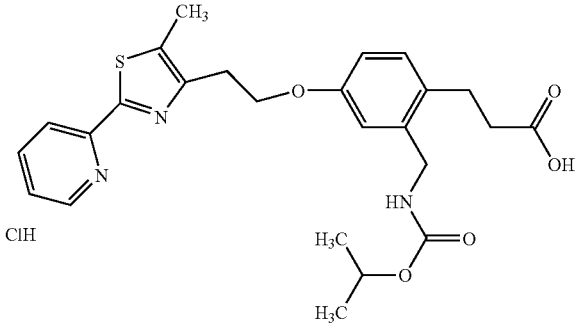 ClH | 484 |
| 264 | 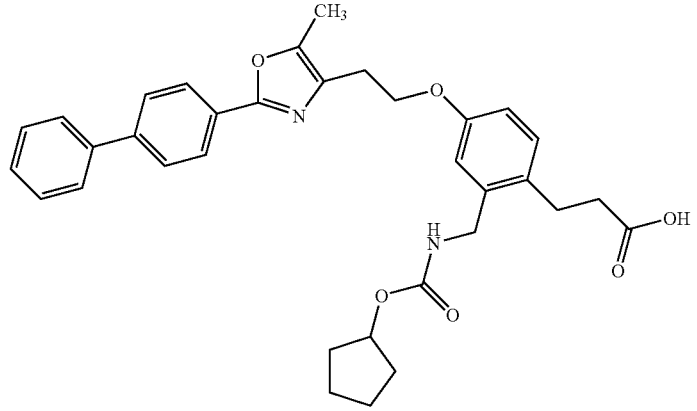 | 569 |

| No. | Compounds | MS (ES+) |
|---|---|---|
| 265 | 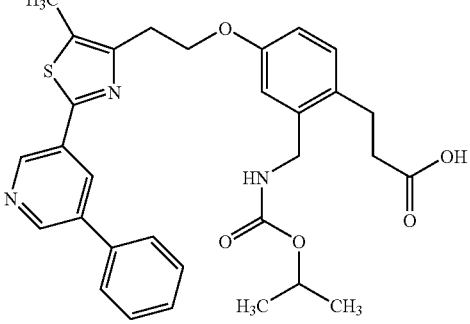 | 560 |
| 266 | 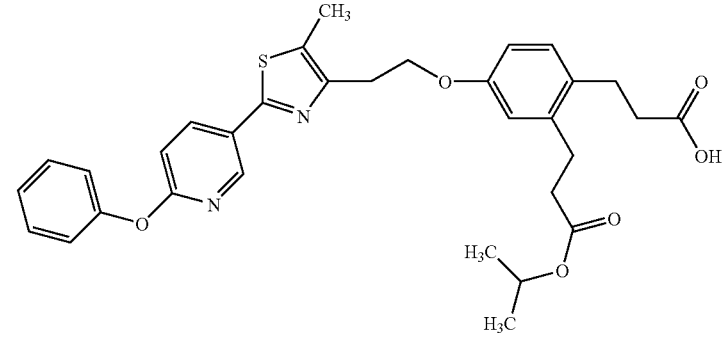 | 576.1 |
| 267 | 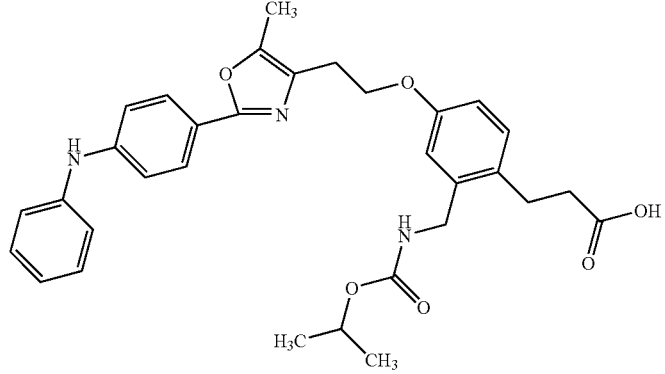 | 558.4 |
| 268 | 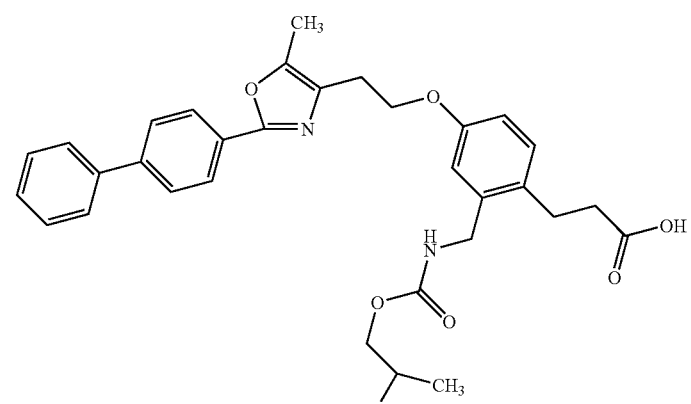 | 557.2 |

-continued
| No. | Compounds | MS (ES+) |
|---|---|---|
| 269 | 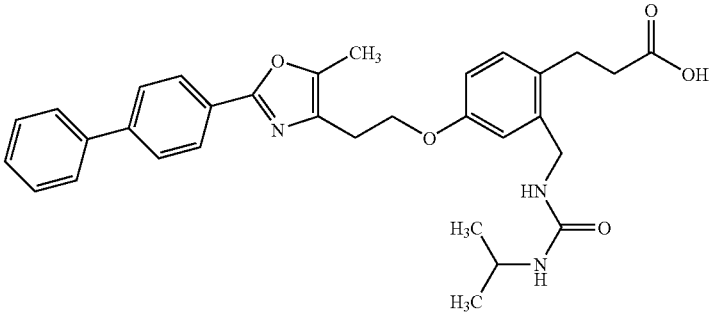 | 542 |
| 270 | 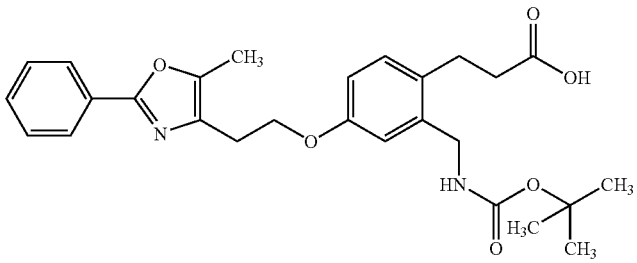 | 481.3 |
| 271 | 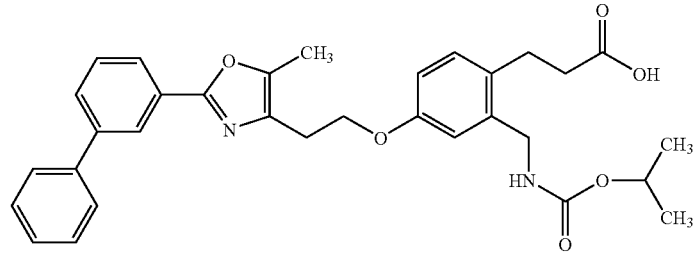 | 543.2 |
| 272 | 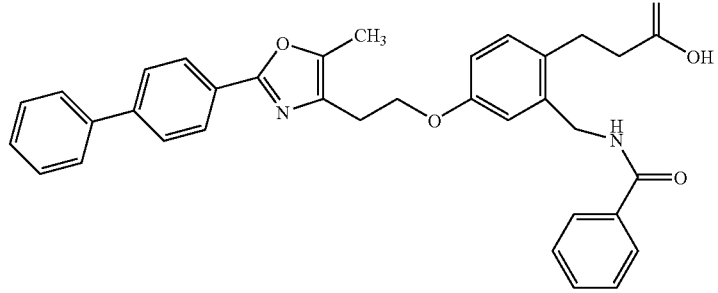 | 561.3 |
| 273 | 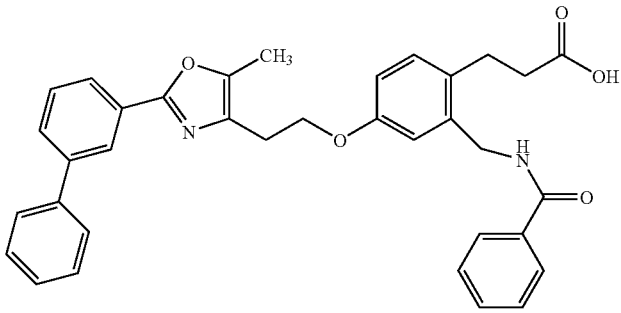 | 561.3 |

-continued

| No. | Compounds | MS (ES+) |
|---|---|---|
| 274 | | 491.3 |
| 275 | | 491.2 |
| 276 | | 539.3 |
| 278 | | 539.3 |
| 279 | | 469.3 |

-continued

| No. | Compounds | MS (ES+) |
|---|---|---|
| 280 | | 469.3 |
| 281 | | 488.1 |
| 282 | | 473.3 |
| 283 | | 473.2 |
| 284 | | 562.2 |

-continued

| No. | Compounds | MS (ES+) |
|---|---|---|
| 285 | | 562.3 |
| 286 | | 492.2 |
| 287 | | 492.2 |
| 288 | | 511.2 |

| No. | Compounds | MS (ES+) |
|---|---|---|
| 289 | 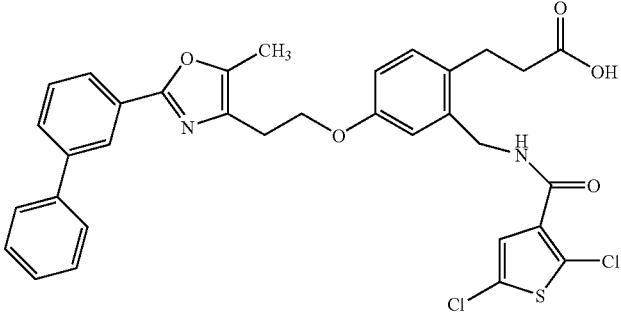 | 635.2 |
| 290 | 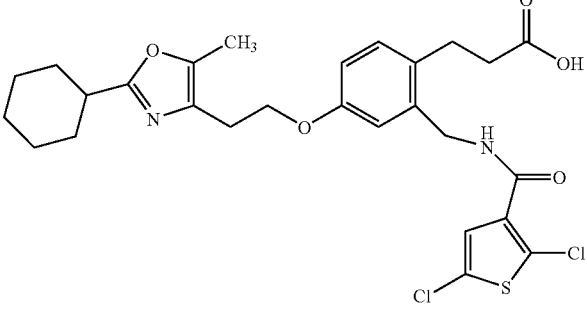 | 565.2 |
| 291 | 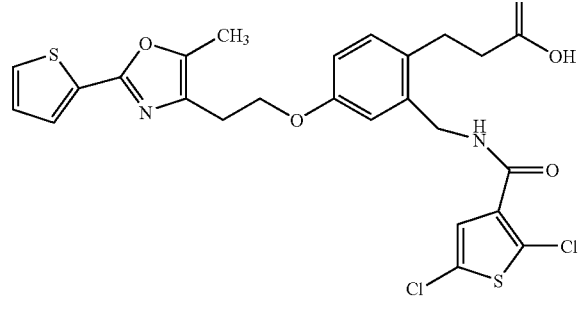 | 565 |
| 292 | 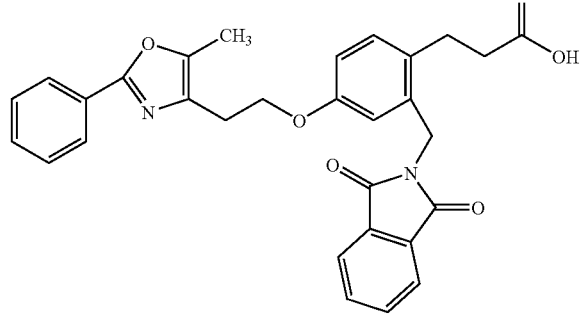 | 511 |

| No. | Compounds | MS (ES+) |
|---|---|---|
| 293 | 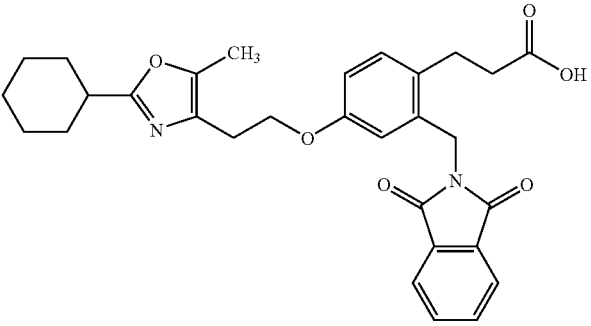 | 517 |
| 294 | 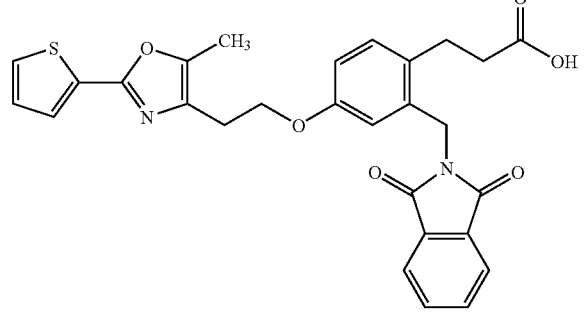 | 517 |
| 295 | 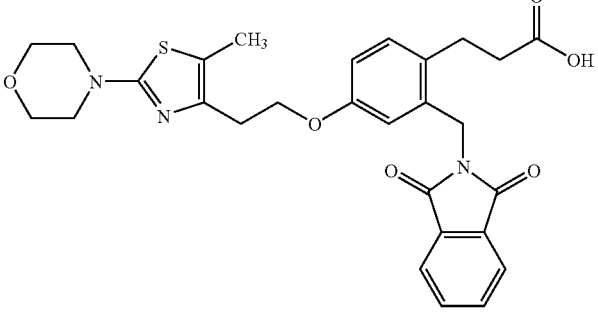 | 536 |
| 296 | 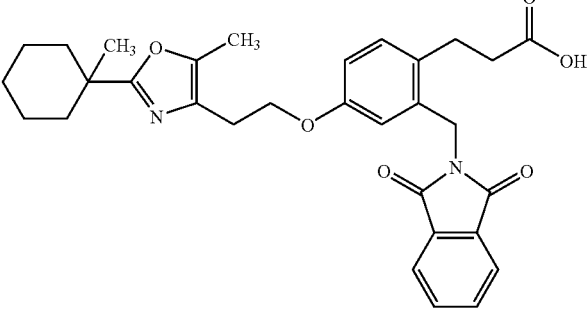 | 531 |

| No. | Compounds | MS (ES+) |
|---|---|---|
| 297 | 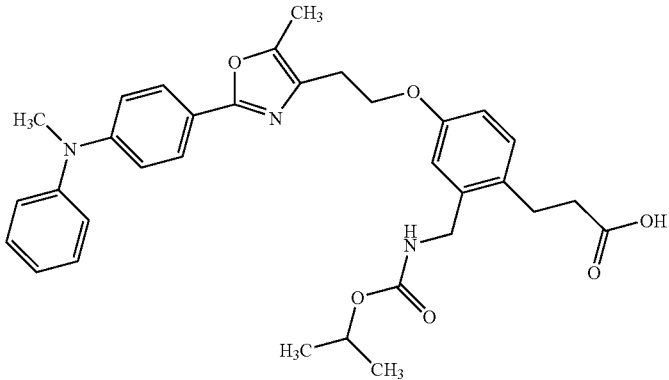 | 572.2 |
| 298 | 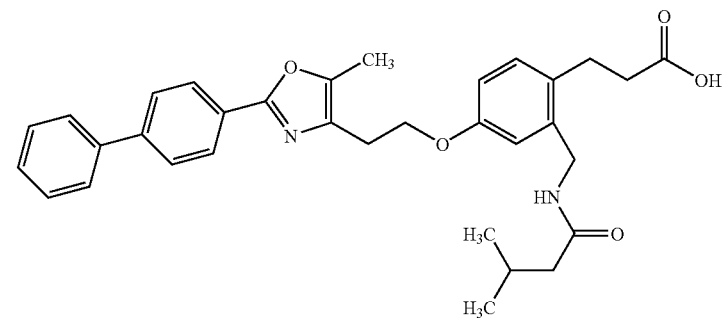 | 541 |
| 299 | 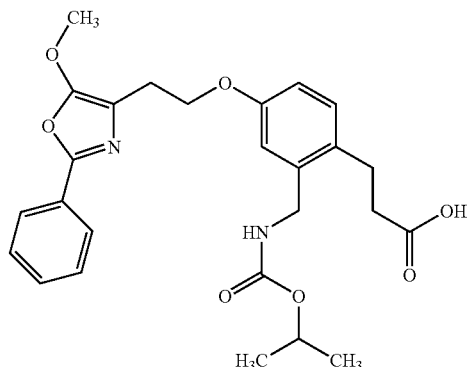 | 483 |
| 300 | 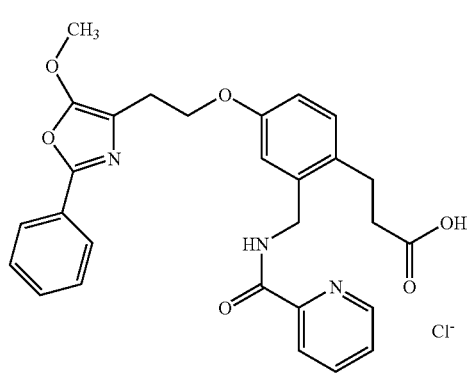 | 502 |

-continued
| No. | Compounds | MS (ES+) |
|---|---|---|
| 301 | 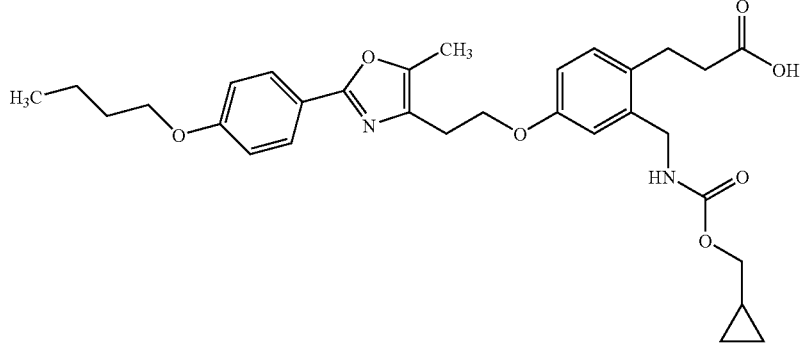 | 551.2770 (HRMS) |
| 302 | 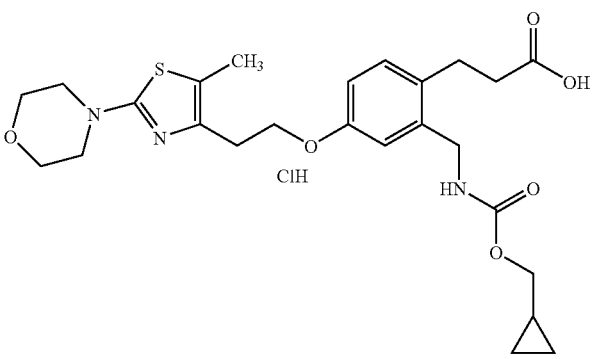 | 504.2171 (HRMS) |
| 303 | 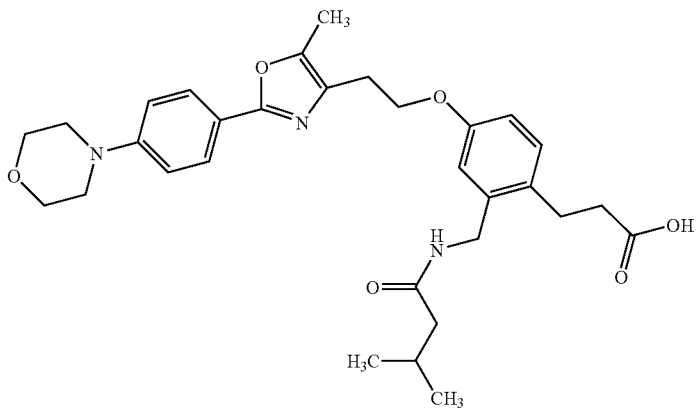 | 550.2 |
| 304 | 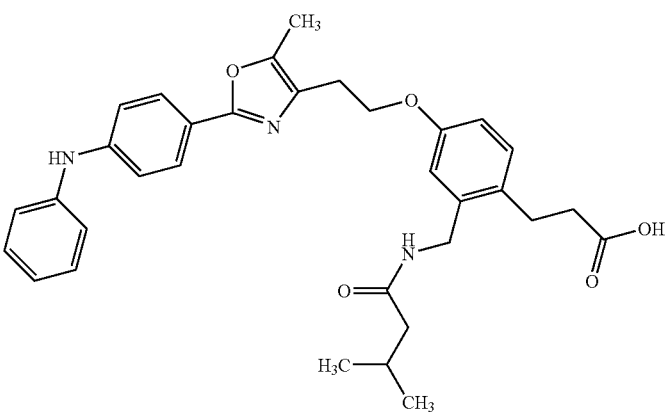 | 554 |

-continued

| No. | Compounds | MS (ES+) |
|---|---|---|
| 305 | | 557.2 |
| 306 | | 490.2 |
| 307 | | 555.2426 (HRMS) |
| 308 | | 571.2436 (HRMS) |

| No. | Compounds | MS (ES+) |
|---|---|---|
| 309 | 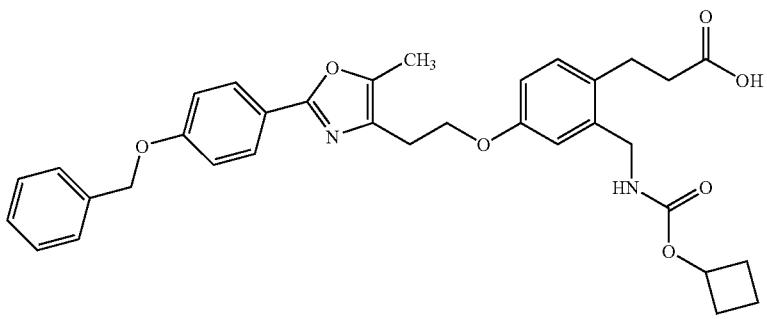 | 585.2595 (HRMS) |
| 310 | 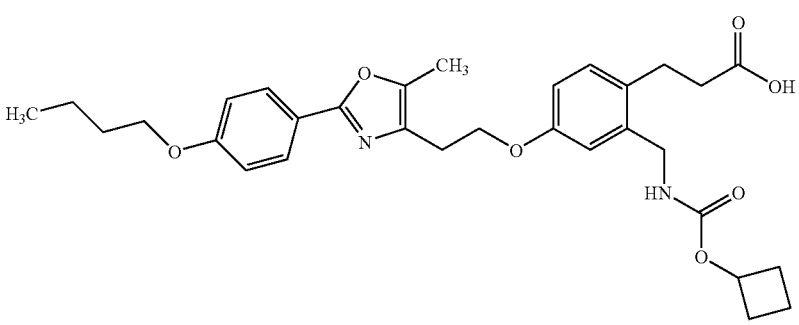 | 551.2753 (HRMS) |
| 311 | 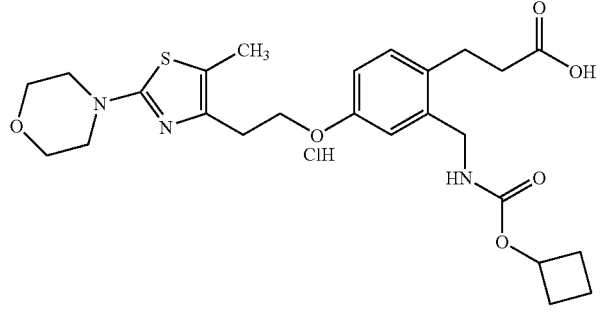 | 504.2144 (HRMS) |
| 312 | 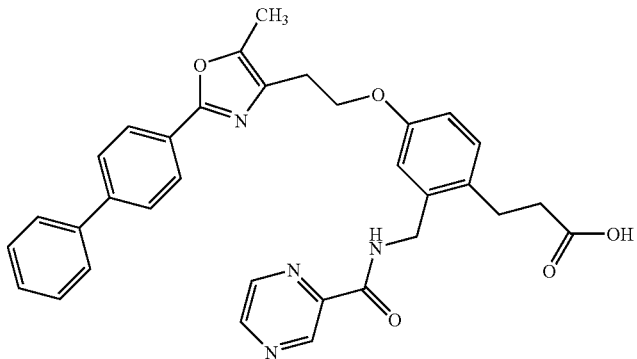 | 563.2 |

-continued

| No. | Compounds | MS (ES+) |
|---|---|---|
| 313 | | 579.2 |
| 314 | | 572.2 |
| 315 | | 495.2 |
| 316 | | 512.2 |

| No. | Compounds | MS (ES+) |
|---|---|---|
| 317 | 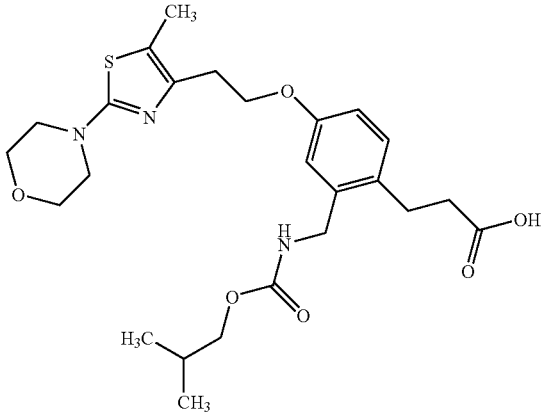 | 506.2 |
| 318 | 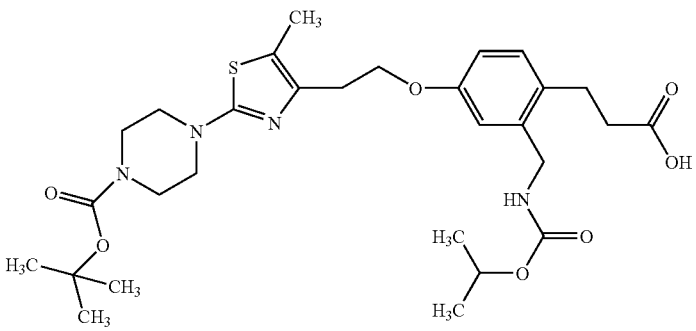 | ¹H NMR |
¹H NMR data for Example 318: (400 MHz, CDCl₃): d 6.98 (1H, d, J=7.9 Hz), 6.71 (1H, s), 6.68 (1H, d, J=7.9 Hz), 4.97 (1H, m), 4.86 (2H, m), 4.31 (2H, bs), 4.08 (2H, t, J=6.5 Hz), 3.45 (4H, m), 3.27 (4H, m), 2.86 (4H, m), 2.55 (2H, bs), 2.18 (3H, s), 1.42 (9H, s), 1.16 (6H, d, J=7.2 Hz).
Example 319
{4-[2-(5-Methyl-2-(4-phenyl)phenyl-oxazol-4-yl)-ethoxy]-2-(isopropylcarbamate)-methyl}-propionic acid
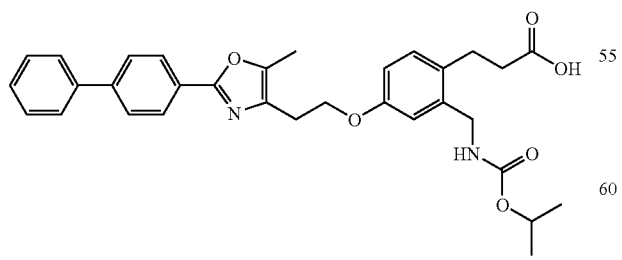

Step A: {4-[2-(5-Methyl-2-(4-phenyl)phenyl-oxazol-4-yl)-ethoxy]-2-(isopropylcarbamate)methyl}-propionic acid tert-butyl ester

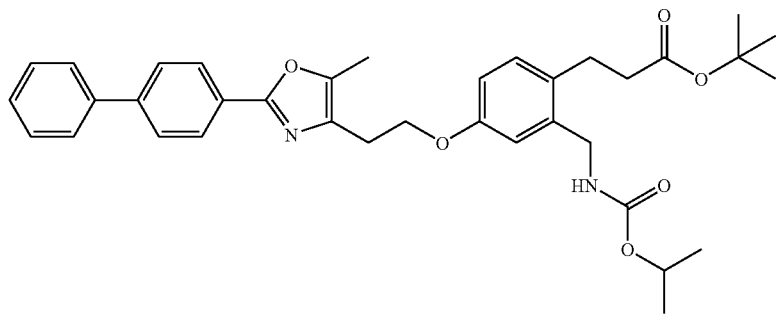

3-[4-hydroxy-2-(isopropoxycarbonylamino-methyl)-phenyl]-propionic acid tert-butyl ester (258 mg, 0.763 mmol) and toluene-4-sulfonic acid 2-(2-biphenyl-4-yl-5-methyl-oxazol-4-yl)-ethyl ester (654 mg, 1.51 mmol) were reacted according to Standard procedure A. Purification by radial chromatography (CH$_2$Cl$_2$/EtOAc 98/2 to 90/10) gave the title compound in quantitative yield. $^1$H NMR (400 MHz, CDCl$_3$): δ 1.14 (d, 6H, J=5.9 Hz), 1.31 (s, 9H), 2.30 (s, 3H), 2.39 (t, 2H, J=7.6 Hz), 2.89 (t, 2H, J=6.6 Hz), 4.14 (t, 2H, J=6.6 Hz), 4.25 (d, 2H, J=5.4 Hz), 4.85 (heptet, 1H, J=5.8 Hz), 6.67 (dd, 1H, J=8.3 Hz, J=2.4 Hz), 6.75 (d, 1H, J=2.4 Hz), 6.99 (d, 1H, J=8.3 Hz), 7.26-7.30 (m, 1H), 7.37 (t, 2H, J=7.6 Hz), 7.53-7.58 (m, 4H), 7.95 (d, 2H, J=8.3 Hz). MS (ES) m/e 599.4 [M+1].

Step B: {4-[2-(5-Methyl-2-(4-phenyl)phenyl-oxazol-4-yl)-ethoxy]-2-(isopropylcarbamate)methyl}-propionic acid A solution of {4-[2-(5-methyl-2-(4-phenyl)phenyl-oxazol-4-yl)-ethoxy]-2-(isopropylcarbamate)methyl}-propionic acid (414 mg, 0.763 mmol) in CH$_2$Cl$_2$ (10 mL) was treated with anisole (1.0 mL) then trifluoroacetic acid (TFA, 3.0 mL). The solution was stirred at room temperature for 2 h and concentrated. The residue was co-evaporated with CCl$_4$ twice, dried under vacuum, triturated with ether, and filtered to obtain the title compound as a white solid (287 mg, 69%). $^1$H NMR (400 MHz, CDCl$_3$) δ 1.11 (d, 6H, J=5.9 Hz), 2.28 (s, 3H), 2.46 (t, 2H, J=7.6 Hz), 2.79 (t, 2H, J=7.6 Hz), 2.86 (t, 2H, J=6.6 Hz), 4.11 (t, 2H, J=6.8 Hz), 4.24 (d, 2H, J=5.4 Hz), 4.82 (heptet, 1H, J=6.1 Hz), 5.05 (bs, 1H), 6.66 (dd, 1H, J=2.4, 8.3 Hz), 6.73 (d, 1H, J=2.4 Hz), 6.99 (d, 1H, J=8.3 Hz), 7.24-7.28 (m, 1H), 7.35 (t, 2H, J=7.6 Hz), 7.51-7.56 (m, 4H), 7.98 (d, 2H, J=8.3 Hz). MS (ES) m/e 543.1 [M+1].

Example 320

3-{2-(Isopropoxycarbonylaminomethyl)-4-[2-(5-methyl-2-morpholin-4-yl-thiazol-4-yl)ethoxy]-phenyl}propionic acid

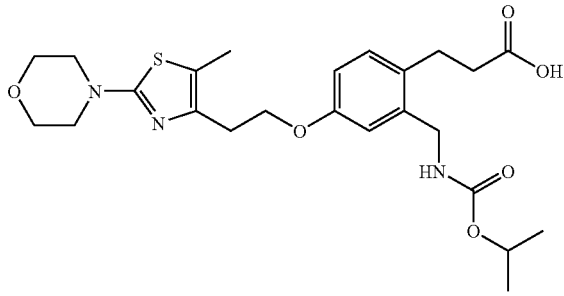

Step A: 3-{2-(Isopropoxycarbonylamino-methyl)-4-[2-(5-methyl-2-morpholin-4-yl-thiazol-4-yl)-ethoxy]-phenyl}-propionic acid tert-butyl ester

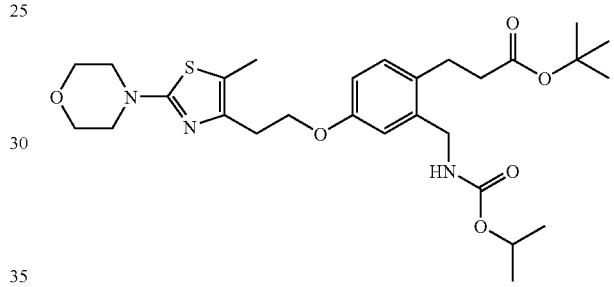

3-[4-hydroxy-2-(isopropoxycarbonylamino-methyl)-phenyl]-propionic acid tert-butyl ester (272 mg, 0.806 mmol) and toluene-4-sulfonic acid 2-(5-methyl-2-morpholin-4-yl-thiazol-4-yl)-ethyl ester (522 mg, 1.36 mmol) were reacted according to Standard procedure A. Purification using radial chromatography (CH$_2$Cl$_2$/EtOAc 98:2 to 75:25) gave the title compound as a white solid (387 mg, 98%). $^1$H NMR (400 MHz, CDCl$_3$) δ 1.14 (d, 6H, J=5.9 Hz), 1.32 (s, 9H), 2.16 (s, 3H), 2.39 (t, 2H, J=7.6 Hz), 2.77 (t, 2H, J=7.6 Hz), 2.84 (t, 2H, J=7.1 Hz), 3.28 (t, 4H, J=4.9 Hz), 3.70 (t, 4H, J=4.9 Hz), 4.08 (t, 2H, J=7.1 Hz), 4.25 (d, 2H, J=5.4 Hz), 4.83 (heptet, 1H, J=4.9 Hz), 6.66 (dd, 1H, J=2.4, 8.3 Hz), 6.72 (d, 1H, J=2.4 Hz), 6.98 (d, 1H, J=8.3 Hz). MS (ES) m/e 548.3 [M+1].

Step B: 3-{2-(Isopropoxycarbonylaminomethyl)-4-[2-(5-methyl-2-morpholin-4-yl-thiazol-4-yl)ethoxy]-phenyl}propionic acid A solution of 3-{2-(isopropoxycarbonylamino-methyl)-4-[2-(5-methyl-2-morpholin-4-yl-thiazol-4-yl)-ethoxy]-phenyl}-propionic acid tert-butyl ester (387 mg, 0.706 mmol) in CH$_2$Cl$_2$ (10 mL) was treated with anisole (1 mL) then TFA (3 mL). The solution was stirred at room temperature for 2 h and concentrated. The residue was co-evaporated with CCl$_4$ twice, dried under vacuum, triturated with ether, and filtered to obtain the title compound as a white solid (236 mg, 60%), isolated as the trifluoracetic acid salt: $^1$H NMR (400 MHz, CDCl$_3$) δ 1.12 (d, 6H, J=6.4 Hz), 2.16 (s, 3H), 2.47 (t, 2H, J=7.6 Hz), 2.79 (t, 2H, J=7.6 Hz), 2.87 (t, 2H, J=6.4 Hz), 3.35 (t, 4H, J=4.9 Hz), 3.70 (t, 4H, J=4.9 Hz), 4.07 (t, 2H, J=6.6 Hz), 4.23 (d, 2H, J=5.4 Hz), 4.82 (heptet, 1H, J=6.1 Hz), 5.07 (bs, 1H), 6.63 (dd, 1H, J=2.7, 8.6 Hz), 6.69 (d, 1H, J=2.9 Hz), 6.98 (d, 1H, J=8.3 Hz). MS (ES) m/e 492.1 [M+1].

Example 321

3-(2-(2-Isopropoxycarbonyl-ethyl)-4-{2-[5-methyl-2-(6-phenoxy-pyridin-3-yl)-oxazol-4-yl]ethoxy}-phenyl)-propionic acid

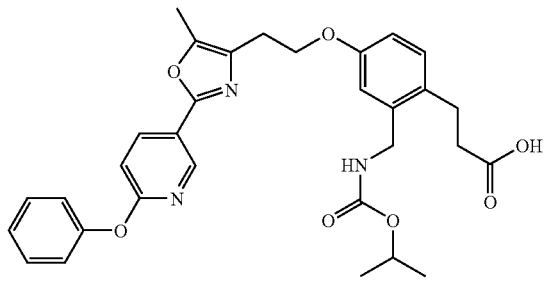

Step A: 3-(2-(2-Isopropoxycarbonyl-ethyl)-4-{2-[5-methyl-2-(6-chloro-pyridin-3-yl)-oxazol-4-yl]ethoxy}-phenyl)-propionic acid t-butyl ester

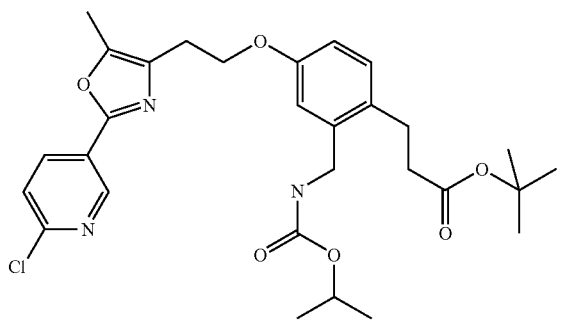

Toluene-4-sulfonic acid 2-[2-(6-chloro-pyridn-3-yl)-5-methyl-oxaxol-4-yl]-ethyl ester tosylate (290 mg, 0.74 mmol) and 3-[4-hydroxy-2-(2-isopropoxycarbonyl-ethyl)-phenyl]-propionic acid t-butyl ester (274 mg, 0.81 mmol) were converted to the title compound (183 mg, 44%) according to Standard procedure A. MS (ESI) m/z 559 (M+H)$^+$.

Step B: 3-(2-(2-Isopropoxycarbonyl-ethyl)-4-{2-[5-methyl-2-(6-phenoxy-pyridin-3-yl)-oxazol-4-yl]ethoxy}-phenyl)-propionic acid To a suspension of NaH (20 mg, 0.48 mmol) in DMF (10 mL) at ambient temperature was added phenol (45 mg, 0.48 mmol). The mixture was stirred at 60° C. for 20 min, and 3-(2-(2-isopropoxycarbonyl-ethyl)-4-{2-[5-methyl-2-(6-chloro-pyridin-3-yl)-oxazol-4-yl]ethoxy}-phenyl)-propionic acid t-butyl ester (180 mg, 0.32 mmol) was added. The resulting mixture was stirred at 60° C. overnight, cooled, diluted with EtOAc, and washed with water/brine (4×). The organic layer was dried (MgSO$_4$), filtered and concentrated. The residue was purified by silica gel chromatography (hexanes/EtOAc 3/1 to 1/1) to afford the intermediate ester as an oil (60 mg, 30%). The title compound was generated using Standard hydrolysis procedure C. MS (ESI) m/z 560 (M+H)$^+$. $^1$H NMR (CDCl$_3$, 250 MHz) δ 1.25 (d, J=0.5 Hz, 6H), 2.42 (s, 3H), 2.65 (m, 2H), 2.96 (m, 4H), 4.38 (m, 2H), 4.18 (m, 2H), 4.38 (m, 1H), 5.00 (m, 2H), 6.82 (m, 3H), 6.96 (m, 1H), 7.12 (m, 1H), 7.20 (m, 2H), 7.45 (m, 2H), 8.28 (m, 1H), 8.80 (m, 1H).

Example 322

3-[4-[2-(3-Biphenyl-4-yl-5-methyl-pyrazol-1-yl)-ethoxy]-2-(isopropoxycarbonyl-amino-methyl)-phenyl]-propionic acid

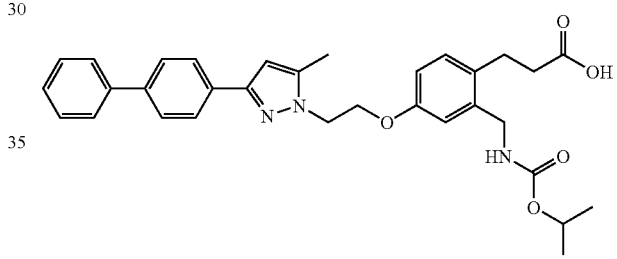

The title compound was prepared from 3-[4-hydroxy-2-(isopropoxycarbonyl-amino-methyl)-phenyl]-propionic acid tert-butyl ester (Prep 16) and 2-(3-biphenyl-4-yl-5-methyl-pyrazol-1-yl)-ethanol (Prep 11) using Standard coupling procedure B followed by Standard hydrolysis procedure C. MS [ES] m/e 542 (M+1)$^+$.

The following Examples 323 to 333 are prepared by following a substantially similar procedure as described in Example 322.

EXAMPLES 323

3-{2-(Isopropoxycarbonylamino-methyl)-4-[2-(5-methyl-3-phenyl-pyrazol-1-yl)-ethoxy]-phenyl}-propionic acid

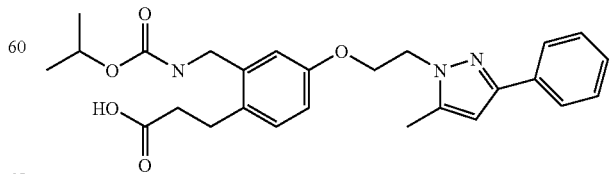

HRMS Calculated for C$_{26}$H$_{32}$N$_3$O$_5$: m/z 466.2342. Found: 466.2331.

EXAMPLES 324

3-(4-[2-(3-Biphenyl-4-yl-5-methyl-pyrazol-1-yl)-ethoxy]-2-{[(pyridine-2-carbonyl)-amino]-methyl}-phenyl)-propionic acid trifluoroacetate

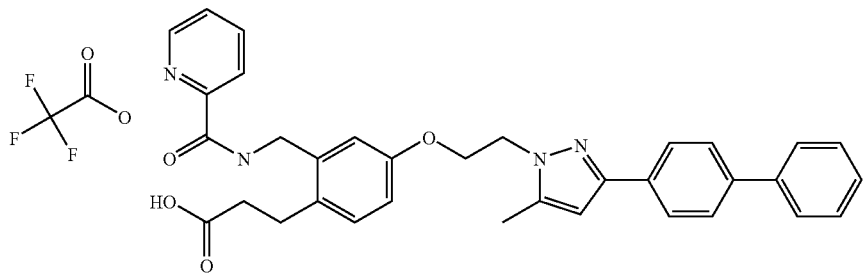

HRMS Calculated for $C_{28}H_{30}N_4O_4$: m/z 486.2267. Found: 486.2233.

EXAMPLES 325

3-[4-[2-(5-Biphenyl-4-yl-3-methyl-pyrazol-1-yl)-ethoxy]-2-(isopropoxycarbonylamino-methyl)-phenyl]-propionic acid

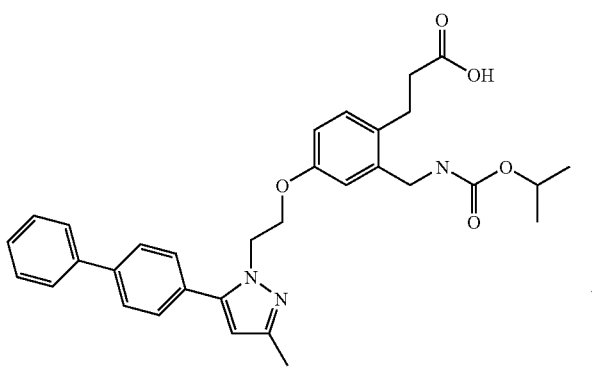

HRMS Calculated for $C_{32}H_{36}N_3O_5$: m/z 542.2655. Found: 542.2678.

EXAMPLES 326

3-[4-{2-[3-(4-Bromo-phenyl)-5-methyl-pyrazol-1-yl]-ethoxy}-2-(isopropoxycarbonylamino-methyl)-phenyl]-propionic acid tert-butyl ester

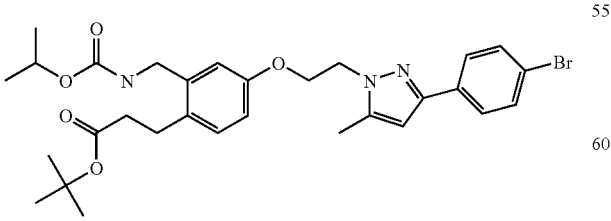

HRMS Calculated for $C_{30}H_{39}BrN_3O_5$: m/z 600.2073. Found: 600.2064;

EXAMPLES 327

3-[4-{2-[3-(4-Bromo-phenyl)-5-methyl-pyrazol-1-yl]-ethoxy}-2-(isopropoxycarbonylamino-methyl)-phenyl]-propionic acid

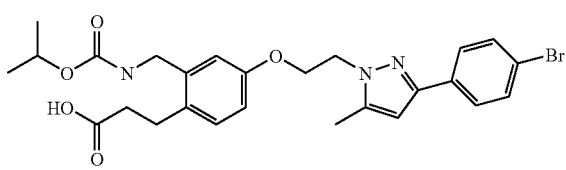

HRMS Calculated for $C_{26}H_{31}BrN_3O_5$: m/z 544.1447. Found: 544.1456.

EXAMPLES 328

3-(4-[2-(5-Methyl-3-naphthalen-2-yl-pyrazol-1-yl)-ethoxy]-2-{[(pyridine-2-carbonyl)-amino]-methyl}-phenyl)-propionic acid hydrochloride

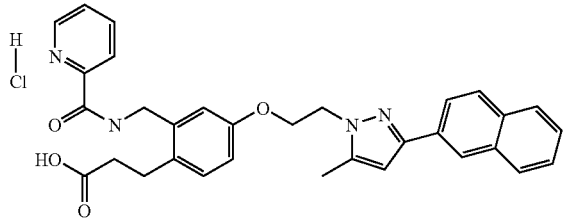

The above compound is prepared by using Standard hydrolysis procedure D. HRMS Calculated for $C_{32}H_{31}N_4O_4$: m/z 535.2345. Found: 535.2343.

EXAMPLES 329

3-{2-(Isopropoxycarbonylamino-methyl)-4-[2-(5-methyl-3-naphthalen-2-yl-pyrazol-1-yl)-ethoxy]-phenyl}-propionic acid

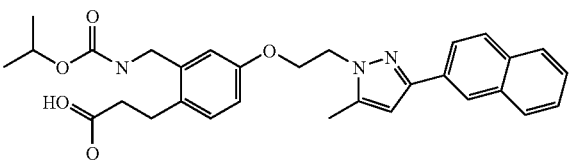

HRMS Calculated for $C_{30}H_{34}N_3O_5$: m/z 516.2498. Found: 516.2485.

EXAMPLES 330

3-{2-(Isopropoxycarbonylamino-methyl)-4-[2-(5-methyl-3-naphthalen-1-yl-pyrazol-1-yl)-ethoxy]-phenyl}-propionic acid

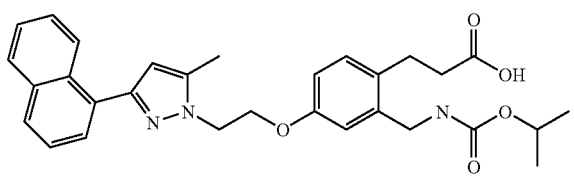

HRMS Calculated for $C_{30}H_{34}N_3O_5$: m/z 516.2498. Found: 516.2529.

EXAMPLES 331

3-{2-(Isopropoxycarbonylamino-methyl)-4-[2-(5-methyl-2-naphthalen-2-yl-oxazol-4-yl)-ethoxy]-phenyl}-propionic acid

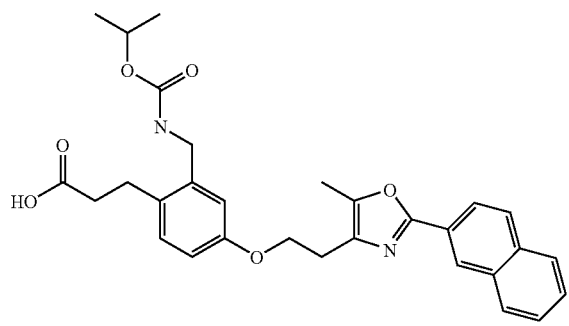

HRMS Calculated for $C_{30}H_{33}N_2O_6$: m/z 517.2339. Found: 517.2328.

EXAMPLES 332

3-{4-[2-(3-Biphenyl-4-yl-5-methyl-pyrazol-1-yl)-ethoxy]-2-[(isopropoxy-carbonyl-methyl-amino)-methyl]-phenyl}-propionic acid

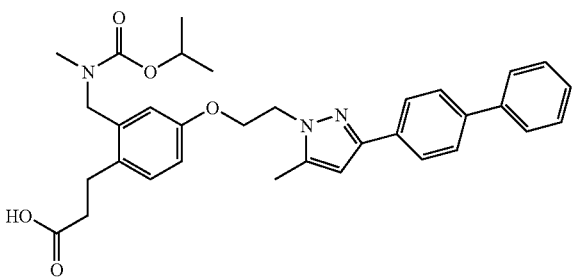

HRMS Calculated for $C_{33}H_{38}N_3O_5$: m/z 556.2811. Found: 556.2819.

EXAMPLES 333

3-{4-{2-[3-(4-Bromo-phenyl)-5-methyl-pyrazol-1-yl]-ethoxy}-2-[(isopropoxy-carbonyl-methyl-amino)-methyl]-phenyl}-propionic acid

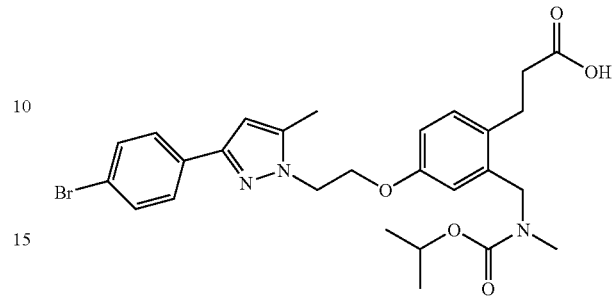

HRMS Calculated for $C_{27}H_{33}BrN_3O_5$: m/z 558.1604. Found: 558.1608.

Example 334

3-{2-(Isopropoxycarbonylamino-methyl)-4-[2-(1-methyl-4-phenyl-1H-imidazol-2-yl)-ethoxy]-phenyl}-propionic acid

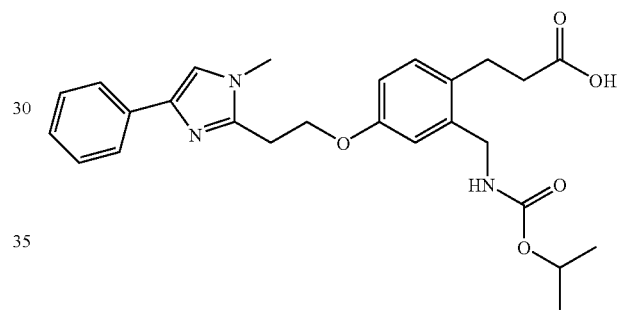

The title compound was prepared from 3-[4-hydroxy-2-(isopropoxycarbonyl-amino-methyl)-phenyl]-propionic acid tert-butyl ester (Prep 16) and 2-(1-Methyl-4-phenyl-1H-imidazol-2-yl)-ethanol (*J. Med. Chem.* 1998, 41(25), 5037-5054) using Standard coupling procedure B followed by Standard hydrolysis procedure D affording an off-white finely-crystalline solid. HRMS Calculated for C26H31N3O5: m/z 466.2342. Found: 466.2355.

Tail Piece Aryl Ring Modifications

Example 335

3-[4-{2-[2-(4-Bromo-phenyl)-5-methyl-oxazol-4-yl]-ethoxy}-2-(isopropoxycarbonyl-amino-methyl)-phenyl]-propionic acid tert-butyl ester

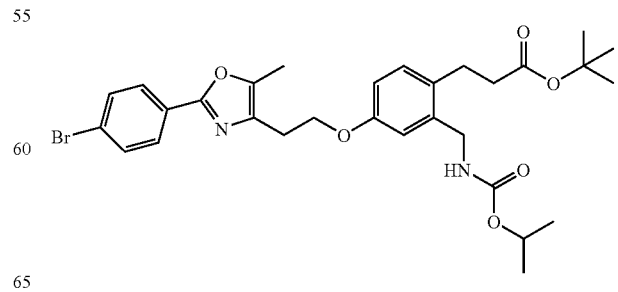

Toluene-4-sulfonic acid 2-[2-(4-bromo-phenyl)-5-methyl-oxazol-4-yl]-ethyl ester (5.06 g, 11.6 mmol) and 3-[4- hydroxy-2-(isopropoxycarbonylamino-methyl)-phenyl]-propionic acid tert-butyl ester (3.01 g, 8.92 mmol) were coupled using Standard procedure A to give the title compound as a white solid (3.41 g, 64%). MS [ES] m/z 601.603 (M+H).

The following Examples 336 to 337 are prepared by following a substantially similar procedure as described in Example 335.

Example 336

3-[4-{2-[2-(3-Bromo-phenyl)-5-methyl-oxazol-4-yl]-ethoxy}-2-(isopropoxy-carbonylamino-methyl)-phenyl]-propionic acid tert-butyl ester

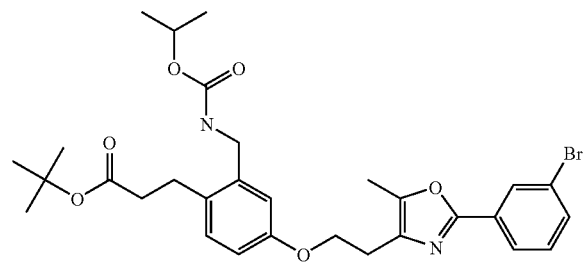

MS [ES] m/z 601.603 (M+H).

Example 337

3-[4-{2-[2-(2-Bromo-phenyl)-5-methyl-oxazol-4-yl]-ethoxy}-2-(isopropoxy-carbonylamino-methyl)-phenyl]-propionic acid tert-butyl ester

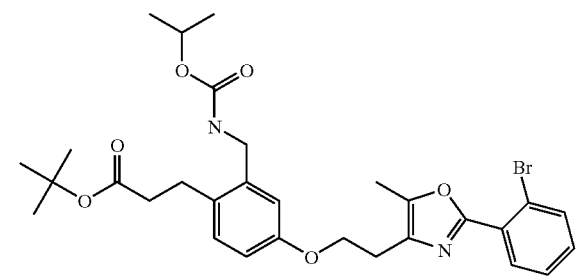

Example 338

3-(2-(Isopropoxycarbonylamino-methyl)-4-{2-[5-methyl-2-(4-pyridin-3-yl-phenyl)-oxazol-4-yl]-ethoxy}-phenyl)-propionic acid

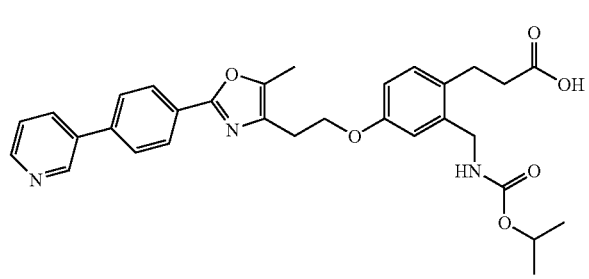

Suzuki Coupling Using Aryl Boronic Acids: A mixture of 3-[4-{2-[2-(4-bromo-phenyl)-5-methyl-oxazol-4-yl]-ethoxy}-2-(isopropoxycarbonylamino-methyl)-phenyl]-propionic acid tert-butyl ester (450 mg, 0.75 mmol), 3-pyridineboronic acid (120 mg, 0.97 mmol), triphenylphosphine (6 mg, 0.024 mmol), 2M aqueous sodium carbonate (3 mL) in n-propanol (15 mL) was sparged with nitrogen for 5 min. Palladium acetate (2 mg, 0.008 mmol) was added, and the reaction was heated to reflux under a blanket of nitrogen for 4 h. The reaction mixture was concentrated and then partitioned between water/EtOAc. The organic layer was dried (MgSO$_4$) and concentrated to crude product (290 mg). This material was purified by silica gel column chromatography to yield 3-(2-(isopropoxycarbonylamino-methyl)-4-{2-[5-methyl-2-(4-pyridin-3-yl-phenyl)-oxazol-4-yl]-ethoxy}-phenyl)-propionic acid tert-butyl ester was obtained as a white solid (230 mg, 51%). $^1$H NMR (CDCl3) δ1.25 (d, 6H), 1.42 (s, 9H), 2.42 (s, 3H), 2.51 (t, 2H), 2.89 (t, 2H), 3.05 (t, 2H), 4.26 (t, 2H), 4.36 (d, 2H), 4.96 (m, 2H), 6.78 (dd, 1H), 6.87 (d, 1H), 7.21 (d, 1H), 7.47 (dd, 1H), 7.67 (d, 2H), 8.00 (dt, 1H), 8.12 (d, 2H), 8.65 (dd, 1H), 8.94 (s, 1H). MS [EI+] m/z 600 (M+H).

This ester (225 mg, 0.375 mmol) was dissolved in THF (15 mL) and treated with 1N HCl (1 mL). The mixture was heated at reflux for 7 h, cooled, and concentrated. The residue was azeotroped twice with acetonitrile and dried in a vacuum oven to give the title compound, isolated as the HCl salt (140 mg, 64%). $^1$H NMR (DMSO-d$_6$) δ1.15 (d, 6H), 2.41 (s, 3H), 2.45 (t, 2H), 2.76 (t, 2H), 2.95 (t, 2H), 4.17 (overlapping t and d, 4H), 4.75 q, 1H), 6.77 (m, 2H), 7.07 (dd, 1H), 7.55 (t, 1H), 8.02 (m, 4H), 8.73 (d, 1H), 8.85 (d, 1H), 9.25 (s, 1H). MS [EI+] m/z 544 (M+H).

The following Examples 339 to 367 are prepared by following a substantially similar procedure as described in Example 338

Example 339

3-(2-(Isopropoxycarbonylaminomethyl)-4-{2-[5-methyl-2-(4-pyridin-3-ylphenyl)oxazol-4-yl]ethoxy}phenyl)propionic acid

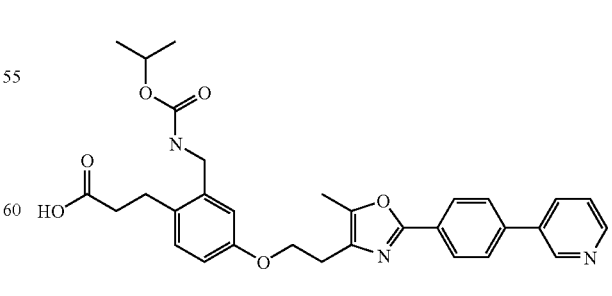

MS (ES) m/z 544 (M+1).

Example 340

3-(2-(Isopropoxycarbonylaminomethyl)-4-{2-[5-methyl-2-(4-pyridin-4-yl-phenyl)oxazol-4-yl]ethoxy}phenyl)propionic acid

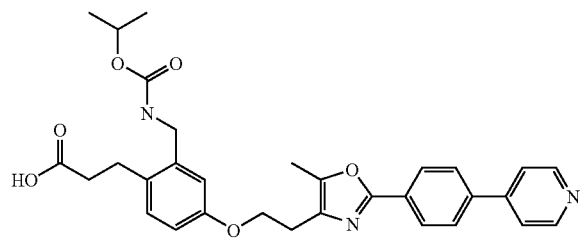

MS (ES) m/z 544 (M+1).

Example 341

3-(2-(Isopropoxycarbonylaminomethyl)-4-{2-[5-methyl-2-(3-pyridin-3-ylphenyl)oxazol-4-yl]ethoxy}phenyl)propionic acid

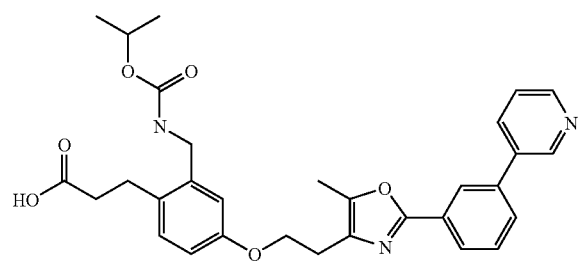

MS (ES) m/z 544 (M+1).

Example 342

3-(2-(Isopropoxycarbonylaminmethyl)-4-{2-[5-methyl-2-(3-pyridin-4-ylphenyl)oxazol-4-yl]ethoxy}phenyl)propionic acid

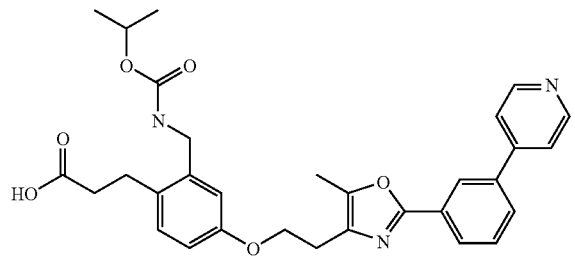

MS (ES) m/z 544 (M+1).

Example 343

3-[4-{2-[2-(4'-Fluorobiphenyl-4-yl)-5-methyloxazol-4-yl]ethoxy}-2-(isopropoxycarbonylaminomethyl)phenyl]propionic acid

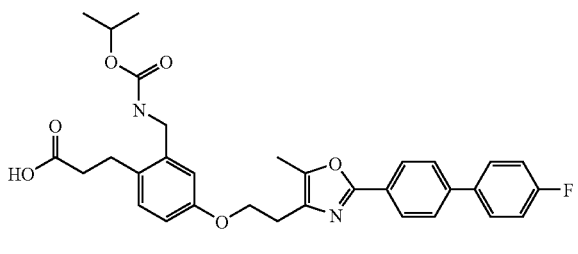

MS (ES) m/z 559 (M+1).

Example 344

3-(2-(Isopropoxycarbonylaminomethyl)-4-{2-[5-methyl-2-(4'-trifluoromethylbiphenyl-4-yl)oxazol-4-yl]ethoxy}phenyl)propionic acid

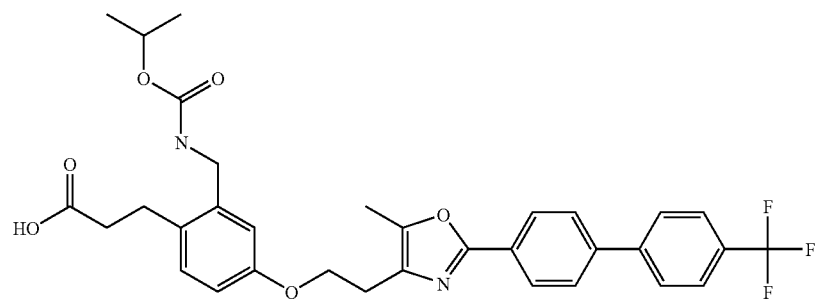

MS (ES) m/z 609 (M+1).

Example 345

3-(2-(Isopropoxycarbonylaminomethyl)-4-{2-[5-methyl-2-(2'-trifluoromethylbiphenyl-4-yl)oxazol-4-yl]ethoxy}phenyl)propionic acid

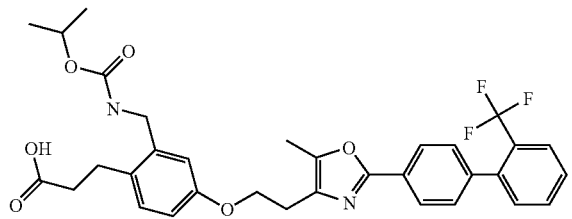

MS (ES) m/z 609 (M+1).

Example 346

3-(2-(Isopropoxycarbonylaminomethyl)-4-{2-[2-(4'-methoxybiphenyl-4-yl)-5-methyloxazol-4-yl]ethoxy}phenyl)propionic acid

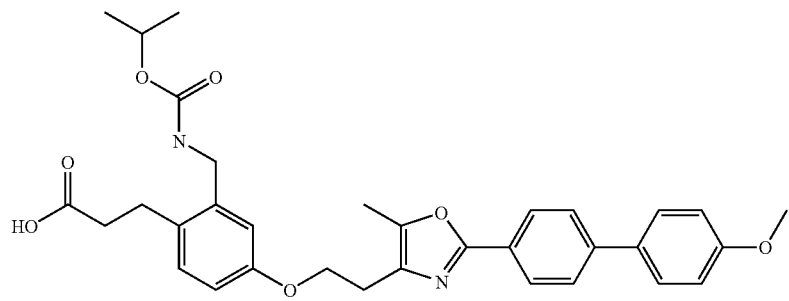

MS (ES) m/z 571 (M+1).

Example 347

3-(2-(Isopropoxycarbonylaminomethyl)-4-{2-[2-(3'-methoxybiphenyl-4-yl)-5-methyloxazol-4-yl]ethoxy}phenyl)propionic acid

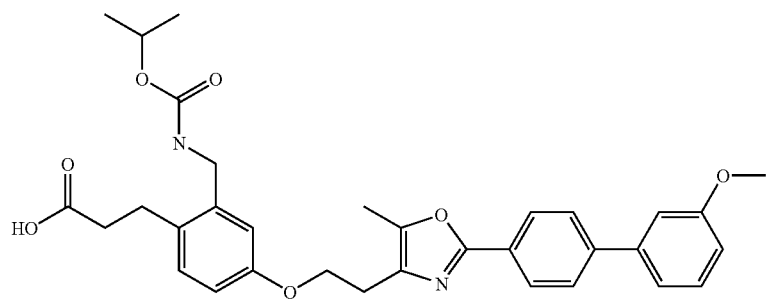

$^1$H-NMR (DMSO-d6) δ 1.16 (d, 6H), 2.39 (s, 3H), 2.45 (t, 2H), 2.76 (t, 2H), 2.95 (t, 2H), 3.85 s, 3H), 4.17 (m, 4H), 4.77 (m, 1H), 6.74–7.55 (m, 7H), 7.83 (d, 2H), 7.99 (d, 2H).

Example 348

3-[4-{2-[2-(4'-Fluorobiphenyl-3-yl)-5-methyloxazol-4-yl]ethoxy}-2-(isopropoxycarbonylaminomethyl)phenyl]propionic acid

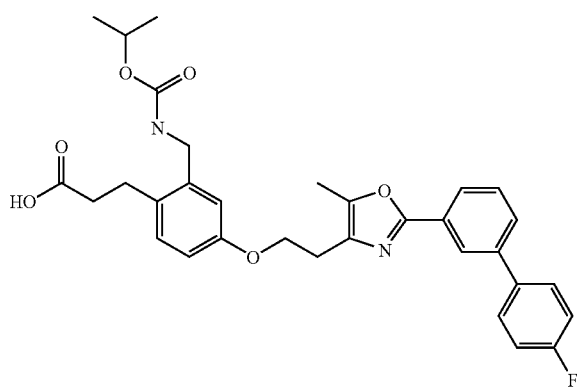

MS (ES) m/z 559 (M+1).

Example 349

3-[4-{2-[2-(3'-Fluorobiphenyl-3-yl)-5-methyloxazol-4-yl]ethoxy}-2-(isopropoxycarbonylaminomethyl)phenyl]propionic acid

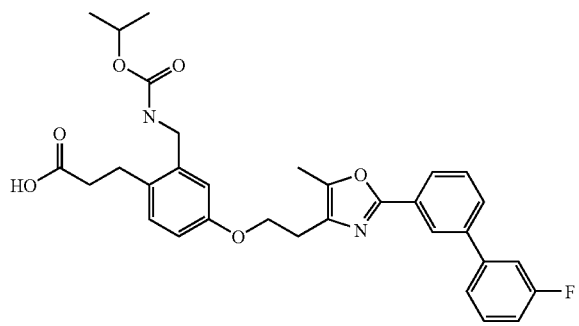

MS (ES) m/z 546 (M+1).

Example 350

3-(2-(Isopropoxycarbonylaminomethyl)-4-{2-[5-methyl-2-(4'-trifluoromethylbiphenyl-3-yl)oxazol-4-yl]ethoxy}phenyl)propionic acid

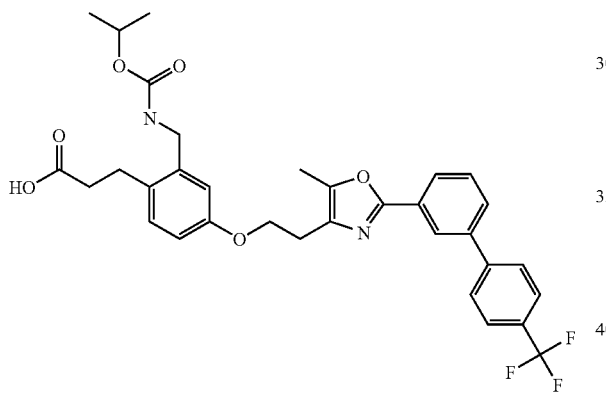

$^1$H-NMR (DMSO-d6) δ 1.15 (d, 6H), 2.40 (s, 3H), 2.45 (t, 2H), 2.79 (t, 2H), 2.96 (t, 2H), 4.17 (m, 4H), 4.75 (m, 1H), 6.77 (m, 2H), 7.08 (d, 1H), 7.53 (m, 1H), 7.66 (m, 1H), 7.83-8.05 (m, ES), 8.20 (s, 1H).

Example 351

3-(2-(Isopropoxycarbonylaminomethyl)-4-{2-[5-methyl-2-(3'-trifluoromethylbiphenyl-3-yl)oxazol-4-yl]ethoxy}phenyl)propionic acid

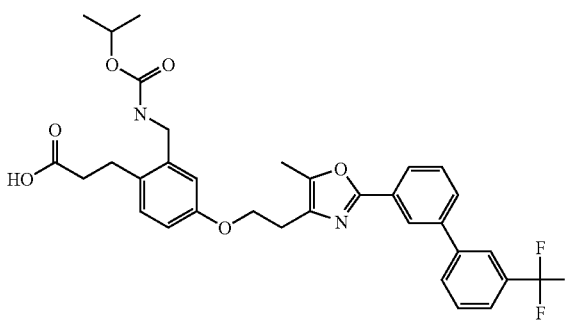

$^1$H-NMR (DMSO-d6) δ 1.14 (d, 6H), 2.40 (s, 3H), 2.45 (t, 2H), 2.67 (t, 2H), 2.95 (t, 2H), 4.16 (m, 4H), 4.74 (m, 1H), 6.77 (m, 2H), 7.09 d, 1H), 7.47-8.20 (m, 8H).

Example 352

3-(2-(Isopropoxycarbonylaminomethyl)-4-{2-[5-methyl-2-(2'-trifluoromethylbiphenyl-3-yl)oxazol-4-yl]ethoxy}phenyl)propionic acid

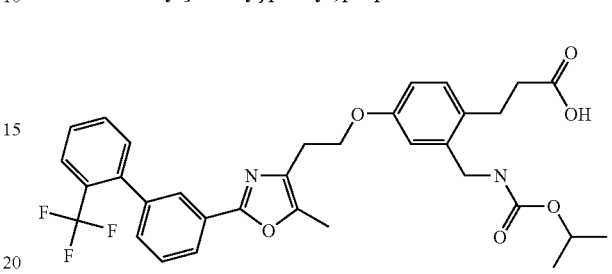

$^1$H-NMR (DMSO-d6) δ 1.13 (d, 6H), 2.36 (s, 3H), 2.44 (t, 2H), 2.77 (t, 2H), 2.93 (t, 2H), 4.15 (m, 4H), 4.74 (m, 1H), 6.76 (m, 2H), 7.06 (d, 1H), 7.40-8.00 (m, 8H).

Example 353

3-(2-(Isopropoxycarbonylaminomethyl)-4-{2-[2-(3'-methoxybiphenyl-3-yl)-5-methyloxazol-4-yl]ethoxy}phenyl)propionic acid

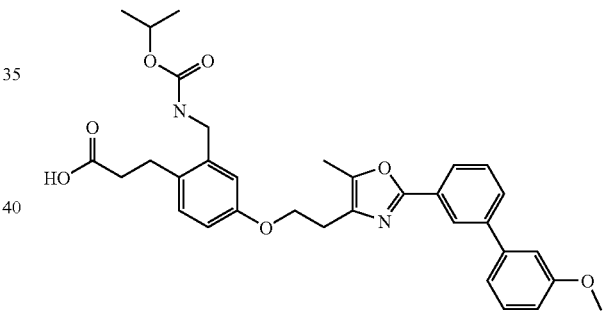

MS (ES) m/z 573 (M+1).

Example 354

3-(2-(Isopropoxycarbonylaminomethyl)-4-{2-[2-(2'-methoxybiphenyl-3-yl)-5-methyloxazol-4-yl]ethoxy}phenyl)propionic acid

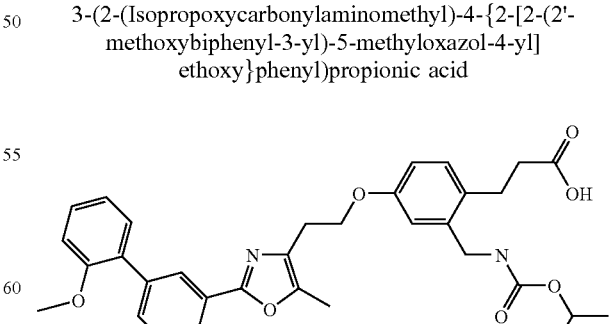

$^1$H-NMR (DMSO-d6) δ 1.13 (d, 6H), 2.40 (s, 2H), 2.45 (t, 2H), 2.78 (t, 2H), 2.93 (t, 2H), 3.80 (s, 3H), 4.16 (m, 4H), 4.75 (m, 1H), 6.76 (m, 2H), 7.07 (m, 2H), 7.16 (d, 1H), 7.32-8.05 (m, 6H).

Example 355

3-[4-{2-[2-(3'-Fluorobiphenyl-4-yl)-5-methyloxazol-4-yl]ethoxy}-2-(isopropoxycarbonylaminomethyl)phenyl]propionic acid

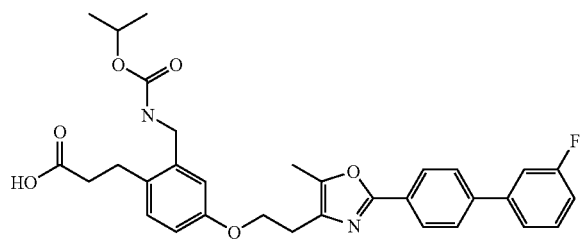

MS (ES) m/z 559 (M+1).

Example 356

3-[4-{2-[2-(2'-Fluoro-biphenyl-4-yl)-5-methyl-oxazol-4-yl]-ethoxy}-2-(isopropoxycarbonylaminomethyl)-phenyl]-propionic acid

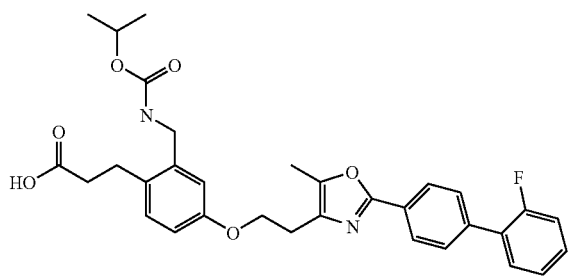

$^1$H-NMR (CDCl3) δ 1.25 (d, 6H), 2.41 (s, 3H), 2.65 (t, 2H), 2.95 (t, 2H), 3.01 (t, 2H), 4.24 (t, 2H), 4.38 (br d, 2H), 4.96 (m, 1H), 5.03 (br s, 1H), 6.78 (dd, 1H), 6.84 (d, 1H), 7.19-7.55 (m, 6H), 7.65 (dd, 2H), 8.06 dd, 2H).

Example 357

3-(2-(Isopropoxycarbonylaminomethyl)-4-{2-[5-methyl-2-(3'-trifluoromethylbiphenyl-4-yl)oxazol-4-yl]ethoxy}phenyl)propionic acid

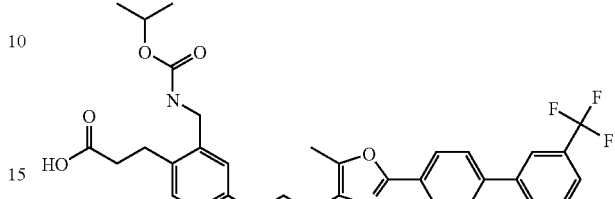

MS (ES) m/z 561 (M+1).

Example 358

3-[4-[2-(2-Biphenyl-2-yl-5-methyl-oxazol-4-yl)-ethoxy]-2-(isopropoxycarbonylamino-methyl)-phenyl]-propionic acid

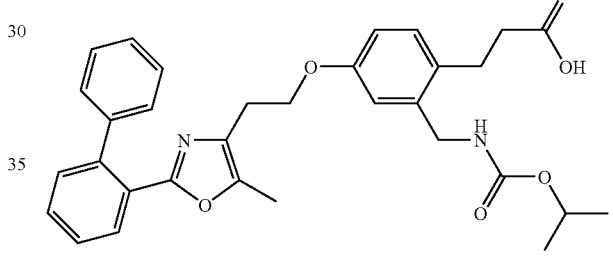

MS (ES) m/z 543.2 (M+1)$^+$.

Example 359

4'-(4-{2-[4-(2-Carboxy-ethyl)-3-(isopropoxycarbonylamino-methyl)-phenoxy]-ethyl}-5-methyl-oxazol-2-yl)-biphenyl-3-carboxylic acid

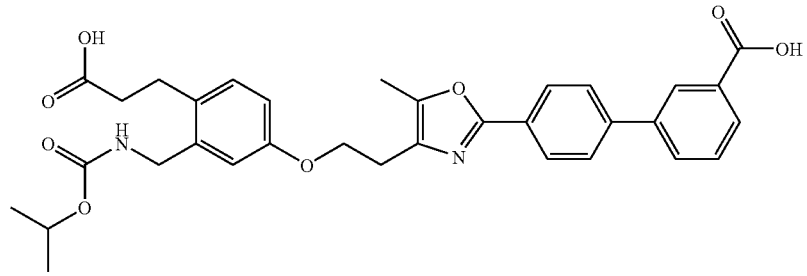

The above compound is prepared after an additional hydrolysis step using Standard procedure E. MS (ES) m/z 587.3 (M+1)⁺.

Example 360

4'-(4-{2-[4-(2-Carboxy-ethyl)-3-(isopropoxycarbonylamino-methyl)-phenoxy]-ethyl}-5-methyl-oxazol-2-yl)-biphenyl-4-carboxylic acid

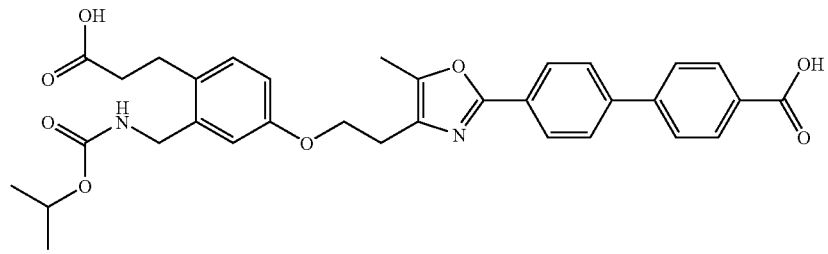

The above compound is prepared after an additional hydrolysis step using Standard procedure E. MS (ES) m/z 587.2 (M+1)⁺.

Example 361

3-(2-(Isopropoxycarbonylamino-methyl)-4-{2-[5-methyl-3-(4-pyridin-4-yl-phenyl)-pyrazol-1-yl]-ethoxy}-phenyl)-propionic acid hydrochloride

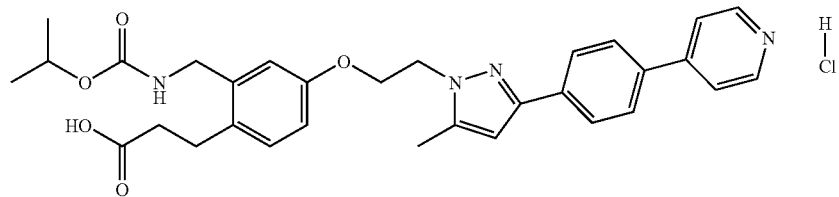

HRMS Calculated for $C_{31}H_{35}N_4O_5$: m/z 543.2607. Found: 543.2614.

Example 362

3-(2-(Isopropoxycarbonylamino-methyl)-4-{2-[5-methyl-3-(4-pyridin-3-yl-phenyl)-pyrazol-1-yl]-ethoxy}-phenyl)-propionic acid hydrochloride

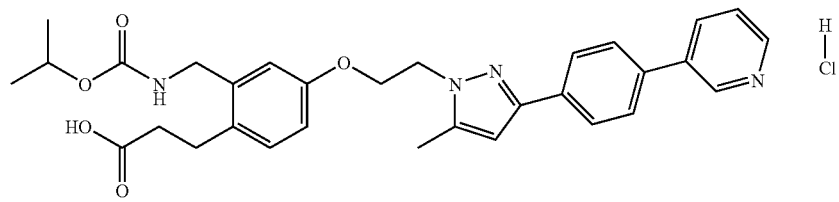

HRMS Calculated for $C_{31}H_{35}N_4O_5$: m/z 543.2607. Found: 543.2612.

Example 363

3-[4-{2-[3-(4'-Fluoro-biphenyl-4-yl)-5-methyl-pyrazol-1-yl]-ethoxy}-2-(isopropoxycarbonylaminomethyl)-phenyl]-propionic acid

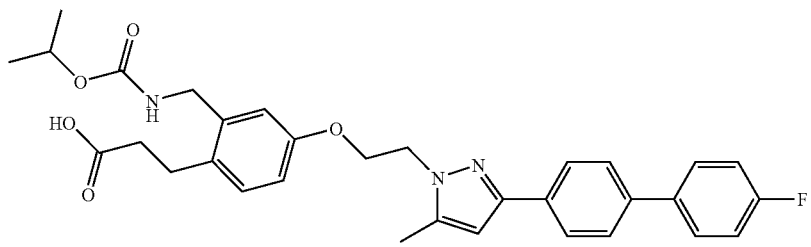

HRMS Calculated for $C_{28}H_{35}FN_3O_5$: m/z 560.2561. Found: 560.2575.

Example 364

3-[4-{2-[3-(4'-Methoxy-biphenyl-4-yl)-5-methyl-pyrazol-1-yl]-ethoxy}-2-(isopropoxycarbonylaminomethyl)-phenyl]-propionic acid

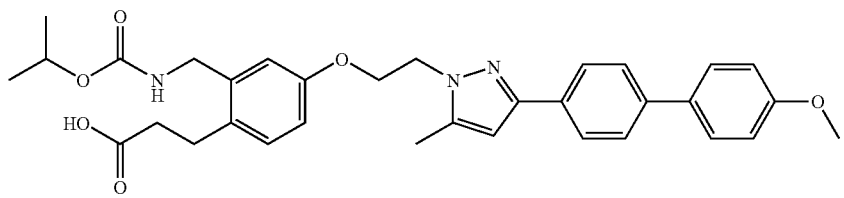

HRMS Calculated for $C_{33}H_{38}N_3O_6$: m/z 572.2761. Found: 572.2752.

Example 365

3-[4-{2-[3-(3'-Methoxy-biphenyl-4-yl)-5-methyl-pyrazol-1-yl]-ethoxy}-2-(isopropoxycarbonylaminomethyl)-phenyl]-propionic acid

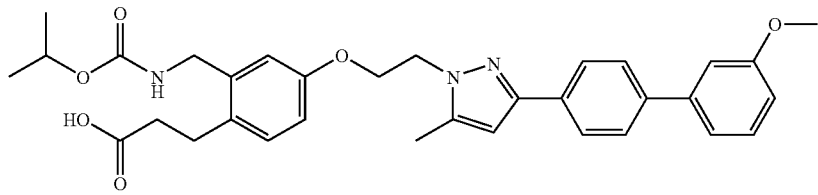

HRMS Calculated for $C_{33}H_{38}N_3O_6$: m/z 572.2761. Found: 572.2776.

Example 366

3-[4-{2-[3-(2'-Fluoro-biphenyl-4-yl)-5-methyl-pyrazol-1-yl]-ethoxy}-2-(isopropoxycarbonylaminomethyl)-phenyl]-propionic acid

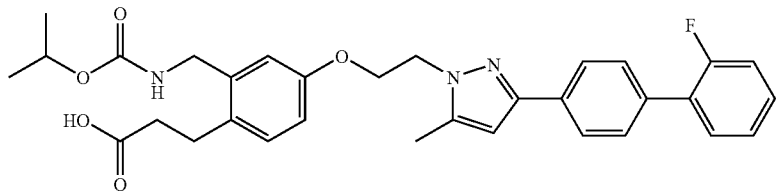

HRMS Calculated for $C_{32}H_{35}FN_4O_5$: m/z 560.2561. Found: 560.2540.

Example 367

3-[4-{2-[3-(2'-Methyl-biphenyl-4-yl)-5-methyl-pyrazol-1-yl]-ethoxy}-2-(isopropoxycarbonylaminomethyl)-phenyl]-propionic acid

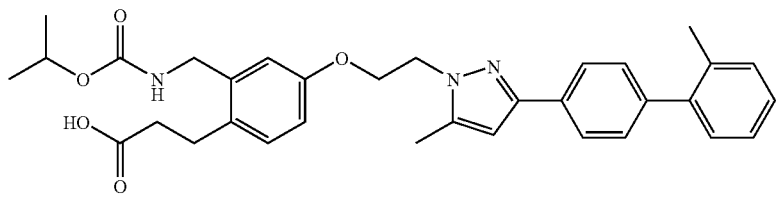

HRMS Calculated for $C_{33}H_{38}N_3O_5$: m/z 556.2811. Found: 556.2802.

Example 368

3-(2-(Isopropoxycarbonylamino-methyl)-4-{2-[5-methyl-2-(4-pyrazin-2-yl-phenyl)-oxazol-4-yl]-ethoxy}-phenyl)-propionic acid

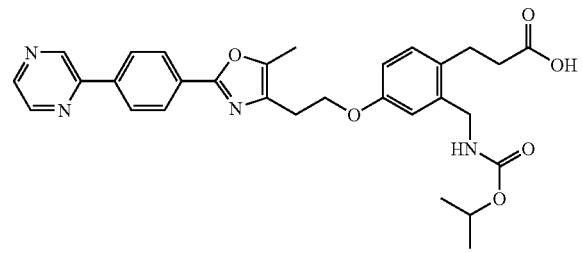

Step A: 3-[2-(Isopropoxycarbonylamino-methyl)-4-(2-{5-methyl-2-[4-(4,4,5,5-tetramethyl-[1,3,2]dioxaborolan-2-yl)-phenyl]-oxazol-4-yl}-ethoxy)-phenyl]-propionic acid

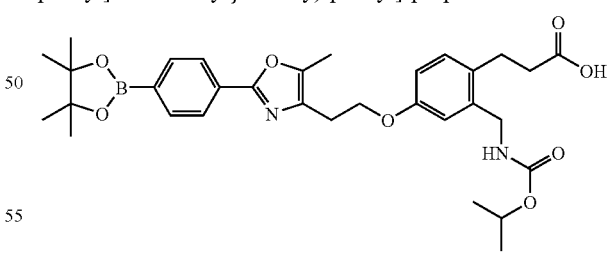

A solution of 3-[4-{2-[2-(4-bromo-phenyl)-5-methyl-oxazol-4-yl]-ethoxy}-2-(isopropoxycarbonylamino-methyl)-phenyl]-propionic acid tert-butyl ester (4.00 g, 6.65 mmol) in DMSO (50 mL) was treated with bis(pinacolato)diborane (2.20 g, 8.64 mmol) and potassium acetate (1.96 g, 19.95 mmol). The solution was sparged with nitrogen for 10 min, Pd(dppf)Cl$_2$ (980 mg, 1.20 mmol; 1:1 complex with CH$_2$Cl$_2$) was added, and the reaction mixture was heated at 80° C. for 4 h. The mixture was partitioned between water and ethyl acetate. The organic layer was dried (MgSO$_4$), filtered, and concentrated. Purification by silica gel chromatography (9:1 hexanes:ethyl acetate) yielded the title compound as a yellow oil (2.81 g). $^1$H NMR (300 MHz CDCl$_3$) δ 1.25 (d, 6H), 1.26 (s, 9H), 1.37 (s, 12H), 2.40 (s, 3H), 2.51 (t, 2H), 2.88 (t, 2H), 2.98 (t, 2H), 4.26 (t, 2H), 4.35 (d, 2H), 4.97 (br m, 2H), 6.77 (dd, 1H), 6.85 (d, 1H), 7.10 (d, 1H), 7.87 (d, 2H), 7.99 (d, 2H). MS [EI+] 649 (M+H).

Step B: 3-(2-(Isopropoxycarbonylamino-methyl)-4-{2-[5-methyl-2-(4-pyrazin-2-yl-phenyl)-oxazol-4-yl]-ethoxy}-phenyl)-propionic acid Suzuki coupling using haloaryl compounds: 3-[2-(Isopropoxycarbonylamino-methyl)-4-(2-{5-methyl-2-[4-(4,4,5,5-tetramethyl-[1,3,2]-dioxaborolan-2-yl)-phenyl]-oxazol-4-yl}-ethoxy)-phenyl]-propionic acid (500 g, 0.771 mmol), CsF (258 g, 1.69 mmol), PdCl$_2$(dppf) (0.057 g, 0.07 mmol), and 2-chloropyrazine (0.0971 g, 0.85 mmol) were added to a 3-neck flask and were dissolved in anhydrous dioxane (25 mL). The reaction mixture was stirred at 100° C. under a stream of N$_2$ for about 12 h. The reaction mixture was diluted with ethyl acetate (200 mL) and washed with saturated NaCl (100 mL) and water (100 mL). The organic layer was filtered through Celite, dried (Na$_2$SO$_4$), filtered, and concentrated. The crude product (1.2 g) was purified by radial chromatography (10-70% EtOAc/hexanes) to give the intermediate ester (0.312 g): MS (ES) m/z 601 (M+H)$^+$. The ester was dissolved in of 4M HCl/dioxane (10 mL). The mixture was stirred N$_2$ for 16 h and concentrated to give the title compound (305 mg, 72%): MS (ES) m/z 545 (M+H)$^+$. Anal. Calculated for C, 66.16%; H, 5.92%; N, 10.29%. Found C, 65.97%; H, 6.07%; N, 10.45%.

The following Examples 369 to 382 are prepared by following a substantially similar procedure as described in Example 368.

Example 369

3-(2-(Isopropoxycarbonylaminomethyl)-4-{2-[5-methyl-2-(4-pyridin-2-ylphenyl)oxazol-4-yl]ethoxy}phenyl)propionic acid

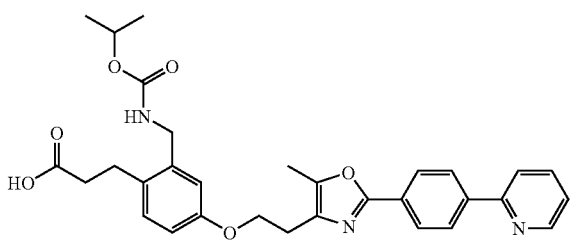

MS (ES) m/z 544 (M+1).

Example 370

3-[2-(Isopropoxycarbonylaminomethyl)-4-(2-{5-methyl-2-[4-(5-methylpyridin-2-yl)phenyl]oxazol-4-yl}ethoxy)phenyl]propionic acid

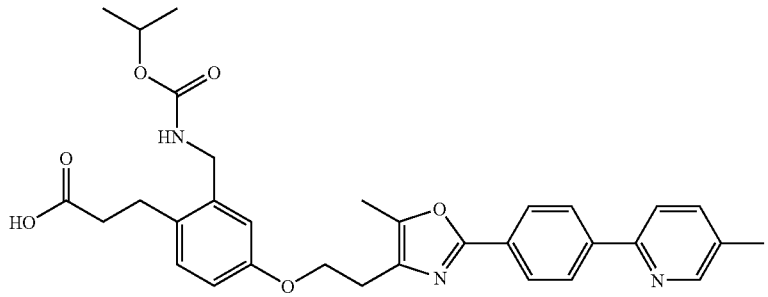

MS (ES) m/z 558 (M+1).

Example 371

3-[2-(Isopropoxycarbonylaminomethyl)-4-(2-{5-methyl-2-[4-(3-methylpyridin-2-yl)phenyl]oxazol-4-yl}ethoxy)phenyl]propionic acid

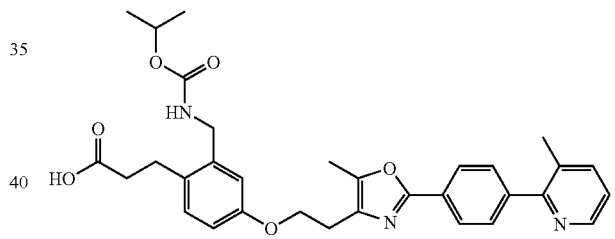

MS (ES) m/z 558 (M+1).

Example 372

3-[2-(Isopropoxycarbonylaminomethyl)-4-(2-{5-methyl-2-[4-(6-methylpyridin-2-yl)phenyl]oxazol-4-yl}ethoxy)phenyl]propionic acid

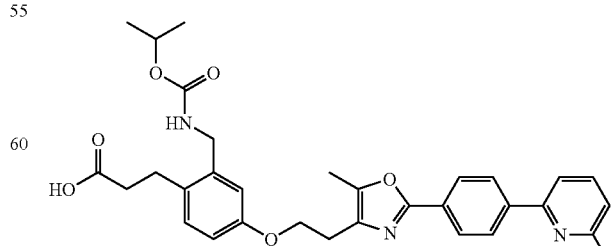

MS (ES) m/z 492 (M+1).

Example 373

3-[2-(Isopropoxycarbonylaminomethyl)-4-(2-{5-methyl-2-[4-(4-methylpyridin-2-yl)phenyl]oxazol-4-yl}ethoxy)phenyl]propionic acid

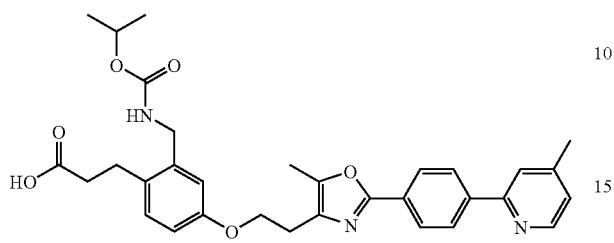

MS (ES) m/z 558 (M+1).

Example 374

3-[2-(Isopropoxycarbonylaminomethyl)-4-(2-{5-methyl-2-[4-(4-trifluoromethylpyridin-2-yl)phenyl]oxazol-4-yl}ethoxy)phenyl]propionic acid

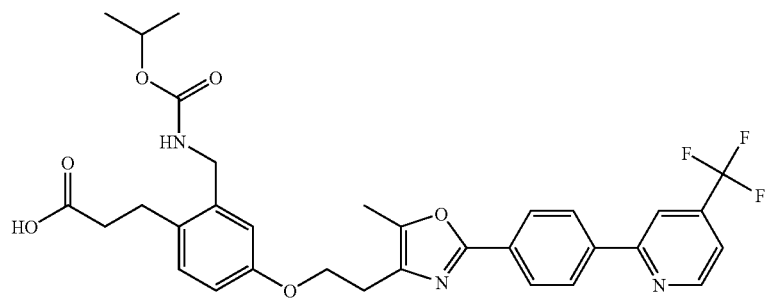

MS (ES) m/z 612 (M+1).

Example 375

3-[2-(Isopropoxycarbonylaminomethyl)-4-(2-{5-methyl-2-[4-(5-trifluoromethylpyridin-2-yl)phenyl]oxazol-4-yl}ethoxy)phenyl]propionic acid

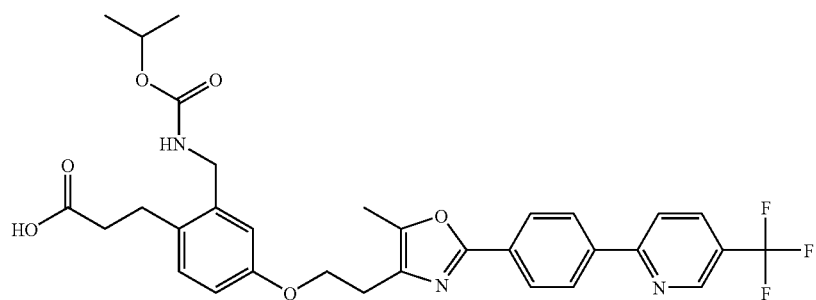

MS (ES) m/z 612 (M+1).

Example 376

3-[2-(Isopropoxycarbonylaminomethyl)-4-(2-{2-[4-(6-methoxypyridin-3-yl)phenyl]-5-methyloxazol-4-yl}ethoxy)phenyl]propionic acid

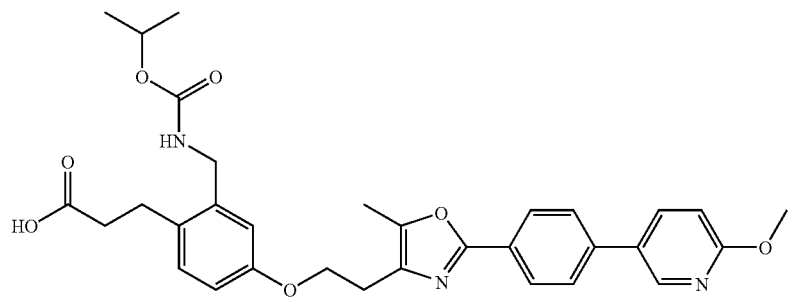

MS (ES) m/z 574 (M+1).

Example 377

3-[2-(Isopropoxycarbonylaminomethyl)-4-(2-{2-[4-(6-methoxypyridin-2-yl)phenyl]-5-methyloxazol-4-yl}ethoxy)phenyl]propionic acid

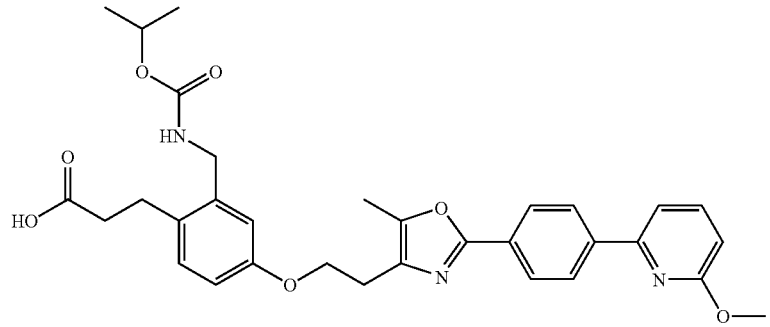

MS (ES) m/z 574 (M+1).

Example 378

3-(2-(Isopropoxycarbonylaminomethyl)-4-{2-[5-methyl-2-(4-quinolin-4-ylphenyl)oxazol-4-yl]ethoxy}phenyl)propionic acid

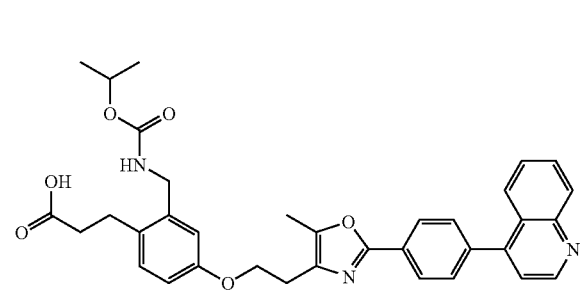

MS (ES) m/z 594 (M+1).

Example 379

3-(2-(Isopropoxycarbonylaminomethyl)-4-{2-[5-methyl-2-(4-pyrazin-2-ylphenyl)oxazol-4-yl]ethoxy}phenyl)propionic acid

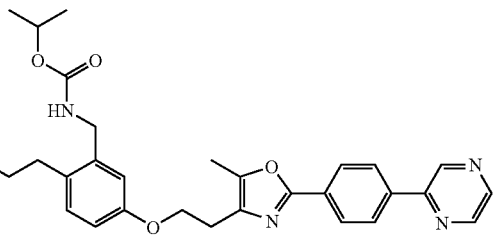

MS (ES) m/z 545 (M+1).

Example 380

3-[2-(Isopropoxycarbonylaminomethyl)-4-(2-{2-[4-(4-methoxypyridin-2-yl)phenyl]-5-methyloxazol-4-yl}ethoxy)phenyl]propionic acid

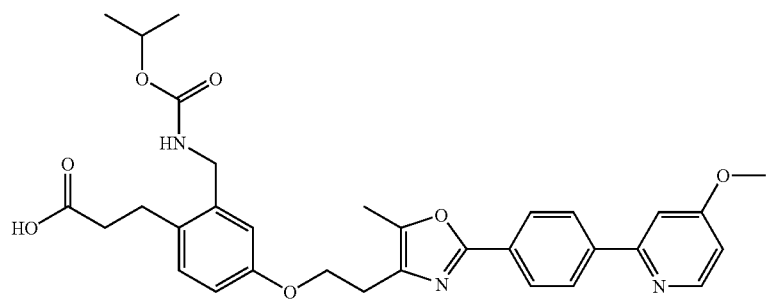

MS (ES) m/z 574 (M+1).

Example 381

3-[4-(2-{2-[4-(5-Cyanopyridin-2-yl)phenyl]-5-methyloxazol-4-yl}ethoxy)-2-(isopropoxycarbonylaminomethyl)phenyl]propionic acid

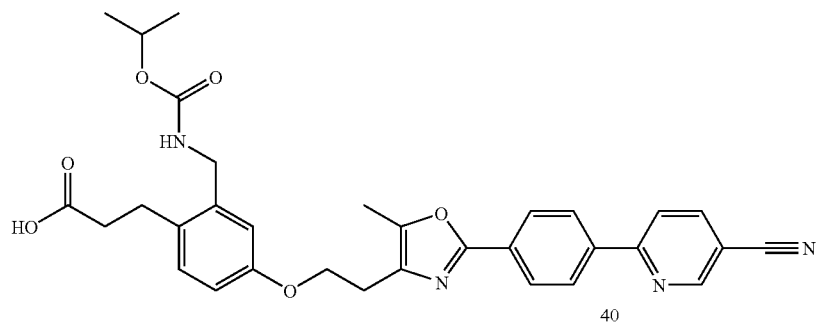

MS (ES) m/z 569 (M+1).

Example 382

3-(2-(Isopropoxycarbonylamino-methyl)-4-{2-[5-methyl-2-(4-pyrimidin-2-yl-phenyl)-oxazol-4-yl]-ethoxy}-phenyl)-propionic acid

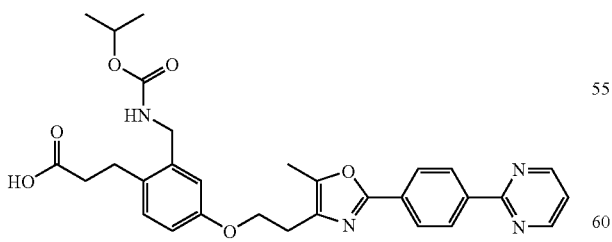

MS (ES) m/z 545 (M+H)$^+$. Anal. Calculated for C, 66.16%; H, 5.92%; N, 10.29%. Found C, 65.87%; H, 6.17%; N, 10.53%.

Example 383

3[4-(2-{2-[4-(4-Fluoro-phenylamino)-phenyl]-5-methyl-oxazol-4-yl}-ethoxy)-2-(isopropoxycarbonylamino-methyl)-phenyl]-propionic acid

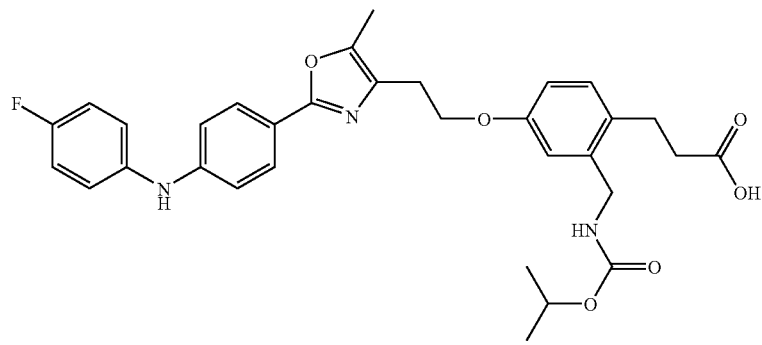

3-[4-{2-[2-(4-bromo-phenyl)-5-methoxy-oxazol-4-yl]-ethoxy}-2-(isopropoxy-carbonylamino-methyl)-propionic acid tert-butyl ester (0.10 g, 0.17 mmol) was dissolved in DME (5 mL) in a sealed tube apparatus. $N_2$ was bubbled through the solution, and 4-fluoroaniline (24 mg, 0.20 mmol), 2-(di-t-butylphosphino)-biphenyl (20 mg), $Pd_2$ $(dba)_3$ (10 mg), and $K_3PO_4$ (50 mg, 0.24 mmol) were added. The tube was sealed and heated at 100° C. for 16 h. The reaction mixture was cooled, diluted with EtOAc, and washed with water. The organic layer was dried ($MgSO_4$), filtered, and concentrated. The residue was purified using silica gel chromatography (hexanes/EtOAc 2/1 to 1/1). Using the Standard hydrolysis procedure C, this material was converted into the title compound as an oil (25 mg): MS (ESI) m/z 594 (M+H)$^+$.

The following Examples 384 to 387 are prepared by following a substantially similar procedure as described in Example 383.

Example 384

3-[4-(2-{2-[4-(4-Cyano-phenylamino)-phenyl]-5-methyl-oxazol-4-yl}-ethoxy)-2-(isopropoxycarbonylamino-methyl)-phenyl]-propionic acid

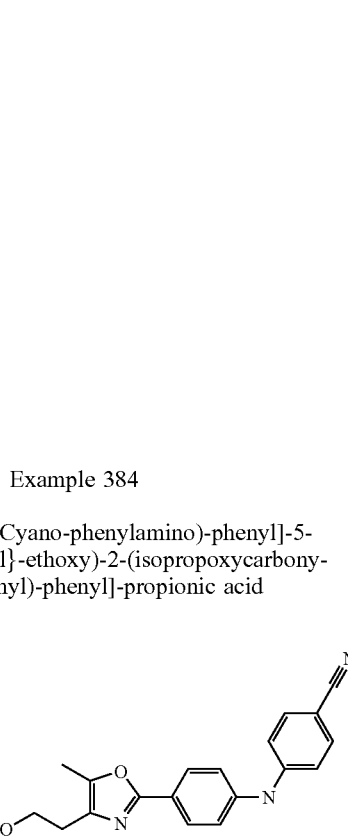

MS (ES) m/z 583 (M+1).

Example 385

3-[4-(2-{2-[4-(3,5-Difluoro-phenylamino)-phenyl]-5-methyl-oxazol-4-yl}-ethoxy)-2-(isopropoxycarbonylamino-methyl)-phenyl]-propionic acid

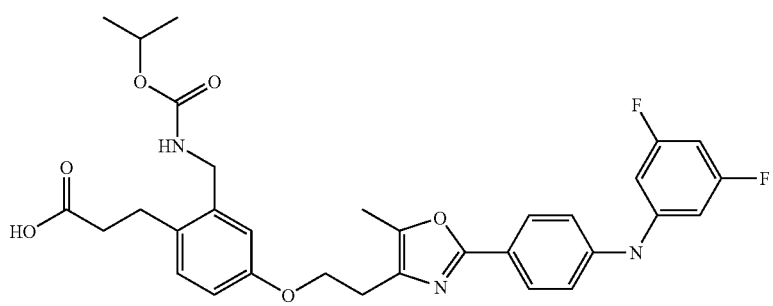

MS (ES) m/z 594 (M+1).

Example 386

3-(2-(Isopropoxycarbonylamino-methyl)-4-{2-[5-methyl-2-(4-p-tolylamino-phenyl)-oxazol-4-yl]-ethoxy}-phenyl)-propionic acid

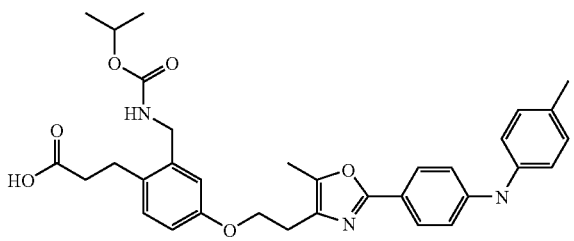

MS (ES) m/z 572 (M+J).

Example 387

3-[2-(Isopropoxycarbonylamino-methyl)-4-(2-{2-[4-(4-methoxy-phenylamino)-phenyl]-5-methyl-oxazol-4-yl}-ethoxy)-phenyl]-propionic acid

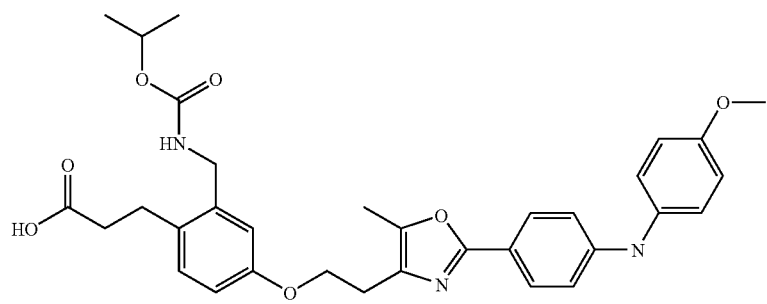

MS (ES) m/z 588 (M+1).

Example 390

3[4-(2-{2-[3-Benzylamino-phenyl]-5-methyl-oxazol-4-yl}-ethoxy)-2-(isopropoxycarbonylamino-methyl)-phenyl]-propionic acid

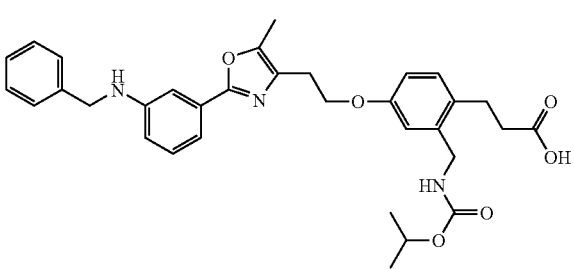

3-[4-{2-[2-(3-bromo-phenyl)-5-methoxy-oxazol-4-yl]-ethoxy}-2-(isopropoxy-carbonylamino-methyl)-propionic acid tert-butyl ester (0.10 g, 0.17 mmol) was dissolved in toluene (5 mL) in a sealed tube apparatus. N₂ was bubbled through the solution, and benzylamine (46 µL, 0.42 mmol), 2-(dicyclohexylphosphino)-biphenyl (12 mg), Pd₂(dba)₃ (16 mg) and t-BuONa (23 mg, 0.24 mmol) were added. The tube was sealed and heated at 100° C. for 16 h. The reaction mixture was cooled, diluted with EtOAc, and washed with water. The organic layer was dried (MgSO₄), filtered, and concentrated. The residue was purified using silica gel chromatography (hexanes/EtOAc 2/1 to 1/1). Using the Standard hydrolysis procedure C, this material was converted into the corresponding carboxylic acid; the title compound was isolated as the HCl salt by treatment with 1M HCl in ether (15 mg). MS (ES) m/z 572 (M+H)⁺.

Example 391

3-[4-{2-[2-(4-Diethylamino-phenyl)-5-methyl-oxazol-4-yl]-ethoxy}-2-(isopropoxycarbonylamino-methyl)-phenyl]-propionic acid

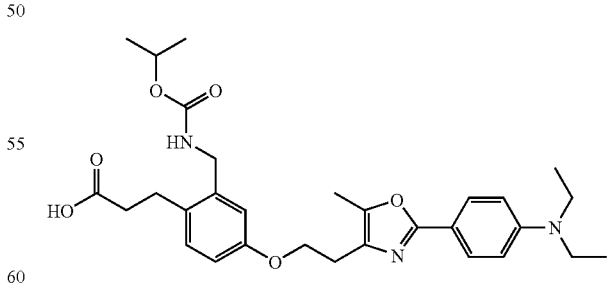

The above compound is prepared by following a substantially similar procedure as described in Example 390 except that the reaction is carried out in DME at 80° C. MS (ES) m/z 538.2 (M+H)⁺.

Example 392

3-(2-(Isopropoxycarbonylamino-methyl)-4-{2-[5-methyl-2-(4-morpholin-4-yl-phenyl)-oxazol-4-yl]-ethoxy}-phenyl)-propionic acid

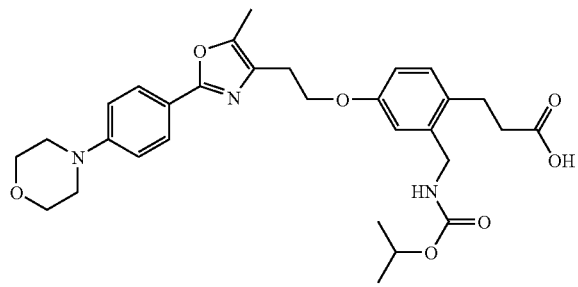

A solution of 3-[4-{2-[2-(4-bromo-phenyl)-5-methyl-oxazol-4-yl]-ethoxy}-2-(isopropoxycarbonylamino-methyl)-phenyl]-propionic acid tert-butyl ester (60 mg, 0.100 mmol) in toluene (3.0 mL) in a sealed tube apparatus under a flow of $N_2$ was treated with $Pd(OAc)_2$ (5 mg), 2-(di-t-butylphosphino)biphenyl (10 mg), morpholine (17 mg, 0.20 mmol), and sodium t-butoxide (19 mg, 0.200 mmol). The tube was sealed and heated at 105° C. for 14 h. The mixture was cooled and purified directly using silica gel chromatography (30-50% EtOAc/hexanes) to yield the intermediate ester. A solution of ester in TFA (1.0 ml)/$CH_2Cl_2$ (1.5 ml)/$H_2O$ (0.1 mL) and stirred 14 h and concentrated. The residue was and purified using silica gel chromatography (hexanes/EtOAc/HOAc, 5/5/0.02) to afford the title compound (36 mg, 65%): MS (ESI) m/z 552.3 (M+H)⁺.

The following Examples 393 to 395 are prepared by following a substantially similar procedure as described in Example 392.

Example 393

3-(2-(Isopropoxycarbonylamino-methyl)-4-{2-[5-methyl-2-(3-morpholin-4-yl-phenyl)-oxazol-4-yl]-ethoxy}-phenyl)-propionic acid

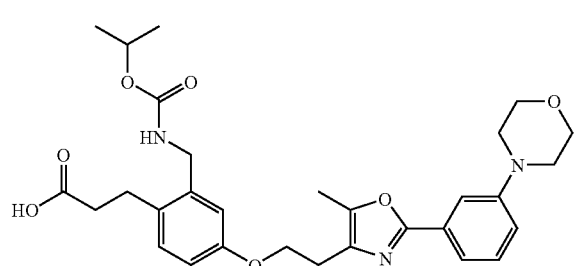

MS (ESI) m/z 552.2 (M+H)⁺.

Example 394

3-(2-(Isopropoxycarbonylamino-methyl)-4-{2-[5-methyl-2-(4-piperidin-1-yl-phenyl)-oxazol-4-yl]-ethoxy}-phenyl)-propionic acid

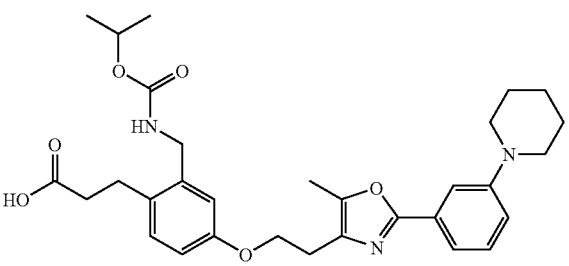

MS (ESI) m/z 550.3 (M+H)⁺.

Example 395

3-(2-(Isopropoxycarbonylamino-methyl)-4-{2-[5-methyl-2-(3-piperidin-1-yl-phenyl)-oxazol-4-yl]-ethoxy}-phenyl)-propionic acid

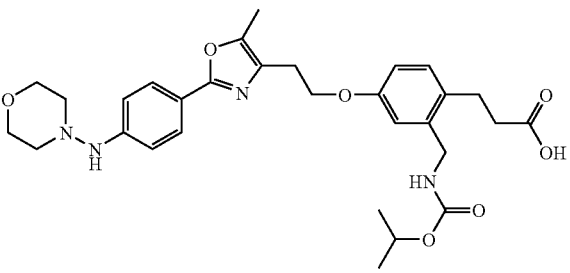

MS (ESI) m/z 550.3 (M+H)⁺.

Example 396

3-[2-(Isopropoxycarbonylamino-methyl)-4-(2-{5-methyl-2-[4-(morpholin-4-ylamino)-phenyl]-oxazol-4-yl}-ethoxy)-phenyl]-propionic acid A solution of 3-[4-{2-[2-(4-bromo-phenyl)-5-methyl-oxazol-4-yl]-ethoxy}-2-(isopropoxycarbonylamino-methyl)- phenyl]-propionic acid tert-butyl ester (120 mg, 0.200 mmol) in toluene (2.0 mL) in a sealed tube under a flow of N₂ was treated Pd₂(dba)₃ (10 mg), 2-(di-t-butylphosphino)biphenyl (10 mg), N-aminomorpholine (29 mg, 0.28 mmol), and sodium t-butoxide (38 mg, 0.40 mmol). The tube was sealed and heated at 100° C. for 60 min. The mixture was cooled and purified using silica gel chromatography (5-10% MeOH/EtOAc) to yield the title compound directly (22 mg, 21%): MS (ESI) m/z 567.3 (M+H)⁺.

Example 397

3-(2-(Isopropoxycarbonylamino-methyl)-4-{2-[5-methyl-2-(4-phenoxy-phenyl)-oxazol-4-yl]-ethoxy}-phenyl)-propionic acid

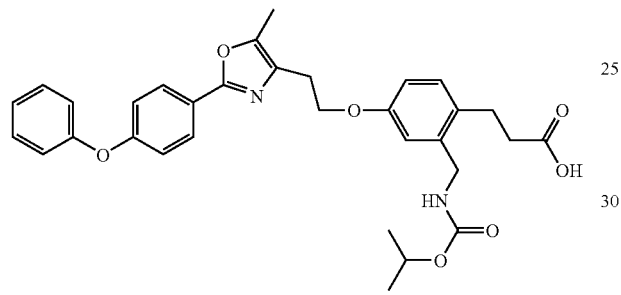

A mixture of 3-[4-{2-[2-(4-bromo-phenyl)-5-methyl-oxazol-4-yl]-ethoxy}-2-(isopropoxycarbonylamino-methyl)-phenyl]-propionic acid tert-butyl ester (0.44 mmol, 0.24 g), phenol (0.53 mmol, 0.050 g), K₃PO₄ (0.88 mmol, 0.19 g), 2-(di-t-butylphosphino)biphenyl (0.066 mmol, 0.020 g), and Pd(OAc)₂ (0.044 mmol, 0.010 g) in toluene (7 mL) was degassed under vacuum and backfilled with nitrogen (3×) and heated at 110° C. for 18 h. Additional Pd(OAc)₂ (10 mg) and 2-(di-t-butylphosphino)biphenyl (20 mg) were added to ensure complete reaction, and the mixture was heated 5 h. Upon cooling, the mixture was placed directly onto a silica gel column and eluted with 30%-50% EtOAc/hexanes to give 3-(2-(isopropoxycarbonylamino-methyl)-4-{2-[5-methyl-2-(4-phenoxy-phenyl)-oxazol-4-yl]-ethoxy}-phenyl)-propionic acid tert-butyl ester (0.11 g).

The tert-butyl ester (0.18 mmol, 0.11 g) was dissolved in CH₂Cl₂ (3 mL), and 90% TFA/water (5 mL) was added. The mixture was stirred for 3 h and concentrated. The residue was purified by silica gel chromatography (50% ethyl acetate/hexanes) to give an oil. Trituration with Et₂O gave the title compound as a white solid (90 mg, 90%): ¹H NMR (250 MHz, CDCl₃) δ 8.11 (d, 2H, J=8.8 Hz), 7.56 (t, 2H, J=7.9 Hz), 7.37-7.20 (m, 6H), 7.0-6.93 (m, 2H), 5.11 (heptet, 1H, J=6.3 Hz), 4.53 (d, 2H, J=5.1 Hz), 4.38 (t, 2H, J=6.7 Hz), 3.12 (q, 4H, J=7.3 Hz), 2.80 (t, 2H, J=7.6 Hz), 2.54 (s, 3H), 1.41 (d, 6H, J=6.3 Hz).

The following Examples 398 to 405 are prepared by following a substantially similar procedure as described in Examples 396 and 397.

Example 398

3-(2-(Isopropoxycarbonylamino-methyl)-4-{2-[5-methyl-2-(3-phenoxy-phenyl)-oxazol-4-yl]-ethoxy}-phenyl)-propionic acid

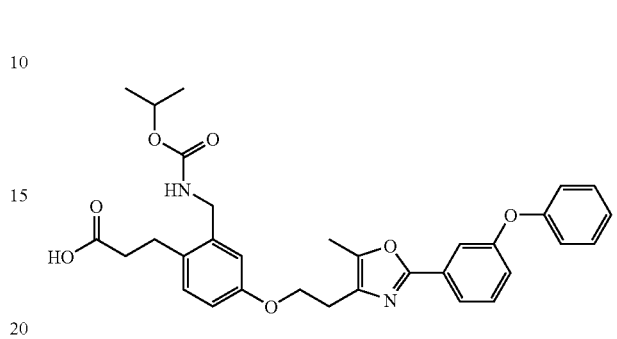

MS (ESI) m/z 559.2 (M+H)⁺.

Example 399

3-(2-(Isopropoxycarbonylamino-methyl)-4-{2-[5-methyl-2-(2-phenoxy-phenyl)-oxazol-4-yl]-ethoxy}-phenyl)-propionic acid

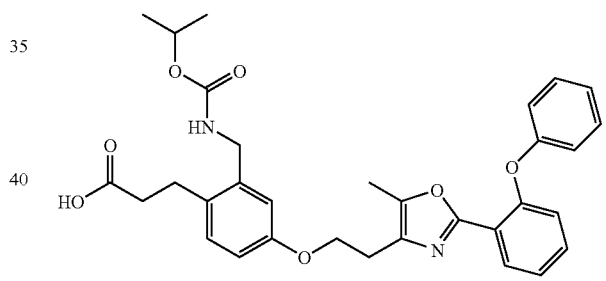

MS (ESI) 559 (M+H)⁺. Anal Calculated for C₃₂H₃₄N₂O₇: C, 68.8; H, 6.1; N, 5.0. Found: C, 67.9; H, 6.2; N, 5.3.

Example 400

3-[4-(2-{2-[4-(4-Cyano-phenoxy)-phenyl]-5-methyl-oxazol-4-yl}-ethoxy)-2-(isopropoxycarbonylamino-methyl)-phenyl]-propionic acid

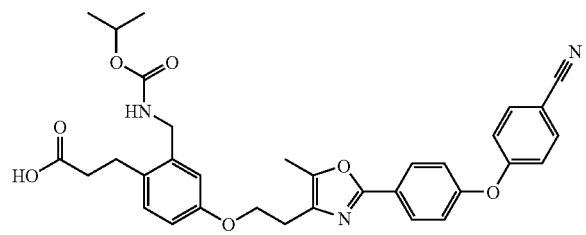

MS (ES) m/z 584.

Example 401

3-[2-(Isopropoxycarbonylamino-methyl)-4-(2-{5-methyl-2-[4-(4-trifluoromethyl-phenoxy)-phenyl]-oxazol-4-yl}-ethoxy)-phenyl]-propionic acid

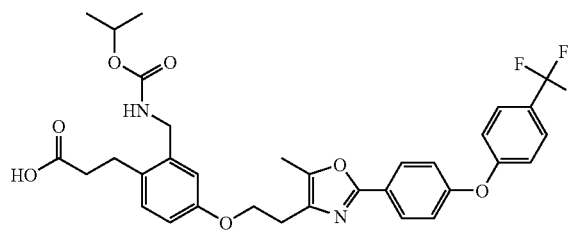

MS (ES) m/z 627 (M+1).

Example 402

3-[4-(2-{2-[4-(4-Fluoro-phenoxy)-phenyl]-5-methyl-oxazol-4-yl}-ethoxy)-2-(isopropoxycarbonylamino-methyl)-phenyl]-propionic acid

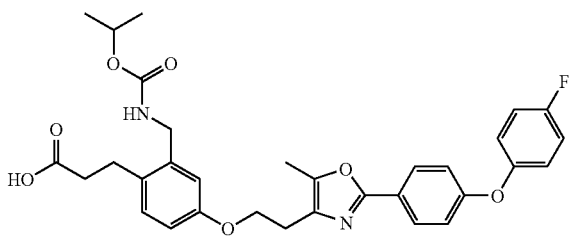

MS (ES) m/z 577 (M+1).

Example 403

3-[4-(2-{2-[4-(3,4-Difluoro-phenoxy)-phenyl]-5-methyl-oxazol-4-yl}-ethoxy)-2-(isopropoxycarbony-lamino-methyl)-phenyl]-propionic acid

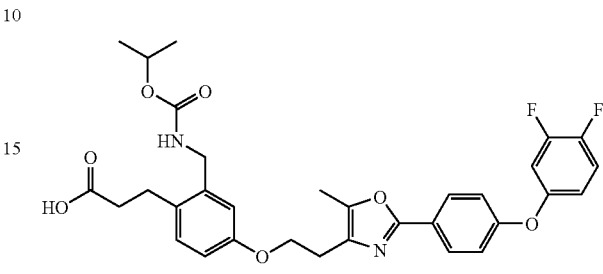

MS (ES) m/z 595 (M+1).

Example 404

3-(2-(Isopropoxycarbonylamino-methyl)-4-{2-[5-methyl-2-(4-m-tolyloxy-phenyl)-oxazol-4-yl]-ethoxy}-phenyl)-propionic acid

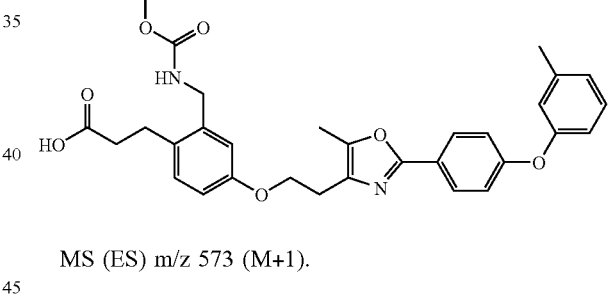

MS (ES) m/z 573 (M+1).

Example 405

3-[4-(2-{2-[4-(4-Acetyl-phenoxy)-phenyl]-5-methyl-oxazol-4-yl}-ethoxy)-2-(isopropoxycarbonylamino-methyl)-phenyl]-propionic acid

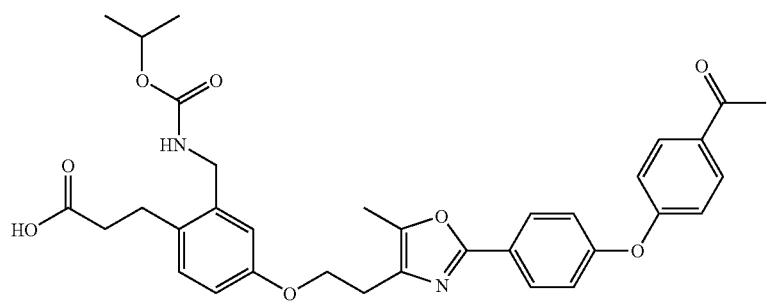

MS (ES) m/z 601 (M+1).

Example 406

3-[4-{2-[2-(4-Hydroxy-phenyl)-5-methyl-oxazol-4-yl]-ethoxy}-2-(isopropoxycarbonylamino-methyl)-phenyl]-propionic acid tert-butyl ester

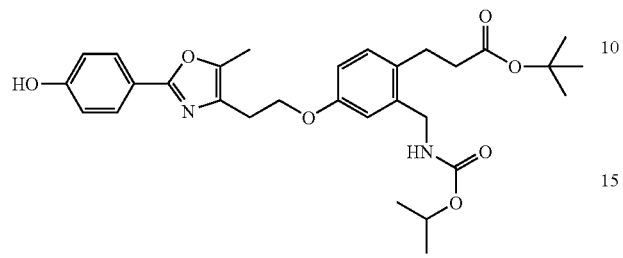

According to the procedure in *Organic Synthesis*, vol. V, p. 918, a solution of 3-[2-(isopropoxycarbonylamino-methyl)-4-(2-{5-methyl-2-[4-(4,4,5,5-tetramethyl-[1,3,2]dioxaborolan-2-yl)-phenyl]-oxazol-4-yl}-ethoxy)-phenyl]-propionic acid tert-butyl ester (1.4 g, 2.16 mmol, Example 368, Step A) in THF (8 mL) was treated with glacial acetic acid (194 mg, 3.24 mmol) at 0° C. A solution of 30% H₂O₂ in water (4.75 mL) was diluted with H₂O (1 mL) and added to the reaction mixture. The mixture was warmed to room temperature and treated with 1M aqueous Na₂S₂O₃ solution (50 mL). The THF was removed under vacuum and the aqueous phase was extracted with ethyl acetate. The organic layer was washed with 1M Na₂S₂O₃ (2×50 mL), dried (MgSO₄), filtered, and concentrated to an oil containing (1.21 g). Purification using silica gel chromatography (1:1 ηεξανεσ:ετηψλ acetate) yielded the title compound as a white solid (1.10 g, 95%). ¹H NMR (300 MHz CDCl₃) δ 1.15 (d, 6H), 1.19 (s, 9H), 2.26 (s, 3H), 2.39 (t, 2H), 2.75 (t, 2H), 2.85 (t, 2H), 4.10 (t, 2H), 4.28 (d, 2H), 4.85 (m, 1H), 5.01 (br d, 1H), 6.63 (dd, 1H), 6.74 (m, 3H), 6.96 (d, 1 h), 7.70 (d, 2H); MS [EI+] m/z 539 (M+H).

Example 407

3-[4-{2-[2-(3-Hydroxy-phenyl)-5-methyl-oxazol-4-yl]-ethoxy}-2-(isopropoxycarbonylamino-methyl)-phenyl]-propionic acid tert-butyl ester

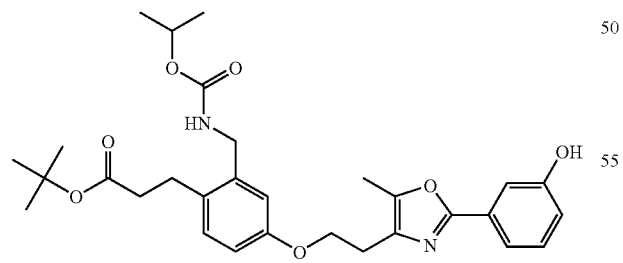

The above compound is prepared by following a substantially similar procedure as described in Example 406. MS [EI+] m/z 539 (M+H).

The following Examples 408 to 409 are prepared by following a substantially similar procedure as described in Example 406 and the corresponding carboxylic acids are obtained from Standard hydrolysis procedure C:

Example 408

3-[4-{2-[2-(4-Hydroxyphenyl)-5-methyloxazol-4-yl]ethoxy}-2-(isopropoxycarbonylaminomethyl)phenyl]propionic acid

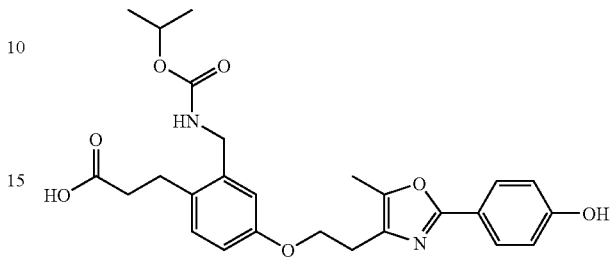

MS (ES) m/z 483 (M+1).

Example 409

3-[4-{2-[2-(3-Hydroxyphenyl)-5-methyloxazol-4-yl]ethoxy}-2-(isopropoxycarbonylaminomethyl)phenyl]propionic acid

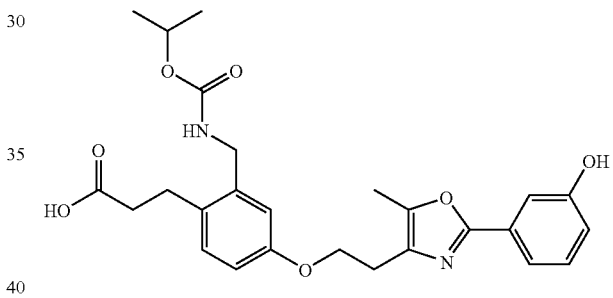

MS (ES) m/z 483 (M+1).

Example 410

3-(2-(Isopropoxycarbonylamino-methyl)-4-{2-[2-(4-isopropoxy-phenyl)-5-methyl-oxazol-4-yl]-ethoxy}-phenyl)-propionic acid

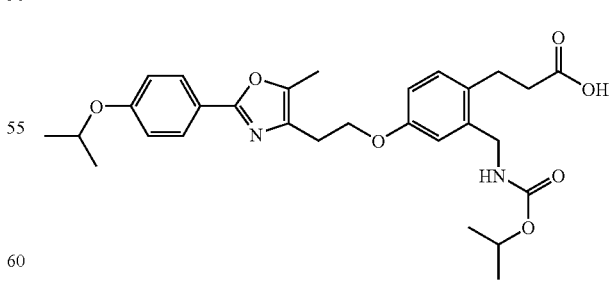

A solution of 3-[4-{2-[2-(4-hydroxy-phenyl)-5-methyl-oxazol-4-yl]-ethoxy}-2-(isopropoxycarbonylamino-methyl)-phenyl]-propionic acid tert-butyl ester (300 mg, 0.557 mmol, Example 406) in ethanol (20 mL) was treated with 2-iodopropane (473 mg, 2.78 mmol) and K₂CO₃ (231 mg, 1.67 mmol) and was heated at reflux overnight. The reaction mixture was cooled and concentrated. The residue was diluted with H₂O and ethyl acetate. The layers were separated, and the aqueous layer was extracted with ethyl acetate (2×). The combined organic layers were dried (MgSO₄), filtered, and concentrated to yield an oil. Purification using silica gel chromatography (3:1 hexane:ethyl acetate) yielded 3-(2-(isopropoxycarbonylamino-methyl)-4-{2-[2-(4-isopropoxy-phenyl)-5-methyl-oxazol-4-yl]-ethoxy}-phenyl)-propionic acid tert-butyl ester as a yellow oil (210 mg). ¹H NMR (300 MHz CDCl₃) δ 1.28 (d, 6H), 1.40 (d, 6H), 1.45 (s, 9H), 2.38 (s, 3H), 2.53 (t, 2H), 2.91 (t, 2H), 2.99 (t, 2H), 4.25 (t, 2H), 4.39 (d, 2H), 4.66 (m, 1H), 5.00 (br m, 2H), 6.80 (dd, 1H), 6.87 (d, 1H), 6.95 (d, 2H), 7.13 (d, 1H), 7.95 (d, 2H) MS [ES] 581 (M+H).

This ester was converted to the title compound according to Standard Procedure C; a white solid (134 mg). ¹H NMR (300 MHz CDCl₃) δ 1.15 (d, 6H), 1.29 (d, 6H), 2.31 (s, 3H), 2.53 (t, 2H), 2.82 (t, 2H), 2.97 (t, 2H), 4.15 (t, 2H), 4.26 (d, 2H), 4.55 (m, 1H), 4.84 (m, 1H), 4.99 (br s, 1H), 6.68 (dd, 1H), 6.73 (d, 1H), 6.87 (d, 2H), 7.00 (d, 1H), 7.90 (d, 2H) MS [ES] m/z 525 (M+H).

The following Examples 411 to 422 are prepared by following a substantially similar procedure as described in Example 410.

Example 411

3-(2-(Isopropoxycarbonylaminomethyl)-4-{2-[5-methyl-2-(4-propoxyphenyl)oxazol-4-yl]ethoxy}phenyl)propionic acid

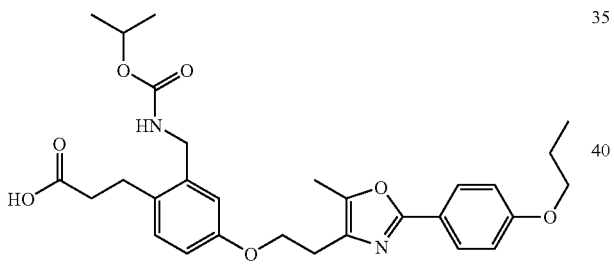

MS (ES) m/z 525 (M+1).

Example 412

3-[4-{2-[2-(4-Ethoxyphenyl)-5-methyloxazol-4-yl]ethoxy}-2-(isopropoxycarbonylaminomethyl)phenyl]propionic acid

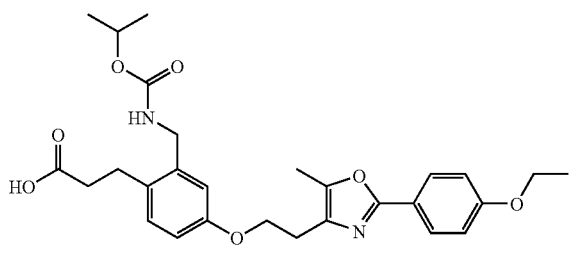

MS (ES) m/z 511 (M+1).

Example 413

3-(2-(Isopropoxycarbonylaminomethyl)-4-{2-[2-(4-methoxyphenyl)-5-methyoxazol-4-yl]ethoxy}phenyl)propionic acid MS (ES) m/z 497 (M+1).

Example 414

3-(2-(Isopropoxycarbonylaminomethyl)-4-{2-[2-(3-methoxyphenyl)-5-methyoxazol-4-yl]ethoxy}phenyl)propionic acid MS (ES) m/z 497 (M+1)

Example 415

3-[4-{2-[2-(3-Ethoxyphenyl)-5-methyloxazol-4-yl]-ethoxy}-2-(isopropoxycarbonylaminomethyl)phenyl]propionic acid

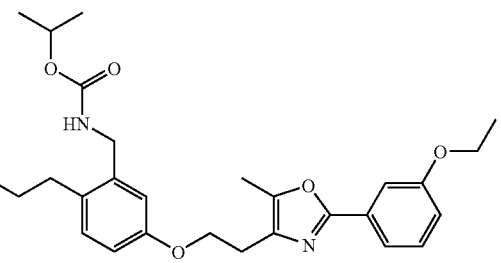

MS (ES) m/z 511 (M+1).

Example 416

3-(2-(Isopropoxycarbonylaminomethyl)-4-{2-[2-(3-isopropoxyphenyl)-5-methyloxazol-4-yl]ethoxy}phenyl)propionic acid

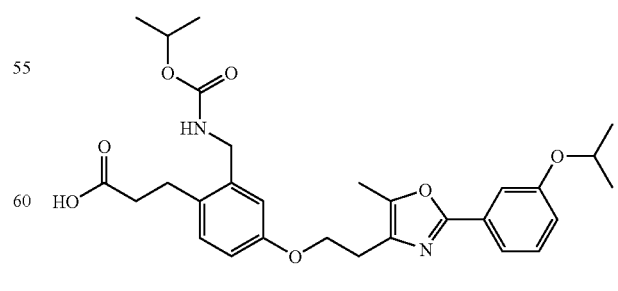

MS (ES) m/z 525 (M+1).

Example 417

3-(2-(Isopropoxycarbonylaminomethyl)-4-{2-[5-methyl-2-(3-propoxyphenyl)oxazol-4-yl]ethoxy}phenyl)propionic acid

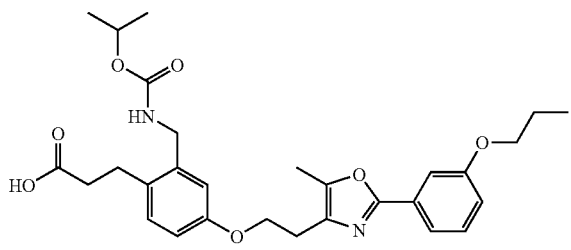

MS (ES) m/z 525 (M+1).

Example 418

3-[4-{2-[2-(3-Butoxyphenyl)-5-methyloxazol-4-yl]ethoxy}-2-(isopropoxycarbonylaminomethyl)phenyl]propionic acid

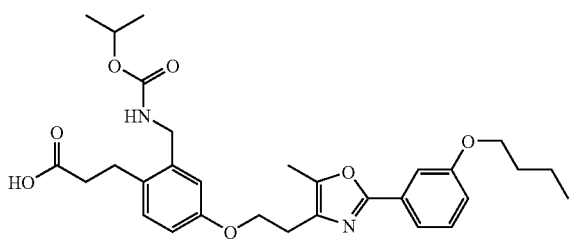

MS (ES) m/z 539 (M+1).

Example 419

3-[4-{2-[2-(3-Cyclopentyloxyphenyl)-5-methyloxazol-4-yl]ethoxy}-2-(isopropoxycarbonylaminomethyl)phenyl]propionic acid

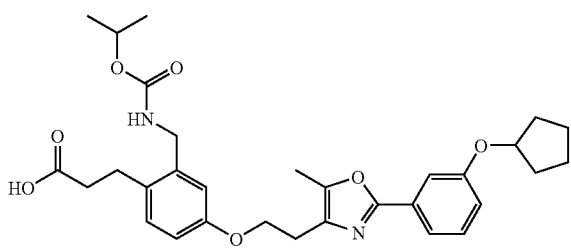

MS (ES) m/z 551 (M+1).

Example 420

3-[4-{2-[2-(3-Cyclohexyloxyphenyl)-5-methyloxazol-4-yl]ethoxy}-2-(isopropoxycarbonylaminomethyl)-phenyl]propionic acid

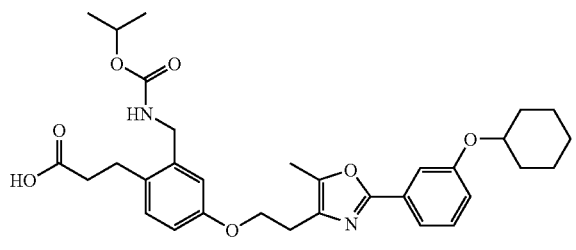

MS (ES) m/z 565 (M+1).

Example 421

3-[4-{2-[2-(4-Cyclopentyloxyphenyl)-5-methyloxazol-4-yl]ethoxy}-2-(isopropoxycarbonylaminomethyl)phenyl]propionic acid

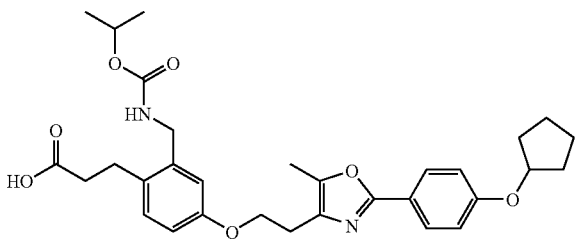

MS (ES) m/z 551 (M+1).

Example 422

3-[4-{2-[2-(4-Cyclohexyloxyphenyl)-5-methyloxazol-4-yl]ethoxy}-2-(isopropoxycarbonylaminomethyl)phenyl]propionic acid

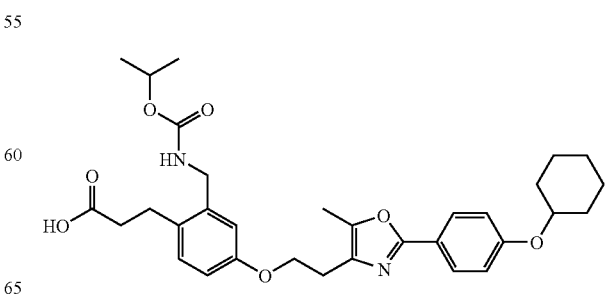

MS (ES) m/z 565 (M+1).

Example 423

3-[2-(Isopropoxycarbonylamino-methyl)-4-(2-{5-methyl-2-[4-(tetrahydro-pyran-4-yloxy)-phenyl]-oxazol-4-yl}-ethoxy)-phenyl]-propionic acid

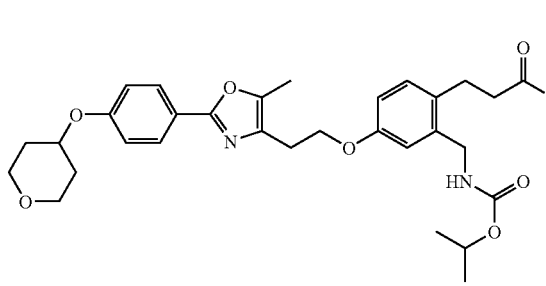

A mixture of 3-[4-{2-[2-(4-hydroxy-phenyl)-5-methyl-oxazol-4-yl]-ethoxy}-2-(isopropoxycarbonylamino-methyl)-phenyl]-propionic acid tert-butyl ester (120 mg, 0.223 mmol, Example 406), tetrahydro-pyran-4-ol (22.7 mg, 0.223 mmol), triphenylphosphine (58.4 mg, 0.223 mmol) and toluene (10 mL) was treated dropwise with DIAD (45 mg, 0.223 mmol). The mixture was stirred under $N_2$ at ambient temperature for 16 h and concentrated. The crude product was purified by radial chromatography (10-70% EtOAc/hexanes) to give 3-[2-(isopropoxycarbonylamino-methyl)-4-(2-{5-methyl-2-[4-(tetrahydro-pyran-4-yloxy)-phenyl]-oxazol-4-yl}-ethoxy)-phenyl]-propionic acid tert-butyl ester. The ester product was dissolved 4M HCl/dioxane (5 mL), stirred for 16 h and concentrated to give the title compound: MS [ES] m/z 525 (M+H).

The following Examples 424 to 431 are prepared by following a substantially similar procedure as described in Example 423.

Example 424

3-[2-(Isopropoxycarbonylaminomethyl)-4-(2-{5-methyl-2-[4-(1-methylpiperidin-4-yloxy)phenyl]oxazol-4-yl}ethoxy)phenyl]propionic acid

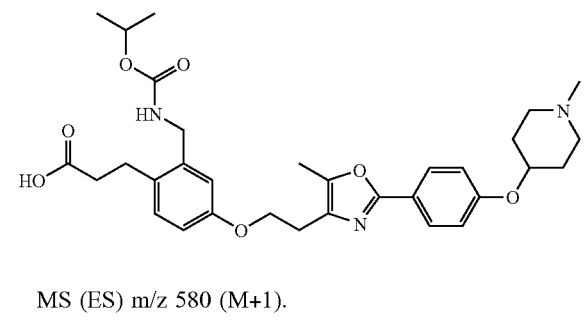

MS (ES) m/z 580 (M+1).

Example 425

3-[2-(Isopropoxycarbonylaminomethyl)-4-(2-{5-methyl-2-[3-(tetrahydropyran-4-yloxy)phenyl]oxazol-4-yl}ethoxy)phenyl]propionic acid

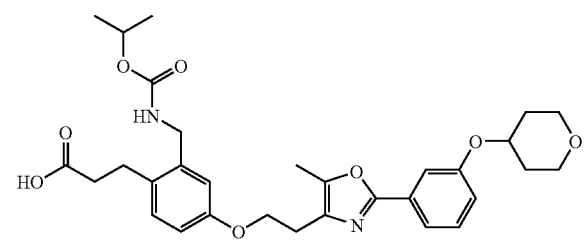

MS (ES) m/z 567 (M+1).

Example 426

3-[2-(Isopropoxycarbonylaminomethyl)-4-(2-{5-methyl-2-[3-(1-methylpiperidin-4-yloxy)phenyl]oxazol-4-yl}ethoxy)phenyl]propionic acid

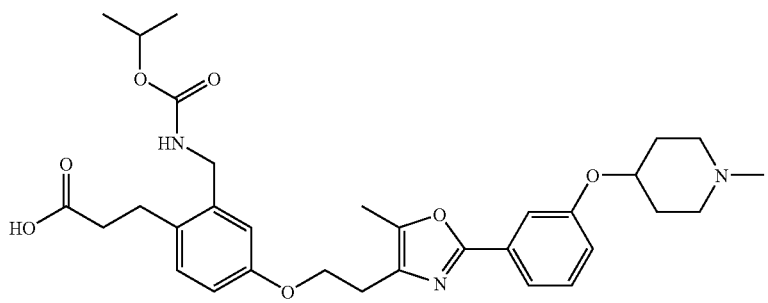

MS (ES) m/z 580 (M+1).

Example 427

3-[2-(Isopropoxycarbonylaminomethyl)-4-(2-{5-methyl-2-[3-(piperidin-4-yloxy)phenyl]oxazol-4-yl}ethoxy)phenyl]propionic acid

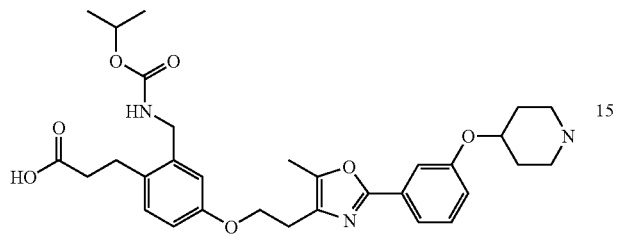

MS (ES) m/z 566 (M+1).

Example 428

3-[4-(2-{2-[3-(3-Dimethylaminopropoxy)phenyl]-5-methyloxazol-4-yl}ethoxy)-2-(isopropoxycarbonylaminomethyl)phenyl]propionic acid

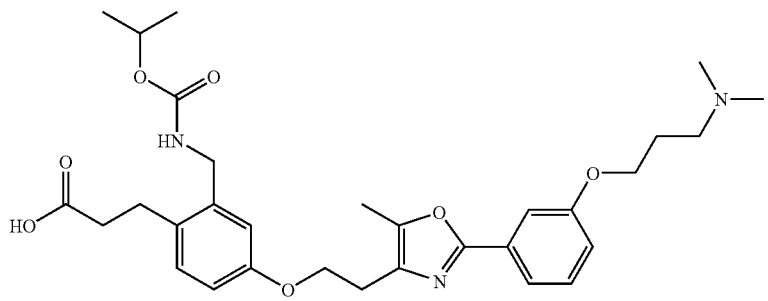

MS (ES) m/z 568 (M+1).

Example 429

3-[2-(Isopropoxycarbonylaminomethyl)-4-(2-{5-methyl-2-[4-(piperidin-4-yloxy)phenyl]oxazol-4-yl}ethoxy)phenyl]propionic acid

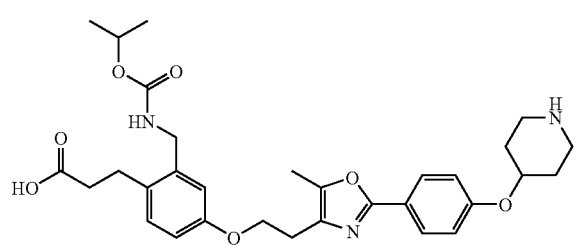

MS (ES) m/z 566 (M+1).

Example 430

3-[4-(2-{2-[4-(2-Dimethylaminoethoxy)phenyl]-5-methyloxazol-4-yl}ethoxy)-2-(isopropoxycarbonylaminomethyl)phenyl]propionic acid

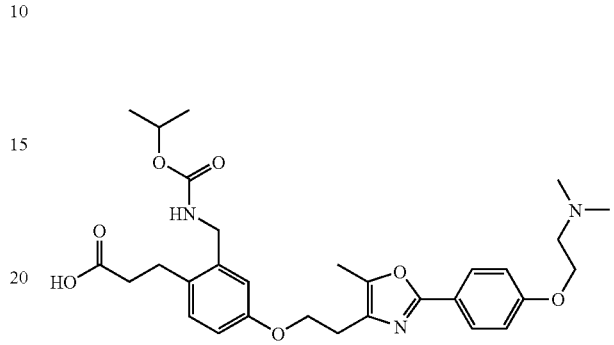

MS (ES) m/z 554 (M+1).

Example 431

3-[4-(2-{2-[4-(3-Dimethylaminopropoxy)phenyl]-5-methyloxazol-4-yl}ethoxy)-2-(isopropoxycarbonylaminomethyl)phenyl]propionic acid

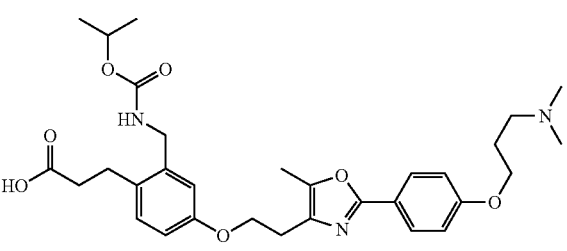

MS (ES) m/z 568 (M+1).

Example 432

3-[2-(Isopropoxycarbonylaminomethyl)-4-(2-{5-methyl-2-[4-(pyridin-2-yloxy)phenyl]oxazol-4-yl}ethoxy)phenyl]propionic acid

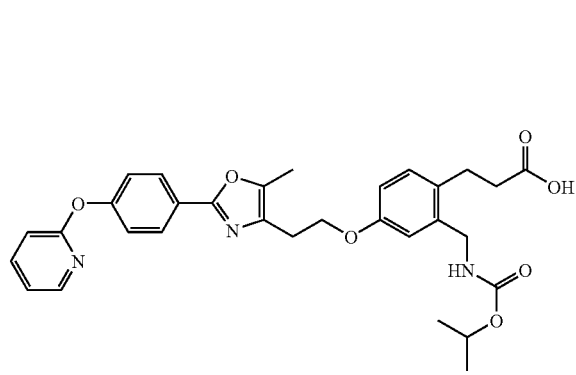

3-[4-{2-[2-(4-hydroxy-phenyl)-5-methyl-oxazol-4-yl]-ethoxy}-2-(isopropoxy-carbonylamino-methyl)-phenyl]-propionic acid tert-butyl ester (Example 406) was reacted with 2-bromopyridine by the procedure in Example 397 to give the title compound. MS (ES) m/z 560 (M+1).

The following Examples 433 to 435 are prepared by following a substantially similar procedure as described in Example 432.

Example 433

3-[2-(Isopropoxycarbonylaminomethyl)-4-(2-{5-methyl-2-[4-(pyridin-4-yloxy)phenyl]oxazol-4-yl}ethoxy)phenyl]propionic acid

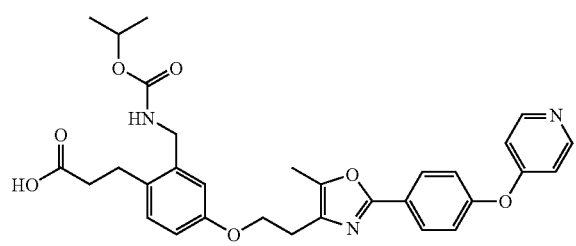

MS (ES) m/z 560 (M+1).

Example 434

3-[2-(Isopropoxycarbonylaminomethyl)-4-(2-{5-methyl-2-[4-(pyridin-3-yloxy)phenyl]oxazol-4-yl}ethoxy)phenyl]propionic acid

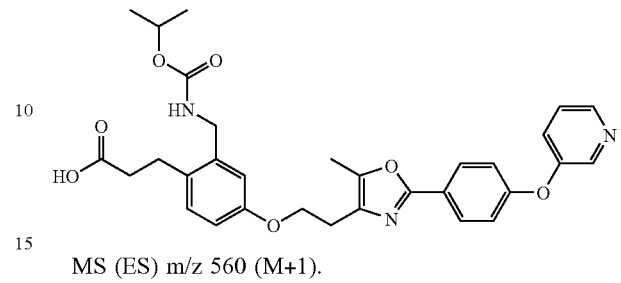

MS (ES) m/z 560 (M+1).

Example 435

3-[2-(Isopropoxycarbonylaminomethyl)-4-(2-{5-methyl-2-[4-(pyrimidin-2-yloxy)phenyl]oxazol-4-yl}ethoxy)phenyl]propionic acid

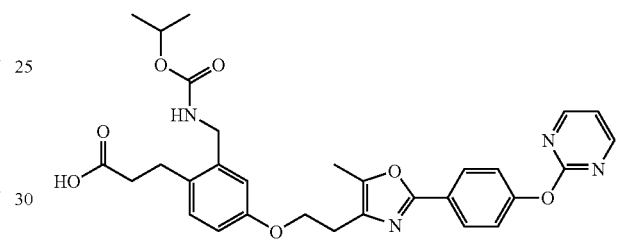

MS (ES) m/z 561 (M+1).

Example 436

3-(2-(Isopropoxycarbonylamino-methyl)-4-{2-[5-methyl-2-(4-carbamoyl-phenyl)-oxazol-4yl]-ethoxy}-phenyl)-propionic acid

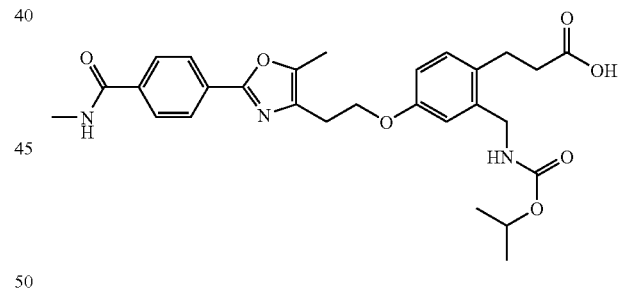

Step A: 4-(4-{2-[4-(2-tert-Butoxycarbonyl-ethyl)-3-(isopropoxycarbonylamino-methyl)-phenoxy]-ethyl}-5-methyl-oxazol-2-yl)-benzoic acid methyl ester

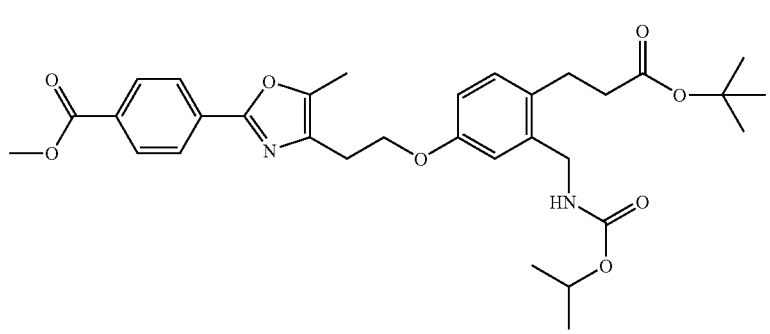

A mixture of 3-[4-{2-[2-(4-bromo-phenyl)-5-methoxy-oxazol-4-yl]-ethoxy}-2-(isopropoxy-carbonylamino-methyl-phenyl)-propionic acid tert-butyl ester (0.25 g, 0.42 mmol), 1,1'-bis(diphenylphosphino)-ferrocene palladium (II) chloride (50 mg), MeOH (0.1 mL) and triethylamine (0.12 mL, 0.66 mmol) in acetonitrile (2 mL) was stirred and heated at 70° C. under CO gas (balloon) for 16 h. The reaction mixture was cooled and concentrated. The residue was purified by silica gel chromatography (hexanes/EtOAc, 5/1 to 1/1) to afford a the title compound as a white solid (0.12 g, 50%): MS (ESI) m/z 581 (M+H)$^+$.

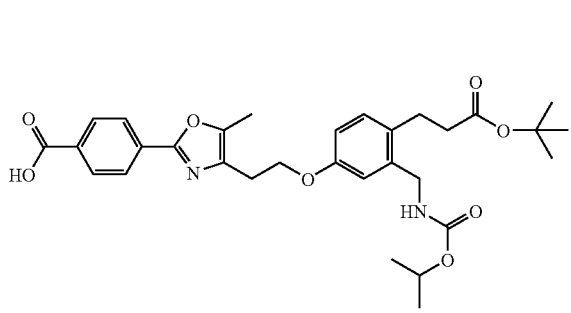

A solution of 4-(4-{2-[4-(2-tert-Butoxycarbonyl-ethyl)-3-(isopropoxycarbonyl-amino-methyl)-phenoxy]-ethyl}-5-methyl-oxazol-2-yl)-benzoic acid methyl ester (100 mg, 0.17 mmol) in methanol (2 mL) was treated with 1.5 N aqueous LiOH (1.0 mL) and stirred at ambient temperature for 3 h. The reaction mixture was acidified with 1N HCl and extracted with CH$_2$Cl$_2$. The organic layer was dried (MgSO$_4$), concentrated, and purified by silica gel chromatography (hexanes/EtOAc, 1/1 to 0/1) to afford the title compound (55 mg, 57%). MS (ESI) m/z 567 (M+H)$^+$.

Step C: 3-(2-(Isopropoxycarbonylamino-methyl)-4-{2-[5-methyl-2-(4-carbamoyl-phenyl)-oxazol-4yl]-ethoxy}-phenyl)-propionic acid A solution of 4-(4-{2-[4-(2-tert-Butoxycarbonyl-ethyl)-3-(isopropoxycarbonyl-amino-methyl)-phenoxy]-ethyl}-5-methyl-oxazol-2-yl)-benzoic acid (40 mg, 0.07 mmol) in CH$_2$Cl$_2$ (2 mL) was treated with oxalyl chloride (1.0 μL, 0.12 mmol) and one drop of DMF. The reaction mixture was stirred at ambient temperature for 30 min, concentrated, and co-evaporated with toluene. The residue was dissolved in CH$_2$Cl$_2$ (2 mL) and was added to a flask charged with 2.0 M methylamine in THF (2M, 0.04 mL) and triethylamine (20 μL, 0.12 mmol). The mixture was stirred at ambient temperature for 16 h, diluted with CH$_2$Cl$_2$ (10 mL), and washed with H$_2$O. The organic layer was dried (MgSO$_4$), concentrated, and purified by silica gel chromatography (hexanes/EtOAc, 3:1 to 0:1) to afford the intermediate tert-butyl ester. The ester was converted to the acid by Standard procedure C; purification by mass directed HPLC yielded the title compound. MS (ESI) m/z 524 (M+H)$^+$.

The following Examples 437 to 448 are prepared by following a substantially similar procedure as described in Example 436.

Example 437

3-(2-(Isopropoxycarbonylamino-methyl)-4-{2-[5-methyl-2-(3-methylcarbamoyl-phenyl)-oxazol-4-yl]-ethoxy}-phenyl)-propionic acid

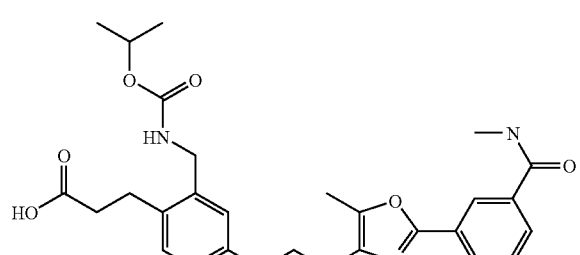

MS (ES) m/z 524 (M+1).

Example 438

3-(2-(Isopropoxycarbonylamino-methyl)-4-{2-[5-methyl-2-(3-propylcarbamoyl-phenyl)-oxazol-4-yl]-ethoxy}-phenyl)-propionic acid

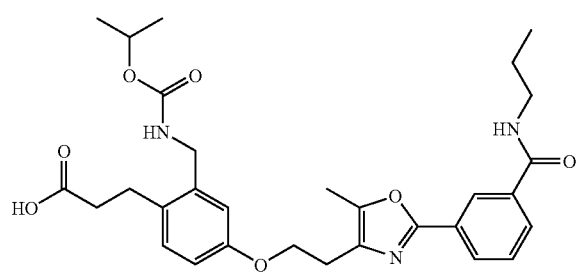

MS (ES) m/z 552 (M+1).

Example 439

3-[4-{2-[2-(3-Cyclobutylcarbamoyl-phenyl)-5-methyl-oxazol-4-yl]-ethoxy}-2-(isopropoxycarbonylamino-methyl)-phenyl]-propionic acid

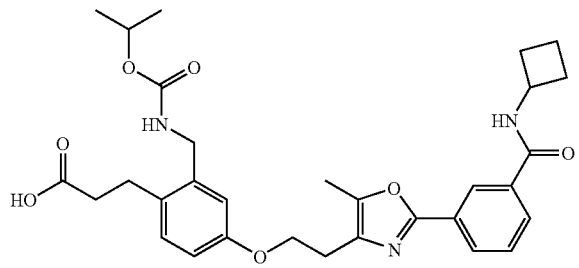

MS (ES) m/z 564 (M+1).

Example 440

3-[4-{2-[2-(3-Isobutylcarbamoyl-phenyl)-5-methyl-oxazol-4-yl]-ethoxy}-2-(isopropoxycarbonylamino-methyl)-phenyl]-propionic acid

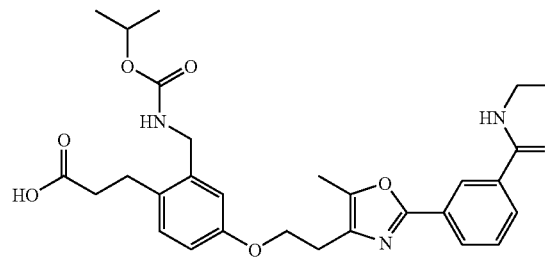

MS (ES) m/z 566 (M+1).

Example 441

3-(2-(Isopropoxycarbonylamino-methyl)-4-{2-[5-methyl-2-(3-phenylcarbamoyl-phenyl)-oxazol-4-yl]-ethoxy}-phenyl)-propionic acid

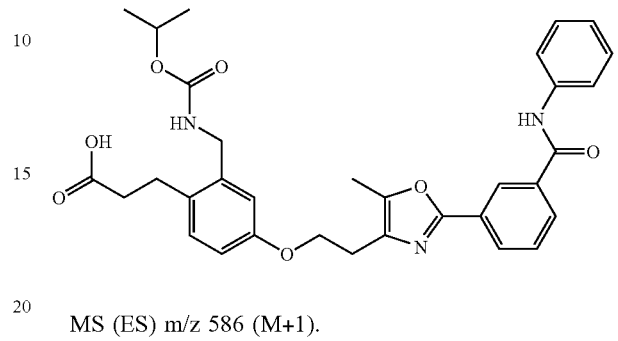

MS (ES) m/z 586 (M+1).

Example 442

3-[2-(Isopropoxycarbonylamino-methyl)-4-(2-{5-methyl-2-[3-(morpholine-4-carbonyl)-phenyl]-oxazol-4-yl}-ethoxy)-phenyl]-propionic acid

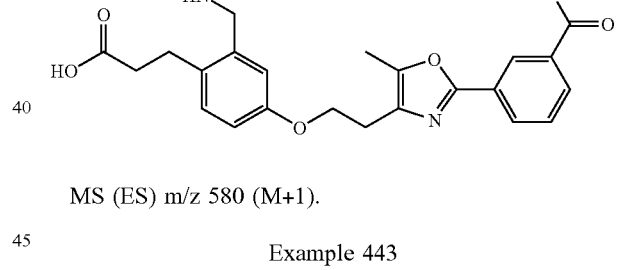

MS (ES) m/z 580 (M+1).

Example 443

3-(2-(Isopropoxycarbonylamino-methyl)-4-{2-[5-methyl-2-(4-propylcarbamoyl-phenyl)-oxazol-4-yl]-ethoxy}-phenyl)-propionic acid

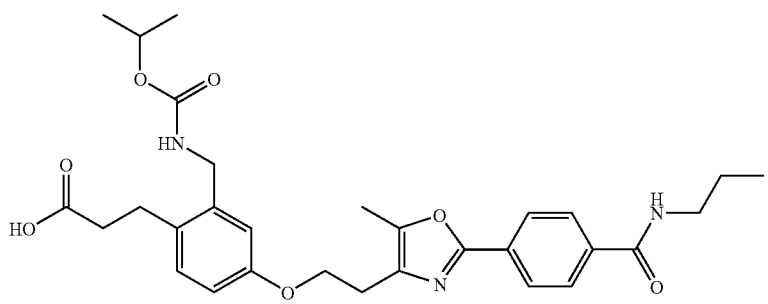

MS (ES) m/z 552 (M+1).

Example 444

3-[4-{2-[2-(4-Cyclobutylcarbamoyl-phenyl)-5-methyl-oxazol-4-yl]-ethoxy}-2-(isopropoxycarbonylamino-methyl)-phenyl]-propionic acid

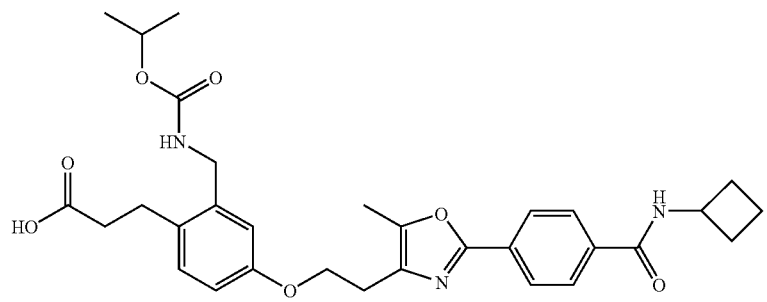

MS (ES) m/z 564 (M+1).

Example 445

3-[4-{2-[2-(4-Cyclohexylcarbamoyl-phenyl)-5-methyl-oxazol-4-yl]-ethoxy}-2-(isopropoxycarbonylamino-methyl)-phenyl]-propionic acid

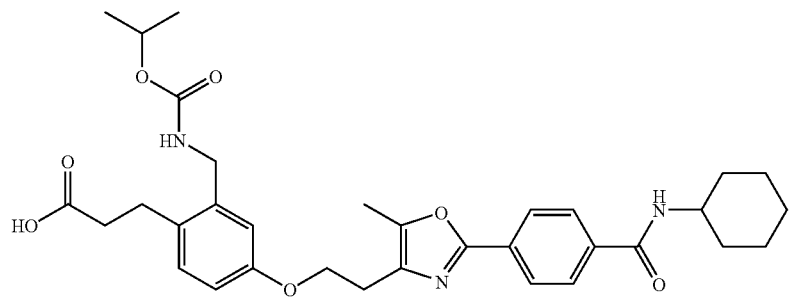

MS (ES) m/z 592 (M+1).

Example 446

3-(2-(Isopropoxycarbonylamino-methyl)-4-{2-[5-methyl-2-(4-phenylcarbamoyl-phenyl)-oxazol-4-yl]-ethoxy}-phenyl)-propionic acid

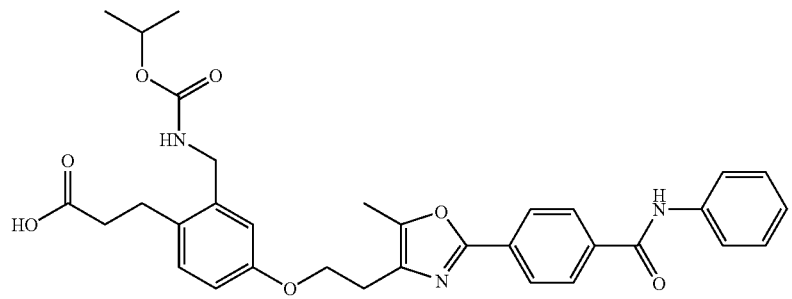

MS (ES) m/z 586 (M+1).

Example 447

3-[2-(Isopropoxycarbonylamino-methyl)-4-(2-{5-methyl-2-[4-(pyridin-3-ylcarbamoyl)-phenyl]-oxazol-4-yl}-ethoxy)-phenyl]-propionic acid

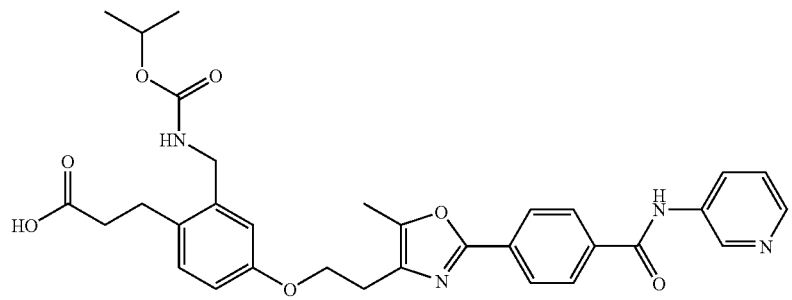

MS (ES) m/z 587 (M+1).

Example 448

3-[2-(Isopropoxycarbonylamino-methyl)-4-(2-{5-methyl-2-[4-(pyrrolidine-1-carbonyl)-phenyl]-oxazol-4-yl}-ethoxy)-phenyl]-propionic acid

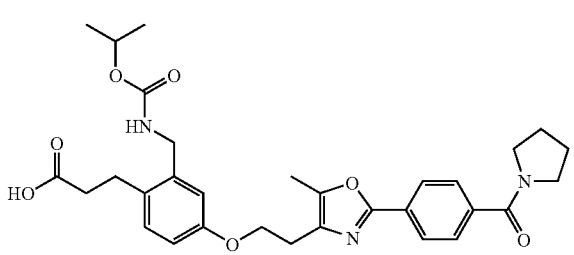

MS (ES) m/z 564 (M+1).

Example 449

4-(4-{2-[4-(2-Carboxy-ethyl)-3-(isopropoxycarbonylamino-methyl)-phenoxy]-ethyl}-5-methyl-oxazol-2-yl)-benzoic acid

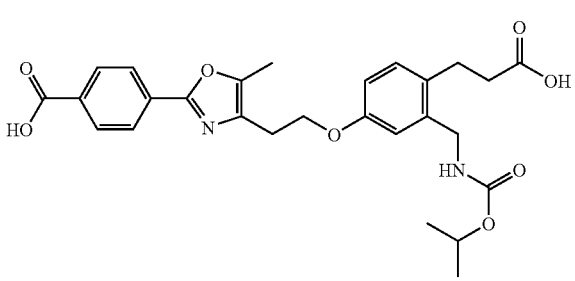

4-(4-{2-[4-(2-tert-Butoxycarbonyl-ethyl)-3-(isopropoxycarbonylamino-methyl)-phenoxy]-ethyl}-5-methyl-oxazol-2-yl)-benzoic acid (50 mg, 0.09 mmol, Example 436, Step B) was converted to the title compound using Standard Procedure C (40 mg, 95%): MS (ESI) m/z 525 (M+H)⁺.

Example 450

3-(4-{2-[4-(2-Carboxy-ethyl)-3-(isopropoxycarbonylamino-methyl)-phenoxy]-ethyl}-5-methyl-oxazol-2-yl)-benzoic acid

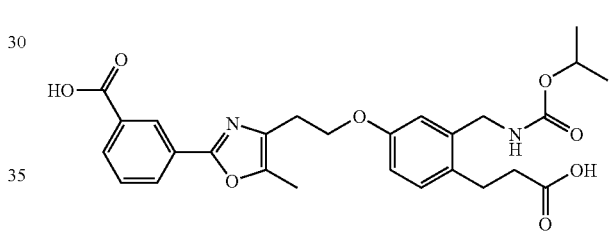

The above compound is prepared by following a substantially similar procedure as described in Example 449. MS (ESI) m/z 525 (M+H)⁺.

Example 451

3-[4-{2-[2-(3-Cyclohexylcarbamoyl-phenyl)-5-methyl-oxazol-4-yl]-ethoxy}-2-(isopropoxycarbonylamino-methyl)-phenyl]-propionic acid

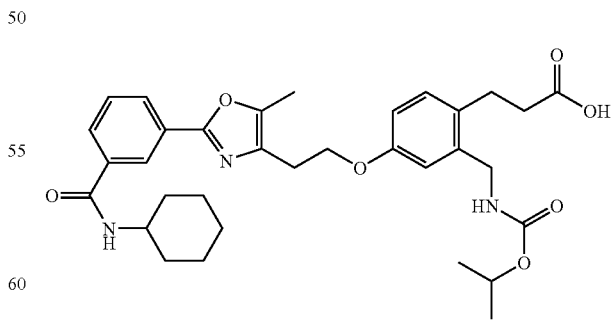

A solution of 3-[4-{2-[2-(4-bromo-phenyl)-5-methoxy-oxazol-4-yl]-ethoxy}-2-(isopropoxy-carbonylamino-methyl)-propionic acid tert-butyl ester (230 mg, 0.38 mmol) in acetonitrile (20 ml) in a dry 3-neck flask was treated with 2-hydroxypyridine (44 mg, 0.46 mmol) and 1,1'-bis(diphenylphosphino)-ferrocene palladium (II) chloride (47 mg, 0.057 mmol). The mixture was stirred for about 5 minutes under N$_2$, and triethylamine (58 mg, 0.57 mmol) was added dropwise. CO gas was bubbled through the mixture, and the reaction was heated at 70° C. for 4 h. The CO bubbling was replaced by a balloon filled with CO, and the reaction was stirred an additional 16 h. The mixture was cooled and partitioned equally into 2 flasks. One portion was treated with cyclohexylamine (46 mg, 0.46 mmol) and triethylamine (58 mg, 0.57 mmol). The mixture was stirred at 70° C. for 16 h, cooled, filtered through Celite, and concentrated to a brown solid (196 mg). The solid was purified by radial chromatography (10-70% EtOAc/hexanes) to give the penultimate tert-butyl ester (78 mg; MS (ESI) m/z 648.6 (M+H)$^+$). The ester was converted to the title compound by Standard procedure D (72 mg, 64%). MS (ESI) m/z 592.0 (M+H)$^+$.

Example 452

3-[4-(2-{2-[4-(3-Fluoro-benzoylamino)-phenyl]-5-methyl-oxazol-4-yl}-ethoxy)-2-(isopropoxycarbonylamino-methyl)-phenyl]-propionic acid Step A: 3-(2-(Isopropoxycarbonylamino-methyl)-4-{2-[5-methyl-2-(4-nitro-phenyl)-oxazol-4-yl]-ethoxy}-phenyl)-propionic acid tert-butyl ester

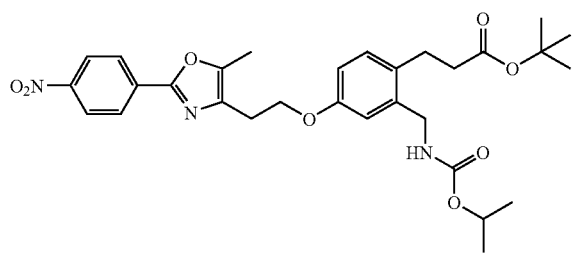

4-Methyl-3-nitro-benzenesulfonic acid 2-[5-methyl-2-(4-nitro-phenyl)-oxazol-4-yl]-ethyl ester (Preparation 7) and 3-[4-hydroxy-2-(isopropoxycarbonylamino-methyl)-phenyl]-propionic acid tert-butyl ester were coupled by Standard procedure A to give the title compound.

Step B: 3-[4-{2-[2-(4-Amino-phenyl)-5-methyl-oxazol-4-yl]-ethoxy}-2-(isopropoxycarbonylamino-methyl)-phenyl]-propionic acid tert-butyl ester

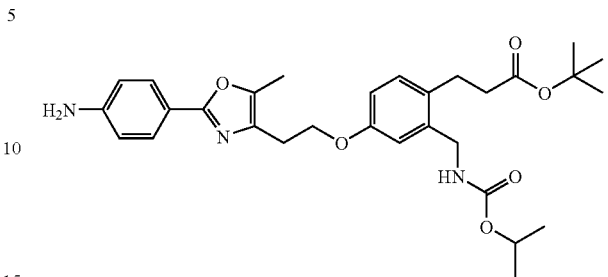

A mixture of 3-(2-(isopropoxycarbonylamino-methyl)-4-{2-[5-methyl-2-(4-nitro-phenyl)-oxazol-4-yl]-ethoxy}-phenyl)-propionic acid tert-butyl ester (207 mg, 0.365 mmol) and 10% Pd—C (27 mg) in EtOAc (20 mL) was stirred under H$_2$ (1 atm) for 18 h. The reaction mixture was filtered through Celite and concentrated (75° C.) to give the title compound as a colorless oil (196 mg, 100%): MS (ESI) m/z 538 (M+H)$^+$.

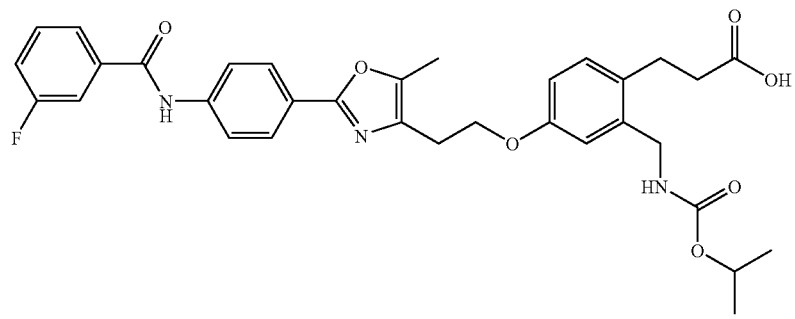

Step C: 3-[4-(2-{2-[4-(3-Fluoro-benzoylamino)-phenyl]-5-methyl-oxazol-4-yl}-ethoxy)-2-(isopropoxycarbonylamino-methyl)-phenyl]-propionic acid 3-Fluorobenzoyl chloride (31 mg, 0.20 mmol, 1.8 equiv) was added to a solution of 3-[4-{2-[2-(4-amino-phenyl)-5-methyl-oxazol-4-yl]-ethoxy}-2-(isopropoxycarbonyl-amino-methyl)-phenyl]-propionic acid tert-butyl ester (58 mg, 0.11 mmol, 1 equiv) and triethylamine (30 µL, 22 mg, 0.22 mmol, 2.0 equiv) in CH$_2$Cl$_2$ (5 mL). After 16 h, the reaction solution was washed with 1 M aqueous HCl (5 mL) and saturated aq NaHCO$_3$ (5 mL). The organic layer was dried (MgSO$_4$) and concentrated (75° C.) to the intermediate ester as a light yellow oil. The oil was diluted with 4 M HCl in 1,4-dioxane (5 mL), stirred for 64 h, and concentrated to give the title compound (73 mg, 110%). HRMS Calculated for C$_{33}$H$_{35}$FN$_3$O$_7$: m/z 604.2459. Found: 604.2453.

The following Examples 453 to 475 are prepared by following a substantially similar procedure as described in Examples 451 and 452.

Example 453

3-[4-(2-{2-[4-(4-Fluoro-benzoylamino)-phenyl]-5-methyl-oxazol-4-yl}-ethoxy)-2-(isopropoxycarbonylamino-methyl)-phenyl]-propionic acid

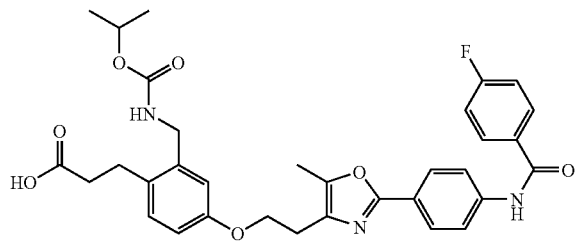

HRMS Calculated for $C_{33}H_{35}FN_3O_7$: m/z 604.2459. Found: 604.2454.

Example 454

3-[4-(2-{2-[4-(3,5-Difluoro-benzoylamino)-phenyl]-5-methyl-oxazol-4-yl}-ethoxy)-2-(isopropoxycarbonylamino-methyl)-phenyl]-propionic acid

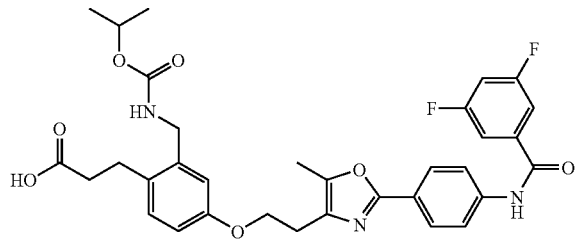

HRMS Calculated for $C_{33}H_{34}F_2N_3O_7$: m/z 622.2365. Found: 622.2352.

Example 455

3-[4-(2-{2-[4-(3,4-Difluoro-benzoylamino)-phenyl]-5-methyl-oxazol-4-yl}-ethoxy)-2-(isopropoxycarbonylamino-methyl)-phenyl]-propionic acid

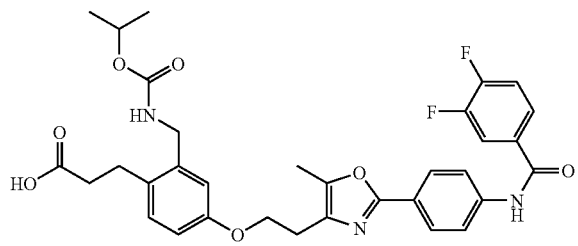

HRMS Calculated for $C_{33}H_{34}F_2N_3O_7$: m/z 622.2365. Found: 622.2382.

Example 456

3-(4-{2-[2-(4-Acetylamino-phenyl)-5-methyl-oxazol-4-yl]-ethoxy}-2-{[(pyridine-2-carbonyl)-amino]-methyl}-phenyl)-propionic acid

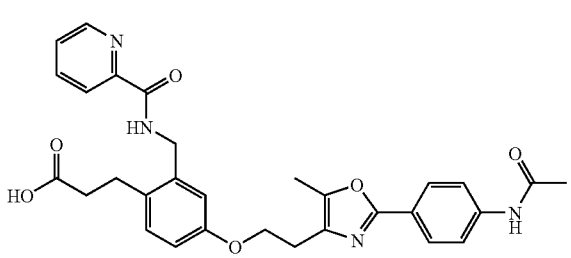

MS (ES) m/z 543 (M+1).

Example 457

3-(4-{2-[2-(4-Amino-phenyl)-5-methyl-oxazol-4-yl]-ethoxy}-2-{[(pyridine-2-carbonyl)-amino]-methyl}-phenyl)-propionic acid

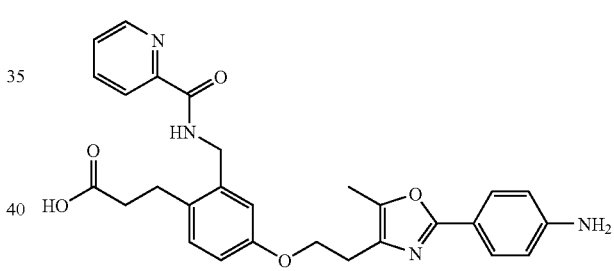

MS (ES) m/z 501 (M+1).

Example 458

3-(4-{2-[2-(4-Isobutoxycarbonylamino-phenyl)-5-methyl-oxazol-4-yl]-ethoxy}-2-{[(pyridine-2-carbonyl)-amino]-methyl}-phenyl)-propionic acid

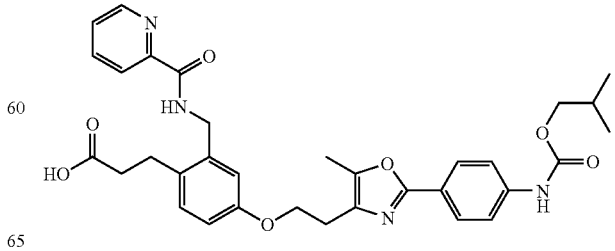

MS (ES) m/z 601 (M+1).

Example 459

3-[4-{2-[2-(4-Amino-phenyl)-5-methyl-oxazol-4-yl]-ethoxy}-2-(isopropoxycarbonylamino-methyl)-phenyl]-propionic acid

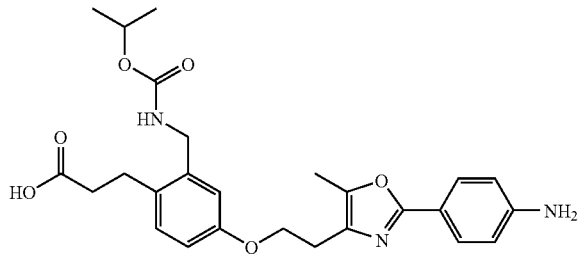

MS (ES) m/z 482 (M+1).

Example 460

3-[4-{2-[2-(4-Benzoylamino-phenyl)-5-methyl-oxazol-4-yl]-ethoxy}-2-(isopropoxycarbonylamino-methyl)-phenyl]-propionic acid

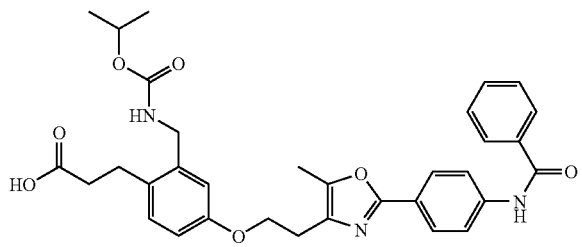

MS (ES) m/z 586 (M+1).

Example 461

3-(4-{2-[2-(4-Benzoylamino-phenyl)-5-methyl-oxazol-4-yl]-ethoxy}-2-{[(pyridine-2-carbonyl)-amino]-methyl}-phenyl)-propionic acid

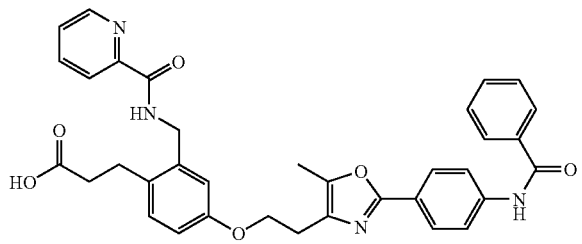

MS (ES) m/z 661 (M+1).

Example 462

3-(4-(2-{2-[4-(4-Methoxy-benzoylamino)-phenyl]-5-methyl-oxazol-4-yl}-ethoxy)-2-{[(pyridine-2-carbonyl)-amino]-methyl}-phenyl)-propionic acid

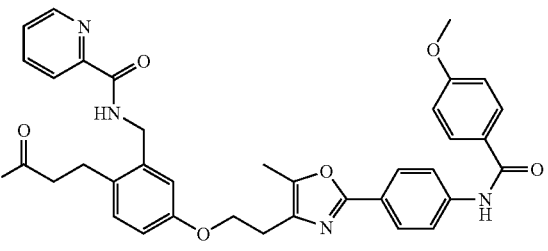

MS (ES) m/z 635 (M+1).

Example 463

3-(4-[2-(5-Methyl-2-{4-[(pyridine-3-carbonyl)-amino]-phenyl}-oxazol-4-yl)-ethoxy]-2-{[(pyridine-2-carbonyl)-amino]-methyl}-phenyl)-propionic acid

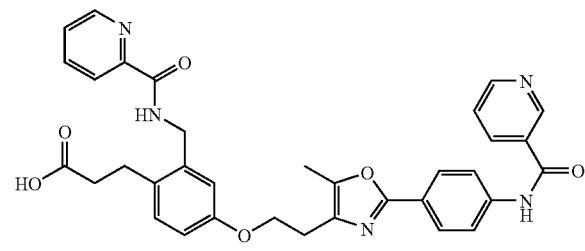

MS (ES) m/z 606 (M+1).

Example 464

3-(4-[2-(2-{4-[(2,5-Dichloro-thiophene-3-carbonyl)-amino]-phenyl}-5-methyl-oxazol-4-yl)-ethoxy]-2-{[(pyridine-2-carbonyl)-amino]-methyl}-phenyl)-propionic acid

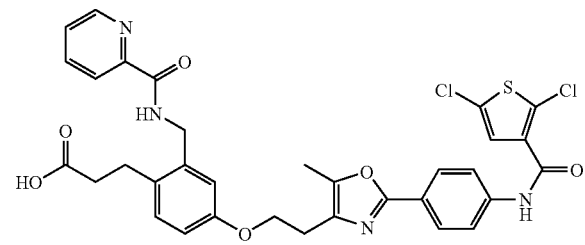

MS (ES) m/z 680 (M+1).

Example 465

3-(4-(2-{2-[4-(N,N-Di-(butane-1-sulfonyl)amino)-phenyl]-5-methyl-oxazol-4-yl}-ethoxy)-2-{[(pyridine-2-carbonyl)-amino]-methyl}-phenyl)-propionic acid

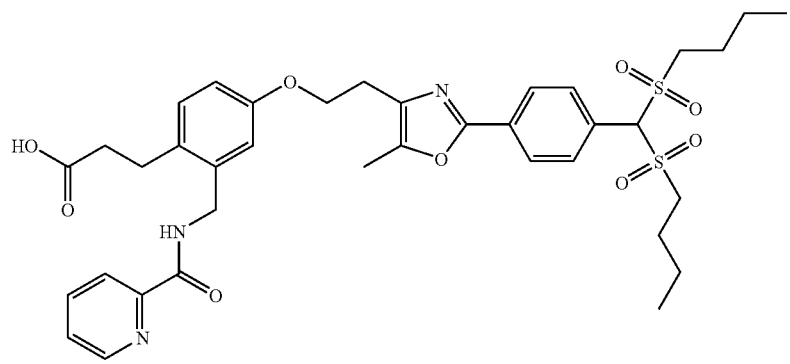

MS (ES) m/z 741 (M+1).

Example 466

3-(4-(2-{2-[4-(Butane-1-sulfonylamino)-phenyl]-5-methyl-oxazol-4-yl}-ethoxy)-2-{[(pyridine-2-carbonyl)-amino]-methyl}-phenyl)-propionic acid

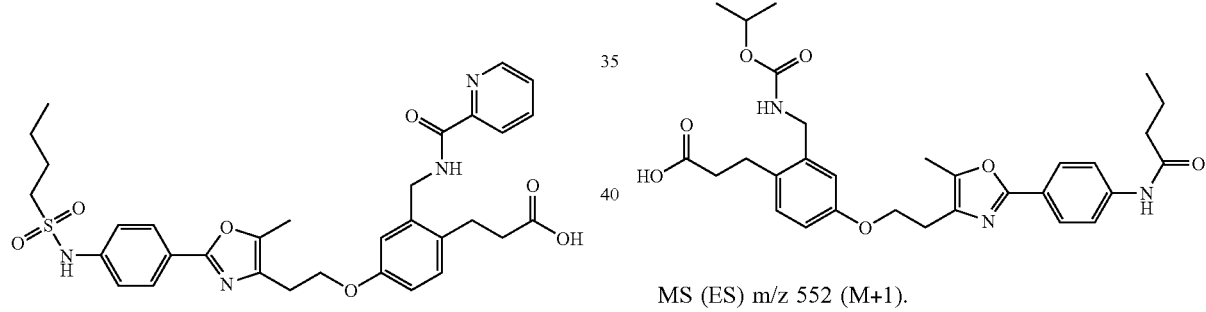

MS (ES) m/z 621 (M+1).

Example 467

3-[4-{2-[2-(4-Acetylamino-phenyl)-5-methyl-oxazol-4-yl]-ethoxy}-2-(isopropoxycarbonylamino-methyl)-phenyl]-propionic acid

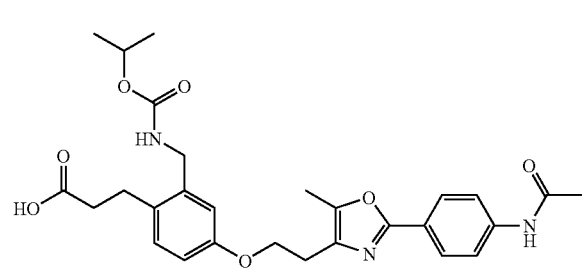

MS (ES) m/z 524 (M+1).

Example 468

3-[4-{2-[2-(4-Butyrylamino-phenyl)-5-methyl-oxazol-4-yl]-ethoxy}-2-(isopropoxycarbonylamino-methyl)-phenyl]-propionic acid

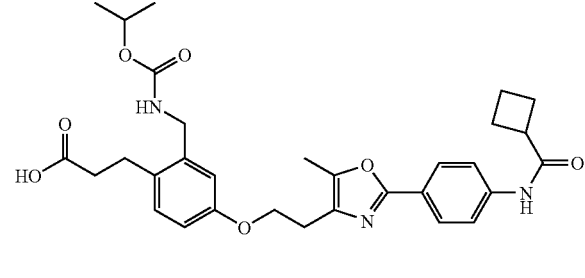

MS (ES) m/z 552 (M+1).

Example 469

3-[4-(2-{2-[4-(Cyclobutanecarbonyl-amino)-phenyl]-5-methyl-oxazol-4-yl}-ethoxy)-2-(isopropoxycarbonylamino-methyl)-phenyl]-propionic acid MS (ES) m/z 564 (M+1).

Example 470

3-[2-(Isopropoxycarbonylamino-methyl)-4-(2-{2-[4-(4-methoxy-benzoylamino)-phenyl]-5-methyl-oxazol-4-yl}-ethoxy)-phenyl]-propionic acid

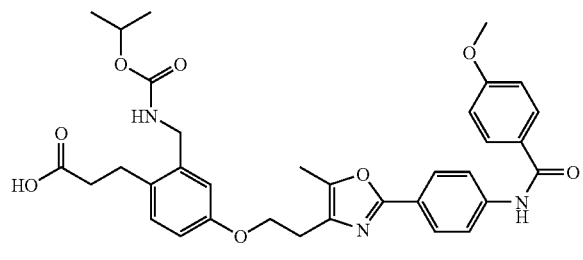

MS (ES) m/z 616 (M+1).

Example 471

3-[4-(2-{2-[4-(3,5-Dimethoxy-benzoylamino)-phenyl]-5-methyl-oxazol-4-yl}-ethoxy)-2-(isopropoxycarbonylamino-methyl)-phenyl]-propionic acid

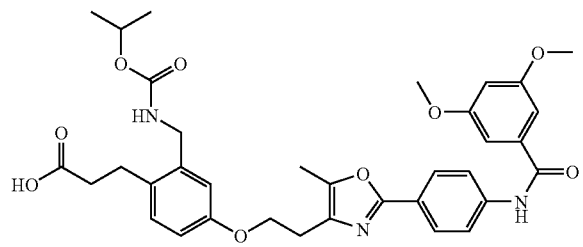

MS (ES) m/z 646 (M+1).

Example 472

3-{2-(Isopropoxycarbonylamino-methyl)-4-[2-(5-methyl-2-{4-[(pyridine-3-carbonyl)-amino]-phenyl}-oxazol-4-yl)-ethoxy]-phenyl}-propionic acid

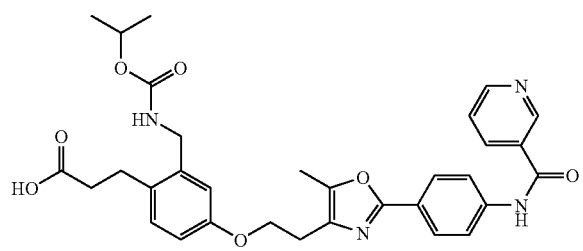

MS (ES) m/z 587 (M+1).

Example 473

3-[4-[2-(2-{4-[(2,5-Dichloro-thiophene-3-carbonyl)-amino]-phenyl}-5-methyl-oxazol-4-yl)-ethoxy]-2-(isopropoxycarbonylamino-methyl)-phenyl]-propionic acid

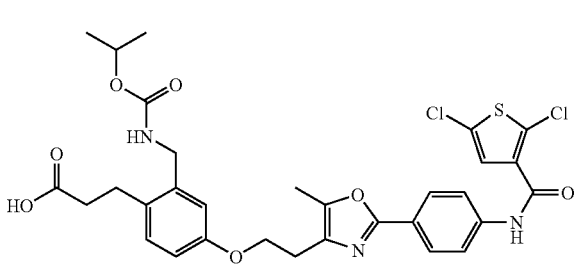

MS (ES) m/z 661 (M+1).

Example 474

3-{2-(Isopropoxycarbonylamino-methyl)-4-[2-(5-methyl-2-{4-[(pyridine-2-carbonyl)-amino]-phenyl}-oxazol-4-yl)-ethoxy]-phenyl}-propionic acid

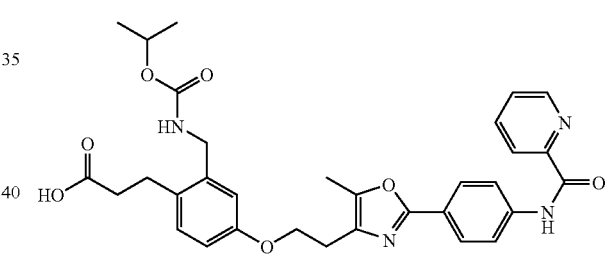

MS (ES) m/z 587 (M+1).

Example 475

3-[4-[2-(2-{4-[(Furan-2-carbonyl)-amino]-phenyl}-5-methyl-oxazol-4-yl)-ethoxy]-2-(isopropoxycarbonylamino-methyl)-phenyl]-propionic acid

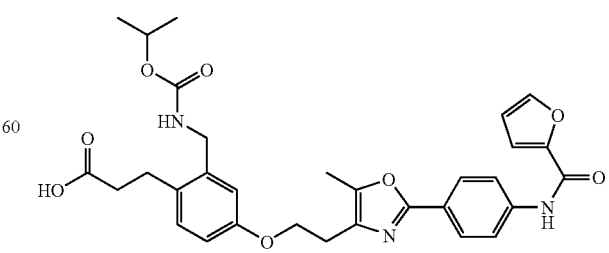

MS (ES) m/z 576 (M+1).

Example 476

3-[4-[2-(5-Methyl-2-phenyl-oxazol-4-yl)-ethoxy]-2-(pyrimidin-2-ylaminomethyl)-phenyl]-propionic acid

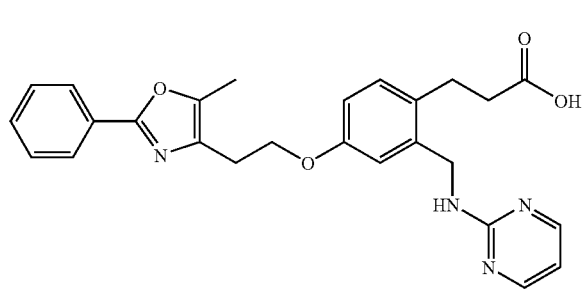

A solution of 3-{2-Aminomethyl-4-[2-(5-methyl-2-phenyl-oxazol-4-yl)-ethoxy]-phenyl}-propionic acid tert-butyl ester: acetic acid salt (0.40 mmol, 0.20 g, Example 1 Step B) in DMF (2 mL) was treated with $K_2CO_3$ (1.0 mmol, 0.14 g) and 2-chloropyrimidine (1.2 mmol, 0.14 g). The mixture was heated at 60° C. for 18 h, cooled, diluted with water (50 mL, and extracted with EtOAc (3×15 mL). The combined organic layers were dried ($Na_2SO_4$), concentrated and purified by silica gel chromatography to give the tert-butyl ester intermediate. This material was converted into the title compound (80 mg) using Standard procedure C. MS (ESI) m/z 459.2 $(M+H)^+$.

Example 477

3-{4-[2-(5-Methyl-2-phenyl-oxazol-4-yl)-ethoxy]-2-[(2-methylsulfanyl-pyrimidin-4-ylamino)-methyl]-phenyl}-propionic acid

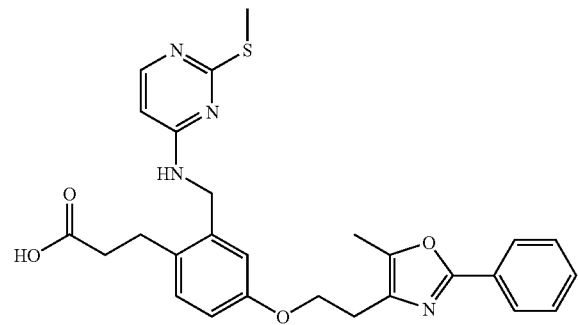

The above compound is prepared by following a substantially similar procedure as described in Example 476. MS (ESI) m/z 505.1 $(M+H)^+$.

Example 478

3-{2-(Benzothiazol-2-ylaminomethyl)-4-[2-(5-methyl-2-phenyl-oxazol-4-yl)-ethoxy]-phenyl}-propionic acid

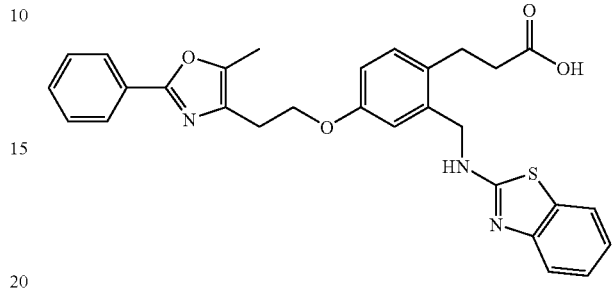

A solution of 3-{2-aminomethyl-4-[2-(5-methyl-2-phenyl-oxazol-4-yl)-ethoxy]-phenyl}-propionic acid tert-butyl ester acetic acid salt (150 mg, 0.302 mmol; Example 1 Step B) and 2-chloro-benzothiazole (154 mg, 0.907 mmol) in toluene (5 mL) was treated with $K_2CO_3$ (42 mg). The suspension was heated at 110° C. for 48 h and concentrated. The residue was purified by silica gel chromatography (25-50% EtOAc/hexanes) to afford the tert-butyl ester intermediate (15 mg). This material was converted into the title compound (80 mg) using Standard procedure C. The intermediate was treated with TFA (0.25 ml)/$CH_2Cl_2$ (1.0 ml)/$H_2O$ (0.1 mL), stirred for 3 h, and concentrated. The residue was dissolved in $CH_2Cl_2$ (10 ml), washed with aqueous buffer (pH=7), dried ($Na_2SO_4$), and concentrated to afford the title compound (12 mg, 8%). MS (ESI) m/z 514.3 $(M+H)^+$.

Example 479

3-{2-[(2-Benzoyl-phenylamino)-methyl]-4-[2-(5-methyl-2-phenyl-oxazol-4-yl)-ethoxy]-phenyl}-propionic acid

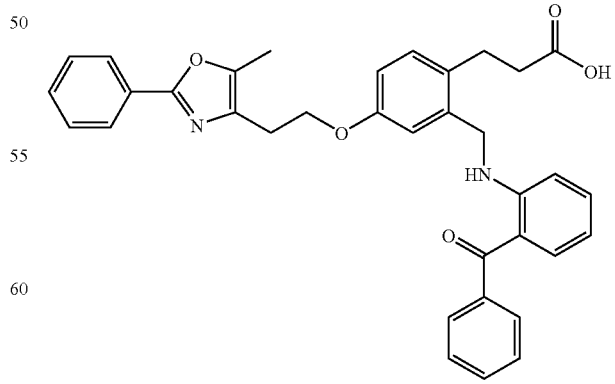

A solution of 3-{2-aminomethyl-4-[2-(5-methyl-2-phenyl-oxazol-4-yl)-ethoxy]-phenyl}-propionic acid tert-butyl ester acetic acid salt (290 mg, 0.665 mmol, Example 1, Step B) and 2-benzoyl-cyclohexanone (161 mg, 0.797 mmol) in anisole (20 mL) was treated with a slurry of Pd/C (60 mg) in anisole (2 mL). The mixture was refluxed at 200° C. with azeotropic removal of water for 2 h and cooled to room temperature. The catalyst was filtered and a fresh slurry of Pd/C (60 mg) in anisole was added. The mixture was heated at 110° C. for 72 h and filtered through a pad of Celite. The filtrate was concentrated, purified by silica gel chromatography-(25% EtOAc/hexanes) to afford a mixture of starting material and desired tert butyl ester intermediate. The mixture was treated with TFA (1.0 ml)/CH$_2$Cl$_2$ (1.0 ml)/H$_2$O (0.1 mL), stirred for 3 h, and concentrated. The residue was and purified using silica gel chromatography (MeOH/EtOAc 1/9) to give the title compound (38 mg, 10%). MS (ESI) m/z 561.3 (M+H)$^+$.

Example 480

3-{4-[2-(5-Methyl-2-phenyl-oxazol-4-yl)-ethoxy]-2-[(4-trifluoromethyl-phenylamino)-methyl]-phenyl}-propionic acid

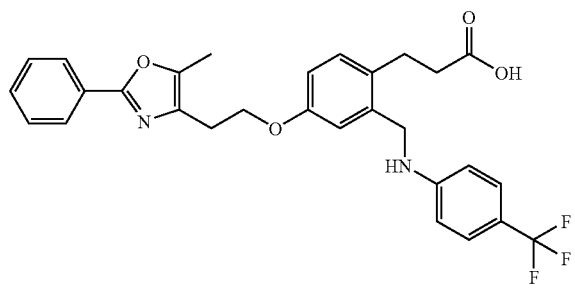

A solution of 3-{2-aminomethyl-4-[2-(5-methyl-2-phenyl-oxazol-4-yl)-ethoxy]-phenyl}-propionic acid tert-butyl ester (174 mg, 0.40 mmol, Example 1 and Procedure 1) in toluene (5.0 mL) in a sealed tube apparatus under a flow of N$_2$ was added Pd(OAc)$_2$ (15 mg), 2-(di-t-butylphosphino) biphenyl (10 mg), sodium t-butoxide (54 mg, 0.56 mmol) and 4-trifluoromethylchlorobenzene (29 mg, 0.16 mmol). The tube was sealed and heated at 110° C. for 14 b. The reaction mixture was cooled, quenched with water (1.0 mL), and extracted with EtOAc (2×15 mL). The combined organics were concentrated and purified using silica gel chromatography column (10-50% EtOAc/hexanes) to yield the tert-butyl ester intermediate (80 mg). This material was converted into the title compound (40 mg, 48%) using Standard procedure C. MS (ESI) m/z 525.4 (M+H)$^+$.

The following Examples 481 to 484 are prepared by following a substantially similar procedure as described in Examples 478 to 480.

Example 481

3-{2-[(4-Methanesulfonyl-phenylamino)-methyl]-4-[2-(5-methyl-2-phenyl-oxazol-4-yl)-ethoxy]-phenyl}-propionic acid

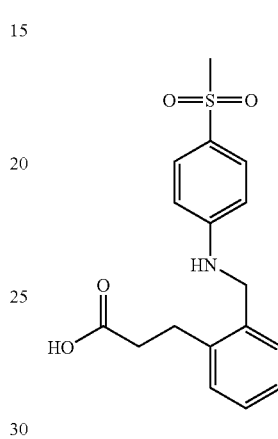

MS (ESI) m/z 535.1 (M+H)$^+$.

Example 482

3-{4-[2-(5-Methyl-2-phenyl-oxazol-4-yl)-ethoxy]-2-[(4-propionyl-phenylamino)-methyl]-phenyl}-propionic acid

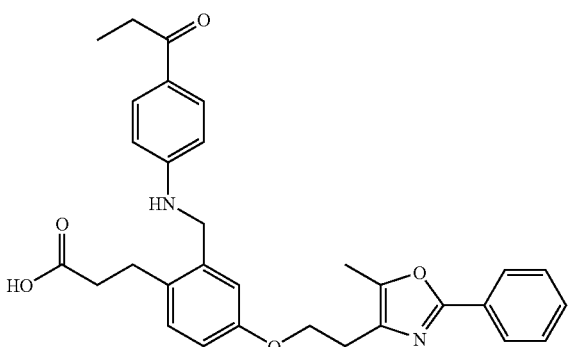

MS (ESI) m/z 513.2 (M+H)$^+$.

Example 483

3-{2-{[Bis-(4-methoxy-phenyl)-amino]-methyl}-4-[2-(5-methyl-2-phenyl-oxazol-4-yl)-ethoxy]-phenyl}-propionic acid

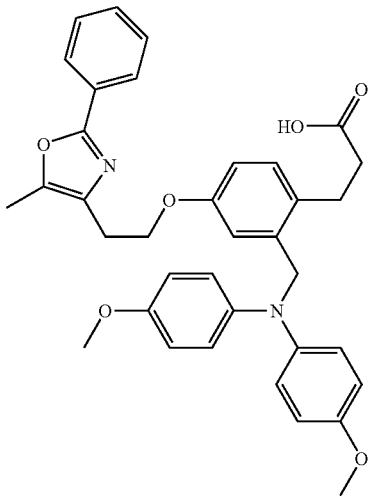

MS (ESI) m/z 593.3 (M+H)+.

Example 484

3-[4-[2-(5-Methyl-2-phenyl-oxazol-4-yl)-ethoxy]-2-(pyridin-2-ylaminomethyl)-phenyl]-propionic acid

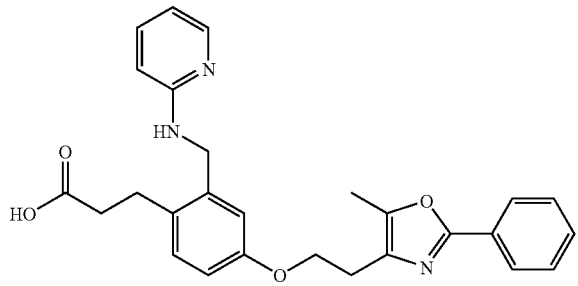

MS (ESI) m/z 458.2 (M+H)+.

Example 485

3-{2-{[(2,5-Dichloro-thiophene-3-carbonyl)-methyl-amino]-methyl}-4-[2-(5-methyl-2-phenyl-oxazol-4-yl)-ethoxy]-phenyl}-propionic acid

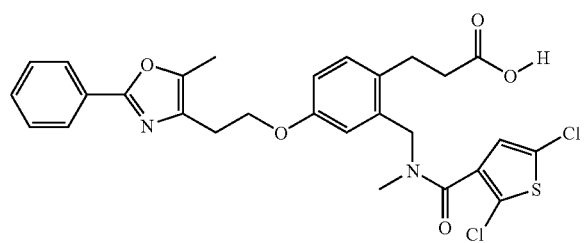

Step A: 3-{4-[2-(5-Methyl-2-phenyl-oxazol-4-yl)-ethoxy]-2-[(2,2,2-trifluoro-acetylamino)-methyl]-phenyl}-propionic acid tert-butyl ester

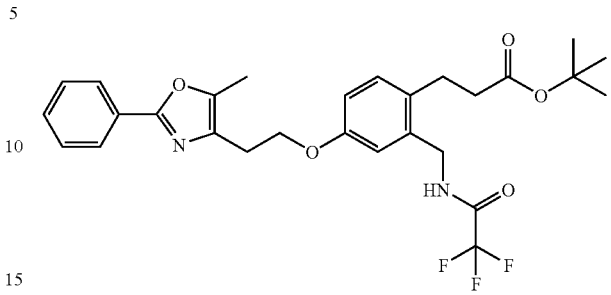

3-{2-Aminomethyl-4-[2-(5-methyl-2-phenyl-oxazol-4-yl)-ethoxy]-phenyl}-propionic acid tert-butyl ester: acetic acid salt (894 mg, 1.80 mmol) was dissolved in CH$_2$Cl$_2$ (25 mL) and washed with saturated NaHCO$_3$ solution (15 mL). The organic layer was dried (NaSO$_4$), filtered, and concentrated to a yellow oil (681 mg). The crude amine was dissolved in CH$_2$Cl$_2$ (25 mL) and treated with trifluoroacetic anhydride (0.66 mL, 4.7 mmol) then pyridine (0.37 mL, 4.6 mmol). The reaction mixture was stirred at ambient temperature for 4 h and concentrated. The residue was partitioned between EtOAc and 1N HCl, and the organic layer was washed with saturated NaHCO$_3$ solution then brine. The organic layer was dried (Na$_2$SO$_4$) and concentrated to give a pale yellow solid (839 mg, 88%).

Step B: 3-(4-[2-(5-Methyl-2-phenyl-oxazol-4-yl)-ethoxy]-2-{[methyl-(2,2,2-trifluoro-acetyl)-amino]-methyl}-phenyl)-propionic acid tert-butyl ester

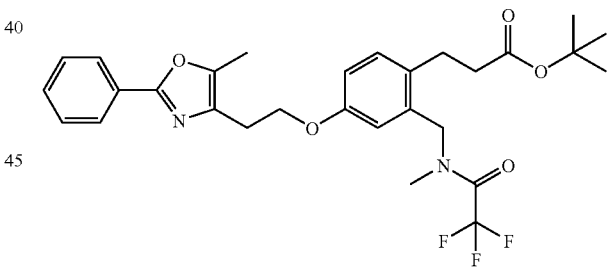

A solution of 3-{4-[2-(5-methyl-2-phenyl-oxazol-4-yl)-ethoxy]-2-[(2,2,2-trifluoro-acetylamino)-methyl]-phenyl}-propionic acid tert-butyl ester (151 mg, 0.28 mmol) in dry DMF (10 mL) was cooled in an ice bath and treated with NaH (22 mg, 0.55 mmol, 60% oil dispersion). After the reaction mixture was stirred for 25 min, iodomethane (0.15 mL, 3.0 mmol) was added, and the reaction was allowed to warm to ambient temperature gradually. After 4 h, more iodomethane (0.10 mL, 2 mmol) was added. The mixture was stirred overnight and was partitioned between EtOAc and aqueous LiCl solution. The organic layer was washed with brine, dried (Na$_2$SO$_4$), and concentrated. The residue was purified by silica gel radial chromatography (CH$_2$Cl$_2$/EtOAc 100/0 to 95/5) to give the title compound (111 mg, 73%).

Step C: 3-{2-Methylaminomethyl-4-[2-(5-methyl-2-phenyl-oxazol-4-yl)-ethoxy]-phenyl}-propionic acid tert-butyl ester

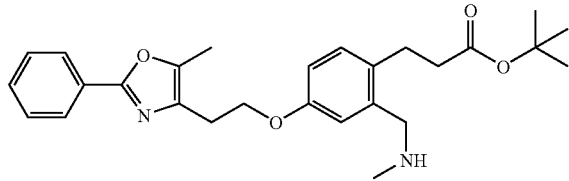

A solution of 3-(4-[2-(5-methyl-2-phenyl-oxazol-4-yl)-ethoxy]-2-{[methyl-(2,2,2-trifluoro-acetyl)-amino]-methyl}-phenyl)-propionic acid tert-butyl ester (111 mg, 0.20 mmol) in methanol (5 mL) and THF (5 mL) was treated with 2N NaOH (1.0 mL, 2.0 mmol) and heated at 55° C. for 1 h. The reaction mixture was cooled, concentrated, neutralized with 1N HCl and extracted into EtOAc. The organic layer was washed with saturated $NaHCO_3$ solution and brine, dried ($Na_2SO_4$), and concentrated. The residue was purified by silica gel radial chromatography ($CH_2Cl_2$/methanol 95/5 to 90/10) to the title compound (37 mg, 42%). MS (ES) m/z 451.3 [M+1].

Step D: 3-{2-{[(2,5-Dichloro-thiophene-3-carbonyl)-methyl-amino]-methyl}-4-[2-(5-methyl-2-phenyl-oxazol-4-yl)-ethoxy]-phenyl}-propionic acid tert butyl ester

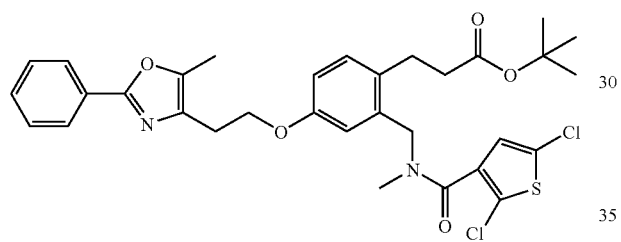

A solution of 3-{2-methylaminomethyl-4-[2-(5-methyl-2-phenyl-oxazol-4-yl)-ethoxy]-phenyl}-propionic acid tert-butyl ester (37 mg, 0.083 mmol) in $CH_2Cl_2$ (5 mL) was treated with triethylamine (0.035 mL, 0.25 mmol) then 2,5-dichloro-thiophene-3-carbonyl chloride (0.054 mL, 0.25 mmol) and stirred at ambient temperature overnight. The mixture was diluted with EtOAc (25 mL) and washed with brine (3×10 mL). The organic layer was dried ($Na_2SO_4$) and concentrated to the title compound (50 mg, 96%). MS (ES) m/z 629, 631 [M+1].

Step E: 3-{2-{[(2,5-Dichloro-thiophene-3-carbonyl)-methyl-amino]-methyl}-4-[2-(5-methyl-2-phenyl-oxazol-4-yl)-ethoxy]-phenyl}-propionic acid A solution of 3-{2-{[(2,5-dichloro-thiophene-3-carbonyl)-methyl-amino]-methyl}-4-[2-(5-methyl-2-phenyl-oxazol-4-yl)-ethoxy]-phenyl}-propionic acid tert butyl ester (50 mg, 0.079 mmol) in $CH_2Cl_2$ (2 mL) was treated with anisole (1.0 mL) then TFA (0.6 mL). The solution was stirred at ambient temperature 2 h, and more TFA (1.0 mL) was added. After 15 min, the reaction was concentrated and co-evaporated with $CCl_4$ (3×). The residue was triturated with hexanes to yield a foam (43 mg, 95%). $^1$H NMR (400 MHz, $CDCl_3$) δ 2.36 (s, 3H), 2.48 (t, 0.6H, J=7.8 Hz), 2.58 (t, 1.4H, J=7.8 Hz), 2.72 (t, 0.6H, J=7.8 Hz), 2.84 (s, 2H), 2.90 (t, 1.4H, J=7.8 Hz), 2.93 (s, 1H), 2.98 (brs, 2H), 4.17 (t, 2H, J=6.4 Hz), 4.47 (s, 0.6H), 4.71 (s, 1.4H), 6.61 (brs, 0.3H), 6.71-6.76 (m, 2H), 6.79 (s, 0.7H), 7.04 (d, 0.3H, J=8.3 Hz), 7.08 (d, 0.7H, J=8.3 Hz), 7.41-7.43 (m, 3H), 7.94 (brs, 2H).

The following Examples 486 to 488 are prepared by following a substantially similar procedure as described in Example 485.

Example 486

3-{2-[(Butyryl-methyl-amino)-methyl]4-[2-(5-methyl-2-phenyl-oxazol-4-yl)-ethoxy]-phenyl}-propionic acid

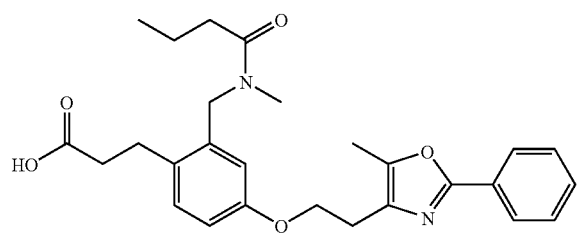

MS (ES) m/z 465 (M+1).

Example 487

3-{2-[(Cyclobutanecarbonyl-methyl-amino)-methyl]-4-[2-(5-methyl-2-phenyl-oxazol-4-yl)-ethoxy]-phenyl}-propionic acid

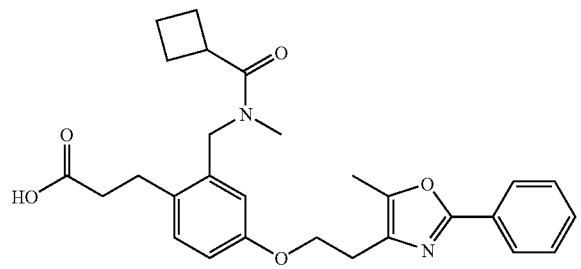

MS (ES) m/z 477 (M+1).

Example 488

3-{2-[(Benzyloxycarbonyl-methyl-amino)-methyl]-4-[2-(5-methyl-2-phenyl-oxazol-4-yl)-ethoxy]-phenyl}-propionic acid

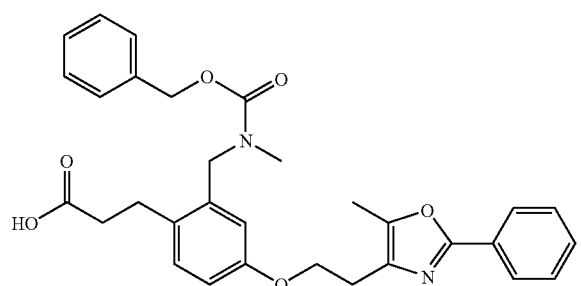

MS (ES) m/z 529 (M+1).

Example 489

3-{4-[2-(2-Biphenyl-3-yl-5-methyl-oxazol-4-yl)-ethoxy]-2-[(isopropoxycarbonyl-methyl-amino)-methyl]-phenyl}-propionic acid

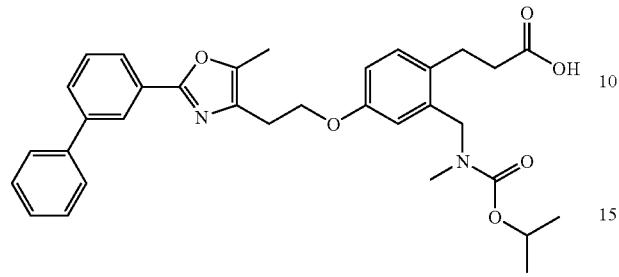

3-{4-Hydroxy-2-[(isopropoxycarbonyl-methyl-amino)-methyl]-phenyl}-propionic acid tert-butyl ester (500 mg, 1.4 mmol; Preparation 22) and toluene-4-sulfonic acid 2-(2-biphenyl-3-yl-5-methyl-oxazol-4-yl)ethyl ester (617 mg, 1.4 mmol; Preparation 1/2) were coupled using Standard procedure A to give the penultimate tert-butyl ester. This ester was converted to the title compound using Standard procedure D (326 mg): MS (ESI) m/z 557 (M+H)$^+$.

The following Examples 490 to 501 are prepared by following a substantially similar procedure as described in Example 489.

Example 490

3-{4-{2-[2-(3-Bromophenyl)-5-methyloxazol-4-yl]ethoxy}-2-[(isopropoxycarbonylmethylamino)methyl]phenyl}propionic acid

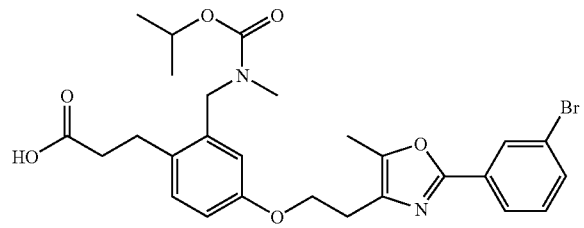

MS (ES) m/z 560 (M+1).

Example 491

3-{4-[2-(2-Biphenyl-3-yl-5-methyloxazol-4-yl)ethoxy]-2-[(isopropoxycarbonylmethylamino)methyl]phenyl}propionic acid

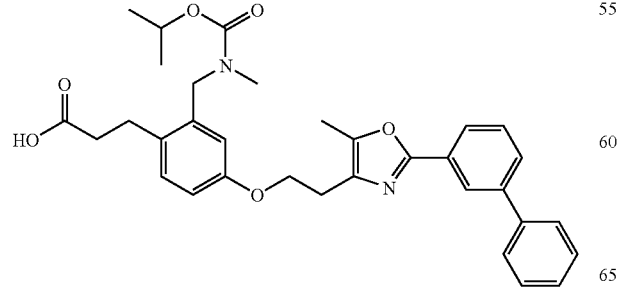

MS (ES) m/z 577 (M+1).

Example 492

3-{4-[2-(2-Cyclohexyl-5-methyloxazol-4-yl)ethoxy]-2-[(isopropoxycarbonylmethylamino)methyl]phenyl}propionic acid MS (ES) m/z 487 (M+1).

Example 493

3-{2-[(Isopropoxycarbonylmethylamino)methyl]-4-[2-(5-methyl-2-morpholin-4-ylthiazol-4-yl)ethoxy]phenyl}propionic acid MS (ES) m/z 506 (M+1).

Example 494

3-{4-{2-[2-(4-Bromophenyl)-5-methyloxazol-4-yl]ethoxy}-2-[(isopropoxycarbonylmethylamino)methyl]phenyl}propionic acid MS (ES) m/z 560 (M+1).

Example 495

3-{2-[(Isopropoxycarbonylmethylamino)methyl]-4-[2-(5-methyl-2-phenylthiazol-4-yl)ethoxy]phenyl}propionic acid

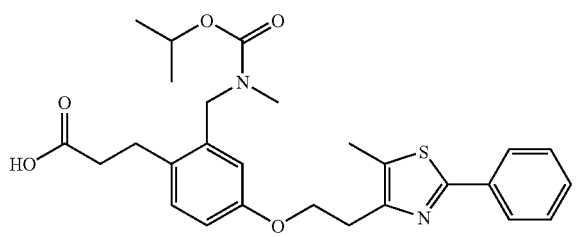

MS (ES) m/z 497 (M+1).

Example 496

3-{4-[2-(2-Biphenyl-4-yl-5-methylthiazol-4-yl)ethoxy]-2-[(isopropoxycarbonylmethylamino)methyl]phenyl}propionic acid

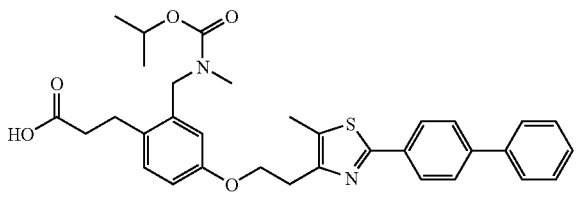

MS (ES) m/z 573 (M+1).

Example 497

3-(2-[(Isopropoxycarbonylmethylamino)methyl]-4-{2-[5-methyl-2-(1-methyl-cyclohexyl)oxazol-4-yl]ethoxy}phenyl)propionic acid

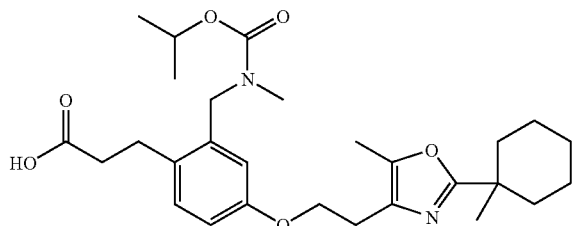

MS (ES) m/z 501 (M+1).

Example 498

3-{2-[(Isopropoxycarbonylmethylamino)methyl]-4-[2-(5-methyl-2-phenethyl-oxazol-4-yl)ethoxy]phenyl}propionic acid

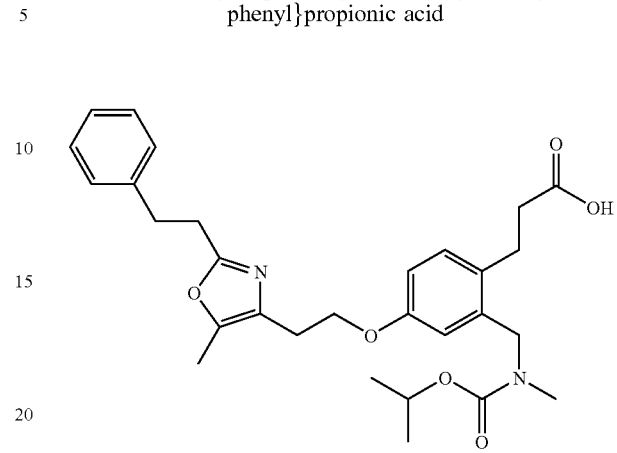

MS (ES) m/z 509 (M+1).

Example 499

3-{2-[(Isopropoxycarbonylmethylamino)methyl]-4-[2-(5-methyl-2-phenyl-oxazol-4-yl)ethoxy]phenyl}propionic acid

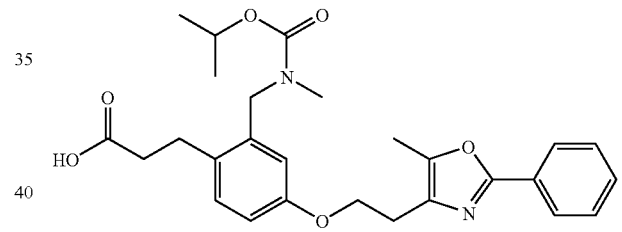

MS (ES) m/z 481 (M+1).

Example 500

3-(4-[2-(2-Biphenyl-3-yl-5-methyloxazol-4-yl)ethoxy]-2-{[methyl(pyridine-2-carbonyl)amino]methyl}phenyl)propionic acid

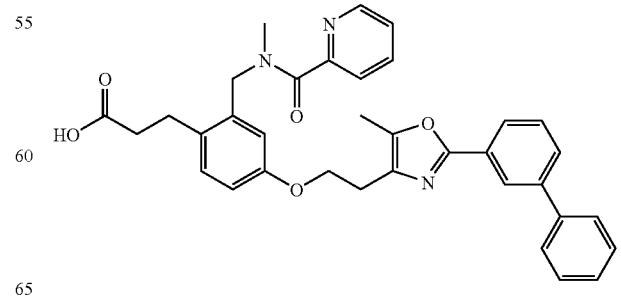

MS (ES) m/z 576 (M+1).

Example 501

3-[4-{2-[2-(2-Bromophenyl)-5-methyloxazol-4-yl]ethoxy}-2-(isopropoxycarbonylaminomethyl)phenyl]propionic acid

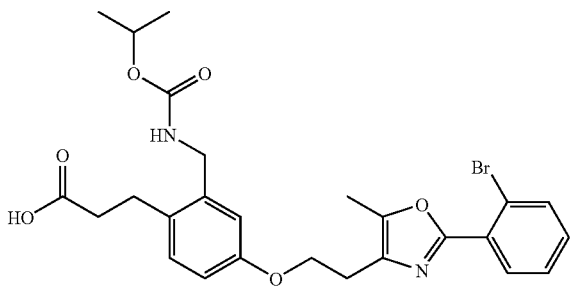

MS (ES) m/z 546 (M+1).

Example 502

3-{4-[2-(2-Biphenyl-4-yl-5-methyl-oxazol-4-yl)-ethoxy]-2-[(ethyl-isopropoxycarbonyl-amino)-methyl]-phenyl}-propionic acid

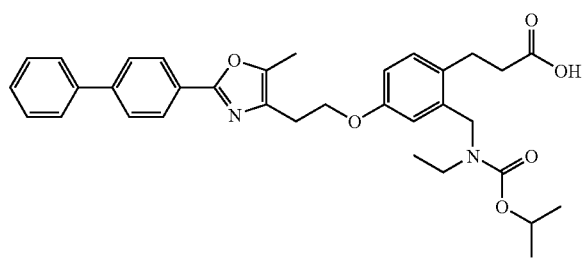

Step A: 3-[4-[2-(2-Biphenyl-4-yl-5-methyl-oxazol-4-yl)-ethoxy]-2-(isopropoxycarbonylamino-methyl)-phenyl]-propionic acid methyl ester

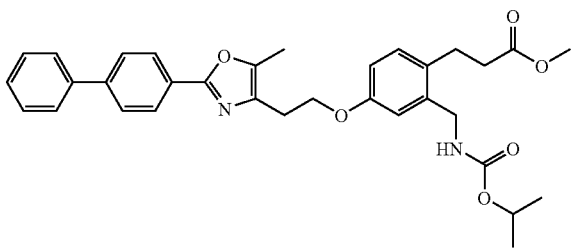

3-[4-Hydroxy-2-(isopropoxycarbonylamino-methyl)-phenyl]-propionic acid methyl ester (Preparation 17) and toluene-4-sulfonic acid 2-(2-biphenyl-4-yl-5-methyl-oxazol-4-yl)ethyl ester (Preparation 1) were combined according to Standard procedure A to give the title compound.

Step B: 3-(4-[2-(2-Biphenyl-4-yl-5-methyl-oxazol-4-yl)-ethoxy]-2-[(ethyl-isopropoxycarbonyl-amino)-methyl]-phenyl)-propionic acid A solution of 3-[4-[2-(2-biphenyl-4-yl-5-methyl-oxazol-4-yl)-ethoxy]-2-(isopropoxycarbonylamino-methyl)-phenyl]-propionic acid methyl ester (200 mg, 0.36 mmol) in DMF (15 mL) was treated with sodium bis(trimethylsilyl)amide (132 mg, 0.719 mmol). Ethyl iodide (112 mg, 0.719 mmol) was added, and the reaction mixture was stirred overnight at room temperature under N$_2$. The mixture was diluted with EtOAc (100 mL) and washed with brine (100 mL), then water (100 mL). The organic layer was dried (MgSO$_4$) and concentrated to the penultimate ester as white solid (179 mg). The material was dissolved in EtOH (20 mL), treated with 5N NaOH (20 mL), and stirred at room temperature overnight. The mixture was acidified with 1N HCl (10 mL) and extracted with EtOAc (50 mL). The organics were dried (MgSO$_4$) and concentrated to give a white solid (201 mg). MS [EI+] m/z 571 (M+H)$^+$. Anal. Calculated for C$_{34}$H$_{38}$N$_2$O$_6$: C, 71.6; H, 6.7; N, 4.9. Found: C, 70.8; H, 6.8; N, 5.0.

The following Examples 503 to 504 are prepared by following a substantially similar procedure as described in Example 502.

Example 503

3-{4-[2-(2-Biphenyl-4-yl-5-methyl-oxazol-4-yl)-ethoxy]-2-[(isopropoxycarbonyl-methyl-amino)-methyl]-phenyl}-propionic acid

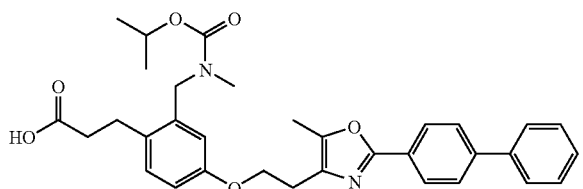

MS [EI+] m/z 557 (M+H)$^+$. Anal. Calculated for C$_{33}$H$_{36}$N$_2$O$_6$: C, 71.2; H, 6.5; N, 5.0. Found: C, 70.6; H, 6.6; N, 5.1.

Example 504

3-{2-[(Isopropoxycarbonyl-methyl-amino)-methyl]-4-[2-(5-methyl-3-phenyl-pyrazol-1-yl)-ethoxy]-phenyl}-propionic acid

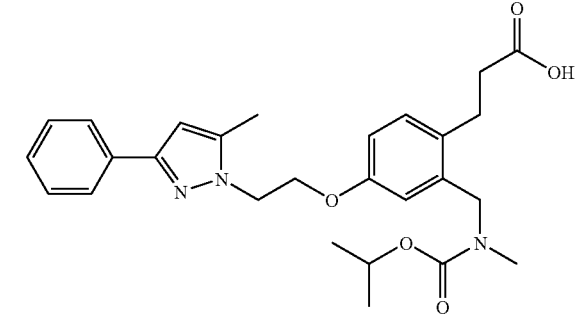

MS [EI+] m/z 480.1 (M+H)$^+$.

Example 505

3-(2-[(Isopropoxycarbonyl-methyl-amino)-methyl)-4-{2-[5-methyl-2-(3-pyridin-3-yl-phenyl)-oxazol-4-yl]-ethoxy}-phenyl)-propionic acid

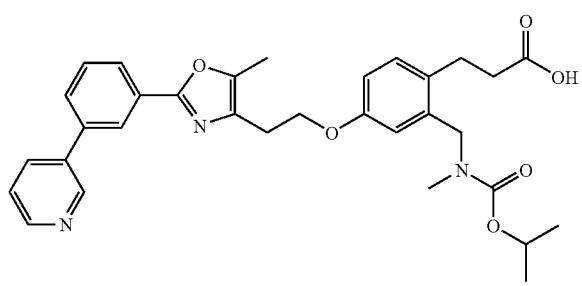

N-Methylation of carbamates: In a small screw cap vial was placed 3-(2(isopropoxycarbonylamino-methyl)-4-{2-[5-methyl-2-(3-pyridin-3-yl-phenyl)-oxazol-4-yl]-ethoxy}-phenyl)-propionic acid tert-butyl ester (0.5 mmol). A 1/1 mixture of CHCl$_3$/TFA (1.6 mL) was added followed by 37% HCHO (50 µL). The reaction mixture was shaken at ambient temperature for 0.5 h and triethylsilane (110 µL, 0.7 mmol) was added. The mixture was shaken for another 0.5 h and was concentrated. The product mixture was purified

Example 506

3-(2-[(Isopropoxycarbonyl-methyl-amino)-methyl]-4-{2-[5-methyl-2-(4-trifluoromethyl-phenyl)-oxazol-4-yl]-ethoxy}-phenyl)-propionic acid

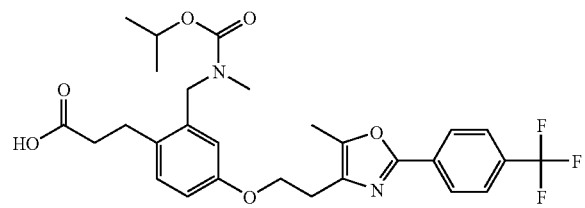

MS (ES) m/z 549 (M+H)+.

Example 507

3-{4-{2-[2-(4-Butoxy-phenyl)-5-methyl-oxazol-4-yl]-ethoxy}-2-[(isopropoxycarbonyl-methyl-amino)-methyl]-phenyl}-propionic acid

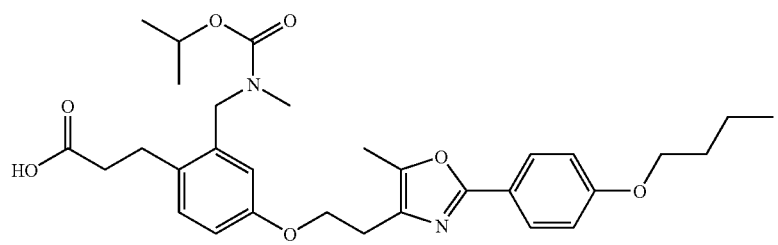

MS (ES) m/z 553 (M+H)+.

Example 508

3-(2-[(Isopropoxycarbonyl-methyl-amino)-methyl]4-{2-[5-methyl-2-(3-pyridin-3-yl-phenyl)-oxazol-4-yl]-ethoxy}-phenyl)-propionic acid

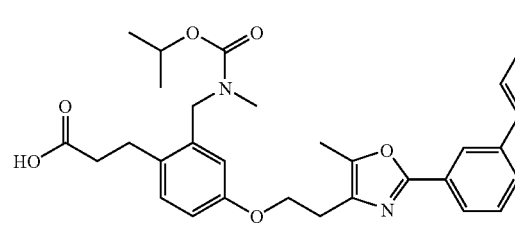

MS (ES) m/z 558 (M+H)+.

Example 509

3-{2-[(Isopropoxycarbonyl-methyl-amino)-methyl]-4-[2-(5-methyl-2-pyridin-4-yl-thiazol-4-yl)-ethoxy]-phenyl}-propionic acid

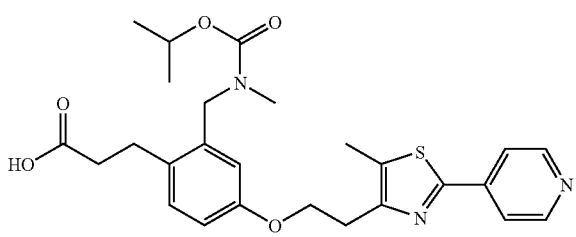

MS (ES) m/z 498 (M+H)+.

Example 510

3-{3-{[(2,5-Dichloro-thiophene-3-carbonyl)-amino]-methyl}-4-[2-(5-methyl-2-phenyl-oxazol-4-yl)-ethoxy]-phenyl}-propionic acid

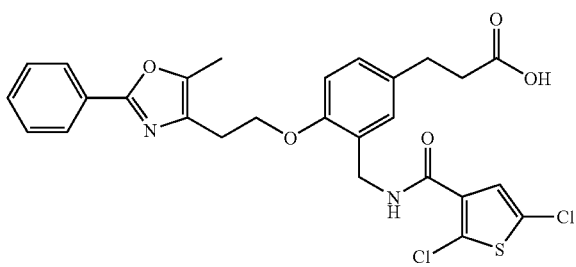

Step, A: 3-(3-Allyl-4-benzyloxy-phenyl)-propionic acid methyl ester

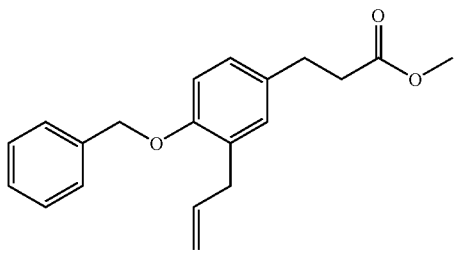

A solution of 3-(3-allyl-4-hydroxy-phenyl)-propionic acid methyl ester (20.5 g, 93.0 mmol; Brown G R, et al. *Bioorg. and Med. Chem. Lett.* 1997, 7, 597) in DMF (50 mL) was treated with $Cs_2CO_3$ (32.6 g, 100 mmol) then benzyl bromide (12.8 mL, 108 mmol) and heated at 55° C. for 16 h. $Cs_2CO_3$ (16.3 g, 50 mmol) and benzyl bromide (6.4 mL, 54 mmol) were added. The mixture was stirred at 55° C. for 23 h, cooled, and partitioned between EtOAc (250 mL) and water (100 mL). The organic layer was washed with brine (75 mL). The combined aqueous layers were back-extracted with EtOAc (100 mL). The combined organic layers were dried ($Na_2SO_4$), and concentrated. The residue was purified by silica gel column chromatography ($CH_2Cl_2$/hexanes 1/1 to 100/0) to the title compound (27.0 g, 93%).

Step B: 3-(4-Benzyloxy-3-carboxymethyl-phenyl)-propionic acid methyl ester

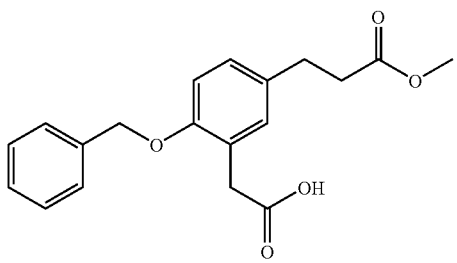

A solution of 3-(3-allyl-4-benzyloxy-phenyl)-propionic acid methyl ester (25.0 g, 80.5 mmol) in acetone (300 mL) and water (30 mL) was treated with 4-methyl-morpholine 4-oxide (12.96 g, 95.8 mmol) then osmium (IV) oxide (5 chips). The flask was covered with foil and stirred 20 h. The solution was diluted with EtOAc (1 L) and washed with 1N $Na_2S_2O_3$ (2×150 mL) and brine (125 mL). The organic layer was concentrated to a yellow oil (28.9 g). The oil was dissolved in THF (190 mL) and water (125 mL), and sodium periodate (49.0 g, 229 mmol) was added. THF (190 mL) and water (125 mL) were added. The thick white slurry was stirred for 2 h and filtered. The filtrate was extracted with EtOAc (1 L). The organic layer was washed successively with brine, 1N $Na_2S_2O_3$, and brine (150 mL each) and was concentrated to an orange oil (25.3 g). The oil was diluted with tert-butanol (400 mL) and 2-methyl-2-butene (100 mL) and was cooled in an ice bath. The mixture was treated with sodium chlorite (68 g, 0.76 mol), and a solution of $NaH_2PO_4$ (68 g, 0.49 mol) in water (250 mL) was added over 5 min. After 15 min, the ice bath was removed. The mixture was stirred for 2 h and was partitioned between EtOAc (1 L) and water (125 mL). The organic layer was washed with 1N $Na_2S_2O_3$ (125 mL) and brine (125 mL), dried (NaSO4), and concentrated to the title compound as a tan solid (31.4 g, 119%). This material was used in subsequent reactions without further purification.

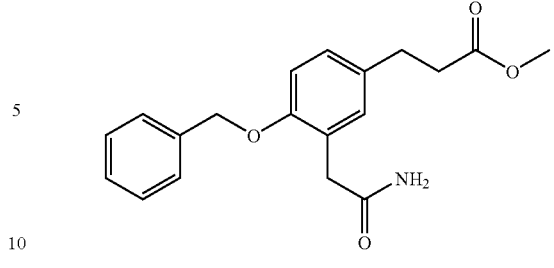

3-(4-Benzyloxy-3-carboxymethyl-phenyl)-propionic acid methyl ester (80.5 mmol), ammonium chloride (7.75 g, 145 mmol), EDC (27.7 g, 144 mmol), and N-hydroxybenzotriazole hydrate (19.6 g, 145 mmol) were combined in a flask and diluted with DMF (320 mL). Ethyl-diisopropyl-amine (51 mL, 293 mmol) was added. The solution was stirred for 20 h and partitioned between EtOAc (1.2 L) and 1N HCl (250 mL). The organic layer was washed with saturated $NaHCO_3$ solution (200 mL) and brine (200 mL), dried (NaSO4), and concentrated. The crude product was slurred with ethyl ether and filtered to give the title compound (15.9 g, 60%).

Step C: 3-[4-Benzyloxy-3-(tert-butoxycarbonylamino-methyl)-phenyl]-propionic acid methyl ester

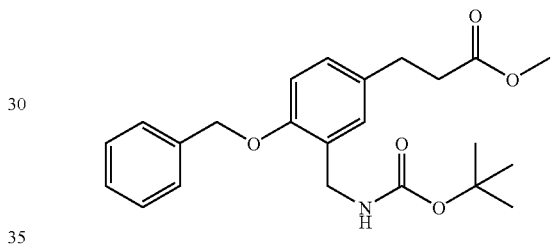

3-(4-benzyloxy-3-carbamoylmethyl-phenyl)-propionic acid methyl ester (15.9 g, 48.6 mmol) was dissolved in $CH_3CN$ (850 mL) and DMF (8 mL) with warming. Water was added, the solution was cooled to ambient temperature, and [bis(trifluoroacetoxy)iodo]benzene (31.32 g, 72.8 mmol) was added. After 30 min, pyridine (8.2 mL) was added, and the solution was stirred for 17 h. Triethylamine (28 mL, 200 mmol) and di-tert-butyl dicarbonate (16.0 g, 73.3 mmol) were added. The mixture was stirred for 2.5 h and was concentrated. The residue was partitioned between EtOAc (1 L) and brine (150 mL). The organic layer was washed with ice-cold 1N HCl (150 mL), saturated $NaHCO_3$ solution (150 mL) and brine (100 mL); dried (NaSO4); and concentrated. The residue was purified by silica gel column chromatography ($CH_2Cl_2$/EtOAc 100/0 to 95/5) to a yellow oil (11.0 g, 57%).

Step D: 3-[3-(tert-Butoxycarbonylamino-methyl)-4-hydroxy-phenyl]-propionic acid methyl ester

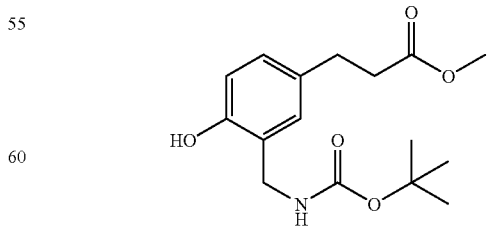

A solution of 3-[4-benzyloxy-3-(tert-butoxycarbonylamino-methyl)-phenyl]-propionic acid methyl ester (8.50 g, 21.3 mmol) in THF (100 mL) was treated with 5% Pd-on-carbon (1.1 g) and shaken under a hydrogen atmosphere (60 psi) at ambient temperature for 6 h. The mixture was filtered through Celite and concentrated to a pale yellow solid (5.63 g, 85%).

Step E: 3-{3-(tert-Butoxycarbonylamino-methyl)-4-[2-(5-methyl-2-phenyl-oxazol-4-yl)-ethoxy]-phenyl}-propionic acid methyl ester

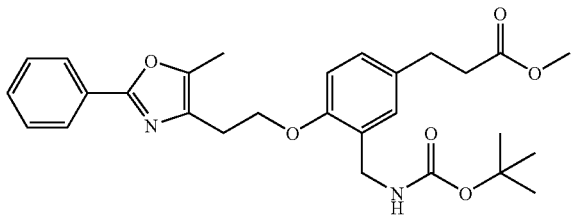

3-[3-(tert-Butoxycarbonylamino-methyl)-4-hydroxy-phenyl]-propionic acid methyl ester (5.50 g, 17.8 mmol), toluene-4-sulfonic acid 2-(5-methyl-2-phenyl-oxazol-4-yl)-ethyl ester (7.93 g, 22.2 mmol) and $Cs_2CO_3$ (7.23 g, 22.2 mmol) were suspended in DMF (40 mL) and stirred at 55° C. for 18 h. Additional toluene-4-sulfonic acid 2-(5-methyl-2-phenyl-oxazol-4-yl)-ethyl ester (3.00 g, 8.39 mmol) and $Cs_2CO_3$ (2.73 g, 8.39 mmol) were added and stirring was continued for 22 h. The reaction mixture was cooled and partitioned between EtOAc (125 mL) and water (50 mL). The organic layer was washed with brine (50 mL), dried ($NaSO_4$), and concentrated. The residue was purified by silica gel column chromatography ($CH_2Cl_2$/EtOAc 97/3 to 80/20) to give pure product (3.33 g, 38%) and slightly impure product (7.08 g).

Step F: 3-{3-Aminomethyl-4-[2-(5-methyl-2-phenyl-oxazol-4-yl)-ethoxy]-phenyl}-propionic acid methyl ester: trifluoroacetic acid salt

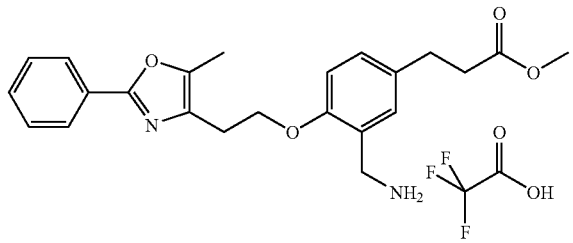

A solution of 3-{3-(tert-butoxycarbonylamino-methyl)-4-[2-(5-methyl-2-phenyl-oxazol-4-yl)-ethoxy]-phenyl}-propionic acid methyl ester (3.33 g, 6.73 mmol) in $CH_2Cl_2$ (24 mL) was treated at ambient temperature with TFA (10 mL) and stirred for 3 h. The solution was concentrated and co-evaporated with $CCl_4$ (3×) to yield the title compound as a foam (4.13 g, quantitative)

Step G: 3-{3-{[(2,5-Dichloro-thiophene-3-carbonyl)-amino]-methyl}-4-[2-(5-methyl-2-phenyl-oxazol-4-yl)-ethoxy]-phenyl}-propionic acid General Parallel Synthesis Procedure: 3-{3-Aminomethyl-4-[2-(5-methyl-2-phenyl-oxazol-4-yl)-ethoxy]-phenyl}-propionic acid methyl ester: trifluoroacetic acid salt (565 mg, 1.1 mmol) was dissolved in $CH_2Cl_2$ (25 mL) and washed with saturated $NaHCO_3$ solution (15 mL). The organic layer was dried ($NaSO_4$), filtered, and concentrated to 3-{3-aminomethyl-4-[2-(5-methyl-2-phenyl-oxazol-4-yl)-ethoxy]-phenyl}-propionic acid methyl ester (368 mg, 0.93 mmol, 84%). A portion of this free base (26 mg, 0.071 mmol) in $CH_2Cl_2$ (0.5 mL) was treated with triethylamine (0.075 mL, 0.54 mmol) then 2,5-dichloro-thiophene-3-carbonyl chloride (0.049 mL, 0.22 mmol). The reaction mixture was shaken overnight and dimethylethylenediamine (0.15 mL, 1.4 mmol) was added. The reaction mixture was shaken for 2 h and passed through an SCX column (1 g, equilibrated with 2 mL MeOH then 2 mL MeOH/$CH_2Cl_2$ 1/1). The methyl ester-amide product was eluted with MeOH/$CH_2Cl_2$ (1:1, 10 mL) and concentrated. The residue was dissolved in THF (2 mL) and MeOH (2 mL) and treated with 5N NaOH (1 mL). The solution was heated at 55° C. for 2.5 h, cooled, and acidified with 5N HCl (1.5 mL). The mixture was transferred to a ChemElute cartridge and eluted with $CH_2Cl_2$. The solvent was removed under a stream of $N_2$. The crude product was dried under vacuum and purified by mass-directed HPLC to give the title compound as a foam (9.9 mg, 26%).) MS (ESI) m/z 559.1 (M+H)⁺.

EXAMPLES 511-543

Examples 511 to 543 are prepared by following a substantially similar procedure as described in Example 510.

| No. | Compounds | MS (ES+) |
|---|---|---|
| 511 | (structure) | 541.3 |

-continued
| No. | Compounds | MS (ES+) |
|---|---|---|
| 512 | 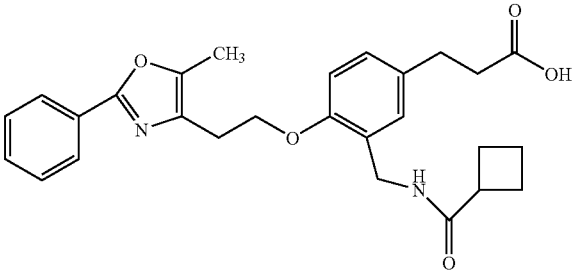 | 463.3 |
| 513 | 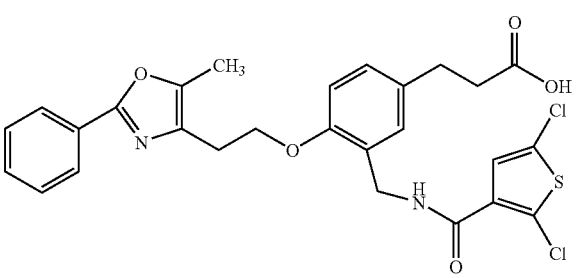 | 559.1 |
| 514 | 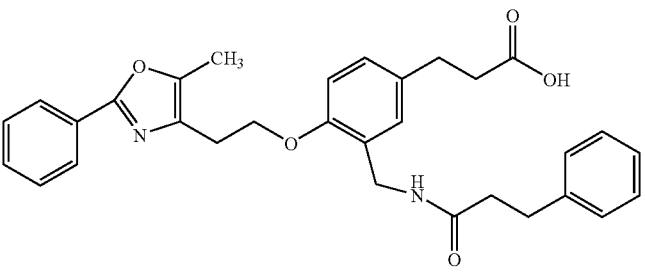 | 513.3 |
| 515 | 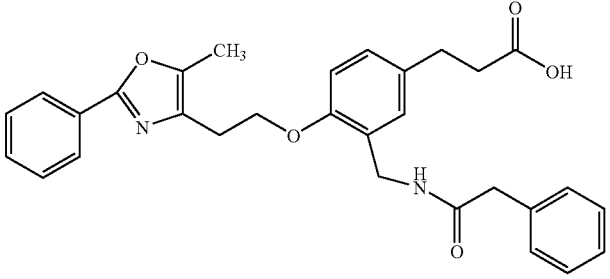 | 499.3 |
| 516 | 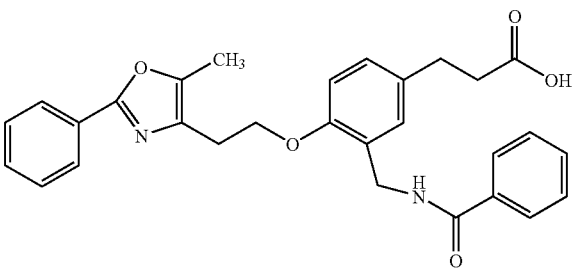 | 485.3 |

-continued
| No. | Compounds | MS (ES+) |
|---|---|---|
| 517 | 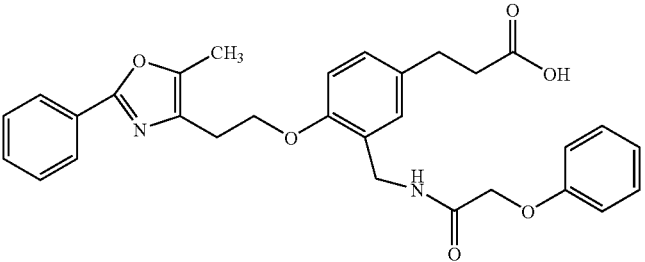 | 515.3 |
| 518 | 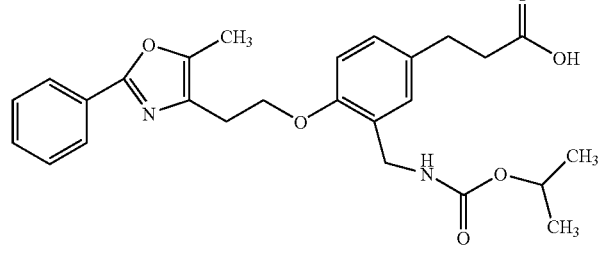 | 481.3 |
| 519 | 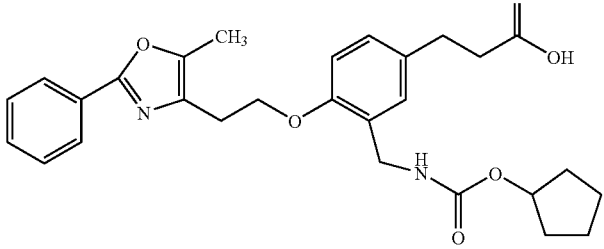 | 493.3 |
| 520 | 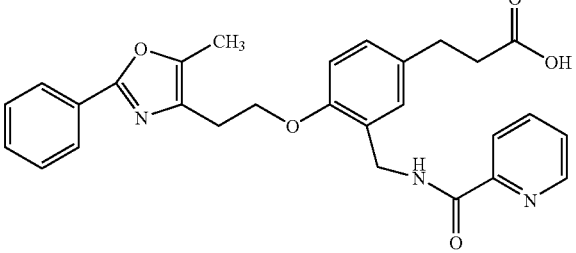 | 486.2 |
| 521 | 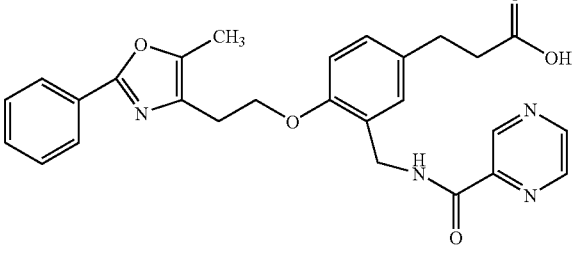 | 487.2 |

-continued

| No. | Compounds | MS (ES+) |
|---|---|---|
| 522 | | 475.2 |
| 523 | | 535.2 |
| 524 | | 536.2 |
| 525 | | 499.2 |
| 526 | | 515.2 |

-continued
| No. | Compounds | MS (ES+) |
|---|---|---|
| 527 | 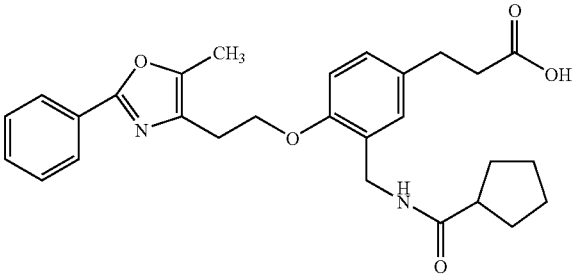 | 477.3 |
| 528 | 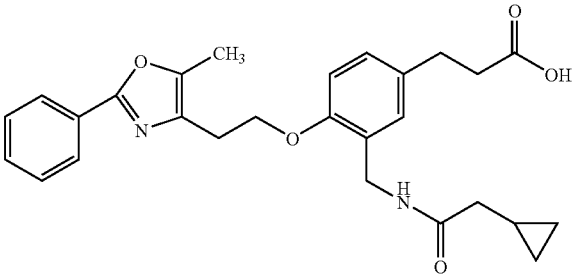 | 463.3 |
| 529 | 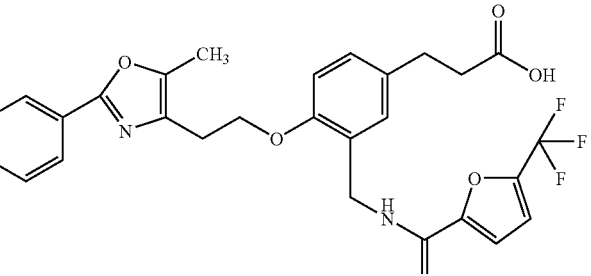 | 543.2 |
| 530 | 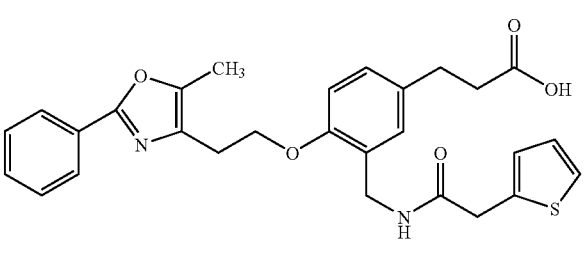 | 505.3 |
| 531 | 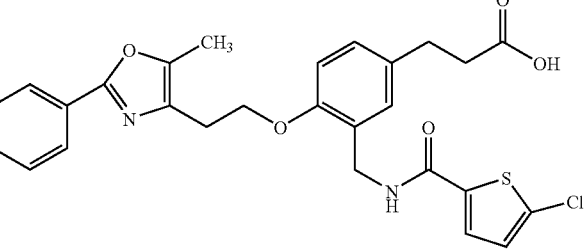 | 525.2 |

-continued
| No. | Compounds | MS (ES+) |
|---|---|---|
| 532 | 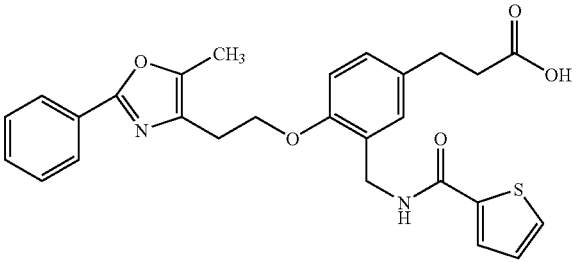 | 491.2 |
| 533 | 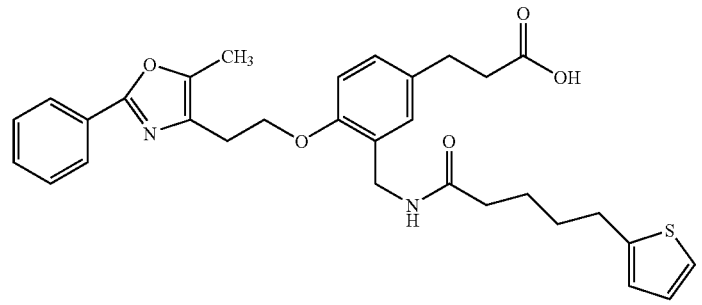 | 547.3 |
| 534 | 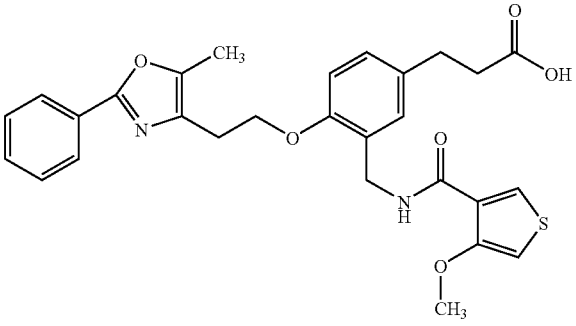 | 521.3 |
| 535 | 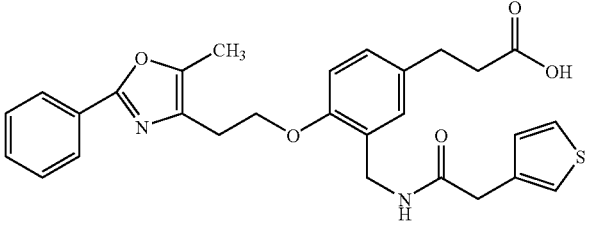 | 505.3 |
| 536 | 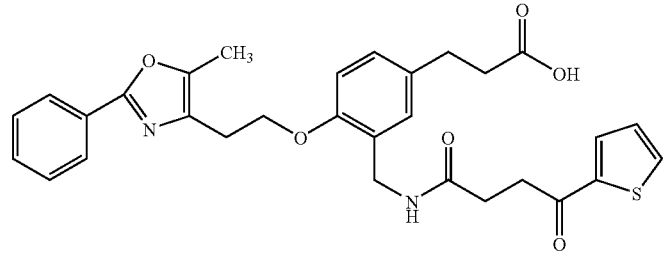 | 547.3 |

-continued

| No. | Compounds | MS (ES+) |
|---|---|---|
| 537 | | 505.3 |
| 538 | | 505.3 |
| 539 | | 491.3 |
| 540 | | 505.3 |
| 541 | | 525.2 |

-continued

| No. | Compounds | MS (ES+) |
|---|---|---|
| 542 | 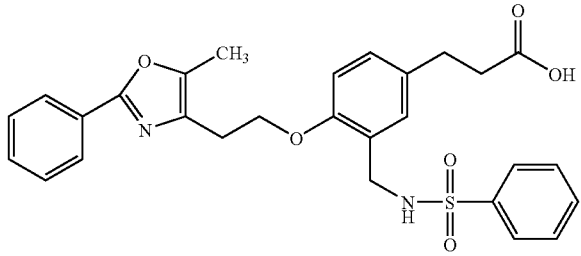 | 521.2 |
| 543 | 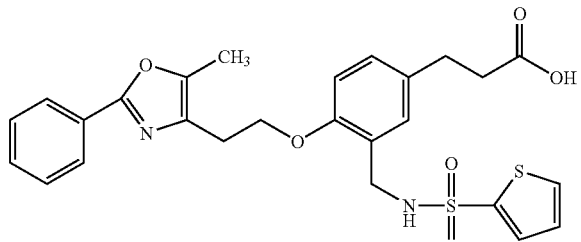 | 527.1 |

Example 544

3-{2-(2-Isopropoxycarbonylamino-ethyl)-4-[2-(5-methyl-2-phenyl-oxazol-4-yl)-ethoxy)-phenyl}-propionic acid

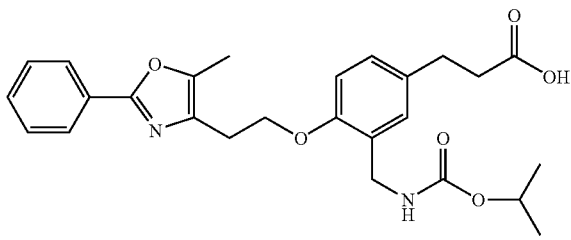

Step A: 5-Benzyloxy-2-bromo-(2-nitrovinyl)benzene

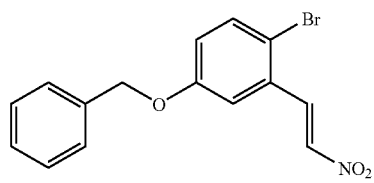

A solution of 2-bromo-5-hydroxy-benzaldehyde (5.99 g, 29.8 mmol, Preparation 13 Step A) in DMF (50 mL) was treated with benzyl bromide (7.65 g, 44.7 mmol) and Cs$_2$CO$_3$ (15.1 g, 44.7 mmol). The resulting mixture was heated at 80° C. for 60 min and was quenched with water (200 mL). The mixture was extracted with EtOAc (2×100 mL), dried (Na$_2$SO$_4$), and concentrated to a residue, which was purified on silica gel chromatography (hexanes/EtOAc 9/1) to afford 5-benzyloxy-2-bromo-benzaldehyde as white solid in quantitative yield.

A solution of nitromethane (2.02 mL, 37.3 mmol) in ethanol (10 mL) was treated with 10N NaOH (3.0 mL) at ambient temperature. A white solid precipitated immediately, and a solution of 5-benzyloxy-2-bromo-benzaldehyde (8.67 g, 29.8 mmol) in CH$_2$Cl$_2$ (50 mL) was added. The reaction mixture was stirred for 18 h and quenched with water (100 mL). The mixture was extracted with CH$_2$Cl$_2$ (2×50 mL), dried (Na$_2$SO$_4$), and concentrated to a residue, which was then purified by silica gel chromatography (hexanes/EtOAc 8/2) to afford 1-(5-benzyloxy-2-bromo-phenyl)-2-nitro-ethanol as yellow oil.

This intermediate was dissolved in CH$_2$Cl$_2$ (150 mL) and cooled to 0° C. Methanesulfonyl chloride (2.55 mL, 60.0 mmol) was added, and the mixture was stirred for 15 min. Triethylamine (8.41 mL) was added, and the mixture was stirred for 60 min. The reaction was quenched with water (200 mL) and extracted with CH$_2$Cl$_2$ (150 mL). The organic layer was dried (Na$_2$SO$_4$) and concentrated. The residue was purified by silica gel chromatography (hexanes/EtOAc 8/2) to afford the title compound (8.60 g, 86%). $^1$H NMR (400 MHz, CDCl$_3$): δ 5.04 (s, 2H), 6.93 (dd, 1H, J=2.7 Hz, 9.0 Hz), 7.11 (d, 1H, J=3.2 Hz), 7.34-7.37 (m, 5H), 7.48 (d, 1H, J=13.7 Hz), 7.51 (d, 1H, J=9.0 Hz), 8.28 (d, 1H, J=13.7 Hz).

Step B: 2-(5-Benzyloxy-2-bromo-phenyl)-ethylamine

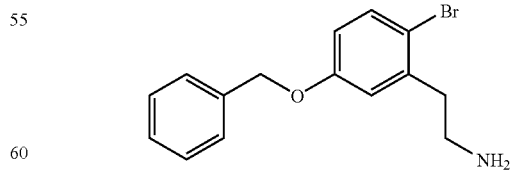

To a solution of 5-benzyloxy-2-bromo-(2-nitrovinyl)benzene (8.60 g, 25.6 mmol) in THF (100 mL) at −78° C. was added LAH (4.1 g, 102 mmol) portion wise over 30 min. The reaction mixture was allowed to warm gradually to ambient temperature. After 18 h, the mixture was carefully quenched with water (4 mL), 2N NaOH (4 mL), and water (12 mL), successively. The slurry was filtered and the precipitate was washed with CH$_2$Cl$_2$ (3×150 mL), dried (Na$_2$SO$_4$), and concentrated. The residue was purified by silica gel chromatography (EtOAc, then CH$_2$Cl$_2$/MeOH/NH$_4$OH 10/1/0.01) to afford the title compound as an oil (3.36 g, 43%). $^1$H NMR (400 MHz, CDCl$_3$): δ 2.84 (t, 2H, J=6.7 Hz), 2.96 (t, 2H, J=6.7 Hz), 5.03 (s, 2H), 6.71 (dd, 1H, J=2.7 Hz, 8.6 Hz), 6.86 (d, 1H, J=2.4 Hz), 7.33-7.43 (m, 6H).

Step C: 2-(5-Benzyloxy-2-bromo-phenyl)-ethyl]-carbamic acid tert-butyl ester

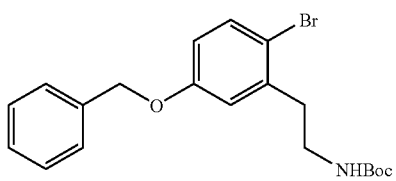

A solution of 2-(5-benzyloxy-2-bromo-phenyl)-ethylamine (3.36 g, 10.97 mmol) in CH$_2$Cl$_2$ (50 mL) at 0° C. was treated with Et$_3$N (3.08 mL, 21.9 mmol) and di-tert-butyl dicarbonate (2.87 g, 13.2 mmol). The mixture was stirred for 2 h while being allowed to warm gradually to ambient temperature and was concentrated. The residue was purified by silica gel chromatography (EtOAc/hexanes, 65:35) to afford the title compound as an oil (4.45 g, 100%). $^1$H NMR (400 MHz, CDCl$_3$): δ 1.44 (s, 9H), 2.90 (t, 2H, J=6.7 Hz), 3.39 (dt, 2H, J=6.3 Hz, 6.7 Hz), 5.02 (s, 2H), 6.72 (dd, 1H, J=3.1 Hz, 8.6 Hz), 6.87 (br s, 1H), 7.33-7.43 (m, 6H).

Step D: 3-[4-Benzyloxy-2-(2-tert-butoxycarbonylamino-ethyl)-phenyl]-acrylic acid methyl ester

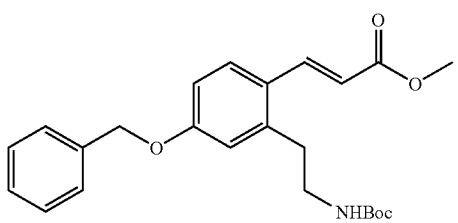

A solution of 2-(5-benzyloxy-2-bromo-phenyl)-ethyl]-carbamic acid tert-butyl ester (4.40 g, 10.8 mmol) in propionitrile (100 mL) was degassed (vacuum/Ar purge, 3×). Tri-ortho-tolylphosphine (0.660 g, 2.17 mmol), methyl acrylate (2.93 mL, 32.5 mmol), and diisopropylethyl amine (3.76 mL, 21.6 mmol) were added. The mixture was de-gassed (vacuum/Ar purge, 3×). Pd(OAc)$_2$ (242 mg, 1.08 mmol) was added, and the reaction mixture was degassed again. The mixture was stirred at 95° C. for 18 h and concentrated to a residue, which was purified by silica gel chromatography (EtOAc/hexanes, 7/3) to afford the title compound (4.15 g, 93%). $^1$H NMR (400 MHz, CDCl$_3$) (major isomer): δ 1.43 (s, 9H), 2.94 (t, 2H, J=6.8 Hz), 3.33 (dt, 2H, J=6.3 Hz, 6.8 Hz), 3.79 (s, 3H), 5.08 (s, 2H), 6.28 (d, 1H, J=15.6 Hz), 6.84 (br s, 1H), 6.86 (d, 1H, J=8.3 Hz), 7.34-7.43 (m, 5H), 7.55 (d, 1H, J=8.3 Hz), 7.91 (d, 1H, J=15.6 Hz).

Step E: 3-[2-(2-tert-Butoxycarbonylamino-ethyl)-4-hydroxy-phenyl]-propionic acid methyl ester

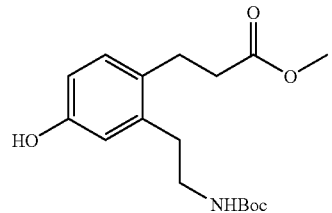

To a solution of 3-[4-benzyloxy-2-(2-tert-butoxycarbonylamino-ethyl)-phenyl]-acrylic acid methyl ester (4.15 g, 10.1 mmol) in THF (100 mL) and MeOH (10 mL) was added 5% Pd—C (200 mg) in THF (10 mL). The resulting suspension was treated with hydrogen under balloon pressure for 18 h. The mixture was filtered through a pad of Celite and concentrated. The residue was purified by silica gel chromatography (EtOAc/hexanes, 6/4) to afford the title compound (1.20 g, 34%). $^1$H NMR (400 MHz, CDCl$_3$): δ 1.44 (s, 9H), 2.57 (t, 2H, J=7.8 Hz), 2.77 (t, 2H, J=7.3 Hz), 2.88 (t, 2H, J=7.8 Hz), 3.33 (br s, 2H), 3.68 (s, 3H), 6.65 (br s, 1H), 6.67 (d, 1H, J=8.3 Hz), 7.02 (d, 1H, J=8.3 Hz). MS (ES$^+$) m/z 324.1 [M+H]$^+$.

Step F: 3-{2-(2-tert-Butoxycarbonylamino-ethyl)-4-[2-(5-methyl-2-phenyl-oxazol-4-yl)-ethoxy]-phenyl}-propionic acid methyl ester

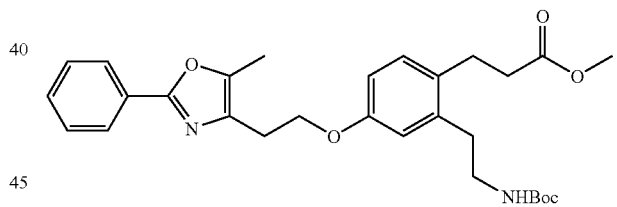

To a solution of 3-[2-(2-tert-butoxycarbonylamino-ethyl)-4-hydroxy-phenyl]-propionic acid methyl ester (0.807 g, 2.50 mmol) and toluene-4-sulfonic acid 2-(5-methyl-2-phenyl-oxazol-4-yl)-ethyl ester (1.34 g, 3.74 mmol) in DMF (5 mL) was added Cs$_2$CO$_3$ (1.22 g, 3.74 mmol). The suspension was stirred at 65° C. for 48 h, quenched with H$_2$O (200 mL), and extracted with EtOAc (3×100 mL). The combined organics were dried (Na$_2$SO$_4$) and concentrated to a residue, which was purified on silica gel chromatography (hexanes/EtOAc 9/1 to 8/2 to 6/4) to afford the title compound as a colorless oil (0.90 g, 71%). $^1$H NMR (400 MHz, CDCl$_3$): δ 1.42 (s, 9H), 2.37 (s, 3H), 2.54 (t, 2H, J=7.8 Hz), 2.77 (t, 2H, J=7.8 Hz), 2.88 (t, 2H, J=6.8 Hz), 2.96 (t, 2H, J=6.8 Hz), 3.33 (~dt, 2H, J=6.8 Hz), 3.65 (s, 3H), 4.20 (t, 2H, J=6.8 Hz), 6.70 (br s, 1H), 6.72 (d, 1H, J=8.3 Hz), 7.05 (d, 1H, J=8.3 Hz), 7.39-7.44 (m, 3H), 7.95-7.98 (m, 2H). MS (ES$^+$) m/z [M+H]$^+$.

Step G: 3-{2-(2-Amino-ethyl)-4-[2-(5-methyl-2-phenyl-oxazol-4-yl)-ethoxy]-phenyl}-propionic acid methyl ester

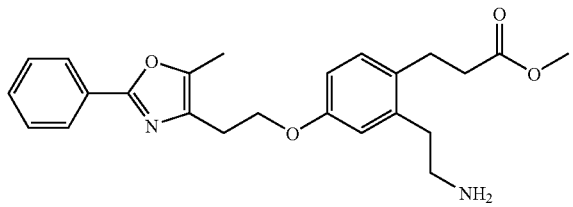

A solution of 3-{2-(2-tert-butoxycarbonylamino-ethyl)-4-[2-(5-methyl-2-phenyl-oxazol-4-yl)-ethoxy]-phenyl}-propionic acid methyl ester (0.90 g, 1.77 mmol) in $CH_2Cl_2$ (10 mL) at 0° C. was treated with TFA (5.0 mL) and water (0.2 mL). The resulting solution was allowed to warm gradually to ambient temperature. After 18 h, the mixture was concentrated. The residue was partitioned between $CH_2Cl_2$ (30 mL) and 5N NaOH (2 mL), and the aqueous layer was extracted with $CH_2Cl_2$ (3×30 mL). The combined organics were dried ($K_2CO_3$) and concentrated to a residue, which was purified by silica gel chromatography ($CH_2Cl_2$/MeOH/$NH_4OH$, 8/2/0.05) to afford the title compound as a colorless oil (0.42 g, 58%). $^1$H NMR (400 MHz, CDCl$_3$): δ 2.34 (s, 3H), 2.52 (t, 2H, J=7.8 Hz), 2.81 (t, 2H, J=7.8 Hz), 2.91 (t, 4H, J=6.4 Hz), 3.06 (t, 2H, J=7.3 Hz), 3.60 (s, 3H), 4.20 (t, 2H, J=6.8 Hz), 6.68 (br s, 1H), 6.71 (d, 1H, J=8.3 Hz), 7.01 (d, 1H, J=8.3 Hz), 7.37-7.39 (m, 3H), 7.89-7.92 (m, 2H).

Step H: 3-{2-(2-Isopropoxycarbonylamino-ethyl)-4-[2-(5-methyl-2-phenyl-oxazol-4-yl)-ethoxy]-phenyl}-propionic acid

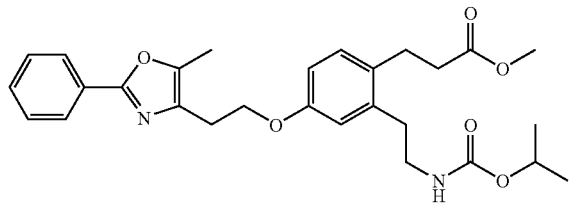

A solution of 3-{2-(2-amino-ethyl)-4-[2-(5-methyl-2-phenyl-oxazol-4-yl)-ethoxy]-phenyl}-propionic acid methyl ester (26 mg, 0.064 mmol) in $CH_2Cl_2$ (2 mL) at 0° C. was treated with TEA (0.2 mL) and isopropyl chloroformate (0.13 mL, 1.0 M in ether). The resulting mixture was allowed to warm gradually to ambient temperature. After 2 h, the mixture was concentrated to a residue, which was purified by silica gel chromatography (hexanes/EtOAc 7/3) to afford the isopropyl carbamate as a colorless oil. $^1$H NMR (400 MHz, CDCl$_3$): δ 1.19 (d, 6H, J=5.9 Hz), 2.42 (s, 3H), 2.54 (t, 2H, J=7.8 Hz), 2.79 (t, 2H, J=6.8 Hz), 2.89 (t, 2H, J=7.8 Hz), 3.05 (br s, 2H), 3.38 (br s, 2H), 3.60 (s, 3H), 4.26 (t, 2H, J=6.8 Hz), 4.68 (br s, 1H), 4.89 (q, 1H, J=6.4 Hz), 6.70 (br s, 1H), 6.71 (d, 1H, J=8.3 Hz), 7.05 (d, 1H, J=8.3 Hz), 7.47 (m, 3H), 8.10 (m, 2H).

This compound was dissolved in THF (1.0 mL) and MeOH (0.5 mL). The solution was treated with 2N NaOH (0.32 mL) and heated at 60° C. for 60 min. The reaction mixture was neutralized with 2N HCl (0.40 mL), and extracted with EtOAc (3×5 mL). The combined organics were dried ($Na_2SO_4$), and concentrated to a residue, which was purified by silica gel chromatography (hex-anes/EtOAc 9/1, then EtOAc/MeOH 95/5) to afford the title compound as a white solid (12 mg, 32% over two steps). $^1$H NMR (400 MHz, CDCl$_3$): δ 1.17 (d, 6H, J=5.9 Hz), 2.36 (s, 3H), 2.52 (br s, 2H), 2.79 (t, 2H, J=6.8 Hz), 2.89 (t, 2H, J=7.8 Hz), 2.93 (t, 2H, J=6.8 Hz), 3.31 (br s, 2H), 4.16 (t, 2H, J=6.8 Hz), 4.68 (br s, 1H), 4.89 (q, 1H, J=6.4 Hz), 6.67 (br s, 1H), 6.71 (d, 1H, J=8.3 Hz), 7.05 (d, 1H, J=8.3 Hz), 7.47 (m, 3H), 8.10 (m, 2H). MS [ES] m/z 481.4 (M+1).

The following Examples 545 to 552 are prepared by following a substantially similar procedure as described in Example 544.

Example 545

3-{2-[2-(Butane-1-sulfonylamino)-ethyl]-4-[2-(5-methyl-2-phenyl-oxazol-4-yl)-ethoxy]-phenyl}-propionic acid

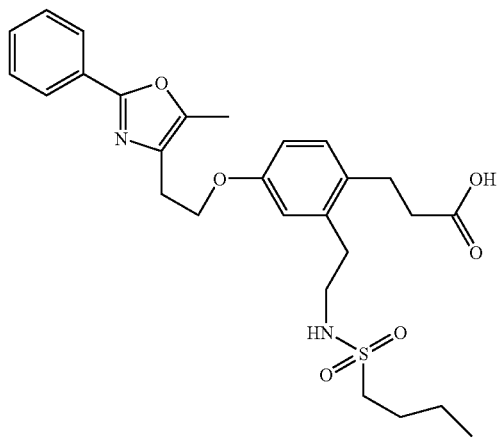

MS [ES] m/z 515.3 (M+1).

Example 546

3-(4-[2-(5-Methyl-2-phenyl-oxazol-4-yl)-ethoxy]-2-{2-[(pyridine-2-carbonyl)-amino]-ethyl}-phenyl)-propionic acid

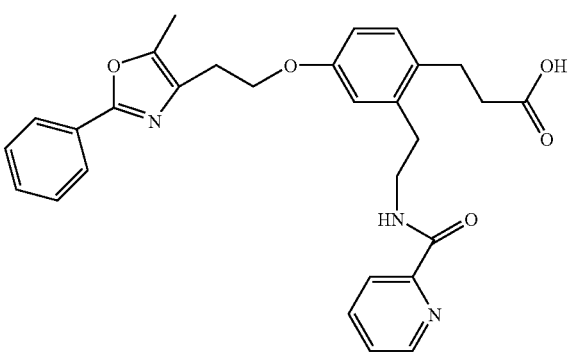

MS [ES] m/z 500.3 (M+1).

Example 547

3-{2-{2-[(2,5-Dichloro-thiophene-3-carbonyl)-amino]-ethyl}-4-[2-(5-methyl-2-phenyl-oxazol-4-yl)-ethoxy]-phenyl}-propionic acid

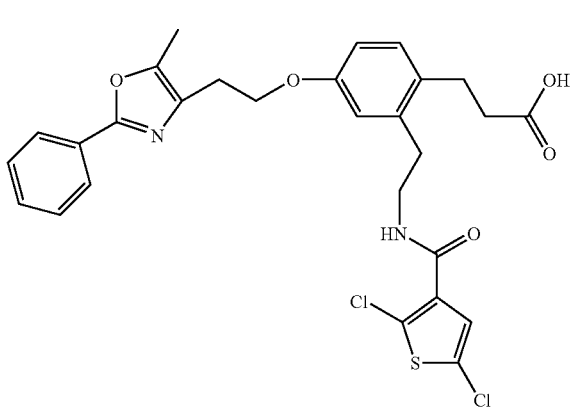

MS [ES−] m/z 573.0 (M−1).

Example 548

3-[4-[2-(5-Methyl-2-phenyl-oxazol-4-yl)-ethoxy]-2-(2-phenylacetylamino-ethyl)-phenyl]-propionic acid

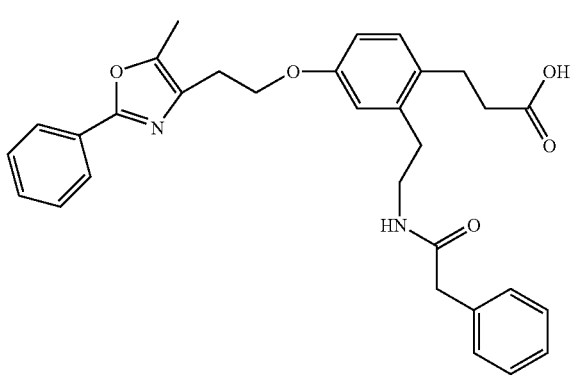

MS [ES] m/z 513.2 (M+1).

Example 549

3-{2-[2-(Cyclobutanecarbonyl-amino)-ethyl]-4-[2-(5-methyl-2-phenyl-oxazol-4-yl)-ethoxy]-phenyl}-propionic acid

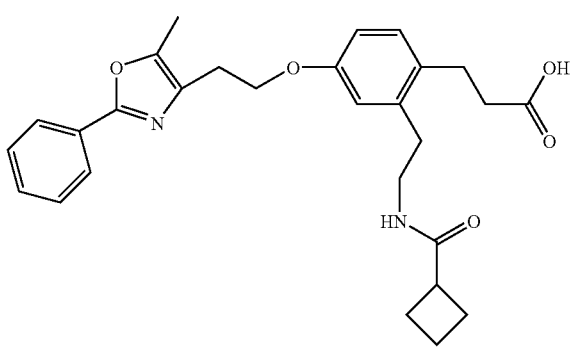

MS [ES] m/z 477.1 (M+1).

Example 550

3-{2-(2-Benzoylamino-ethyl)-4-[2-(5-methyl-2-phenyl-oxazol-4-yl)-ethoxy]-phenyl}-propionic acid

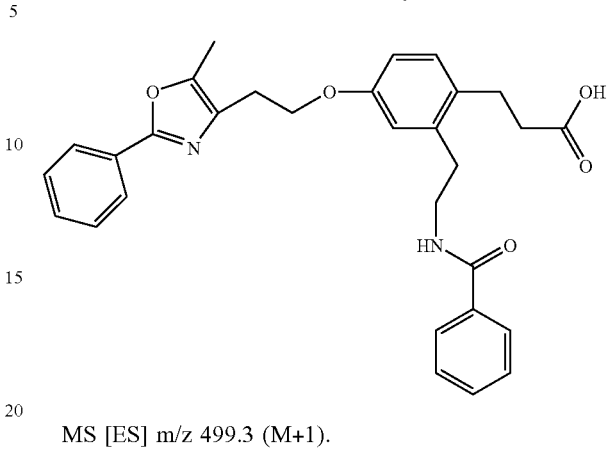

MS [ES] m/z 499.3 (M+1).

Example 551

3-{2-(2-Isobutoxycarbonylamino-ethyl)-4-[2-(5-methyl-2-phenyl-oxazol-4-yl)-ethoxy]-phenyl}-propionic acid

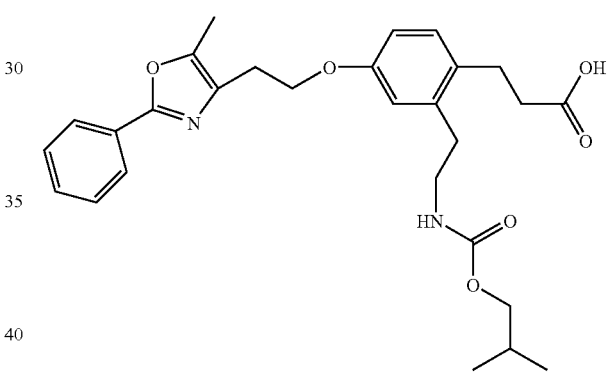

MS [ES] m/z 495.3 (M+1).

Example 552

3-{2-(2-Benzyloxycarbonylamino-ethyl)-4-[2-(5-methyl-2-phenyl-oxazol-4-yl)-ethoxy]-phenyl}-propionic acid

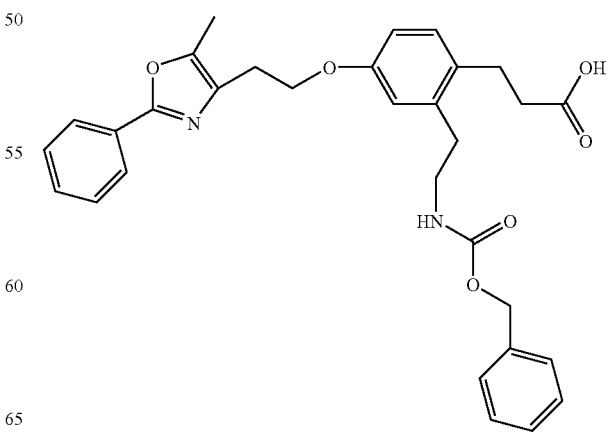

MS [ES] m/z 529.0 (M+1).

Example 553

3-(2-(2-Isopropoxycarbonylamino-ethyl)-4-{2-[5-methyl-2-(4-morpholin-4-yl-phenyl)-oxazol-4-yl]-ethoxy}-phenyl)-propionic acid

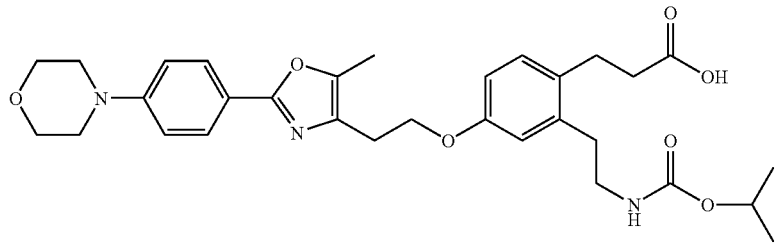

Step A: 3-[4-Hydroxy-2-(2-isopropoxycarbonylamino-ethyl)-phenyl]-propionic acid methyl ester

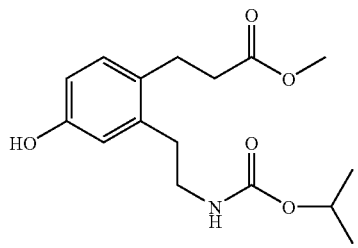

A solution of 3-[2-(2-tert-butoxycarbonylamino-ethyl)-4-hydroxy-phenyl]-propionic acid methyl ester (282 mg, 0.876 mmol; Example 544, Step E) in CH$_2$Cl$_2$ (10 mL) at ambient temperature was treated with TFA (5.0 mL), stirred for 60 min, and concentrated. The residue in CH$_2$Cl$_2$ (10 mL) was treated with triethyl amine (2.0 mL) and iso-propyl chloroformate (0.97 mL, 1.0 M in toluene). The reaction mixture was stirred at ambient temperature for 16 h and concentrated. The crude material was purified using silica gel chromatography (50% EtOAc/hexanes) to yield the title compound (180 mg, 67%).

Step B: 3-(2-(2-Isopropoxycarbonylamino-ethyl)-4-{2-[5-methyl-2-(4-morpholin-4-yl-phenyl)-oxazol-4-yl]-ethoxy}-phenyl)-propionic acid A solution of toluene-4-sulfonic acid 2-[5-methyl-2-(4-morpholin-4-yl-phenyl)-oxazol-4-yl]-ethyl ester (44 mg, 0.10 mmol; Preparation 5) and 3-[4-hydroxy-2-(2-isopropoxycarbonylamino-ethyl)-phenyl]-propionic acid methyl ester (31 mg, 0.10 mmol) in DMF (1.0 mL) was treated with K$_2$CO$_3$ (30 mg). The resulting suspension was stirred at 65° C. for 16 h and diluted with water (10 mL). The mixture was extracted with EtOAc (3×10 mL). The combined organic layers were dried (Na$_2$SO$_4$), concentrated, and purified using silica gel chromatography (50% EtOAc/hexanes to yield 3-(2-(2-isopropoxycarbonylamino-ethyl)-4-{2-[5-methyl-2-(4-morpholin-4-yl-phenyl)-oxazol-4-yl]-ethoxy}-phenyl)-propionic acid methyl ester.

This ester intermediate was dissolved in THF (0.6 mL) and MeOH (0.4 mL) and treated with aqueous 2M LiOH (1.0 mL, 2.0 mmol). The mixture was stirred for 16 h at ambient temperature, neutralized with HCl (1.0 mL, 2.0 M), and concentrated. The residue was extracted with EtOAc (3×5 mL). The combined organic layers were dried (Na$_2$SO$_4$), concentrated, and purified using silica gel chromatography column (hexanes/EtOAc/HOAc, 5/5/0.02) to afford the title compound (10 mg, 18%). MS (ES+) m/z 566.2 (M+H)$^+$.

The following Examples 554 to 560 are prepared by following a substantially similar procedure as described in Example 553.

Example 554

3-[4-[2-(2-Biphenyl-3-yl-5-methyl-oxazol-4-yl)-ethoxy]-2-(2-isopropoxycarbonyl-amino-ethyl)-phenyl]-propionic acid

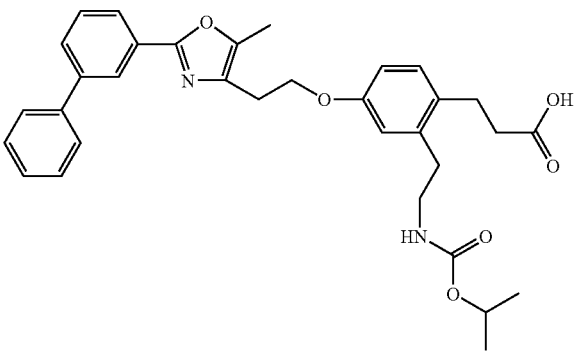

MS [ES] m/z 557.5 (M+1).

Example 555

3-[4-[2-(2-Biphenyl-4-yl-5-methyl-oxazol-4-yl)-ethoxy]-2-(2-isopropoxycarbonyl-amino-ethyl)-phenyl]-propionic acid

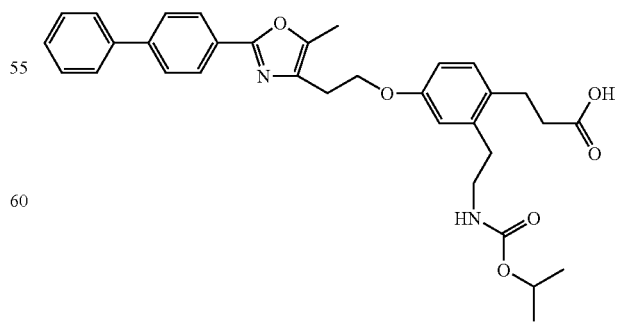

MS [ES] m/z 557.2 (M+1).

Example 556

3-{2-(2-Isopropoxycarbonyl-amino-ethyl)-4-[2-(5-methyl-2-morpholin-4-yl-thiazol-4-yl)-ethoxy]-phenyl}-propionic acid

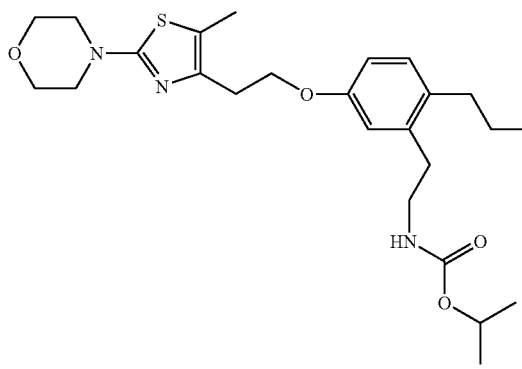

MS [ES] m/z 506.2 (M+1).

Example 557

3-{2-(2-Isopropoxycarbonylamino-ethyl)-4-[2-(5-methyl-2-pyridin-2-yl-thiazol-4-yl)-ethoxy]-phenyl}-propionic acid

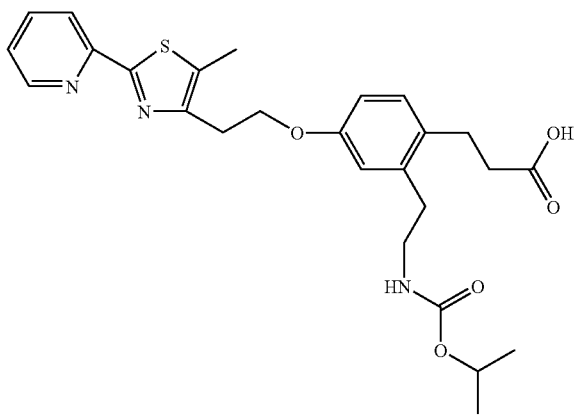

MS [ES] m/z 498.3 (M+1).

Example 558

3-{2-(2-Isopropoxycarbonylamino-ethyl)-4-[2-(5-methyl-3-phenyl-pyrazol-1-yl)-ethoxy]-phenyl}-propionic acid

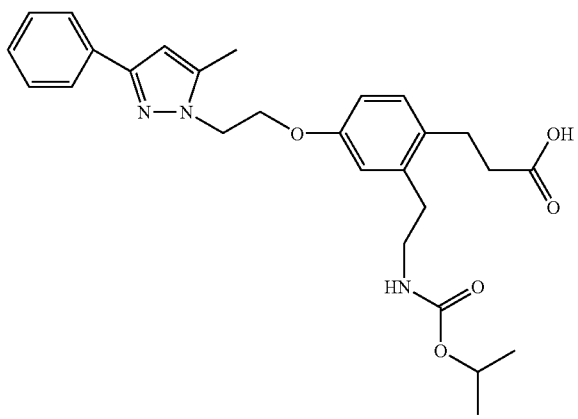

MS [ES] m/z 480.3 (M+1).

Example 559

3-(2-(2-Isopropoxycarbonylamino-ethyl)-4-{2-[5-methyl-2-(4-phenylamino-phenyl)-oxazol-4-yl]-ethoxy}-phenyl)-propionic acid

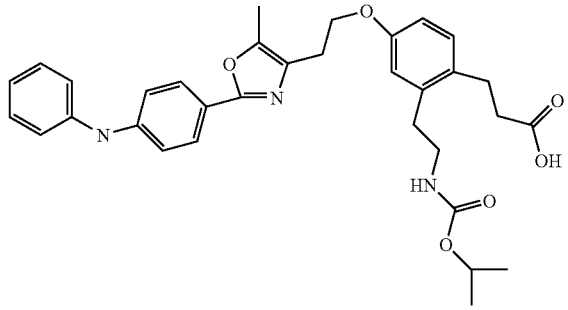

MS [ES] m/z 572.2 (M+1).

Example 560

3-[2-(2-Isopropoxycarbonylamino-ethyl)-4-(2-{5-methyl-2-[4-(methyl-phenyl-amino)-phenyl]-oxazol-4-yl}-ethoxy)-phenyl]-propionic acid

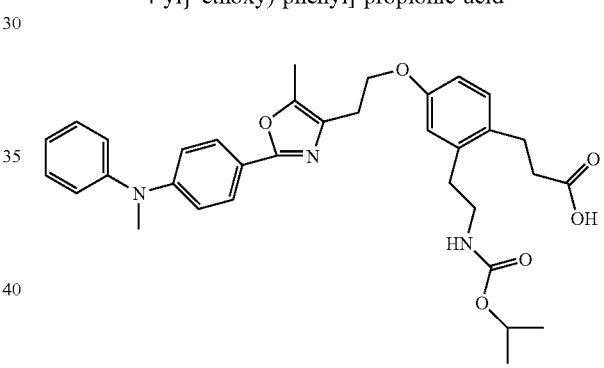

MS [ES] m/z 586.2 (M+1).

Example 561

2-{2-(tert-Butoxycarbonylamino-methyl)-4-[2-(5-methyl-2-phenyl-oxazol-4-yl)-ethoxy]-phenoxy}-2-methyl-propionic acid

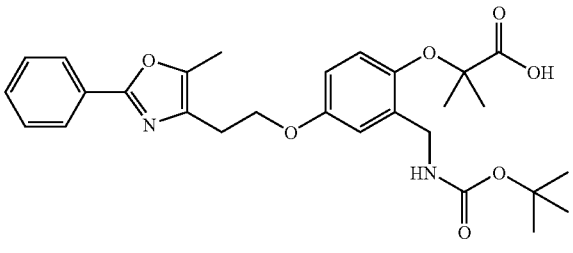

Step A: 2-(2-Allyl-4-benzyloxy-phenoxy)-2-methyl-propionic acid ethyl ester

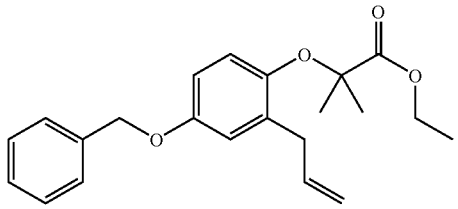

2-Allyl-4-benzyloxy-phenol (WO 9728137 A1 19970807, Adams et al.) (6.04 g, 25.1 mmol) in dry DMF (75 mL) was cooled in an ice bath and treated with NaH (1.78 g, 44.5 mmol, 60% oil dispersion). After 30 min, the red reaction mixture was treated over 5 min with ethyl bromoisobutyrate (7.4 mL, 50 mmol). The cold bath was removed after 5 min. The reaction was stirred 20 min and placed in an oil bath (T=85° C.). After 18 h, the mixture was cooled and partitioned between brine (75 mL) and ether (200 mL). The organic layer was washed with brine (50 mL), dried (Na$_2$SO$_4$), and concentrated to a brown oil (12 g). The crude product was purified by flash chromatography using hexanes:ethyl acetate (100:0 to 5:1) to give the desired product (8.47 g, 95%).

Step B: 2-(4-Benzyloxy-2-carboxymethyl-phenoxy)-2-methyl-propionic acid ethyl ester

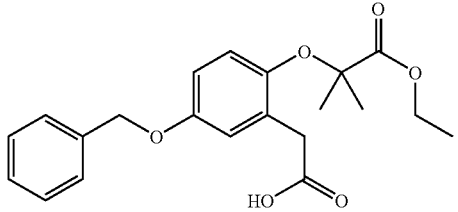

A solution of 2-(2-allyl-4-benzyloxy-phenoxy)-2-methyl-propionic acid ethyl ester (8.07 g, 22.8 mmol) in acetone (85 mL) and water (8.5 mL) was treated with 4-methyl-morpholine 4-oxide (3.68 g, 27.2 mmol) then osmium (IV) oxide (2 chips). The flask was covered with foil and stirred 5 h. The solution was diluted with EtOAc (600 mL) and washed with 1N Na$_2$S$_2$O$_3$ (2×75 mL) and brine (75 mL). The organic layer was concentrated to a tan oil (8.74 g). The oil was dissolved in THF (54 mL) and water (36 mL), and sodium periodate (15.4 g, 72.0 mmol) was added. THF (54 mL) and water (36 mL) were added. The thick white slurry was stirred for 3 h and filtered. The filtrate was extracted with EtOAc (500 mL). The organic layer was washed successively with brine, 1N Na$_2$S$_2$O$_3$, and brine (75 mL each) and was concentrated to an orange oil (7.65 g). The oil was diluted with tert-butanol (180 mL) and 2-methyl-2-butene (60 mL) and was cooled in an ice bath. The mixture was treated with sodium chlorite (19 g, 0.21 mol), and a solution of NaH$_2$PO$_4$ (19 g, 0.14 mol) in water (120 mL) was added over 5 min. After 15 min, the ice bath was removed. The mixture was stirred for 2 h and was partitioned between EtOAc (500 mL) and water (50 mL). The organic layer was washed with 1N Na$_2$S$_2$O$_3$ (75 mL) and brine (75 mL), dried (NaSO4), and concentrated to the title compound as a pale yellow solid (6.52 g, 77%). This material was used in subsequent reactions without further purification.

Step C: 2-(4-Benzyloxy-2-carbamoylmethyl-phenoxy)-2-methyl-propionic acid ethyl ester

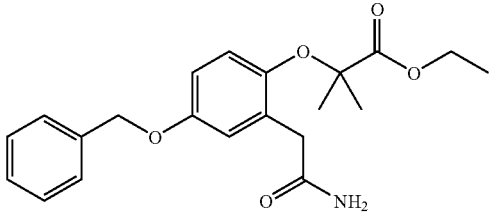

2-(4-Benzyloxy-2-carboxymethyl-phenoxy)-2-methyl-propionic acid ethyl ester (500 mg, 1.34 mmol), ammonium chloride (108 mg, 2.02 mmol), EDC (3.86 mg, 2.01 mmol), and N-hydroxybenzotriazole hydrate (272 mg, 2.01 mmol) were combined in a flask and diluted with DMF (5 mL). Ethyl diisopropyl amine (0.70 mL, 4.0 mmol) was added. The solution was stirred for 18 h and partitioned between EtOAc (25 mL) and 1N HCl (10 mL). The organic layer was washed with saturated NaHCO$_3$ solution (10 mL) then brine (10 mL), dried (Na$_2$SO$_4$), and concentrated. The crude product was purified by radial chromatography (hexanes/EtOAc 1/2 to 1/4) to give the title compound (430 mg, 86%).

Step D: 2-[4-Benzyloxy-2-(tert-butoxycarbonylamino-methyl)-phenoxy]-2-methyl-propionic acid ethyl ester

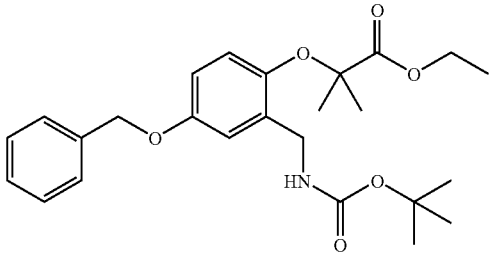

2-(4-Benzyloxy-2-carbamoylmethyl-phenoxy)-2-methyl-propionic acid ethyl-ester (430 mg, 1.16 mmol) was dissolved in CH$_3$CN (4.5 mL) and water (4.5 mL), and [bis(trifluoroacetoxy)iodo]benzene (745 mg, 1.73 mmol) was added. After 10 min, pyridine (0.19 mL, 2.3 mmol) was added, and the solution was stirred for 17 h. Triethylamine (0.60 mL, 4.3 mmol) and di-tert-butyl dicarbonate (506 mg, 2.32 mmol) were added. The mixture was stirred for 1 h and was concentrated. The residue was partitioned between ether (50 mL) and brine (15 mL). The organic layer was washed with ice-cold 1N HCl, saturated NaHCO$_3$ solution, and brine (15 mL each); dried (NaSO$_4$); and concentrated. The residue was purified by silica gel column chromatography (hexanes/EtOAc 4/1 to 3/2) to a yellow oil (345 g, 67%).

Step E: 2-[2-(tert-Butoxycarbonylamino-methyl)-4-hydroxy-phenoxy]-2-methyl-propionic acid ethyl ester

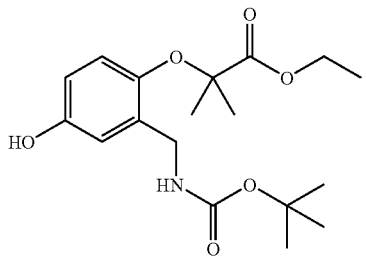

A solution of 2-[4-benzyloxy-2-(tert-butoxycarbonylamino-methyl)-phenoxy]-2-methyl-propionic acid ethyl ester (0.38 g, 0.86 mmol) in THF (15 mL) was treated with 5% Pd-on-carbon (47 mg) and shaken under a hydrogen atmosphere (60 psi) at ambient temperature for 18 h. The mixture was filtered through Celite and concentrated. The crude product was purified by radial chromatography (hexanes/EtOAc 2.5/1) to give the title compound (208 mg g, 69%).

Step F: 2-{2-(tert-Butoxycarbonylamino-methyl)-4-[2-(5-methyl-2-phenyl-oxazol-4-yl)-ethoxy]-phenoxy}-2-methyl-propionic acid 2-[2-(tert-Butoxycarbonylamino-methyl)-4-hydroxy-phenoxy]-2-methyl-propionic acid ethyl ester (200 mg, 0.566 mmol), toluene-4-sulfonic acid 2-(5-methyl-2-phenyl-oxazol-4-yl)-ethyl ester (245 mg, 686 mmol) and $Cs_2CO_3$ (185 mg, 0.567 mmol) were suspended in DMF (5 mL) and stirred at 55° C. for 39 h. The reaction mixture was cooled and partitioned between $Et_2O$ (50 mL) and water (10 mL). The organic layer was washed with brine (10 mL), dried ($NaSO_4$), and concentrated. The residue was purified by radial chromatography (hexanes/EtOAc 4/1) to give an oil (280 mg). A solution of the product in MeOH (6 mL) and THF (3 mL) was treated with 2.5N aqueous NaOH solution (2 mL) and heated at 55° C. for 2 h. The mixture was cooled and concentrated. Ice chips were added (~5) and the mixture was acidified using 5N aqueous HCL solution (2 mL). The reaction mixture was partitioned between EtOAc (30 mL) and brine (15 mL). The organic layer was washed with brine (2×10 mL), dried ($NaSO_4$), and concentrated. The residue was purified by silica gel column chromatography (hexanes/EtOAc/HOAc 3/2/0 to 3/2/0.05) to give the title compound as a white foam (156 mg, 54%). MS (ES⁻) m/z 509.1 [M–H]⁻. Anal. Calcd. For $C_{28}H_{34}N_2O_7$: C, 65.88; H, 6.71; N, 5.49. Found: C, 65.67; H, 6.79; N, 5.52.

Example 562

{2-(tert-Butoxycarbonylamino-methyl)-4-[2-(5-methyl-2-phenyl-oxazol-4-yl)-ethoxy]-phenoxy}-acetic acid

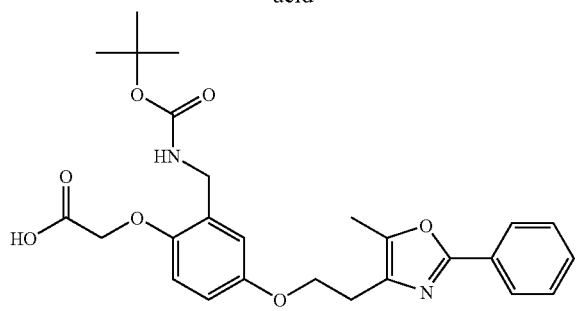

The above compound is prepared by following a substantially similar procedure as described in Example 561. MS [ES] m/z 483.2 (M+1).

Example 563

2-{2-(Ethoxycarbonylamino-methyl)-4-[2-(5-methyl-2-phenyl-oxazol-4-yl)-ethoxy]-phenoxy}-2-methyl-propionic acid

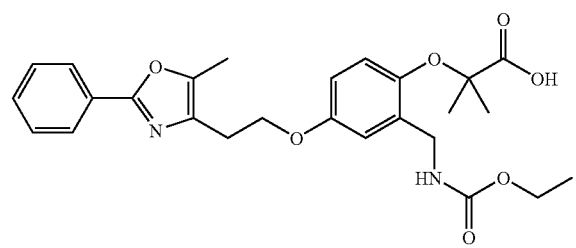

Step A: 2-{2-Aminomethyl-4-[2-(5-methyl-2-phenyl-oxazol-4-yl)-ethoxy]-phenoxy}-2-methyl-propionic acid ethyl ester: trifluoroacetic acid salt

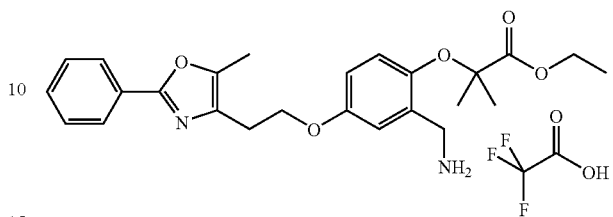

A solution of 2-{2-(tert-butoxycarbonylamino-methyl)-4-[2-(5-methyl-2-phenyl-oxazol-4-yl)-ethoxy]-phenoxy}-2-methyl-propionic acid ethyl ester (350 mg, 0.650 mmol) in $CH_2Cl_2$ (10 mL) was treated at ambient temperature with TFA (4 mL) and stirred for 2.5 h. The solution was concentrated and co-evaporated with $CCl_4$ (3×) to yield the title compound as a foam (381 mg, quantitative).

Step B: 2-{2-(Ethoxycarbonylamino-methyl)-4-[2-(5-methyl-2-phenyl-oxazol-4-yl)-ethoxy]-phenoxy}-2-methyl-propionic acid General Parallel Synthesis Procedure: 2-{2-Aminomethyl-4-[2-(5-methyl-2-phenyl-oxazol-4-yl)-ethoxy]-phenoxy}-2-methyl-propionic acid ethyl ester: trifluoroacetic acid salt (381 mg, 0.650 mmol max.) was dissolved in $CH_2Cl_2$ (25 mL) and washed with saturated $NaHCO_3$ solution (15 mL). The organic layer was dried ($NaSO_4$), filtered, and concentrated to 2-{2-aminomethyl-4-[2-(5-methyl-2-phenyl-oxazol-4-yl)-ethoxy]-phenoxy}-2-methyl-propionic acid ethyl ester (245 mg, 0.59 mmol, 86%). A portion of this free base (13 mg, 0.030 mmol) in $CH_2Cl_2$ (0.8 mL) was treated with triethylamine (0.050 mL, 0.36 mmol) then ethyl chloroformate (0.020 mL, 0.21 mmol). The reaction mixture was shaken overnight and dimethylethylenediamine (0.050 mL, 0.47 mmol) was added. The reaction mixture was shaken for 2 h, diluted with MeOH (0.5 mL), and passed through an SCX column (1 g, equilibrated with 4 mL MeOH/$CH_2Cl_2$ 1/1). The methyl ester-amide product was eluted with MeOH/$CH_2Cl_2$ (1:1, 8 mL) and concentrated. The residue was dissolved in THF (1 mL) and EtOH (1 mL) and treated with 2N NaOH (0.5 mL). The solution was heated at 45° C. for 45 min, cooled, concentrated, and acidified with 1N HCl (2.5 mL). The mixture was diluted with diluted with $CH_2Cl_2$ (0.5 mL), transferred to a 3-mL ChemElute cartridge, and eluted with $CH_2Cl_2$ (8 mL). The solvent was removed under a stream of $N_2$. The crude product was dried under vacuum and purified by mass-directed HPLC to give a foam (2.7 mg, 19%). %). MS (ES+) m/z 483.5 [M+H]⁺.

The following Examples 564 to 570 are prepared by following a substantially similar procedure as described in Example 563.

Example 564

{2-(Benzyloxycarbonylamino-methyl)-4-[2-(5-methyl-2-phenyl-oxazol-4-yl)-ethoxy]-phenoxy}-acetic acid

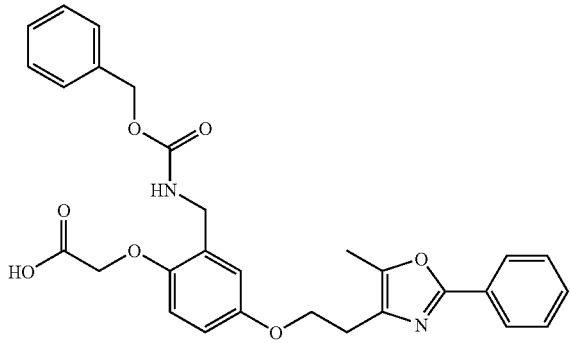

MS [ES] m/z 517.2 (M+1).

Example 565

{2-{[(2,5-Dichloro-thiophene-3-carbonyl)-amino]-methyl}-4-[2-(5-methyl-2-phenyl-oxazol-4-yl)-ethoxy]-phenoxy-}-acetic acid

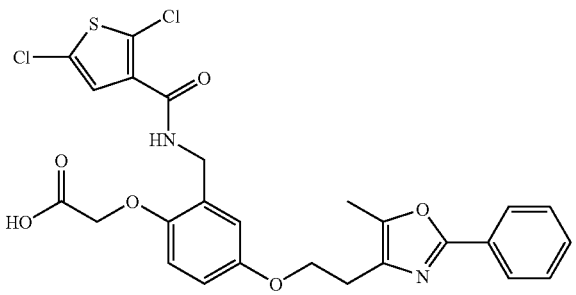

MS [ES] m/z 561.1 (M+1).

Example 566

{2-[(Cyclobutanecarbonyl-amino)-methyl]-4-[2-(5-methyl-2-phenyl-oxazol-4-yl)-ethoxy]-phenoxy}-acetic acid

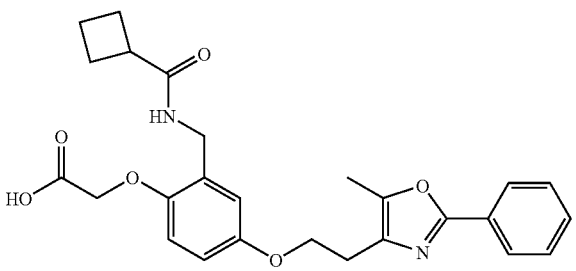

MS [ES] m/z 465.2 (M+1).

Example 567

2-{2-(Butyrylamino-methyl)-4-[2-(5-methyl-2-phenyl-oxazol-4-yl)-ethoxy]-phenoxy}-2-methyl-propionic acid

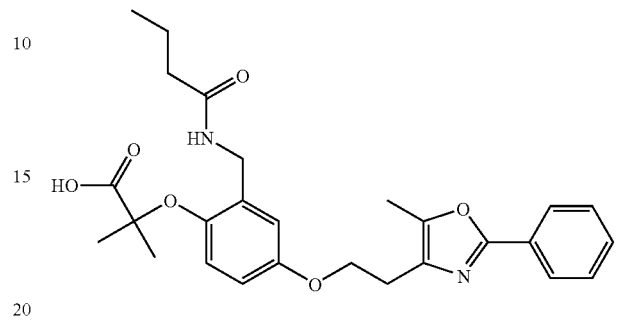

MS [ES] 481 m/z (M+1).

Example 568

2-{2-{[(2,5-Dichloro-thiophene-3-carbonyl)-amino]-methyl}-4-[2-(5-methyl-2-phenyl-oxazol-4-yl)-ethoxy]-phenoxy}-2-methyl-propionic acid

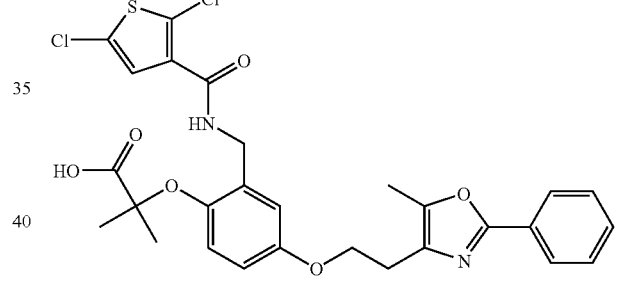

MS [ES] m/z 481 (M+1).

Example 569

2-{2-(Ethoxycarbonylamino-methyl)-4-[2-(5-methyl-2-phenyl-oxazol-4-yl)-ethoxy]-phenoxy}-2-methyl-propionic acid

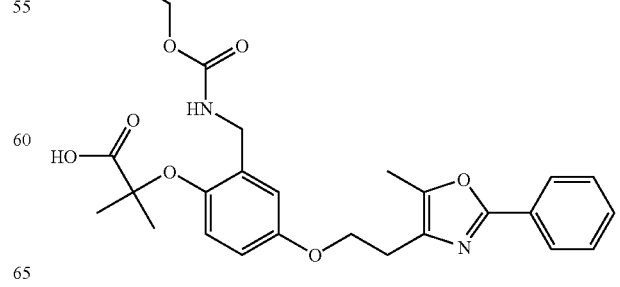

MS [ES] m/z 483 (M+1).

Example 570

2-{2-[(Cyclobutanecarbonyl-amino)-methyl]4-[2-(5-methyl-2-phenyl-oxazol-4-yl)-ethoxy]-phenoxy}-2-methyl-propionic acid

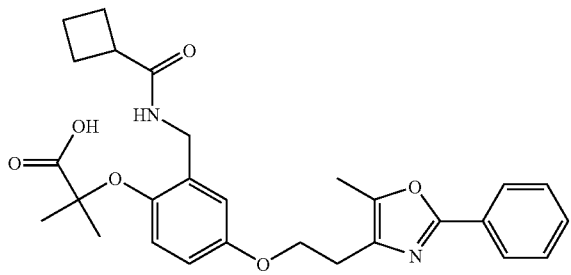

MS [ES] m/z 493 (M+1).

Example 571

3-(2-Cyano-4-{2-[5-methyl-2-(4-phenoxyphenyl)oxazol-4-yl]ethoxy}phenyl)propionic acid

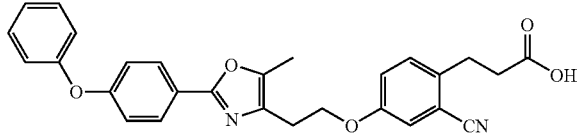

Step A: 2-Bromo-5-hydroxy-benzonitrile

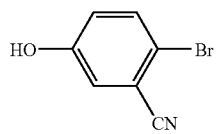

To a stirred solution of 3-cyanophenol (2.00 g, 18.0 mmol) in anhydrous acetonitrile (20 mL) under $N_2$ at −30° C. was added dropwise 54% $HBF_4 \cdot Et_2O$ (2.48 mL, 18.0 mmol). The temperature was maintained below −20° C. during addition. To this stirred solution was added NBS (3.27 g, 18.0 mmol) portion wise keeping the temperature below −10° C. After the addition was complete, the solution was allowed to warm to 19° C. The reaction mixture was diluted with 38% $NaHSO_3$ (10 mL) and extracted with MTBE (2×25 mL). The organic layer was washed with $H_2O$ (2×25 mL) and brine (25 mL), dried ($MgSO_4$), filtered, and concentrated to give a white solid (3.15 g). Purification of a portion of this product (1.0 g) by radial chromatography (30% EtOAc/hexane) gave 0.51 g of the title compound as a white solid. mp 183-184° C. Anal. Calculated for $C_7H_4BrNO$: C, 42.46; H, 2.04; N, 7.07. Found: C, 42.44; H, 1.93; N, 6.90.

Step B: 2-(3-Ethoxy-buta-1,3-dienyl)-5-hydroxy-benzonitrile

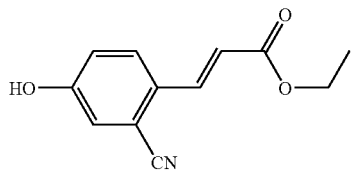

To a stirred solution of 2-bromo-5-hydroxy-benzonitrile (1.4 g, 7.1 mmol), ethyl acrylate (2.12 g, 21.2 mmol), palladium(II) acetate (0.159 g, 7.0 mmol), diisopropylethylamine (0.82 g, 14.1 mmol), and tri-ortho-tolylphosphine (0.430 g, 14.1 mmol) was added propionitrile (50 mL). The reaction was stirred overnight at 80° C. under a stream of $N_2$. The mixture was cooled, filtered, and concentrated. The crude material (3.0 g) was purified by radial chromatography (10-70% EtOAc/hexanes) to give the title compound as a white solid (1.1 g). MS [EI] m/z 216 (M+H)⁺.

Step C: 2-(3-Ethoxy-but-3-enyl)-5-hydroxy-benzonitrile

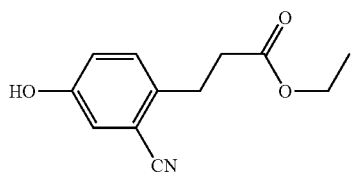

To a solution of 2-(3-ethoxy-buta-1,3-dienyl)-5-hydroxy-benzonitrile (600 mg) in EtOAc (50 mL) was added 5% Pd/C (0.3 g). The reaction was exposed to hydrogen gas in a Parr apparatus at 60 psi overnight at ambient temperature. The reaction mixture was filtered and concentrated to give the title compound (410 mg). MS [EI] m/z 218 (M+H)⁺.

Step D: 3-(2-Cyano-4-{2-[5-methyl-2-(4-phenoxyphenyl)oxazol-4-yl]ethoxy}phenyl)propionic acid A mixture of 2-(3-ethoxy-but-3-enyl)-5-hydroxy-benzonitrile (220 mg, 1.00 mmol), toluene-4-sulfonic acid 2-[5-methyl-2-(4-phenoxy-phenyl)-oxazol-4-yl]-ethyl ester (450 mg, 1.00 mmol; Preparation 6), and $CsCO_3$ (978 mg, 3.00 mmol) in DMF (10 mL) was stirred overnight at 60° C. under an $N_2$. The mixture was cooled, diluted with EtOAc (20 mL) and washed with brine (20 mL). The organic layer was dried ($Na_2SO_4$) and concentrated. The product mixture was purified by radial chromatography (10-70% EtOAc/hexanes) to give 3-(2-cyano-4-{2-[5-methyl-2-(4-phenoxyphenyl)oxazol-4-yl]ethoxy}phenyl)propionic acid ethyl ester (201 mg). A solution of this ester in EtOH (10 mL) and 5N NaOH (10 mL) was heated at 70° C. overnight, concentrated, acidified with 1N HCl, and extracted with EtOAc. The organic layer dried ($Na_2SO_4$) and concentrated to give the title compound (192 mg); MS [ES] m/z 469 (M+1).

The following Examples 572 to 573 and 575 to 581 are prepared by following a substantially similar procedure as described in Example 571.

Example 572

3-{4-[2-(2-Biphenyl-4-yl-5-methyloxazol-4-yl)ethoxy]-2-cyanophenyl}propionic acid

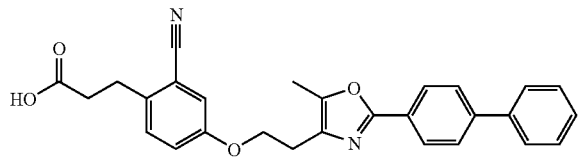

MS [ES] m/z 453 (M+1).

Example 573

3-{4-[3-(Biphenyl-4-yloxy)propoxy]-2-cyanophenyl}propionic acid

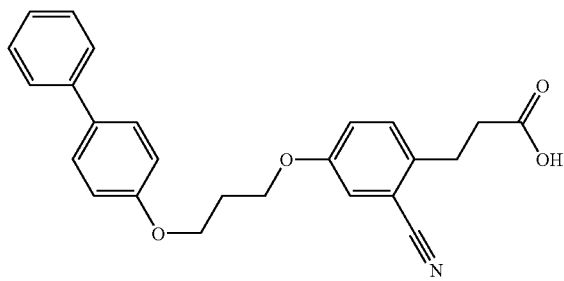

MS [ES] m/z 402 (M+1).

Example 575

3-(4-{2-[2-(4-Bromo-phenyl)-5-methyloxazol-4-yl]ethoxy}-2-cyanophenyl)propionic acid

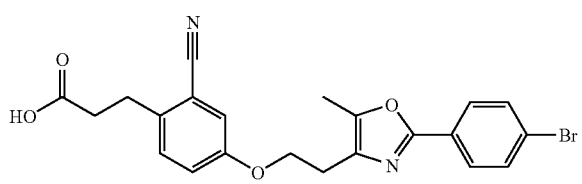

MS [ES] m/z 456 (M+1).

Example 576

3-{4-[2-(2-Biphenyl-3-yl-5-methyloxazol-4-yl)ethoxy]-2-cyanophenyl}propionic acid

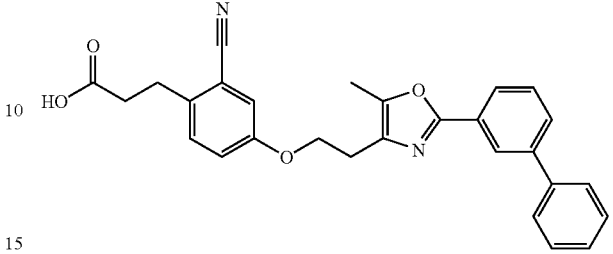

MS [ES] m/z 453 (M+1).

Example 577

3-{2-Cyano-4-[2-(5-methyl-2-morpholin-4-ylthiazol-4-yl)ethoxy]phenyl}propionic acid

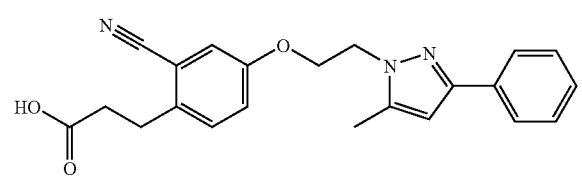

MS [ES] m/z 402 (M+1).

Example 578

3-{2-Cyano-4-[2-(5-methyl-3-phenylpyrazol-1-yl)ethoxy]phenyl}propionic acid

MS [ES] m/z 376 (M+1).

Example 579

3-(4-{2-[2-(4-Butoxyphenyl)-5-methyloxazol-4-yl]ethoxy}-2-cyanophenyl)propionic acid

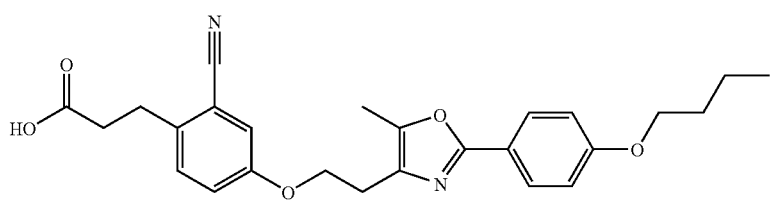

MS [ES] m/z 449 (M+1).

Example 580

3-(2-Cyano-4-{2-[5-methyl-2-(6-phenylpyridin-3-yl)thiazol-4-yl]ethoxy}phenyl)propionic acid

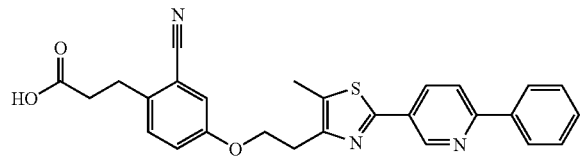

MS [ES] m/z 470 (M+1).

Example 581

3-{2-Cyano-4-[2-(5-methyl-2-phenylthiazol-4-yl)ethoxy]phenyl}propionic acid

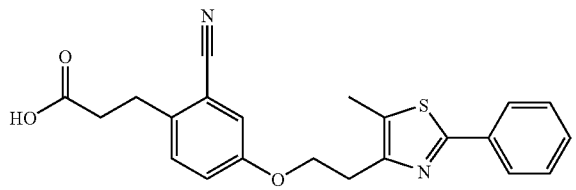

MS [ES] m/z 393 (M+1).

Example 582

3-{2-Benzylcarbamoyl-4-[2-(5-methyl-2-phenyl-oxazol-4-yl)-ethoxy]-phenyl}-propionic acid

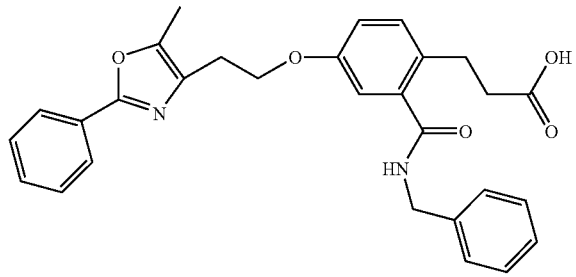

Step A: 3-(4-Benzyloxy-2-formyl-phenyl)-acrylic acid tert-butyl ester

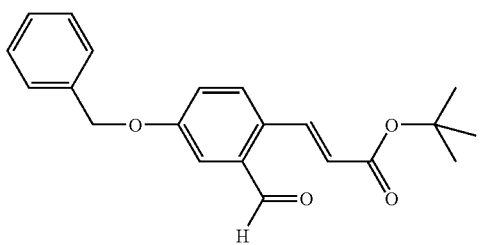

To a solution of 3-(2-formyl-4-hydroxy-phenyl)-acrylic acid tert-butyl ester (4.97 g, 20.0 mmol) in DMF (40 mL) was added benzyl bromide (2.85 mL, 24.0 mmol) and $Cs_2CO_3$ (7.82 g, 24.0 mmol). The suspension was stirred at 80° C. for 30 min, and TLC indicated the reaction was complete. The mixture was quenched with $H_2O$ (500 mL) and extracted with EtOAc (2×100 mL). The combined organics were dried ($Na_2SO_4$) and concentrated to a residue, which was purified by silica gel chromatography (hexanes/EtOAc 9/1) to afford the title compound as yellow solid (6.70 g, 99%).

Step B: 5-Benzyloxy-2-(2-tert-butoxycarbonyl-vinyl)-benzoic acid

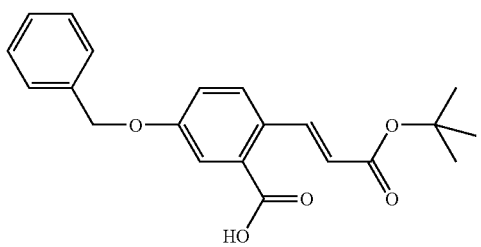

A solution of 3-(4-benzyloxy-2-formyl-phenyl)-acrylic acid tert-butyl ester (6.70 g, 19.8 mmol) in tert-butanol (150 mL) was treated with 2-methyl-2-butene (50 mL) and cooled to 0° C. A solution of $NaClO_2$ (17.0 g, 188 mmol) and $NaH_2PO_4$ (17.0 g, 142 mmol) in $H_2O$ (200 mL) was added, and the mixture was stirred at 0° C. for 15 min. The ice bath was removed, and the mixture was stirred at room temperature for 2 h. The organic layer was separated, and the aqueous layer was extracted with EtOAc (2×100 mL). The combined organic layers were dried ($Na_2SO_4$) and concentrated. The residue was purified using silica gel chromatography (hexanes/EtOAc 9/1 to 0/10) to afford the title compound as white solid (6.78 g, 96%). $^1$H NMR (400 MHz, $CDCl_3$): δ 1.52 (s, 9H), 5.12 (s, 2H), 6.20 (d, 1H, J=16.2 Hz), 7.13 (dd, 1H, J=3.6, 9.0 Hz), 7.34-7.45 (m, 5H), 7.58 (d, 1H, J=8.8 Hz), 7.64 (d, 1H, J=2.4 Hz), 8.41 (d, 1H, J=16.2 Hz).

Step C: 5-Benzyloxy-2-(2-tert-butoxycarbonyl-vinyl)-benzoic acid 2-trimethylsilanyl-ethyl ester

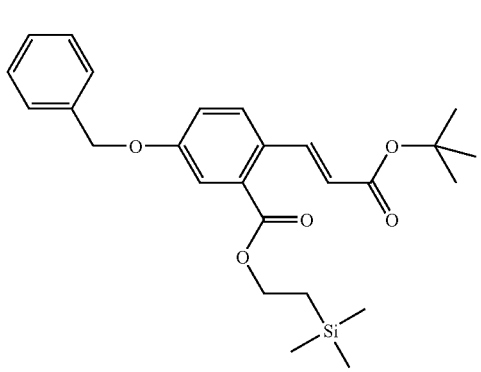

To a solution of 5-benzyloxy-2-(2-tert-butoxycarbonyl-vinyl)-benzoic acid (5.50 g, 15.5 mmol) in $CH_2Cl_2$ (100 mL) was added 2-trimethylsilyl-ethanol (3.67 g, 31.0 mmol), EDC (5.36 g, 27.9 mmol), and DMAP (3.67 g, 31.0 mmol). The resulting mixture was stirred at room temperature for 12 h, washed with aqueous $NH_4Cl$ (150 mL), and extracted with $CH_2Cl_2$ (100 mL). The combined organics were dried ($Na_2SO_4$) and concentrated. The residue was purified using silica gel chromatography (hexanes/EtOAc 9/1) to afford the title compound as an oil (5.90 g, 84%). $^1$H NMR (400 MHz, $CDCl_3$): δ 0.07 (s, 9H), 1.14 (t, 2H, J=8.8 Hz), 1.52 (s, 9H), 4.41 (t, 2H, J=8.8 Hz), 5.10 (s, 2H), 6.20 (d, 1H, J=15.6 Hz), 7.13 (dd, 1H, J=3.0, 8.3 Hz), 7.34-7.44 (m, 5H), 7.50 (d, 1H, J=3.0 Hz), 7.53 (d, 1H, J=8.8 Hz), 8.41 (d, 1H, J=16.1 Hz).

Step D: 2-(2-tert-Butoxycarbonyl-ethyl)-5-hydroxy-benzoic acid 2-trimethylsilanyl-ethyl ester

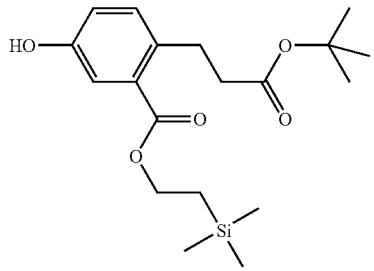

A solution of 5-benzyloxy-2-(2-tert-butoxycarbonyl-vinyl)-benzoic acid 2-trimethylsilanyl-ethyl ester (6.20 g, 13.6 mmol) in EtOH (95 mL) was treated with Pd/C (5%, 0.775 g). The resulting suspension was treated with hydrogen at 60 psi for 6 h at room temperature. The catalyst was filtered through a pad of Celite, and the filtrate was concentrated to an oil (4.30 g, 86%). $^1$H NMR (400 MHz, CDCl$_3$): δ 0.07 (s, 9H), 0.96 (t, 1H, J=8.8 Hz), 1.12 (t, 1H, J=8.8 Hz), 1.40 (s, 9H), 2.52 (t, 1H, J=7.8 Hz), 3.13 (t, 1H, J=7.8 Hz), 3.73 (t, 1H, J=8.5 Hz), 4.36 (t, 1H, J=8.5 Hz), 5.00 (br s, 1H), 6.88 (dd, 1H, J=2.4, 8.3 Hz), 7.14 (d, 1H, J=8.3 Hz), 7.35 (d, 1H, J=2.4 Hz).

Step E: 2-(2-tert-Butoxycarbonyl-ethyl)-5-[2-(5-methyl-2-phenyl-oxazol-4-yl)-ethoxy]-benzoic acid 2-trimethylsilanyl-ethyl ester

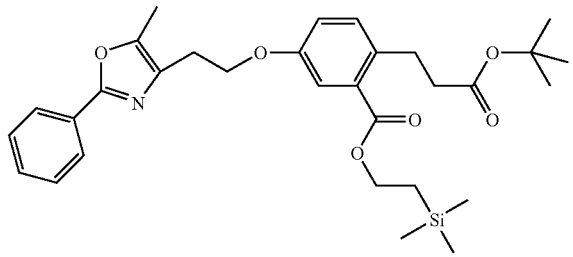

To a solution of 2-(2-tert-butoxycarbonyl-ethyl)-5-hydroxy-benzoic acid 2-trimethylsilanyl-ethyl ester (4.30 g, 11.7 mmol) and toluene-4-sulfonic acid 2-(5-methyl-2-phenyl-oxazol-4-yl)-ethyl ester (4.61 g, 12.9 mmol) in DMF (30 mL) was added Cs$_2$CO$_3$ (4.59 g, 14.1 mmol). The suspension was stirred at 55° C. for 12 h. The reaction mixture was quenched with H$_2$O (200 mL) and extracted with EtOAc (3×100 mL). The combined organics were dried (Na$_2$SO$_4$) and concentrated to a residue, which was purified using silica gel chromatography (hexanes/EtOAc 9/1 to 8/2) to afford the title compound as a colorless oil (5.04 g, 78%). $^1$H NMR (400 MHz, CDCl$_3$): δ 0.06 (s, 9H), 1.11 (t, 2H, J=8.8 Hz), 1.40 (s, 9H), 2.36 (s, 3H), 2.51 (t, 1H, J=7.8 Hz), 2.97 (t, 2H, J=6.8 Hz), 3.12 (t, 1H, J=7.8 Hz), 4.24 (t, 2H, J=6.8 Hz), 4.35 (t, 2H, J=8.8 Hz), 6.88 (dd, 1H, J=3.0, 8.3 Hz), 7.15 (d, 1H, J=8.3 Hz), 7.37-7.44 (m, 4H), 7.97 (d, 2H, J=7.8 Hz).

Step F: 2-(2-tert-Butoxycarbonyl-ethyl)-5-[2-(5-methyl-2-phenyl-oxazol-4-yl)-ethoxy]-benzoic acid

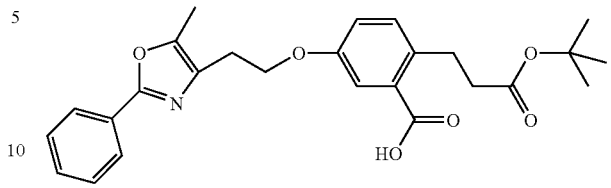

A solution of 2-(2-tert-butoxycarbonyl-ethyl)-5-[2-(5-methyl-2-phenyl-oxazol-4-yl)-ethoxy]-benzoic acid 2-trimethylsilanylethyl ester (5.04 g, 9.13 mmol) in THF (100 mL) was treated with TBAF (20 mL, 1.0 M) at room temperature for 1 h. The reaction mixture was concentrated and purified using silica gel chromatography (hexanes/EtOAc 1/1) to afford the title compound as a colorless oil (4.04 g, 98%). $^1$H NMR (400 MHz, CDCl$_3$): δ 1.38 (s, 9H), 2.37 (s, 3H), 2.55 (t, 2H, J=7.3 Hz), 2.98 (t, 2H, J=6.5 Hz), 3.15 (t, 2H, J=7.3 Hz), 4.26 (t, 2H, J=6.5 Hz), 4.35 (t, 2H, J=8.8 Hz), 6.99 (dd, 1H, J=2.9, 8.8 Hz), 7.18 (d, 1H, J=8.3 Hz), 7.38-7.43 (m, 3H), 7.49 (d, 1H, J=2.9 Hz), 7.97 (d, 2H, J=7.8 Hz). MS (ES) m/z 522.3 [M+H]$^+$.

Step G: 3-{2-Benzylcarbamoyl-4-[2-(5-methyl-2-phenyl-oxazol-4-yl)-ethoxy]-phenyl}-propionic acid To a solution of 2-(2-tert-butoxycarbonyl-ethyl)-5-[2-(5-methyl-2-phenyl-oxazol-4-yl)-ethoxy]-benzoic acid (93 mg, 0.200 mmol) in CH$_2$Cl$_2$ (2 mL) was added benzylamine (52 mg g, 0.49 mmol), EDC (54 mg, 0.28 mmol), triethylamine (0.057 ml, 0.40 mmol), and DMAP (catalyst). The resulting mixture was stirred at room temperature for 12 h and washed with aqueous NH$_4$Cl (2 mL). The organic layer was purified using a silica gel column (Sep-Pak column, 10 g; hexanes/EtOAc 1/1) to afford the tert-butyl ester intermediate. The ester was treated a mixture of CH$_2$Cl$_2$ (1.0 mL), TFA (0.8 mL), and water (0.1 mL) at room temperature for 2 h. The reaction mixture was concentrated and dried under vacuum to afford the title product as a white solid (35 mg, 36%). $^1$H NMR (400 MHz, CDCl$_3$): δ 2.32 (s, 3H), 2.59 (t, 2H, J=7.3 Hz), 2.88-2.98 (m, 4H, J=6.5 Hz), 4.16 (t, 2H, J=6.5 Hz), 4.52 (s, 2H), 6.83 (dd, 1H, J=2.6, 8.4 Hz), 6.87 (d, 1H, J=2.4 Hz), 7.10 (d, 1H, J=8.3 Hz), 7.20-7.30 (m, 3H), 7.37-7.40 (m, 3H), 7.88-7.91(m, 2H). MS (ES) m/z 485.2 [M+H]$^+$, m/z 483.4 [M−H]$^−$.

Example 583

3-{2-Benzylcarbamoyl-4-[2-(2-biphenyl-4-yl-5-methyl-oxazol-4-yl)-ethoxy]-phenyl}-propionic acid

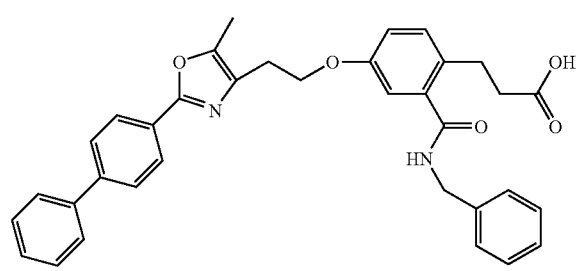

Step A: 3-(2-Benzylaminocarbonyl-4-benzyloxy-phenyl)-acrylic acid tert-butyl ester

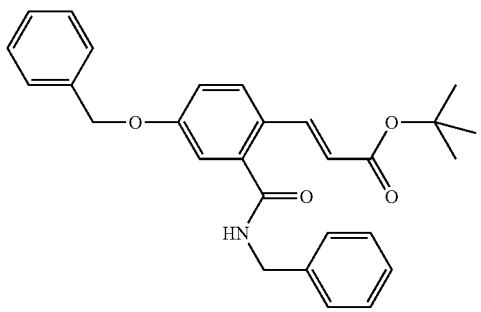

To a solution of 5-benzyloxy-2-(2-tert-butoxycarbonyl-vinyl)-benzoic acid (1.45 g, 4.09 mmol) in CH$_2$Cl$_2$ (40 mL) was added benzylamine (0.613 g, 5.73 mmol), EDC (1.254 g, 6.54 mmol), and DMAP (1.00 g, 8.18 mmol). The resulting mixture was stirred at room temperature for 12 h, washed with aqueous NH$_4$Cl (50 mL), and extracted with CH$_2$Cl$_2$ (2×50 mL). The combined organic layers were dried (Na$_2$SO$_4$) and concentrated. The residue was then purified using silica gel chromatography (hexanes/EtOAc 8/2) to afford the title compound as an oil (720 mg, 40%). $^1$H NMR (400 MHz, CDCl$_3$): δ 1.52 (s, 9H), 4.63 (d, 2H, J=5.5 Hz), 5.09 (s, 2H), 5.97 (br s, 1H), 6.22 (d, 1H, J=15.6 Hz), 7.01 (dd, 1H, J=2.7, 8.6 Hz), 7.10 (d, 1H, J=2.8 Hz), 7.28-7.42 (m, 10H), 7.55 (d, 1H, J=9.0 Hz), 7.88 (d, 1H, J=16.0 Hz).

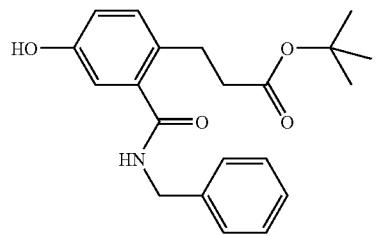

A solution of 3-(2-benzylaminocarbonyl-4-benzyloxy-phenyl)-acrylic acid tert-butyl ester (720 mg, 1.625 mmol) in EtOH (15 mL) and THF (5 mL) was treated with Pd/C (5%, 70 mg). The resulting suspension was treated with hydrogen using a balloon for 4 h at room temperature. The catalyst was filtered through a pad of celite and the filtrate was concentrated to an oil (450 mg, 78%). $^1$H NMR (400 MHz, CDCl$_3$): δ 1.34 (s, 9H), 2.56 (t, 2H, J=7.0 Hz), 2.90 (t, 2H, J=7.0 Hz), 4.59 (d, 1H, J=5.9 Hz), 6.74 (dd, 1H, J=2.7, 8.2 Hz), 6.89 (d, 1H, J=2.7 Hz), 7.01 (d, 1H, J=8.2 Hz), 7.25-7.36 (m, 5H). MS (ES) m/z 356.2 [M+H]$^+$, m/z 354.0 [M−H]$^−$.

Step C: 3-{2-Benzylcarbamoyl-4-[2-(2-biphenyl-4-yl-5-methyl-oxazol-4-yl)-ethoxy]-phenyl}-propionic acid To a solution of 3-(2-benzylaminocarbonyl-4-hydroxy-phenyl)-propionic acid tert-butyl ester (50 mg, 0.140 mmol) and toluene-4-sulfonic acid 2-(5-methyl-2-(4-phenylphenyl)-oxazol-4-yl)-ethyl ester (73 mg, 0.168 mmol) in DMF (1.0 mL) was added K$_2$CO$_3$ (100 mg, 0.724 mmol). The suspension was stirred at 65° C. for 12 h. The reaction mixture was quenched with H$_2$O (10 mL) and extracted with EtOAc (3×10 mL). The combined organic layers were dried (Na$_2$SO$_4$) and concentrated to a residue, which was purified using silica gel chromatography (hexanes/EtOAc 7/3) to afford the tert-butyl ester intermediate as an oil. The ester was treated a mixture of CH$_2$Cl$_2$ (1.0 mL), TFA (0.8 mL) and water (0.1 mL) at room temperature for 2 h. The reaction mixture was concentrated and dried under vacuum to afford the title product as a white solid (37 mg, 47%). $^1$H NMR (400 MHz, CDCl$_3$): δ 2.36 (s, 3H), 2.59 (t, 2H, J=7.3 Hz), 2.94 (t, 4H, J=7.2 Hz), 4.20 (t, 2H, J=6.5 Hz), 4.55 (s, 2H), 6.85 (dd, 1H, J=2.9, 8.2 Hz), 6.90 (d, 1H, J=2.4 Hz), 7.12 (d, 1H, J=8.6 Hz), 7.20-7.36 (m, 6H), 7.42 (t, 2H, J=7.4 Hz), 7.59 (d, 2H, J=8.6 Hz), 7.64 (d, 2H, J=8.2 Hz), 8.00 (d, 2H, J=8.6 Hz). MS (ES) m/z 561.3 [M+H]$^+$, m/z 559.5 [M−H]$^−$.

EXAMPLES 584-643

Examples 584 to 643 are prepared by following a substantially similar procedure as described in Examples 582 and 583. Examples 584 to 628 are prepared by following a substantially similar procedure as described in Example 582. Examples 629 to 643 are prepared by following a substantially similar procedure as described in Example 583.

| No. | Compounds | Name | MS (ES+) |
|---|---|---|---|
| 584 | | 3-{4-[2-(5-Methyl-2-phenyl-oxazol-4-yl)-ethoxy]-2-phenyl-carbamoyl-phenyl}-propionic acid | 471.2 |

-continued
| No. | Compounds | Name | MS (ES+) |
|---|---|---|---|
| 585 | 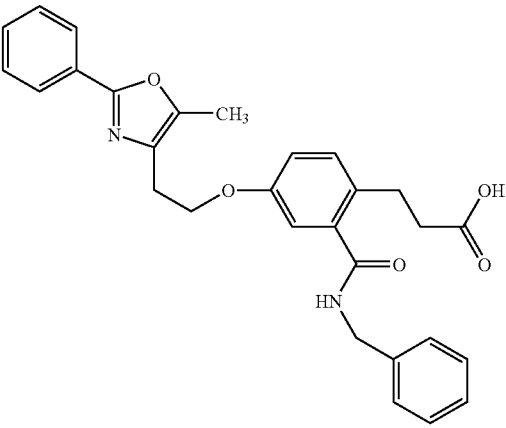 | 3-{2-Benzyl-carbamoyl-4-[2-(5-methyl-2-phenyl-oxazol-4-yl)-ethoxy]-phenyl}-propionic acid | 485.2 |
| 586 | 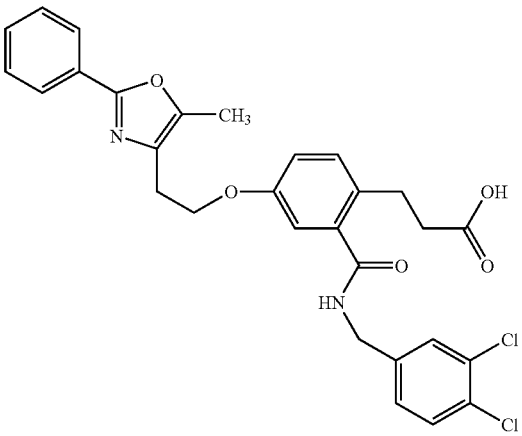 | 3-{2-(3,4-Dichloro-benzyl-carbamoyl)-4-[2-(5-methyl-2-phenyl-oxazol-4-yl)-ethoxy]-phenyl}-propionic acid | 553 |
| 587 | 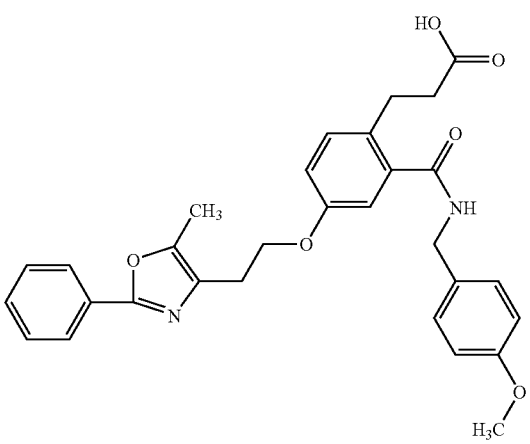 | 3-{2-(4-Methoxy-benzyl-carbamoyl)-4-[2-(5-methyl-2-phenyl-oxazol-4-yl)-ethoxy]-phenyl}-propionic acid | 515.2 |

-continued
| No. | Compounds | Name | MS (ES+) |
|---|---|---|---|
| 588 | 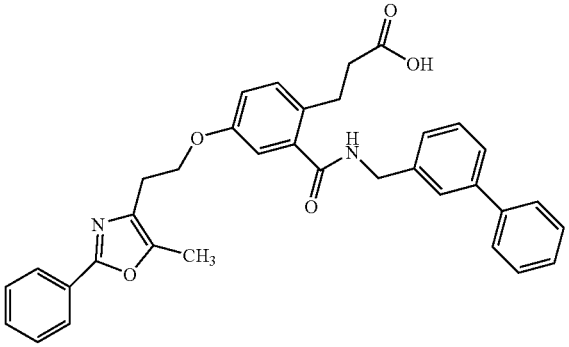 | 3-{2-[(Biphenyl-3-ylmethyl)-carbamoyl]-4-[2-(5-methyl-2-phenyl-oxazol-4-yl)-ethoxy]-phenyl}-propionic acid | 561.2 |
| 589 | 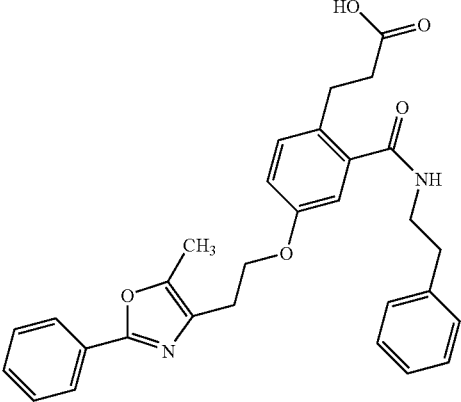 | 3-{4-[2-(5-Methyl-2-phenyl-oxazol-4-yl)-ethoxy]-2-phenethyl-carbamoyl-phenyl}-propionic acid | 499.3 |
| 590 | 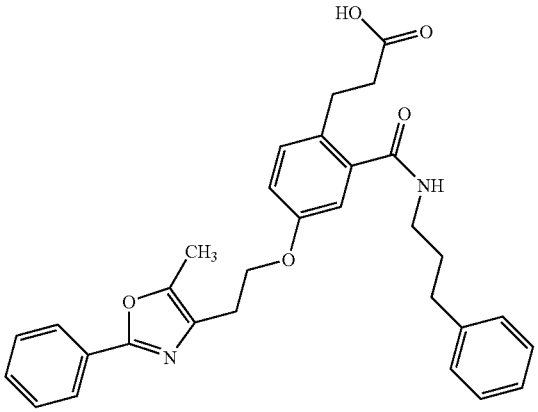 | 3-[4-[2-(5-Methyl-2-phenyl-oxazol-4-yl)-ethoxy]-2-(3-phenyl-propyl-carbamoyl)-phenyl]-propionic acid | 513.3 |

-continued

| No. | Compounds | Name | MS (ES+) |
|---|---|---|---|
| 591 | | 3-{4-[2-(5-Methyl-2-phenyl-oxazol-4-yl)-ethoxy]-2-[(thiophen-2-ylmethyl)-carbamoyl]-phenyl}-propionic acid | 491.2 |
| 592 | | 3-{2-Hexyl-carbamoyl-4-[2-(5-methyl-2-phenyl-oxazol-4-yl)-ethoxy]-phenyl}-propionic acid | 479.3 |
| 593 | | 3-{2-Methyl-carbamoyl-4-[2-(5-methyl-2-phenyl-oxazol-4-yl)-ethoxy]-phenyl}-propionic acid | 409.1 |
| 594 | | 3-{2-Butyl-carbamoyl-4-[2-(5-methyl-2-phenyl-oxazol-4-yl)-ethoxy]-phenyl}-propionic acid | 451.1 |
| 595 | | 3-{2-Isopropyl-carbamoyl-4-[2-(5-methyl-2-phenyl-oxazol-4-yl)-ethoxy]-phenyl}-propionic acid | 437.2 |

| No. | Compounds | Name | MS (ES+) |
|---|---|---|---|
| 596 | | 3-{2-(Cyclohexylmethyl-carbamoyl)-4-[2-(5-methyl-2-phenyl-oxazol-4-yl)-ethoxy]-phenyl}-propionic acid | 491.2 |
| 597 | | 3-{2-tert-Butyl-carbamoyl-4-[2-(5-methyl-2-phenyl-oxazol-4-yl)-ethoxy]-phenyl}-propionic acid | 451.2 |
| 598 | | 3-{2-Carbamoyl-4-[2-(5-methyl-2-phenyl-oxazol-4-yl)-ethoxy]-phenyl}-propionic acid | 395.1 |
| 599 | | 3-{2-(2-Fluoro-benzyl-carbamoyl)-4-[2-(5-methyl-2-phenyl-oxazol-4-yl)-ethoxy]-phenyl}-propionic acid | 503.1 |
| 600 | | 3-{2-(2-Chloro-benzyl-carbamoyl)-4-[2-(5-methyl-2-phenyl-oxazol-4-yl)-ethoxy]-phenyl}-propionic acid | 519.1 |
| 601 | | 3-{2-(2,4-Dichloro-benzyl-carbamoyl)-4-[2-(5-methyl-2-phenyl-oxazol-4-yl)-ethoxy]-phenyl}-propionic acid | 553 |
| 602 | | 3-{2-(2-Methoxy-benzyl-carbamoyl)-4-[2-(5-methyl-2-phenyl-oxazol-4-yl)-ethoxy]-phenyl}-propionic acid | 515.1 |

-continued

| No. | Compounds | Name | MS (ES+) |
|---|---|---|---|
| 603 | | 3-{2-(Indan-1-yl-carbamoyl)-4-[2-(5-methyl-2-phenyl-oxazol-4-yl)-ethoxy]-phenyl}-propionic acid | 511.1 |
| 604 | | 3-{2-(3-Fluoro-benzyl-carbamoyl)-4-[2-(5-methyl-2-phenyl-oxazol-4-yl)-ethoxy]-phenyl}-propionic acid | 503.1 |
| 605 | | 3-[4-[2-(5-Methyl-2-phenyl-oxazol-4-yl)-ethoxy]-2-(4-trifluoromethyl-benzylcarbamoyl)-phenyl]-propionic acid | 553 |
| 606 | | 3-{2-(3-Methyl-benzyl-carbamoyl)-4-[2-(5-methyl-2-phenyl-oxazol-4-yl)-ethoxy]-phenyl}-propionic acid | 499.1 |
| 607 | | 3-{2-(4-Fluoro-benzyl-carbamoyl)-4-[2-(5-methyl-2-phenyl-oxazol-4-yl)-ethoxy]-phenyl}-propionic acid | 503.1 |
| 608 | | 3-{4-[2-(5-Methyl-2-phenyl-oxazol-4-yl)-ethoxy]-2-[(naphthalen-1-yl-methyl)-carbamoyl]-phenyl}-propionic acid | 535.1 |
| 609 | | 3-{2-(4-Methanesulfonyl-benzyl-carbamoyl)-4-[2-(5-methyl-2-phenyl-oxazol-4-yl)-ethoxy]-phenyl}-propropionic acid | 563.1 |

-continued

| No. | Compounds | Name | MS (ES+) |
|---|---|---|---|
| 610 | | 3-[4-[2-(5-Methyl-2-phenyl-oxazol-4-yl)-ethoxy]-2-(2-trifluoromethyl-benzylcarbamoyl)-phenyl]-propionic acid | 553.1 |
| 611 | | 3-{2-(4-Nitro-benzylcarbamoyl)-4-[2-(5-methyl-2-phenyl-oxazol-4-yl)-ethoxy]-phenyl}-propionic acid | 530.1 |
| 612 | | 3-[4-[2-(5-Methyl-2-phenyl-oxazol-4-yl)-ethoxy]-2-(4-sulfamoyl-benzylcarbamoyl)-phenyl]-propionic acid | 564.1 |
| 613 | | 3-{2-(3,5-Dimethyl-benzylcarbamoyl)-4-[2-(5-methyl-2-phenyl-oxazol-4-yl)-ethoxy]-phenyl}-propionic acid | 513.2 |
| 614 | | 3-{2-(4-tert-Butyl-benzylcarbamoyl)-4-[2-(5-methyl-2-phenyl-oxazol-4-yl)-ethoxy]-phenyl}-propionic acid | 541.2 |
| 615 | | 3-{2-(2-Methyl-benzylcarbamoyl)-4-[2-(5-methyl-2-phenyl-oxazol-4-yl)-ethoxy]-phenyl}-propionic acid | 499.2 |

-continued

| No. | Compounds | Name | MS (ES+) |
|---|---|---|---|
| 616 | | 3-{4-[2-(5-Methyl-2-phenyl-oxazol-4-yl)-ethoxy]-2-[(pyridin-4-yl-methyl)-carbamoyl]-phenyl}-propionic acid | 486.2 |
| 617 | | 3-{2-(3-Methoxy-benzylcarbamoyl)-4-[2-(5-methyl-2-phenyl-oxazol-4-yl)-ethoxy]-phenyl}-propionic acid | 515.2 |
| 618 | | 3-[4-[2-(5-Methyl-2-phenyl-oxazol-4-yl)-ethoxy]-2-(3-trifluoromethyl-benzylcarbamoyl)-phenyl]-propionic acid | 553.1 |
| 619 | | 3-{2-(3,5-Bis-trifluoromethyl-benzyl-carbamoyl)-4-[2-(5-methyl-2-phenyl-oxazol-4-yl)-ethoxy]-phenyl}-propionic acid | 621.1 |
| 620 | | 3-{2-(3-Chloro-benzylcarbamoyl)-4-[2-(5-methyl-2-phenyl-oxazol-4-yl)-ethoxy]-phenyl}-propionic acid | 519.1 |

-continued

| No. | Compounds | Name | MS (ES+) |
|---|---|---|---|
| 621 | | 3-{2-(3-Fluoro-5-trifluoromethyl-benzyl carbamoyl)-4-[2-(5-methyl-2-phenyl-oxazol-4-yl)-ethoxy]-phenyl}-propionic acid | 571.1 |
| 622 | | 3-{2-(3,5-Difluoro-benzyl-carbamoyl)-4-[2-(5-methyl-2-phenyl-oxazol-4-yl)-ethoxy]-phenyl}-propionic acid | 521.1 |
| 623 | | 3-{2-(3,5-Dichloro-benzyl-carbamoyl)-4-[2-(5-methyl-2-phenyl-oxazol-4-yl)-ethoxy]-phenyl}-propionic acid | 553 |
| 624 | Chiral | (R)-3-[4-[2-(5-Methyl-2-phenyl-oxazol-4-yl)-ethoxy]-2-(1-phenyl-ethylcarbamoyl)-phenyl]-propionic acid | 499.2 |
| 625 | | 3-{2-(Benzyl-ethyl-carbamoyl)-4-[2-(5-methyl-2-phenyl-oxazol-4-yl)-ethoxy]-phenyl}-propionic acid | 513.2 |
| 626 | | 3-{2-(Benzyl-methyl-carbamoyl)-4-[2-(5-methyl-2-phenyl-oxazol-4-yl)-ethoxy]-phenyl}-propionic acid | 499.2 |
| 627 | Chiral | (S)-3-{2-[(Carboxy-phenyl-methyl)carbamoyl]-4-[2-(5-methyl-2-phenyl-oxazol-4-yl)-ethoxy]-phenyl}-propionic acid | 529.1 |

-continued

| No. | Compounds | Name | MS (ES+) |
|---|---|---|---|
| 628 | 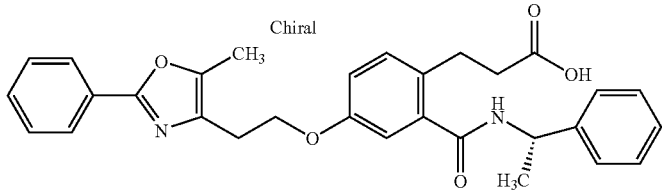 | (S)-3-[4-[2-(5-Methyl-2-phenyl-oxazol-4-yl)-ethoxy]-2-(1-phenyl-ethylcarbamoyl)-phenyl]-propionic acid | 499.2 |
| 629 | 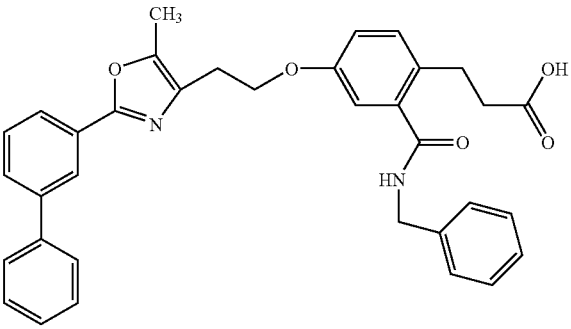 | 3-{2-Benzylcarbamoyl-4-[2-(2-biphenyl-3-yl-5-methyl-yl-oxazol-4-yl)-ethoxy]-phenyl}-propionic acid | 561.3 |
| 630 | 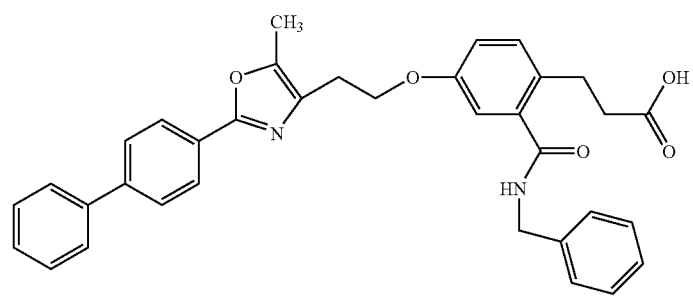 | 3-{2-Benzylcarbamoyl-4-[2-(2-biphenyl-4-yl-5-methyl-yl-oxazol-4-yl)-ethoxy]-phenyl}-propionic acid | 561.3 |
| 631 | 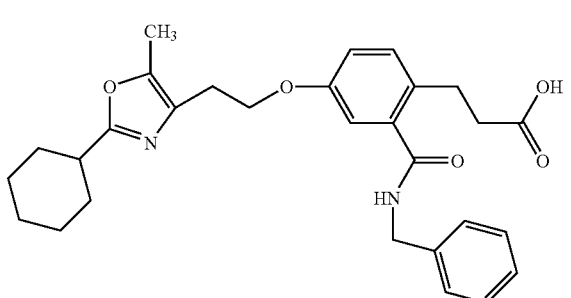 | 3-{2-Benzyl-carbamoyl-4-[2-(2-cyclohexyl-5-methyl-oxazol-4-yl)-ethoxy]-phenyl}-propionic acid | 491.3 |
| 632 | 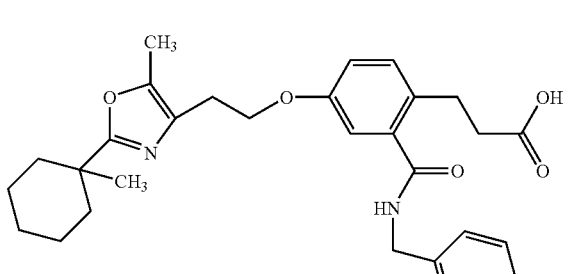 | 3-(2-Benzyl-carbamoyl-4-{2-[5-methyl-2-(1-methyl-cyclohexyl)-oxazol-4-yl]-ethoxy}-phenyl)-propionic acid | 505.4 |

-continued

| No. | Compounds | Name | MS (ES+) |
|---|---|---|---|
| 633 | | 3-{2-Benzyl-carbamoyl-4-[2-(5-methyl-2-morpholin-4-yl-thiazol-4-yl)-ethoxy]-phenyl}-propionic acid | 510.3 |
| 634 | Chiral | (R)-3-[4-[2-(2-Biphenyl-4-yl-5-methyl-oxazol-4-yl)-ethoxy]-2-(1-phenyl-ethylcarbamoyl)-phenyl]-propionic acid | 575.3 |
| 635 | Chiral | (R)-3-[4-[2-(2-Biphenyl-3-yl-5-methyl-oxazol-4-yl)-ethoxy]-2-(1-phenyl-ethylcarbamoyl)-phenyl]-propionic acid | 575.3 |
| 636 | Chiral | (R)-3-[4-[2-(5-Methyl-2-morpholin-4-yl-thiazol-4-yl)-ethoxy]-2-(1-phenylethylcarbamoyl)-phenyl]-propionic acid | 524.2 |
| 637 | | 3-[4-[2-(2-Biphenyl-4-yl-5-methyl-oxazol-4-yl)-ethoxy]-2-(3,5-difluoro-benzylcarbamoyl)-phenyl]-propionic acid | 597.3 |

-continued
| No. | Compounds | Name | MS (ES+) |
|---|---|---|---|
| 638 | 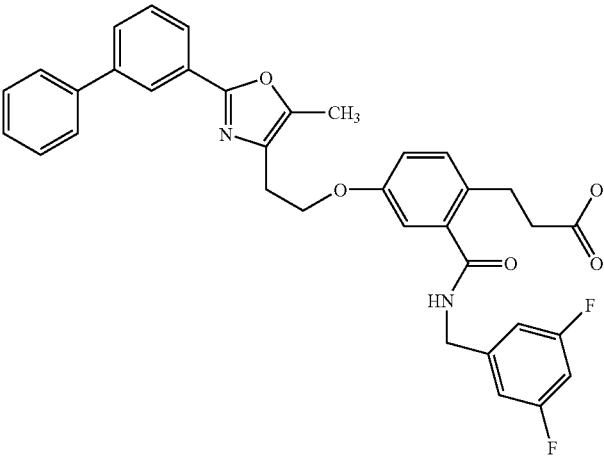 | 3-[4-[2-(2-Biphenyl-3-yl-5-methyl-oxazol-4-yl)-ethoxy]-2-(3,5-difluoro-benzylcarbamoyl)-phenyl]-propionic acid | 597.3 |
| 639 | 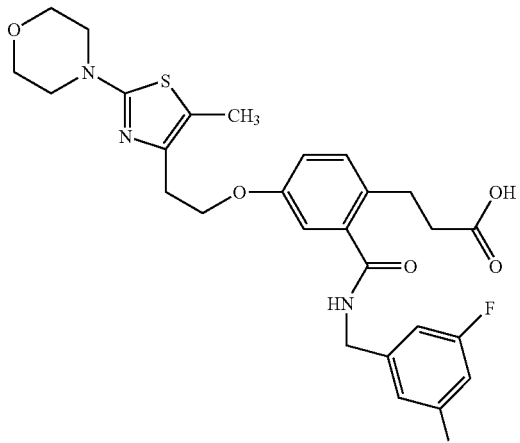 | 3-{2-(3,5-Difluoro-benzylcarbamoyl)-4-[2-(5-methyl-2-morpholin-4-yl-thiazol-4-yl)-ethoxy]-phenyl}-propionic acid | 546.1 |
| 640 | 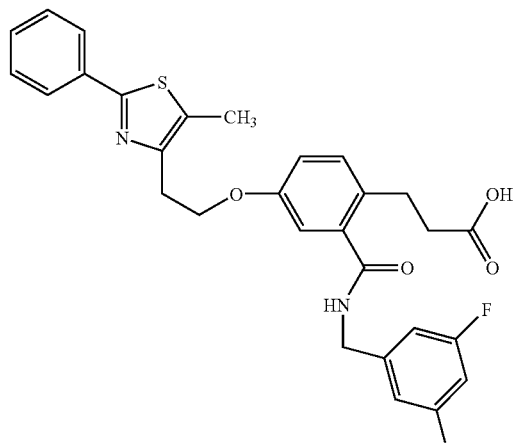 | 3-{2-(3,5-Difluoro-benzylcarbamoyl)-4-[2-(5-methyl-2-phenyl-thiazol-4-yl)-ethoxy]-phenyl}-propionic acid | 537.1 |

-continued
| No. | Compounds | Name | MS (ES+) |
|---|---|---|---|
| 641 | 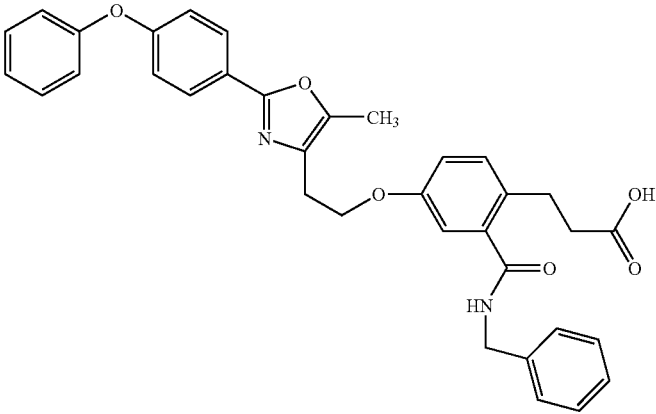 | 3-(2-Benzyl-carbamoyl-4-{2-[5-methyl-2-(4-phenoxy-phenyl)-oxazol-4-yl]-ethoxy}-phenyl)-propionic acid | 577.3 |
| 642 | 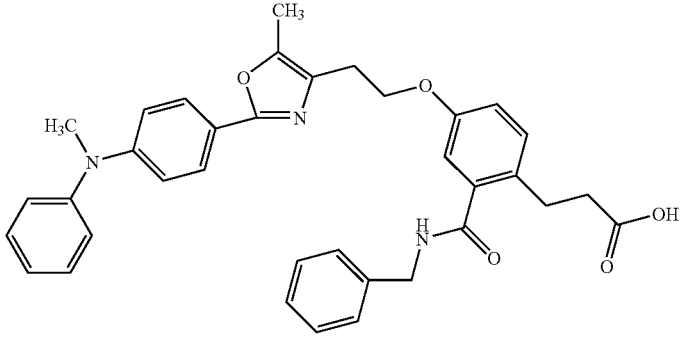 | 3-[2-Benzyl-carbamoyl-4-(2-{5-methyl-2-[4-(methyl-phenyl-amino)-phenyl]-oxazol-4-yl}-ethoxy)-phenyl]-propionic acid | 590.2 |
| 643 | 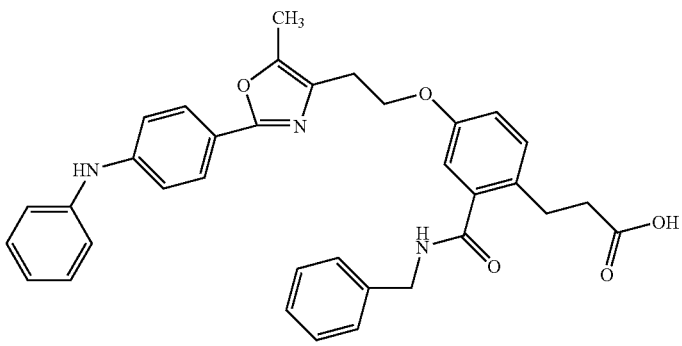 | 3-(2-Benzyl-carbamoyl-4-{2-[5-methyl-2-(4-phenyl-amino-phenyl)-oxazol-4-yl]-ethoxy}-phenyl)-propionic acid | 576.2 |

Example 644

3-{2-Cyclopentylcarbamoyloxymethyl-4-[2-(2-phenyloxazol-4-yl)ethoxy]phenyl}-propionic acid

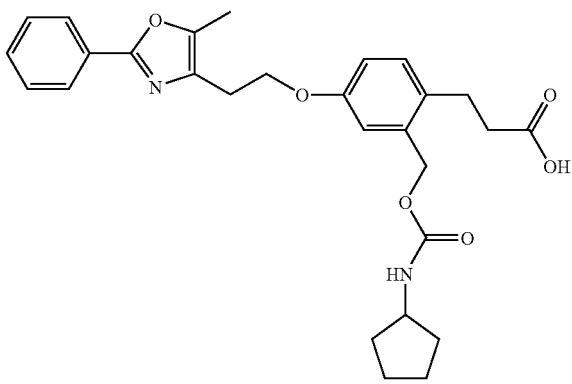

Step A: 3-{2-Formyl-4-[2-(5-methyl-2-phenyloxazol-4-yl)ethoxy]phenyl}acrylic acid tert-butyl ester

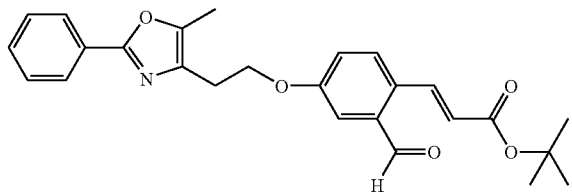

A flame-dried 100 mL round bottomed flask was charged with toluene-4-sulfonic acid 2-(5-methyl-2-phenyloxazol-4-yl)ethyl ester (3.74 g, 10.5 mmol), 3-(2-formyl-4-hydroxyphenyl)acrylic acid tert-butyl ester (2.0 g, 8.05 mmol), and anhydrous DMF (40 mL). Cesium carbonate (3.94 g, 12.1 mmol) was added, and the reaction was heated to 55° C. under a nitrogen atmosphere for 18 h. The volatiles were removed in vacuo, and the crude residue was dissolved in EtOAc (250 mL). The organic layer was washed with brine (2×), dried (Na$_2$SO$_4$), and concentrated to a yellow oil (1.70 g, 49%). $^1$H NMR (400 MHz, CDCl$_3$) δ 1.54 (s, 9H), 2.38 (s, 3H), 3.01 (t, J=6.6 Hz, 2H), 4.34 (t, J=6.6 Hz, 2H), 6.24 (d, J=15.6 Hz, 1H), 7.12 (dd, J=8.8, 2.9 Hz, 1H), 7.38 (d, J=2.9 Hz, 1H), 7.40-7.45 (m, 3H), 7.58 (d, J=8.8 Hz, 1H), 7.98 (dd, J=6.4, 2.0 Hz, 2H), 8.33 (d, J=15.6 Hz, 1H), 10.3 (s, 1H). MS (ES) m/e 434 (M+1).

Step B: 3-{2-Formyl-4-[2-(5-methyl-2-phenyloxazol-4-yl)ethoxy]phenyl}acrylic acid tert-butyl ester

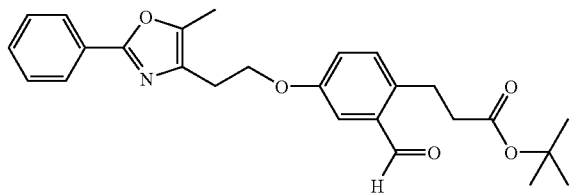

A 100 mL round bottomed flask was charged with 3-{2-formyl-4-[2-(5-methyl-2-phenyloxazol-4-yl)-ethoxy]phenyl}acrylic acid tert-butyl ester (1.69 g, 3.90 mmol), THF (40 mL), and then 10% Pd/C catalyst (0.17 g). The reaction was stirred vigorously under a hydrogen atmosphere at one atmosphere for 18 h. The mixture was filtered through Celite and concentrated to a yellow solid (1.70 g, quantitative). $^1$H NMR (400 MHz, CDCl$_3$) δ 1.39 (d, J=4.9 Hz, 9H), 2.37 (d, J=2.9 Hz, 3H), 2.51 (t, J=7.6 Hz, 2H), 2.99 (t, J=6.6 Hz, 2H), 3.23 (t, J=7.1 Hz, 2H), 4.29 (t, J=6.6 Hz, 2H), 7.04-7.10 (m, 1H), 7.21 (d, J=8.3 Hz, 1H), 7.34 (d, J=2.4 Hz, 1H), 7.38-7.45 (m, 3H), 7.97 (dd, J=7.3, 2.0 Hz, 2H), 10.2 (s, 1H). MS (ES) m/e 436 (M+1).

Step C: 3-{2-Hydroxymethyl-4-[2-(2-phenyl-oxazol-4-yl)ethoxy]phenyl}propionic acid tert-butyl ester

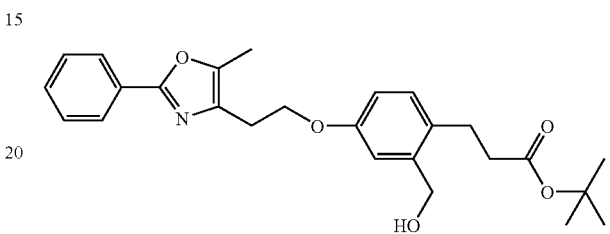

A 100 mL round bottomed flask was charged with 3-{2-formyl-4-[2-(2-phenyloxazol-4-yl)ethoxy]phenyl}propionic acid tert-butyl ester (1.82 g, 4.18 mmol) and absolute ethanol (20 mL). The stirring solution was cooled in an ice/ethanol bath and treated with sodium borohydride (0.31 g, 8.36 mmol). The cold bath was removed, and the mixture was stirred at ambient temperature under a nitrogen atmosphere for 2 h. The reaction mixture was poured into EtOAc (100 mL) and ice water (100 mL). The organic layer was washed with brine, dried (Na$_2$SO$_4$), and concentrated to a yellow oil (1.62 g, 88%). $^1$H NMR (400 MHz, CDCl$_3$) δ 1.38 (s, 9H), 2.37 (s, 3H), 2.54 (t, J=7.6 Hz, 2H), 2.88 (t, J=7.6 Hz, 2H), 2.97 (t, J=6.6 Hz, 2H), 4.23 (t, J=6.6 Hz, 2H), 4.66 (s, 2H), 6.78 (dd, J=8.3, 2.9 Hz, 1H), 6.94 (d, J=2.4 Hz, 1H), 7.09 (d, J=8.3 Hz, 1H), 7.38-7.45 (m, 3H), 7.97 (dd, J=8.1, 1.7 Hz, 2H). MS (ES) m/e 438 (M+1).

Step D: 3-{2-Cyclopentylcarbamoyloxymethyl-4-[2-(2-phenyloxazol-4-yl)ethoxy]phenyl}-propionic acid tert-butyl ester

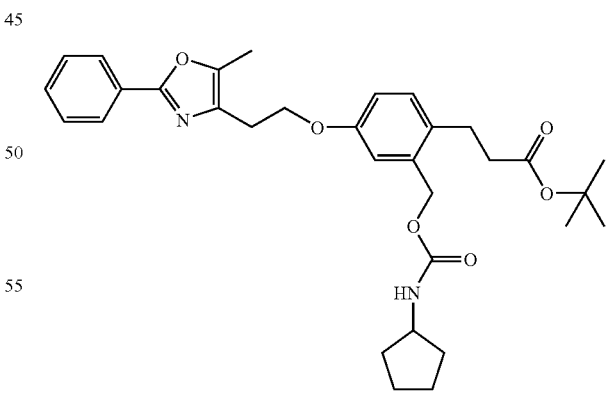

A 15 mL round bottomed flask was charged with 3-{2-hydroxymethyl-4-[2-(2-phenyloxazol-4-yl)ethoxy]phenyl}propionic acid tert-butyl ester (0.10 g, 0.23 mmol), cyclopentylisocyanate (0.15 mL, 1.38 mmol), and anhydrous CH$_2$Cl$_2$ (0.75 mL). A 1.0 M HCl solution in ether (0.115 mL, 0.115 mmol) was added, and the reaction mixture was stirred at ambient temperature under a nitrogen atmosphere for 24 h. The reaction mixture was diluted with CH₂Cl₂, (30 mL), washed with brine, dried (Na₂SO₄), and concentrated to an oil. The crude product was purified using radial chromatography (EtOAc:hexanes 10:90 to 35:65) to a colorless oil (0.105 g, 83%). ¹H NMR (400 MHz, CDCl₃) δ1.42 (s, 9H), 1.56-1.65 (m, 4H), 1.94-2.04 (m, 2H), 2.37 (s, 3H), 2.46 (t, J=7.6 Hz, 2H), 2.87 (t, J=8.1 Hz, 2H), 2.96 (t, J=6.6 Hz, 2H), 3.97 (br s, 1H), 4.22 (t, J=6.6 Hz, 2H), 4.76 (br s, 1H), 5.07 (s, 2H), 6.90 (dd, J=8.3, 2.4 Hz, 1H), 6.89 (s, 1H), 7.10 (d, J=8.8 Hz, 1H), 7.40-7.45 (m, 3H), 7.96-7.98 (m, 2H). MS (ES) m/e 549 (M+1).

Step E: 3-{2-Cyclopentylcarbamoyloxymethyl-4-[2-(2-phenyloxazol-4-yl)ethoxy]phenyl}-propionic acid A 15 mL round bottom flask was charged with 3-{2-cyclopentylcarbamoyloxymethyl-4-[2-(2-phenyloxazol-4-yl)ethoxy]phenyl}propionic acid tert-butyl ester (0.097 g, 0.18 mmol), CH₂Cl₂ (1.2 mL), and then trifluoroacetic acid (1.2 mL). The solution was stirred at ambient temperature under a nitrogen atmosphere for 4 h and was concentrated. The residue was purified using radial chromatography (MeOH:CH₂Cl₂ 2:98 to 10:90) to give a white solid (0.085 g, 93%). ¹H NMR (400 MHz, CDCl₃) δ 1.37 (br s, 2H), 1.63 (br s, 4H), 1.93-2.05 (m, 2H), 2.39 (s, 3H), 2.64 (br s, 2H), 2.91-3.18 (m, 4H), 3.99 (br s, 1H), 4.21 (s, 2H), 4.87 (br s, 1H), 5.10 (br s, 2H), 6.80 (s, 1H), 6.89 (s, 1H), 7.00-7.25 (br s, 1H), 7.36-7.52 (m, 3H), 7.95 (s, 2H). MS (ES) m/e 493 (M+1).

The following Examples 645 to 651 are prepared by following a substantially similar procedure as described in Example 644.

Example 645

3-{2-Isopropylcarbamoyloxymethyl-4-[2-(5-methyl-2-phenyloxazol-4-yl)ethoxy]phenyl}propionic acid tert-butyl ester MS (ES) m/e 523 (M+1).

Example 646

3-{2-Isopropylcarbamoyloxymethyl-4-[2-(5-methyl-2-phenyloxazol-4-yl)ethoxy]phenyl}propionic acid

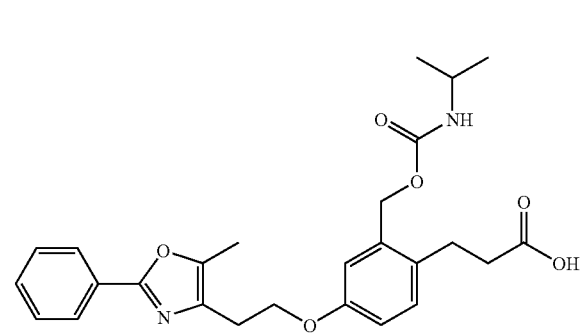

¹H NMR (400 MHz, CDCl₃) δ 1.13 (d, J=5.4 Hz, 6H), 2.37 (s, 3H), 2.61 (t, J=7.8 Hz, 2H), 2.92-2.98 (m, 4H), 3.80 (br s, 1H), 4.21 (t, J=6.6 Hz, 2H), 4.66 (br s, 1H), 5.08 (s, 2H), 6.81 (dd, J=8.6, 2.7 Hz, 1H), 6.90 (s, 1H), 7.11 (d, J=8.3 Hz, 1H), 7.41-7.44 (m, 3H), 7.97 (dd, J=4.4, 2.9 Hz, 2H). MS (ES) m/e 467 (M+1).

Example 647

3-{2-Benzylcarbamoyloxymethyl-4-[2-(5-methyl-2-phenyloxazol-4-yl)ethoxy]phenyl}propionic acid tert-butyl ester MS (ES) m/e 571 (M+1).

Example 648

3-{2-Benzylcarbamoyloxymethyl-4-[2-(5-methyl-2-phenyloxazol-4-yl)ethoxy]phenyl}propionic acid

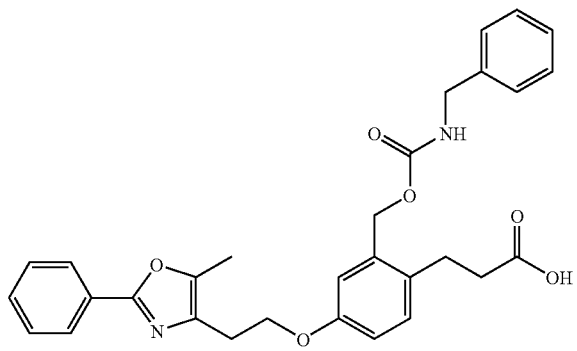

¹H NMR (400 MHz, CDCl₃) δ2.37 (s, 3H), 2.60 (t, J=7 Hz, 2H), 2.92-2.97 (m, 4H), 4.20 (t, J=7 Hz, 2H), 4.36 (d, J=5.9 Hz, 2H), 5.13 (s, 2H), 5.18 (br s, 1H), 6.80 (d, J=8.3 Hz, 1H), 6.91 (s, 1H), 7.10 (d, J=8.3 Hz, 1H), 7.24-7.30 (m, 5H), 7.42 (s, 3H), 7.97 (s, 2H). MS (ES) m/e 515 (M+1).

Example 649

Morpholine-4-carboxylic acid 2-(2-carboxyethyl)-5-[2-(5-methyl-2-phenyloxazol-4-yl)ethoxy]benzyl ester

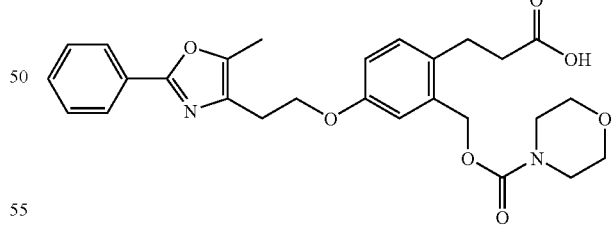

MS (ES) m/e 495 (M+1).

Example 650

3-{2-Cyclohexylcarbamoyloxymethyl-4-[2-(5-methyl-2-phenyloxazol-4-yl)ethoxy]phenyl}propionic acid tert-butyl ester MS (ES) m/e 563 (M+1)

Example 651

3-{2-Cyclohexylcarbamoyloxymethyl-4-[2-(5-methyl-2-phenyloxazol-4-yl)ethoxy]phenyl}propionic acid

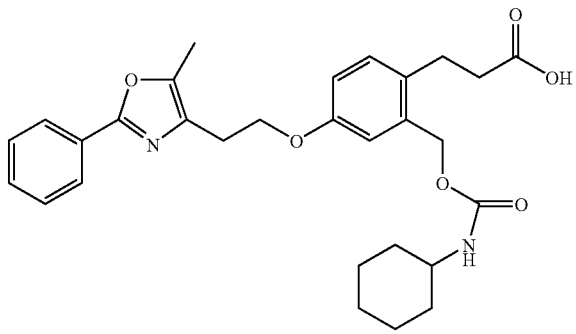

$^1$H NMR (400 MHz, CDCl$_3$) δ 1.08-1.18 (m 3H), 1.21-1.42 (m, 2H), 1.57 (br s, 1H), 1.66-1.70 (m, 2H), 1.90 (br s, 2H), 2.40 (s, 3H), 2.61 (t, J=7.7 Hz, 2H), 2.94 (t, J=7.8 Hz, 2H), 3.01 (t, J=6.4 Hz, 2H), 3.48 (br s, 1H), 4.22 (t, J=6.4 Hz, 2H), 4.74 (br s, 1H), 5.07 (s, 2H), 6.79-6.89 (m, 1H), 6.90 (s, 1H), 7.11 (d, J=8.3 Hz, 1H), 7.44-7.46 (m, 3H), 7.98 (dd, J=6.7, 2.8 Hz, 2H). MS (ES) m/e 507 (M+1).

Example 652

3-{2-Cyclohexylcarbamoyloxymethyl-4-[2-(2-phenyloxazol-4-yl)ethoxy]phenyl}-propionic acid

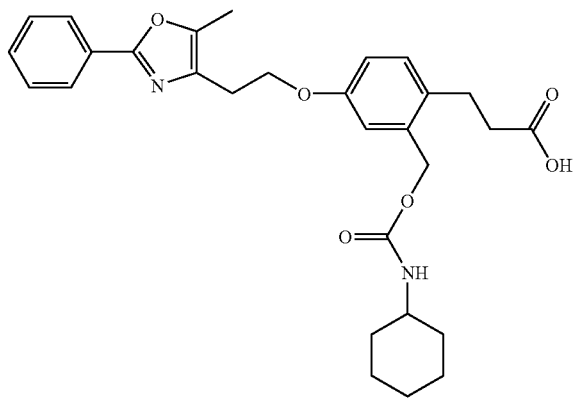

Step A: 3-[4-(tert-Butyldiphenylsilanyloxy)-2-formylphenyl]acrylic acid tert-butyl ester

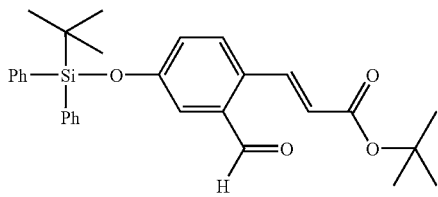

A flame-dried 200 mL round bottomed flask was charged with 3-(2-formyl-4-hydroxyphenyl)acrylic acid tert-butyl ester (10.0 g, 40.3 mmol), tert-butylchlorodiphenylsilane (12.6 mL, 48.3 mmol), and dry CH$_2$Cl$_2$ (150 mL). Triethylamine (11.2 mL, 80 mmol) and N,N-dimethylaminopyridine (1.0 g, 1.0 mmol) were added, and the mixture was stirred at ambient temperature under a nitrogen atmosphere for 16 h. The reaction mixture was diluted with additional CH$_2$Cl$_2$, washed with brine (2×), dried (Na$_2$SO$_4$), and concentrated to an oil. The crude product was purified using the Biotage medium pressure chromatography system (EtOAc:hexanes 5:95) to give a pale yellow oil (18.3 g, 93%). $^1$H NMR (400 MHz, CDCl$_3$) δ 1.12 (s, 9H), 1.51 (d, J=15.1 Hz, 9H), 6.15 (d, J=5.1 Hz, 1H), 6.87 (dd, J=8.6, 2.7 Hz, 1H), 7.34-7.47 (m, 7H), 7.68-7.73 (m, 5H), 8.28 (d, J=15.6 Hz, 1H), 10.1 (s, 1H). MS (ES) m/e 487 (M+1).

Step B: 3-[4-(tert-Butyldiphenylsilanyloxy)-2-hydroxymethylphenyl]propionic acid tert-butyl ester

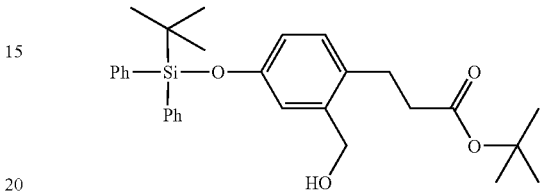

A 500 mL Parr hydrogenation bottle was charged with 3-[4-(tert-butyldiphenylsilanyloxy)-2-formylphenyl]acrylic acid tert-butyl ester (18.3 g, 37.6 mmol), THF (60 mL), and methanol (120 mL). Triethylamine (2 mL) and then 5% Pd/C (5.9 g) were added. The mixture was shaken with hydrogen at 60 psi pressure for 48 h. The mixture was filtered through Celite and concentrated to an oil. This oil was purified using the Biotage medium pressure chromatography (EtOAc:hexanes 15:85) to a pale yellow oil (12.8 g, 69%). $^1$H NMR (400 MHz, CDCl$_3$) δ 1.09 (s, 9H), 1.35 (s, 9H), 2.49 (t, J=7.6 Hz, 2H), 2.83 (t, J=7.6 Hz, 2H), 4.55 (s, 2H), 6.56 (dd, J=8.3, 2.4 Hz, 1H), 6.83 (d, J=2.9 Hz, 1H), 6.87 (d, J=8.3 Hz, 1H), 7.33-7.44 (m, 6H), 7.70 (dd, J=7.8, 1.5 Hz, 4H). MS (ES) m/e 508 (M+NH$_4$).

Step C: 3-[4-(tert-Butyldiphenylsilanyloxy)-2-cyclohexylcarbamoyloxymethylphenyl]propionic acid tert-butyl ester

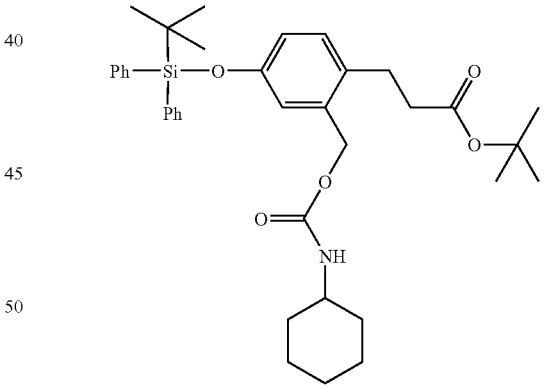

A 100 mL round bottomed flask under N$_2$ were charged with 3-[4-(tert-butyldiphenylsilanyloxy)-2-hydroxymethylphenyl]propionic acid tert-butyl ester (3.0 g, 6.11 mmol), cyclohexylisocyanate (4.7 mL, 36.7 mmol), and anhydrous CH$_2$Cl$_2$ (25 mL). A 1.0 M HCl solution in ether (3.06 mL, 3.06 mmol) was added, and the reaction mixture was stirred at ambient temperature under a nitrogen atmosphere for 16 h. The mixture was diluted with CH$_2$Cl$_2$ (100 mL), washed with brine, dried (Na$_2$SO$_4$), and concentrated to a brown oil. This crude oil was purified using the Biotage medium pressure chromatography system (EtOAc:hexanes 5:95) to a colorless oil (3.1 g, 82%). $^1$H NMR (400 MHz, CDCl$_3$) δ 1.08-1.24 (m, 1H), 1.26-1.40 (m, 11H), 1.56-1.62 (m, 2H), 1.68-1.72 (m, 2H), 2.41 (t, J=8.3 Hz, 2H), 2.80 (t, J=7.8 Hz, 2H), 3.47 (br s, 1H), 4.56 (br s, 1H), 4.95 (s, 2H), 6.57 (dd, J=8.3, 2.7 Hz, 1H), 6.80 (s, 1H), 6.87 (d, J=8.6 Hz, 1H), 7.33-7.44 (m, 6H), 7.69-7.72 (m, 4H). MS (ES) m/e 616 (M+1).

Step D: 3-(2-Cyclohexylcarbamoyloxymethyl-4-hydroxyphenyl)propionic acid tert-butyl ester

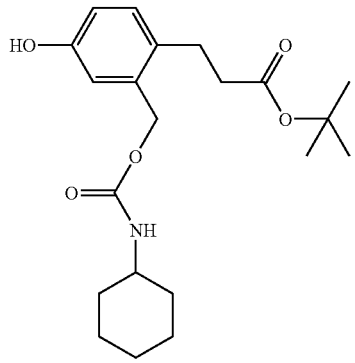

A 500 mL round bottomed flask was charged with 3-[4-(tert-butyldiphenylsilanyloxy)-2-cyclohexylcarbamoyloxymethylphenyl]propionic acid tert-butyl ester (3.1 g, 5.03 mmol) and anhydrous THF (180 mL). Tetrabutylammonium fluoride (15.1 mL, 15.1 mmol, 1.0M in THF) was added, and the reaction mixture was stirred at ambient temperature under a nitrogen atmosphere for 4 h. The mixture was concentrated, and the residue was diluted with EtOAc (100 mL), washed with brine, dried over (Na₂SO₄), and concentrated to give an oil. This crude oil was purified using the Biotage medium pressure chromatography system (EtOAc: hexanes 10:90 to 50:50) to a colorless oil (1.67 g, 88%). ¹H NMR (400 MHz, CDCl₃) δ 1.04-1.19 (m, 3H), 1.24-1.38 (m, 2H), 1.42 (s, 9H), 1.57-1.62 (m, 1H), 1.66-1.71 (m, 2H), 1.91-2.05 (m, 2H), 2.47 (t, J=7.8 Hz, 2H), 2.88 (t, J=7.8 Hz, 2H), 3.48-3.50 (m, 1H), 4.77-4.78 (m, 1H), 5.07 (s, 2H), 5.40 (s, 1H), 6.73 (dd, J=8.3, 2.9 Hz, 1H), 6.84 (d, J=2.4 Hz, 1H), 7.07 (d, J=8.3 Hz, 1H). MS (ES) m/e 378 (M+1).

Step E: 3-{2-Cyclohexylcarbamoyloxymethyl-4-[2-(5-methyl-2-phenyloxazol-4-yl)ethoxy]phenyl}propionic acid tert-butyl ester

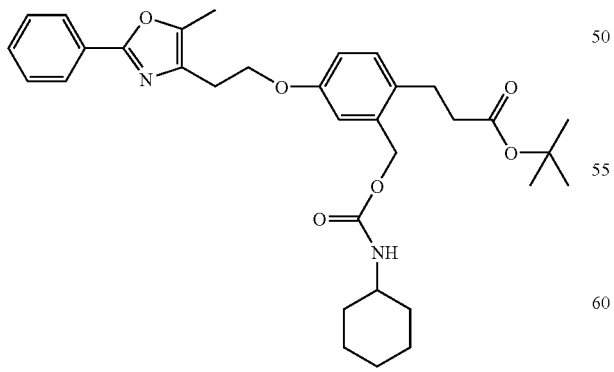

A 40 mL Carousel tube was charged with 3-(2-cyclohexylcarbamoyloxymethyl-4-hydroxyphenyl)propionic acid tert-butyl ester (0.10 g, 0.26 mmol) in anhydrous DMF (1.0 mL).

Toluene-4-sulfonic acid 2-(5-methyl-2-phenyloxazol-4-yl) ethyl ester (0.104 g, 0.292 mmol) and cesium carbonate (0.13 g, 0.40 mmol) were added. The mixture was stirred and heated at 55° C. under a nitrogen atmosphere for 30 h and was concentrated. The residue was diluted with EtOAc (50 mL) and washed twice with brine (2×), dried (Na₂SO₄), and concentrated. The crude residue was purified using radial chromatography (EtOAc: CH₂Cl₂ 2:98 to 5:95) to give a white solid (0.085 g, 57%). ¹H NMR (400 MHz, CDCl₃) δ 1.07-1.19 (m, 3H), 1.24-1.38 (m, 2H), 1.42 (s, 9H), 1.56-1.60 (m, 1H), 1.67-1.70 (m, 2H), 1.91-1.93 (m, 2H), 2.37 (s, 3H), 2.46 (t, J=7.8 Hz, 2H), 2.88 (t, J=7.8 Hz, 2H), 2.96 (t, J=7.8 Hz, 2H), 3.48-3.50 (m, 1H), 4.22 (t, J=6.8 Hz, 2H), 4.69-4.71 (m, 1H), 5.07 (s, 2H), 6.80 (dd, J=8.3, 2.4 Hz, 1H), 6.90 (d, J=2.4 Hz, 1H), 7.10 (d, J=8.3 Hz, 1H), 7.39-7.45 (m, 3H), 7.98 (dd, J=4.2, 2.2 Hz, 2H). MS (ES) m/e 563 (M+1).

Step F: 3-{2-Cyclohexylcarbamoyloxymethyl-4-[2-(5-methyl-2-phenyloxazol-4-yl)ethoxy]phenyl}propionic acid A 25 mL round bottomed flask was charged with 3-{2-cyclohexylcarbamoyloxymethyl-4-[2-(5-methyl-2-phenyloxazol-4-yl)ethoxy]phenyl}-propionic acid tert-butyl ester (0.080 g, 0.14 mmol) and CH₂Cl₂ (2 mL). Trifluoroacetic acid (2 mL) was added, and the solution was stirred at ambient temperature under a nitrogen atmosphere for 1.5 h. The solution was concentrated to give a white solid (0.068 g, 94%). ¹H NMR (400 MHz, CDCl₃) δ 1.08-1.18 (m 3H), 1.21-1.42 (m, 2H), 1.57 (br s, 1H), 1.66-1.70 (m, 2H), 1.90 (br s, 2H), 2.40 (s, 3H), 2.61 (t, J=7.7 Hz, 2H), 2.94 (t, J=7.8 Hz, 2H), 3.01 (t, J=6.4 Hz, 2H), 3.48 (br s, 1H), 4.22 (t, J=6.4 Hz, 2H), 4.74 (br s, 1H), 5.07 (s, 2H), 6.79-6.89 (m, 1H), 6.90 (s, 1H), 7.11 (d, J=8.3 Hz, 1H), 7.44-7.46 (m, 3H), 7.98 (dd, J=6.7, 2.8 Hz, 2H). MS (ES) m/e 507 (M+1).

The following Examples 653 to 661 are prepared by following a substantially similar procedure as described in Example 652.

Example 653

3-{4-[2-(2-Biphenyl-4-yl-5-methyloxazol-4-yl)ethoxy]-2-cyclohexylcarbamoyloxymethylphenyl}propionic acid tert-butyl ester

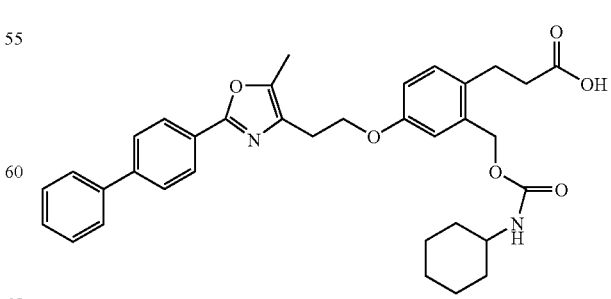

MS (ES) m/e 639 (M+1).

Example 654

3-{4-[2-(2-Biphenyl-4-yl-5-methyloxazol-4-yl)ethoxy]-2-cyclohexylcarbamoyloxymethylphenyl}propionic acid

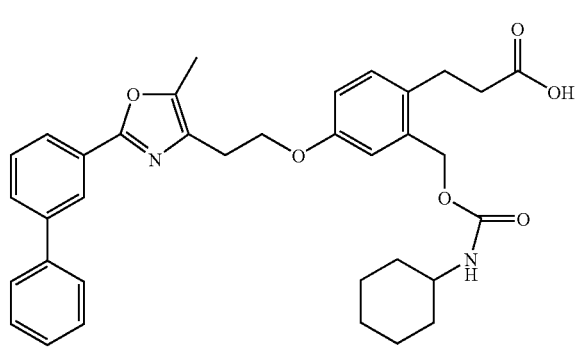

$^1$H NMR (400 MHz, CDCl$_3$) δ1.14-1.25 (m, 3H), 1.31-1.34 (m, 2H), 1.56-1.66 (m, 1H), 1.69-1.70 (m, 2H), 1.89 (br s, 2H), 2.46 (s, 3H), 2.62 (t, J=7.6 Hz, 2H), 2.93 (t, J=7.8 Hz, 2H), 3.11 (t, J=5.9 Hz, 2H), 3.47 (br s, 1H), 4.24 (t, J=5.9 Hz, 2H), 4.83 (br s, 1H), 5.08 (s, 2H), 6.80 (d, J=6.8 Hz, 1H), 6.90 (d, J=2.9 Hz, 1H), 7.11 (d, J=8.3 Hz, 1H), 7.41 (d, J=7.3 Hz, 1H), 7.48 (t, J=7.6 Hz, 2H), 7.64 (d, J=7.3 Hz, 2H), 7.74 (d, J=8.3 Hz, 2H), 8.09 (d, J=8.3 Hz, 2H). MS (ES) m/e 583 (M+1).

Example 655

3-{4-[2-(2-Biphenyl-3-yl-5-methyloxazol-4-yl)ethoxy]-2-cyclohexylcarbamoyloxymethylphenyl}propionic acid tert-butyl ester MS (ES) m/e 639 (M+1)

Example 656

3-{4-[2-(2-Biphenyl-3-yl-5-methyloxazol-4-yl)ethoxy]-2-cyclohexylcarbamoyloxymethylphenyl}propionic acid $^1$H NMR (400 MHz, CDCl$_3$) δ1.26-1.41 (m, 3H), 1.44-1.56 (m, 2H), 1.75 (br s, 1H), 1.84-1.88 (m, 2H), 2.08-2.10 (m, 2H), 2.63 (s, 3H), 2.80 (t, J=7.8 Hz, 2H), 3.12 (t, J=7.9 Hz, 2H), 3.27 (t, J=6.1 Hz, 2H), 3.66 (br s, 4.42 (t, J=6.1 Hz, 2H), 4.97 (br s, 1H), 5.27 (s, 2H), 7.04 (d, J=6.4 Hz, 1H), 7.08 (d, J=2.4 Hz, 1H), 7.30 (d, J=8.3 Hz, 1H), 7.55-7.76 (m, 4H), 7.85-7.86 (m, 2H), 7.92 (d, J=7.8 Hz, 1H), 8.15 (d, J=7.8 Hz, 1H), 8.44 (d, J=1.5 Hz, 1H). MS (ES) m/e 583 (M+1).

Example 657

3-{2-Cyclohexylcarbamoyloxymethyl-4-[2-(5-methyl-2-morpholin-4-ylthiazol-4-yl)ethoxy]phenyl}propionic acid tert-butyl ester MS (ES) m/e 588 (M+1)

Example 658

3-{2-Cyclohexylcarbamoyloxymethyl-4-[2-(5-methyl-2-morpholin-4-ylthiazol-4-yl)ethoxy]phenyl}propionic acid

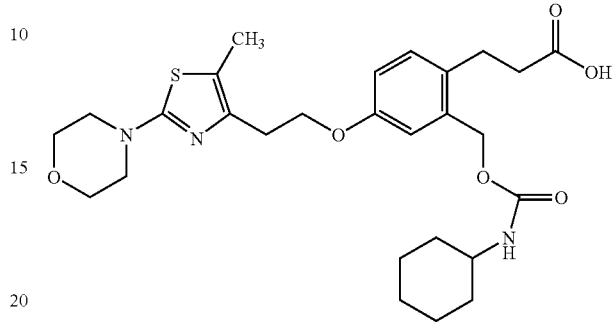

$^1$H NMR (400 MHz, CDCl$_3$) δ1.11-1.37 (m, 5H), 1.57-1.61 (m, 1H), 1.68-1.72 (m, 2H), 1.90-1.93 (m, 2H), 2.29 (s, 3H), 2.58 (t, J=7.8 Hz, 2H), 2.90 (t, J=7.6 Hz, 2H), 3.06 (t, J=5.1 Hz, 2H), 3.47-3.50 (m, 1H), 3.66 (t, J=4.6 Hz, 4H), 3.85 (t, J=4.9 Hz, 4H), 4.20 (t, J=5.4 Hz, 2H), 5.06 (s, 2H), 6.74 (d, J=8.3 Hz, 1H), 6.86 (s, 1H), 7.08 (d, J=8.3 Hz, 1H). MS (ES) m/e 532 (M+1).

Example 659

3-(2-Cyclohexylcarbamoyloxymethyl-4-{2-[5-methyl-2-(4-phenoxyphenyl)oxazol-4-yl]ethoxy}phenyl)propionic acid tert-butyl ester MS (ES) m/e 655 (M+1)

Example 660

3-(2-Cyclohexylcarbamoyloxymethyl-4-{2-[5-methyl-2-(4-phenoxyphenyl)oxazol-4-yl]ethoxy}phenyl)propionic acid

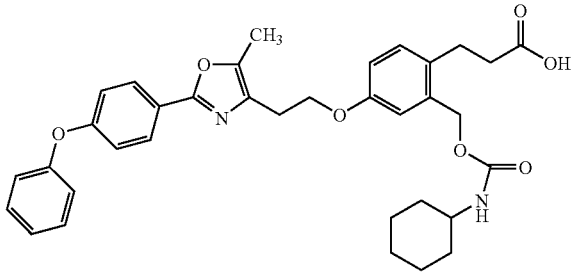

$^1$H NMR (400 MHz, CDCl$_3$) δ1.15-1.24 (m, 3H), 1.26-1.34 (m, 2H), 1.57 (br s, 1H), 1.67-1.70 (m, 2H), 1.90 (br s, 2H), 2.43 (s, 3H), 2.61 (t, 7.6 Hz, 2H), 2.93 (t, J=7.3 Hz, 2H), 3.08 (t, J=5.6 Hz, 2H), 3.47-3.52 (m, 1H), 4.22 (t, J=5.6 Hz, 1H), 4.84 (br s, 1H, 1H), 6.79 (d, 2.4 Hz, 1H), 6.88 (d, J=2.4 Hz, 1H), 7.00-7.12 (m, 5H), 7.21 (t, J=7.6 Hz, 1H), 7.41 (t, J=7.8 Hz, 2H), 7.99 (d, 8.8 Hz, 2H). MS (ES) m/e 599 (M+1).

Example 661

3-(4-{2-[2-(4-Bromophenyl)-5-methyloxazol-4-yl]ethoxy}-2-cyclohexylcarbamoyloxymethylphenyl)propionic acid tert-butyl ester

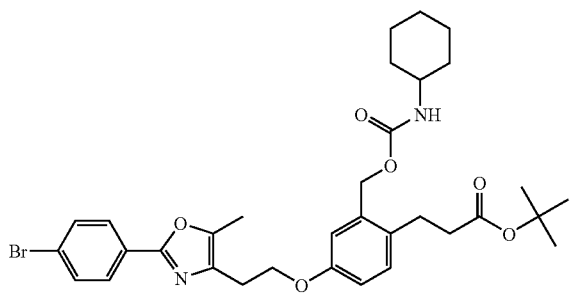

MS (ES) m/e 641 (M+1).

Example 662

3-(2-Cyclohexylcarbamoyloxymethyl-4-{2-[5-methyl-2-(4-morpholin-4-ylphenyl)oxazol-4-yl]ethoxy}phenyl)propionic acid

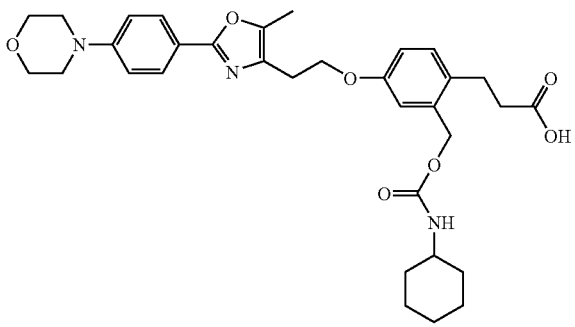

Step A: 3-(2-Cyclohexylcarbamoyloxymethyl-4-{2-[5-methyl-2-(4-morpholin-4-ylphenyl)oxazol-4-yl]ethoxy}phenyl)propionic acid tert-butyl ester

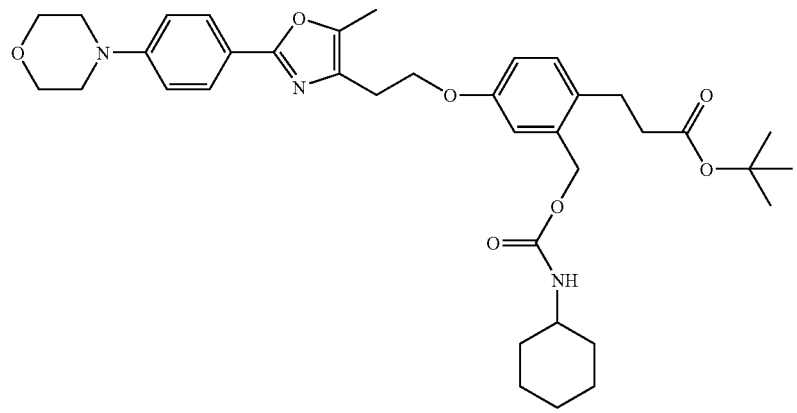

A 1 mL microvial under a nitrogen atmosphere was charged with 3-(4-{2-[2-(4-bromophenyl)-5-methyloxazol-4-yl]ethoxy}-2-cyclohexylcarbamoyloxymethylphenyl)propionic acid tert-butyl ester (0.30 g, 0.468 mmol; Example 39), anhydrous toluene (0.5 mL), and then morpholine (0.053 mL, 0.61 mmol). Tris(dibenzylideneacetone)-dipalladium(0) (0.004 g, 0.0044 mmol), 2-(di-tert-butylphosphine)biphenyl (0.006 g, 0.020 mmol), and sodium tert-butoxide (0.063 g, 0.655 mmol) were added sequentially. The mixture was stirred at ambient temperature under a nitrogen atmosphere for 5 h and was poured into EtOAc (50 mL). The organic layer was washed with brine (2×), dried (Na$_2$SO$_4$), and concentrated to a dark yellow oil. This crude product was purified using radial chromatography (EtOAc:hexanes 15:85 to 50:50) to give a yellow oil (0.058 g, 19%). $^1$H NMR (400 MHz, CDCl$_3$) δ1.07-1.18 (m, 3H), 1.29-1.40 (m, 1H), 1.42 (s, 9H), 1.52-1.70 (m, 4H), 1.91-1.93 (m, 2H), 2.34 (s, 3H), 2.46 (t, J=8.1 Hz, 2H), 2.87 (t, J=7.8 Hz, 2H), 2.94 (t, J=6.8 Hz, 2H), 3.24 (t, J=4.9 Hz, 4H), 3.48-3.50 (m, 1H), 3.86 (t, J=4.9 Hz, 4H), 4.20 (t, J=6.6 Hz, 2H), 5.07 (s, 2H), 6.79 (dd, J=8.6, 2.7 Hz, 1H), 6.85-6.93 (m, 3H), 7.09 (d, J=8.3 Hz, 1H), 7.87 (dd, J=11.5, 2.7 Hz, 2H). MS (ES) m/e 648 (M+1).

Step B: 3-(2-Cyclohexylcarbamoyloxymethyl-4-{2-[5-methyl-2-(4-morpholin-4-ylphenyl)oxazol-4-yl]ethoxy}phenyl)propionic acid A 15 mL round bottomed flask was charged with 3-(2-cyclohexylcarbamoyloxymethyl-4-{2-[5-methyl-2-(4-morpholin-4-ylphenyl)oxazol-4-yl]ethoxy}phenyl)propionic acid (0.058 g, 0.09 mmol) and CH$_2$Cl$_2$ (1 mL). Trifluoroacetic acid (0.5 mL) was added, and the solution was stirred at ambient temperature under a nitrogen atmosphere for 1.5 h. The mixture was concentrated to give a yellow solid (0.052 g, 98%). $^1$H NMR (400 MHz, CDCl$_3$) δ1.03-1.11 (m, 3H), 1.18-1.30 (m, 2H), 1.45-1.50 (m, 1H), 1.60-1.63 (m, 2H), 1.82-1.85 (m, 2H), 2.38 (s, 3H), 2.52 (t, J=7.6 Hz, 2H), 2.84 (t, J=7.6 Hz, 2H), 3.04 (t, J=5.6 Hz, 2H), 3.30 (t, J=4.9 Hz, 4H), 3.39 (br s, 1H), 3.80 (t, J=4.9 Hz, 4H), 4.17 (t, J=5.9 Hz, 2H), 4.86 (br s, 1H), 4.99 (s, 2H), 6.70 (d, J=8.3 Hz, 1H), 6.81 (d, J=2.4 Hz, 1H), 7.03 (d, J=8.3 Hz, 1H), 7.90 (d, J=9.3 Hz, 2H). MS (ES) m/e 592 (M+1).

The following Examples 663 to 664 are prepared by following a substantially similar procedure as described in Example 662.

Example 663

3-(2-Cyclohexylcarbamoyloxymethyl-4-{2-[5-methyl-2-(4-phenylaminophenyl)oxazol-4-yl]ethoxy}phenyl)propionic acid

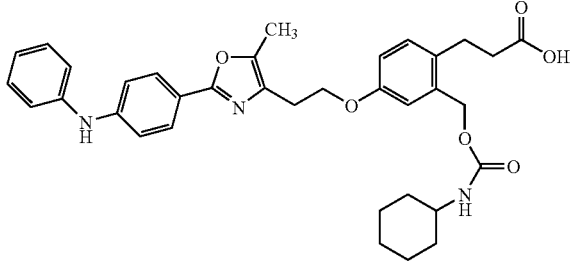

$^1$H NMR (400 MHz, CDCl$_3$) δ1.11-1.42 (m, 5H), 1.56 (br s, 1H), 1.66-1.69 (m, 2H), 1.89-1.92 (m, 2H), 2.38 (s, 3H), 2.60 (t, J=7 Hz, 2H), 2.91 (t, J=7 Hz, 2H), 3.03 (t, J=5.6 Hz, 2H), 4.22 (t, J=6.1 Hz, 2H), 4.86 (br s, 1H), 5.06 (s, 2H), 6.78 (d, J=7.8 Hz, 1H), 6.89 (s, 1H), 7.04-7.10 (m, 4H), 7.16 (d, J=7.8 Hz, 2H), 7.34 (t, J=7.8 Hz, 2H), 7.88 (d, J=8.3 Hz, 2H). MS (ES) m/e 598 (M+1).

Example 664

3-[2-Cyclohexylcarbamoyloxymethyl-4-(2-{5-methyl-2-[4-(methylphenylamino)phenyl]oxazol-4-yl}ethoxy)phenyl]propionic acid

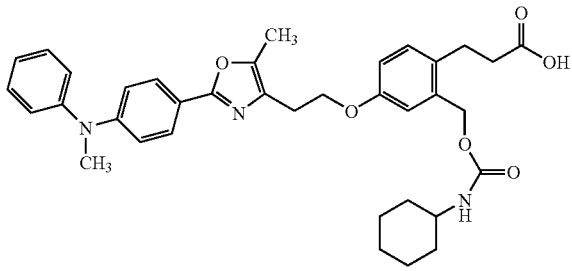

$^1$H NMR (400 MHz, CDCl$_3$) δ1.02-1.35 (m, 5H), 1.56(br s, 1H), 1.67-1.70 (m, 2H), 1.89 (br s, 2H), 2.41 (s, 3H), 2.60 (t, J=7 Hz, 2H), 2.91 (t, J=7 Hz, 2H), 3.09 (t, J=7 Hz, 2H), 3.39 (s, 3H), 3.47 (br s, 1H), 4.24 (t, J=7 Hz, 2H), 4.95 (br s, 1H), 5.06 (s, 2H), 6.81 (d, J=8.3 Hz, 2H), 6.89 (s, 1H), 7.09 (d, J=7.8 Hz, 1H), 7.23 (t, J=7.6 Hz, 3H), 7.43 (t, J=7.8 Hz, 3H), 7.87 (d, J=8.8 Hz, 2H). MS (ES) m/e 612 (M+1).

Example 665

3-{2-Methoxymethyl-4-[2-(5-methyl-2-phenyloxazol-4-yl)ethoxy]phenyl}propionic acid

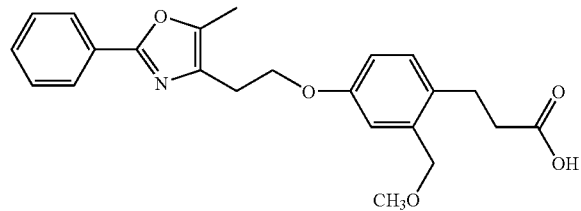

Step A: 3-{2-Methoxymethyl-4-[2-(5-methyl-2-phenyloxazol-4-yl)ethoxy]phenyl}propionic acid tert-butyl ester

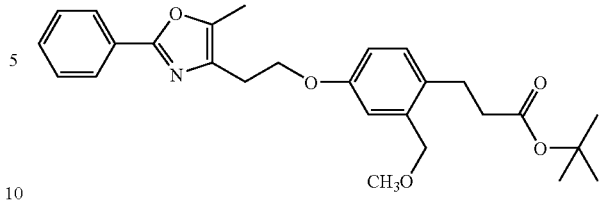

A 15 mL round bottomed flask was charged with 3-{2-hydroxymethyl-4-[2-(5-methyl-2-phenyloxazol-4-yl)ethoxy]phenyl}propionic acid tert-butyl ester (0.10 g, 0.23 mmol) and methyl iodide (0.21 mL, 2.3 mmol) in anhydrous DMF (1 mL) under a nitrogen atmosphere. The mixture was cooled in an ice bath and treated in one portion with NaH (0.018 g, 0.25 mmol, 60% oil dispersion). The reaction mixture was stirred for 2 h, concentrated, and diluted with EtOAc (40 mL). The organic layer was washed with brine (2×), dried (Na$_2$SO$_4$), and concentrated. The crude product was purified using radial chromatography (EtOAc:hexanes 10:90 to 25:75) to give a yellow oil (0.060 g, 58%). MS (ES) m/e 648 (M+1).

Step B: 3-{2-Methoxymethyl-4-[2-(5-methyl-2-phenyloxazol-4-yl)ethoxy]phenyl}propionic acid A 15 mL round bottomed flask was charged 3-{2-methoxymethyl-4-[2-(5-methyl-2-phenyloxazol-4-yl)ethoxy]phenyl}propionic acid tert-butyl ester (0.060 g, 0.13 mmol), CH$_2$Cl$_2$ (1.2 mL), and then trifluoroacetic acid (0.6 mL). The solution was stirred at ambient temperature under a nitrogen atmosphere for 16 h and was concentrated. The residue was diluted with CH$_2$Cl$_2$ (30 mL) and washed with brine. The organic layer was dried (Na$_2$SO$_4$), filtered, and concentrated to give a white solid (0.046 g, 89%). MS (ES) m/e 648 (M+1).

The following Examples 666 to 673 are prepared by following a substantially similar procedure as described in Example 665.

Example 666

3-{2-Benzyloxymethyl-4-[2-(5-methyl-2-phenyloxazol-4-yl)ethoxy]phenyl}propionic acid tert-butyl ester MS (ES) m/e 528 (M+1)

Example 667

3-{2-Benzyloxymethyl-4-[2-(5-methyl-2-phenyloxazol-4-yl)ethoxy]phenyl}propionic acid

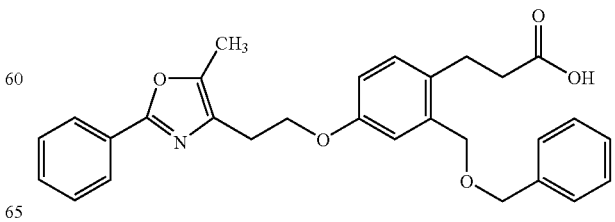

MS (ES) m/e 472 (M+1).

Example 668

3-{2-Ethoxymethyl-4-[2-(5-methyl-2-phenyloxazol-4-yl)ethoxy]phenyl}propionic acid tert-butyl ester MS (ES) m/e 466 (M+1)

Example 669

3-{2-Ethoxymethyl-4-[2-(5-methyl-2-phenyloxazol-4-yl)ethoxy]phenyl}propionic acid

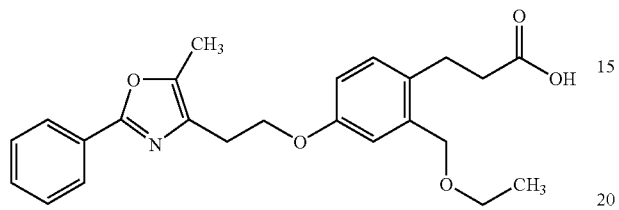

MS (ES) m/e 410 (M+1).

Example 670

3-{2-(4-tert-Butyl-benzyloxymethyl)-4-[2-(5-methyl-2-phenyloxazol-4-yl)ethoxy]phenyl}propionic acid tert-butyl ester MS (ES) m/e 584 (M+1)

Example 671

3-{2-(4-tert-Butyl-benzyloxymethyl)-4-[2-(5-methyl-2-phenyloxazol-4-yl)ethoxy]phenyl}propionic acid

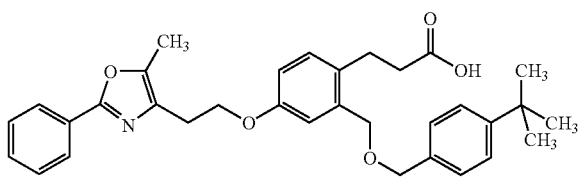

MS (ES) m/e 410 (M+1).

Example 672

3-{2-(Biphenyl-4-ylmethoxymethyl)-4-[2-(5-methyl-2-phenyloxazol-4-yl)ethoxy]phenyl}propionic acid tert-butyl ester MS (ES) m/e 604 (M+1)

Example 673

3-{2-(Biphenyl-4-ylmethoxymethyl)-4-[2-(5-methyl-2-phenyloxazol-4-yl)ethoxy)phenyl}propionic acid

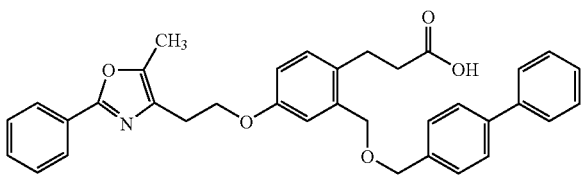

MS (ES) m/e 410 (M+1).

Example 674

3-{2-sec-Butoxymethyl-4-[2-(5-methyl-2-phenyloxazol-4-yl)ethoxy]phenyl}propionic acid

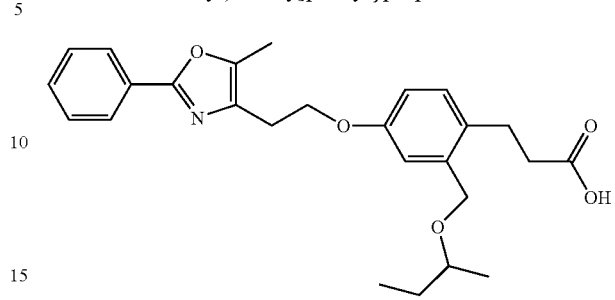

Step A: 3-{2-Bromomethyl-4-[2-(5-methyl-2-phenyloxazol-4-yl)ethoxy]phenyl}propionic acid tert-butyl ester

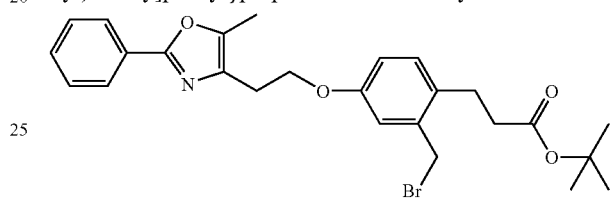

A 100 mL round bottomed flask was charged with 3-{2-hydroxymethyl-4-[2-(5-methyl-2-phenyloxazol-4-yl)ethoxy]phenyl}propionic acid tert-butyl ester (1.0 g, 2.29 mmol), anhydrous THF (25 mL), and then triphenylphosphine (1.20 g, 4.57 mmol) and CBr$_4$ (1.52 g, 4.57 mmol). The yellow mixture was stirred at ambient temperature under a nitrogen atmosphere for 1 h and was poured into EtOAc (100 mL). The organic layer was washed with brine, dried (Na$_2$SO$_4$), and concentrated. The crude product was purified using radial chromatography (EtOAc:hexanes 15:85 to 25:75) to give a colorless oil (0.95 g, 83%). MS (ES) m/e 501 (M+1).

Step B: 3-{2-sec-Butoxymethyl]4-[2-(5-methyl-2-phenyloxazol-4-yl)ethoxy]phenyl}propionic acid A flame-dried 15 mL round bottomed flask was charged with 2-butanol (0.92 mL, 1.0 mmol), anhydrous DMF (1 mL), and then NaH (0.013 g, 0.2 mmol, 60% oil dispersion). The reaction mixture was cooled in an ice bath for 15 min, and 3-{2-bromomethyl-4-[2-(5-methyl-2-phenyloxazol-4-yl)ethoxy]phenyl}propionic acid tert-butyl ester ((0.050 g, 0.10 mmol) in anhydrous DMF (0.5 mL) was added. The reaction mixture was stirred under a nitrogen atmosphere for 2 h. A product mixture of free acid and tert-butyl ester formed. The reaction was poured into EtOAc (40 mL), washed with brine (3×), dried (Na$_2$SO$_4$), and concentrated. The crude oil was then dissolved directly in CH$_2$Cl$_2$ (1 mL) and treated with TFA (1.5 mL). The solution was stirred at ambient temperature for 16 h and concentrated. The crude product residue was purified using radial chromatography (EtOAc:hexanes 15:85 to 1:1) to give a yellow oil (0.012 g, 27%). MS (ES) m/e 438 (M+1).

The following Examples 675 to 680 are prepared by following a substantially similar procedure as described in Example 674.

Example 675

3-{2-Isopropoxymethyl-4-[2-(5-methyl-2-phenyloxazol-4-yl)ethoxy]-phenyl}propionic acid

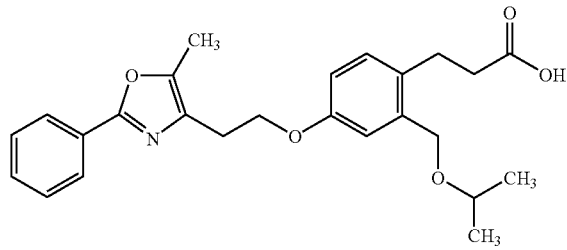

MS (ES) m/e 424 (M+1).

Example 676

3-{2-Cyclohexyloxymethyl-4-[2-(5-methyl-2-phenyloxazol-4-yl)ethoxy]phenyl}propionic acid

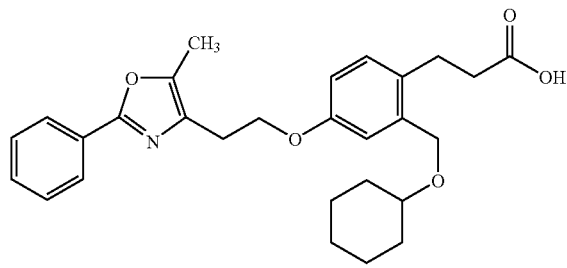

MS (ES) m/e 464 (M+1).

Example 677

3-{2-Isobutoxymethyl-4-[2-(5-methyl-2-phenyloxazol-4-yl)ethoxy]phenyl}propionic acid

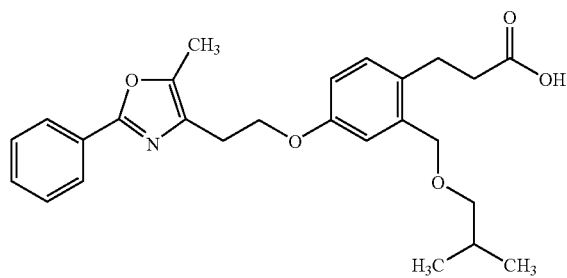

MS (ES) m/e 438 (M+1).

Example 678

3-{2-Cyclohexylmethoxymethyl-4-[2-(5-methyl-2-phenyloxazol-4-yl)ethoxy]phenyl}propionic acid

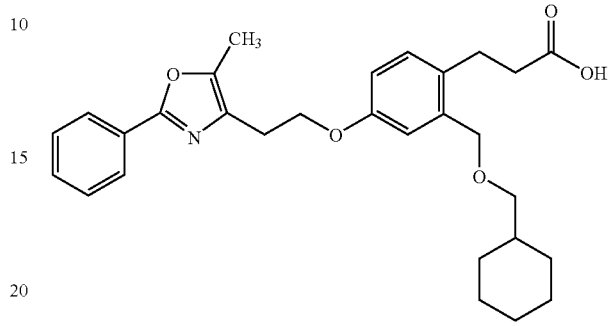

MS (ES) m/e 478 (M+1).

Example 679

3-{2-(Biphenyl-4-yloxymethyl)-4-[2-(5-methyl-2-phenyloxazol-4-yl)ethoxy]phenyl}propionic acid

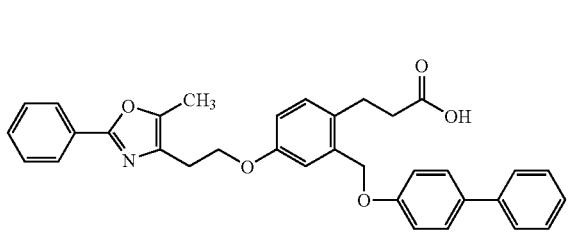

MS (ES) m/e 534 (M+1).

Example 680

3-{2-(3-Methylbutoxymethyl)-4-[2-(5-methyl-2-phenyloxazol-4-yl)ethoxy]phenyl}propionic acid

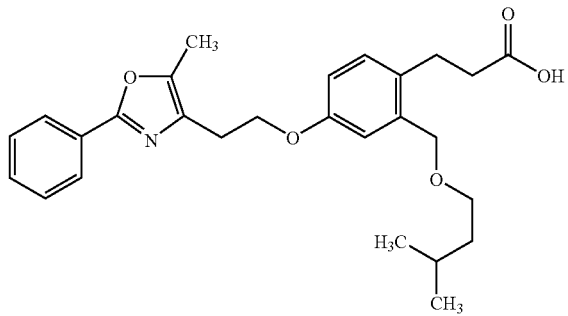

MS (ES) m/e 452 (M+1).

Example 681

3-[4-[2-(5-Methyl-2-phenyloxazol-4-yl)ethoxy]-2-(4-trifluoromethylphenoxymethyl)-phenyl]propionic acid

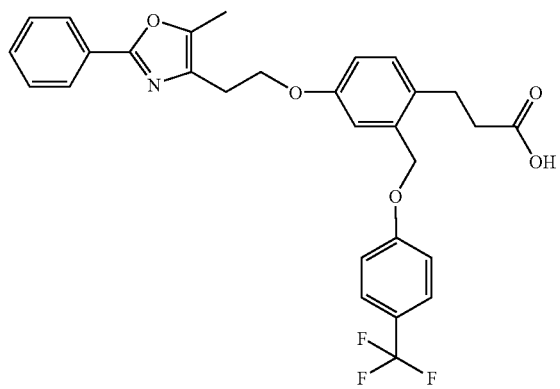

General procedure for parallel synthesis using the Dyna-Vac Carousel apparatus. A 50 mL glass tube with screw cap and nitrogen inlet was charged with 3-{2-bromomethyl-4-[2-(5-methyl-2-phenyloxazol-4-yl)ethoxy]phenyl}propionic acid tert-butyl ester (0.040 g, 0.080 mmol), 4-trifluoromethylphenol (0.019 g 0.12 mmol), anhydrous DMF (0.5 mL), and then cesium carbonate (0.039 g, 0.12 mmol). The mixture was stirred at ambient temperature for 16 h. MS analysis of the reaction indicated formation of the intermediate ester product [MS (ES) m/e 582 (M+1)]. The reaction mixture was poured into ether (30 mL). The organic layer was washed with brine (2×), dried (Na$_2$SO$_4$), and concentrated. The residue was diluted with CH$_2$Cl$_2$ (1 mL) and trifluroacetic acid (0.25 mL) was added. The mixture was stirred at ambient temperature for 1.5 h and was concentrated. The crude product mixture was purified by mass-directed reverse phase HPLC to provide the title compound (0.045 g, 64%). MS (ES) m/e 526 (M+1).

The following Examples 682 to 691 are prepared by following a substantially similar procedure as described in Example 681.

Example 682

3-{2-(4-Fluorophenoxymethyl)-4-[2-(5-methyl-2-phenyloxazol-4-yl)ethoxy]phenyl}propionic acid

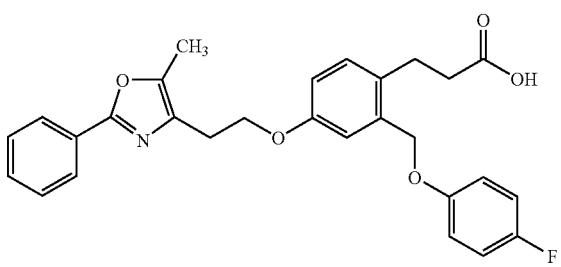

MS (ES) m/e 476 (M+1).

Example 683

3-{2-(3-Fluorophenoxymethyl)-4-[2-(5-methyl-2-phenyloxazol-4-yl)ethoxy]phenyl}propionic acid

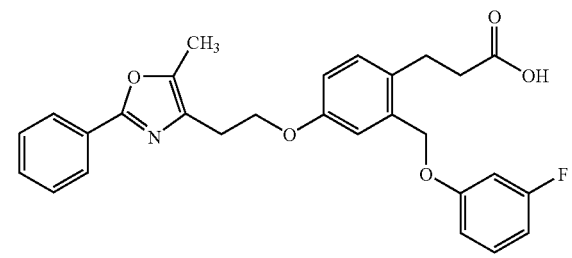

MS (ES) m/e 476 (M+1).

Example 684

3-{2-(2-Fluorophenoxymethyl)-4-[2-(5-methyl-2-phenyloxazol-4-yl)ethoxy]phenyl}propionic acid

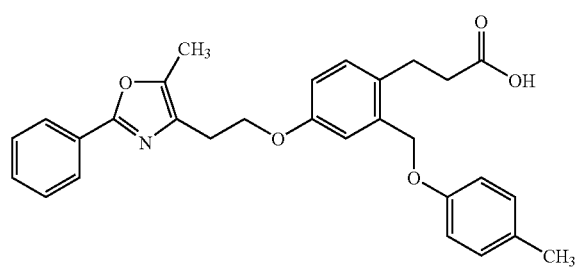

MS (ES) m/e 476 (M+1).

Example 685

3-{4-[2-(5-Methyl-2-phenyloxazol-4-yl)ethoxy]-2-p-tolyloxymethylphenyl}propionic acid MS (ES) m/e 472 (M+1).

Example 686

3-{4-[2-(5-Methyl-2-phenyloxazol-4-yl)ethoxy]-2-m-tolyloxymethylphenyl}propionic acid

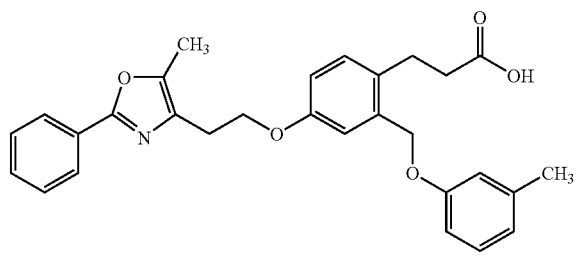

MS (ES) m/e 472 (M+1).

Example 687

3-{4-[2-(5-Methyl-2-phenyloxazol-4-yl)ethoxy]-2-o-tolyloxymethylphenyl}propionic acid

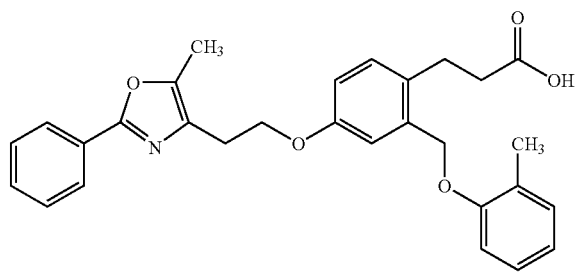

MS (ES) m/e 472 (M+1).

Example 688

3-{2-(4-Methoxyphenoxymethyl)-4-[2-(5-methyl-2-phenyloxazol-4-yl)ethoxy]phenyl}propionic acid

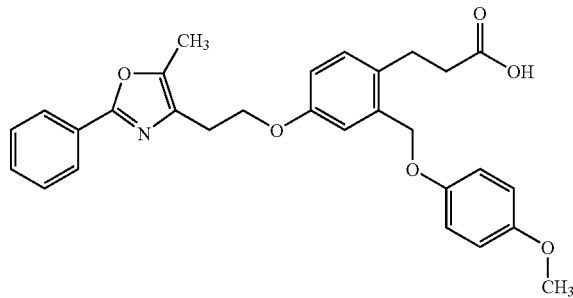

MS (ES) m/e 488 (M+1).

Example 689

3-{2-(Biphenyl-2-yloxymethyl)-4-[2-(5-methyl-2-phenyloxazol-4-yl)ethoxy]phenyl}propionic acid

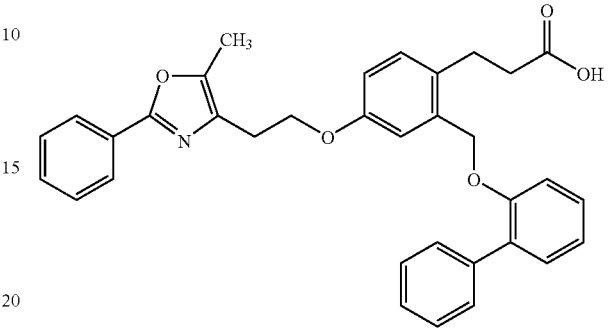

MS (ES) m/e 534 (M+1).

Example 690

3-{4-[2-(5-Methyl-2-phenyloxazol-4-yl)ethoxy]-2-phenylsulfanylmethylphenyl}propionic acid

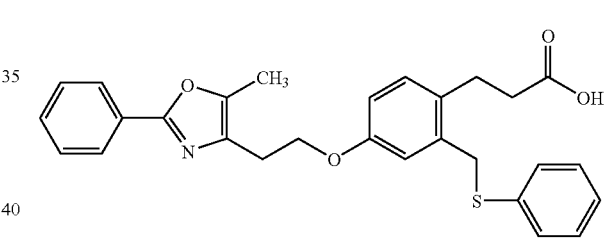

MS (ES) m/e 474 (M+1).

Example 691

3-{2-Benzenesulfonylmethyl-4-[2-(5-methyl-2-phenyloxazol-4-yl)ethoxy]phenyl}propionic acid

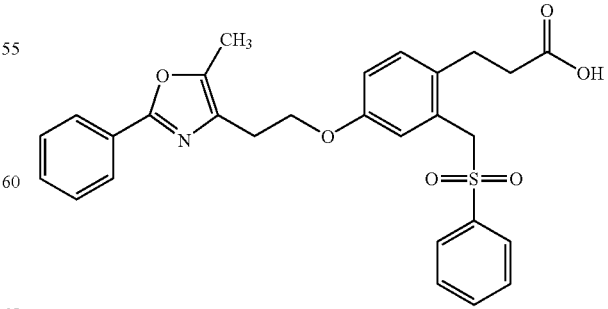

MS (ES) m/e 506 (M+1).

Example 692

3-[4-[2-(2-Biphenyl-4-yl-5-methyloxazol-4-yl)ethoxy]-2-(4-trifluoromethylphenoxy-methyl)-phenyl]-propionic acid

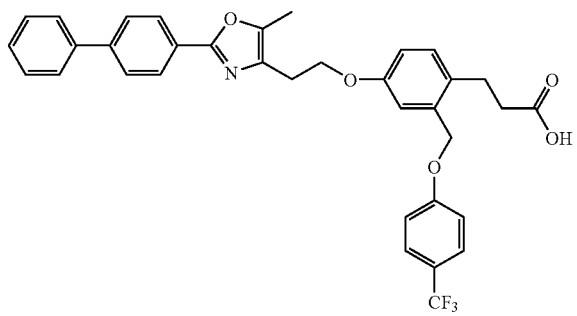

Step A: 3-[2-Bromomethyl-4-(tert-butyldiphenylsilanyloxy)phenyl]propionic acid tert-butyl ester

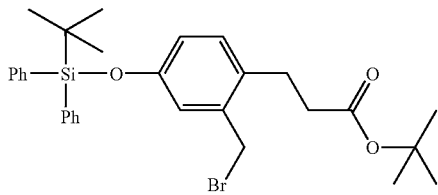

A 200 mL round bottomed flask was charged with 3-[4-(tert-butyldiphenylsilanyloxy)-2-hydroxymethylphenyl]propionic acid tert-butyl ester (3.03 g, 6.18 mmol), anhydrous THF (75 mL), and then triphenylphosphine (3.24 g, 12.4 mmol) and CBr₄ (4.10 g, 12.4 mmol). The yellow mixture was stirred at ambient temperature under a nitrogen atmosphere for 1 h and was concentrated. The residue was diluted with EtOAc (500 mL). The organic layer was washed with brine (2×), dried (Na₂SO₄), and concentrated to a solid. The crude product was purified using a Biotage medium pressure chromatography system (EtOAc:hexanes 10:90) to give a yellow oil (2.95 g, 86%), MS (ES) m/e 572 (M+NH₄).

Step B: 3-[4-(tert-Butyldiphenylsilanyloxy)-2-(4-trifluoromethylphenoxymethyl)phenyl]-propionic acid tert-butyl ester

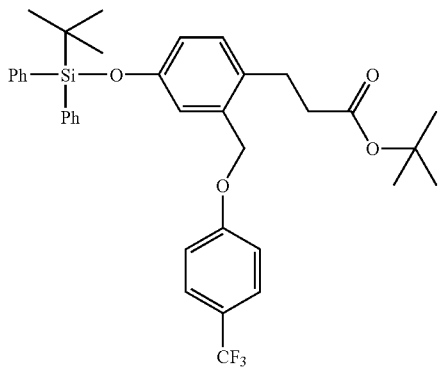

A 50 mL round bottomed flask was charged with 3-[2-bromomethyl-4-(tert-butyldiphenylsilanyloxy)phenyl]propionic acid tert-butyl ester (1.0 g, 1.81 mmol), anhydrous DMF (10 mL), and then 4-trifluoromethylphenol (0.44 g, 2.7 mmol) and cesium carbonate (0.88 g, 2.7 mmol). The reaction mixture was stirred at ambient temperature under a nitrogen atmosphere for 18 h and concentrated. The residue was diluted with EtOAc (100 mL). The organic layer was washed with brine (2×), dried (Na₂SO₄), and concentrated to a yellow oil. The crude residue was purified using radial (EtOAc:hexanes 15:85 to 50:50) to give a yellow oil (0.66 g, 58%). MS (ES) m/e 635 (M+1).

Step C: 3-[4-Hydroxy-2-(4-trifluoromethylphenoxymethyl)phenyl]propionic acid tert-butyl ester

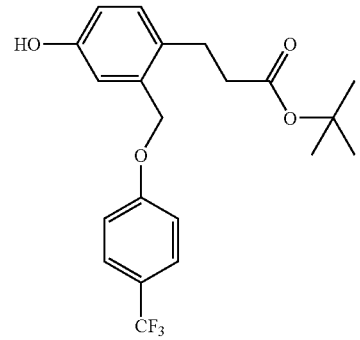

A 100 mL round bottomed flask was charged with 3-[4-(tert-butyldiphenylsilanyloxy)-2-(4-trifluoromethylphenoxymethyl)phenyl]propionic acid tert-butyl ester (0.65 g, 1.02 mmol), anhydrous THF (40 mL), and then tetrabutylammonium fluoride (3.1 mL, 3.1 mmol, 1.0 M in THF). The reaction was stirred under a nitrogen atmosphere for 1.5 h and was concentrated. The residue was diluted with EtOAc (100 mL). The organic layer was washed with brine (2×), dried (Na₂SO₄), and concentrated to an orange oil. The crude oil was purified using radial chromatography (EtOAc:hexanes 15:85) to give a white solid (0.31 g, 77%). MS (ES) m/e 395 (M−1).

Step D: 3-[4-[2-(2-Biphenyl-4-yl-5-methyloxazol-4-yl)ethoxy]-2-(4-trifluoromethylphenoxy-methyl)-phenyl]-propionic acid General procedure for parallel synthesis using, the Dyna-Vac Carousel apparatus: A 50 mL glass tube with screw cap and nitrogen inlet was charged with 3-[4-hydroxy-2-(4-trifluoromethylphenoxymethyl)phenyl]propionic acid tert-butyl ester (0.050 g, 0.146 mmol), toluene-4-sulfonic acid 2-(2-biphenyl-4-yl-5-methyloxazol-4-yl)ethyl ester (0.078 g, 0.18 mmol), anhydrous DMF (0.5 mL), and then cesium carbonate (0.072 g, 0.22 mmol). The mixture was stirred at ambient temperature for 16 h. MS analysis of the reaction indicated formation of the ester intermediate MS (ES) m/e 658 (M+1). The reaction mixture was poured into ether (30 mL). The organic layer was washed with brine (2×), dried (Na₂SO₄), and concentrated. The crude residue was diluted with CH₂Cl₂ (2 mL) and then trifluoroacetic acid (1 mL). The mixture was stirred at ambient temperature for 2 h and concentrated under a stream of N₂. The crude product was purified by mass-directed reverse phase HPLC to provide the title compound (0.053 g, 71%). ¹H NMR (250 MHz, CDCl₃) δ2.41 (s, 3H), 2.70 (t, J=7.7 Hz, 2H), 2.95-3.05 (m, 4H), 4.28 (t, J=6.6 Hz, 2H), 5.09 (s, 2H), 6.90 (dd, J=8.5, 2.8 Hz, 1H), 7.01 (d, J=2.6 Hz, 1H), 7.06 (d, J=8.6 Hz, 2H), 7.21 (d, J=8.5 Hz, 1H), 7.41-7.72 (m, 9H), 8.07 (d, J=8.4 Hz, 2H). MS (ES) m/e 602 (M+1).

The following Examples 693 to 697 are prepared by following a substantially similar procedure as described in Example 692.

Example 693

3-[4-[2-(2-Cyclohexyl-5-methyloxazol-4-yl)ethoxy]-2-(4-trifluoromethylphenoxymethyl)phenyl]propionic acid

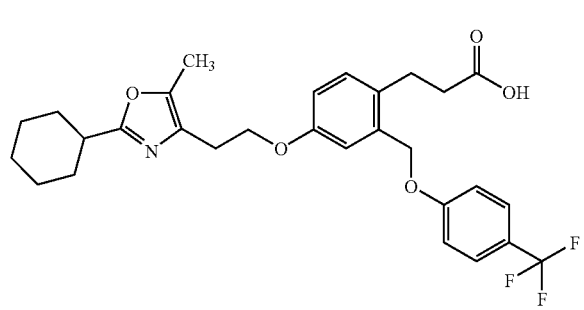

MS (ES) m/e 532 (M+1).

Example 694

3-[4-[2-(5-Methyl-2-morpholin-4-yl-thiazol-4-yl)ethoxy]-2-(4-trifluoromethylphenoxymethyl)phenyl]propionic acid

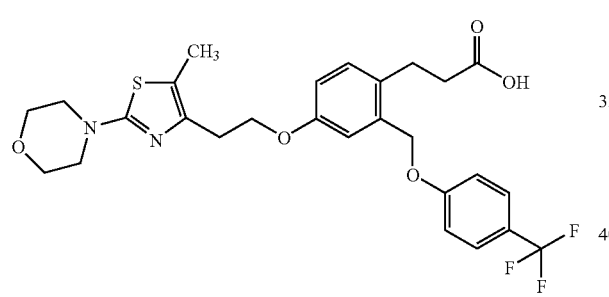

MS (ES) m/e 551 (M+1).

Example 695

3-[4-[2-(2-Biphenyl-3-yl-5-methyloxazol-4-yl)ethoxy]-2-(4-trifluoromethylphenoxymethyl)phenyl]propionic acid

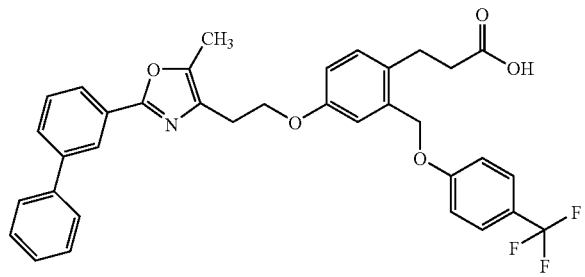

MS (ES) m/e 602 (M+1).

Example 696

3-[4-{2-[5-Methyl-2-(4-phenoxyphenyl)oxazol-4-yl]ethoxy}-2-(4-trifluoromethylphenoxymethyl)phenyl]propionic acid

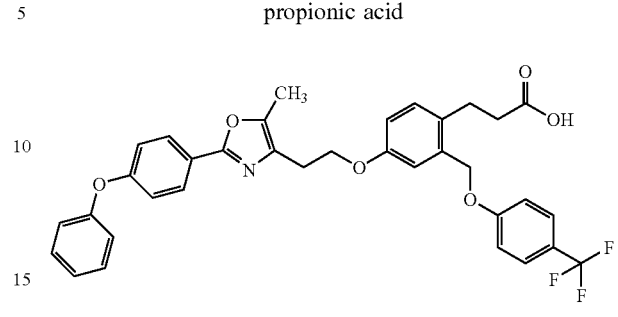

MS (ES) m/e 618 (M+1).

Example 697

3-[4-[4-Methyl-2-(4-trifluoromethylphenyl)thiazol-5-ylmethoxy]-2-(4-trifluoromethylphenoxymethyl)phenyl]propionic acid MS (ES) m/e 596 (M+1)

Example 698

3-{2-Benzyloxymethyl-4-[2-(2-cyclohexyl-5-methyl-oxazol-4-yl)-ethoxy]-phenyl}-propionic acid

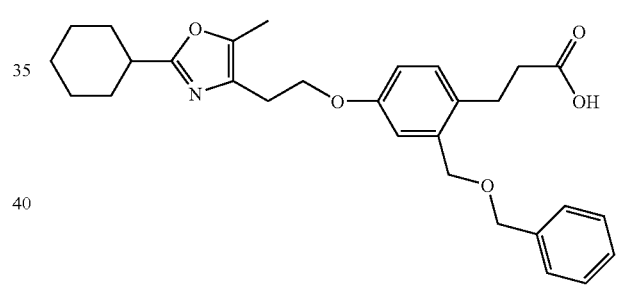

Step A: 3-[2-Benzyloxymethyl-4-(tert-butyl-diphenyl-silanyloxy)-phenyl]-propionic acid tert-butyl ester

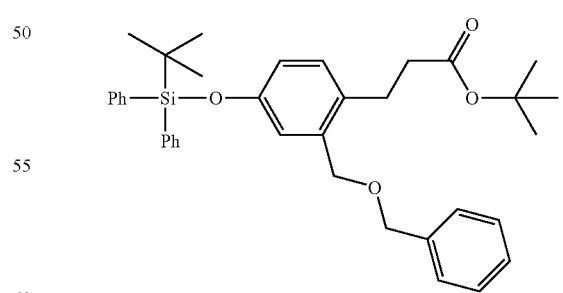

A 100 mL round bottomed flask was charged with 3-[4-(tert-butyldiphenylsilanyloxy)-2-hydroxymethylphenyl]propionic acid tert-butyl ester (1.52 g, 3.10 mmol), anhydrous DMF (15 mL), and then benzyl bromide (1.84 mL, 15.5 mmol) under a nitrogen atmosphere. The solution was cooled to −10° C., and NaH (0.124 g, 3.10 mmol, 60% oil dispersion) was added. The mixture was stirred for 5 h, and was poured into EtOAc (150 mL). The organic layer was washed with brine (2×), dried (Na$_2$SO$_4$), and concentrated to a brown oil. The crude oil was purified using radial chromatography (EtOAc:hexanes 2:98 to 5:95) to give a pale yellow oil (1.04 g, 58%). MS (ES) m/e 598 (M+NH$_4$).

Step B: 3-(2-Benzyloxymethyl-4-hydroxy-phenyl)-propionic acid tert-butyl ester

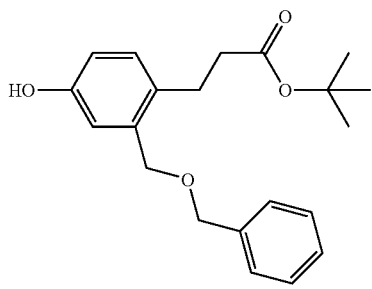

A 250 mL round bottomed flask was charged with 3-[2-benzyloxymethyl-4-(tert-butyl-diphenyl-silanyloxy)-phenyl]-propionic acid tert-butyl ester (1.03 g, 1.77 mmol), anhydrous THF (60 mL), and then tetrabutylammonium fluoride (5.3 mL, 5.3 mmol, 1.0 M in THF). The reaction mixture was stirred under a nitrogen atmosphere for 1 h, concentrated, and diluted with EtOAc (100 mL). The organic layer was washed with brine (2×), dried (Na$_2$SO$_4$), and concentrated to give an oil. The crude oil was purified using radial chromatography (EtOAc:hexanes 10:90 to 50:50) to give a white solid (0.52 g, 86%). MS (ES) m/e 343 (M−1).

Step C: 3-{2-Benzyloxymethyl-4-[2-(2-cyclohexyl-5-methyl-oxazol-4-yl)-ethoxy]-phenyl}-propionic acid General procedure for the parallel synthesis of analogs using the DynaVac Carousel apparatus: A 50 mL glass tube with screw cap and nitrogen inlet was charged with 3-(2-benzyloxymethyl-4-hydroxy-phenyl)-propionic acid tert-butyl ester (0.050 g, 0.146 mmol), toluene-4-sulfonic acid 2-(2-biphenyl-4-yl-5-methyloxazol-4-yl)ethyl ester (0.078 g, 0.18 mmol), anhydrous DMF (0.5 mL), and then cesium carbonate (0.072 g, 0.22 mmol). The mixture was stirred at ambient temperature for 16 h. MS analysis of the reaction indicated that the intermediate ester was formed, MS (ES) m/e 534 (M+1). The crude reaction was poured into ether (30 mL), and washed with brine (2×), dried (Na$_2$SO$_4$), and concentrated in vacuo. The crude residue was dissolved in CH$_2$Cl$_2$ (2 mL) and trifluoroacetic acid was added (1.0 mL). The reaction mixture was stirred at ambient temperature for 2 h and was concentrated under a stream of N$_2$. The crude product was purified by mass-directed reverse phase HPLC to provide 0.053 g (71%) of 3-{4-[2-(2-Cyclohexyl-5-methyloxazol-4-yl)ethoxy]-2-phenoxymethylphenyl}propionic acid. MS (ES) m/e 478 (M+1).

The following Examples 699 to 704 are prepared by following a substantially similar procedure as described in Example 698.

Example 699

3-{2-Benzyloxymethyl-4-[2-(5-methyl-2-morpholin-4-ylthiazol-4-yl)ethoxy]phenyl}propionic acid

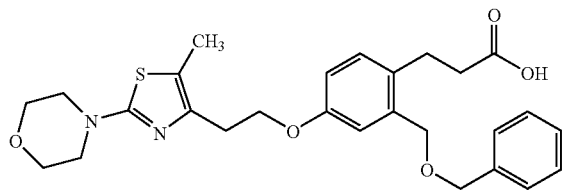

MS (ES) m/e 497 (M+1).

Example 670

3-{2-Benzyloxymethyl-4-[2-(2-biphenyl-4-yl-5-methyloxazol-4-yl)ethoxy]phenyl}propionic acid

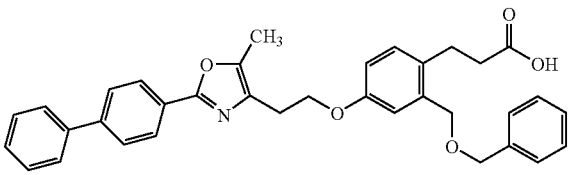

MS (ES) m/e 548 (M+1).

Example 671

3-{2-Benzyloxymethyl-4-[2-(2-biphenyl-3-yl-5-methyloxazol-4-yl)ethoxy]-phenyl}propionic acid

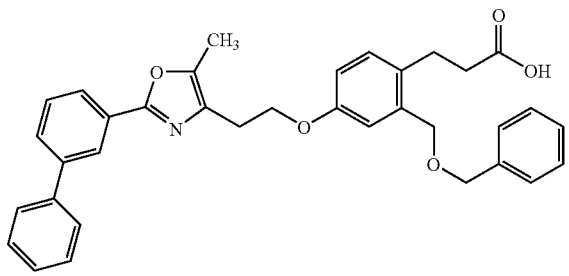

MS (ES) m/e 548 (M+1).

Example 672

3-(2-Benzyloxymethyl-4-{2-[5-methyl-2-(4-phenoxyphenyl)oxazol-4-yl]ethoxy}phenyl)propionic acid

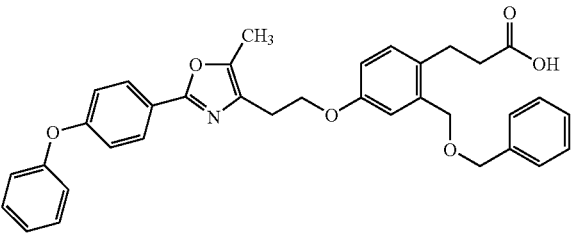

MS (ES) m/e 564 (M+1).

Example 673

3-(2-Benzyloxymethyl-4-{2-[2-(4-butoxyphenyl)-5-methyloxazol-4-yl]ethoxy}phenyl)propionic acid

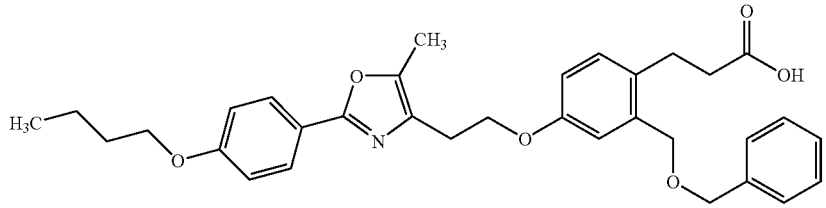

MS (ES) m/e 544 (M+1).

Example 674

3-(2-Benzyloxymethyl-4-{2-[5-methyl-2-(4-trifluoromethylphenyl)oxazol-4-yl]ethoxy}phenyl)propionic acid

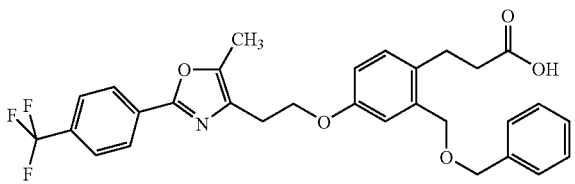

MS (ES) m/e 540 (M+1).

Example 705

3-{4-[3-(Biphenyl-4-yloxy)-propoxy]-2-cyclohexylcarbamoyloxymethyl-phenyl}-propionic acid

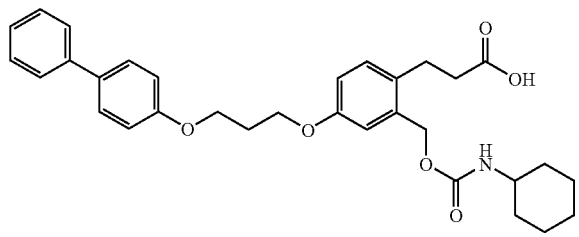

Step A: 3-{4-[3-(Biphenyl-4-yloxy)-propoxy]-2-cyclohexylcarbamoyloxymethyl-phenyl}-propionic acid tert-butyl ester

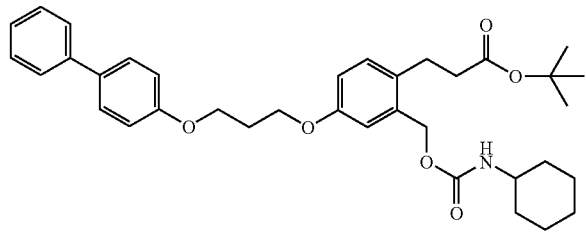

A mixture of 3-(2-cyclohexylcarbamoyloxymethyl-4-hydroxy-phenyl)-propionic acid tert-butyl ester (50 mg, 0.13 mmol; Example 652 Step D), 4-(3-bromo-propoxy)-biphenyl (58 mg, 0.2 mmol; Tetrahedron 1994, 50, 3427, and potassium carbonate (53 mg, 0.39 mmol) in acetonitrile (6 mL) was heated at 80° C. overnight. Ethyl acetate (20 mL) and H$_2$O (20 mL) were added. The organic layer was separated, and the aqueous layer was extracted with ethyl acetate (3×). The combined organic layers were dried (MgSO$_4$), filtered, and concentrated. The crude mixture was purified by silica gel column chromatography (hexane/ethyl acetate 4/1) to give the title compound (50 mg, 65%). $^1$H-NMR (300 MHz, CDCl$_3$): δ 7.54 (m, 4H), 7.42 (t, 2H, J=7.6), 7.32 (d, 1H, J=8.4), 7.12 (d, 1H, J=8.3), 6.99 (d, 2H, J=8.7), 6.93 (d, 1H, J=2.2), 6.82 (dd, 1H, J=8.4, 2.7), 5.09 (s, 2H), 4.74 (d, 1H, J=7.5), 4.18 (m, 4H), 3.56-3.42 (m, 1H), 2.90 (t, 2H, J=7.8), 2.48 (t, 2H, J=7.8), 2.28 (qn, 2H, J=6.0), 1.95-1.88 (m, 2H), 1.75-1.08 (m, 8H), 1.44 (s, 9H).

Step B: 3-{4-[3-(Biphenyl-4-yloxy)-propoxy]-2-cyclohexylcarbamoyloxymethyl-phenyl}-propionic acid Trifluoroacetic acid (0.032 mL, 0.42 mmol) was added to a solution of 3-{4-[3-(biphenyl-4-yloxy)-propoxy]-2-cyclohexylcarbamoyloxymethyl-phenyl}-propionic acid tert-butyl ester (50 mg, 0.085 mmol) in CH$_2$Cl$_2$ (5 mL) at room temperature. The reaction mixture was stirred overnight and concentrated under vacuum to give the title compound (41 mg, 90%). $^1$H-NMR (200 MHz, CDCl$_3$): δ 9.4 (br s, 1H), 7.58-7.49 (m, 4H), 7.42 (m, 2H), 7.32 (m, 1H), 7.13 (d, 1H, J=8.3), 7.00-6.93 (m, 3H), 6.84 (dd, 1H, J=7.8, 2.7), 5.11 (s, 2H), 4.76 (br s, 1H), 4.17 (m, 4H), 3.57-3.35 (m, 1H), 2.95 (t, 2H, J=7.8), 2.63 (t, 2H, J=7.8), 2.27 (qn, 2H, J=6.0), 1.99-1.05 (m, 10H).

Example 706

3-{4-[3-(4-Benzoyl-phenoxy)-propoxy]-2-cyclohexylcarbamoyloxymethyl-phenyl}-propionic acid

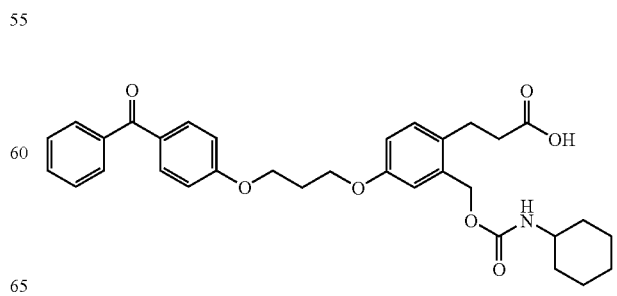

Step A: 3-{4-[3-(4-Benzoyl-phenoxy)-propoxy]-2-cyclo-hexylcarbamoyloxymethyl-phenyl}-propionic acid tert-butyl ester

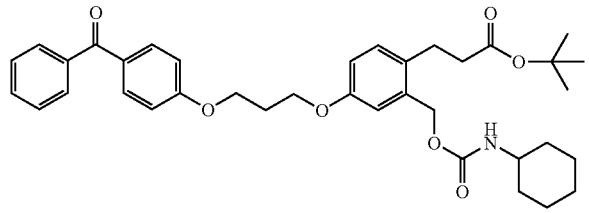

A mixture of 3-(2-cyclohexylcarbamoyloxymethyl-4-hydroxy-phenyl)-propionic acid tert-butyl ester (50 mg, 0.13 mmol; Example 652 Step D), [4-(3-bromo-propoxy)-phenyl]-phenyl-methanone (64 mg, 0.2 mmol, Bull Chem. Soc. Jpn. 1990, 63, 1342) and potassium carbonate (53 mg, 0.39 mmol) in acetonitrile (6 mL) was heated at 80° C. overnight. Ethyl acetate (20 mL) and H$_2$O (20 mL) were added. The organic layer was separated, and the aqueous layer was extracted with ethyl acetate (3×). The combined organic layers were dried (MgSO$_4$), filtered, and concentrated. The crude mixture was purified by silica gel column chromatography (hexane/ethyl acetate 4/1) to give the title compound (50 mg, 62%). $^1$H-NMR (300 MHz, CDCl$_3$): δ 7.74 (d, 2H, J=8.5), 7.68 (d, 2H, J=7.7), 7.48 (d, 1H, J=8.4), 7.40 (m, 2H), 7.05 (d, 1H, J=8.5), 6.90 (d, 2H, J=8.6), 6.85 (s, 1H), 6.74 (dd, 1H, J=8.5, 2.2), 5.04 (s, 2H), 4.68 (d, 1H, J=7.3), 4.17 (t, 2H, J=5.9), 4.09 (t, 2H, J=5.9), 3.43 (m, 1H), 2.82 (t, 2H, J=7.8), 2.40 (t, 2H, J=7.8), 2.21 (qn, 2H, J=5.9), 1.85 (m, 2H), 1.67-1.02 (m, 8H), 1.36 (s, 9H).

Step B: 3-{4-[3-(4-Benzoyl-phenoxy)-propoxy]-2-cyclo-hexylcarbamoyloxymethyl-phenyl}-propionic acid Trifluoroacetic acid (0.031 mL, 0.4 mmol) was added to a solution of 3-{4-[3-(4-benzoyl-phenoxy)-propoxy]-2-cyclohexylcarbamoyloxymethyl-phenyl}-propionic acid tert-butyl ester (50 mg, 0.08 mmol) in CH$_2$Cl$_2$ (5 mL) at room temperature. The reaction mixture was stirred overnight and concentrated under vacuum to give the title compound. (39 mg, 88%). $^1$H-NMR (200 MHz, CDCl$_3$): δ 7.83-7.72 (m, 4H), 7.57-7.43 (m, 3H), 7.12 (d, 1H, J=8.6), 6.98-82 (m, 4H), 5.10 (s, 2H), 4.82 (br s, 1H), 4.23 (t, 2H, J=5.9), 4.15 (t, 2H, J=5.9), 3.57-3.36 (m, 1H), 2.94 (m, 2H), 2.62 (m, 2H), 2.28 (qn, 2H, J=5.9), 1.98-1.02 (m, 10H).

Example 708

2-{2-Methoxymethyl-4-[2-(5-methyl-2-phenyloxazol-4-yl)ethoxy]phenoxy}-2-methylpropionic acid

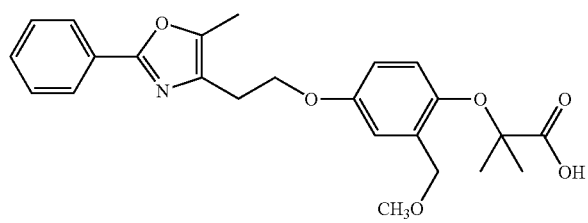

Step A: 2-(4-Benzyloxy-2-formyl-phenoxy)-2-methyl-propionic acid ethyl ester

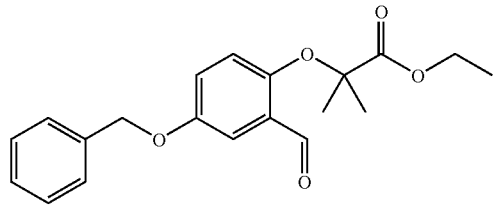

5-Benzyloxy-2-hydroxy-benzaldehyde (Kappe, T.; Witoszynskyj, T. Arch. Pharm., 1975, 308 (5), 339-346) (169 g, 741 mmol), ethyl bromoisobutyrate (164 mL, 1.11 mol), and cesium carbonate (240 g, 741 mmol) in dry DMF (600 mL) were heated at 80° C. for 15 h. Additional cesium carbonate (5 g) and ethyl bromoisobutyrate (20 mL) were added, and the reaction mixture was heated for 6 h. The reaction mixture was cooled, diluted with EtOAc (4 L), and washed with water (3×2 L). The organic layer was dried (Na$_2$SO$_4$) and concentrated to a brown oil. The crude product was recrystallized from EtOAc (150 mL) with hexanes until turbid to give the title compound as a pale yellow solid (210 g, 83%): mp 65° C.; $^1$H NMR (400 MHz, CDCl$_3$) δ 1.24 (t, 3H, J=7.1 Hz), 1.62 (s, 6H), 4.23 (q, 2H, J=7.1 Hz), 6.81 (d, 1H, J=8.8 Hz), 7.10 (dd, 1H, J=4.6, 9.0 Hz), 7.30-7.43 (m, 6H); MS (ES) m/e 343.1 [M+1].

Step B: 2-(4-Hydroxy-2-hydroxymethyl-phenoxy)-2-methyl-propionic acid ethyl ester

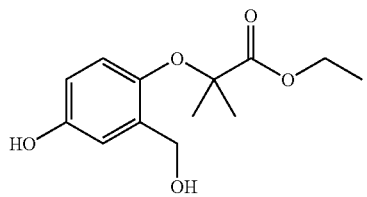

2-(4-Benzyloxy-2-formyl-phenoxy)-2-methyl-propionic acid ethyl ester (185 g, 540 mmol) in ethanol (700 mL) was treated with 10% Pd/C (205 g) and hydrogen (60 psi) at 50° C. for 2 d. The mixture was filtered through Celite, washed with ethanol (1.5 L), and concentrated. The residue was recrystallized from EtOAc/hexanes to give the title compound (116 g). $^1$H NMR (400 MHz, CDCl$_3$) δ 1.26 (t, 3H, J=7.3 Hz), 1.52 (s, 6H), 2.14 (s, 3H), 4.23 (q, 2H, J=7.3 Hz), 4.59 (brs, 2H), 6.61-6.68 (m, 2H), 6.77 (d, 1H, J=2.8 Hz).

Step C: 2-{2-hydroxymethyl-4-[2-(5-methyl-2-phenyloxazol-4-yl)ethoxy]phenoxy}-2-methylpropionic acid ethyl ester

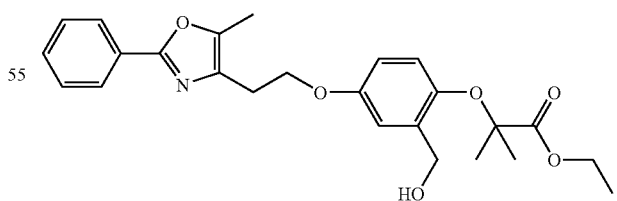

A 25 mL round bottomed flask under a nitrogen atmosphere was charged with toluene-4-sulfonic acid 2-(5-methyl-2-phenyloxazol-4-yl)ethyl ester (0.77 g, 2.17 mmol), 2-(4-hydroxy-2-hydroxymethylphenoxy)-2-methylpropionic acid ethyl ester (0.5 g, 1.97 mmol), and absolute ethanol (10 mL). Potassium carbonate (0.54 g, 3.94 mmol, 325 mesh) was added, and the reaction was heated to 80° C. for 12 h. The mixture was concentrated and the crude residue was diluted with EtOAc (75 mL). The organic layer was washed with brine (2×), dried (Na₂SO₄), and concentrated to an oil. The crude product was purified using radial chromatography (EtOAc:Hex 5:95 to 35:65) to give a colorless oil (0.17 g, 20%). MS (ES) m/e 452 (M+1).

Step D: 2-{2-Methoxymethyl-4-[2-(5-methyl-2-phenyloxazol-4-yl)ethoxy]phenoxy}-2-methylpropionic acid ethyl ester

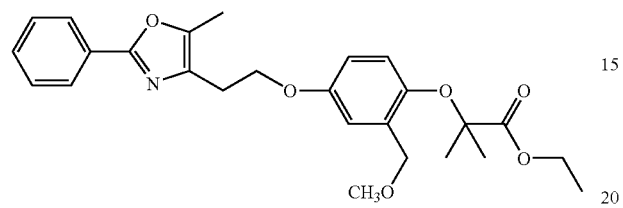

A 15 mL round bottomed flask under a nitrogen atmosphere were charged with 2-{2-hydroxymethyl-4-[2-(5-methyl-2-phenyloxazol-4-yl)ethoxy]phenoxy}-2-methylpropionic acid ethyl ester (0.075 g, 0.17 mmol), anhydrous DMF (1 mL), and then methyl iodide (0.16 mL, 1.7 mmol). The solution was cooled in an ice bath and was treated with NaH (0.014 g, 0.34 mmol, 60% oil dispersion). The mixture was stirred for 2 h, poured into EtOAc (6 mL) and brine (10 mL), and acidified using dilute sulfuric acid. The organic layer was separated, dried (Na₂SO₄), and concentrated to an oil. The crude product was purified using radial chromatography (EtOAc:Hex 15:85) to give a colorless oil (0.039 g, 51%). MS (ES) m/e 454 (M+1).

Step E: 2-{2-Methoxymethyl-4-[2-(5-methyl-2-phenyloxazol-4-yl)ethoxy]phenoxy}-2-methylpropionic acid A 25 mL round bottomed flask was charged with 2-{2-methoxymethyl-4-[2-(5-methyl-2-phenyloxazol-4-yl)ethoxy]phenoxy}-2-methylpropionic acid ethyl ester (0.039 g, 0.087 mmol), ethanol (2 mL), and then aqueous 2N NaOH (0.22 mL, 0.44 mmol). The solution was heated at 55° C. for 1 h. The mixture was concentrated, acidified using 5% H₂SO₄ (1.5 mL), and partitioned between CH₂Cl₂ (15 mL) and brine (15 mL). The organic layer was dried (Na₂SO₄), filtered, and concentrated and to give a white solid (0.024 g, 66%). MS (ES) m/e 426 (M+1).

Example 709

2-{2-Benzyloxymethyl-4-[2-(5-methyl-2-phenyloxazol-4-yl)-ethoxy]phenoxy}-2-methylpropionic acid

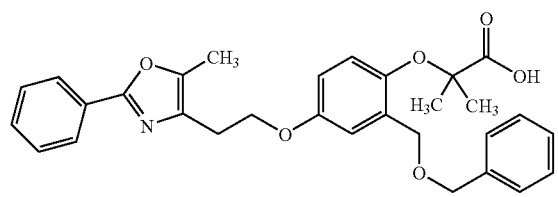

The above compound is prepared by following a substantially similar procedure as described in Example 708. MS (ES) m/e 502 (M+1).

Example 710

2-{2-Cyclohexylcarbamoyloxymethyl-4-[2-(5-methyl-2-phenyl-oxazol-4-yl)-ethoxy]-phenoxy}-2-methyl-propionic acid

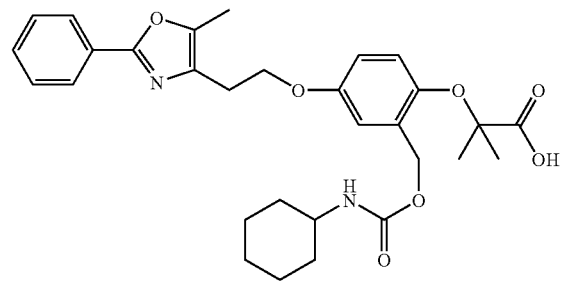

Step A: 3-{2-Cyclohexylcarbamoyloxymethyl-4-[2-(2-phenyloxazol-4-yl)ethoxy]phenyl}-propionic acid ethyl ester

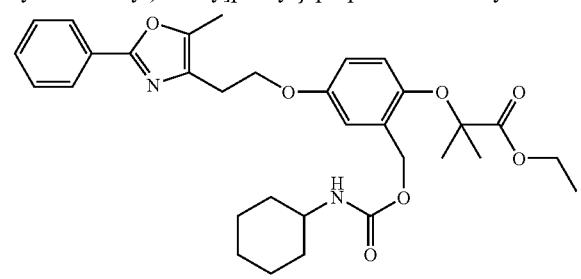

A 15 mL round bottomed flask under N₂ was charged 2-{2-hydroxymethyl-4-[2-(5-methyl-2-phenyloxazol-4-yl)ethoxy]phenoxy}-2-methylpropionic acid ethyl ester (0.075 g, 0.17 mmol), cyclohexylisocyanate (0.13 mL, 1.0 mmol), anhydrous CH₂Cl₂ (0.5 mL), and then 1.0 N HCl in ether (0.086 mL, 0.086 mmol). The reaction mixture was stirred at ambient temperature for 18 h and was diluted with CH₂Cl₂ (10 mL). The organic layer was washed with brine, dried (Na₂SO₄) and concentrated to give 0.10 g of a crude oil, which was used directly in the next step. MS (ES) m/e 564 (M+1).

Step B: 3-{2-Cyclohexylcarbamoyloxymethyl-4-[2-(2-phenyloxazol-4-yl)ethoxy]phenyl}-propionic acid To a 15 mL round bottomed flask was charged with 3-{2-cyclohexylcarbamoyloxymethyl-4-[2-(2-phenyloxazol-4-yl)ethoxy]phenyl}propionic acid ethyl ester (0.10 g, 0.17 mmol), ethanol (2 mL), and then 2N NaOH (0.48 mL, 0.96 mmol). The solution was heated at 55° C. for 2 h. The mixture was concentrated, acidified using 5% H₂SO₄ (1.5 mL), and partitioned between CH₂Cl₂ (15 mL) and brine (15 mL). The organic layer was dried (Na₂SO₄), filtered, and concentrated and was concentrated. The crude residue was submitted for mass-directed HPLC purification to give a white solid (0.058 g, 63%). MS (ES) m/e 537 (M+1).

The following Examples 711 to 713 are prepared by following a substantially similar procedure as described in Example 710.

Example 711

2-{2-Isopropylcarbamoyloxymethyl-4-[2-(5-methyl-2-phenyloxazol-4-yl)ethoxy]phenoxy}-2-methylpropionic acid

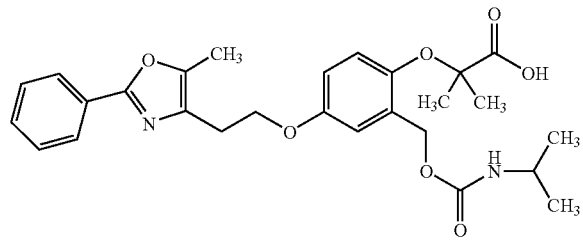

MS (ES) m/e 497 (M+1).

Example 712

2-{2-Benzylcarbamoyloxymethyl-4-[2-(5-methyl-2-phenyloxazol-4-yl)ethoxy]phenoxy}-2-methylpropionic acid

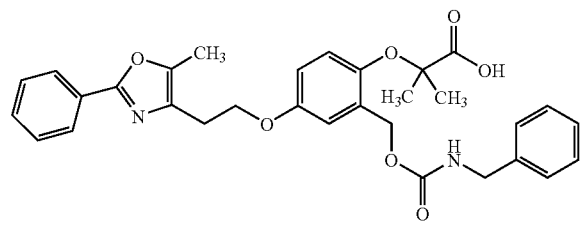

MS (ES) m/e 545 (M+1).

Example 713

2-{2-(4-Fluorobenzylcarbamoyloxymethyl)-4-[2-(5-methyl-2-phenyloxazol-4-yl)ethoxy]phenoxy}-2-methylpropionic acid

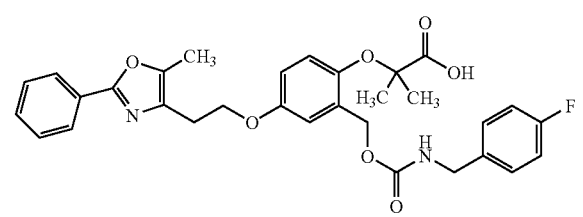

MS (ES) m/e 563 (M+1).

Example 714

2-Methyl-2-{4-[2-(5-methyl-2-phenyl-oxazol-4-yl)-ethoxy]-2-m-tolyloxymethylphenoxy}-propionic acid

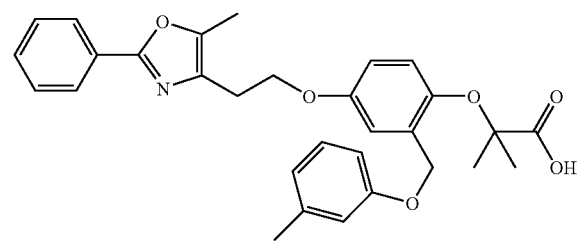

Step A: 2-{2-Bromomethyl-4-[2-(5-methyl-2-phenyl-oxazol-4-yl)-ethoxy]-phenoxy}-2-methyl-propionic acid ethyl ester

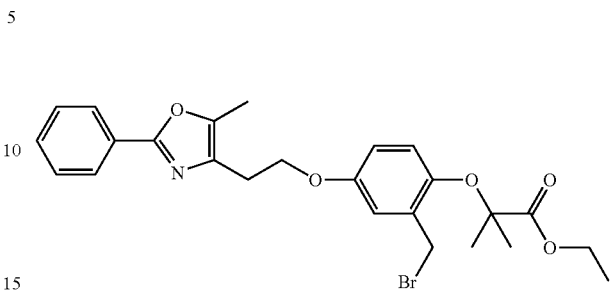

A 100 mL round bottomed flask was charged with 2-{2-hydroxymethyl-4-[2-(5-methyl-2-phenyl-oxazol-4-yl)-ethoxy]-phenoxy}-2-methyl-propionic acid ethyl ester (1.0 g, 2.25 mmol), dissolved in anhydrous THF (75 mL), and then of triphenylphosphine (1.18 g, 4.50 mmol) and CBr$_4$ (1.49 g, 4.50 mmol). The mixture was stirred at ambient temperature under a nitrogen atmosphere for 1 h and was poured into EtOAc (135 mL). The organic layer was washed with brine (50 mL), dried (Na$_2$SO$_4$), and concentrated. The crude product was purified using radial chromatography (EtOAc:hexanes 15:85) to give a the title compound as a colorless oil (0.95 g, 76%).

Step B: 2-Methyl-2-{4-[2-(5-methyl-2-phenyl-oxazol-4-yl)-ethoxy]-2-m-tolyloxymethylphenoxy}-propionic acid General procedure for the parallel synthesis of analogs using the DynaVac Carousel apparatus: A 50 mL glass tube with screw cap and nitrogen inlet was charged with 2-{2-bromomethyl-4-[2-(5-methyl-2-phenyloxazol-4-yl)ethoxy]phenoxy}-2-methyl-propionic acid ethyl ester (0.040 g, 0.080 mmol), m-cresol (0.012 mL, 0.12 mmol), absolute ethanol (1 mL), and then potassium carbonate (0.022 g, 0.16 mmol; 325 mesh). The mixture was heated to 80° C. for 4 h. MS analysis of the reaction indicated that 2-methyl-2-{4-[2-(5-methyl-2-phenyloxazol-4-yl)ethoxy]-2-m-tolyloxymethylphenoxy}-propionic acid ethyl ester: MS (ES) m/e 530 (M+1) had formed. The reaction mixture was treated with 2N NaOH (0.4 mL), heated at 55° C. for 3 h, cooled, and concentrated. The residue was treated with 5N HCl (0.75 mL) and CH$_2$Cl$_2$ (1 mL) and was poured onto a 3-mL ChemElute cartridge to remove the aqueous layer. The cartridge was washed with CH$_2$Cl$_2$, and the solvent was removed in vacuo. The crude residue was purified by mass-directed reverse phase HPLC to provide the title compound (0.032 g, 38%). MS (ES) m/e 502 (M+1).

The following Examples 715 to 723 are prepared by following a substantially similar procedure as described in Example 714.

Example 715

2-{2-(4-Fluorophenoxymethyl)-4-[2-(5-methyl-2-phenyloxazol-4-yl)ethoxy]phenoxy}-2-methylpropionic acid

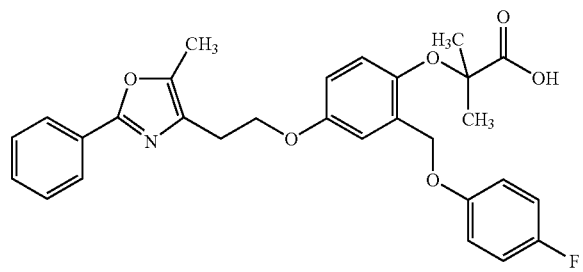

MS (ES) m/e 506 (M+1).

Example 716

2-{2-(3-Fluorophenoxymethyl)-4-[2-(5-methyl-2-phenyloxazol-4-yl)ethoxy]phenoxy}-2-methylpropionic acid

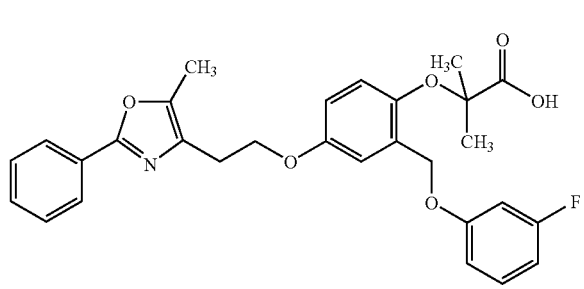

MS (ES) m/e 506 (M+1).

Example 717

2-{2-(2-Fluorophenoxymethyl)-4-[2-(5-methyl-2-phenyloxazol-4-yl)ethoxy]phenoxy}-2-methylpropionic acid

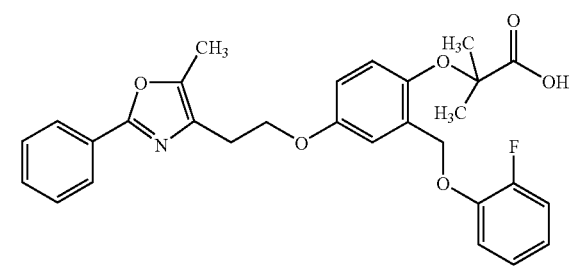

MS (ES) m/e 506 (M+1).

Example 718

2-Methyl-2-{4-[2-(5-methyl-2-phenyloxazol-4-yl)ethoxy]-2-p-tolyloxymethylphenoxy}propionic acid

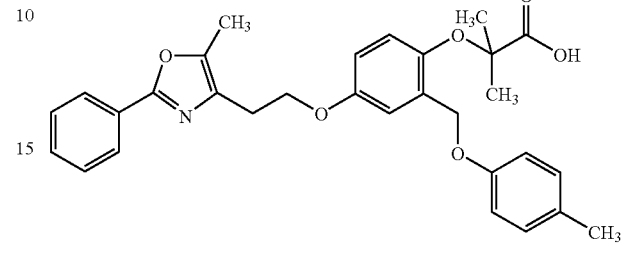

MS (ES) m/e 502 (M+1).

Example 719

2-Methyl-2-{4-[2-(5-methyl-2-phenyloxazol-4-yl)ethoxy]-2-o-tolyloxymethylphenoxy}propionic acid

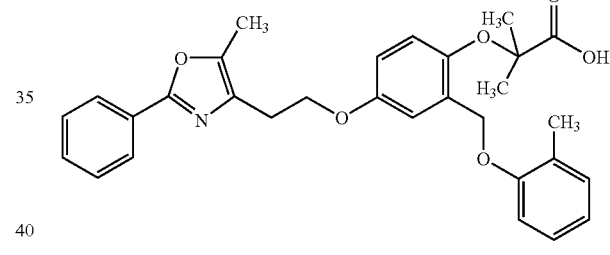

MS (ES) m/e 502 (M+1).

Example 720

2-{2-(4-Methoxyphenoxyethyl)-4-[2-(5-methyl-2-phenyloxazol-4-yl)ethoxy]phenoxy}-2-methylpropionic acid

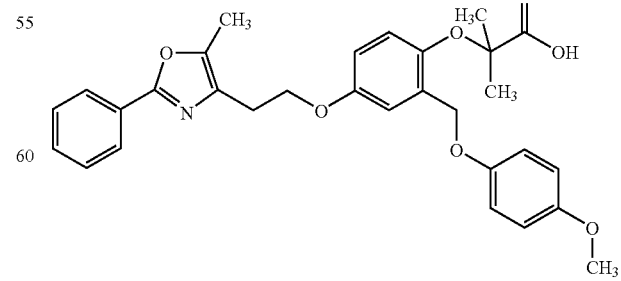

MS (ES) m/e 518 (M+1).

Example 721

2-Methyl-2-[4-[2-(5-methyl-2-phenyloxazol-4-yl)ethoxy]-2-(4-trifluoromethylphenoxymethyl)phenoxy]propionic acid

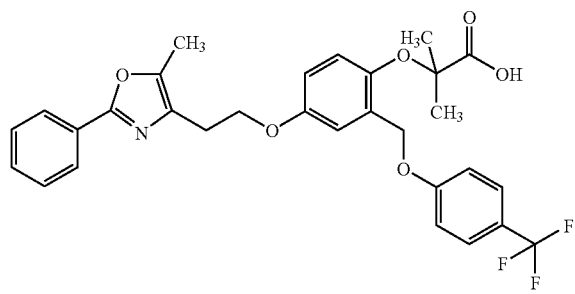

MS (ES) m/e 556 (M+1).

Example 722

2-{2-(Biphenyl-2-yloxymethyl)-4-[2-(5-methyl-2-phenyloxazol-4-yl)ethoxy]phenoxy}-2-methylpropionic acid

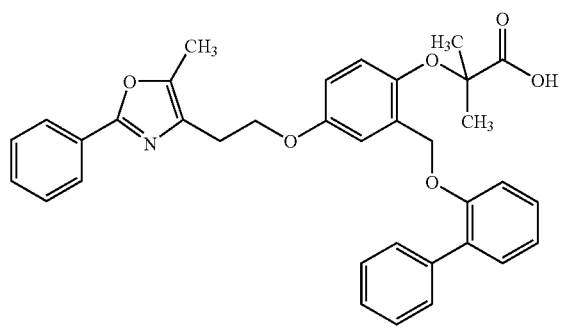

MS (ES) m/e 564 (M+1).

Example 723

2-{2-(Biphenyl-4-yloxymethyl)-4-[2-(5-methyl-2-phenyloxazol-4-yl)ethoxy]phenoxy}-2-methylpropionic acid

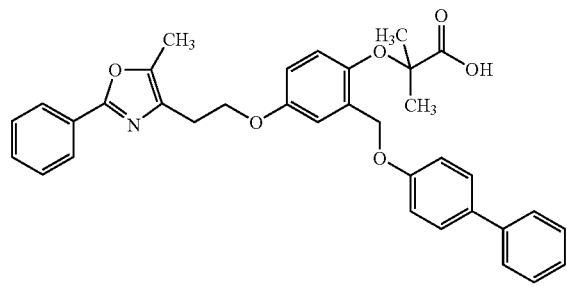

MS (ES) m/e 564 (M+1).

Example 724

3-{2-(Benzoylaminomethyl)-4-[3-(biphenyl-4-yloxy)propoxy]phenyl}propionic acid

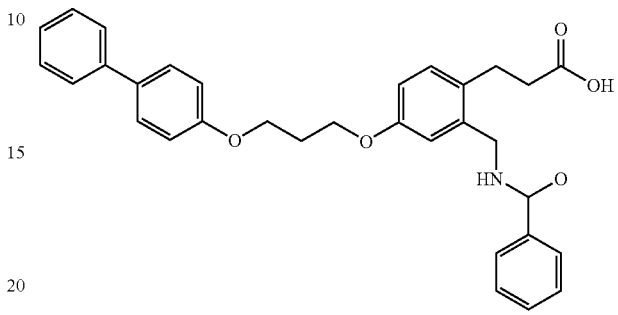

A solution of 4-(3-bromo-propoxy)-biphenyl (291 mg, 1.00 mmol; Preparation 12) and 3-[2-(benzoylamino-methyl)-4-hydroxy-phenyl]-propionic acid tert-butyl ester (320 mg, 0.90 mmol; Preparation 21) in DMF (5 mL) was treated with $K_2CO_3$ (100 mg) and heated at 60° C. for 48 h. The reaction mixture was diluted with water (50 mL) and extracted with EtOAc (3×20 mL). The combined organics were dried ($Na_2SO_4$), concentrated, and purified using silica gel chromatography (10-30% EtOAc/hexanes) to give 3-{2-(benzoylaminomethyl)-4-[3-(biphenyl-4-yloxy)propoxy]phenyl}propionic acid tert-butyl ester (450 mg). This material was treated with a mixture of $CH_2Cl_2$ (1.0 mL)/TFA (0.8 mL)/water (0.1 mL) at ambient temperature for 2 h. The reaction mixture was concentrated and dried under vacuum to afford the title product as a white solid (380 mg, 75%). MS (ES) m/e 510.1 (M+1).

The following Examples 725 to 757 are prepared by following a substantially similar procedure as described in Example 724.

Example 725

3-{2-(Benzoylaminomethyl)-4-[2-(4-phenoxy-phenoxy)ethoxy]phenyl}propionic acid

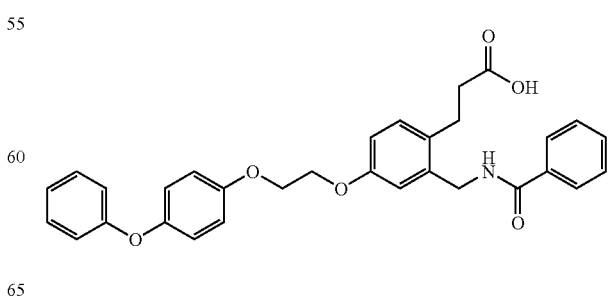

MS [ES] m/z 512 (M+1).

Example 726

3-{2-(Benzoylaminomethyl)-4-[2-(3-phenylbenzofuran-6-yloxy)ethoxy]-phenyl}-propionic acid

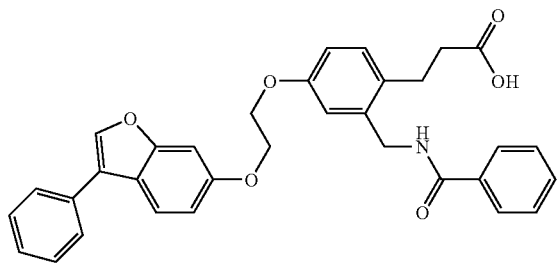

MS [ES] m/z 536 (M+1).

Example 727

3-{2-(Benzoylaminomethyl)-4-[2-(6-methoxynaphthalen-2-yloxy)ethoxy]-phenyl}propionic acid

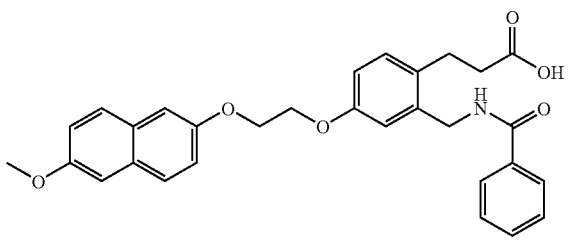

MS [ES] m/z 500 (M+1).

Example 728

3-{2-[(Cyclobutanecarbonylamino)methyl]-4-[2-(4-phenoxyphenoxy)-ethoxy]phenyl}propionic acid

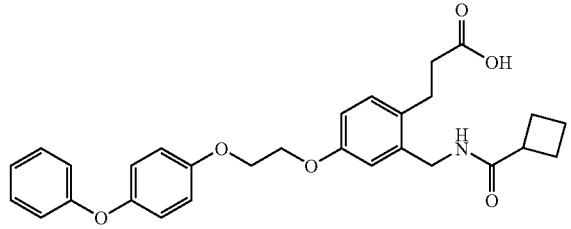

MS [ES] m/z 490 (M+1).

Example 729

3-[4-[2-(Biphenyl-4-yloxy)ethoxy]-2-(isopropoxycarbonylaminomethyl)-phenyl]propionic acid

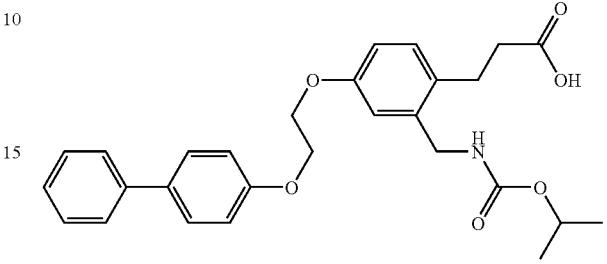

MS [ES] m/z 473 (M+1).

Example 730

3-(4-[2-(Biphenyl-4-yloxy)ethoxy]-2-{[(pyridine-2-carbonyl)amino]methyl}-phenyl)propionic acid

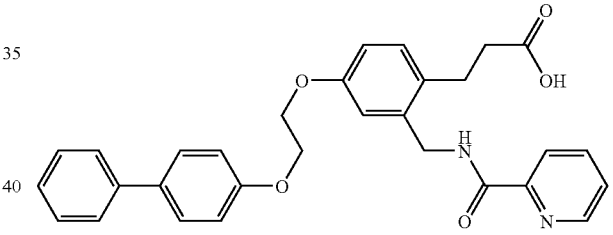

MS [ES] m/z 497 (M+1).

Example 731

3-(4-[2-(Biphenyl-3-yloxy)ethoxy]-2-{[(pyridine-2-carbonyl)amino]methyl}phenyl)propionic acid

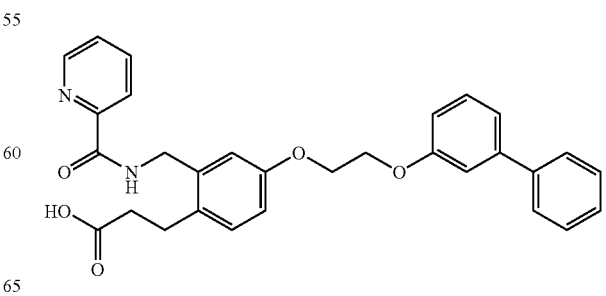

MS [ES] m/z 497 (M+1).

Example 732

3-(4-[2-(4-Phenoxy-phenoxy)ethoxy]-2-{[(pyridine-2-carbonyl)amino]-methyl}phenyl)propionic acid

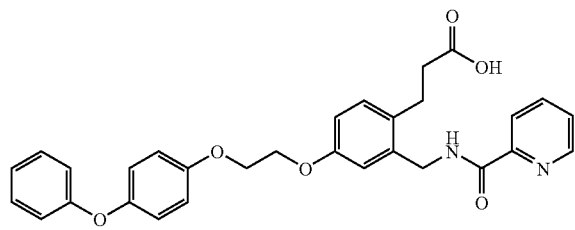

MS [ES] m/z 501 (M+1).

Example 733

3-(4-[2-(3-Phenylbenzofuran-6-yloxy)ethoxy]-2-{[(pyridine-2-carbonyl)-amino]methyl}phenyl)propionic acid

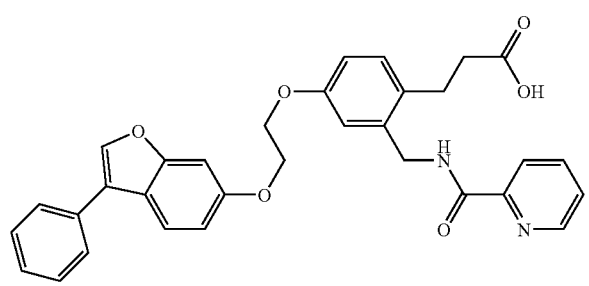

MS [ES] m/z 537 (M+1).

Example 734

3-(4-[2-(6-Methoxynaphthalen-2-yloxy)ethoxy]-2-{[(pyridine-2-carbonyl)-amino]methyl}phenyl)propionic acid

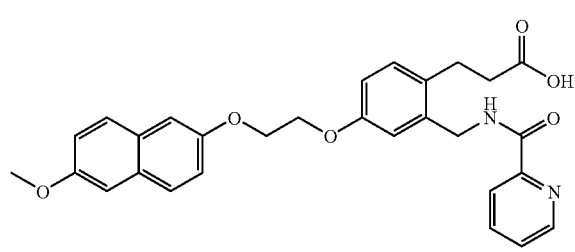

MS [ES] m/z 501 (M+1).

Example 735

3-{2-(Benzoylaminomethyl)-4-[4-(biphenyl-4-yloxy)butoxy]phenyl}propionic acid

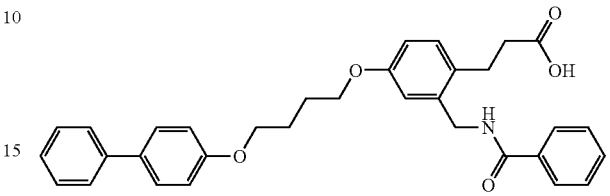

MS [ES] m/z 524 (M+1).

Example 736

3-{2-(Benzoylaminomethyl)-4-[4-(biphenyl-3-yloxy)butoxy]phenyl}propionic acid

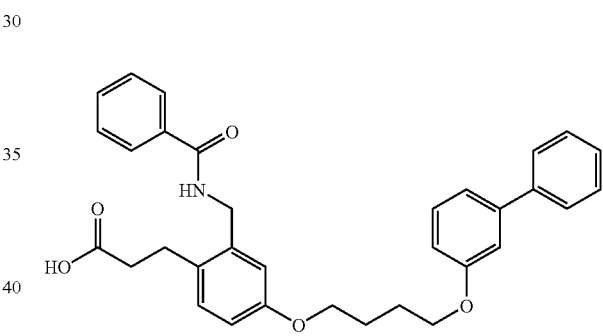

MS [ES] m/z 524 (M+1).

Example 737

3-{2-(Benzoylaminomethyl)-4-[4-(4-phenoxyphenoxy)butoxy]phenyl}propionic acid

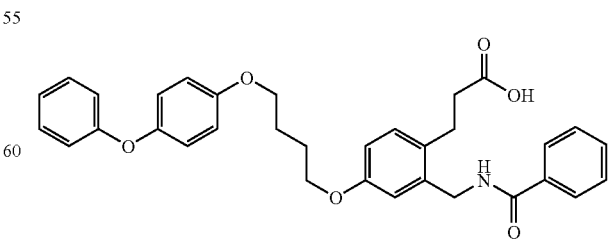

MS [ES] m/z 540 (M+1).

Example 738

3-{2-(Benzoylaminomethyl)-4-[4-(3-phenylbenzofuran-6-yloxy)butoxy]phenyl}-propionic acid

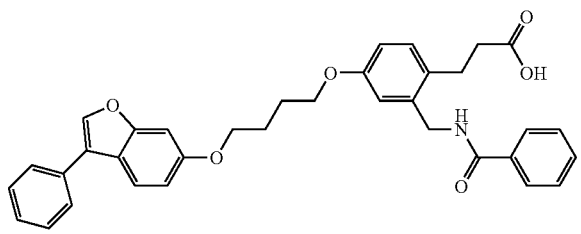

MS [ES] m/z 564 (M+1).

Example 739

3-{2-(Isopropoxycarbonylaminomethyl)-4-[4-(4-phenoxyphenoxy)butoxy]phenyl}propionic acid

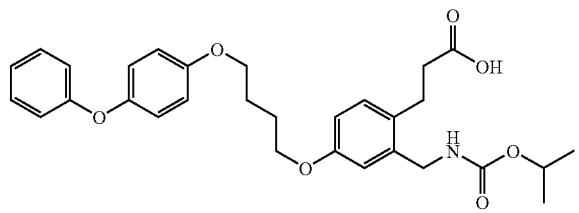

MS [ES] m/z 522 (M+1).

Example 740

3-{2-(Isopropoxycarbonylaminomethyl)-4-[4-(3-phenylbenzofuran-6-yloxy)butoxy]phenyl}propionic acid

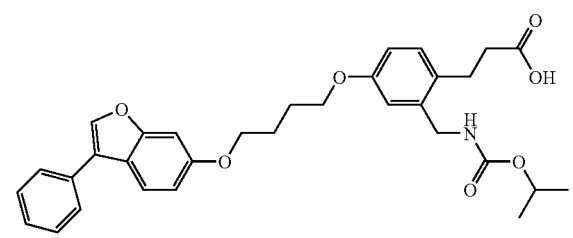

MS [ES] m/z 546 (M+1).

Example 741

3-(4-[4-(Biphenyl-3-yloxy)butoxy]-2-{[(pyridine-2-carbonyl)amino]methyl}-phenyl)propionic acid

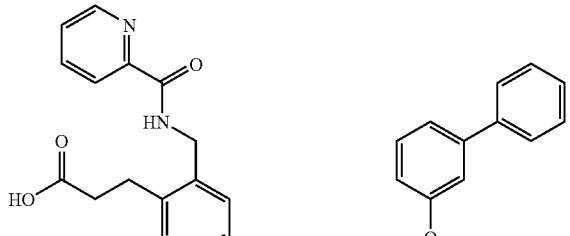

MS [ES] m/z 525 (M+1).

Example 742

3-(4-[4-(4-Phenoxyphenoxy)butoxy]-2-{[(pyridine-2-carbonyl)amino]-methyl}phenyl)propionic acid

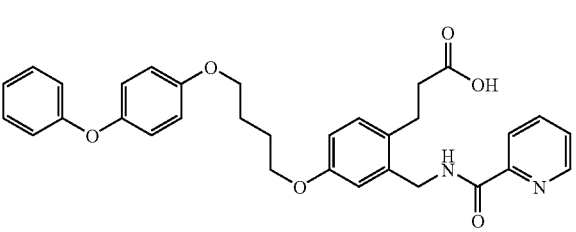

MS [ES] m/z 541 (M+1).

Example 743

3-(4-[4-(3-Phenylbenzofuran-6-yloxy)butoxy]-2-{[(pyridine-2-carbonyl)-amino]methyl}phenyl)propionic acid

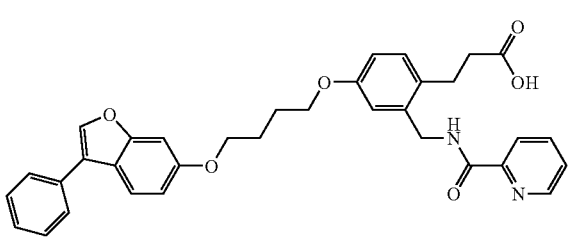

MS [ES] m/z 565 (M+1).

Example 744

3-(4-[4-(6-Methoxynaphthalen-2-yloxy)butoxy]-2-{[(pyridine-2-carbonyl)-amino]methyl}phenyl)propionic acid

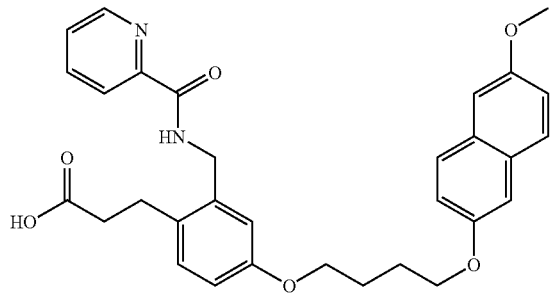

MS [ES] m/z 529 (M+1).

Example 745

3-(4-[4-(Biphenyl-3-yloxy)butoxy]-2-{[(2,5-dichlorothiophene-3-carbonyl)-amino]methyl}phenyl)propionic acid

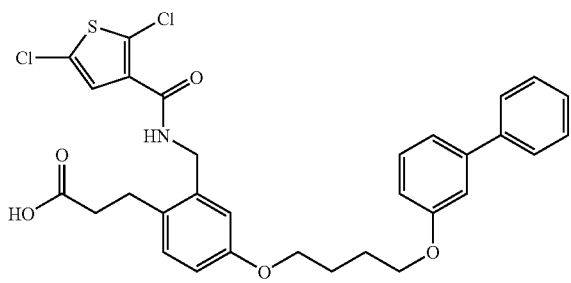

MS [ES] m/z 599 (M+1).

Example 746

3-{2-(Benzoylaminomethyl)-4-[3-(biphenyl-3-yloxy)propoxy]phenyl}propionic acid

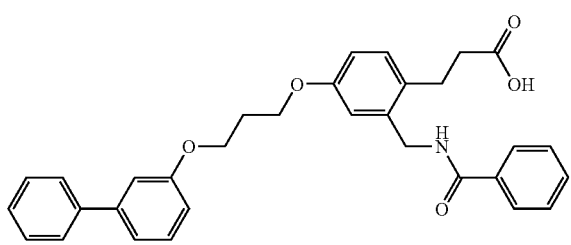

MS [ES] m/z 510 (M+1).

Example 747

3-[4-[3-(Biphenyl-3-yloxy)propoxy]-2-(isopropoxy-carbonylaminomethyl)-phenyl]propionic acid

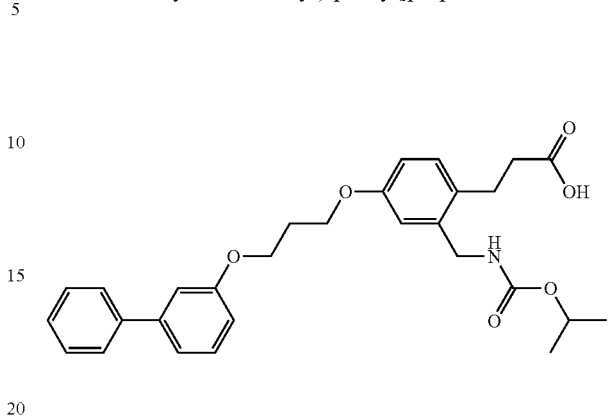

MS [ES] m/z 492 (M+1).

Example 748

3-(4-[3-(Biphenyl-4-yloxy)propoxy]-2-{[(pyridine-2-carbonyl)amino]methyl}-phenyl)propionic acid

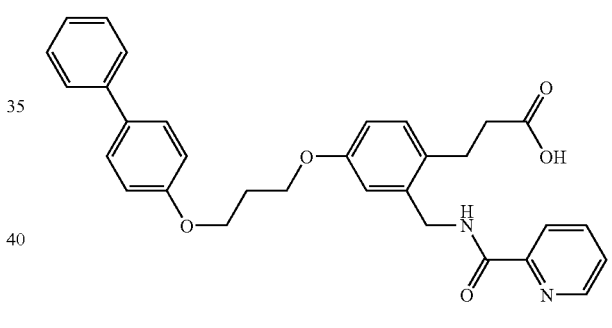

MS [ES] m/z 511 (M+1).

Example 749

3-(4-[3-(Biphenyl-3-yloxy)propoxy]-2-{[(pyridine-2-carbonyl)amino]methyl}phenyl)propionic acid

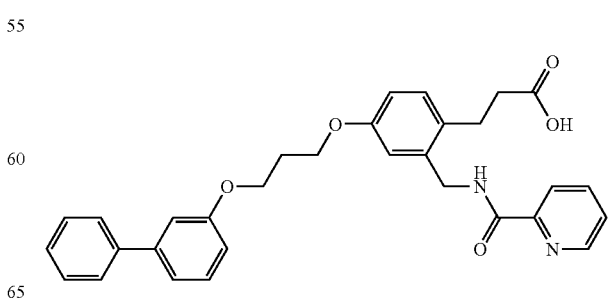

MS [ES] m/z 511 (M+1).

Example 750

3-(4-[3-(6-Methoxynaphthalen-2-yloxy)propoxy]-2-{[(pyridine-2-carbonyl)-amino]methyl}phenyl)propionic acid

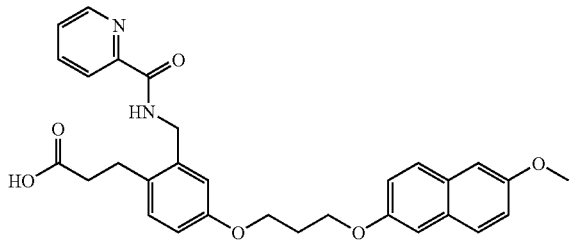

MS [ES] m/z 515 (M+1).

Example 751

3-(4-[3-(Biphenyl-4-yloxy)propoxy]-2-{[(2,5-dichlorothiophene-3-carbonyl)-amino]methyl}phenyl)propionic acid

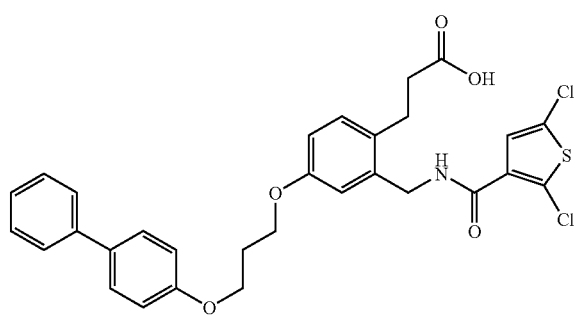

MS [ES] m/z 585 (M+1).

Example 752

3-{2-{[(2,5-Dichlorothiophene-3-carbonyl)amino]methyl}-4-[3-(3-phenyl-benzofuran-6-yloxy)propoxy]phenyl}propionic acid

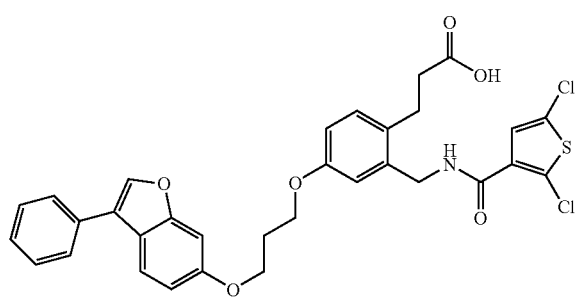

MS [ES] m/z 625 (M+1).

Example 753

3-[4-[3-(Biphenyl-4-yloxy)propoxy]-2-(1,3-dioxo-1,3-dihydroisoindol-2-ylmethyl)phenyl]propionic acid

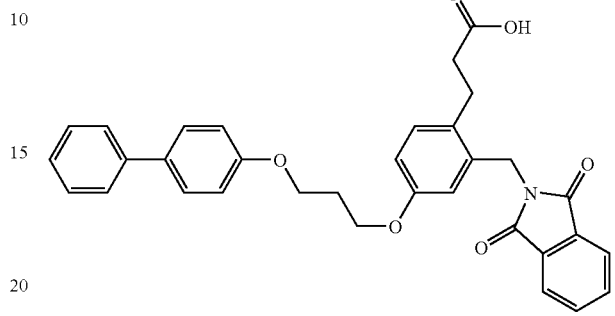

MS [ES] m/z 536 (M+1).

Example 754

3-[4-[3-(Biphenyl-4-yloxy)propoxy]-2-(isopropoxycarbonylaminomethyl)-phenyl]propionic acid

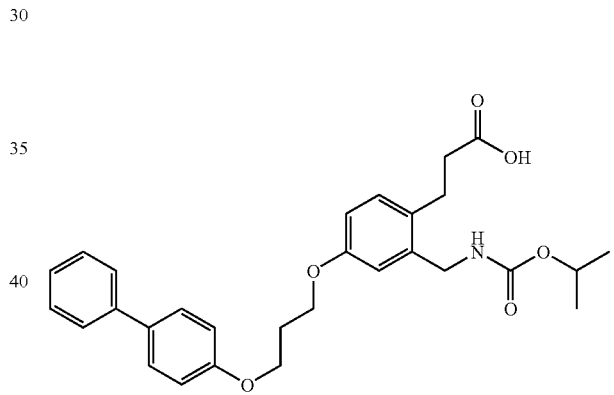

MS [ES] m/z 492 (M+1).

Example 755

3-{2-(Benzoylaminomethyl)-4-[3-(4-phenoxyphenoxy)propoxy]phenyl}propionic acid

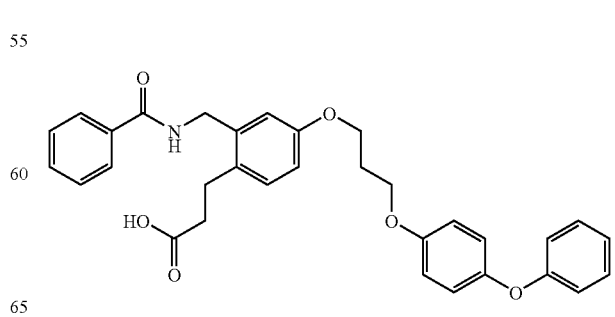

MS [ES] m/z 526 (M+1).

Example 756

3-{2-(Isopropoxycarbonylaminomethyl)-4-[3-(4-phenoxyphenoxy)propoxy]-phenyl}propionic acid

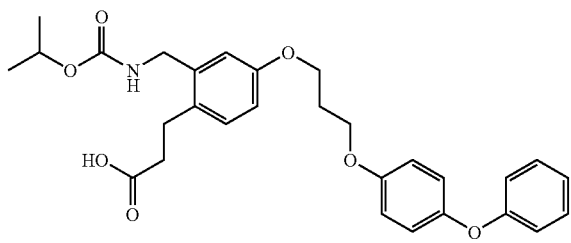

MS [ES] m/z 508 (M+1).

Example 757

3-(4-[3-(4-Phenoxyphenoxy)propoxy]-2-{[(pyridine-2-carbonyl)amino]-methyl}phenyl)propionic acid

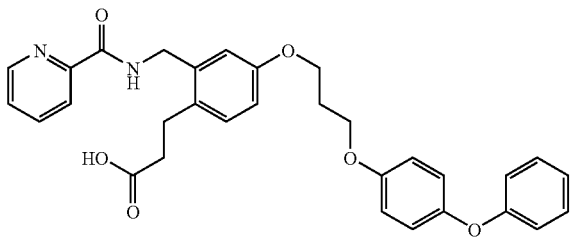

MS [ES] m/z 527 (M+1).

Example 758

(2-Biphenyl-4-yl-5-methyl-oxazol-4-yl)-acetic acid methyl ester

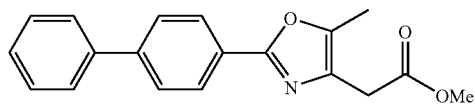

Step 1: 4-Bromo-3-oxo-pentanoic acid methyl ester

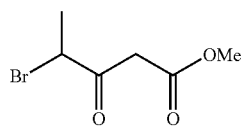

A solution of bromine (28.3 g, 0.177 mol) in chloroform (30 mL) was added dropwise over 2 h to a solution of methyl propionylacetate (23.5 g, 0.177 mol) in chloroform (155 mL) at 0-5° C. The mixture was stirred for 30 min, and the cooling bath was removed. The mixture was stirred for 18 h, and ice water (200 mL) was added. The organic layer was collected and washed with cold water (2×200 mL), 10% aqueous sodium thiosulfate (2×200 mL) and brine (200 mL). The filtered solution was dried (Na$_2$SO$_4$) and concentrated to 36.5 g of the title compound as a clear liquid.

Step 2: Biphenyl-4-carboxylic acid 3-methoxycarbonyl-1-methyl-2-oxo-propyl ester

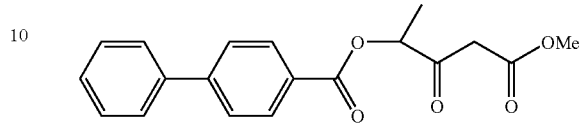

A mixture of biphenyl-4-carboxylic acid (800 g, 4.03 mol) in acetone (4.6 L) was treated with triethylamine (0.6 L, 4.3 mol, 1.07 eq) dropwise over 13 min while maintaining the temperature at 15-30° C. 4-Bromo-3-oxo-pentanoic acid methyl ester (880 g, 4.21 mol, 1.04 eq) was added dropwise over 21 min at 15-30° C. The mixture was stirred overnight at room temperature. Water (9.6 L) was added dropwise over 85 minutes at 15-30° C. The mixture was stirred for 2 h. The precipitated product was collected by filtration and washed twice with water (1 L). The product was dried under vacuum at 50° C. to afford 1291 g (98% yield, 96% HPLC purity) of the title compound.

Step 3: Biphenyl-4-carboxylic acid 2-amino-3-methoxycarbonyl-1-methyl-allyl ester

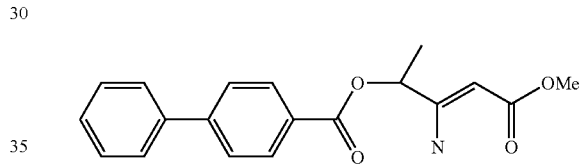

A mixture of biphenyl-4-carboxylic acid 3-methoxycarbonyl-1-methyl-2-oxo-propyl ester (1275 g, 3.9 mol, 1 eq) and ammonium acetate (640 g, 8.3 mol) in ethanol (10 L) was heated with stirring at 70-75° C. until the keto ester compound is completely consumed (1-2 h). The mixture was then kept at 0-5° C. for 1.5 h. The precipitated solid was collected by filtration and washed with hexanes (2.5 L). The product was dried overnight under vacuum at 50° C. to obtain 1244 g (90% yield, 98% HPLC purity) of the title compound.

Step 4: (2-Biphenyl-4-yl-5-methyl-oxazol-4-yl)-acetic acid methyl ester

A mixture of biphenyl-4-carboxylic acid 2-amino-3-methoxycarbonyl-1-methyl-allyl ester (566 g, 1.74 mol, 1 eq) and ammonium acetate (283 g, 3.67 mol) in glacial acetic acid (11.3 L) was heated at reflux for 2 h, cooled, and concentrated. The residue was coevaporated with toluene (2×2.5 L) and EtOAc (2.5 L). The mixture was diluted with EtOAc (6.6 L) and transferred with EtOAc (2.2 L) to a bottom outlet separation flask. The mixture was washed twice with water (2.2 L), saturated aqueous NaHCO$_3$ (1.1 L), and brine (2×2.2 L). The organic layer was dried (Na$_2$SO$_4$, 550 g), filtered with the aid of EtOAc (1.1 L), and concentrated. The residue was dissolved in isopropanol (2 L) at 50° C. and allowed to cool overnight at room temperature. The mixture was kept at 0° C. to 5° C. for 1 h. The precipitated solid was broken up and collected by filtration. The solid was washed with cold isopropanol (4×0.55 L) and dried overnight in a vacuum oven at 50° C. to yield 428 g of the title compound (72% from Step 2).

What is claimed is:
1. A compound of formula I,

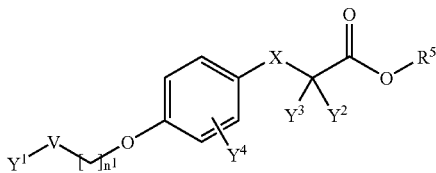

and pharmaceutically acceptable salts, solvates, hydrates or stereoisomers thereof, wherein:

$n^1$ is 2, 3, 4 or 5;
V is a bond or O;
X is $CH_2$ or O;
p is 0 or 1;
m is 1-4;
$Y^1$ is:

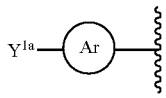

wherein,

is: 1-3-oxazolyl,
wherein 1-3-oxazolyl is optionally substituted with one or more groups independently selected from the group consisting of:
hydrogen, $C_1$-$C_6$ alkyl, $C_1$-$C_6$ alkoxy, halo, haloalkyl and haloalkyloxy;

$Y^{1a}$ is: hydrogen,
($C_0$-$C_3$)alkyl-aryl,
C(O)-aryl,
heteroaryl,
cycloalkyl,
heterocycloalkyl,
aryloxy,
$NR^5(CH_2)_mOR^5$,
aryl-Z-aryl,
aryl-Z-heteroaryl,
aryl-Z-cycloalkyl,
aryl-Z-heterocycloalkyl,
heteroaryl-Z-aryl,
heteroaryl-Z-heterocycloalkyl or
heterocycloalkyl-Z-aryl,
wherein aryl, cycloalkyl, aryloxy, heteroaryl, and heterocycloalkyl are optionally substituted with one or more substituents independently selected from the group consisting of:
halo,
hydroxyl,
nitro,
cyano,
$C_1$-$C_6$ alkyl,
$C_1$-$C_6$ alkoxy optionally substituted with $N(R^5)_2$,
haloalkyl,
$N(R^5)_2$,
$N[C(O)R^5]_2$,
$N[S(O)_2R^5]_2$,
$NR^5S(O)_2R^5$,
$NR^5C(O)R^5$,
$NR^5C(O)OR^5$,
$C(O)N(R^5)_2$,
$C(O)OR^5$ and
$C(O)R^5$;

Z is: a bond,
-oxygen-
—$C(O)NR^5$—
—$NR^5C(O)$—,
—$NR^5C(O)O$—,
—$C(O)$—,
—$NR^5$—,
—$[O]_p(CH_2)_m$—,
—$(CH_2)_m[O]_p$—,
—$NR^5(CH_2)_m$— or
—$(CH_2)_mNR^5$—;

$Y^2$ and $Y^3$ are each independently:
hydrogen,
$C_1$-$C_6$ alkyl or
$C_1$-$C_6$ alkoxy;

$Y^4$ is: ($C_1$-$C_3$)alkyl-$NR^5C(O)$—($C_0$-$C_5$)alkyl-$Y^7$,
($C_1$-$C_3$)alkyl-$NR^5C(O$—($C_2$-$C_5$)alkenyl-$Y^7$,
($C_1$-$C_3$)alkyl-$NR^5C(O$—($C_2$-$C_5$)alkynyl-$Y^7$;
($C_1$-$C_3$)alkyl-$NR^5C(O)O$—($C_0$-$C_5$)alkyl-$Y^7$,
($C_1$-$C_3$)alkyl-$NR^5C(O)NR^5$—($C_0$-$C_5$)alkyl-$Y^7$,
($C_1$-$C_3$)alkyl-$NR^5C(S)NR^5$—($C_0$-$C_5$)alkyl-$Y^7$,
($C_0$-$C_3$)alkyl—$C(O)NR^5$—($C_0$-$C_5$)alkyl-$Y^7$,
($C_1$-$C_3$)alkyl-$OC(O)NY^{10}Y^{11}$,
($C_1$-$C_3$)alkyl-$NY^{10}Y^{11}$,
($C_1$-$C_3$)alkyl-O—($C_0$-$C_5$)alkyl-$Y^7$,
($C_1$-$C_3$)alkyl-S—($C_0$-$C_5$)alkyl-$Y^7$ or
CN;

$Y^7$ is: hydrogen,
aryl,
heteroaryl,
$C_1$-$C_{12}$ alkyl,
$C_1$-$C_6$ alkoxy,
cycloalkyl,
heterocycloalkyl,
aryloxy,
C(O)-heteroaryl or
$SR^6$,
wherein alkyl, aryl, aryloxy, alkoxy, heteroaryl, cycloalkyl, and heterocycloalkyl are optionally substituted with one or more groups independently selected from $R^7$:

$Y^{10}$ and $Y^{11}$ are each independently:
hydrogen,
aryl,
heteroaryl,
$C_1$-$C_{10}$ alkyl,
cycloalkyl,
$SO_2(R^6)$; or
$Y^{10}$ and $Y^{11}$ together are a 5- to 10-membered heterocycloalkyl ring or heterocycloalkyl ring fused with aryl, and the heterocycloalkyl ring optionally containing one or more heteroatoms selected from N, O or S; and wherein,
aryl, heteroaryl, heterocycloalkyl and alkyl are optionally substituted with one or more substituents independently selected from $R^7$;

$R^5$ is hydrogen or $C_1$-$C_6$ alkyl;
$R^6$ is: hydrogen,

C$_1$-C$_{10}$ alkyl,
cycloalkyl,
aryl, or
heteroaryl,
  wherein alkyl, cycloalkyl, aryl and heteroaryl are optionally substituted with one or more substituents independently selected from R$^7$;
R$^7$ is: halo,
nitro,
oxo,
cyano,
hydroxyl,
benzyl,
phenyl,
phenoxy,
heteroaryl,
C(O)R$^6$,
C$_1$-C$_{10}$ alkyl,
C$_1$-C$_6$ alkoxy,
C$_1$-C$_6$ haloalkyl,
C$_1$-C$_6$ haloalkyloxy,
O(CH$_2$)$_m$-phenyl,
(CH$_2$)$_m$OC(O-aryl,
C(O)OR$^5$,
S(O)$_2$R$^5$,
S(O)$_2$N(R$^5$)$_2$,
SR$^5$ or
N(R$^5$)$_2$,
  wherein phenyl and phenoxy are optionally substituted with one or more groups independently selected from halo or trifluoromethyl.

2. The compound of claim 1, wherein Y$^{1a}$ is selected from the group consisting of: aryl, heteroaryl, cycloalkyl, heterocycloalkyl, aryloxy,

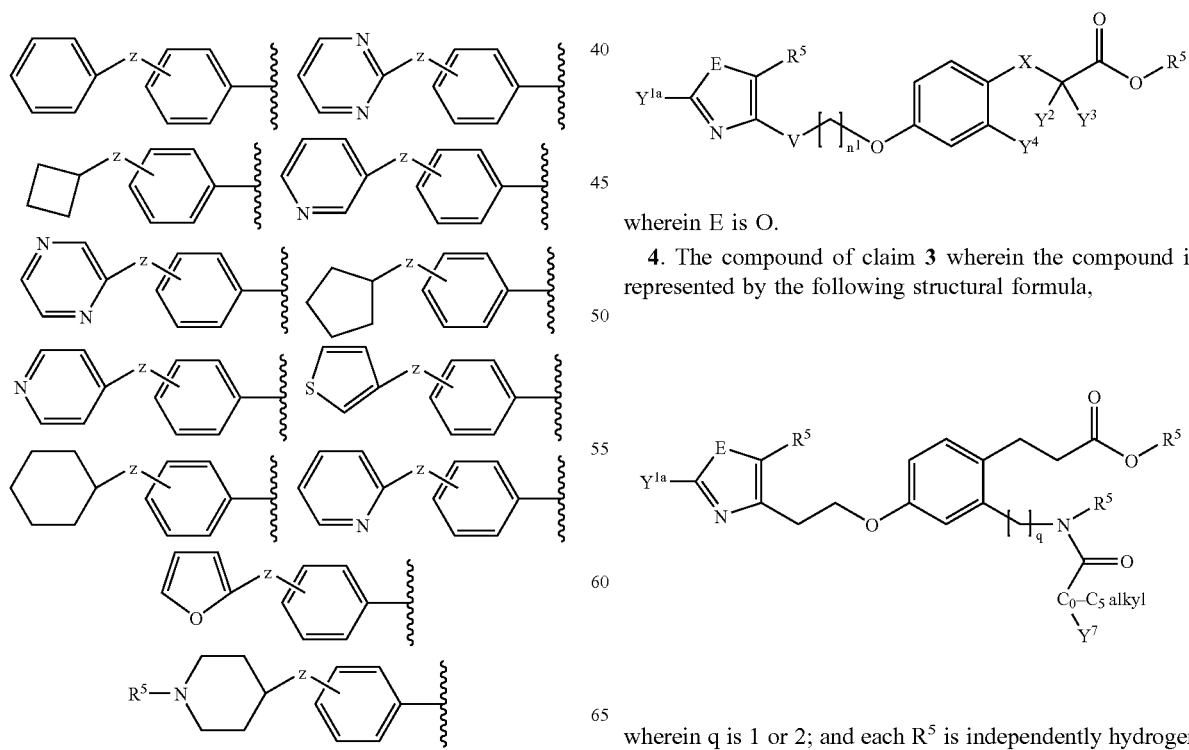

3. The compound of claim 1, wherein the compound is represented by the following structural formula,

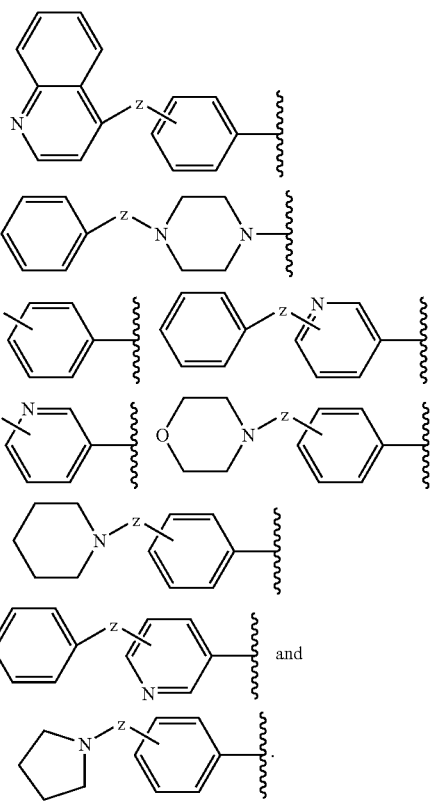

wherein E is O.

4. The compound of claim 3 wherein the compound is represented by the following structural formula, wherein q is 1 or 2; and each R$^5$ is independently hydrogen or methyl.

5. The compound of claim 3 wherein the compound is represented by the following structural formula,

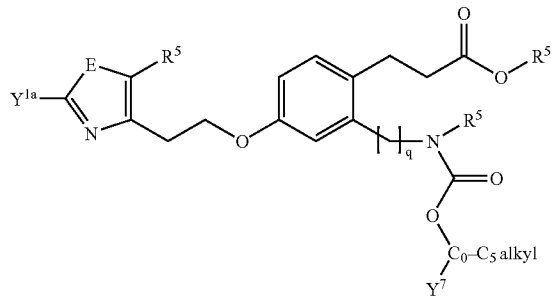

wherein q is 1 or 2; and each $R^5$ is independently hydrogen or methyl.

6. The compound of claim 3 wherein the compound is represented by the following structural formula,

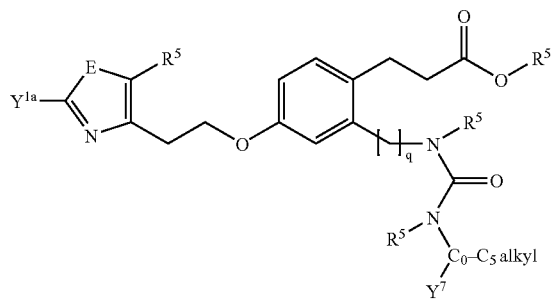

wherein q is 1 or 2; and each $R^5$ is independently hydrogen or methyl.

7. The compound of claim 3 wherein the compound is represented by the following structural formula,

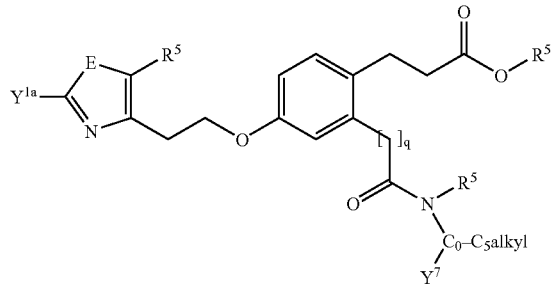

wherein q is 0 or 1; and each $R^5$ is independently hydrogen or methyl.

8. The compound of claim 3 wherein the compound is represented by the following structural formula,

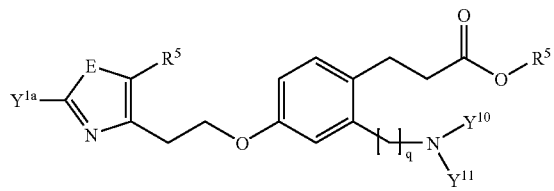

wherein q is 1 or 2; and each $R^5$ is independently hydrogen or methyl.

9. The compound of claim 3 wherein the compound is represented by the following structural formula,

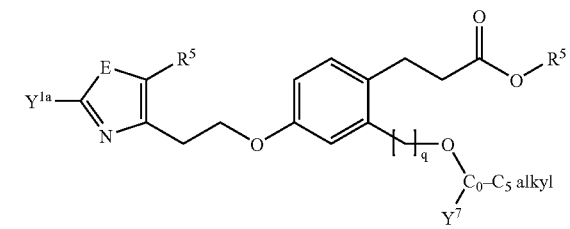

wherein q is 1 or 2; and each $R^5$ is independently hydrogen or methyl.

10. The compound of claim 3 wherein the compound is represented by the following structural formula,

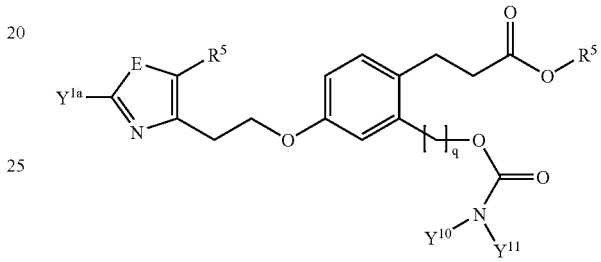

wherein q is 1 or 2; and each $R^5$ is independently hydrogen or methyl.

11. The compound of claim 3 wherein the compound is represented by the following structural Formula,

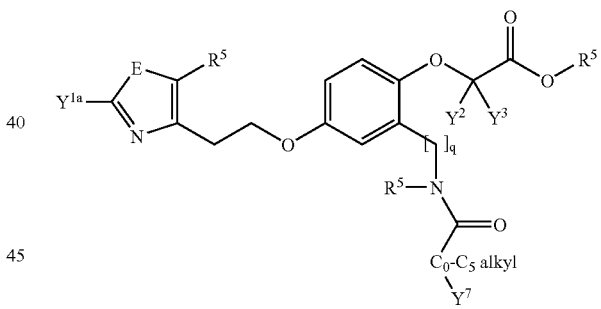

wherein q is 1 or 2; and each $R^5$, $Y^2$ and $Y^3$ are independently hydrogen or methyl.

12. The compound of claim 3 represented by the following structural formula,

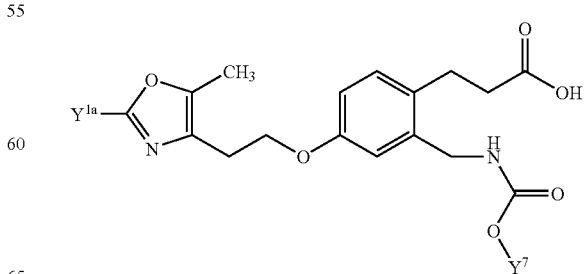

wherein $Y^{1a}$ is optionally substituted phenyl, naphthyl,

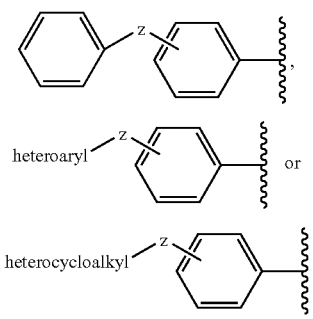

and Z is a bond, oxygen, —NH—, —N(CH$_3$)—, —NHC(O)— or —C(O)NH—.

13. The compound of claim 3 represented by the following structural formula,

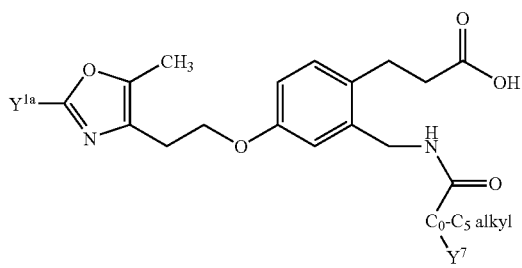

wherein $Y^{1a}$ is optionally substituted phenyl, naphthyl or

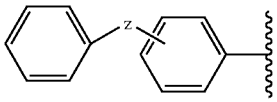

and Z is a bond, oxygen, —NH—, —N(CH$_3$)—, —NHC(O)— or —C(O)NH—.

14. The compound of claim 1 represented by the following structural formula,

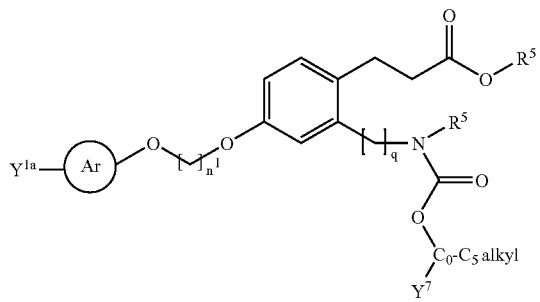

wherein,
$Y^{1a}$ is hydrogen, aryl, heteroaryl, or aryloxy; q is 1 or 2; and $n^1$ is 2, 3, or 4.

15. The compound of claim 1 represented by the following structural formula,

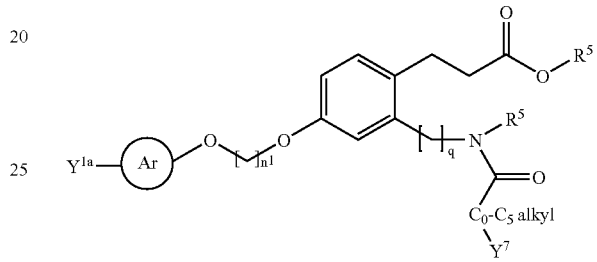

wherein,
$Y^{1a}$ is hydrogen, aryl, heteroaryl or aryloxy; q is 1 or 2; and $n^1$ is 2, 3, or 4.

16. The compound of claim 1 represented by a following structural formula,

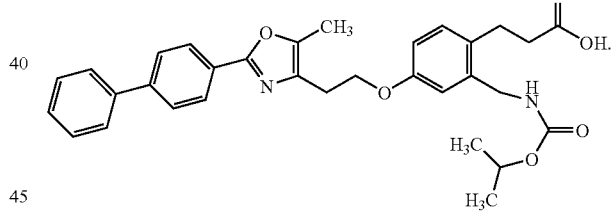

17. A compound selected from the group consisting of:

| No. | Compound | Name |
|---|---|---|
| 1 | ![compound structure] | 3-{2-(Diphenylacetyl-aminomethyl)-4-[2-(5-methyl-2-phenyloxazol-4-yl)ethoxy]phenyl} propionic acid, |

-continued

| No. | Compound | Name |
|---|---|---|
| 2 | | 3-{2-[(2-Cyclopropylacetylamino)methyl]-4-[2-(5-methyl-2-phenyloxazol-4-yl)ethoxy]phenyl} propionic acid |
| 3 | | 3-{2-[(3-Methoxybenzoylamino)methyl]-4-[2-(5-methyl-2-phenyloxazol-4-yl)ethoxy]phenyl} propionic acid, |
| 4 | | 3-{2-{[(Biphenyl-2-carbonyl)amino]methyl}-4-[2-(5-methyl-2-phenyloxazol-4-yl)ethoxy]phenyl} propionic acid, |
| 5 | | 3-(4-[2-(2-Biphenyl-4-yl-5-methyloxazol-4-yl)ethoxy]-2-{[(2,5-dichlorothiophene-3-carbonyl)amino]methyl}phenyl) propionic acid, |

-continued

| No. | Compound | Name |
|---|---|---|
| 6 | | 3-{2-(Isopropoxycarbonyl-aminomethyl)-4-[2-(5-methyl-2-phenyloxazol-4-yl)ethoxy]phenyl} propionic acid, |
| 7 | | 3-{2-(1,3-Dioxo-1,3-dihydroisoindol-2-ylmethyl)-4-[2-(5-methyl-2-phenyloxazol-4-yl)ethoxy]phenyl} propionic acid |
| 8 | | 3-{4-[2-(5-Methyl-2-phenyloxazol-4-yl)ethoxy]-2-[(3-phenylureido)methyl]phenyl} propionic acid, |
| 9 | | 3-[4-[2-(2-Biphenyl-4-yl-5-methyloxazol-4-yl)ethoxy]-2-(isopropoxycarbonyl-aminomethyl)phenyl]propionic acid |

-continued
| No. | Compound | Name |
|---|---|---|
| 13 | 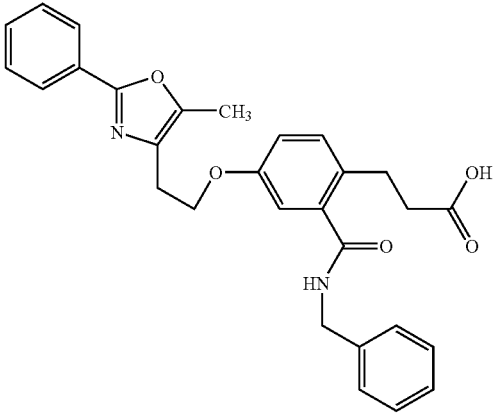 | 3-{2-Benzylcarbamoyl-4-[2-(5-methyl-2-phenyloxazol-4-yl)ethoxy]phenyl} propionic acid, |
| 14 | 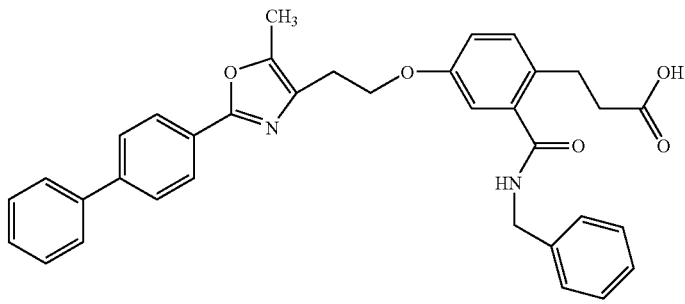 | 3-{2-Benzylcarbamoyl-4- [2-(2-biphenyl-4-yl-5-methyloxazol-4-yl)ethoxy]phenyl} propionic acid |
| 15 | 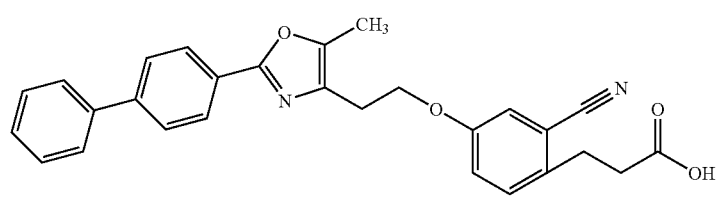 | 3-{4[2-(2-Biphenyl-4-yl-5-methyloxazol-4-yl)ethoxy]-2-cyanophenyl} propionic acid, |
| 16 | 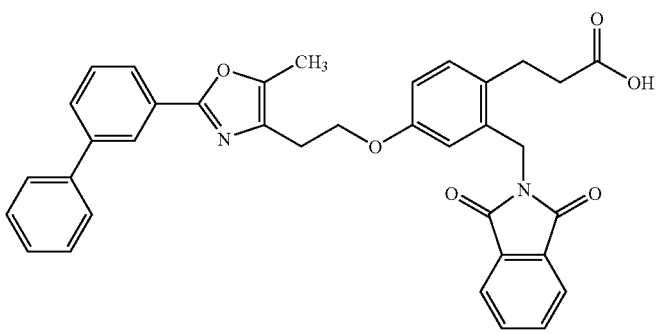 | 3-[4-[2-(2-Biphenyl-3-yl-5-methyloxazol-4-yl)ethoxy]-2-(1,3-dioxo-1,3-dihydroisoindol-2-ylmethyl)phenyl]propionic acid |

-continued
| No. | Compound | Name |
|---|---|---|
| 17 | 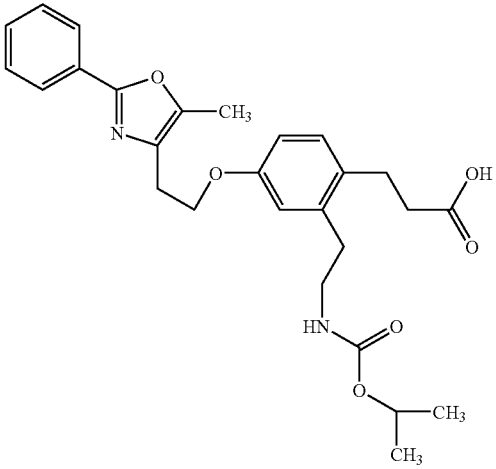 | 3-{2-(2-Isopropoxycarbonyl-aminoethyl)-4-[2-(5-methyl-2-phenyloxazol-4-yl)ethoxy]phenyl} propionic acid, |
| 18 | 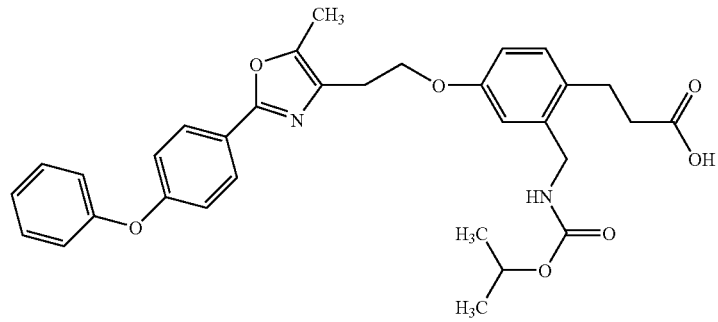 | 3-(2-(Isopropoxycarbonyl-aminomethyl)-4-{2-[5-methyl-2-(4-phenoxyphenyl)oxazol-4-yl]ethoxy}phenyl) propionic acid |
| 19 | 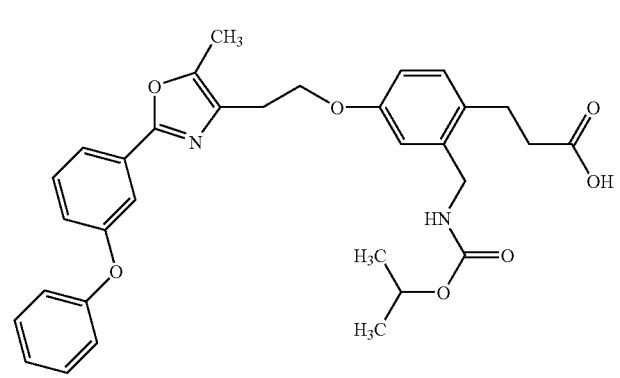 | 3-(2-(Isopropoxycarbonyl-aminomethyl)-4-{2-[5-methyl-2-(3-phenoxyphenyl)oxazol-4-yl]ethoxy}phenyl) propionic acid, |

-continued

| No. | Compound | Name |
|---|---|---|
| 21 | | 3-[4-[2-(2-Biphenyl-4-yl-5-methyloxazol-4-yl)ethoxy]-2-(2-isopropoxycarbonylaminoethyl)phenyl] propionic acid, |
| 22 | | 3-[4-[2-(2-Biphenyl-4-yl-5-methyloxazol-4-yl)ethoxy]-2-(isobutoxycarbonyl-aminomethyl)phenyl] propionic acid |
| 23 | | 3-[4-[2-(2-Biphenyl-4-yl-5-methyloxazol-4-yl)ethoxy]-2-(cyclopentyloxycarbonyl-aminomethyl)phenyl] propionic acid |

-continued

| No. | Compound | Name |
|---|---|---|
| 24 | | 3-(2-(Isopropoxycarbonyl-aminomethyl)-4-{2-[2-(4-isopropoxyphenyl)-5-methyloxazol-4-yl]ethoxy}phenyl) propionic acid, |
| 25 | | 3-(2-Benzylcarbamoyl-4-{2-[5-methyl-2-(4-phenoxyphenyl)oxazol-4-yl]ethoxy}phenyl) propionic acid, |
| 26 | | 3-(2-(Isopropoxycarbonyl-aminomethyl)-4-{2-[5-methyl-2-(4-morpholin-4-ylphenyl)oxazol-4-yl]ethoxy}phenyl) propionic acid |
| 27 | | 3-(2-(Isopropoxycarbonyl-aminomethyl)-4-{2-[5-methyl-2-(4-piperidin-1-ylphenyl)oxazol-4-yl]ethoxy}phenyl) propionic acid |

-continued

| No. | Compound | Name |
|---|---|---|
| 28 | | 3-(2-(Isopropoxycarbonyl-aminomethyl)-4-{2-[5-methyl-2-(4-pyrimidin-2-ylphenyl)oxazol-4-yl]ethoxy}phenyl) propionic acid |
| 29 | | 3-(2-(Isopropoxycarbonyl-aminomethyl)-4-{2-[5-methyl-2-(4-pyrazin-2-ylphenyl)oxazol-4-yl]ethoxy}phenyl) propionic acid |
| 31 | | 3-{2-Cyclohexylcarbamoyl-oxymethyl-4-[2-(5-methyl-2-phenyloxazol-4-yl)ethoxy]phenyl}propionic acid, |
| 32 | | 3-(2-(Isopropoxycarbonyl-aminomethyl)-4-{2-[5-methyl-2-(4-phenylaminophenyl)oxazol-4-yl]ethoxy}phenyl) propionic acid |

-continued

| No. | Compound | Name |
|---|---|---|
| 34 | 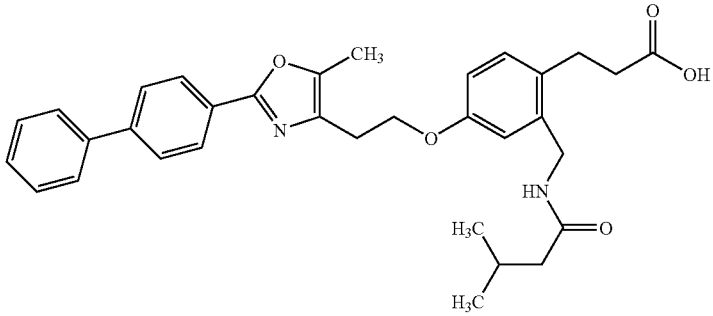 | 3-{4-[2-(2-Biphenyl-4-yl-5-methyloxazol-4-yl)ethoxy]-2-[(3-methylbutyrylamino)methyl]phenyl} propionic acid, |
| 35 | 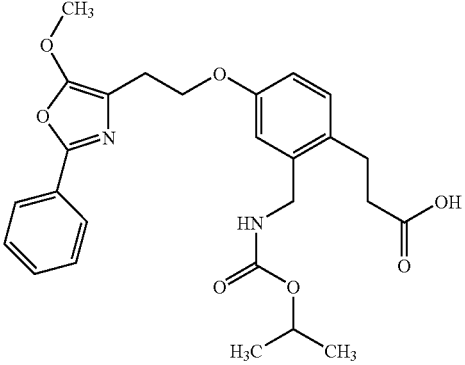 | 3-{2-(Isopropoxycarbonyl-aminomethyl)-4-[2-(5-methoxy-2-phenyloxazol-4-yl)ethoxy]phenyl} propionic acid, |
| 36 | 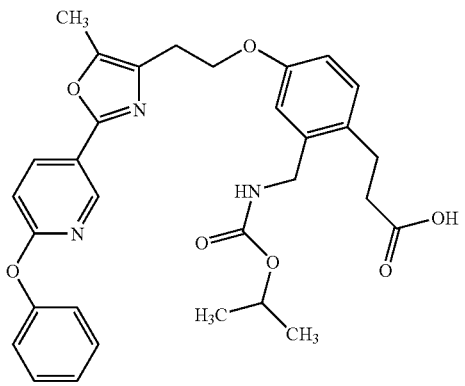 | 3-(2-(Isopropoxycarbonyl-aminomethyl)-4-{2-[5-methyl-2-(6-phenoxypyridin-3-yl)oxazol-4-yl]ethoxy}phenyl) propionic acid |
| 37 | 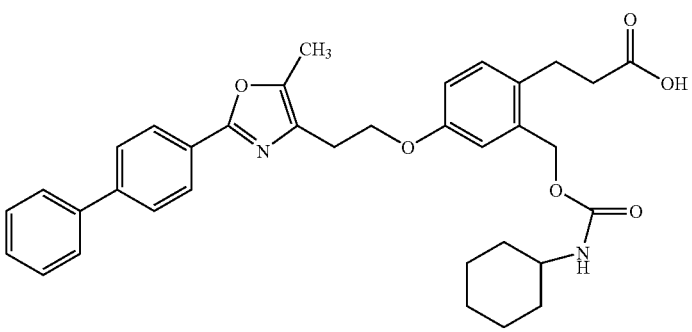 | 3-{4-[2-(2-Biphenyl-4-yl-5-methyloxazol-4-yl)ethoxy]-2-cyclohexylcarbamoyloxymethyl phenyl} propionic acid, |

-continued

| No. | Compound | Name |
|---|---|---|
| 39 | | 3-(2-Cyclohexylcarbamoyl-oxymethyl-4-{2-[5-methyl-2-(4-phenoxyphenyl)oxazol-4-yl]ethoxy}phenyl) propionic acid, |
| 40 | | 3-(2-Cyclohexylcarbamoyl-oxymethyl-4-{2-[5-methyl-2-(4-morpholin-4-ylphenyl)oxazol-4-yl]ethoxy}phenyl) propionic acid |
| 41 | | 3-[2-(Isopropoxycarbonyl-aminomethyl)-4-(2-{5-methyl-2-[3-(tetrahydropyran-4-yloxy)phenyl]oxazol-4-yl} ethoxy)phenyl] propionic acid, |
| 42 | | 3-[4-[2-(2-Biphenyl-4-yl-5-methyloxazol-4-yl)ethoxy]-2-(cyclopropylmethoxycarbonyl-aminomethyl)phenyl] propionic acid |

-continued

| No. | Compound | Name |
|---|---|---|
| 44 | 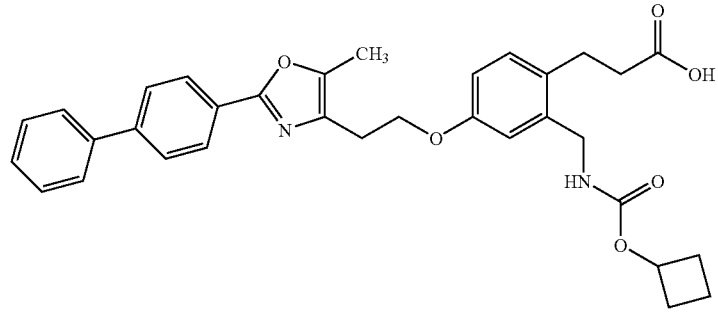 | 3-[4-[2-(2-Biphenyl-4-yl-5-methyloxazol-4-yl)ethoxy]-2-(cyclobutoxycarbonylamino-methyl)phenyl]propionic acid, HCl salt |
| 46 | 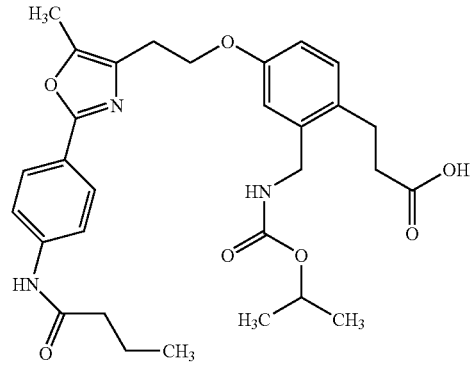 | 3[4-{2-[2-(4-Butyrylaminophenyl)-5-methyloxazol-4-yl]ethoxy}-2-(isopropoxycarbonyl-aminomethyl)phenyl]propionic acid |
| 47 | 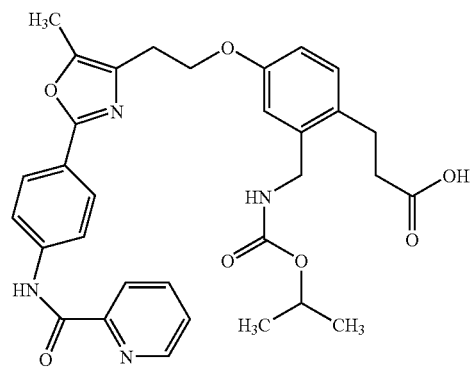 | 3-{2-(Isopropoxycarbonyl-amino-methyl)-4-[2-(5-methyl-2-{4-[(pyridine-2-carbonyl)-amino]-phenyl}-oxazol-4-yl)-ethoxy]-phenyl}-propionic acid, |
| 48 | 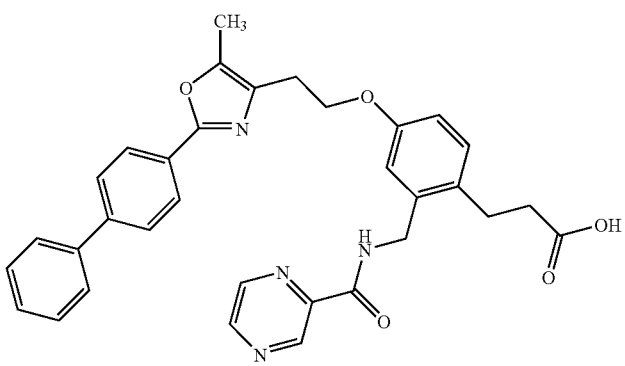 | 3-(4-[2-(2-Biphenyl-4-yl-5-methyloxazol-4-yl)ethoxy]-2-{[(pyrazine-2-carbonyl)amino]methyl}phenyl) propionic acid |

-continued

| No. | Compound | Name |
|---|---|---|
| 49 | | 3-[4-{2-[2-(3-Cyclohexylcarbamoylphenyl)-5-methyloxazol-4-yl]ethoxy}-2-(isopropoxycarbonyl-aminomethyl)phenyl] propionic acid |
| 50 | | 3-(2-(Isopropoxycarbonyl-aminomethyl)-4-{2-[5-methyl-2-(2-phenoxyphenyl)oxazol-4-yl]ethoxy}phenyl) propionic acid |
| 51 | | 3-(2-Cyano-4-{2-[5-methyl-2-(4-phenoxy-phenyl)-oxazol-4-yl-ethoxy}-phenyl) propionic acid |
| 52 | | 3-[2-(Isopropoxycarbonyl-aminomethyl)-4-(2-{5-methyl-2-[4-(pyridin-2-yloxy)phenyl]oxazol-4-yl}ethoxy)phenyl] propionic acid, |

-continued

| No. | Compound | Name |
|---|---|---|
| 53 | 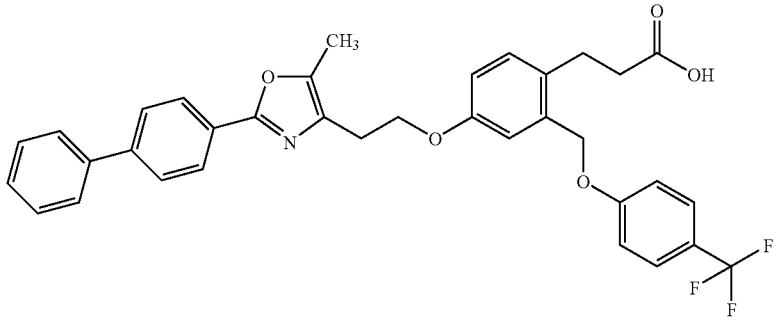 | 3-[4-[2-(2-Biphenyl-4-yl-5-methyloxazol-4-yl)ethoxy]-2-(4-trifluoromethylphenoxymethyl)phenyl] propionic acid, |
| 55 | 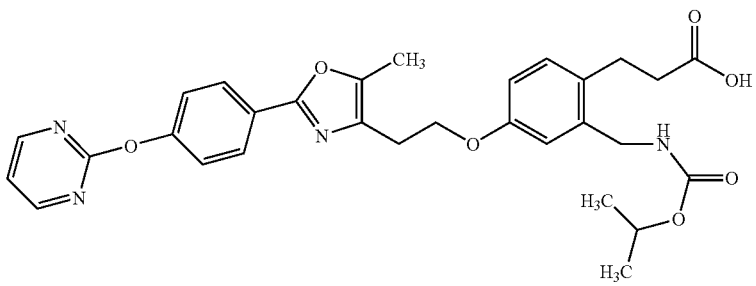 | 3-[2-(Isopropoxycarbonyl-aminomethyl)-4-(2-{5-methyl-2-[4-(pyrimidin-2-yloxy)phenyl]oxazol-4-yl}ethoxy)phenyl] propionic acid, |
| 56 | 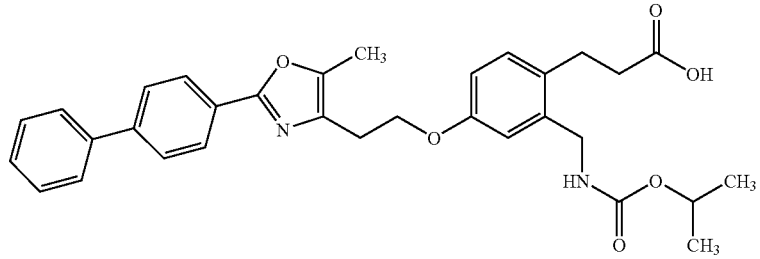 | 3-[4-[2-(2-Biphenyl-4-yl-5-methoxyoxazol-4-yl)ethoxy]-2-(isopropoxycarbonylaminomethyl)phenyl] propionic acid, |
| 57 | 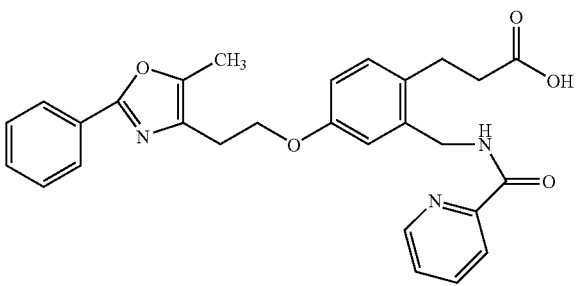 | 3-(4-[2-(5-Methyl-2-phenyl-oxazol-4-yl)-ethoxy]-2-{[(pyridine-2-carbonyl)-amino]-methyl}-phenyl)-propionic acid, |
| 58 | 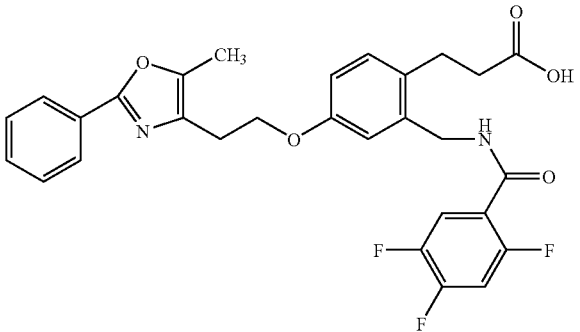 | 3-{4-[2-(5-Methyl-2-phenyl-oxazol-4-yl)-ethoxy]-2-[(2,4,5-trifluoro-benzoylamino)-methyl]-phenyl}-propionic acid, |

| No. | Compound | Name |
|---|---|---|
| 59 | | 3-{2-[(2,4-Difluoro-benzoylamino)-methyl]-4-[2-(5-methyl-2-phenyl-oxazol-4-yl)-ethoxy]-phenyl}-propionic acid, |
| 60 | | 3-(4-[2-(5-Methyl-2-phenyl-oxazol-4-yl)-ethoxy]-2-{[(thiophene-2-carbonyl)-amino]-methyl}-phenyl)-propionic acid, |
| 61 | | 3-(4-[2-(5-Methyl-2-phenyl-oxazol-4-yl)-ethoxy]-2-{[(thiophene-2-carbonyl)-amino]-methyl}-phenyl)-proprionic acid |
| 62 | | 3-{2-(Butyrylamino-methyl)-4-[2-(5-methyl-2-phenyl-oxazol-4-yl)-ethoxy]-phenyl}-propionic acid |
| 63 | | 3-{2-[(Cyclobutanecarbonyl-amino)-methyl]-4-[2-(5-methyl-2-phenyl-oxazol-4-yl)-ethoxy]-phenyl}-propionic acid, |

-continued

| No. | Compound | Name |
|---|---|---|
| 64 | | 3-{2-(Benzyloxycarbonylamino-methyl)-4-[2-(5-methyl-2-phenyl-oxazol-4-yl)-ethoxy]-phenyl}-propionic acid, |
| 65 | | 3-{2-(tert-Butoxycarbonylamino-methyl)-4-[2-(5-methyl-2-phenyl-oxazol-4-yl)-ethoxy]-phenyl}-propionic acid, |
| 66 | | 3-{4-[2-(5-Methyl-2-phenyl-oxazol-4-yl)-ethoxy]-2-[(2-phenoxy-acetylamino)-methyl]-phenyl}-propionic acid, |
| 67 | | 3-{2-[(Cyclopentanecarbonyl-amino)-methyl]-4-[2-(5-methyl-2-phenyl-oxazol-4-yl)-ethoxy]-phenyl}-propionic acid. |

18. A pharmaceutical composition comprising a pharmaceutically acceptable carrier and a compound of claim 1 or a pharmaceutically acceptable salt, solvate or hydrate thereof.

* * * * *